US009687448B2

(12) United States Patent
Akinc et al.

(10) Patent No.: US 9,687,448 B2
(45) Date of Patent: Jun. 27, 2017

(54) NUCLEIC ACID LIPID PARTICLE FORMULATIONS

(71) Applicant: ALNYLAM PHARMACEUTICALS, INC., Cambridge, MA (US)

(72) Inventors: Akin Akinc, Cambridge, MA (US); Martin Maier, Cambridge, MA (US); Varun Kumar, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/650,264

(22) PCT Filed: Dec. 4, 2013

(86) PCT No.: PCT/US2013/073181

§ 371 (c)(1),
(2) Date: Jun. 5, 2015

(87) PCT Pub. No.: WO2014/089239

PCT Pub. Date: Jun. 12, 2014

(65) Prior Publication Data

US 2015/0306039 A1 Oct. 29, 2015

Related U.S. Application Data

(60) Provisional application No. 61/734,736, filed on Dec. 7, 2012.

(51) Int. Cl.

| | |
|---|---|
| *A61K 9/16* | (2006.01) |
| *A61K 9/00* | (2006.01) |
| *A61K 9/127* | (2006.01) |
| *C12N 15/88* | (2006.01) |
| *A61K 31/713* | (2006.01) |

(52) U.S. Cl.

CPC .......... *A61K 9/1617* (2013.01); *A61K 9/0019* (2013.01); *A61K 9/1272* (2013.01); *A61K 9/1641* (2013.01); *A61K 31/713* (2013.01); *C12N 15/88* (2013.01)

(58) Field of Classification Search

None

See application file for complete search history.

(56) References Cited

U.S. PATENT DOCUMENTS

| | | | | |
|---|---|---|---|---|
| 2010/0267806 | A1* | 10/2010 | Bumcrot | C12N 15/111 514/44 A |
| 2010/0324120 | A1* | 12/2010 | Chen | A61K 9/1272 514/44 A |
| 2012/0183602 | A1 | 7/2012 | Chen et al. | |

FOREIGN PATENT DOCUMENTS

| | | | |
|---|---|---|---|
| WO | WO-02087541 | A1 | 11/2002 |
| WO | WO-2005007196 | A2 | 1/2005 |
| WO | WO-2010056403 | A1 | 5/2010 |
| WO | WO-2010057155 | A1 | 5/2010 |
| WO | WO-2011153493 | A2 | 12/2011 |
| WO | WO-2013086354 | A1 | 6/2013 |
| WO | WO-2014008334 | A1 | 1/2014 |

OTHER PUBLICATIONS

Allen, et al., Liposomes Containing Synthetic Lipid Derivatives of Poly(ethylene glycol) Show Prolonged Circulation Half-lives in vivo, Biochmica et Biophysica Acta (BBA), 1991, 1066:1:29-36.

International Search Report issued in PCT/US2013/073181 on Mar. 27, 2014.

* cited by examiner

*Primary Examiner* — Susan Tran

(74) *Attorney, Agent, or Firm* — Blank Rome LLP

(57) ABSTRACT

The present invention relates to lipid nanoparticles containing a biodegradable cationic lipid which provide improved delivery of active pharmaceutical ingredients, such as siRNA.

7 Claims, 1 Drawing Sheet

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (3)..(4)
<223> OTHER INFORMATION: 2'F modified nucleobase
<220> FEATURE:
<221> NAME/KEY: modified_base
<222> LOCATION: (6)..(9)
<223> OTHER INFORMATION: 2'F modified nucleobase
<220> FEATURE:
<221> NAME/KEY: modified_base
<222> LOCATION: (13)..(16)
<223> OTHER INFORMATION: 2'F modified nucleobase
<220> FEATURE:
<221> NAME/KEY: modified_base
<222> LOCATION: (18)..(18)
<223> OTHER INFORMATION: 2'F modified nucleobase
<220> FEATURE:
<221> NAME/KEY: modified_base
<222> LOCATION: (20)..(21)
<223> OTHER INFORMATION: Deoxyribothymine
<220> FEATURE:
<221> NAME/KEY: misc_feature
<222> LOCATION: (20)..(21)
<223> OTHER INFORMATION: /note="Phosphothioate linkage between residues"

<400> SEQUENCE: 1

ggaucaucuc aagucuuact t                                              21


<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'F modified nucleobase
<220> FEATURE:
<221> NAME/KEY: modified_base
<222> LOCATION: (6)..(8)
<223> OTHER INFORMATION: 2'F modified nucleobase
<220> FEATURE:
<221> NAME/KEY: modified_base
<222> LOCATION: (13)..(13)
```

<223> OTHER INFORMATION: 2'F modified nucleobase
<220> FEATURE:
<221> NAME/KEY: modified_base
<222> LOCATION: (16)..(18)
<223> OTHER INFORMATION: 2'F modified nucleobase
<220> FEATURE:
<221> NAME/KEY: modified_base
<222> LOCATION: (20)..(21)
<223> OTHER INFORMATION: Deoxyribothymine
<220> FEATURE:
<221> NAME/KEY: misc_feature
<222> LOCATION: (20)..(21)
<223> OTHER INFORMATION: /note="Phosphothioate linkage between residues"

<400> SEQUENCE: 2
guaagacuug agaugaucct t 21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"
<220> FEATURE:
<221> NAME/KEY: modified_base
<222> LOCATION: (2)..(2)
<223> OTHER INFORMATION: 2'-OMe modified nucleobase
<220> FEATURE:
<221> NAME/KEY: modified_base
<222> LOCATION: (5)..(6)
<223> OTHER INFORMATION: 2'-OMe modified nucleobase
<220> FEATURE:
<221> NAME/KEY: modified_base
<222> LOCATION: (12)..(12)
<223> OTHER INFORMATION: 2'-OMe modified nucleobase
<220> FEATURE:
<221> NAME/KEY: modified_base
<222> LOCATION: (14)..(17)
<223> OTHER INFORMATION: 2'-OMe modified nucleobase
<220> FEATURE:
<221> NAME/KEY: modified_base
<222> LOCATION: (19)..(19)
<223> OTHER INFORMATION: 2'-OMe modified nucleobase
<220> FEATURE:
<221> NAME/KEY: modified_base
<222> LOCATION: (20)..(21)
<223> OTHER INFORMATION: Deoxyribothymine

<400> SEQUENCE: 3
guaaccaaga guauuccaut t 21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"
<220> FEATURE:
<221> NAME/KEY: modified_base
<222> LOCATION: (7)..(7)
<223> OTHER INFORMATION: 2'-OMe modified nucleobase
<220> FEATURE:
<221> NAME/KEY: modified_base -continued

```
<222> LOCATION: (17)..(17)
<223> OTHER INFORMATION: 2'-OMe modified nucleobase
<220> FEATURE:
<221> NAME/KEY: modified_base
<222> LOCATION: (20)..(21)
<223> OTHER INFORMATION: Deoxyribothymine

<400> SEQUENCE: 4

auggaauacu cuugguuact t                                    21
```

NUCLEIC ACID LIPID PARTICLE FORMULATIONS

This application is the national stage phase of International Patent Application No. PCT/US2013/073181, filed Dec. 4, 2013, which claims the benefit of U.S. Provisional Application No. 61/734,736, filed Dec. 7, 2012, which is hereby incorporated by reference.

FIELD OF THE INVENTION

The present invention relates to lipid nanoparticles containing a biodegradable cationic lipid which provide improved delivery of active pharmaceutical ingredients, such as siRNA.

BACKGROUND OF THE INVENTION

The development of short interfering RNA sequences (siRNAs) as therapeutics has been hindered by problems in delivering the siRNA to its target. siRNA rapidly undergoes enzymatic degradation resulting in a short half-life in the blood, and has poor cellular update and tissue bioavailability. As a result, there has been significant research on delivering siRNA in lipid nanoparticles (LNPs).

Many LNPs include components to minimize aggregation. The inclusion of pegylated lipids into LNPs is known to inhibit aggregation, however, PEG can affect the intracellular delivery and trafficking of non-viral vectors. See, e.g., Heyes et al., *J. Control. Release,* 112 (2006) 280-290. The instructions for some pharmaceuticals indicate that the formulation should be shaken before use in order to break up aggregates and minimize their effect during dosing. However, shaking may not sufficiently break-up aggregates, and there is a risk that the medical practitioner will not perform this function.

There is, therefore, a need for improved stable LNP formulations with minimal aggregation.

SUMMARY OF THE INVENTION

The present invention is directed to lipid nanoparticles comprising a biodegradable cationic lipid and polyethylene glycol-dipalmitoylglycerol (PEG-DPG). It has been discovered that such lipid nanoparticles exhibit improved delivery of active pharmaceutical ingredients, such as a nucleic acid (e.g., siRNA).

One embodiment of the invention are lipid nanoparticles comprising (a) a biodegradable cationic lipid, (b) PEG-DPG, (c) a non-cationic lipid (such as a neutral lipid), (d) optionally, a sterol, and (e) an active pharmaceutical ingredient.

Another embodiment is a pharmaceutical formulation suitable for parenteral administration comprising (a) lipid nanoparticles of the present invention in (b) a medium (such as de-ionized water). The formulation has one or more of the following characteristics:

(i) the medium is substantially free of anions, (ii) the medium is non-ionic or substantially non-ionic, and (iii) the formulation has a pH less than the pKa of the cationic lipid.

In one preferred embodiment, the formulation has a pH ranging from about 4 to about 6.

In addition or as an alternative to the three characteristics above, the formulation is sufficiently stable such that, when the formulation is subjected to vortexing for 60, 90, or 120 seconds the particle size distribution of the lipid nanoparticles does not substantially change. For instance, the $d_{50}$ of the lipid nanoparticles after vortexing is not more than 40 or 50% greater than that of the lipid nanoparticles before vortexing. In one particular embodiment, when the lipid nanoparticles have a unimodal particle size distribution before vortexing, the lipid nanoparticles also exhibit a unimodal particle size distribution after vortexing.

In certain embodiments, the lipid nanoparticles in the formulation have a $d_{98}$ of less than 1 micron, such as less than about 500 nm, less than about 400 nm, less than about 300 nm, less than about 250 nm, less than about 200 nm, less than about 150 nm or less than about 100 nm. For example, the lipid nanoparticles have a $d_{99}$ of less than 1 micron, such as less than about 500 nm, less than about 400 nm, less than about 300 nm, less than about 250 nm, less than about 200 nm, less than about 150 nm or less than about 100 nm. In additional embodiments, the particle has a $d_{50}$ of less than about 100 nm, such as less than about 75 nm, less than about 50 nm, less than about 40 nm, less than about 30 nm, less than about 20 nm or less than about 10 nm. For instance, the lipid nanoparticles may have a $d_{99}$ ranging from about 50 to about 200 nm, or from about 75 to about 150 nm. The lipid nanoparticles may have a $d_{50}$ ranging from about 5 to about 50 nm, such as from about 10 to about 40 nm or from about 20 to about 30 nm.

According to another aspect, the present invention relates to a pharmaceutical formulation suitable for parenteral administration comprising lipid nanoparticles of the present invention in a medium, where the lipid nanoparticles have a $d_{98}$ of less than 1 micron, such as less than about 500 nm, less than about 400 nm, less than about 300 nm, less than about 250 nm, less than about 200 nm, less than about 150 nm or less than about 100 nm. For instance, the lipid nanoparticles may have a $d_{99}$ of less than 1 micron, such as less than about 500 nm, less than about 400 nm, less than about 300 nm, less than about 250 nm, less than about 200 nm, less than about 150 nm or less than about 100 nm. In additional embodiments, the particle has a $d_{50}$ of less than about 100 nm, such as less than about 75 nm, less than about 50 nm, less than about 40 nm, less than about 30 nm, less than about 20 nm or less than about 10 nm. In one embodiment, the lipid nanoparticles may have a $d_{99}$ ranging from about 50 to about 200 nm, or from about 75 to about 150 nm. The lipid nanoparticles may have a $d_{50}$ ranging from about 5 to about 50 nm, such as from about 10 to about 40 nm or from about 20 to about 30 nm.

In one preferred embodiment, the $d_{50}$, $d_{98}$ or $d_{99}$ of the lipid nanoparticles in the formulation does not vary by more than 40, 30, 20, 10, or 5% after 1 month of storage at 4° C. In one embodiment, after 1 month of storage at 4° C., the lipid nanoparticles in the formulation have $d_{50}$, $d_{98}$ and/or $d_{99}$ values as set forth above. For instance, after 1 month storage at 4° C., the lipid nanoparticles in the formulation have $d_{98}$ or $d_{99}$ of less than 1 micron, such as less than about 500 nm, less than about 400 nm, less than about 300 nm, less than about 250 nm, less than about 200 nm, less than about 150 nm or less than about 100 nm.

In yet another embodiment, the lipid nanoparticles in the formulation of the present invention have a single mode particle size distribution (i.e., they are not bi- or poly-modal).

The formulation preferably has a low ionic strength, for example, an ionic strength less than about 50 mM, about 40 mM, about 30 mM, about 20 mM, about 15 mM, about 10 mM, about 5 mM, about 2 mM, or about 1 mM. (The ionic strength of the formulation can be measured using techniques known to the skilled person, for example using a conductivity meter.)

The medium may comprise a non-ionic or substantially non-ionic diluent, and preferably includes a non-ionic or substantially non-ionic diluent that does not destabilize the formulation. In one embodiment, the non-ionic or substantially non-ionic diluent increases the stability of the lipid nanoparticles, such as against mechanical disturbances, and/or inhibits the aggregation of the lipid nanoparticles. The medium may comprise water. In a preferred embodiment, the medium is deionized (e.g., deionized water). The water in the medium may have been purified by reverse osmosis. In a preferred embodiment, the medium contains less than about 50 ppm of mineral acid(s), such as less than about 40 ppm, less than about 30 ppm, less than about 20 ppm, less than about 10 ppm, less than about 5 ppm or less than about 1 ppm of mineral acid(s).

In one embodiment, the formulation further comprises an acid, wherein the molar concentration ratio of (a) the concentration of the anions formed from the acid to (b) the concentration of the acid is less than about 0.5, such as less than about 0.4, less than about 0.3, less than about 0.2 or less than about 0.1. In a particular embodiment, the molar ratio of anion concentration to acid concentration is less than about 0.2 to about 0.5. The anions present in the formulation may be derived from the acid in the medium. In one embodiment, the anion is a monovalent anion (such as an anion derived from acetic acid).

In another embodiment, the medium is free or substantially free of buffer. In one embodiment, the medium contains less than 2, 1, 0.5, 0.2, 0.1, or 0.05% by weight of buffer (based upon 100% total weight of the medium).

In yet another embodiment, the medium is free or substantially free of all or one or more of citrate, saline, L-histidine HCl, histidine, phosphate, and imidazole HCl. In one embodiment, the medium contains less than 2, 1, 0.5, 0.2, 0.1, or 0.05% by weight of each these components or of these components in total (based upon 100% total weight of the medium)

In one embodiment, the formulation further comprises one or more isotonicity agents. Preferably, the formulation includes a sufficient amount of the isotonicity agent(s) to render the formulation physiologically isotonic (i.e., have a pharmaceutically acceptable osmolality) in order to avoid cell distortion or lysis.

In a preferred embodiment, the active pharmaceutical ingredient in the lipid nanoparticles is a nucleic acid, such as a siRNA. The nucleic acid-lipid particle preferably has an encapsulation efficiency of greater than about 90, 92, 95, or 98%, after storage of the formulation for 1 month at about 4° C.

The formulations described herein may be solutions or suspensions.

In one preferred embodiment, the formulation has a pH ranging from about 4 to about 6, such as a pH ranging from about 4 to about 5 or a pH ranging from about 5 to about 6.

DETAILED DESCRIPTION OF THE INVENTION

Definitions

Figure 1:
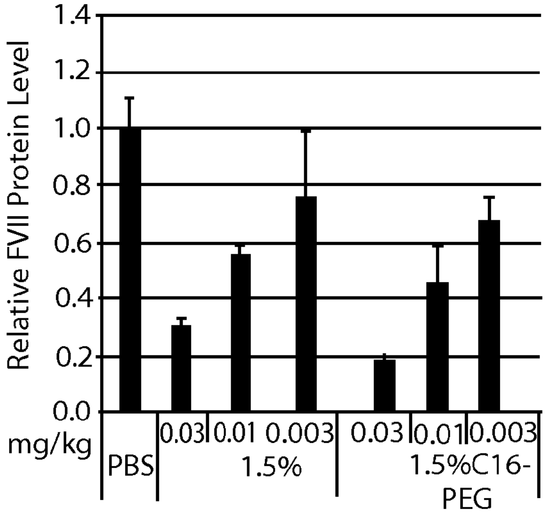
FIG. 1 shows the relative Factor VII protein level 48 hours after intravenous administration of the formulations prepared in Example 1 and Comparative Example 1 in mice.

The term "biodegradable cationic lipid" refers to a cationic lipid having one or more biodegradable groups located in the mid- or distal section of a lipidic moiety (e.g., a hydrophobic chain) of the cationic lipid. The incorporation of the biodegradable group(s) into the cationic lipid results in faster metabolism and removal of the cationic lipid from the body following delivery of the active pharmaceutical ingredient to a target area.

The term "subject" or "patient" refers to a mammal, such as a human, domestic animal, such as a feline or canine subject, farm animal (e.g., bovine, equine, caprine, ovine, and porcine subject), wild animal (whether in the wild or in a zoological garden), research animal, such as mouse, rat, rabbit, goat, sheep, pig, dog, and cat, avian species, such as chicken, turkey, and songbird. The "subject" or "patient" can also be a plant.

The terms "treat" and "treatment" refer to (a) relief from or alleviation of at least one symptom of a disorder in a subject, (b) relieving or alleviating the intensity and/or duration of a manifestation of a disorder experienced by a subject, (c) slowing or reversing the progression of such condition, and (d) arresting, delaying the onset (i.e., the period prior to clinical manifestation of a disorder) and/or reducing the risk of developing or worsening a disorder.

As used herein, the term "intravenous infusion" or "IV infusion" refers to a method of administration of a composition directly into the vein of a patient. IV infusion allows for direct administration of a pharmaceutical formulation to the bloodstream of a patient. This can be performed, for example, via subcutaneous or intradermal infusion. IV infusion can be performed in many ways, including through the use of an injection needle, or with an infusion pump. It can be provided as, for example, a continuous infusion, an intermittent infusion, a patient-controlled infusion, or a circadian infusion.

An "isotonicity agent" generally refers to a compound that is physiologically tolerated and imparts a suitable tonicity to a formulation to prevent the net flow of water across cell membranes that are in contact with the formulation.

The term "encapsulation efficiency" as used herein refers to the percentage of nucleic acid in the lipid nanoparticles that is not degraded after exposure to serum or a nuclease assay that would significantly degrade free nucleic acids. Encapsulation efficiency can be measured as follows:

Dilute the lipid nanoparticle formulation to ~5 μg/mL in 1×TE buffer. Place 50 μL of the sample in a well in a polystyrene 96 well plate, and 50 μL in the well below it. Add 50 μL of 1×TE buffer to the top well, and 50 μL of 2% Triton X-100 to the bottom well. For the reference wells, replace the sample with 50 μL of 1×TE buffer.

Allow the 96 well plate to incubate at 35° C. for 15 minutes. During this time, remove the Quant-iT™ RiboGreen® from the −20° C. storage and allow it to thaw. Once thawed, dilute the RiboGreen 1:100 in 1×TE buffer. After the 15 minute incubation, add 100 μL of diluted RiboGreen reagent to each well, mixing thoroughly by pipetting up and down. Try to avoid creating bubbles while mixing; the samples containing Triton X-100 are especially prone to bubble formation.

Once addition of the RiboGreen is complete, the plate is then read by a fluorescence plate reader (FITC settings); after subtracting the fluorescence values of the blanks from each sample well, the percent of free siRNA may be determined by dividing the fluorescence of the intact liposome sample (no Triton X-100) by the fluorescence value of the disrupted liposome sample (with Triton X-100).

Entrapped fraction=1−free fraction

Encapsulation efficiency=100*Entrapped fraction

The term "fully encapsulated" as used herein indicates that the nucleic acid in the particles is not significantly degraded after exposure to serum or a nuclease assay that would significantly degrade free nucleic acids. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

As used herein, the term "biodegradable group" reefers to a group that include one or more bonds that may undergo bond breaking reactions in a biological environment, e.g., in an organism, organ, tissue, cell, or organelle. For example, the biodegradable group may be metabolizable by the body of a mammal, such as a human (e.g., by hydrolysis). Some groups that contain a biodegradable bond include, for example, but are not limited to esters, dithiols, and oximes. Non-limiting examples of biodegradable groups are —OC(O)—, —C(O)O—, —SC(O)—, —C(O)S—, —OC(S)—, —C(S)O—, —S—S—, —C($R^5$)═N—, —N═C($R^5$)—, —C($R^5$)═N—O—, —O—N═C($R^5$)—, —C(O)($NR^5$)—, —N($R^5$)C(O)—, —C(S)($NR^5$)—, —N($R^5$)C(O)—, —N($R^5$)C(O)N($R^5$)—, —OC(O)O—, —OSi($R^5$)$_2$O—, —C(O)($CR^3R^4$)C(O)O—, or —OC(O)($CR^3R^4$)C(O)—.

As used herein, an "aliphatic" group is a non-aromatic group in which carbon atoms are linked into chains, and is either saturated or unsaturated.

The terms "alkyl" and "alkylene" refer to a straight or branched chain saturated hydrocarbon moiety. In one embodiment, the alkyl group is a straight chain saturated hydrocarbon. Unless otherwise specified, the "alkyl" or "alkylene" group contains from 1 to 24 carbon atoms. Representative saturated straight chain alkyl groups include methyl, ethyl, n-propyl, n-butyl, n-pentyl, and n-hexyl. Representative saturated branched alkyl groups include isopropyl, sec-butyl, isobutyl, tert-butyl, and isopentyl.

The term "alkenyl" refers to a straight or branched chain hydrocarbon moiety having one or more carbon-carbon double bonds. In one embodiment, the alkenyl group contains 1, 2, or 3 double bonds and is otherwise saturated. Unless otherwise specified, the "alkenyl" group contains from 2 to 24 carbon atoms. Alkenyl groups include both cis and trans isomers. Representative straight chain and branched alkenyl groups include ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

The term "alkynyl" refers to a straight or branched chain hydrocarbon moiety having one or more carbon-carbon triple bonds. Unless otherwise specified, the "alkynyl" group contains from 2 to 24 carbon atoms. Representative straight chain and branched alkynyl groups include acetylenyl, propynyl, 1-butynyl, 2-butynyl, 1-pentynyl, 2-pentynyl, and 3-methyl-1-butynyl.

Unless otherwise specified, the terms "branched alkyl", "branched alkenyl", and "branched alkynyl" refer to an alkyl, alkenyl, or alkynyl group in which one carbon atom in the group (1) is bound to at least three other carbon atoms and (2) is not a ring atom of a cyclic group. For example, a spirocyclic group in an alkyl, alkenyl, or alkynyl group is not considered a point of branching.

The term "acyl" refers to a carbonyl group substituted with hydrogen, alkyl, partially saturated or fully saturated cycloalkyl, partially saturated or fully saturated heterocycle, aryl, or heteroaryl. For example, acyl groups include groups such as ($C_1$-$C_{20}$)alkanoyl (e.g., formyl, acetyl, propionyl, butyryl, valeryl, caproyl, and t-butylacetyl), ($C_3$-$C_{20}$)cycloalkylcarbonyl (e.g., cyclopropylcarbonyl, cyclobutylcarbonyl, cyclopentylcarbonyl, and cyclohexylcarbonyl), heterocyclic carbonyl (e.g., pyrrolidinylcarbonyl, pyrrolid-2-one-5-carbonyl, piperidinylcarbonyl, piperazinylcarbonyl, and tetrahydrofuranylcarbonyl), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, and benzo[b]thiophenyl-2-carbonyl).

The term "aryl" refers to an aromatic monocyclic, bicyclic, or tricyclic hydrocarbon ring system. Unless otherwise specified, the "aryl" group contains from 6 to 14 carbon atoms. Examples of aryl moieties include, but are not limited to, phenyl, naphthyl, anthracenyl, and pyrenyl.

The terms "cycloalkyl" and "cycloalkylene" refer to a saturated monocyclic or bicyclic hydrocarbon moiety such as cyclopropyl, cyclobutyl, cyclopentyl, and cyclohexyl. Unless otherwise specified, the "cycloalkyl" or "cycloalkylene" group contains from 3 to 10 carbon atoms.

The term "cycloalkylalkyl" refers to a cycloalkyl group bound to an alkyl group, where the alkyl group is bound to the rest of the molecule.

The term "heterocycle" (or "heterocyclyl") refers to a non-aromatic 5- to 8-membered monocyclic, or 7- to 12-membered bicyclic, or 11- to 14-membered tricyclic ring system which is either saturated or unsaturated, and which contains from 1 to 3 heteroatoms if monocyclic, 1-6 heteroatoms if bicyclic, or 1-9 heteroatoms if tricyclic, independently selected from nitrogen, oxygen and sulfur, and wherein the nitrogen and sulfur heteroatoms may be optionally oxidized, and the nitrogen heteroatom may be optionally quaternized. For instance, the heterocycle may be a cycloalkoxy group. The heterocycle may be attached to the rest of the molecule via any heteroatom or carbon atom in the heterocycle. Heterocycles include, but are not limited to, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

The term "heteroaryl" refers to an aromatic 5-8 membered monocyclic, 7-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively). The heteroaryl groups herein described may also contain fused rings that share a common carbon-carbon bond.

The term "substituted", unless otherwise indicated, refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and an aliphatic group. It is understood that the substituent may be further substituted. Exemplary substituents include amino, alkylamino, dialkylamino, and cyclic amino compounds.

The term "halogen" or "halo" refers to fluoro, chloro, bromo and iodo.

The terms "alkylamine" and "dialkylamine" refer to —NH(alkyl) and —$N(alkyl)_2$ radicals respectively.

The term "hydroxyalkyl" refers to —O-alkyl radical.

The term "alkylheterocycle" refers to an alkyl where at least one methylene has been replaced by a heterocycle.

The following abbreviations are used in this application: DSPC: distearoylphosphatidylcholine; DPPC: 1,2-Dipalmitoyl-sn-glycero-3-phosphocholine; POPC: 1-palmitoyl-2-oleoyl-sn-phosphatidylcholine; DOPE: 1,2-dileoyl-sn-3-phosphoethanolamine; PEG-DMG generally refers to 1,2-dimyristoyl-sn-glycerol-methoxy polyethylene glycol (e.g., PEG 2000); TBDPSCl: tert-Butylchlorodiphenylsilane; DMAP: dimethylaminopyridine; NMO: N-methylmorpholin-N-oxide; LiHDMS: lithium bis(trimethylsilyl)amide; HMPA: hexamethylphosphoramide; EDC: 1-ethyl-3-(3-dimethylaminopropyl) carbodiimide; DIPEA: diisopropylethylamine; DCM: dichloromethane; TEA: triethylamine; TBAF: tetrabutylammonium fluoride Active Pharmaceutical Ingredients The active pharmaceutical ingredient can be any compound suitable for incorporation into a lipid nanoparticle. In one embodiment, the active pharmaceutical ingredient is encapsulated within an aqueous interior of the lipid nanoparticle. In another embodiment, the active pharmaceutical ingredient is present within one or more lipid layers of the lipid nanoparticle. In yet another embodiment, the active pharmaceutical ingredient is bound to the exterior or interior of the lipid surface of the lipid nanoparticle.

The active pharmaceutical ingredient can be any compound capable of exerting a desired effect on a cell, tissue, organ, or subject. Such effects may be biological, physiological, or cosmetic, for example. The active pharmaceutical ingredient can be a nucleic acid, peptide, polypeptide (e.g., an antibody), cytokine, growth factor, apoptotic factor, differentiation-inducing factor, cell surface receptor or a corresponding ligand, or hormone. Suitable active pharmaceutical ingredient include, but are not limited to, anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs (e.g., anti-arrhythmic agents), vasoconstrictors, hormones, steroids, and oncology drugs (e.g., an anti-tumor agent, an anti-cancer drug, or anti-neoplatic agent).

In a preferred embodiment, the active pharmaceutical ingredient is a nucleic acid. The nucleic acid can be an interfering RNA (such as a siRNA), an antisense oligonucleotide, a DNAi oligonucleotide, a ribozyme, an aptamer, a plasmid, or any combination of any of the foregoing. For example, the nucleic acid can be encoded with a product of interest including, but not limited to, RNA, antisense oligonucleotide, an antagomir, a DNA, a plasmid, a ribosomal RNA (rRNA), a micro RNA (miRNA) (e.g., a miRNA which is single stranded and 17-25 nucleotides in length), transfer RNA (tRNA), a small interfering RNA (siRNA), small nuclear RNA (snRNA), antigens, fragments thereof, proteins, peptides, and vaccines or mixtures thereof. In one embodiment, the nucleic acid is an oligonucleotide (e.g., 15-50 nucleotides in length (or 15-30 or 20-30 nucleotides in length)). An siRNA can have, for instance, a duplex region that is 16-30 nucleotides long (e.g., 17-21 or 19-21 nucleotides long). In another embodiment, the nucleic acid is an immunostimulatory oligonucleotide, decoy oligonucleotide, supermir, miRNA mimic, or miRNA inhibitor. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. miRNA mimics represent a class of molecules that can be used to imitate the gene silencing ability of one or more miRNAs. The term "microRNA mimic" refers to synthetic non-coding RNAs (i.e. the miRNA is not obtained by purification from a source of the endogenous miRNA) that are capable of entering the RNAi pathway and regulating gene expression.

The nucleic acid that is present in a lipid nanoparticle can be in any form. The nucleic acid can, for example, be single-stranded DNA or RNA, or double-stranded DNA or RNA, or DNA-RNA hybrids. Non-limiting examples of double-stranded RNA include siRNA. Single-stranded nucleic acids include, e.g., antisense oligonucleotides, ribozymes, microRNA, and triplex-forming oligonucleotides. The nucleic acid can be conjugated to one or more ligands.

In further embodiments, the nucleic acid is selected from an interfering RNA, an antisense oligonucleotide, a DNAi oligonucleotide, a ribozyme, an aptamer, a plasmid, and any combination of any of the foregoing. In one embodiment, the RNA is selected from siRNA, aiRNA, miRNA, Dicer-substrate dsRNA, shRNA, ssRNAi oligonucleotides, and any combination of any of the foregoing.

In a more preferred embodiment, the active pharmaceutical ingredient is an siRNA (e.g., an siRNA having a duplex region that is 17-21 or 19-21 nucleotides long). Formulations containing siRNA are useful in down-regulating the protein levels and/or mRNA levels of target proteins. The siRNA may be unmodified oligonucleotides or modified, and may be conjugated with lipophilic moieties such as cholesterol.

In another embodiment, the active pharmaceutical ingredient is a micro RNA.

In one preferred embodiment, the active pharmaceutical ingredient (e.g., a nucleic acid) is fully encapsulated in the lipid nanoparticle.

Biodegradable Cationic Lipids

The lipid nanoparticle may include any biodegradable cationic lipid suitable for forming a lipid nanoparticle, such as those described in International Publication No. WO 2011/153493, U.S. Patent Publication No. 2012/0027803, and U.S. Provisional Application Nos. 61/568,121 (filed Dec. 7, 2011), 61/568,078 (filed Dec. 7, 2011), 61/568,106 (filed Dec. 7, 2011), 61/568,133 (filed Dec. 7, 2011), 61/623,274 (filed Apr. 12, 2012), and 61/596,093 (filed Feb. 7, 2012), each of which is hereby incorporated by reference. Preferably, the cationic lipid carries a net positive charge at about physiological pH.

The cationic lipid may be an amino lipid. As used herein, the term "amino lipid" is meant to include those lipids having one or two fatty acid or fatty alkyl chains and an amino head group (including an alkylamino or dialkylamino group) that may be protonated to form a cationic lipid at physiological pH.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterrionic, are not excluded from use in the invention.

In certain embodiments, the protonatable lipids have a pKa of the protonatable group in the range of about 4 to about 11, e.g., a pKa of about 5 to about 7. In another embodiment, the cationic lipid has a pKa ranging from about 4 to about 11, and preferably from about 5 to about 7.

In one embodiment, the cationic lipid is a compound of the formula:

Formula (I)

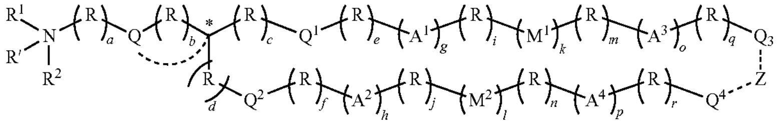

or a salt thereof (e.g., a pharmaceutically acceptable salt thereof), wherein

R' is absent, hydrogen, or alkyl (e.g., $C_1$-$C_4$ alkyl);

with respect to $R^1$ and $R^2$, (i) $R^1$ and $R^2$ are each, independently, optionally substituted alkyl, alkenyl, alkynyl, cycloalkyl, cycloalkylalkyl, or heterocycle;

(ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the $(R)_a$ group adjacent to the nitrogen atom;

each occurrence of R is, independently, —$(CR^3R^4)$—;

each occurrence of $R^3$ and $R^4$ are, independently H, OH, alkyl, alkoxy, —$NH_2$, alkylamino, or dialkylamino (in one preferred embodiment, each occurrence of $R^3$ and $R^4$ are, independently H or $C_1$-$C_4$ alkyl);

or $R^3$ and $R^4$, together with the carbon atom to which they are directly attached, form a cycloalkyl group, wherein no more than three R groups in each chain attached to the carbon C* are cycloalkyl (e.g., cyclopropyl);

the dashed line to Q is absent or a bond;

when the dashed line to Q is absent then Q is absent or is —O—, —NH—, —S—, —C(O)O—, —OC(O)—, —C(O)N($R^4$)—, —N($R^5$)C(O)—, —S—S—, —OC(O)O—, —O—N═C($R^5$)—, —C($R^5$)═N—O—, —OC(O)N($R^5$)—, —N($R^5$)C(O)N($R^5$)—, —N($R^5$)C(O)O—, —C(O)S—, —C(S)O— or —C($R^5$)═N—O—C(O)—; or when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

$Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)($NR^5$)—, —N($R^5$)C(O)—, —C(S)($NR^5$)—, —N($R^5$)C(O)—, —N($R^5$)C(O)N($R^5$)—, or —OC(O)O—;

$Q^3$ and $Q^4$ are each, independently, H, —$(CR^3R^4)$—, aryl, or a cholesterol moiety;

each occurrence of $A^1$, $A^2$, $A^3$ and $A^4$ is, independently, —$(CR^5R^5$—$CR^5$═$CR^5)$—;

each occurrence of $R^5$ is, independently, H or alkyl;

$M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$)═N—, —N═C($R^5$)—, —C($R^5$)═N—O—, —O—N═C($R^5$)—, —C(O)($NR^5$)—, —N($R^5$)C(O)—, —C(S)($NR^5$)—, —N($R^5$)C(O)—, —N($R^5$)C(O)N($R^5$)—, —OC(O)O—, —OSi$(R^5)_2$O—, —C(O)$(CR^3R^4)$C(O)O—, or —OC(O)$(CR^3R^4)$C(O)—);

Z is absent, alkylene or —O—P(O)(OH)—O—;

each - - - attached to Z is an optional bond, such that when Z is absent, $Q^3$ and $Q^4$ are not directly covalently bound together;

a is 1, 2, 3, 4, 5 or 6;

b is 0, 1, 2, or 3;

c, d, e, f, i, j, m, n, q and r are each, independently, 0, 1, 2, 3, 4, 5, 6, 7, 8, 9, or 10;

g and h are each, independently, 0, 1 or 2;

k and l are each, independently, 0 or 1, where at least one of k and l is 1; and o and p are each, independently, 0, 1 or 2, wherein (i) the compound does not contain the following moiety:

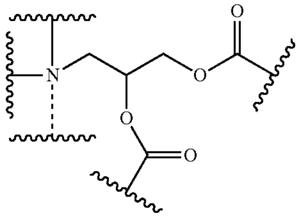

wherein - - - is an optional bond; and (ii) $Q^3$ and $Q^4$ are each, independently, separated from the tertiary carbon atom marked with an asterisk (*) by a chain of 8 or more atoms (e.g., 12 or 14 or more atoms).

In one embodiment, (i) $R^1$ and $R^2$ are each, independently, optionally substituted alkyl, alkenyl, alkynyl, cycloalkyl, cycloalkylalkyl, or heterocycle; or (ii) $R^1$ and $R^2$, together with the nitrogen atom to which they are attached, form an optionally substituted heterocylic ring.

In a preferred embodiment of the compound of formula (I), (a) when $Q^1$ is a biodegradable group (e.g., —C(O)O—), then c is at least 4;

(b) when $Q^2$ is a biodegradable group, then d is at least 4; and (c) $Q^3$ and $Q^4$ are each, independently, separated from the tertiary carbon atom marked with an asterisk (*) by a chain of 10 or more atoms (e.g., 12 or 14 or more atoms).

In another preferred embodiment, a carbon atom alpha or beta to a biodegradable group (e.g., —C(O)O—) in formula (I) may be substituted with one or two alkyl groups (e.g., one $C_1$-$C_4$ alkyl group, such as a —$CH_3$ substituent, or two $C_1$-$C_4$ alkyl groups, such as two —$CH_3$ substituents) or have a spirocyclic group (e.g., a $C_3$-$C_5$ cycloalkyl such as a $C_3$ cycloalkyl). For example, a carbon atom alpha or beta to a biodegradable group can be independently selected from

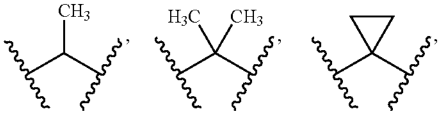

, and

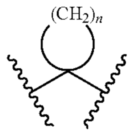

(where n is 4-6).

In one embodiment, the $M^1$ or $M^2$ group and neighboring variable(s) form the group:

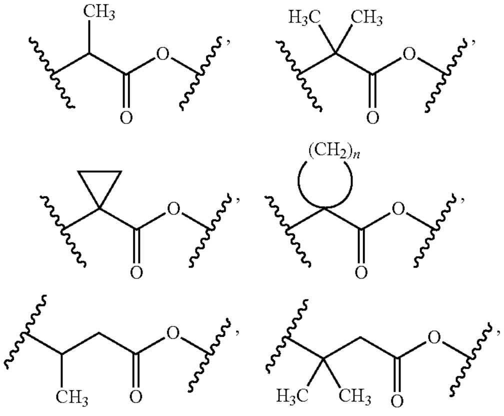

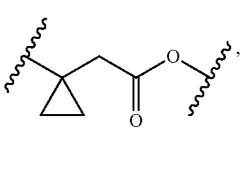

, or

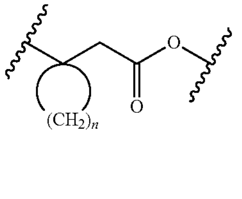

(where n is 4-6).

Yet another embodiment is a cationic lipid of the formula

Formula (IA-1)

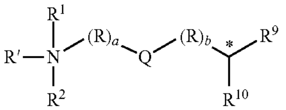

or a salt thereof (e.g., a pharmaceutically acceptable salt thereof), wherein $R^1$, $R^2$, R, a, and b are as defined with respect to formula (I);

Q is absent or is —O—, —NH—, —S—, —C(O)O—, —OC(O)—, —C(O)N($R^4$)—, —N($R^5$)C(O)—, —S—S—, —OC(O)O—, —O—N═C($R^5$)—, —C($R^5$)═N—O—, —OC(O)N($R^5$)—, —N($R^5$)C(O)N($R^5$)—, —N($R^5$)C(O)O—, —C(O)S—, —C(S)O— or —C($R^5$)═N—O—C(O)—;

R' is absent, hydrogen, or alkyl (e.g., $C_1$-$C_4$ alkyl); and each of $R^9$ and $R^{10}$ are independently $C_{12}$-$C_{24}$ alkyl (e.g., $C_{12}$-$C_{20}$ alkyl), $C_{12}$-$C_{24}$ alkenyl (e.g., $C_{12}$-$C_{20}$ alkenyl), or $C_{12}$-$C_{24}$ alkoxy (e.g., $C_{12}$-$C_{20}$ alkoxy) having one or more biodegradable groups; each biodegradable group independently interrupts the $C_{12}$-$C_{24}$ alkyl, alkenyl, or alkoxy group or is substituted at the terminus of the $C_{12}$-$C_{24}$ alkyl, alkenyl, or alkoxy group, wherein (i) the compound does not contain the following moiety:

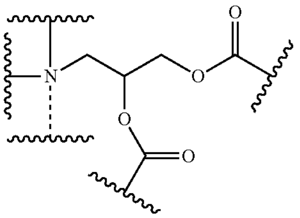

wherein - - - is an optional bond; and (ii) the terminus of $R^9$ and $R^{10}$ is separated from the tertiary carbon atom marked with an asterisk (*) by a chain of 8 or more atoms (e.g., 12 or 14 or more atoms).

In another embodiment, the cationic lipid is a compound of the formula:

Formula (IA-2)

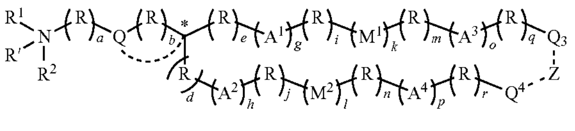

or a salt thereof (e.g., a pharmaceutically acceptable salt thereof), wherein

R' is absent, hydrogen, or alkyl (e.g., $C_1$-$C_4$ alkyl);

$R^1$ and $R^2$ are each, independently, optionally substituted $C_1$-$C_4$ alkyl, $C_2$-$C_4$ alkenyl, $C_2$-$C_4$ alkynyl, $C_3$-$C_6$ cycloalkyl, ($C_3$-$C_6$ cycloalkyl)$C_1$-$C_4$ alkyl, or a monocyclic heterocycle; or $R^1$ and $R^2$, together with the nitrogen atom to which they are attached, form an optionally substituted 5- or 6-membered heterocylic ring (e.g., a $C_5$ or $C_6$ heterocyclic ring);

each occurrence of R is, independently, —($CR^3R^4$)—;

each occurrence of $R^3$ and $R^4$ are, independently H, OH, alkyl, alkoxy, —$NH_2$, alkylamino, or dialkylamino (in one preferred embodiment, each occurrence of $R^3$ and $R^4$ are, independently H or $C_1$-$C_4$ alkyl);

or $R^3$ and $R^4$, together with the carbon atom to which they are directly attached, form a $C_3$-$C_6$ cycloalkyl group, wherein no more than three R groups in each chain attached to the carbon C* are cycloalkyl (e.g., cyclopropyl);

the dashed line to Q is absent or a bond;

when the dashed line to Q is absent, Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or when the dashed line to Q is a bond, b is 0 and Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

$Q^3$ and $Q^4$ are each, independently, H, —($CR^3R^4$)—, aryl, or a cholesterol moiety;

each occurrence of $A^1$, $A^2$, $A^3$ and $A^4$ is, independently, —($CR^5R^5$—$CR^5$=$CR^5$)—;

each occurrence of $R^5$ is, independently, H or alkyl;

$M^1$ and $M^2$ are each, independently, —C(O)—O—, —OC(O)—, —C($R^5$)=N—, —C($R^5$)=N—O—, —O—C(O)O—, —C(O)N($R^5$)—, —C(O)S—, —C(S)O—, —OSi($R^5$)$_2$O—, —C(O)($CR^3R^4$)C(O)O—, or —OC(O)($CR^3R^4$)C(O)—;

Z is absent, alkylene or —O—P(O)(OH)—O—;

each - - - attached to Z is an optional bond, such that when Z is absent, $Q^3$ and $Q^4$ are not directly covalently bound together;

a is 1, 2, 3, 4, 5 or 6;

b is 0, 1, 2, or 3;

d, e, i, j, m, n, q and r are each, independently, 0, 1, 2, 3, 4, 5, 6, 7, 8, 9, or 10;

g and h are each, independently, 0, 1 or 2;

the sum of d+3h is at least 4, and the sum of e+3g is at least 4;

k and l are each, independently, 0 or 1, where at least one of k and l is 1; and o and p are each, independently, 0, 1 or 2, wherein $Q^3$ and $Q^4$ are each, independently, separated from the tertiary carbon atom marked with an asterisk (*) by a chain of 8 or more atoms (e.g., 12 or 14 or more atoms).

In one embodiment, R' in formula (IA-2) is absent or hydrogen. In one embodiment, R' in formula (IA-2) is absent or alkyl (e.g., methyl).

In one embodiment, $R^1$ and $R^2$ in formula (IA-2) are each, independently, $C_1$-$C_4$ alkyl (e.g., methyl or ethyl).

In one embodiment, each occurrence of R in formula (IA-2) is, independently, —$CH_2$— or —CH($CH_3$)—.

In one embodiment, $Q^3$ and $Q^4$ in formula (IA-2) are each, independently, H, aryl, or a cholesterol moiety.

In one embodiment, each occurrence of $A^1$, $A^2$, $A^3$ and $A^4$ in formula (IA-2) is, independently, —($CH_2$—CH=CH)—;

In one embodiment, $M^1$ and $M^2$ in formula (IA-2) are each —C(O)—O—.

In one embodiment of the compound of formula (IA-2), Z is absent and each - - - is absent (i.e., $Q^3$ and $Q^4$ are not directly covalently bound together).

In one embodiment, the sum of e+3g+i+m+3o+q in formula (IA-2) is from about 8 to about 20. In another embodiment, the sum of e+3g+i+m+3o+q in formula (IA-2) is from about 12 to about 20.

In one embodiment, the sum of d+3h+j+n+3p+r in formula (IA-2) is from about 8 to about 20. In another embodiment, the sum of d+3h+j+n+3p+r in formula (IA-2) is from about 12 to about 20.

In another embodiment, the cationic lipid is a compound of the formula

Formula (IB)

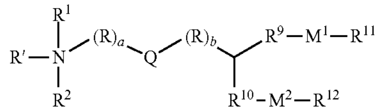

wherein $R^1$, $R^2$, R, a, b, $M^1$, and $M^2$ are as defined with respect to formula (I);

Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—;

R' is absent, hydrogen, or alkyl (e.g., $C_1$-$C_4$ alkyl);

each of $R^9$ and $R^{10}$ are independently alkylene, or alkenylene; and each of $R^{11}$ and $R^{12}$ are independently alkyl or alkenyl, optionally terminated by $COOR^{13}$ where each $R^{13}$ is independently alkyl (e.g., $C_1$-$C_4$ alkyl such as methyl or ethyl);

$R^9$, $M^1$, and $R^{11}$ are together at least 8 carbons atoms in length (e.g., 12 or 14 carbon atoms or longer); and $R^{10}$, $M^2$, and $R^{12}$ are together at least 8 carbons atoms in length (e.g., 12 or 14 carbon atoms or longer).

In a preferred embodiment of the compound of formula (IB), $R^9$ and $R^{10}$ are each independently $C_4$-$C_{12}$ alkylene or $C_4$-$C_{12}$ alkenylene, $M^1$ and $M^2$ are —C(O)O—, and $R^{11}$ and $R^{12}$ are $C_4$-$C_{12}$ alkylene or $C_4$-$C_{12}$ alkenylene. In one embodiment, $R^9$, $M^1$, and $R^{11}$ are together at 12 to 24 carbons atoms in length. In another embodiment, $R^9$, $M^1$, and $R^{11}$ are together at 14 to 18 carbons atoms in length. In one embodiment, $R^{10}$, $M^2$, and $R^{12}$ are together at 12 to 24 carbons atoms in length. In another embodiment, $R^{10}$, $M^2$, and $R^{12}$ are together at 14 to 18 carbons atoms in length.

The $R'R^1R^2N$—$(R)_a$-Q-$(R)_b$— group can be any of the head groups described herein, including those shown in Table 1 below, and salts thereof. In one preferred embodiment, $R'R^1R^2N$—$(R)_a$-Q-$(R)_b$— is $(CH_3)_2N$—$(CH_2)_3$—C(O)O—, $(CH_3)_2N$—$(CH_2)_2$—NH—C(O)O—, $(CH_3)_2N$—$(CH_2)_2$—OC(O)—NH—, or $(CH_3)_2N$—$(CH_2)_3$—C($CH_3$)=N—O—.

In yet another embodiment, the cationic lipid is a compound of the formula

Formula (IC)

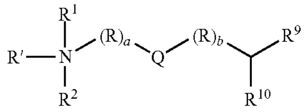

wherein $R^1$, $R^2$, R, a, and b are as defined with respect to formula (I);

Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)═N—O—C(O)—; R' is absent, hydrogen, or alkyl (e.g., $C_1$-$C_4$ alkyl);

each of $R^9$ and $R^{10}$ are independently $C_{12}$-$C_{24}$ alkyl or alkenyl substituted at its terminus with a biodegradable group, such as —COOR$^{13}$ where each $R^{13}$ is independently alkyl (preferably $C_1$-$C_4$ alkyl such as methyl or ethyl).

In a preferred embodiment of the compound of formula (IC), $R^9$ and $R^{10}$ are each independently $C_{14}$-$C_{18}$ alkylene or $C_{14}$-$C_{18}$ alkenylene. In another preferred embodiment, the biodegradable group is —COOR$^3$ where $R^{13}$ is $C_1$-$C_4$ alkyl (such as methyl or ethyl).

The R'$R^1R^2$N—$(R)_a$-Q-$(R)_b$— group can be any of the head groups described herein, including those shown in Table 1 below. In one preferred embodiment, R'$R^1R^2$N—$(R)_a$-Q-$(R)_b$— is $(CH_3)_2N$—$(CH_2)_3$—C(O)O—, $(CH_3)_2N$—$(CH_2)_2$—NH—C(O)O—, $(CH_3)_2N$—$(CH_2)_2$—OC(O)—NH—, or $(CH_3)_2N$—$(CH_2)_3$—C($CH_3$)═N—O—.

Yet another embodiment is intermediates of the formula:

Formula (ID)

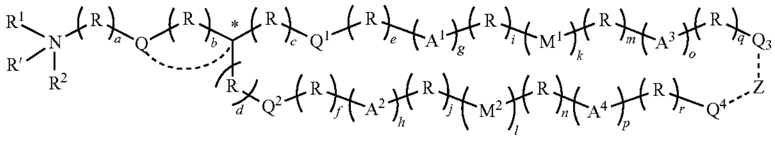

or a salt thereof (e.g., a pharmaceutically acceptable salt thereof), wherein

R' is absent, hydrogen, or alkyl (e.g., $C_1$-$C_4$ alkyl);

$R^1$ and $R^2$ are each, independently, optionally substituted alkyl, alkenyl, alkynyl, cycloalkyl, cycloalkylalkyl, or heterocycle; or $R^1$ and $R^2$, together with the nitrogen atom to which they are attached, form an optionally substituted heterocylic ring;

each occurrence of R is, independently, —($CR^3R^4$)—;

each occurrence of $R^3$ and $R^4$ are, independently H, OH, alkyl, alkoxy, —$NH_2$, alkylamino, or dialkylamino (in one preferred embodiment, each occurrence of $R^3$ and $R^4$ are, independently H or alkyl);

or $R^3$ and $R^4$, together with the carbon atom to which they are directly attached, form a cycloalkyl group, wherein no more than three R groups in each chain attached to the carbon C* are cycloalkyl (e.g., cyclopropyl);

the dashed line to Q is absent or a bond;

when the dashed line to Q is absent, Q is absent or is —O—, —NH—, —S—, —C(O)O—, —OC(O)—, —C(O)N($R^4$)—, —N($R^5$)C(O)—, —S—S—, —OC(O)O—, —O—N═C($R^5$)—, —C($R^5$)═N—O—, —OC(O)N($R^5$)—, —N($R^5$)C(O)N($R^5$)—, —N($R^5$)C(O)O—, —C(O)S—, —C(S)O— or —C($R^5$)═N—O—C(O)—; or when the dashed line to Q is a bond, b is 0 and Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

$Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(N$R^5$)—, —N($R^5$)C(O)—, —N($R^5$)C(O)N($R^5$)—, or —OC(O)O—;

$Q^3$ and $Q^4$ are each, independently, H, —($CR^3R^4$)—, aryl, —OH, or a cholesterol moiety;

each occurrence of $A^1$, $A^2$, $A^3$ and $A^4$ is, independently, —($CR^5R^5$—$CR^5$═$CR^5$)—;

each occurrence of $R^5$ is, independently, H or alkyl;

$M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$)═N—, —N═C($R^5$)—, —C($R^5$)═N—O—, —O—N═C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)($CR^3R^4$)C(O)O—, or —OC(O)($CR^3R^4$)C(O)—);

Z is absent, alkylene or —O—P(O)(OH)—O—;

each - - - attached to Z is an optional bond, such that when Z is absent, $Q^3$ and $Q^4$ are not directly covalently bound together;

a is 1, 2, 3, 4, 5 or 6;

b is 0, 1, 2, or 3;

c, d, e, f, i, j, m, n, q and r are each, independently, 0, 1, 2, 3, 4, 5, 6, 7, 8, 9, or 10;

g and h are each, independently, 0, 1 or 2;

k and l are each, independently, 0 or 1;

o and p are each, independently, 0, 1 or 2, wherein (i) the compound does not contain the following moiety:

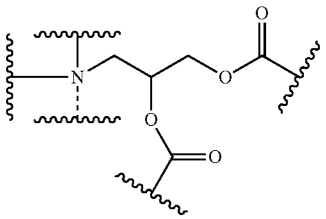

wherein - - - is an optional bond; and (ii) $Q^3$ and $Q^4$ are each, independently, separated from the tertiary carbon atom marked with an asterisk (*) by a chain of 8 or more atoms (e.g., 12 or 14 or more atoms).

In yet a further embodiment, the cationic lipid is a compound of formula IE:

Formula (IE)

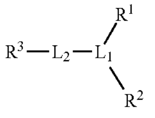

or a salt thereof (e.g., a pharmaceutically acceptable salt thereof), wherein $R^1$ is a $C_{10}$ to $C_{30}$ group having the formula -$L^a$-$(CR^{1a}R^{1b})_\alpha$-$[L^{1b}$-$(CR^{1a}R^{1b})_\beta]_\gamma$-$L^{1c}$-$R^{1c}$, where $L^{1a}$ is a bond, —$CR^{1a}R^{1b}$—, —O—, —CO—, —N$R^{1d}$—, —S—, or a combination thereof;

each $R^{1a}$ and each $R^{1b}$, independently, is H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; —$OR^{1c}$; —$NR^{1c}R^{1d}$; aryl; heteroaryl; or heterocyclyl;

each $L^{1b}$, independently, is a bond, —$(CR^{1a}R^{1b})_{1-2}$—, —O—, —CO—, —$NR^{1d}$—, —S—,

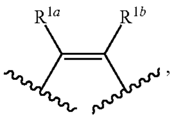, 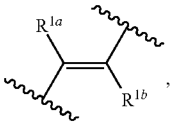, 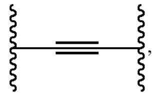, or a combination thereof; or can have the formula

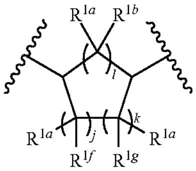

where j, k, and l are each independently 0, 1, 2, or 3, provided that the sum of j, k and l is at least 1 and no greater than 8; and $R^{1f}$ and $R^{1g}$ are each independently $R^{1b}$, or adjacent $R^{1f}$ and $R^{1g}$, taken together, are optionally a bond; or can have the formula

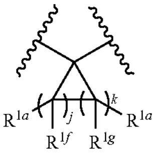

where j and k are each independently 0, 1, 2, 3, or 4 provided that the sum of j and k is at least 1; and $R^{1f}$ and $R^{1g}$ are each independently $R^{1b}$, or adjacent $R^{1f}$ and $R^{1g}$, taken together, are optionally a bond;

or can have the formula:

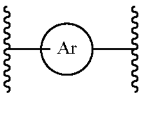

where —Ar— is a 6 to 14 membered arylene group optionally substituted by zero to six independent $R^{1a}$ groups;

or can have the formula:

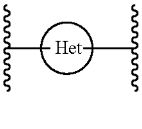

where -Het- is a 3 to 14 membered heterocyclylene or heteroarylene group optionally substituted by zero to six independent $R^{1a}$ groups;

$L^{1c}$ is —$(CR^{1a}R^{1b})_{1-2}$—, —CO—, —$NR^{1d}$—, —S—,

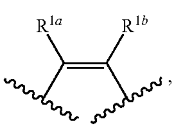, 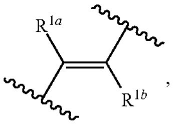, 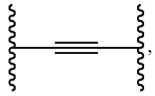, or a combination thereof;

$R^{1c}$ is H; halo; hydroxy; cyano; $C_1$-$C_6$ alkyl optionally substituted by halo, hydroxy, alkoxy, or aryl; $C_3$-$C_8$ cycloalkyl optionally substituted by halo, hydroxy, alkoxy, or aryl; aryl; heteroaryl; or heterocyclyl; or $R^{1c}$ has the formula:

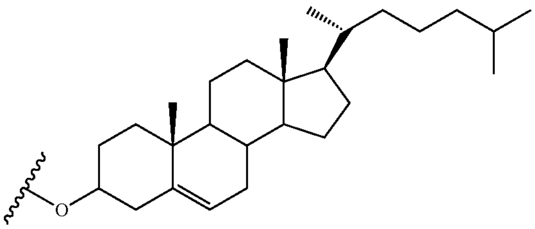;

$R^{1d}$ is H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; aryl; heteroaryl; or heterocyclyl;

α is 0-6, inclusive;

each β, independently, is 0-6, inclusive;

γ is 0-6, inclusive;

$R^2$ is a $C_{10}$ to $C_{30}$ group having the formula -$L^{2a}$-$(CR^{2a}R^{2b})_{\delta}$-$[L^{2b}$-$(CR^{2a}R^{2b})_{\epsilon}]_{\zeta}$-$L^{2c}$-$R^{2c}$, where $L^{2a}$ is a bond, —$CR^{2a}R^{2b}$—, —O—, —CO—, —$NR^{2d}$—, —S—, or a combination thereof;

each $R^{2a}$ and each $R^{2b}$, independently, can be H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; —$OR^{2c}$; —$NR^{2c}R^{2d}$; aryl; heteroaryl; or heterocyclyl;

each $L^{2b}$, independently, can be a bond, —$(CR^{2a}R^{2b})_{1-2}$—, —O—, —CO—, —$NR^{2d}$—, —S—,

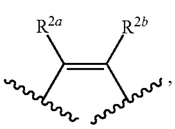, 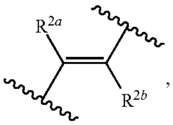, 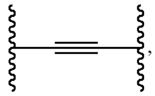, or a combination thereof;

or can have the formula

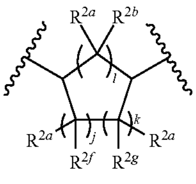

where j, k, and l are each independently 0, 1, 2, or 3, provided that the sum of j, k and l is at least 1 and no greater than 8; and $R^{2f}$ and $R^{2g}$ are each independently $R^{2b}$, or adjacent $R^{2f}$ and $R^{2g}$, taken together, are optionally a bond; or can have the formula

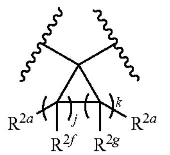

where j and k are each independently 0, 1, 2, 3, or 4 provided that the sum of j and k is at least 1; and $R^{2f}$ and $R^{2g}$ are each independently $R^{2b}$, or adjacent $R^{2f}$ and $R^{2g}$, taken together, are optionally a bond;

or can have the formula:

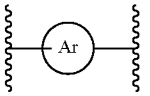

wherein —Ar— is a 6 to 14 membered arylene group optionally substituted by zero to six independent $R^{2a}$ groups; or can have the formula:

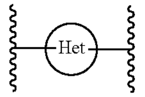

where -Het- is a 3 to 14 membered heterocyclylene or heteroarylene group optionally substituted by zero to six independent $R^{2a}$ groups;

$L^{2c}$ is —$(CR^{2a}R^{2b})_{1-2}$—, —O—, —CO—, —$NR^{2d}$—, —S—,

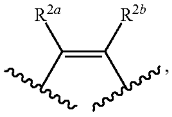,

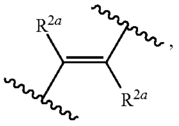,

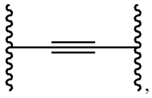, or a combination thereof;

$R^{2c}$ is H; halo; hydroxy; cyano; $C_1$-$C_6$ alkyl optionally substituted by halo, hydroxy, alkoxy or aryl; $C_3$-$C_8$ cycloalkyl optionally substituted by halo, hydroxy, alkoxy or aryl; aryl; heteroaryl; or heterocyclyl; or $R^{2c}$ has the formula:

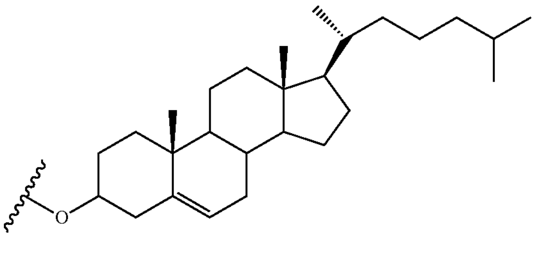;

$R^{2d}$ is H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; aryl; heteroaryl; or heterocyclyl;

δ is 0-6, inclusive;

each ε, independently, is 0-6, inclusive;

ζ is 0-6, inclusive;

$L_1$ is $C(R^a)$, —$(CR^5R^6)_xC(R^a)$—, or $P(Q_2)$;

$R^a$ is H, alkyl, alkoxy, —OH, —N(Q)Q, or —SQ;

$L_2$ is —$(CR^5R^6)_x$—, —C(O)—$(CR^5R^6)_x$—, —$(CR^5R^6)_x$—C(O)—, —$(CR^5R^6)_x$—$CR^5$═$CR^5$—$(CR^5R^6)_y$—, —C(O)—$(CR^5R^6)_x$—$CR^5$═$CR^5$—$(CR^5R^6)_y$—, —$(CR^5R^6)_x$—$CR^5$═$CR^5$—$(CR^5R^6)_y$—C(O)—, —O—, —S—, —N(Q)-, —C(O)O—, —OC(O)—, —C(O)—, —N(Q)C(O)—, —C(O)N(Q)-, —N(Q)C(O)O—, —OC(O)N(Q)-, S(O), —N(Q)S(O)$_2$N(Q)-, —S(O)$_2$—, —N(Q)S(O)$_2$—, —SS—, —O—N═, ═N—O—, —C(O)—N(Q)-N═, —N(Q)-N═, —N(Q)-O—, —C(O)S—, arylene, heteroarylene, cyclalkylene, or heterocyclylene;

each x, independently, can be 0-6, inclusive;

each y, independently, can be 0-6, inclusive;

$R^3$ is of the formula:

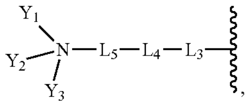,

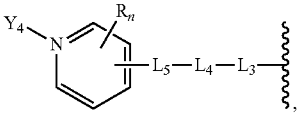, or

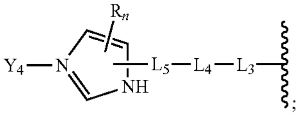;

$Y_1$ is alkyl, cycloalkyl, aryl, aralkyl, or alkynyl, wherein $Y_1$ is optionally substituted by 0 to 6 independent $R_n$;

$Y_2$ is alkyl, cycloalkyl, aryl, aralkyl, or alkynyl, wherein $Y_2$ is optionally substituted by 0 to 6 independent $R_n$;

$Y_3$ is absent, or if present, is alkyl, cycloalkyl, aryl, aralkyl, or alkynyl, wherein $Y_3$ is optionally substituted by 0 to 6 independent $R_n$;

$Y_4$ is absent, or if present, is alkyl, cycloalkyl, aryl, aralkyl, or alkynyl, wherein $Y_4$ is optionally substituted by 0 to 6 independent $R_n$;

or any two of $Y_1$, $Y_2$, and $Y_3$ are taken together with the N atom to which they are attached to form a 3- to 8-member heterocycle optionally substituted by 0 to 6 independent $R_n$;

or $Y_1$, $Y_2$, and $Y_3$ are all be taken together with the N atom to which they are attached to form a bicyclic 5- to 12-member heterocycle optionally substituted by 0 to 6 independent $R_n$;

each $R_n$, independently, can be H, halo, cyano, hydroxy, amino, alkyl, alkoxy, cycloalkyl, aryl, heteroaryl, or heterocyclyl;

$L_3$ is a bond, —N(Q)-, —O—, —S—, —$(CR_7R_8)_a$—, —C(O)—, or a combination of any two of these;

$L_4$ cis a bond, —N(Q)-, —O—, —S—, —$(CR_7R^8)_a$—, —C(O)—, or a combination of any two of these;

$L_5$ is a bond, —N(Q)-, —O—, —S—, —$(CR_7R^8)_a$—, —C(O)—, or a combination of any two of these;

each occurrence of $R_7$ and $R_8$ is, independently, H, halo, cyano, hydroxy, amino, alkyl, alkoxy, cycloalkyl, aryl, heteroaryl, or heterocyclyl;

or two $R_7$ groups on adjacent carbon atoms can be taken together to form a double bond between their respective carbon atoms;

or two $R_7$ groups on adjacent carbon atoms and two $R_8$ groups on the same adjacent carbon atoms can be taken together to form a triple bond between their respective carbon atoms;

or, an $R_7$ or $R_8$ substituent from any of $L_3$, $L_4$, or $L_5$ can be optionally taken with an $R_7$ or $R_8$ substituent from any of $L_3$, $L_4$, or $L_5$ to form a 3- to 8-member cycloalkyl, heterocyclyl, aryl, or heteroaryl group;

or any one of $Y_1$, $Y_2$, or $Y_3$, can be optionally taken together with an $R_7$ or $R_8$ group from any of $L_3$, $L_4$, and $L_5$, and atoms to which they are attached, to form a 3- to 8-member heterocyclyl group;

each a, independently, can be 0, 1, 2, or 3;

each occurrence of $R_5$ and $R_6$ can be, independently, H, halo, cyano, hydroxy, amino, alkyl, alkoxy, cycloalkyl, aryl, heteroaryl, or heterocyclyl;

each Q, independently, is H, alkyl, acyl, cycloalkyl, alkenyl, alkynyl, aryl, heteroaryl or heterocyclyl; and Each $Q_2$, independently, is O, S, N(Q)Q, alkyl or alkoxy.

In some embodiments, $L_1$ can be —$C(R_5R_6)_xC(R_a)$—; or $L_1$ can be —$CH_2$—$C(R_a)$—. $L_2$ can be —C(O)O—, —OC(O)—, —N(Q)C(O)—, —C(O)N(Q)-, —N(Q)C(O)O—, —OC(O)N(Q)-, —SS—, —O—N═, or ═N—O—. $L_2$ can be —C(O)O—, —OC(O)—, —SS—, or ═N—O—.

In some embodiments, $-L^{1a}-(CR^{1a}R^{1b})_{\alpha}$— can be —$(CH_2)_8$—. $-L^{2a}-(CR^{2a}R^{2b})_{\delta}$— can be —$(CH_2)_8$—. $L^{1b}-(CR^{1a}R^{1b})_{\beta}$ can be $CH_2CH_2CH_2$, CH═CH—$CH_2$, or

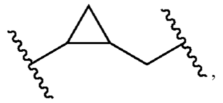 [SMILES: *CC1CC1*]

and β is 1, 2, or 3. $L^{2b}-(CR^{2a}R^{2b})_{\epsilon}$ can be $CH_2CH_2CH_2$, CH═CH—$CH_2$, or

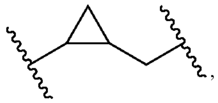 [SMILES: *CC1CC1*]

and ε is 1, 2, or 3.

In one embodiment of the compound of formula IE, at least one $L^{1a}$, $L^{1b}$, $L^{1c}$, $L^{2a}$, $L^{2b}$, or $L^{2c}$ present in the compound is a biodegradable group, such as ester —C(O)O—, —OC(O)—, disulfide (—S—S—), —C($R^5$)═N—, —O—C(O)O—, —C(O)N($R^5$), —N($R^5$)C(O)—, —N($R^5$)C(O)N($R^5$)—, —C(O)S—, —SC(O)—, —C(O)($CR^{1a}R^{1b}$)C(O)O—, or —OC(O)($CR^{1a}R^{1b}$)C(O)—. In another embodiment of the compound of formula IE, at least one $L^{1a}$, $L^{1b}$, and $L^{1c}$ present in the compound is a biodegradable group and at one $L^{2a}$, $L^{2b}$, or $L^{2c}$ present in the compound is a biodegradable group (such as those mentioned above). In yet another embodiment of the compound of formula IE, α in $R^1$ is at least 4, δ in $R^2$ is at least 4, at least one $L^{1a}$, $L^{1b}$, and $L^{1c}$ present in the compound is a biodegradable group and at one $L^{2a}$, $L^{2b}$, or $L^{2c}$ present in the compound is a biodegradable group (such as those mentioned above). In another embodiment, the carbon chain in $R^1$ and/or $R^2$ is saturated. In yet another embodiment, the carbon chain in $R^1$ and/or $R^2$ contains one or two double bonds.

In yet another embodiment, the cationic lipid is a compound selected from compounds of formulas II-XXIII:

(II)

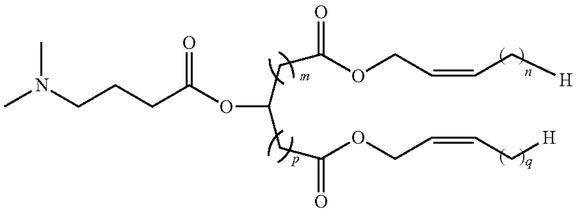

(III)

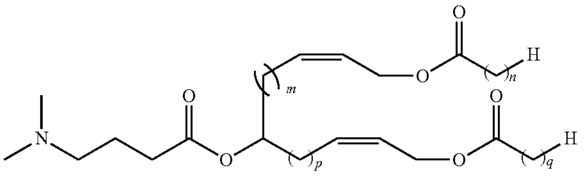

(IV)

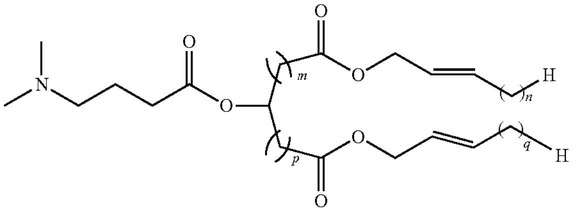

(V)

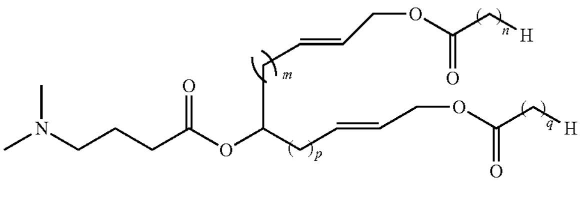

-continued
(VI)
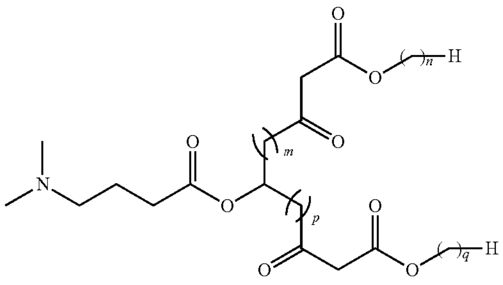
(VII)
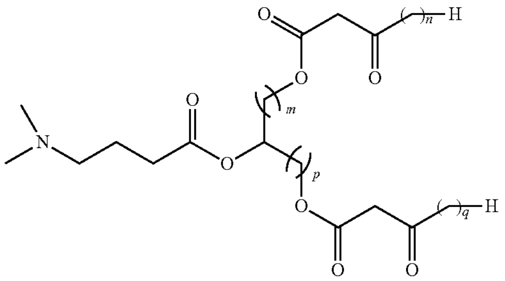
(VIII)
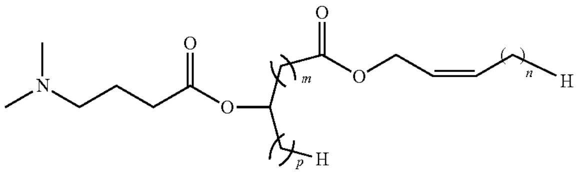
(IX)
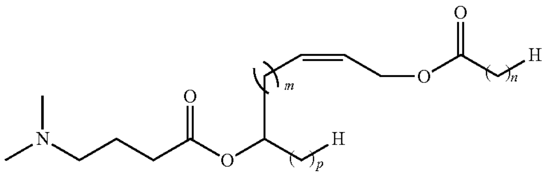
(X)
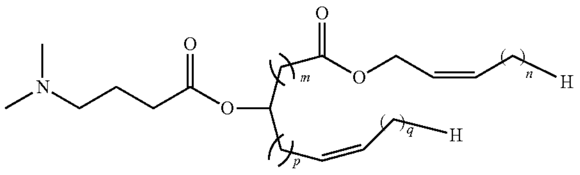
(XI)
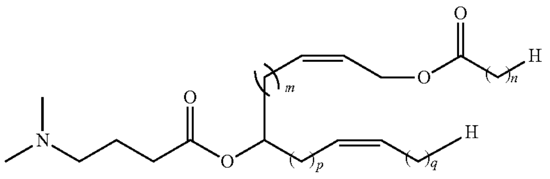
(XII)
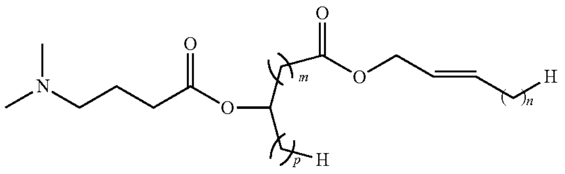
(XIII)
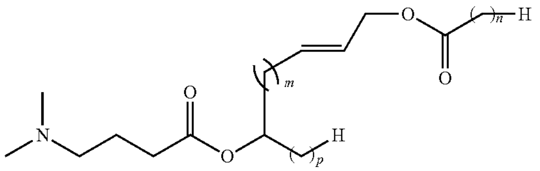
(XIV)
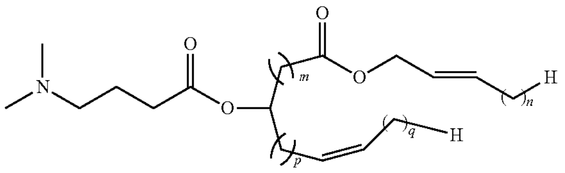
(XV)
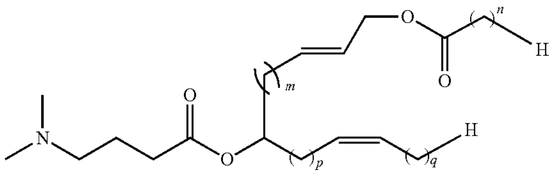
(XVI)
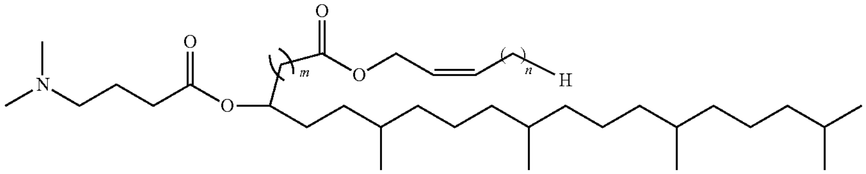
(XVII)
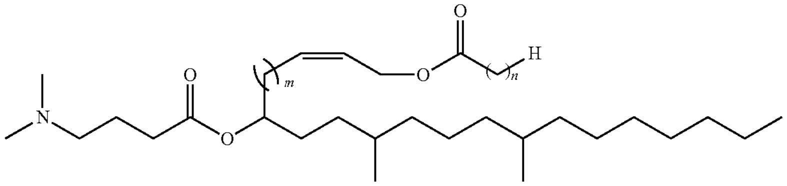

-continued
(XVIII)
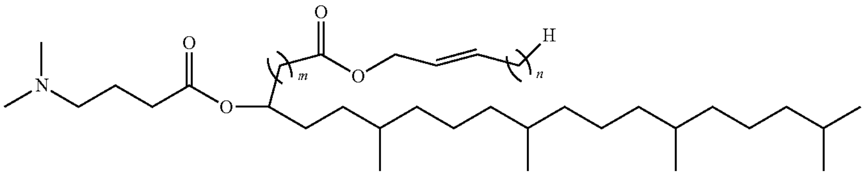
(XIX)
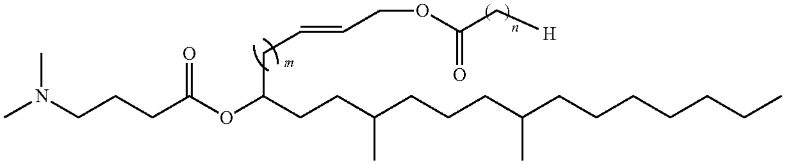
(XX)
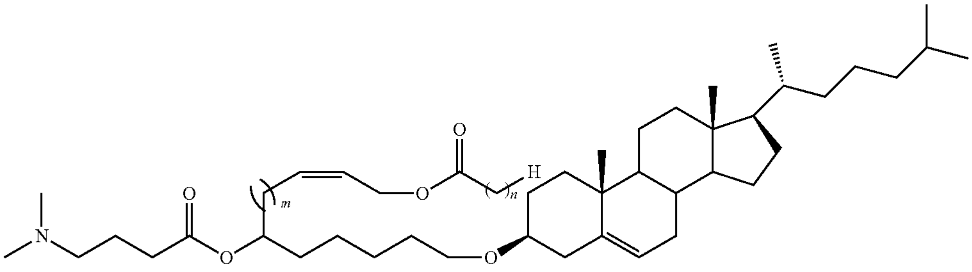
(XXI)
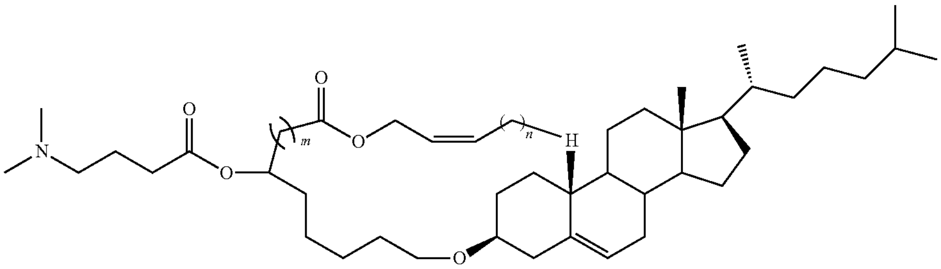
(XXII)
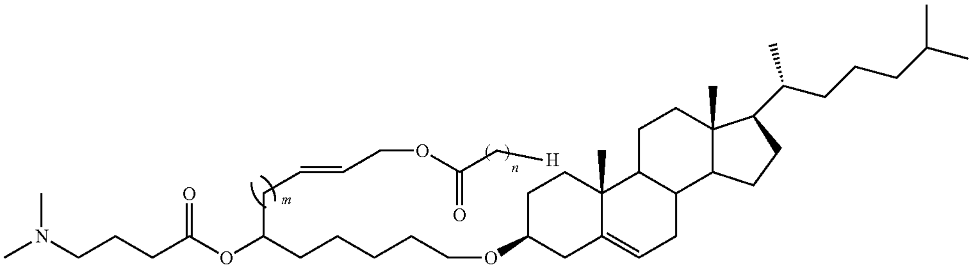
(XXIII)
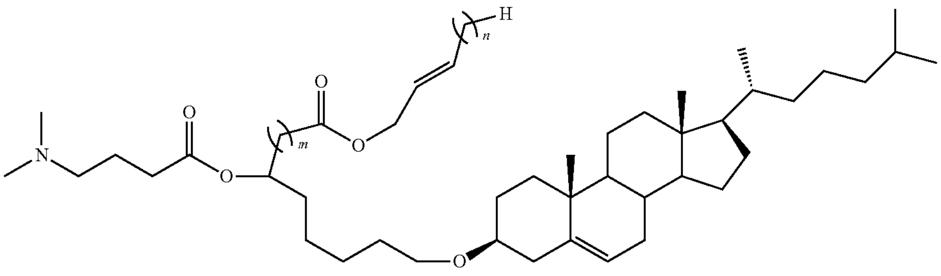
and salts thereof (e.g., pharmaceutically acceptable salts thereof),
wherein
m, n, o and p are each, individually, 1-25, with the proviso that:
(i) in Formulas (II), (IV), (VI) and (VII), m and p are both 4 or greater;
(ii) in Formulas (VIII), (X), (XII), (XIV), (XVI), (XVIII), (XXI) and (XXIII), m is 4 or greater; and
(iii) in Formulas (VIII), (IX), (XII) and (XIII), p is 8 or greater (e.g., 12 or 14 or greater).

In another embodiment, the present invention relates to a cationic lipid or a salt thereof having:

(i) a central atom (e.g., a carbon, nitrogen, or phosphorous central atom)

(ii) a nitrogen containing head group directly bound to the central carbon atom, and (iii) two hydrophobic tails directly bound to the central atom, each hydrophobic tail comprising a $C_8$ or greater aliphatic group (preferably a $C_{14}$ or greater aliphatic group) attached to the central atom, where one or both of the aliphatic group(s) (a) is interrupted by a biodegradable group such that there is a chain of at least four carbon atoms between the biodegradable group and the central atom, or (b) includes a biodegradable group at the terminal end of the hydrophobic tail. For instance, the biodegradable group is selected from —OC(O)—, —C(O)O—, —SC(O)—, —C(O)S—, —OC(S)—, —C(S)O—, —S—S—, —C(O)(NR$^5$)—, —N(R$^5$)C(O)—, —C(S)(NR$^5$)—, —N(R$^5$)C(O)—, —N(R$^5$)C(O)N(R$^5$)—, and —OC(O)O—.

In one embodiment, the cationic lipid is a compound of formula I-XXIII. In another embodiment, the cationic lipid is a compound of one of formulas II-XXIII. In one embodiment, the cationic lipid is a compound of formula I. In another embodiment, the cationic lipid is a compound of formula IA-1, IA-2, IB, IC or ID. The following disclosure represents various embodiments of a compound of Formula I.

In one embodiment, $M^1$ and $M^2$ are each, independently:

—OC(O)—, —C(O)O—, —SC(O)—, —C(O)S—, —OC(S)—, —C(S)O—, —S—S—, —C(R$^5$)═N—, —N═C(R$^5$)—, —C(R$^5$)═N—O—, —O—N═C(R$^5$)—, —C(O)(NR$^5$)—, —N(R$^5$)C(O)—, —C(S)(NR$^5$)—, —N(R$^5$)C(O)—, —N(R$^5$)C(O)N(R$^5$)—, —OC(O)O—, —OSi(R$^5$)$_2$O—, —C(O)(CR$^3$R$^4$)C(O)O—, or —OC(O)(CR$^3$R$^4$)C(O)—.

In another embodiment, $M^1$ and $M^2$ are each, independently:

—OC(O)—, —C(O)—O—, —C(R$^5$)═N—, —N═C(R$^5$)—, —C(R$^5$)═N—O—, —O—N═C(R$^5$)—, —O—C(O)O—, —C(O)N(R$^5$)—, —N(R$^5$)C(O)—, —C(O)S—, —SC(O)—, —C(S)O—, —OC(S)—, —OSi(R$^5$)$_2$O—, —C(O)(CR$^3$R$^4$)C(O)O—, or —OC(O)(CR$^3$R$^4$)C(O)—.

In yet another embodiment, $M^1$ and $M^2$ are each, independently:

—C(O)—O—, —OC(O)—, —C(R$^5$)═N—, —C(R$^5$)═N—O—, —O—C(O)O—, —C(O)N(R$^5$)—, —C(O)S—, —C(S)O—, —OSi(R$^5$)$_2$O—, —C(O)(CR$^3$R$^4$)C(O)O—, or —OC(O)(CR$^3$R$^4$)C(O)—.

In another embodiment, $M^1$ and $M^2$ are each —C(O)O—.

In one embodiment, $R^1$ and $R^2$ are each, individually, optionally substituted alkyl, cycloalkyl, cycloalkylalkyl, or heterocycle. In one embodiment, $R^1$ is alkyl and $R^2$ is alkyl, cycloalkyl or cycloalkylalkyl. In one embodiment, $R^1$ and $R^2$ are each, individually, alkyl (e.g., $C_1$-$C_4$ alkyl, such as methyl, ethyl, or isopropyl). In one embodiment, $R^1$ and $R^2$ are both methyl. In another embodiment, $R^1$ and $R^2$, together with the nitrogen atom to which they are attached, form an optionally substituted heterocylic ring (e.g., N-methylpiperazinyl). In another embodiment, one of $R^1$ and $R^2$ is

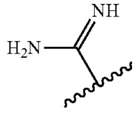

or

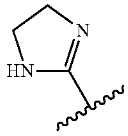

(e.g., $R^1$ is one of the two aforementioned groups and $R^2$ is hydrogen).

In one embodiment, R' is hydrogen or alkyl. In another embodiment, R' is hydrogen or methyl. In one embodiment, R' is absent. In one embodiment, R' is absent or methyl. For compounds in which R' is not absent, the nitrogen atom to which R' is attached carries a positive charge, and the compound also contains a negatively charged counter ion. The counterion can be any anion, such as an organic or inorganic anion. Suitable examples of anions include, but are not limited to, tosylate, methanesulfonate, acetate, citrate, malonate, tartarate, succinate, benzoate, ascorbate, α-ketoglutarate, α-glycerophosphate, halide (e.g., chloride), sulfate, nitrate, bicarbonate, and carbonate. In one embodiment, the counterion is a halide (e.g., Cl).

In one embodiment each R is, independently, —(CR$^3$R$^4$)—, wherein $R^3$ and $R^4$ are each, independently, H or alkyl (e.g., $C_1$-$C_4$ alkyl). For example, in one embodiment each R is, independently, —(CHR$^4$)—, wherein each $R^4$ is, independently H or alkyl (e.g., $C_1$-$C_4$ alkyl). In another embodiment, each R is, independently, —CH$_2$—, —C(CH$_3$)$_2$— or —CH(iPr)- (where iPr is isopropyl). In another embodiment, each R is —CH$_2$—.

In another embodiment $R^5$ is, in each case, hydrogen or methyl. For example, $R^5$ can be, in each case, hydrogen.

In one embodiment, Q is absent, —C(O)O—, —OC(O)—, —C(O)N(R$^4$)—, —N(R$^5$)C(O)—, —S—S—, —OC(O)O—, —C(R$^5$)═N—O—, —OC(O)N(R$^5$)—, —N(R$^5$)C(O)N(R$^5$)—, —N(R$^5$)C(O)O—, —C(O)S—, —C(S)O— or —C(R$^5$)═N—O—C(O)—. In one embodiment, Q is —C(O)O—.

In one embodiment, $Q^1$ and $Q^2$ are each, independently, absent or —O—. For example, in one embodiment, $Q^1$ and $Q^2$ are each absent. In another embodiment, $Q^1$ and $Q^2$ are each —O—.

In one embodiment, the dashed line to Q is absent, b is 0 and R'R$^1$R$^2$N—(R)$_a$-Q- and the tertiary carbon adjacent to it (C*) form the following group:

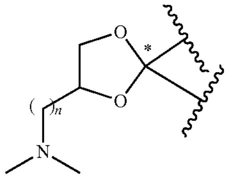

where n is 1 to 4 (e.g., n is 2).

In one embodiment, the dashed line to Q is absent, b is 0 and R'R$^1$R$^2$N—(R)$_a$-Q- and the tertiary carbon adjacent to it form the following group:

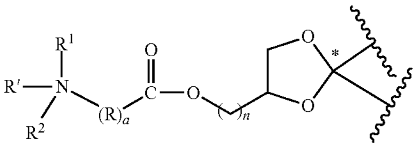

where n is 1 to 4 (e.g., n is 2), and $R^1$, $R^2$, R, a, and b are as defined with respect to formula (I). In one embodiment, a is 3.

In one embodiment, the dashed line to Q is absent, b is 0 and R'R$^1$R$^2$N—(R)$_a$-Q- and the tertiary carbon adjacent to it form the following group:

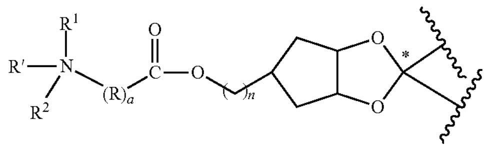

where n is 1 to 4 (e.g., n is 2), and $R^1$, $R^2$, R, a, and b are as defined with respect to formula (I). In one embodiment, a is 0. For example, the group can be:

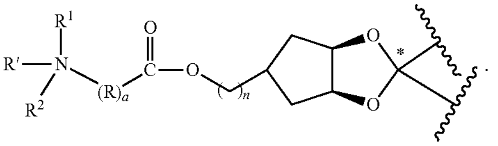

In one embodiment, b is 0. In another embodiment, a is 2, 3, or 4 and b is 0. For example, in one embodiment, a is 3 and b is 0. In another embodiment, a is 3, b is 0, and Q is —C(O)O—.

In one embodiment, the compound of formula (I) is of subformula:

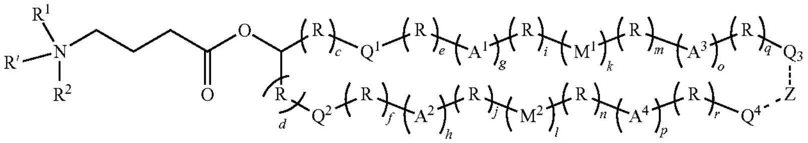

Formula (IF) wherein R, R', $R^1$, $R^2$, $A^1$, $A^2$, $A^3$, $A^4$, $Q^1$, $Q^2$, $Q^3$, $Q^4$, c, d, e, f, g, h, i, j, k, l, m, n, o, p, q and r are as defined in any of the embodiments disclosed herein.

In additional embodiments of the compound of formula (IF), one or more of the following applies:

(i) $Q^1$ and $Q^2$ are absent;

(ii) $M^1$ and $M^2$ are both —C(O)O—;

(iii) g and h are both 1;

(iv) g and h are both 0;

(v) c and e total 7;

(vi) d and f total 7;

(vii) c, e, and i total 7;

(viii) d, f and j total 7;

(ix) i and j are each 7;

(x) k and l are both 1;

(xi) m and n are both 0;

(xii) m and q total 1 or m and q total 2;

(xiii) m and 1 total 6;

(xiv) r and n total 6;

(xv) p and o are both 0;

(xvi) n and r total 2 or n and r total 1; and (xvii) $Q^3$ is H.

In certain embodiments, the biodegradable group present in the cationic lipid is selected from an ester (e.g., —C(O)O— or —OC(O)—), disulfide (—S—S—), oxime (e.g., —C(H)=N—O— or —O—N=C(H)—), —C(O)—O—, —OC(O)—, —C($R^5$)=N—, —N=C($R^5$)—, —C($R^5$)=N—O—, —O—N=C($R^5$)—, —O—C(O)O—, —C(O)N($R^5$), —N($R^5$)C(O)—, —C(S)($NR^5$)—, ($NR^5$)C(S)—, —N($R^5$)C(O)N($R^5$)—, —C(O)S—, —SC(O)—, —C(S)O—, —OC(S)—, —OSi($R^5$)$_2$O—, —C(O)($CR^3R^4$)C(O)O—, or —OC(O)($CR^3R^4$)C(O)—.

In one embodiment, the aliphatic group in one or both of the hydrophobic tails of the cationic lipid includes at least one carbon-carbon double bond.

A suitable cholesterol moiety for the cationic lipids of the present invention (including compounds of formulas (I), IA-2, ID, IE and IF) has the formula:

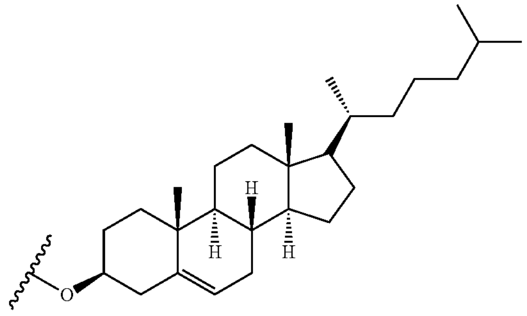

Additional embodiments include a cationic lipid having a head group, one or more hydrophobic tails, and a linker between the head group and the one or more tails. The head group can include an amine; for example an amine having a desired $pK_a$. The $pK_a$ can be influenced by the structure of the lipid, particularly the nature of head group; e.g., the presence, absence, and location of functional groups such as anionic functional groups, hydrogen bond donor functional groups, hydrogen bond acceptor groups, hydrophobic groups (e.g., aliphatic groups), hydrophilic groups (e.g., hydroxyl or methoxy), or aryl groups. The head group amine can be a cationic amine; a primary, secondary, or tertiary amine; the head group can include one amine group (monoamine), two amine groups (diamine), three amine groups (triamine), or a larger number of amine groups, as in an oligoamine or polyamine. The head group can include a functional group that is less strongly basic than an amine, such as, for example, an imidazole, a pyridine, or a guanidinium group. The head group can be zwitterionic. Other head groups are suitable as well.

The one or more hydrophobic tails can include two hydrophobic chains, which may be the same or different. The tails can be aliphatic, for example, they can be composed of carbon and hydrogen, either saturated or unsaturated but without aromatic rings. The tails can be fatty acid tails. Some such groups include octanyl, nonanyl, decyl, lauryl, myristyl, palmityl, stearyl, α-linoleyl, stearidonyl, linoleyl, γ-linolenyl, arachadonyl, and oleyl. Other hydrophobic tails are suitable as well.

The linker can include, for example, a glyceride linker, an acyclic glyceride analog linker, or a cyclic linker (including a spiro linker, a bicyclic linker, and a polycyclic linker). The linker can include functional groups such as an ether, an ester, a phosphate, a phosphonate, a phosphorothioate, a sulfonate, a disulfide, an acetal, a ketal, an imine, a hydrazone, or an oxime. Other linkers and functional groups are suitable as well.

In one embodiment, the cationic lipid is a racemic mixture. In another embodiment, the cationic lipid is enriched in one diastereomer, e.g. the cationic lipid has at least 95%, at least 90%, at least 80% or at least 70% diastereomeric excess. In yet another embodiment, the cationic lipid is enriched in one enantiomer, e.g. the lipid has at least 95%, at least 90%, at least 80% or at least 70% enantiomer excess. In yet another embodiment, the cationic lipid is chirally pure, e.g. is a single optical isomer. In yet another embodiment, the cationic lipid is enriched for one optical isomer.

Where a double bond is present (e.g., a carbon-carbon double bond or carbon-nitrogen double bond), there can be isomerism in the configuration about the double bond (i.e. cis/trans or E/Z isomerism). Where the configuration of a double bond is illustrated in a chemical structure, it is understood that the corresponding isomer can also be present. The amount of isomer present can vary, depending on the relative stabilities of the isomers and the energy required to convert between the isomers. Accordingly, some double bonds are, for practical purposes, present in only a single configuration, whereas others (e.g., where the relative stabilities are similar and the energy of conversion low) may be present as inseparable equilibrium mixture of configurations.

In some cases, a double-bonded unsaturation can be replaced by a cyclic unsaturation. The cyclic unsaturation can be a cycloaliphatic unsaturation, e.g., a cyclopropyl, cyclobutyl, cyclopentyl, cyclohexyl, cycloheptyl, or cyclooctyl group. In some cases, the cyclic group can be a polycyclic group, e.g., a bicyclic group or tricyclic group. A bicyclic group can be bridged, fused, or have a spiro structure.

In some cases, a double bond moiety can be replaced by a cyclopropyl moiety, e.g.,

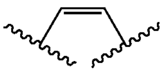

can be replaced by

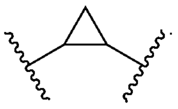 [SMILES: *C1CC1*]

For example, the moiety shown below has two carbon-carbon double bonds, each of which can independently be replaced by a cyclic moiety, e.g., a cyclopropyl moiety. Thus, substitutes for:

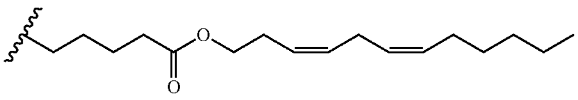 [SMILES: *CCCCC(=O)OCC/C=C\C/C=C\CCCCC]

can include:

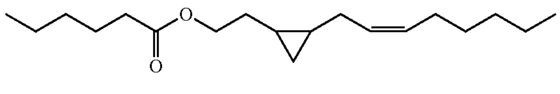

,

-continued

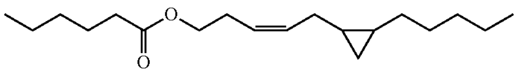

, and

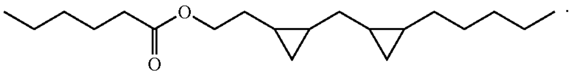

For further example, substitutes for

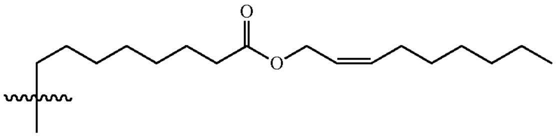 [SMILES: *CCCCCCCC(=O)OC/C=C\CCCCCC]

include:

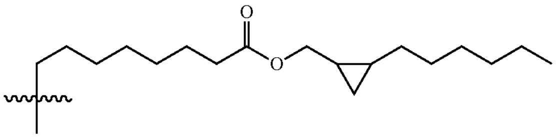 [SMILES: *CCCCCCCC(=O)OCC1CC1CCCCCC]

For further example, substitutes for

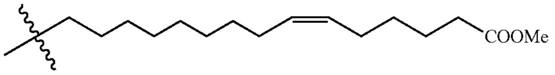 [SMILES: *CCCCCCCC/C=C\CCCCC(=O)OC]

include:

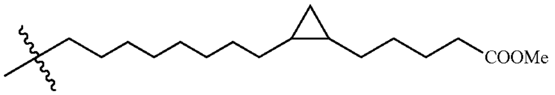 [SMILES: *CCCCCCCCC1CC1CCCCC(=O)OC]

For further example, substitutes for

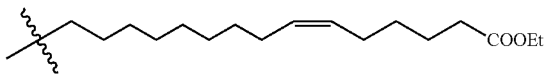

include:

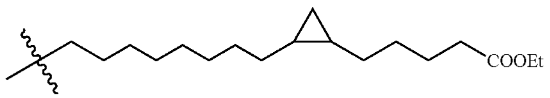 [SMILES: *CCCCCCCCC1CC1CCCCC(=O)OCC]

The cationic lipid includes one or more biodegradable groups. The biodegradable group(s) include one or more bonds that may undergo bond breaking reactions in a biological environment, e.g., in an organism, organ, tissue, cell, or organelle. Functional groups that contain a biodegradable bond include, for example, esters, dithiols, and oximes. Biodegradation can be a factor that influences the clearance of the compound from the body when administered to a subject. Biodegredation can be measured in a cell based assay, where a formulation including a cationic lipid is exposed to cells, and samples are taken at various time points. The lipid fractions can be extracted from the cells and separated and analyzed by LC-MS. From the LC-MS data, rates of biodegradation (e.g., as $t_{1/2}$ values) can be measured.

For example, the compound

Compound 1

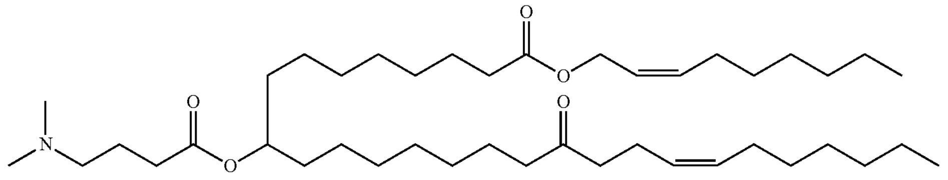

includes an ester linkage in each aliphatic chain, which can undergo hydrolysis in a biological environment, for example, when exposed to, e.g., a lipase or an esterase. The structure of the compound, of course, influences the rate at which the compound undergoes biodegradation. Thus, a related compound such as Compound 2

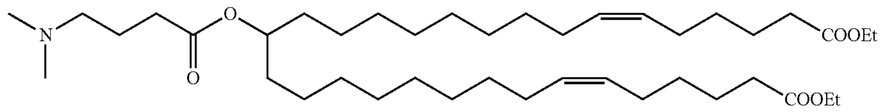

would be expected to exhibit a different rate of biodegradation. Greater effects on that rate would be expected from changes in the structure of the compound at the site of hydrolysis. One modification that can influence the rate of hydrolysis, and thereby influence the rate of biodegradation and clearance from a subject's body, is to make the leaving group of the hydrolysis reaction have a primary, rather than secondary, alcohol.

For example, without wishing to be bound by theory, Compounds 1 and 2 shown above may be metabolized as shown in FIG. 2.

In one embodiment, a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

In another embodiment, a cationic lipid of any of the embodiments described herein containing a biodegradable group or groups has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Some cationic lipids can be conveniently represented as a hydrophobic group combined with a headgroup. By way of example, the compound:

Compound 1

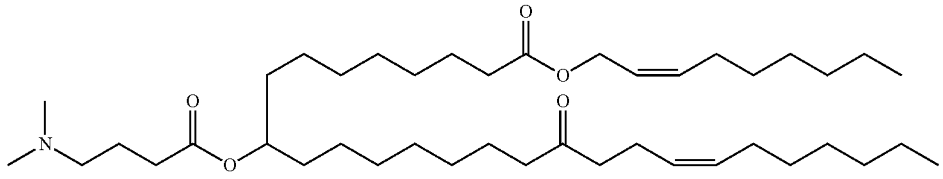

can be thought of as a combination of a headgroup and a hydrophobic group as follows:

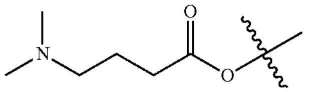

Head Group

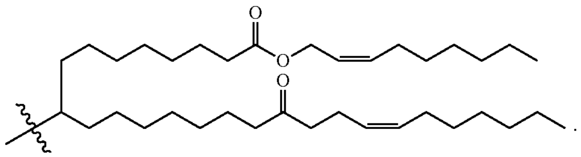

Hydrophobic Group

Thus, some suitable head groups include those depicted in Table 1:

TABLE 1
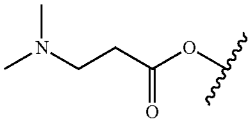 [SMILES: *OC(=O)CCN(C)C]
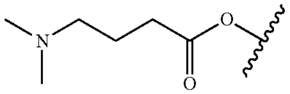 [SMILES: *OC(=O)CCCN(C)C]
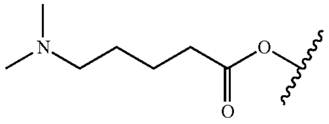 [SMILES: *OC(=O)CCCCN(C)C]
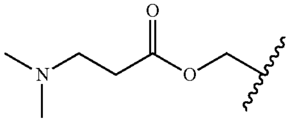 [SMILES: *COC(=O)CCN(C)C]
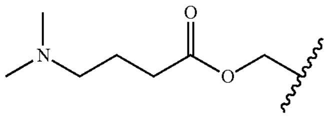 [SMILES: *COC(=O)CCCN(C)C]
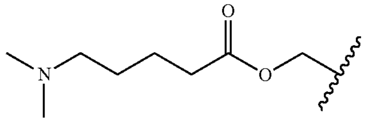 [SMILES: *COC(=O)CCCCN(C)C]
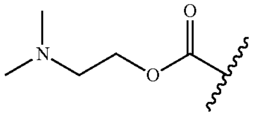 [SMILES: *C(=O)OCCN(C)C]
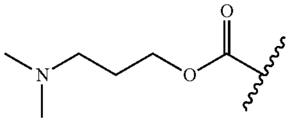 [SMILES: *C(=O)OCCCN(C)C]
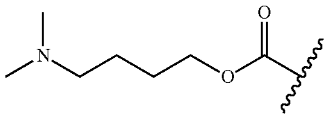 [SMILES: *C(=O)OCCCCN(C)C]
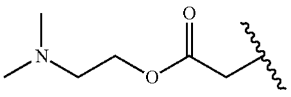 [SMILES: *CC(=O)OCCN(C)C]
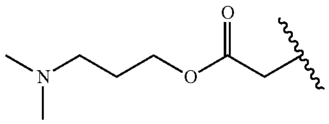 [SMILES: *CC(=O)OCCCN(C)C]
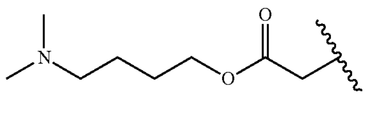 [SMILES: *CC(=O)OCCCCN(C)C]
TABLE 1-continued
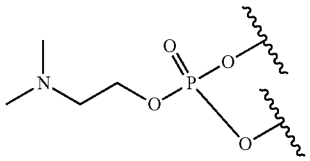 [SMILES: *OP(=O)(O*)OCCN(C)C]
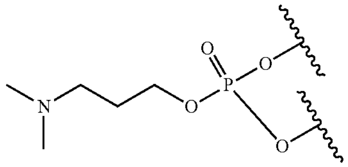 [SMILES: *OP(=O)(O*)OCCCN(C)C]
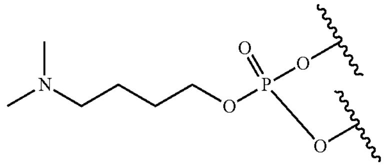 [SMILES: *OP(=O)(O*)OCCCCN(C)C]
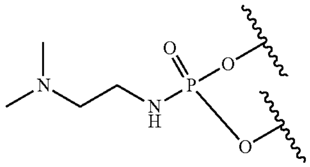 [SMILES: *OP(=O)(NCCN(C)C)O*]
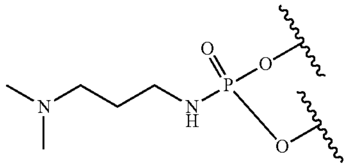 [SMILES: *OP(=O)(NCCCN(C)C)O*]
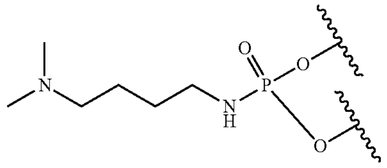 [SMILES: *OP(=O)(NCCCCN(C)C)O*]
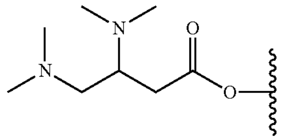 [SMILES: *OC(=O)CC(CN(C)C)N(C)C]
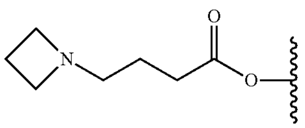 [SMILES: *OC(=O)CCCN1CCC1]
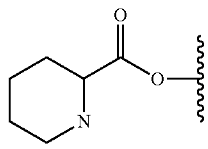 [SMILES: *OC(=O)C1CCCCN1]

TABLE 1-continued
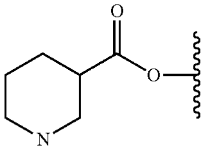 [SMILES: *OC(=O)C1CCCNC1]
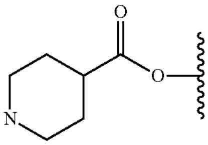 [SMILES: *OC(=O)C1CCNCC1]
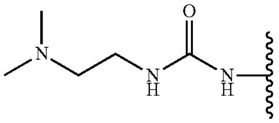 [SMILES: *NC(=O)NCCN(C)C]
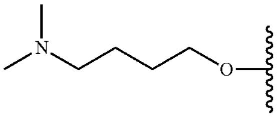 [SMILES: *OCCCCN(C)C]
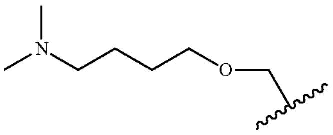 [SMILES: *COCCCCN(C)C]
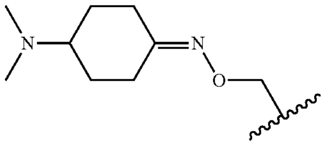 [SMILES: *CON=C1CCC(N(C)C)CC1]
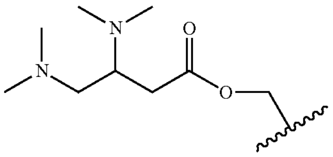 [SMILES: *COC(=O)CC(CN(C)C)N(C)C]
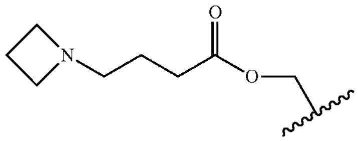 [SMILES: *COC(=O)CCCN1CCC1]
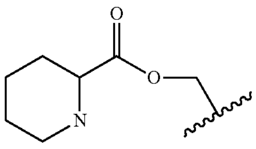 [SMILES: *COC(=O)C1CCCCN1]
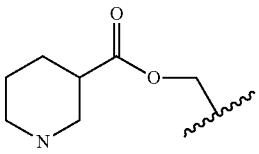 [SMILES: *COC(=O)C1CCCNC1]
TABLE 1-continued
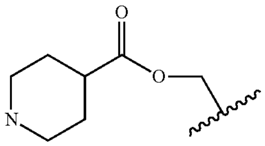 [SMILES: *COC(=O)C1CCNCC1]
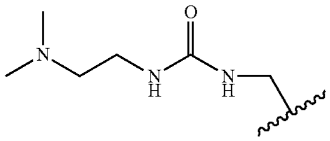 [SMILES: *CNC(=O)NCCN(C)C]
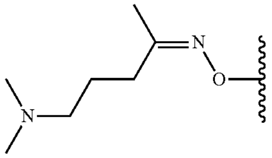 [SMILES: *O/N=C(/C)CCCN(C)C]
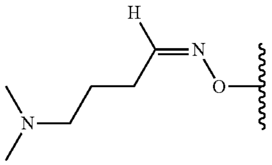 [SMILES: *O/N=C\CCCN(C)C]
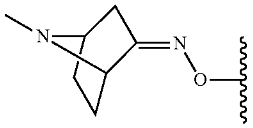 [SMILES: *O/N=C1/CC2CCC1N2C]
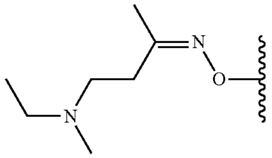 [SMILES: *O/N=C(/C)CCN(C)CC]
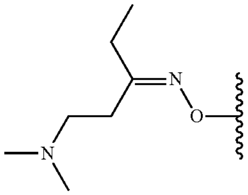 [SMILES: *O/N=C(/CC)CCN(C)C]
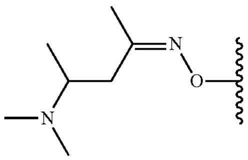 [SMILES: *O/N=C(/C)CC(C)N(C)C]
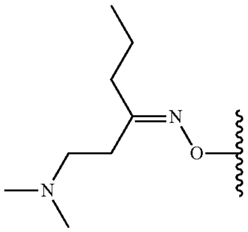 [SMILES: *O/N=C(/CCC)CCN(C)C]

TABLE 1-continued
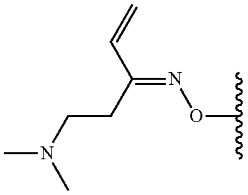 [SMILES: *O/N=C(/C=C)CCN(C)C]
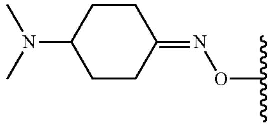 [SMILES: *ON=C1CCC(N(C)C)CC1]
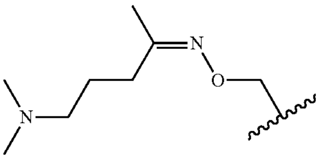 [SMILES: *CO/N=C(/C)CCCN(C)C]
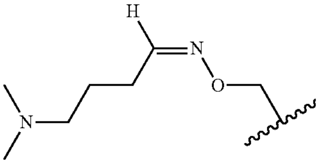 [SMILES: *CO/N=C\CCCN(C)C]
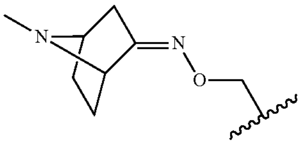 [SMILES: *CO/N=C1/CC2CCC1N2C]
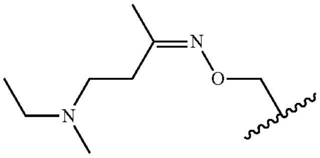 [SMILES: *CO/N=C(/C)CCN(C)CC]
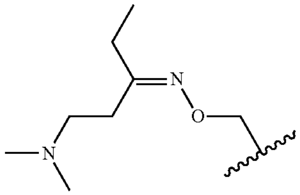 [SMILES: *CO/N=C(/CC)CCN(C)C]
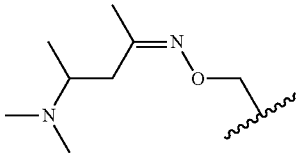 [SMILES: *CO/N=C(/C)CC(C)N(C)C]
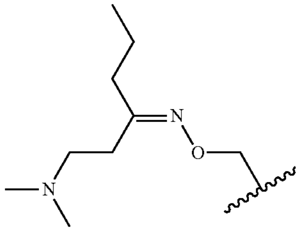 [SMILES: *CO/N=C(/CCC)CCN(C)C]
TABLE 1-continued
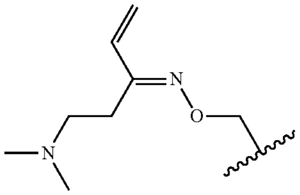 [SMILES: *CO/N=C(/C=C)CCN(C)C]
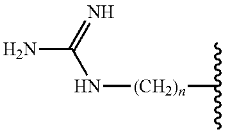
(where n is 0-5)
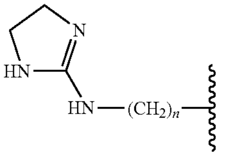
(where n is 0-5)
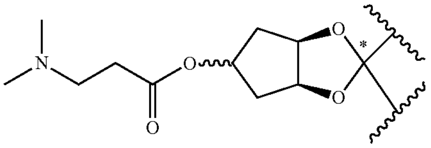
(the carbon with an asterisk is the tertiary carbon of the cation lipid and is not part of the head group)
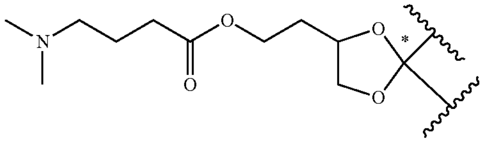
(the carbon with an asterisk is the tertiary carbon of the cation lipid and is not part of the head group)
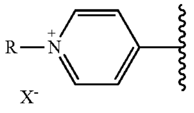
R = H, alkyl (e.g., methyl)
X = halogen (e.g., Cl)

TABLE 1-continued
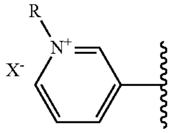
R = H, alkyl (e.g., methyl)
X = halogen (e.g., Cl)
TABLE 1-continued
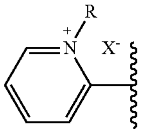
R = H, alkyl (e.g., methyl)
X = halogen (e.g., Cl)
Some suitable hydrophobic tail groups include those depicted in Table 2:
TABLE 2
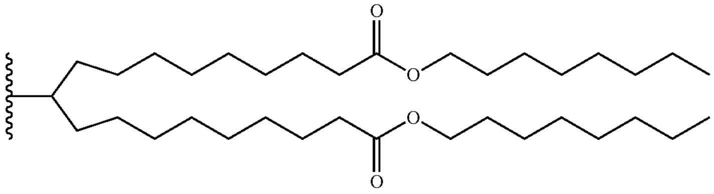 [SMILES: *C(CCCCCCCCC(=O)OCCCCCCCC)CCCCCCCCC(=O)OCCCCCCCC]
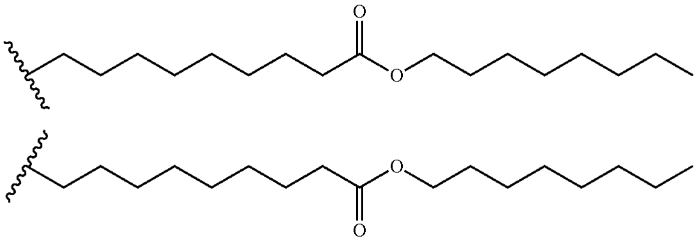 [SMILES: *CCCCCCCCC(=O)OCCCCCCCC ; *CCCCCCCCC(=O)OCCCCCCCC]
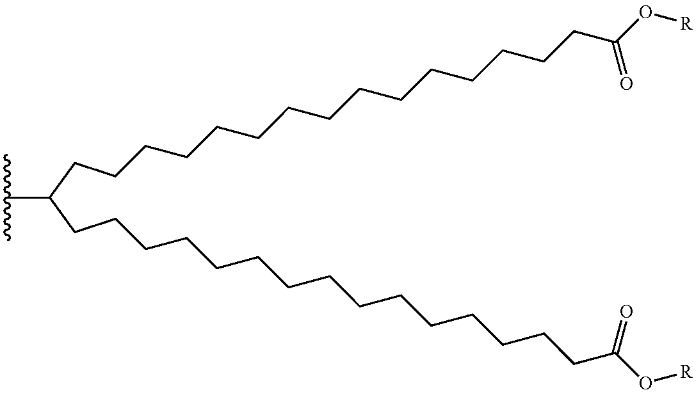
R = Me, Et
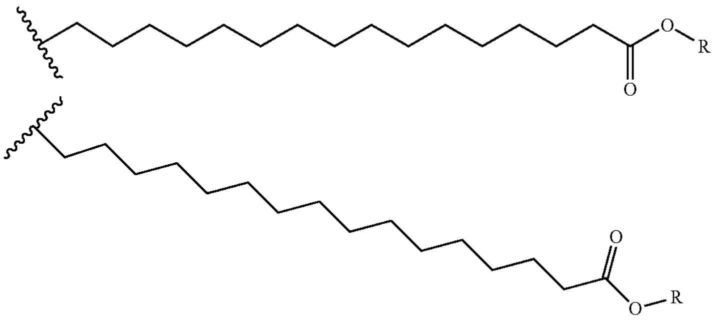
R = Me, Et TABLE 2-continued
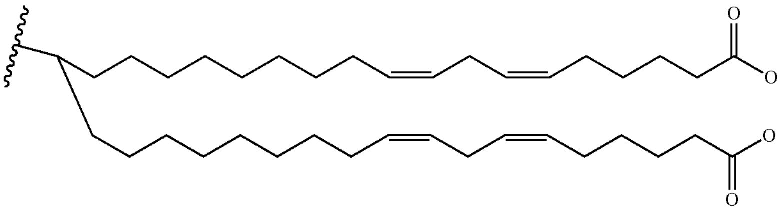
R = Me, Et
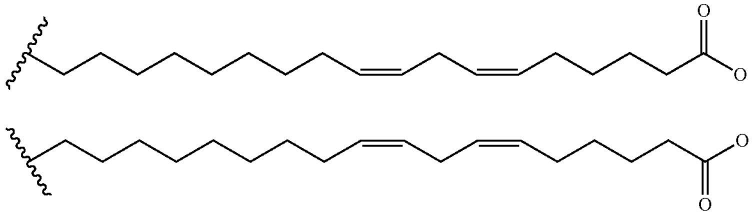
R = Me, Et
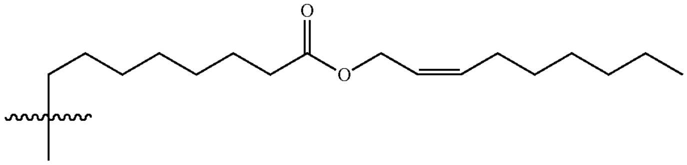 [SMILES: *CCCCCCCC(=O)OC/C=C\CCCCCC]
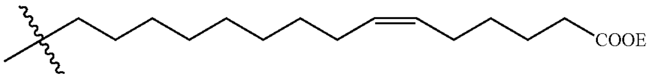
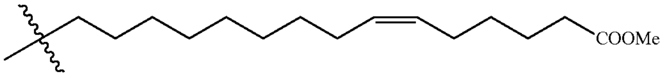
Examples of cationic lipids of the present invention include those shown in Tables 3-13 below, and salts thereof (including pharmaceutically acceptable salts thereof).
TABLE 3
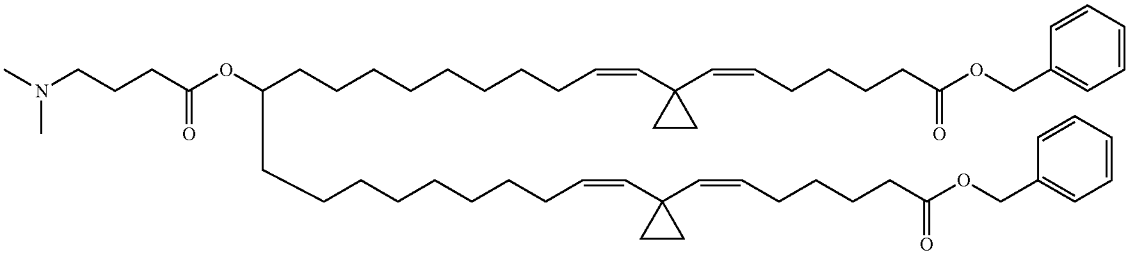 [SMILES: CN(C)CCCC(=O)OC(CCCCCCCC/C=C\C1(/C=C\CCCCC(=O)OCc2ccccc2)CC1)CCCCCCCC/C=C\C1(/C=C\CCCCC(=O)OCc2ccccc2)CC1]
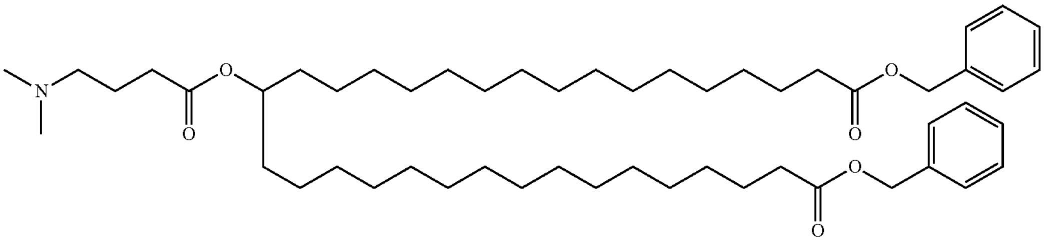 [SMILES: CN(C)CCCC(=O)OC(CCCCCCCCCCCCCCCC(=O)OCc1ccccc1)CCCCCCCCCCCCCCCC(=O)OCc1ccccc1]

TABLE 3-continued
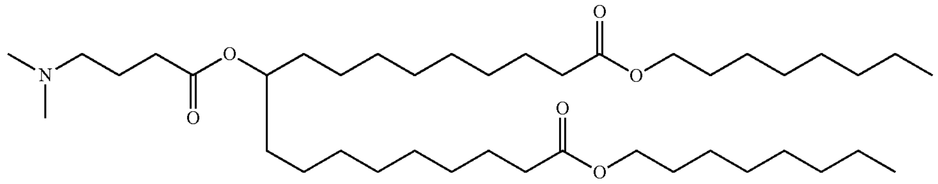 [SMILES: CCCCCCCCOC(=O)CCCCCCCCC(CCCCCCCCC(=O)OCCCCCCCC)OC(=O)CCCN(C)C]
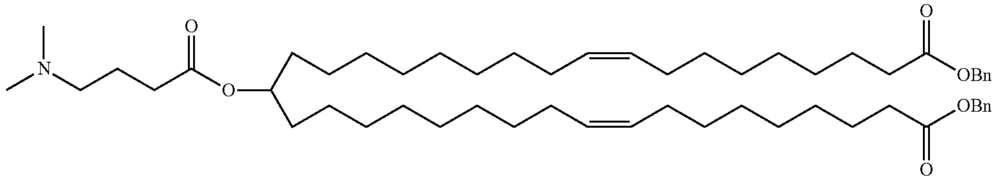 [SMILES: CN(C)CCCC(=O)OC(CCCCCCCC/C=C\CCCCCCCC(=O)OCc1ccccc1)CCCCCCCC/C=C\CCCCCCCC(=O)OCc1ccccc1]
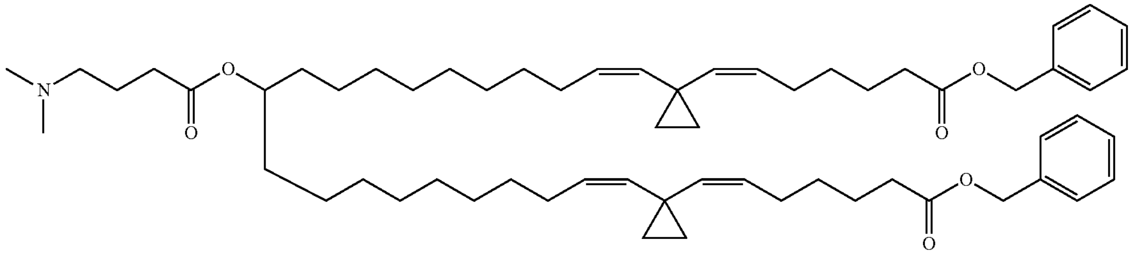 [SMILES: CN(C)CCCC(=O)OC(CCCCCCCC/C=C\C1(/C=C\CCCCC(=O)OCc2ccccc2)CC1)CCCCCCCC/C=C\C1(/C=C\CCCCC(=O)OCc2ccccc2)CC1]
TABLE 4
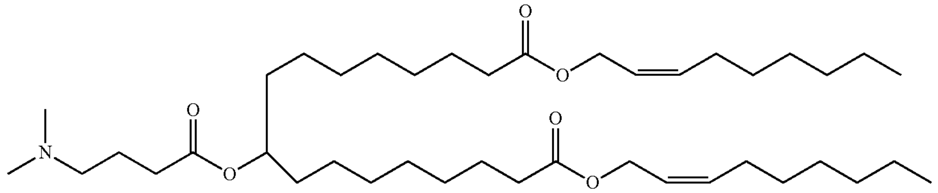
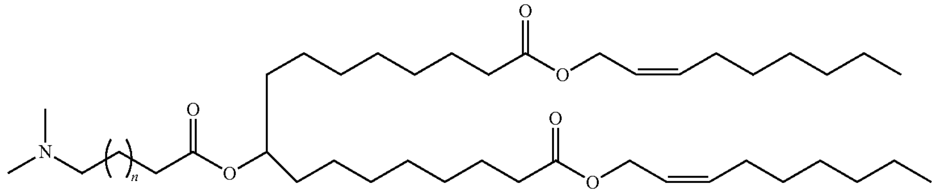 [SMILES: CCCCCC/C=C\COC(=O)CCCCCCCC(CCCCCCCC(=O)OC/C=C\CCCCCC)OC(=O)CCCN(C)C]
n = 0-2
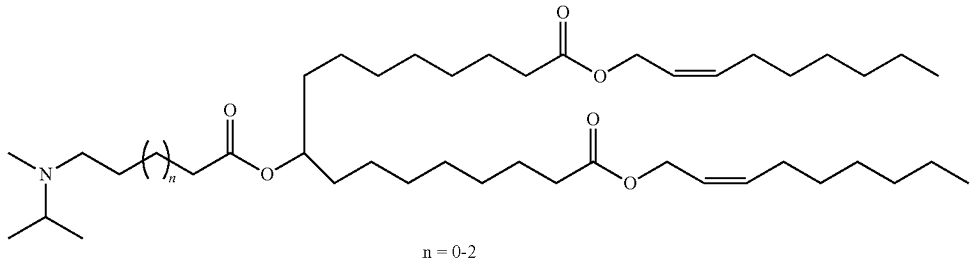
n = 0-2

TABLE 4-continued
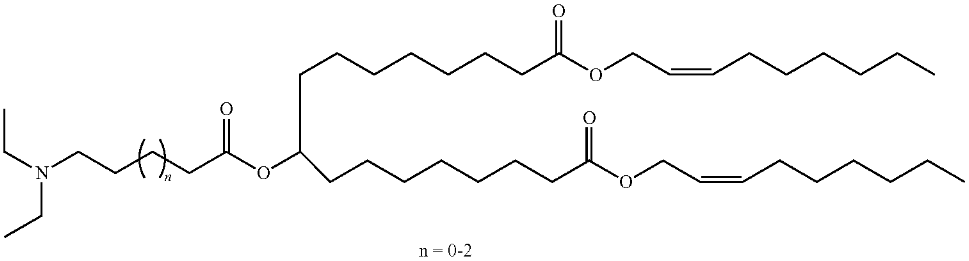
n = 0-2
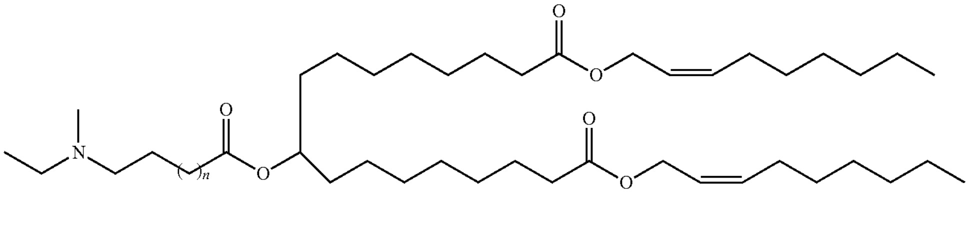
n = 0-2
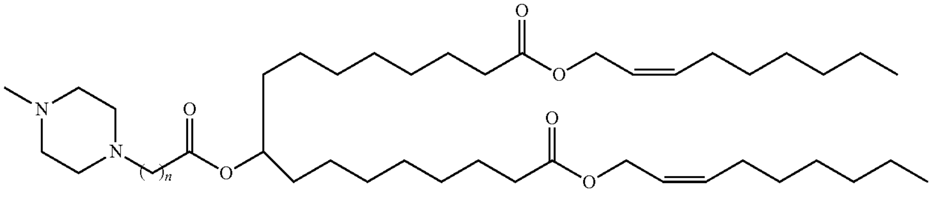
n = 1-3
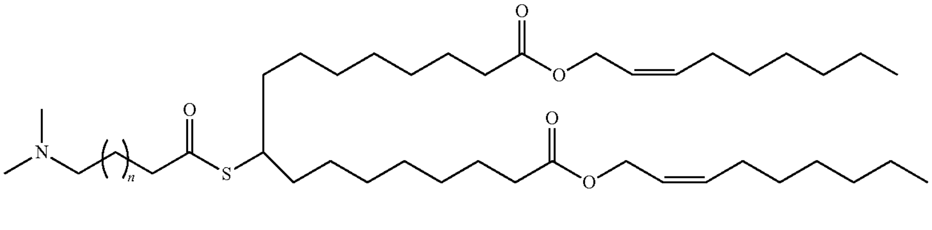
n = 0-2
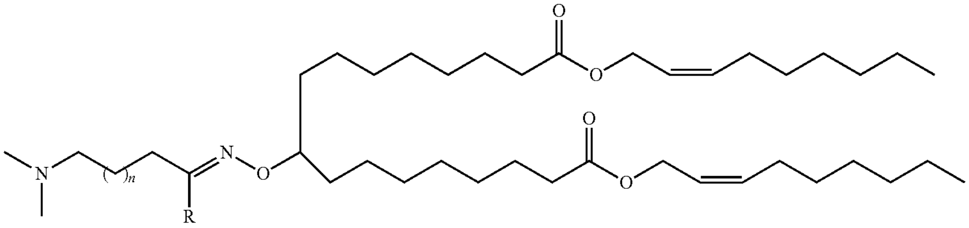
n = 0-2
R = H, Me
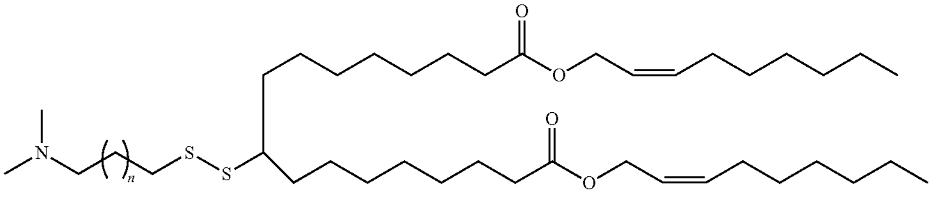
n = 0-2

TABLE 4-continued
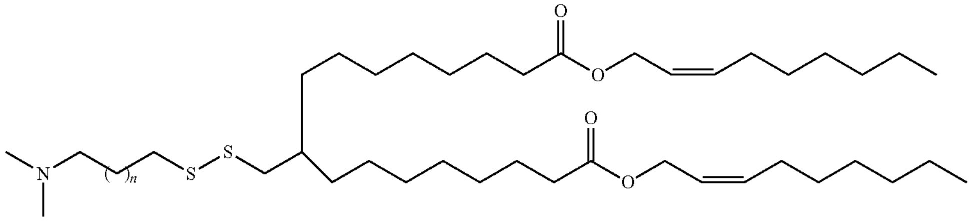
n = 0-2
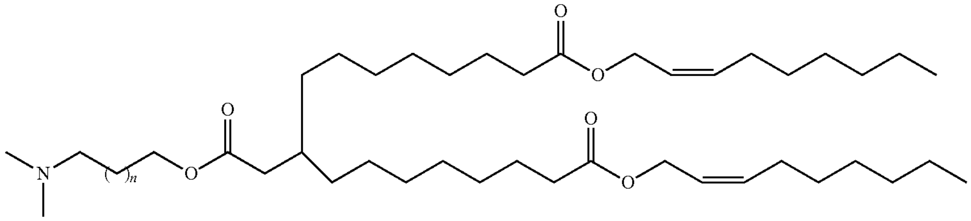
n = 0-2
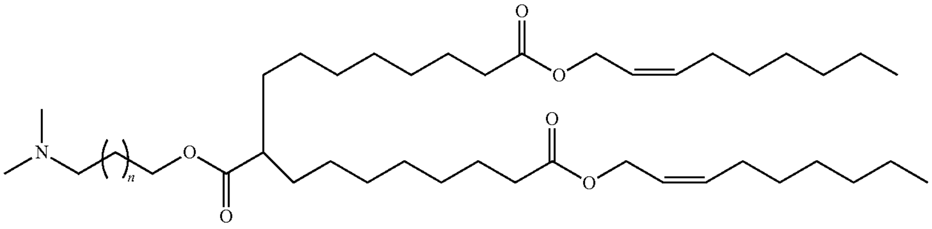
n = 0-2
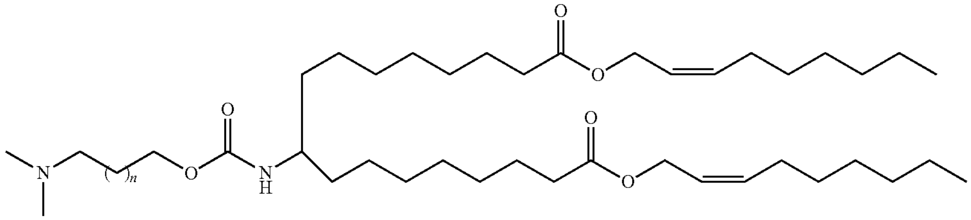
n = 0-2
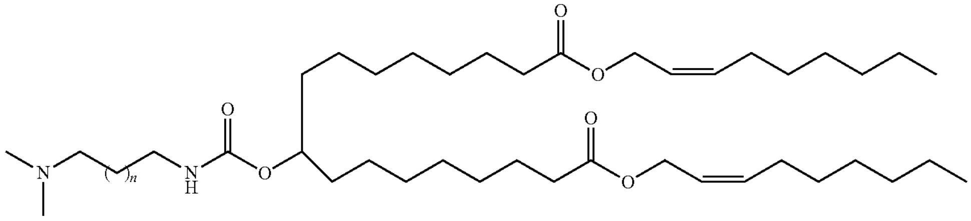
n = 0-2
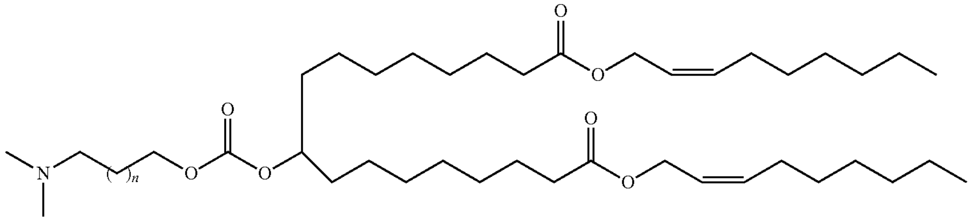
n = 0-2

TABLE 4-continued
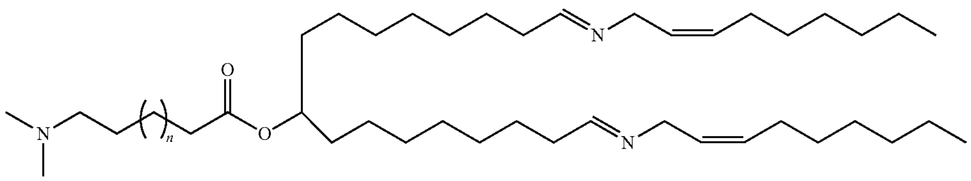
n = 0-2
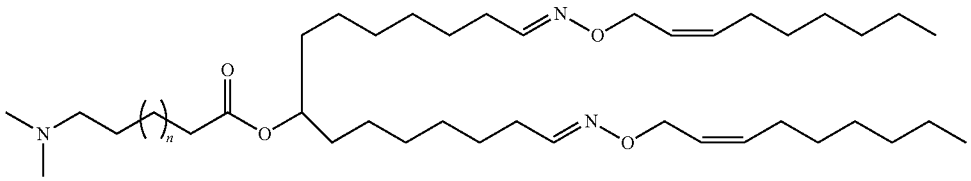
n = 0-2
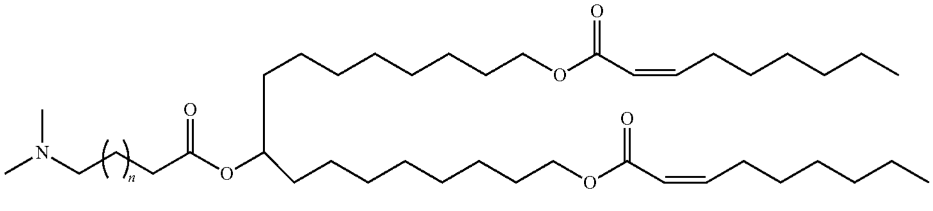
n = 0-2
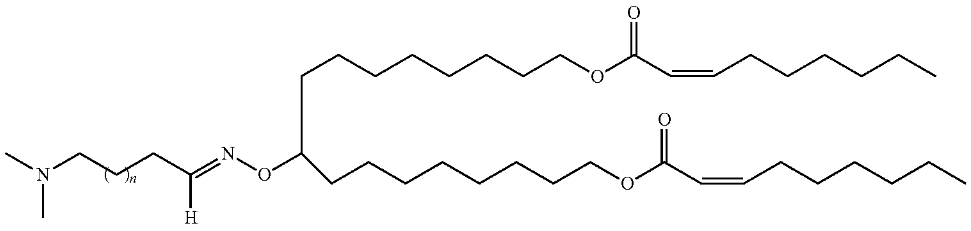
n = 0-2
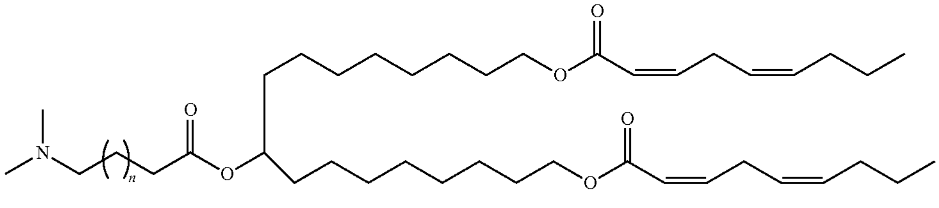
n = 0-2
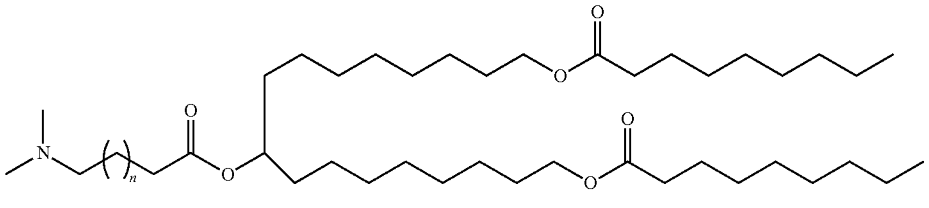
n = 0-2

TABLE 4-continued
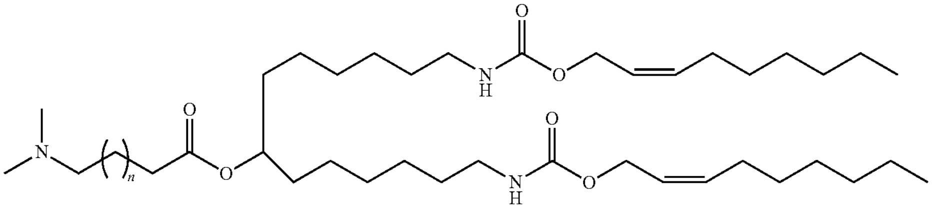
n = 0-2
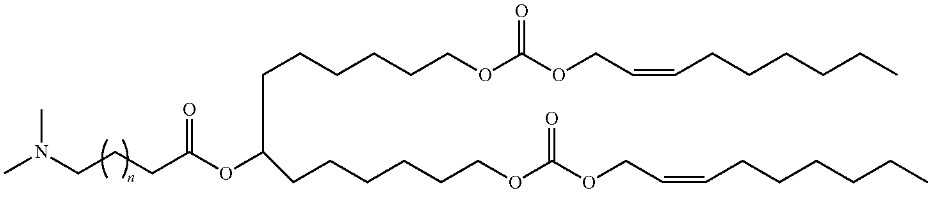
n = 0-2
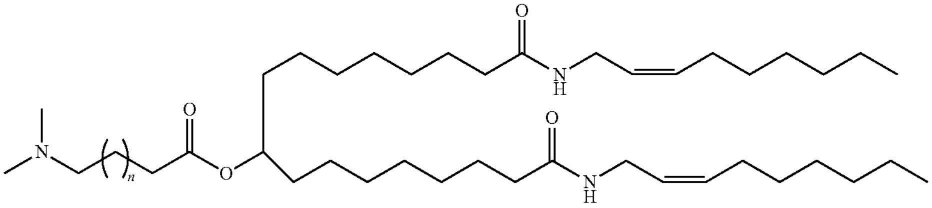
n = 0-2
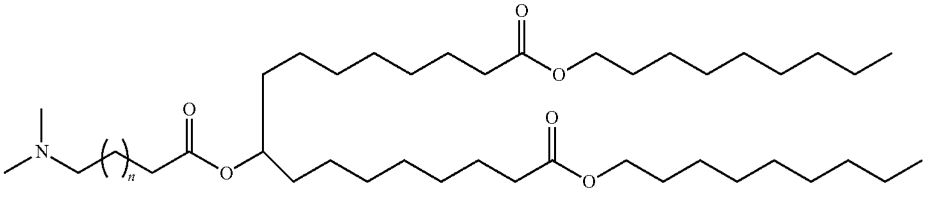
n = 0-2
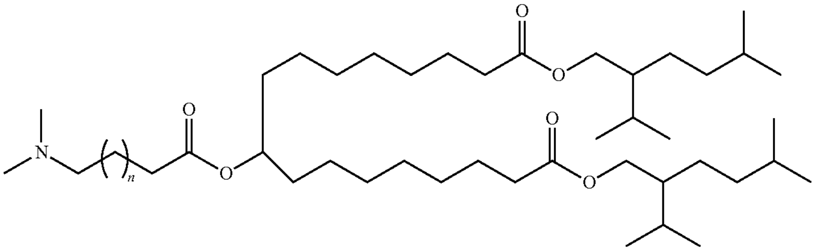
n = 0-2
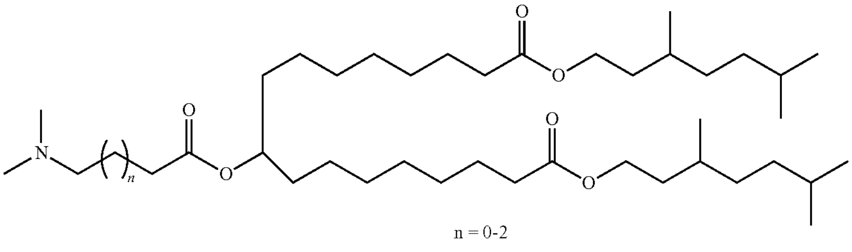
n = 0-2

TABLE 4-continued
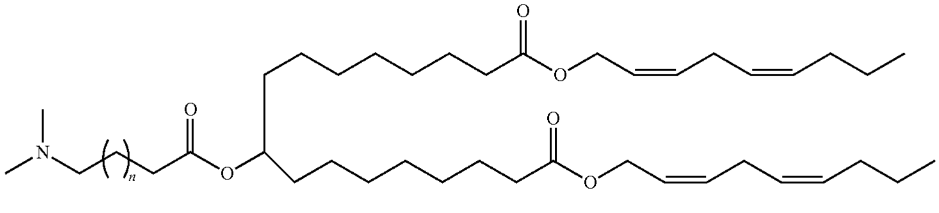
n = 0-2
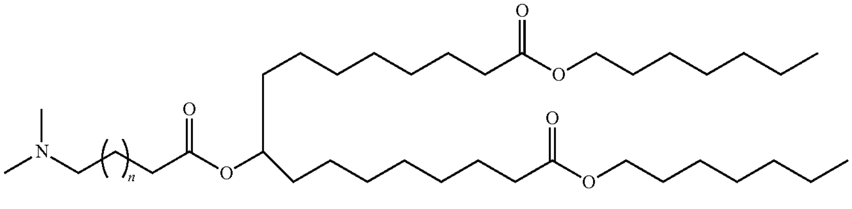
n = 0-2
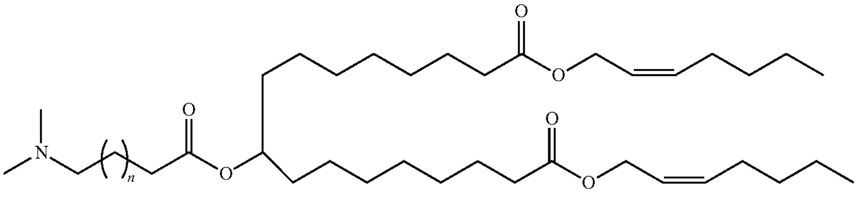
n = 0-2
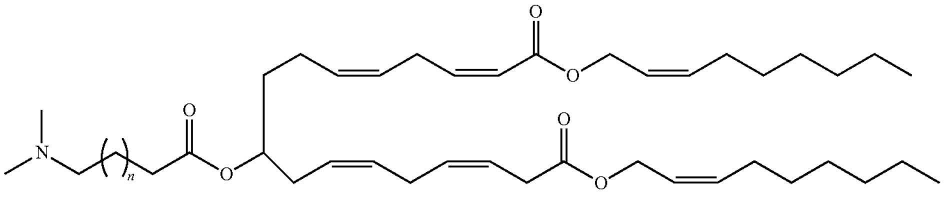
n = 0-2
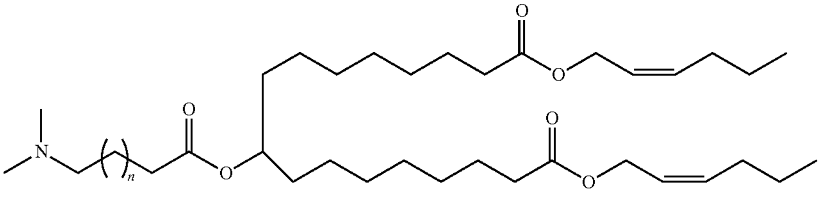
n = 0-2
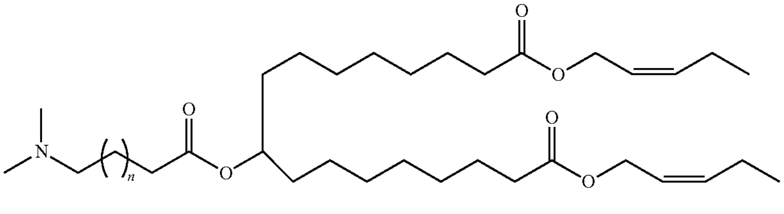
n = 0-2

TABLE 4-continued
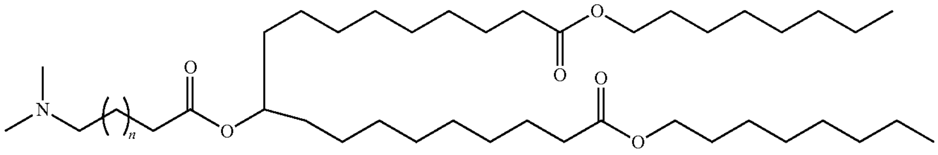
n = 0-2
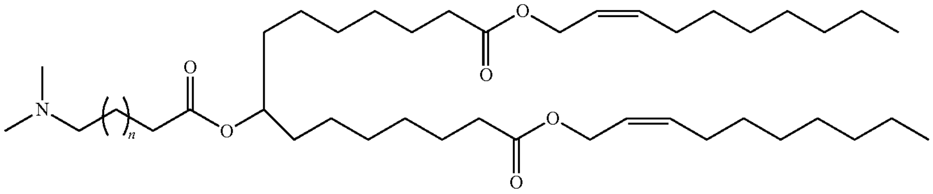
n = 0-2
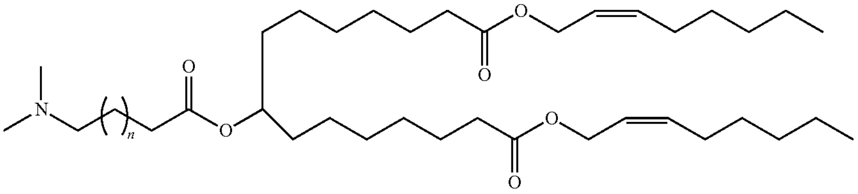
n = 0-2
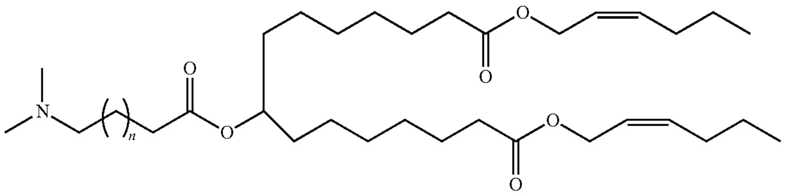
n = 0-2
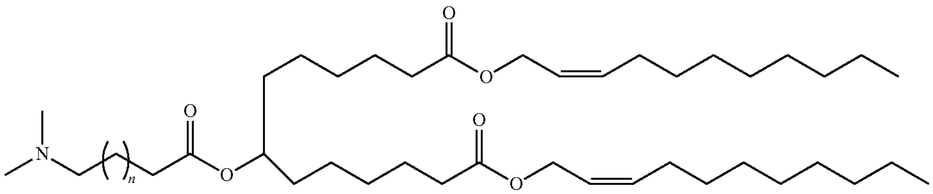
n = 0-2
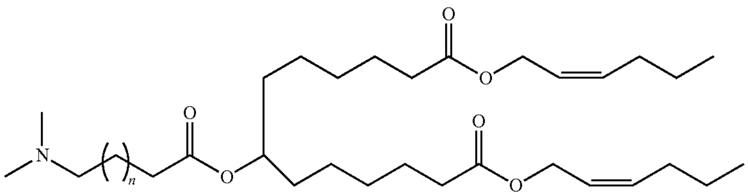
n = 0-2

TABLE 4-continued
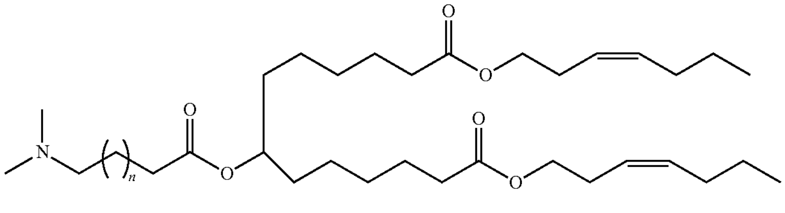
n = 0-2
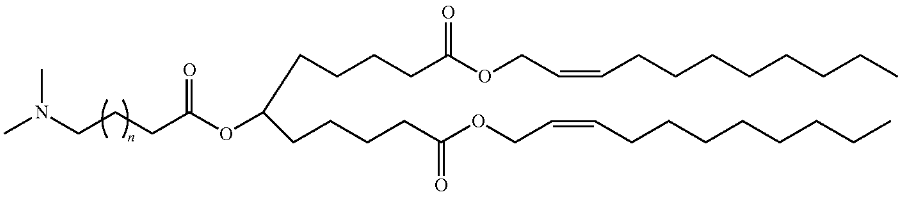
n = 0-2
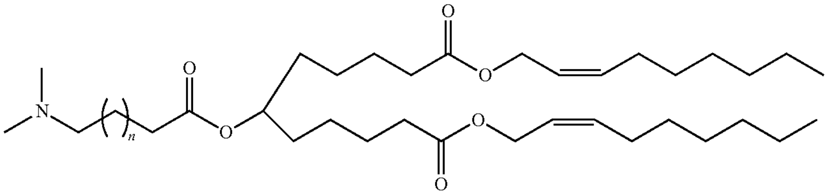
n = 0-2
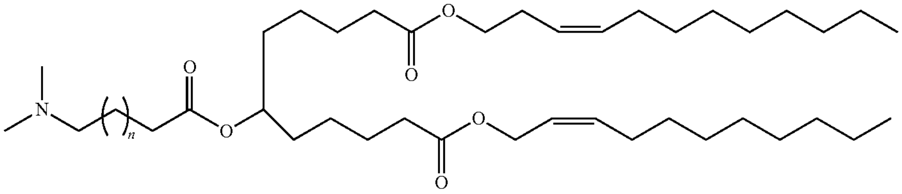
n = 0-2
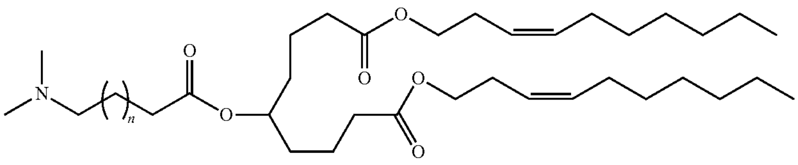
n = 0-2
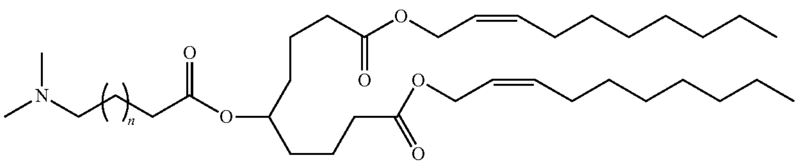
n = 0-2

TABLE 4-continued
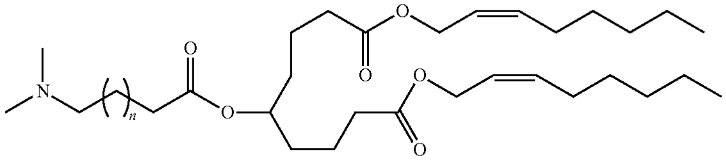
n = 0-2
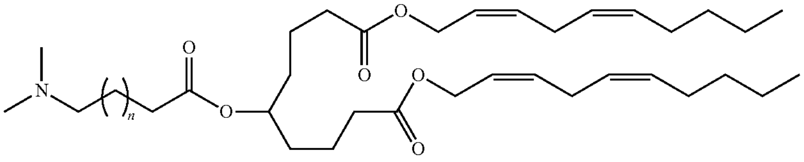
n = 0-2
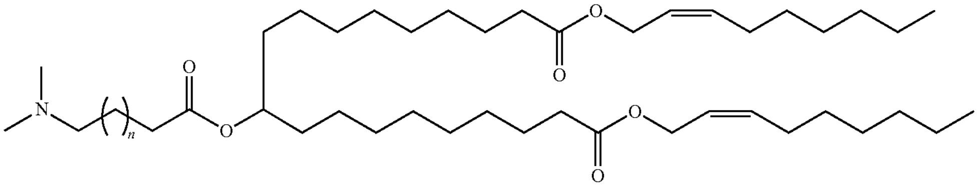
n = 0-2
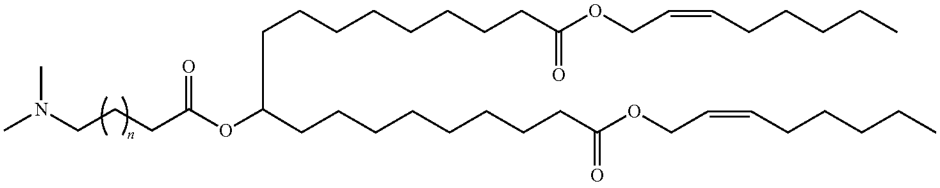
n = 0-2
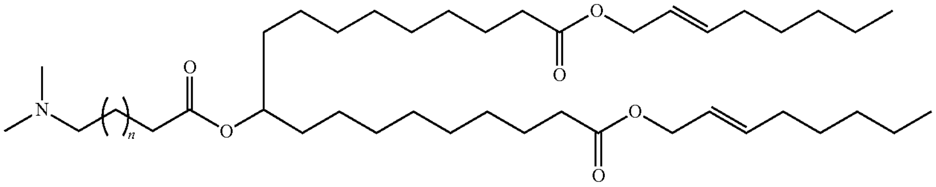
n = 0-2
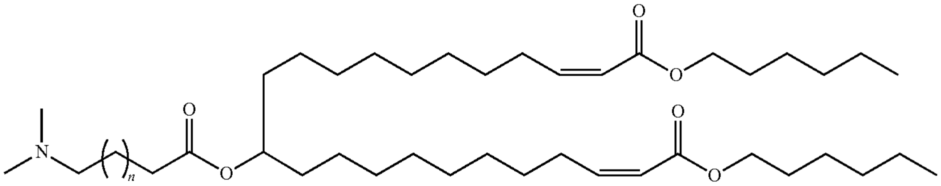
n = 0-2
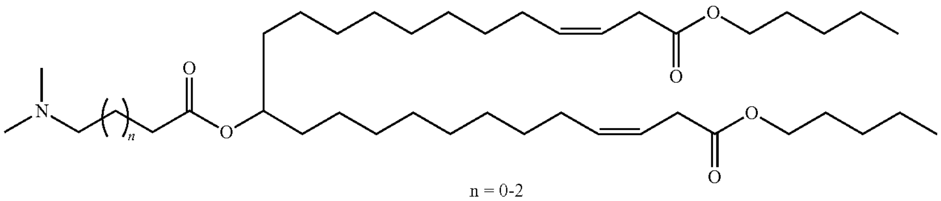
n = 0-2

TABLE 4-continued
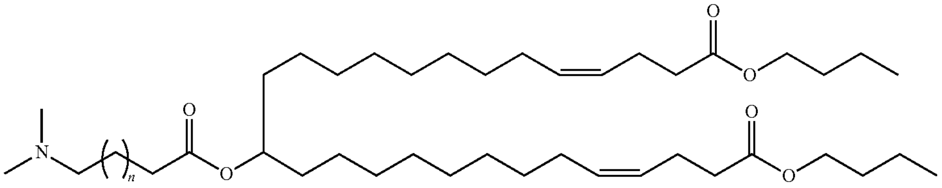
n = 0-2
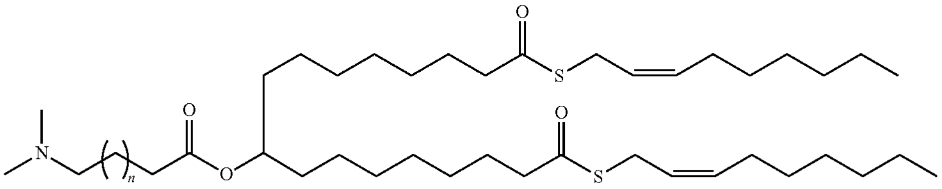
n = 0-2
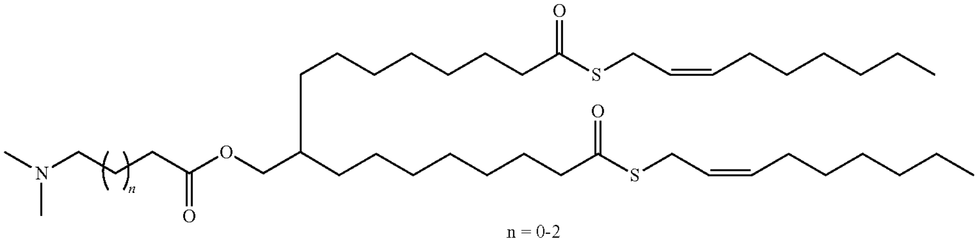
n = 0-2
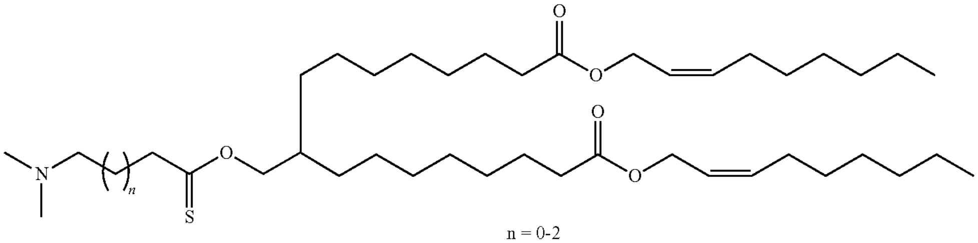
n = 0-2
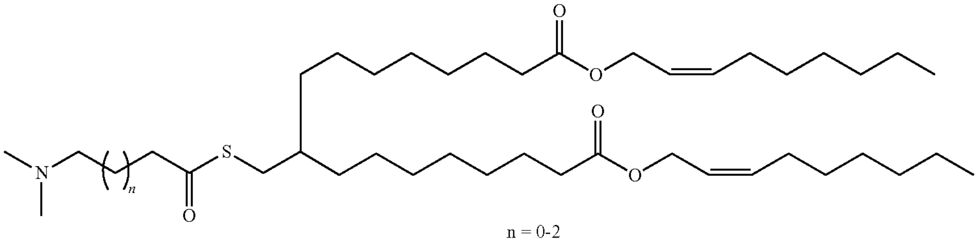
n = 0-2
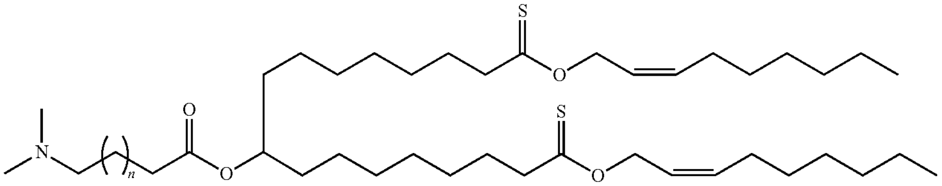
n = 0-2

TABLE 4-continued
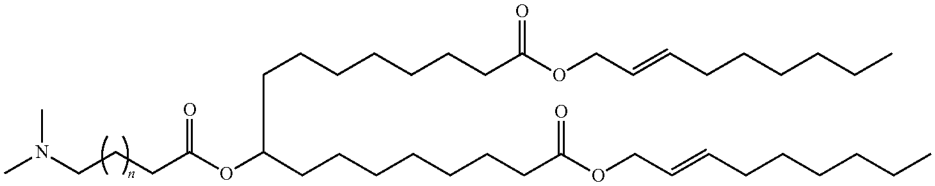
n = 0-2
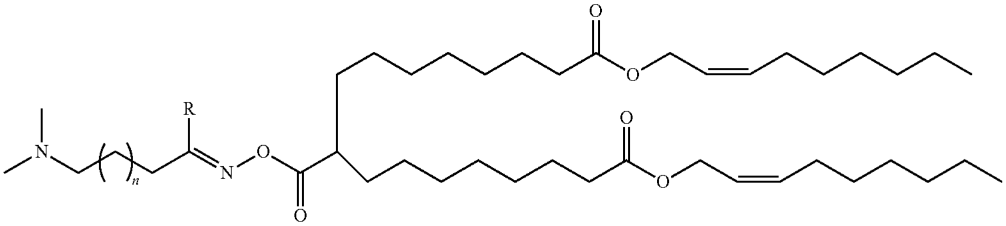
R = H, Me
n = 0-2
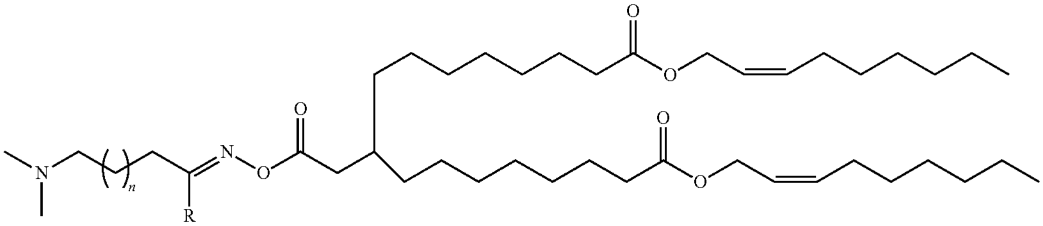
R = H, Me
n = 0-2
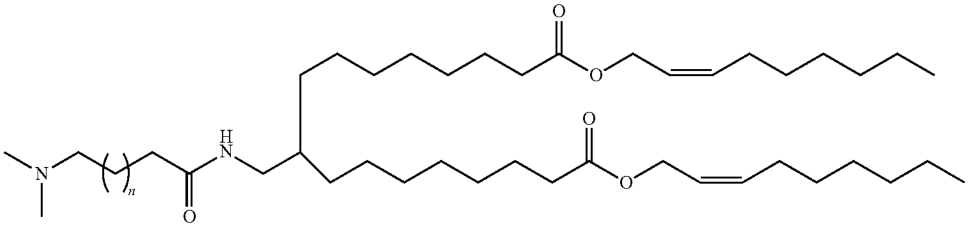
n = 0-2
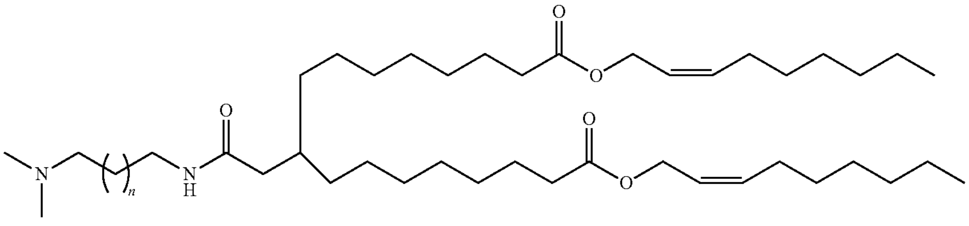
n = 0-2

TABLE 4-continued
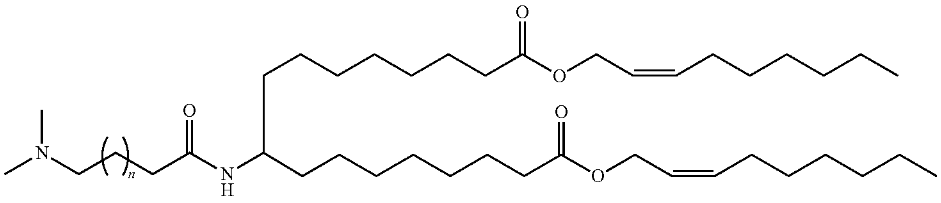
n = 0-2
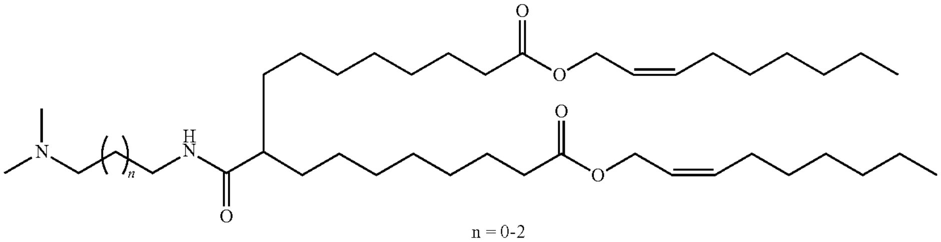
n = 0-2
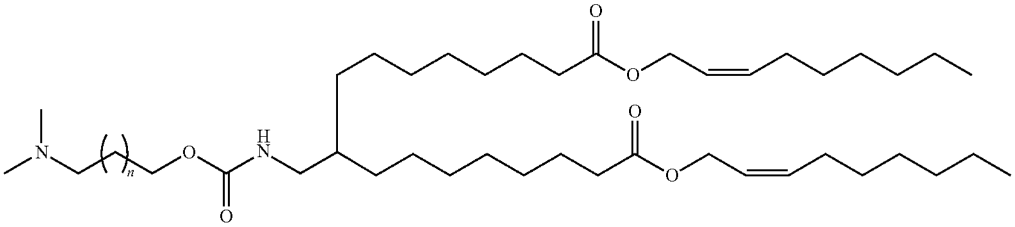
n = 0-2
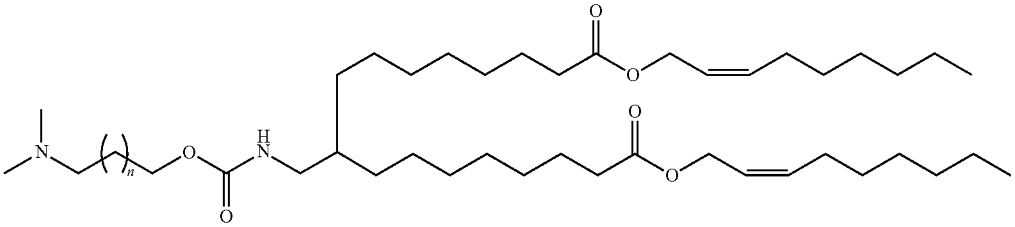
n = 0-2
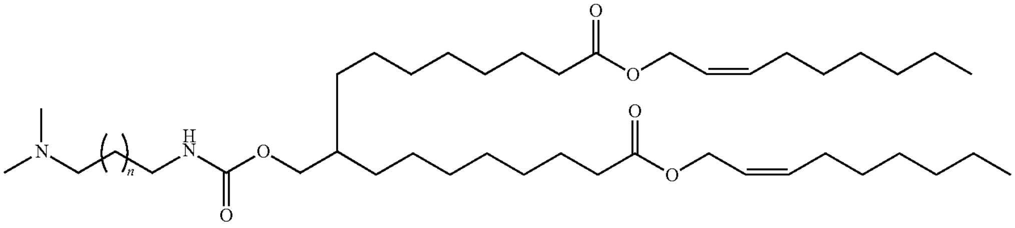
n = 0-2

TABLE 4-continued
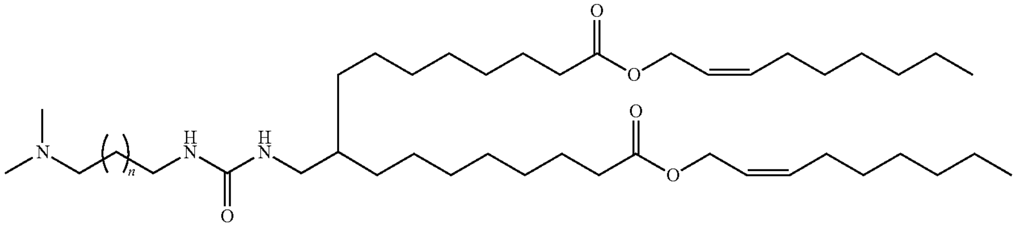
n = 0-2
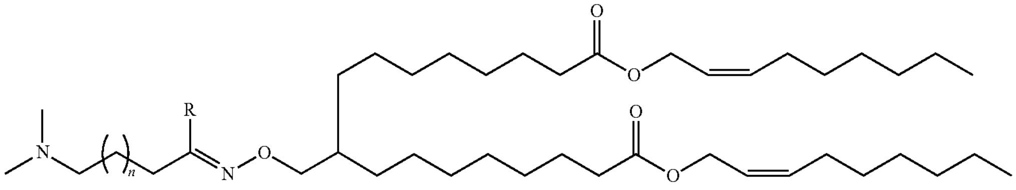
R = H, Me
n = 0-2
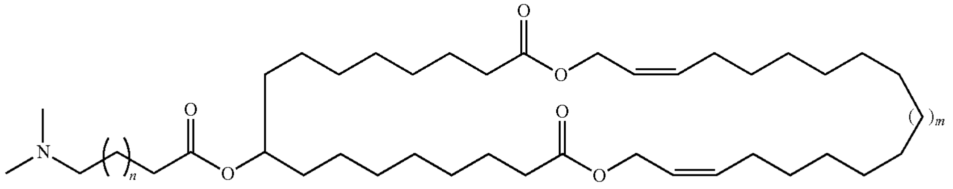
n = 0-2
m = 0-12
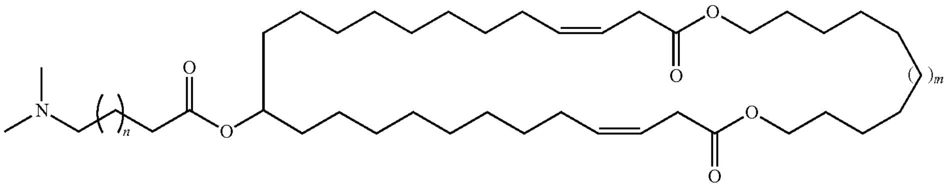
n = 0-2
m = 0-12
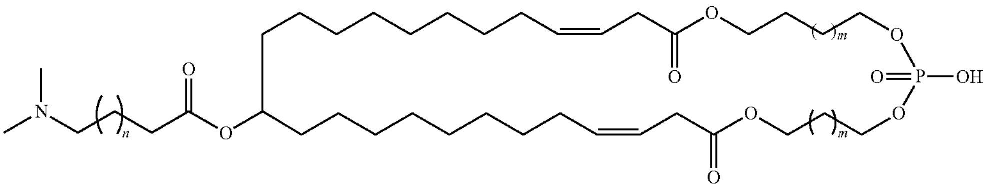
n = 0-2
m = 0-12
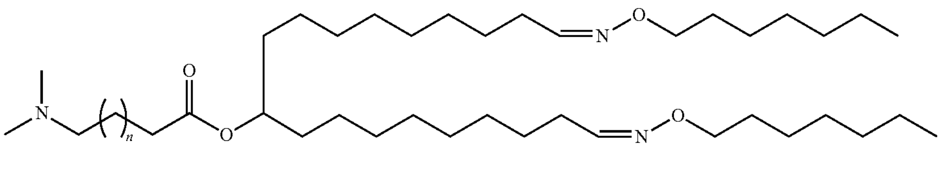
n = 0-2

TABLE 4-continued
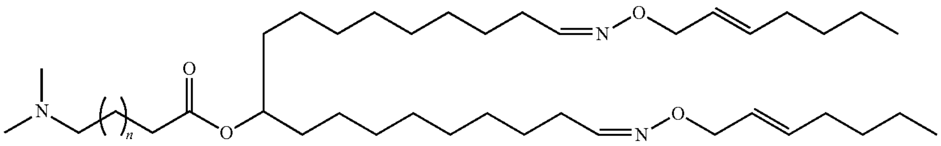
n = 0-2
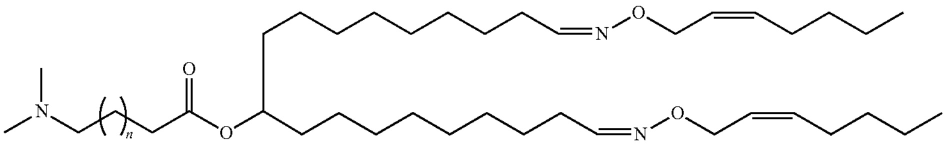
n = 0-2
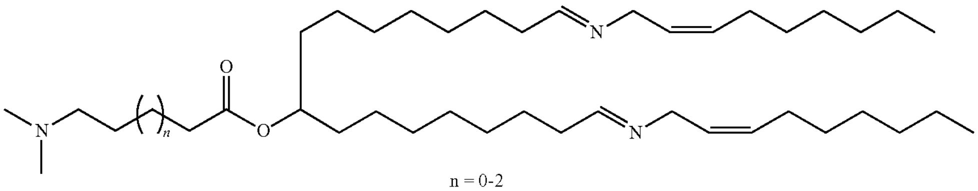
n = 0-2
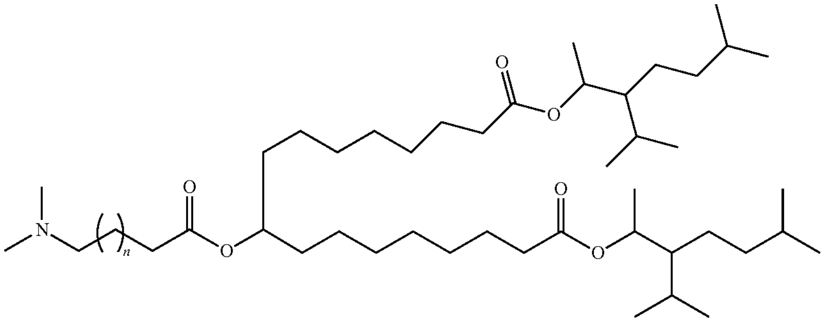
n = 0-2
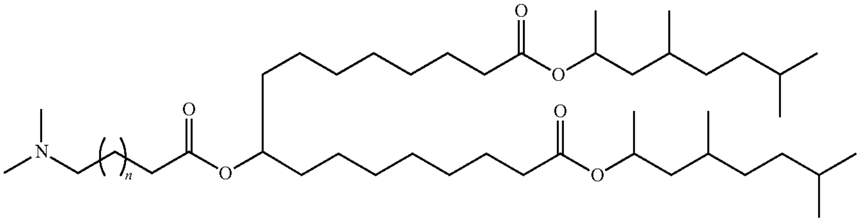
n = 0-2
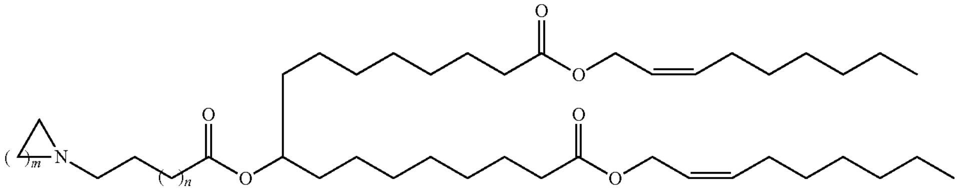
m = 1-6; n = 0-3

TABLE 4-continued
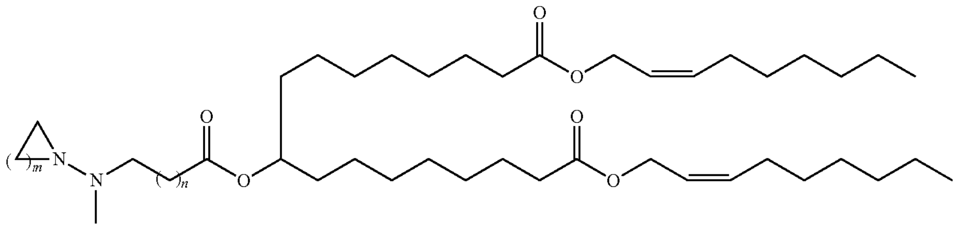
m = 1-6; n = 0-5
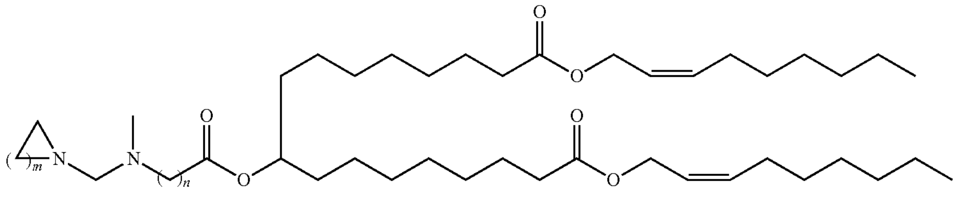
m = 1-6; n = 0-5
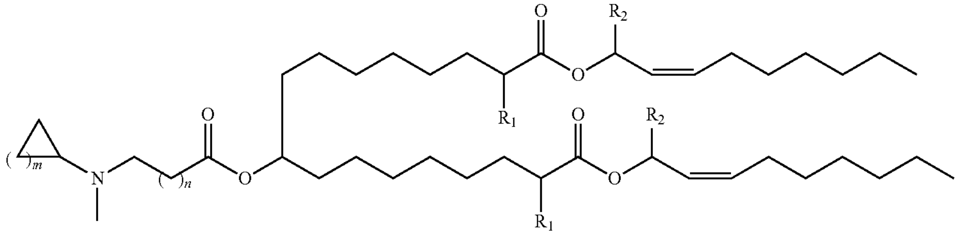
m = 1-6; n = 0-3
$R_1 = R_2$ = Me, Et, iPr etc.
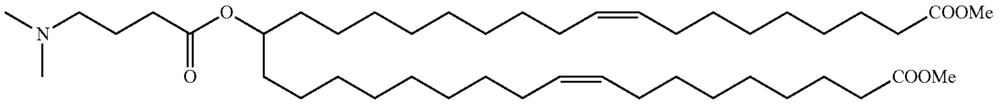 [SMILES: COC(=O)CCCCCCC/C=C\CCCCCCCCC(CCCCCCCC/C=C\CCCCCCCC(=O)OC)OC(=O)CCCN(C)C]
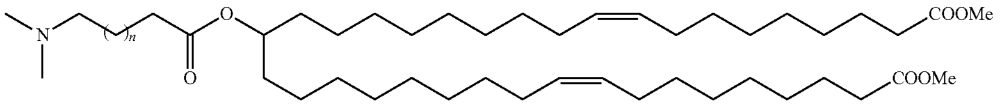
n = 0-2
(n = 1; ALNY-322
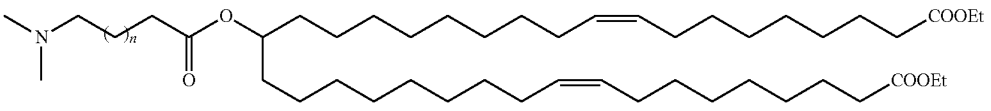
n = 0-2
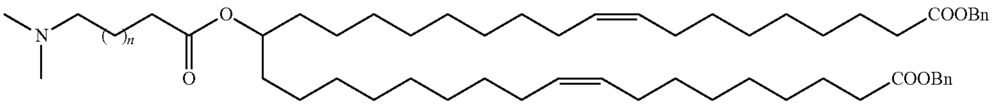
n = 0-2

TABLE 4-continued
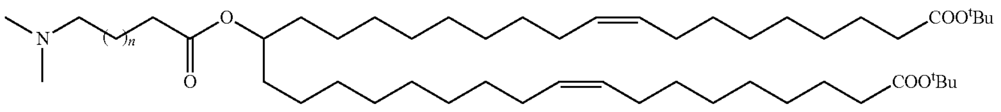
n = 0-2
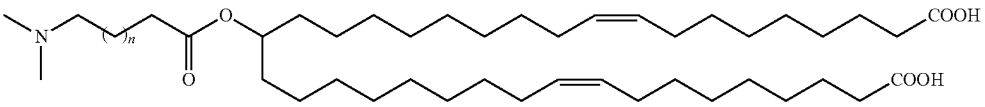
n = 0-2
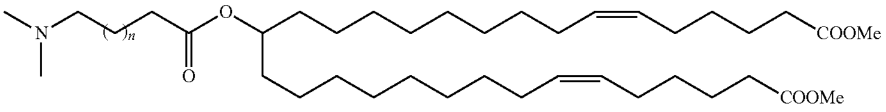
n = 0-2
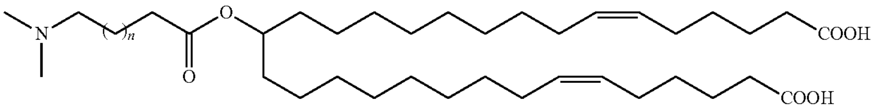
n = 0-2
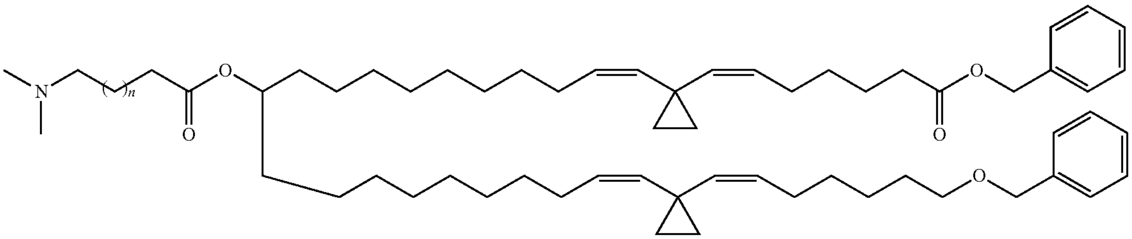
n = 0-2
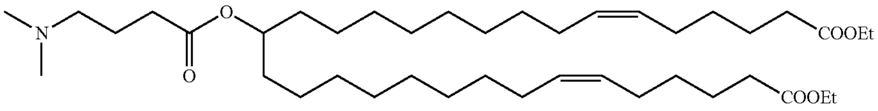 [SMILES: CCOC(=O)CCCC/C=C\CCCCCCCCC(CCCCCCCC/C=C\CCCCC(=O)OCC)OC(=O)CCCN(C)C]
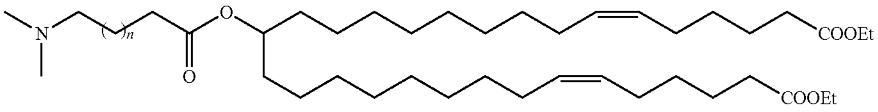
n = 0-2
(n = 1; ALNY-320
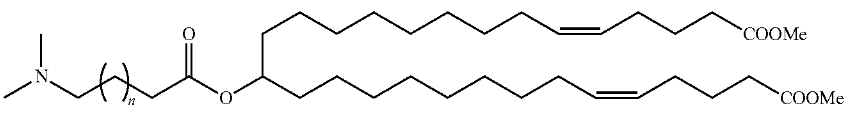
n = 0-2

TABLE 4-continued
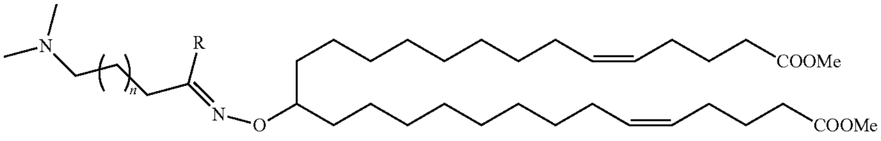
n = 0-2
R = H, Me
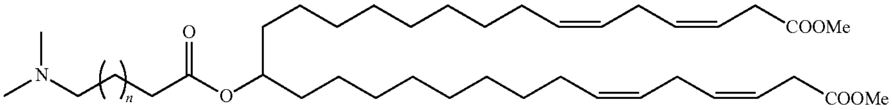
n = 0-2
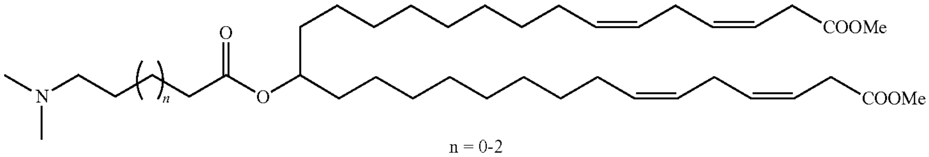
n = 0-2
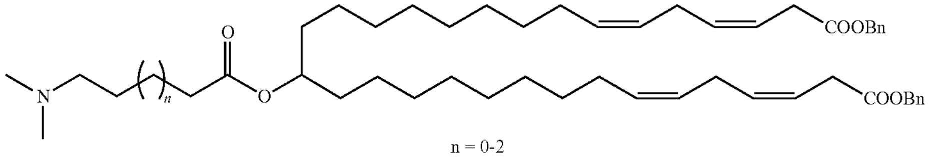
n = 0-2
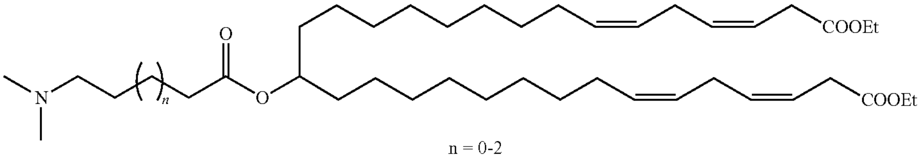
n = 0-2
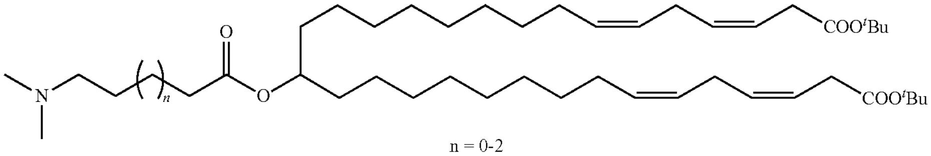
n = 0-2
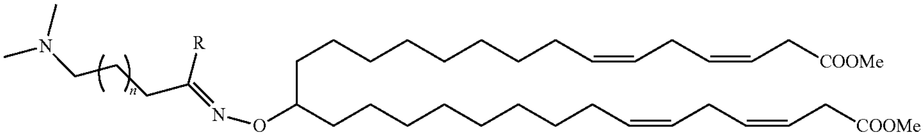
n = 0-2
R = H, Me
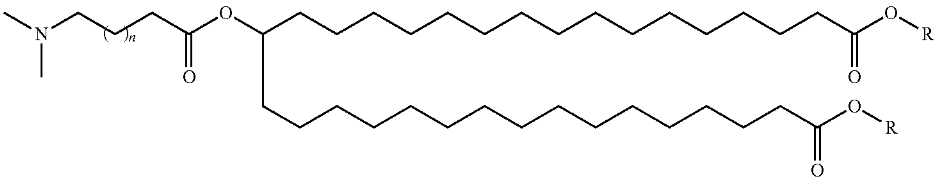
R = Me, Et, Pr, Bn, t-Bu, Ph, alkyl, aryl
n = 0-2

TABLE 4-continued
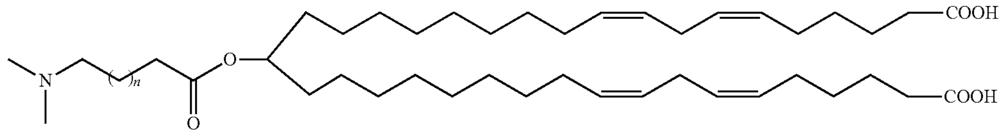
n = 0-2
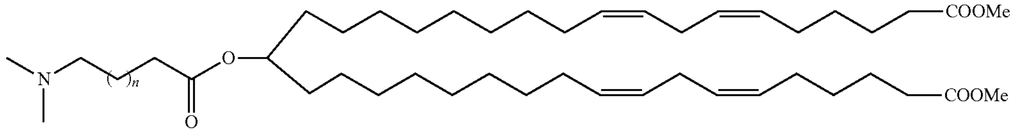
n = 0-2
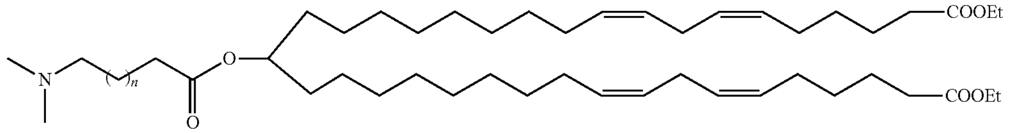
n = 0-2
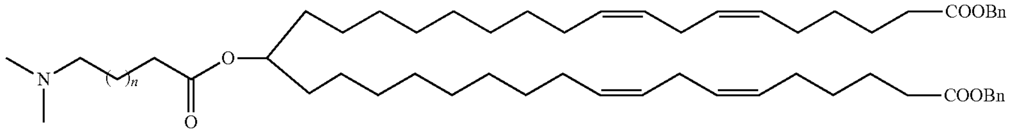
n = 0-2
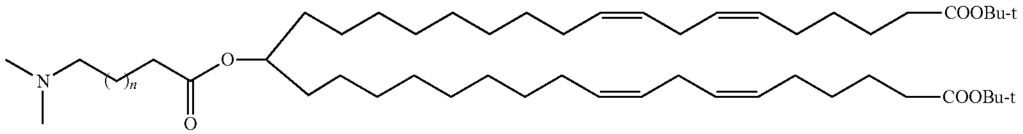
n = 0-2
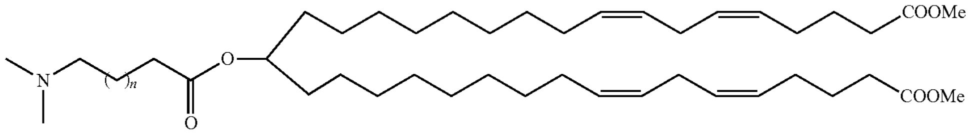
n = 0-2
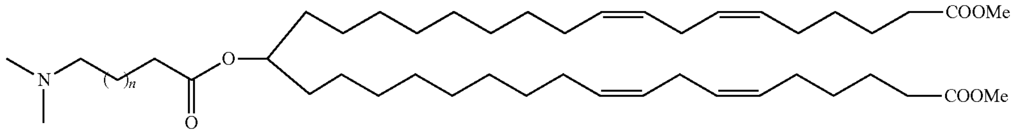
n = 0-2
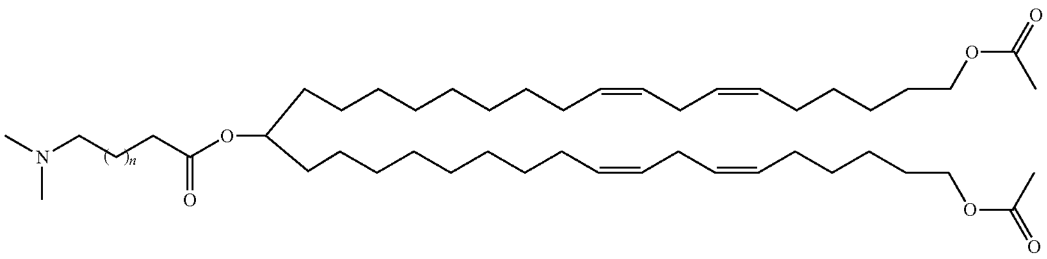
n = 0-2

TABLE 4-continued
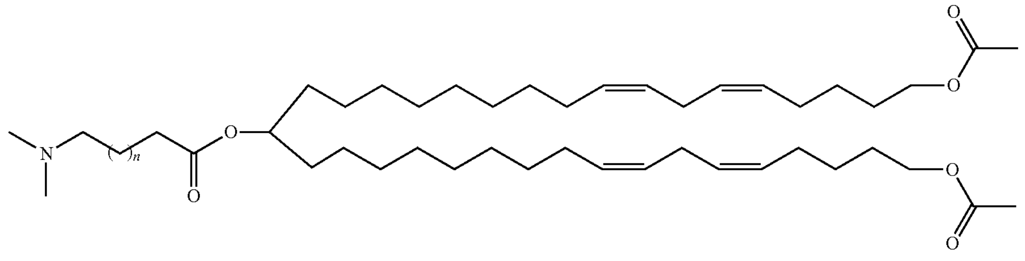
n = 0-2
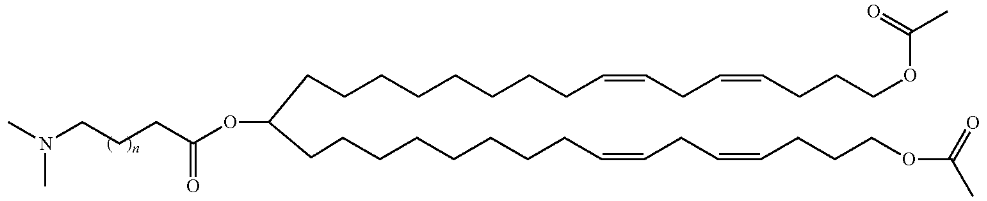
n = 0-2
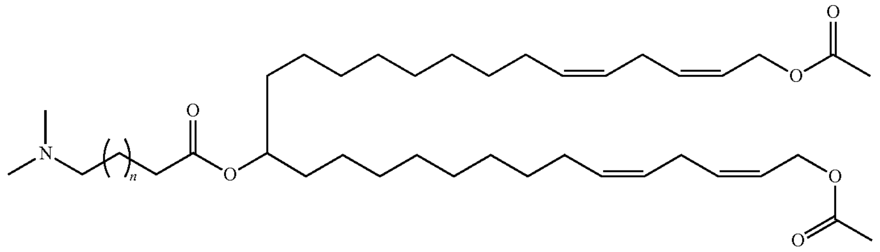
n = 0-2
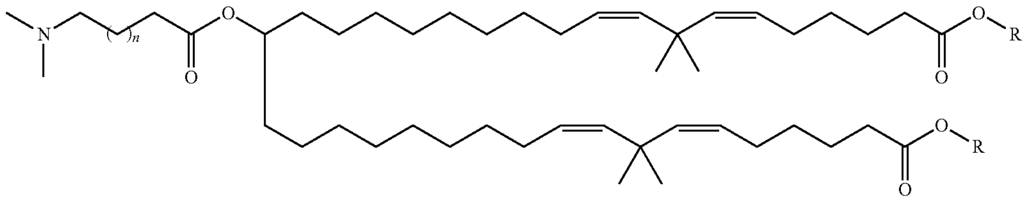
R = Me, Et, Pr, Bn, t-Bu, Ph, alkyl, aryl
n = 0-2
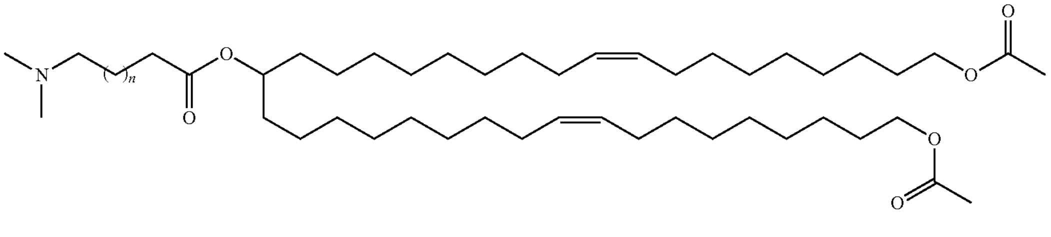
n = 0-2

TABLE 4-continued
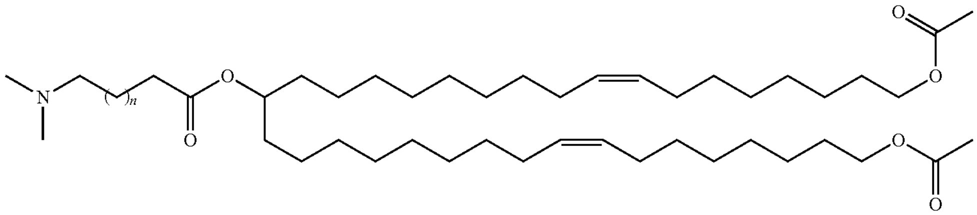
n = 0-2
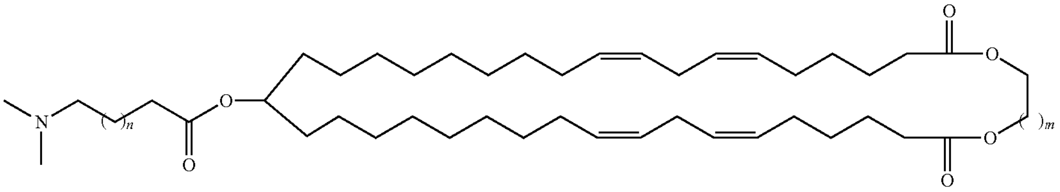
n = 0-2
m = 1-12
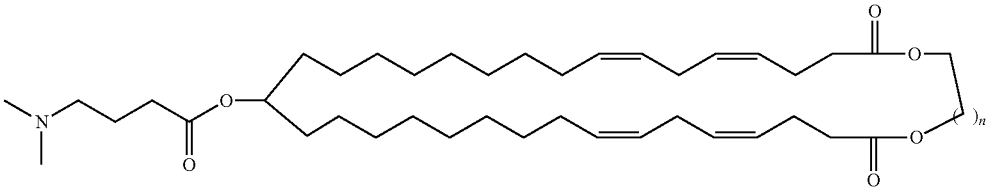
n = 1-12
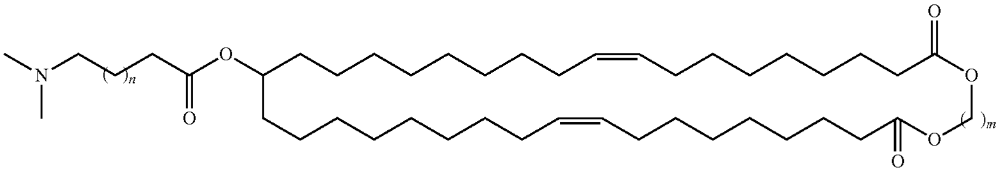
n = 0-2
m = 2-12
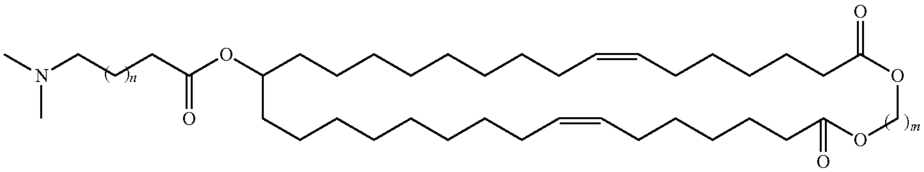
n = 0-2
m = 2-12
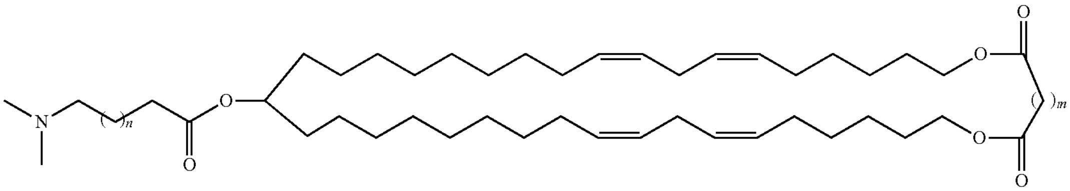
n = 0-2
m = 1-12

TABLE 4-continued
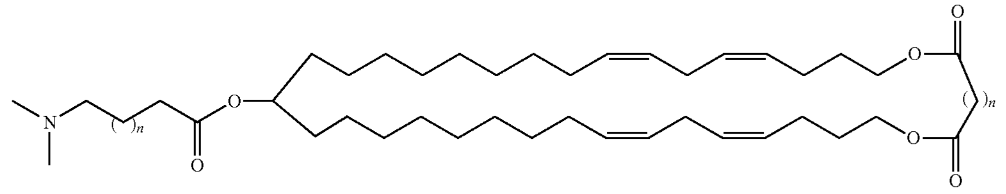
n = 0-2
m = 1-12
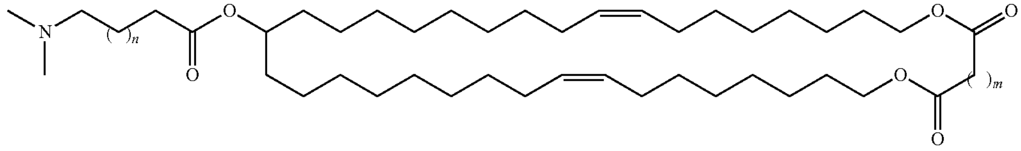
n = 0-2
m = 1-12
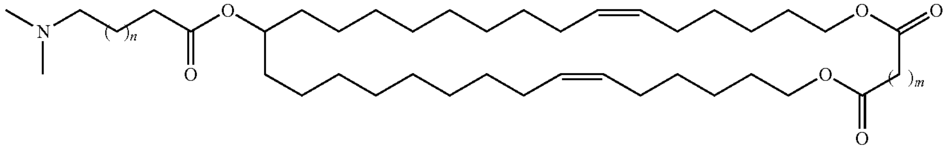
n = 0-2
m = 1-12
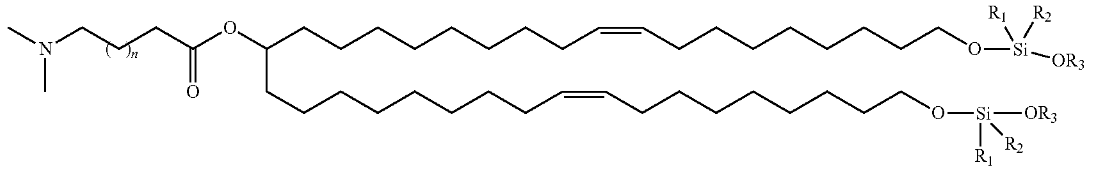
$R_1 = R_2 = R_3$ = Me, Et, iPr
n = 0-2
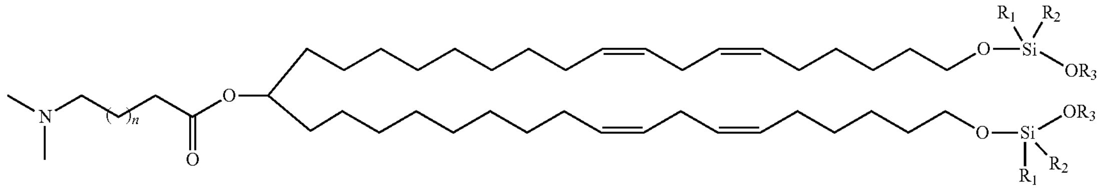
n = 0-2
$R_1 = R_2 = R_3$ = Me, Et, iPr
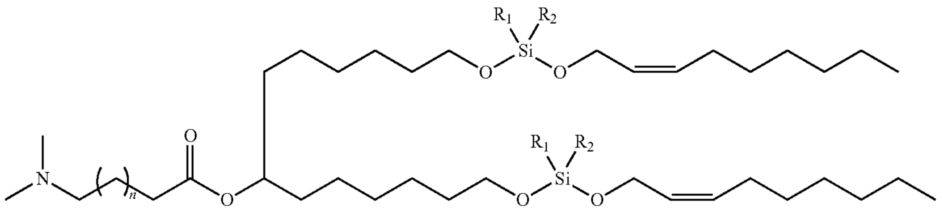
$R_1 = R_2$ = Me, Et, iPr
n = 0-2

TABLE 4-continued
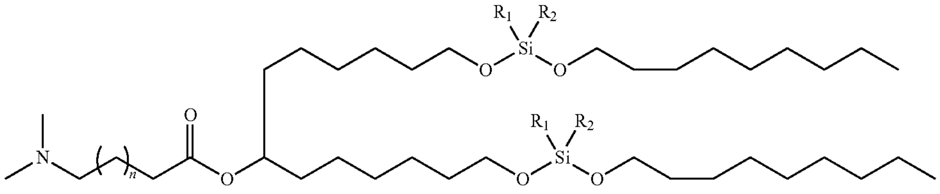
$R_1 = R_2$ = Me, Et, iPr
n = 0-2
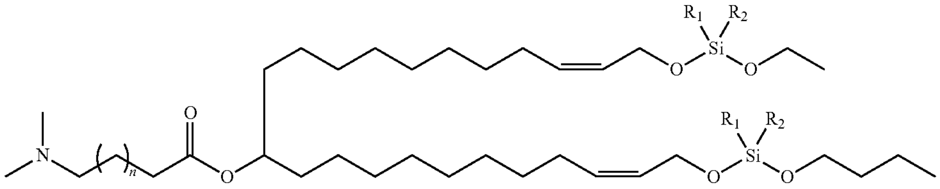
$R_1 = R_2$ = Me, Et, iPr
n = 0-2
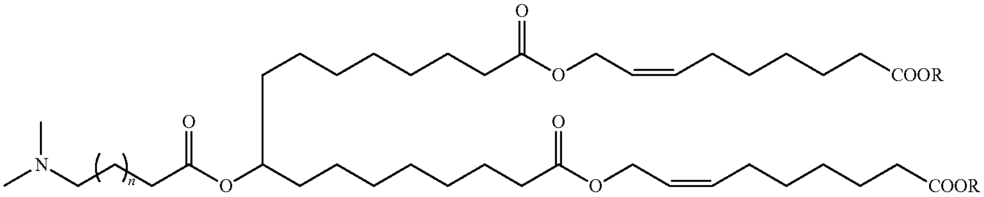
R = Me, Et, Pr, iPr, t-Bu, Bn, Ph, alkyl, aryl
n = 0-2
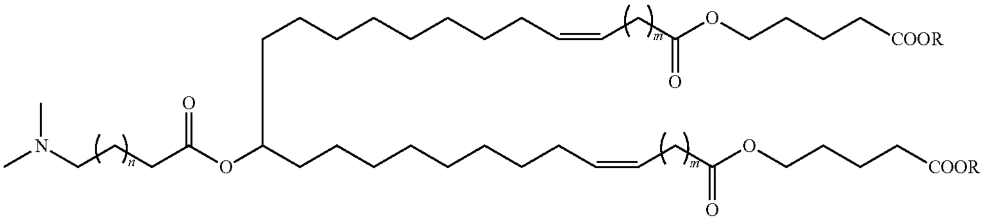
R = Me, Et, Pr, iPr, t-Bu, Bn, Ph, alkyl, aryl
m = 0-2
n = 0-2
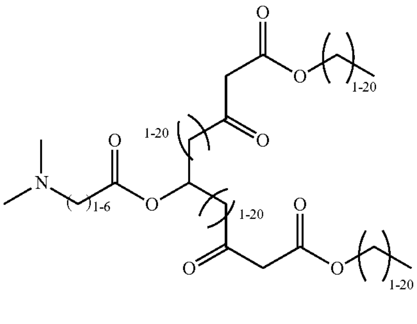

TABLE 4-continued
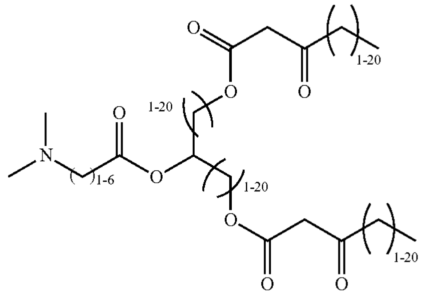
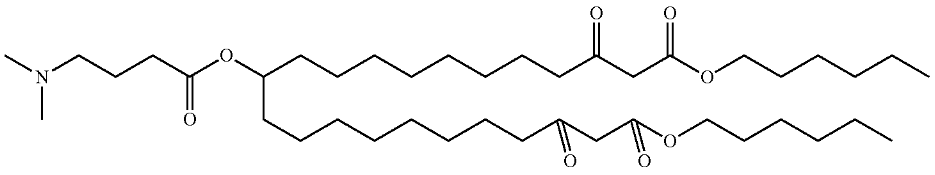 [SMILES: CCCCCCOC(=O)CC(=O)CCCCCCCCC(CCCCCCCCC(=O)CC(=O)OCCCCCC)OC(=O)CCCN(C)C]
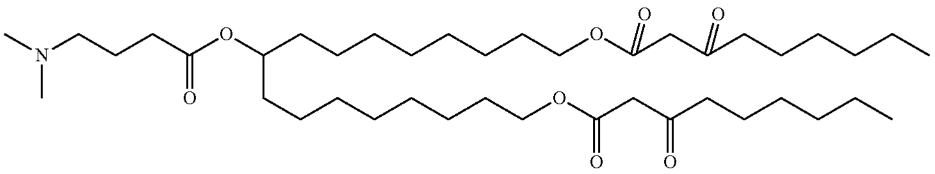 [SMILES: CCCCCCC(=O)CC(=O)OCCCCCCCCC(CCCCCCCCOC(=O)CC(=O)CCCCCC)OC(=O)CCCN(C)C]
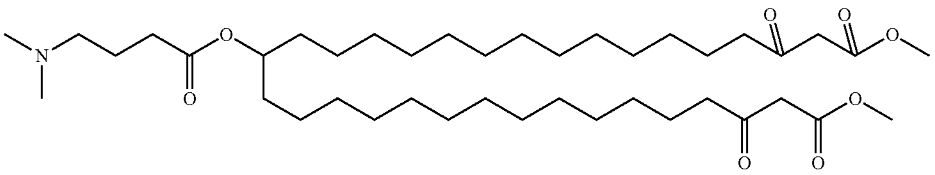
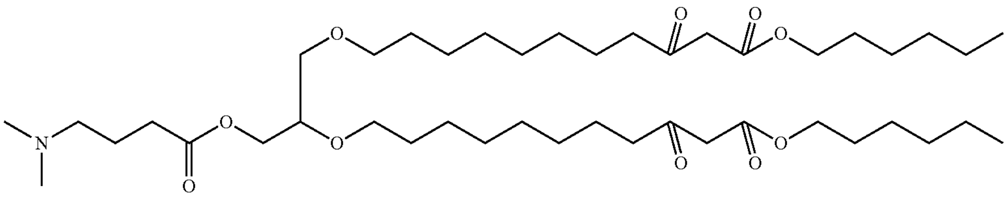 [SMILES: CCCCCCOC(=O)CC(=O)CCCCCCCCOCC(COC(=O)CCCN(C)C)OCCCCCCCCC(=O)CC(=O)OCCCCCC]
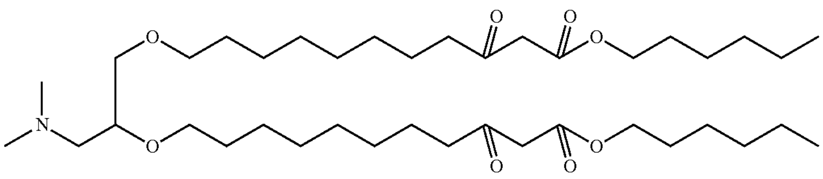 [SMILES: CCCCCCOC(=O)CC(=O)CCCCCCCCOCC(CN(C)C)OCCCCCCCCC(=O)CC(=O)OCCCCCC]
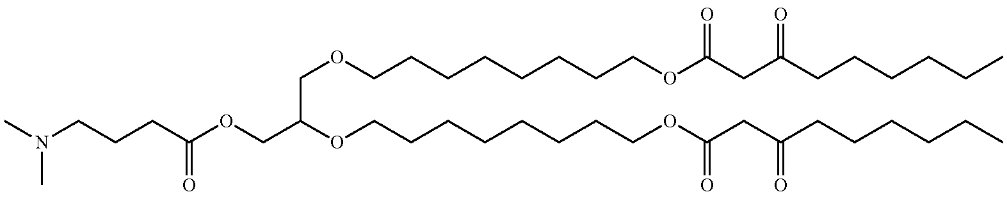 [SMILES: CCCCCCC(=O)CC(=O)OCCCCCCCCOCC(COC(=O)CCCN(C)C)OCCCCCCCCOC(=O)CC(=O)CCCCCC]

TABLE 4-continued
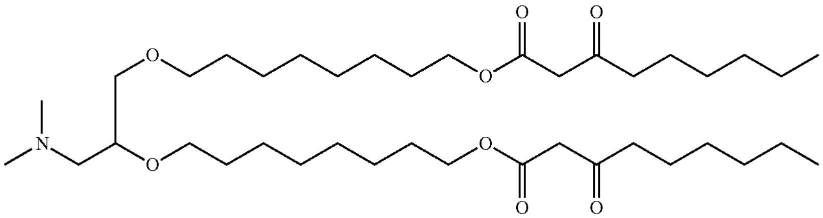 [SMILES: CCCCCCC(=O)CC(=O)OCCCCCCCCOCC(CN(C)C)OCCCCCCCCOC(=O)CC(=O)CCCCCC]
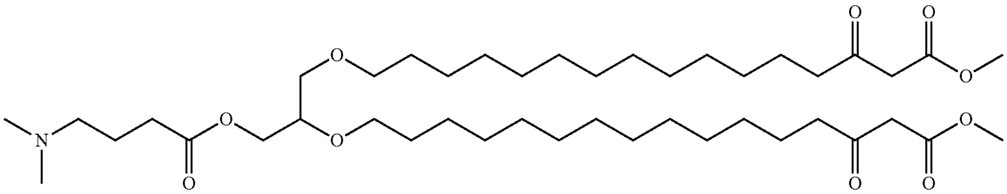
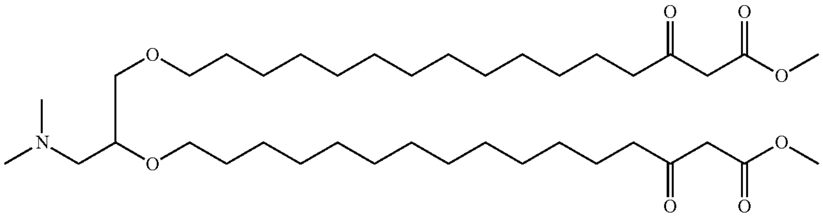
In one embodiment, the cationic lipid of the present invention is selected from the following compounds, and salts thereof (including pharmaceutically acceptable salts thereof):
Compound 1
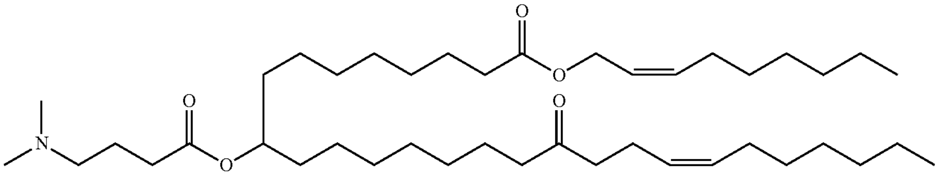
,
Compound 2
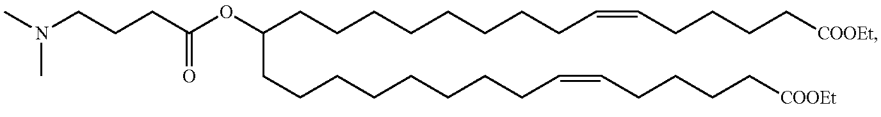
and
Compound 3
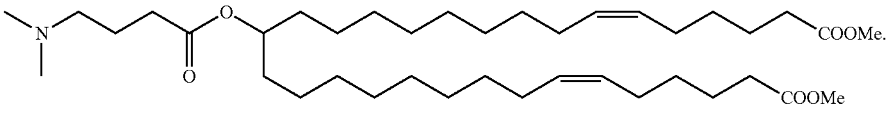

In one embodiment, the cationic lipid is a compound of formula (I), which has a branched alkyl at the alpha position adjacent to the biodegradable group (between the biodegradable group and the tertiary carbon):

Formula (I)

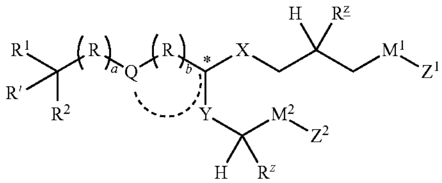

or a salt thereof (e.g., a pharmaceutically acceptable salt thereof), wherein

R' is absent, hydrogen, or alkyl (e.g., $C_1$-$C_4$ alkyl);

with respect to $R^1$ and $R^2$, (i) $R^1$ and $R^2$ are each, independently, optionally substituted alkyl, alkenyl, alkynyl, cycloalkylalkyl, heterocycle, or $R^{10}$;

(ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the $(R)_a$ group adjacent to the nitrogen atom;

each occurrence of R is, independently, $—(CR^3R^4)—$;

each occurrence of $R^3$ and $R^4$ are, independently H, halogen, OH, alkyl, alkoxy, $—NH_2$, $R^{10}$, alkylamino, or dialkylamino (in one preferred embodiment, each occurrence of $R^3$ and $R^4$ are, independently H or $C_1$-$C_4$ alkyl);

each occurrence of $R^{10}$ is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups (preferably at most one $R^{10}$ group);

the dashed line to Q is absent or a bond;

when the dashed line to Q is absent then Q is absent or is —O—, —NH—, —S—, —C(O)—, —C(O)O, —OC(O)—, $—C(O)N(R^4)—$, $—N(R^5)C(O)—$, —S—S—, —OC(O)O—, $—O—N{=}C(R^5)—$, $—C(R^5){=}N—O—$, $—OC(O)N(R^5)—$, $—N(R^5)C(O)N(R^5)—$, $—N(R^5)C(O)O—$, —C(O)S—, —C(S)O— or $—C(R^5){=}N—O—C(O)—$; or when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

each occurrence of $R^5$ is, independently, H or alkyl (e.g. $C_1$-$C_4$ alkyl);

X and Y are each, independently, alkylene or alkenylene (e.g., $C_4$ to $C_{20}$ alkylene or $C_4$ to $C_{20}$ alkenylene);

$M^1$ and $M^2$ are each, independently, a biodegradable group (e.g., —OC(O)—, —C(O)O—, —SC(O)—, —C(O)S—, —OC(S)—, —C(S)O—, —S—S—, $—C(R^5){=}N—$, $—N{=}C(R^5)—$, $—C(R^5){=}N—O—$, $—O—N{=}C(R^5)—$, $—C(O)(NR^5)—$, $—N(R^5)C(O)—$, $—C(S)(NR^5)—$, $—N(R^5)C(O)—$, $—N(R^5)C(O)N(R^5)—$, —OC(O)O—, $—OSi(R^5)_2O—$, $—C(O)(CR^3R^4)C(O)O—$, $—OC(O)(CR^3R^4)C(O)—$, or

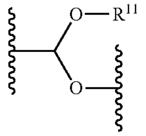

(wherein $R^{11}$ is a $C_2$-$C_8$ alkyl or alkenyl));

each occurrence of $R^z$ is, independently, $C_1$-$C_8$ alkyl (e.g., methyl, ethyl, isopropyl, n-butyl, n-pentyl, or n-hexyl);

a is 1, 2, 3, 4, 5 or 6;

b is 0, 1, 2, or 3; and $Z^1$ and $Z^2$ are each, independently, $C_8$-$C_{14}$ alkyl or $C_8$-$C_{14}$ alkenyl, wherein the alkenyl group may optionally be substituted with one or two fluorine atoms at the alpha position to a double bond which is between the double bond and the terminus of $Z^1$ or $Z^2$ (e.g., (e.g., 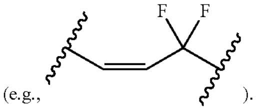 ).

The $R'R^1R^2N—(R)_a$-Q-$(R)_b—$ group can be any of the head groups described herein, including those shown in Table 1 below, and salts thereof. In one preferred embodiment, $R'R^1R^2N—(R)_a$-Q-$(R)_b—$ is $(CH_3)_2N—(CH_2)_3—C(O)O—$, $(CH_3)_2N—(CH_2)_2—NH—C(O)O—$, $(CH_3)_2N—(CH_2)_2—OC(O)—NH—$, or $(CH_3)_2N—(CH_2)_3—C(CH_3){=}N—O—$.

In one embodiment, $R^1$ and $R^2$ are both alkyl (e.g., methyl).

In a further embodiment, a is 3. In another embodiment, b is 0.

In a further embodiment, a is 3, b is 0 and R is $—CH_2—$. In yet a further embodiment, a is 3, b is 0, R is $—CH_2—$ and Q is —C(O)O—. In another embodiment, $R^1$ and $R^2$ are methyl, a is 3, b is 0, R is $—CH_2—$ and Q is —C(O)O—.

In another embodiment, X and Y are each, independently $—(CH_2)_n—$ wherein n is 4 to 20, e.g., 4 to 18, 4 to 16, or 4 to 12. In one embodiment, n is 4, 5, 6, 7, 8, 9, or 10. In one exemplary embodiment, X and Y are $—(CH_2)_6—$. In another embodiment, X and Y are $—(CH_2)_7—$. In yet another embodiment, X and Y are $—(CH_2)_9—$. In yet another embodiment, X and Y are $—(CH_2)_8—$.

In further embodiments, $M^1$ and $M^2$ are each, independently, —OC(O)— or —C(O)O—. For example, in one embodiment, $M^1$ and $M^2$ are each —C(O)O—.

In another embodiment, the cationic lipid is a compound of formula (II), which has a branched alkyl at the alpha position adjacent to the biodegradable group (between the biodegradable group and the terminus of the tail, i.e., $Z^1$ o $Z^2$):

Formula (II)

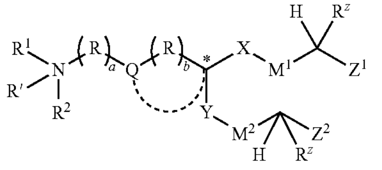

or a salt thereof (e.g., a pharmaceutically acceptable salt thereof), wherein

R' is absent, hydrogen, or alkyl (e.g., $C_1$-$C_4$ alkyl);

with respect to $R^1$ and $R^2$, (i) $R^1$ and $R^2$ are each, independently, optionally substituted alkyl, alkenyl, alkynyl, cycloalkylalkyl, heterocycle, or $R^{10}$;

(ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the $(R)_a$ group adjacent to the nitrogen atom;

each occurrence of R is, independently, —$(CR^3R^4)$—;

each occurrence of $R^3$ and $R^4$ are, independently H, halogen, OH, alkyl, alkoxy, —$NH_2$, $R^{10}$, alkylamino, or dialkylamino (in one preferred embodiment, each occurrence of $R^3$ and $R^4$ are, independently H or $C_1$-$C_4$ alkyl);

each occurrence of $R^{10}$ is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups (preferably at most one $R^{10}$ group);

the dashed line to Q is absent or a bond;

when the dashed line to Q is absent then Q is absent or is —O—, —NH—, —S—, —C(O)—, —C(O)O—, —OC(O)—, —C(O)N($R^4$)—, —N($R^5$)C(O)—, —S—S—, —OC(O)O—, —O—N═C($R^5$)—, —C($R^5$)═N—O—, —OC(O)N($R^5$)—, —N($R^5$)C(O)N($R^5$)—, —N($R^5$)C(O)O—, —C(O)S—, —C(S)O— or —C($R^5$)═N—O—C(O)—; or when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

each occurrence of $R^5$ is, independently, H or alkyl;

X and Y are each, independently, alkylene (e.g., $C_6$-$C_8$ alkylene) or alkenylene, wherein the alkylene or alkenylene group is optionally substituted with one or two fluorine atoms at the alpha position to the $M^1$ or $M^2$ group (e.g., 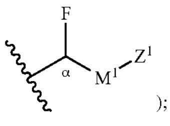 );

$M^1$ and $M^2$ are each, independently, a biodegradable group (e.g., —OC(O)—, —C(O)O—, —SC(O)—, —C(O)S—, —OC(S)—, —C(S)O—, —S—S—, —C(R)═N—, —N═C($R^5$)—, —C($R^5$)═N—O—, —O—N═C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

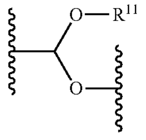

(wherein $R^{11}$ is a $C_2$-$C_8$ alkyl or alkenyl));

each occurrence of $R^z$ is, independently, $C_1$-$C_8$ alkyl (e.g., methyl, ethyl, isopropyl);

a is 1, 2, 3, 4, 5 or 6;

b is 0, 1, 2, or 3; and $Z^1$ and $Z^2$ are each, independently, $C_8$-$C_{14}$ alkyl or $C_8$-$C_{14}$ alkenyl, wherein (i) the alkenyl group may optionally be substituted with one or two fluorine atoms at the alpha position to a double bond which is between the double bond and the terminus of $Z^1$ or $Z^2$ (e.g., 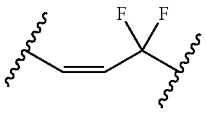 )

and (ii) the terminus of at least one of $Z^1$ and $Z^2$ is separated from the group $M^1$ or $M^2$ by at least 8 carbon atoms.

In another embodiment, X and Y are each, independently —$(CH_2)_n$— wherein n is 4 to 20, e.g., 4 to 18, 4 to 16, or 4 to 12. In one embodiment, n is 4, 5, 6, 7, 8, 9, or 10. In one exemplary embodiment, X and Y are —$(CH_2)_6$—. In another embodiment, X and Y are —$(CH_2)_7$—. In yet another embodiment, X and Y are —$(CH_2)_9$—. In yet another embodiment, X and Y are —$(CH_2)_8$—.

The R'$R^1R^2$N—$(R)_a$-Q-$(R)_b$— group can be any of the head groups described herein, including those shown in Table 1 below, and salts thereof. In one preferred embodiment, R'$R^1R^2$N—$(R)_a$-Q-$(R)_b$— is $(CH_3)_2$N—$(CH_2)_3$—C(O)O—, $(CH_3)_2$N—$(CH_2)_2$—NH—C(O)O—, $(CH_3)_2$N—$(CH_2)_2$—OC(O)—NH—, or $(CH_3)_2$N—$(CH_2)_3$—C($CH_3$)═N—O—.

In another embodiment, the cationic lipid is a compound of formula (III), which has a branching point at a position that is 2-6 carbon atoms (i.e., at the beta (β), gamma (γ), delta (8), epsilon (ϵ) or zeta position (ζ)) adjacent to the biodegradable group (between the biodegradable group and the terminus of the tail, i.e., $Z^1$ or $Z^2$):

Formula (III)

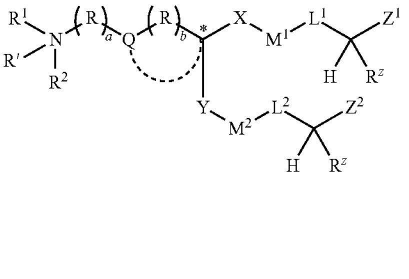

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, $R^z$, a, and b are defined as in formula (I);

$L^1$ and $L^2$ are each, independently, $C_1$-$C_5$ alkylene or $C_2$-$C_5$ alkenylene;

X and Y are each, independently, alkylene (e.g., $C_4$ to $C_{20}$ alkylene or $C_6$-$C_8$ alkylene) or alkenylene (e.g., $C_4$ to $C_{20}$ alkenylene); and $Z^1$ and $Z^2$ are each, independently, $C_8$-$C_{14}$ alkyl or $C_8$-$C_{14}$ alkenyl, wherein the alkenyl group may optionally be substituted with one or two fluorine atoms at the alpha position to a double bond which is between the double bond and the terminus of $Z^1$ or $Z^2$ (e.g.,

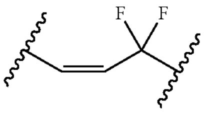

), and with the proviso that the terminus of at least one of $Z^1$ and $Z^2$ is separated from the group $M^1$ or $M^2$ by at least 8 carbon atoms.

In one embodiment, $L^1$ and $L^2$ are each $—CH_2—$. In another embodiment, $L^1$ and $L^2$ are each $—(CH_2)_2—$. In one embodiment, $L^1$ and $L^2$ are each $—(CH_2)_3—$. In yet another embodiment, $L^1$ and $L^2$ are each $—(CH_2)_4—$. In yet another embodiment, $L^1$ and $L^2$ are each $—(CH_2)_5—$. In yet another embodiment, $L^1$ and $L^2$ are each $—CH_2—CH{=}CH—$. In a preferred embodiment, $L^1$ and $L^2$ are each $—CH_2—$ or $—(CH_2)_2$.

In one embodiment, X and Y are each, independently $—(CH_2)_n$ wherein n is 4 to 20, e.g., 4 to 18, 4 to 16, or 4 to 12. In one embodiment, n is 4, 5, 6, 7, 8, 9, or 10. In one exemplary embodiment, X and Y are $—(CH_2)_7—$. In another exemplary embodiment, X and Y are $—(CH_2)_8—$. In yet another exemplary embodiment, X and Y are $—(CH_2)_9—$.

The $R'R^1R^2N—(R)_a$-Q-$(R)_b—$ group can be any of the head groups described herein, including those shown in Table 1 below, and salts thereof. In one preferred embodiment, $R'R^1R^2N—(R)_a$-Q-$(R)_b—$ is $(CH_3)_2N—(CH_2)_3—C(O)O—$, $(CH_3)_2N—(CH_2)_2—NH—C(O)O—$, $(CH_3)_2N—(CH_2)_2—OC(O)—NH—$, or $(CH_3)_2N—(CH_2)_3—C(CH_3){=}N—O—$.

In another embodiment, the cationic lipid is a compound of formula (IIIA), which has a branching point at a position that is 2-6 carbon atoms (i.e., at the beta (β), gamma (γ), delta (δ), epsilon (ϵ) or zeta position (ζ)) from the biodegradable groups $M^1$ and $M^2$ (i.e., between the biodegradable group and the terminus of the tail, i.e., $Z^1$ or $Z^2$):

Formula (IIIA)

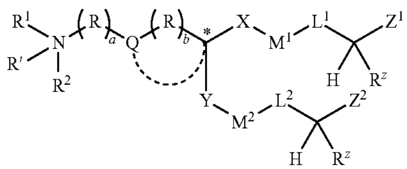

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, a, and b are defined as in formula (I);

each $R^z$ is, independently, $C_1$-$C_8$ alkyl (e.g., $C_3$-$C_6$ alkyl or $C_2$-$C_3$ alkyl);

$L^1$ and $L^2$ are each, independently, $C_1$-$C_5$ alkylene (e.g., $C_2$-$C_3$ alkylene) or $C_2$-$C_5$ alkenylene;

X and Y are each, independently, alkylene (e.g., $C_4$ to $C_{20}$ alkylene or $C_7$-$C_9$ alkylene) or alkenylene (e.g., $C_4$ to $C_{20}$ alkenylene or $C_7$-$C_9$ alkenylene); and $Z^1$ and $Z^2$ are each, independently, $C_1$-$C_8$ alkyl (e.g., $C_1$-$C_6$ alkyl, such as $C_1$, $C_3$ or $C_5$ alkyl) or $C_2$-$C_8$ alkenyl (such as $C_2$-$C_6$ alkenyl);

wherein said cationic lipid is not one selected from:

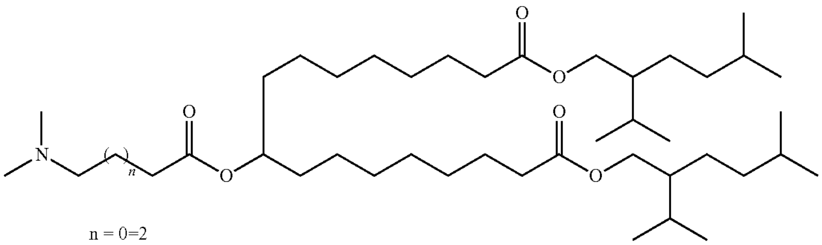

n = 0=2

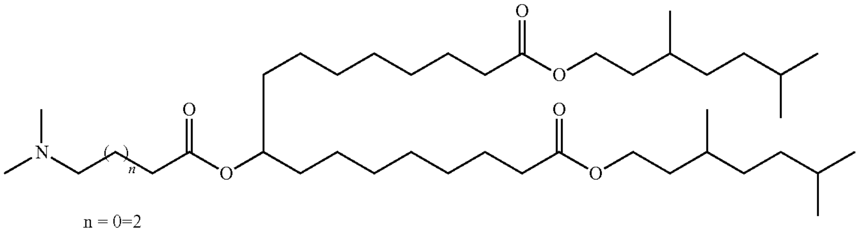

n = 0=2

-continued

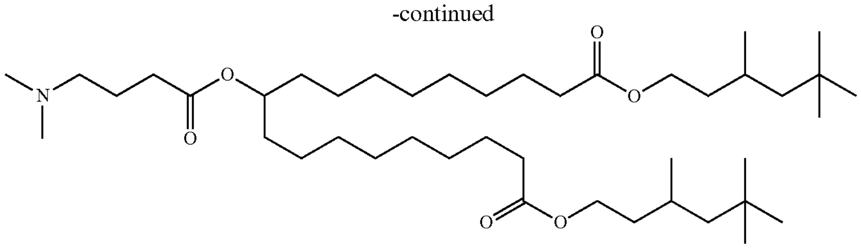

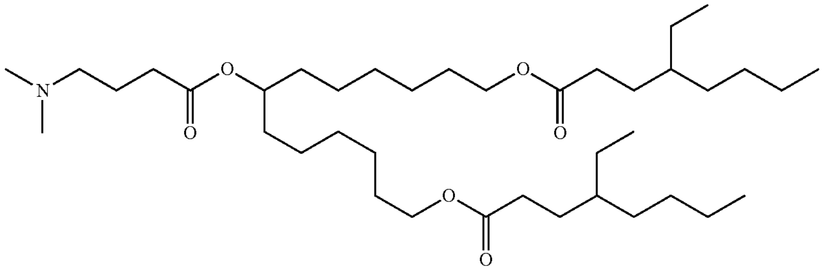

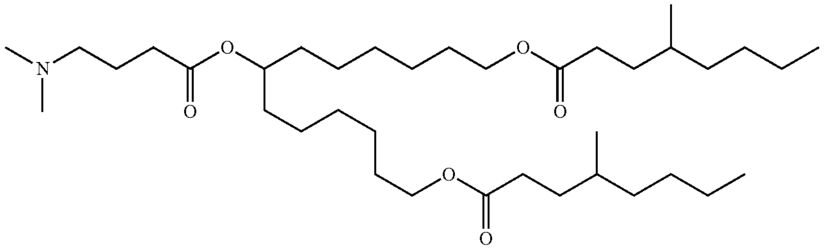

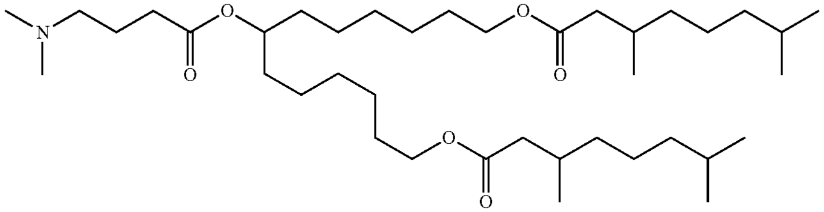

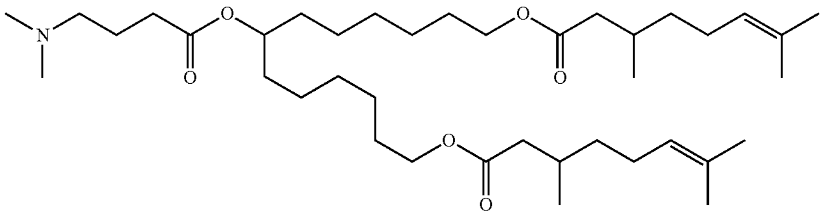

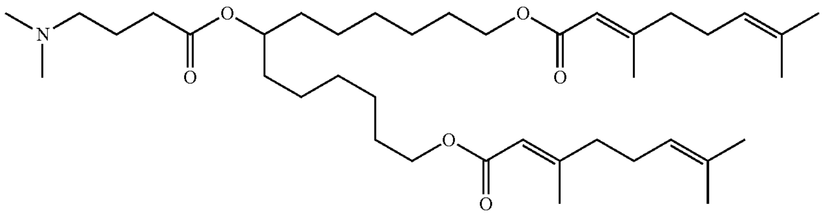

In one embodiment, $L^1$ and $L^2$ are each —$(CH_2)_2$—. In another embodiment, $L^1$ and $L^2$ are each —$(CH_2)_3$—.

In one embodiment, X and Y are each, independently —$(CH_2)_n$ wherein n is 4 to 20, e.g., 4 to 18, 4 to 16, 4 to 12 or 7-9. In one embodiment, n is 4, 5, 6, 7, 8, 9, or 10. In one exemplary embodiment, X and Y are —$(CH_2)_7$—. In yet another exemplary embodiment, X and Y are —$(CH_2)_9$.

In one preferred embodiment, $M^1$ and $M^2$ are —C(O)O— (where the carbonyl group in $M^1$ and $M^2$ is bound to the variable X, and the oxygen atom in $M^1$ and $M^2$ is bound to the variable $L^1$ and $L^2$).

The $R'R^1R^2N$—$(R)_a$-Q-$(R)_b$— group can be any of the head groups described herein, including those shown in Table 1 below, and salts thereof. In one preferred embodiment, $R'R^1R^2N$—$(R)_a$-Q-$(R)_b$— is $(CH_3)_2N$—$(CH_2)_3$—C(O)O—, $(CH_3)_2N$—$(CH_2)_2$—NH—C(O)O—, $(CH_3)_2N$—$(CH_2)_2$—OC(O)—NH—, or $(CH_3)_2N$—$(CH_2)_3$—$C(CH_3)$=N—O—.

In one preferred embodiment, $Z^1$ and $Z^2$ are branched alkyl or branched alkenyl groups.

In one embodiment of formula (IIIA), $Z^1$, $Z^2$, and each $R^z$ are $C_3$-$C_8$ alkyl (such as a $C_3$-$C_6$ alkyl). In another embodiment of formula (IIIA), $Z^1$, $Z^2$, and each $R^z$ are $C_3$-$C_8$ branched alkyl (such as a $C_3$-$C_6$ branched alkyl). In yet another embodiment of formula (IIIA), $Z^1$, $Z^2$, and each $R^z$ are $C_3$-$C_8$ straight alkyl (such as a $C_3$-$C_6$ straight alkyl).

In one embodiment of formula (IIIA), the branching point is at the second position (the (β-position) from the biodegradable groups $M^1$ and $M^2$ in each tail. $Z^1$, $Z^2$, and each $R^z$ can be $C_3$-$C_8$ alkyl (e.g., a $C_3$-$C_6$ alkyl), such as a $C_3$-$C_8$ branched alkyl (e.g., a $C_3$-$C_6$ branched alkyl) or a $C_3$-$C_8$ straight alkyl (e.g., a $C_3$-$C_6$ straight alkyl). In one preferred embodiment, $M^1$ and $M^2$ are —C(O)O— (where the carbonyl group in $M^1$ and $M^2$ is bound to the variable X, and the oxygen atom in $M^1$ and $M^2$ is bound to the variable $L^1$ and/or $L^2$).

In one embodiment of formula (IIIA), the branching point is at the third position (the γ-position) from the biodegradable groups $M^1$ and $M^2$ in each tail. $Z^1$, $Z^2$, and each $R^z$ can be $C_3$-$C_8$ alkyl (e.g., a $C_3$-$C_6$ alkyl), such as a $C_3$-$C_8$ branched alkyl (e.g., a $C_3$-$C_6$ branched alkyl) or a $C_3$-$C_8$ straight alkyl (e.g., a $C_3$-$C_6$ straight alkyl). In one preferred embodiment, $M^1$ and $M^2$ are —C(O)O— (where the carbonyl group in $M^1$ and $M^2$ is bound to the variable X, and the oxygen atom in $M^1$ and $M^2$ is bound to the variable $L^1$ and/or $L^2$).

In one embodiment of formula (IIIA), the branching point is at the third position (the γ-position) from the biodegradable groups $M^1$ and $M^2$ in each tail.

In another embodiment of formula (IIIA), $M^1$ and/or $M^2$ are not —O(C(O)— (where the oxygen atom in $M^1$ and/or $M^2$ is bound to the variable X, and the carbonyl in $M^1$ and/or $M^2$ is bound to the variable $L^1$ and/or $L^2$). In yet another embodiment of formula (IIIA), $Z^1$, $Z^2$, and $R^z$ are not $C_3$-$C_{10}$ cycloalkyl($C_1$-$C_6$ alkyl).

In another embodiment, the cationic lipid is a compound of formula (IV), which has a branching point at a position that is 2-6 carbon atoms (i.e., at beta (β), gamma (γ), delta (δ), epsilon (ε) or zeta position (ζ)) adjacent to the biodegradable group (between the biodegradable group and the terminus of the tail, i.e., $Z^1$ or $Z^2$):

Formula (IV)

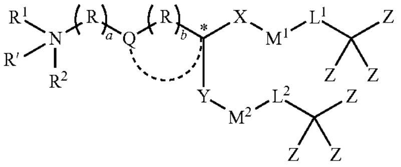

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, $R^z$, a, and b are defined as in formula (I);

$L^1$ and $L^2$ and are each, independently, $C_1$-$C_5$ alkylene or $C_2$-$C_5$ alkenylene;

X and Y are each, independently, alkylene or alkenylene (e.g., $C_{12}$-$C_{20}$ alkylene or $C_{12}$-$C_{20}$ alkenylene); and each occurrence of Z is independently $C_1$-$C_4$ alkyl (preferably, methyl).

For example, in one embodiment, $-L^1-C(Z)_3$ is $—CH_2C(CH_3)_3$. In another embodiment, $-L^1-C(Z)_3$ is $—CH_2CH_2C(CH_3)_3$.

In one embodiment, the total carbon atom content of each tail (e.g., $—X-M^1-L^1-C(Z)_3$ or $—Y-M^2-L^2-C(Z)_3$) is from about 17 to about 26. For example, the total carbon atom content can be from about 19 to about 26 or from about 21 to about 26.

In another embodiment, X and Y are each, independently $—(CH_2)_n—$ wherein n is 4 to 20, e.g., 4 to 18, 4 to 16, or 4 to 12. In one embodiment, n is 4, 5, 6, 7, 8, 9, or 10. In one exemplary embodiment, X and Y are $—(CH_2)_6—$. In another embodiment, X and Y are $—(CH_2)_7—$. In yet another embodiment, X and Y are $—(CH_2)_9—$. In yet another embodiment, X and Y are $—(CH_2)_8—$.

In one embodiment, the cationic lipid is a compound of formula (V), which has an alkoxy or thioalkoxy (i.e., —S-alkyl) group substitution on at least one tail:

Formula (V)

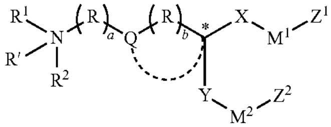

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, a, and b are defined as in formula (I);

X and Y are each, independently, alkylene (e.g., $C_6$-$C_8$ alkylene) or alkenylene, wherein the alkylene or alkenylene group is optionally substituted with one or two fluorine atoms at the alpha position to the $M^1$ or $M^2$ group (e.g., 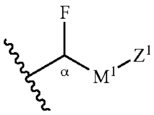);

$Z^1$ and $Z^2$ are each, independently, $C_8$-$C_{14}$ alkyl or $C_8$-$C_{14}$ alkenyl, wherein (i) the $C_8$-$C_{14}$ alkyl or $C_8$-$C_{14}$ alkenyl of at least one of $Z^1$ and $Z^2$ is substituted by one or more alkoxy (e.g., a $C_1$-$C_4$ alkoxy such as $—OCH_3$) or thioalkoxy (e.g., a $C_1$-$C_4$ thioalkoxy such as $—SCH_3$) groups, and (ii) the alkenyl group may optionally be substituted with one or two fluorine atoms at the alpha position to a double bond which is between the double bond and the terminus of $Z^1$ or $Z^2$ (e.g., 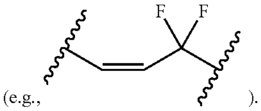 [SMILES: */C=C\C(*)(F)F]).

In one embodiment, the alkoxy substitution on $Z^1$ and/or $Z^2$ is at the beta position from the $M^1$ and/or $M^2$ group.

In another embodiment, X and Y are each, independently $—(CH_2)_n—$ wherein n is 4 to 20, e.g., 4 to 18, 4 to 16, or 4 to 12. In one embodiment, n is 4, 5, 6, 7, 8, 9, or 10. In one exemplary embodiment, X and Y are $—(CH_2)_6—$. In another embodiment, X and Y are $—(CH_2)_7—$. In yet another embodiment, X and Y are $—(CH_2)_9—$. In yet another embodiment, X and Y are $—(CH_2)_8—$.

The $R'R^1R^2N—(R)_a-Q-(R)_b—$ group can be any of the head groups described herein, including those shown in Table 1 below, and salts thereof. In one preferred embodiment, $R'R^1R^2N—(R)_a-Q-(R)_b—$ is $(CH_3)_2N—(CH_2)_3—C(O)O—$, $(CH_3)_2N—(CH_2)_2—NH—C(O)O—$, $(CH_3)_2N—(CH_2)_2—OC(O)—NH—$, or $(CH_3)_2N—(CH_2)_3—C(CH_3)=N—O—$.

In one embodiment, the cationic lipid is a compound of formula (VIA), which has one or more fluoro substituents on at least one tail at a position that is either alpha to a double bond or alpha to a biodegradable group:

Formula (VIA)

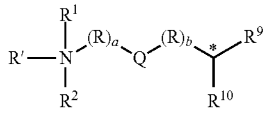

or a salt thereof (e.g., a pharmaceutically acceptable salt thereof), wherein $R^1$, $R^2$, R, a, and b are as defined with respect to formula (I);

Q is absent or is —O—, —NH—, —S—, —C(O)—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—;

R' is absent, hydrogen, or alkyl (e.g., $C_1$-$C_4$ alkyl); and each of $R^9$ and $R^{10}$ are independently $C_{12}$-$C_{24}$ alkyl (e.g., $C_{12}$-$C_{20}$ alkyl), $C_{12}$-$C_{24}$ alkenyl (e.g., $C_{12}$-$C_{20}$ alkenyl), or $C_{12}$-$C_{24}$ alkoxy (e.g., $C_{12}$-$C_{20}$ alkoxy) (a) having one or more biodegradable groups and (b) optionally substituted with one or more fluorine atoms at a position which is (i) alpha to a biodegradable group and between the biodegradable group and the tertiary carbon atom marked with an asterisk (*), or (ii) alpha to a carbon-carbon double bond and between the double bond and the terminus of the $R^9$ or $R^{10}$ group; each biodegradable group independently interrupts the $C_{12}$-$C_{24}$ alkyl, alkenyl, or alkoxy group or is substituted at the terminus of the $C_{12}$-$C_{24}$ alkyl, alkenyl, or alkoxy group, wherein (i) at least one of $R^9$ and $R^{10}$ contains a fluoro group;

(ii) the compound does not contain the following moiety:

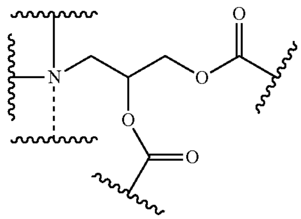

wherein - - - is an optional bond; and (iii) the terminus of $R^9$ and $R^{10}$ is separated from the tertiary carbon atom marked with an asterisk (*) by a chain of 8 or more atoms (e.g., 12 or 14 or more atoms).

In one preferred embodiment, the terminus of $R^9$ and $R^{10}$ is separated from the tertiary carbon atom marked with an asterisk (*) by a chain of 18-22 carbon atoms (e.g., 18-20 carbon atoms).

In another embodiment, the terminus of the $R^9$ and/or $R^{10}$ has the formula —C(O)O—$CF_3$.

In another embodiment, the cationic lipid is a compound of formula (VIB), which has one or more fluoro substituents on at least one tail at a position that is either alpha to a double bond or alpha to a biodegradable group:

Formula (VIB)

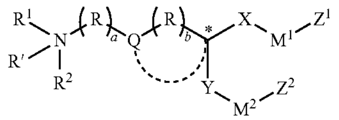

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, a, and b are defined as in formula (I);

X and Y are each, independently, alkylene (e.g., $C_6$-$C_8$ alkylene) or alkenylene, wherein the alkylene or alkenylene group is optionally substituted with one or two fluorine atoms at the alpha position to the $M^1$ or $M^2$ group (e.g., 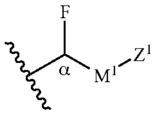);

and $Z^1$ and $Z^2$ are each, independently, $C_8$-$C_{14}$ alkyl or $C_8$-$C_{14}$ alkenyl, wherein said $C_8$-$C_{14}$ alkenyl is optionally substituted by one or more fluorine atoms at a position that is alpha to a double bond (e.g., 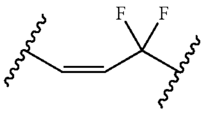), wherein at least one of X, Y, $Z^1$, and $Z^2$ contains a fluorine atom.

In one embodiment, at least one of $Z^1$ and $Z^2$ is substituted by two fluoro groups at a position that is either alpha to a double bond or alpha to a biodegradable group. In one embodiment, at least one of $Z^1$ and $Z^2$ has a terminal —$CF_3$ group at a position that is alpha to a biodegradable group (i.e., at least one of $Z^1$ and $Z^2$ terminates with an —C(O)$OCF_3$ group).

For example, at least one of $Z^1$ and $Z^2$ may include one or more of the following moieties:

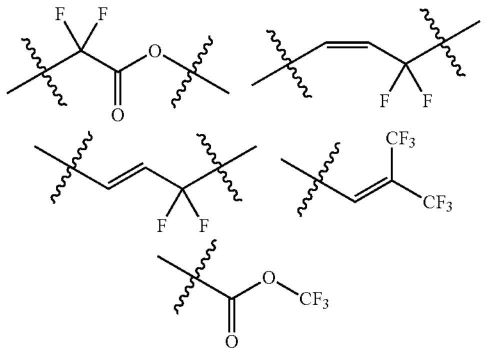

In one embodiment, X and Y are each, independently —$(CH_2)_n$, wherein n is 4 to 20, e.g., 4 to 18, 4 to 16, or 4 to 12. In one embodiment, n is 4, 5, 6, 7, 8, 9, or 10. In one exemplary embodiment, X and Y are $-(CH_2)_7-$. In another exemplary embodiment, X and Y are $-(CH_2)_9-$. In yet another embodiment, X and Y are $-(CH_2)_8-$.

The $R'R^1R^2N-(R)_a$-Q-$(R)_b-$ group can be any of the head groups described herein, including those shown in Table 1 below, and salts thereof. In one preferred embodiment, $R'R^1R^2N-(R)_a$-Q-$(R)_b-$ is $(CH_3)_2N-(CH_2)_3-C(O)O-$, $(CH_3)_2N-(CH_2)_2-NH-C(O)O-$, $(CH_3)_2N-(CH_2)_2-OC(O)-NH-$, or $(CH_3)_2N-(CH_2)_3-C(CH_3)=N-O-$.

In one embodiment, the cationic lipid is a compound of formula (VII), which has an acetal group as a biodegradable group in at least one tail:

Formula (VII)

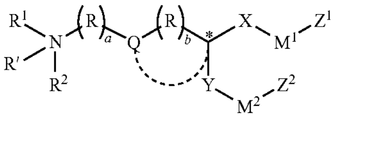

or a salt thereof (e.g., a pharmaceutically acceptable salt thereof), wherein

R', $R^1$, $R^2$, R, $R^3$, $R^4$, $R^{10}$, Q, $R^5$, a, and b are defined as in formula (I);

X and Y are each, independently, alkylene (e.g., $C_6$-$C_8$ alkylene) or alkenylene, wherein the alkylene or alkenylene group is optionally substituted with one or two fluorine atoms at the alpha position to the $M^1$ or $M^2$ group (e.g.,

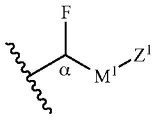

);

$M^1$ and $M^2$ are each, independently, a biodegradable group (e.g., $-OC(O)-$, $-C(O)O-$, $-SC(O)-$, $-C(O)S-$, $-OC(S)-$, $-C(S)O-$, $-S-S-$, $-C(R^5)=N-$, $-N=C(R^5)-$, $-C(R^5)=N-O-$, $-O-N=C(R^5)-$, $-C(O)(NR^5)-$, $-N(R^5)C(O)-$, $-C(S)(NR^5)-$, $-N(R^5)C(O)-$, $-N(R^5)C(O)N(R^5)-$, $-OC(O)O-$, $-OSi(R^5)_2O-$, $-C(O)(CR^3R^4)C(O)O-$, $-OC(O)(CR^3R^4)C(O)-$, or

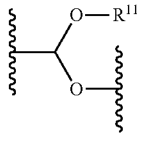

(wherein $R^{11}$ is a $C_4$-$C_{10}$ alkyl or $C_4$-$C_{10}$ alkenyl)); with the proviso that at least one of $M^1$ and $M^2$ is

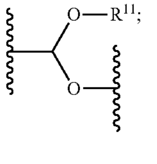

and $Z^1$ and $Z^2$ are each, independently, $C_4$-$C_{14}$ alkyl or $C_4$-$C_{14}$ alkenyl, wherein the alkenyl group may optionally be substituted with one or two fluorine atoms at the alpha position to a double bond which is between the double bond and the terminus of $Z^1$ or $Z^2$ (e.g.,

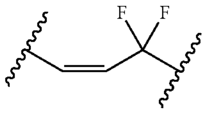

).

In one embodiment, each of $M^1$ and $M^2$ is

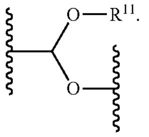

In another embodiment, X and Y are each, independently $-(CH_2)_n-$ wherein n is 4 to 20, e.g., 4 to 18, 4 to 16, or 4 to 12. In one embodiment, n is 4, 5, 6, 7, 8, 9, or 10. In one exemplary embodiment, X and Y are $-(CH_2)_6-$. In another embodiment, X and Y are $-(CH_2)_7-$. In yet another embodiment, X and Y are $-(CH_2)_9-$. In yet another embodiment, X and Y are $-(CH_2)_8-$.

The $R'R^1R^2N-(R)_a$-Q-$(R)_b-$ group can be any of the head groups described herein, including those shown in Table 1 below, and salts thereof. In one preferred embodiment, $R'R^1R^2N-(R)_a$-Q-$(R)_b-$ is $(CH_3)_2N-(CH_2)_3-C(O)O-$, $(CH_3)_2N-(CH_2)_2-NH-C(O)O-$, $(CH_3)_2N-(CH_2)_2-OC(O)-NH-$, or $(CH_3)_2N-(CH_2)_3-C(CH_3)=N-O-$.

In another embodiment, the present invention relates to a cationic lipid or a salt thereof having:

(i) a central carbon atom, (ii) a nitrogen containing head group directly bound to the central carbon atom, and (iii) two hydrophobic tails directly bound to the central carbon atom, wherein each hydrophobic tail is of the formula $-R^e$-M-$R^f$ where $R^e$ is a $C_4$-$C_{14}$ alkyl or alkenyl, M is a biodegradable group, and $R^f$ is a branched alkyl or alkenyl (e.g., a $C_{10}$-$C_{20}$ alkyl or $C_{10}$-$C_{20}$ alkenyl), such that (i) the chain length of $-R^e$-M-$R^f$ is at most 20 atoms (i.e. the total length of the tail from the first carbon atom after the central carbon atom to a terminus of the tail is at most 20), and (ii) the group $-R^e$-M-$R^f$ has at least 20 carbon atoms (e.g., at least 21 atoms).

Optionally, the alkyl or alkenyl group in $R^e$ may be substituted with one or two fluorine atoms at the alpha position to the $M^1$ or $M^2$ group (e.g.,

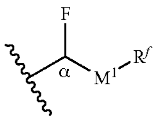

).

Also, optionally, the alkenyl group in $R^f$ may be substituted with one or two fluorine atoms at the alpha position to a double bond which is between the double bond and the terminus of $R^f$ (e.g., 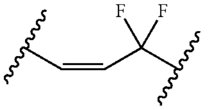 ).

In one embodiment, the cationic lipid of the present invention (such as of formulas I-VII) has asymmetrical hydrophobic groups (i.e., the two hydrophobic groups have different chemical formulas). For example, the cationic lipid can have the formula:

Formula (VIII)

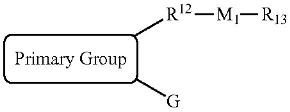

or a salt thereof (e.g., a pharmaceutically acceptable salt thereof), wherein G is branched or unbranched $C_3$-$C_{15}$ alkyl, alkenyl or alkynyl (e.g., a n-$C_8$ alkyl n-$C_9$ alkyl, or n-$C_{10}$ alkyl);

$R^{12}$ is a branched or unbranched alkylene or alkenylene (e.g., $C_6$-$C_{20}$ alkylene or $C_6$-$C_{20}$ alkenylene such as $C_{12}$-$C_{20}$ alkylene or $C_{12}$-$C_{20}$ alkenylene);

$M_1$ is a biodegradable group (e.g., —OC(O)—, —C(O)O—, —SC(O)—, —C(O)S—, —OC(S)—, —C(S)O—, —S—S—, —C($R^5$)═N—, —N═C($R^5$)—, —C($R^5$)═N—O—, —O—N═C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

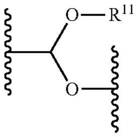

(wherein $R^{11}$ is a $C_2$-$C_8$ alkyl or alkenyl));

$R^3$ and $R^4$ are defined as in formula (I);

each occurrence of $R^5$ is, independently, H or alkyl (e.g., $C_1$-$C_4$ alkyl); and $R^{13}$ is branched or unbranched $C_3$-$C_{15}$ alkyl, alkenyl or alkynyl;

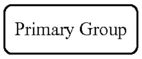

comprises a protonatable group having a $pK_a$ of from about 4 to about 13, more preferably from about 5 to about 8 (e.g. from about 5 to about 7, or from about 5 to about 6.5, or from about 5.5 to about 6.5, or from about 6 to about 6.5).

In one embodiment, the primary group includes (i) a head group, and (ii) a central moiety (e.g., a central carbon atom) to which both the hydrophobic tails are directly bonded. Representative central moieties include, but are not limited to, a central carbon atom, a central nitrogen atom, a central carbocyclic group, a central aryl group, a central hetrocyclic group (e.g., central tetrahydrofuranyl group or central pyrrolidinyl group) and a central heteroaryl group.

Representative

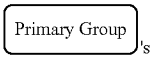's include, but are not limited to,

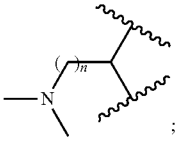 ; 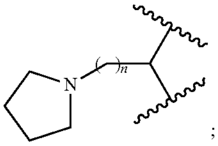 ;

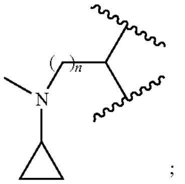 ; 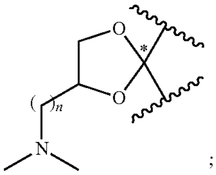 ;

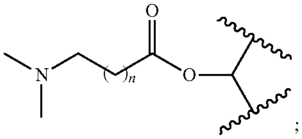 ;

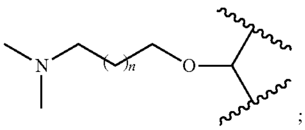 ;

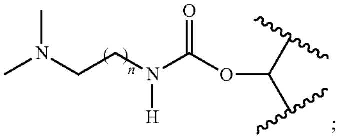 ;

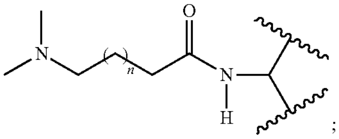 ;

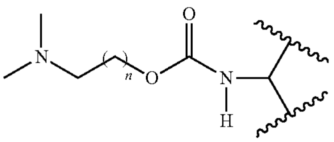

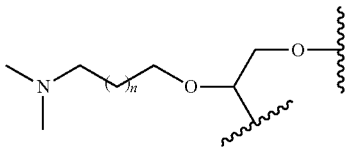 ;

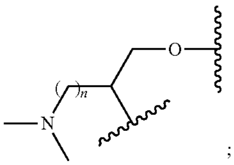 ; 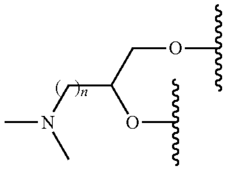 ;

-continued
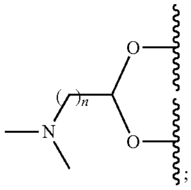
;
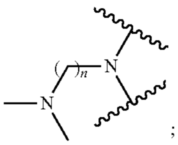
;
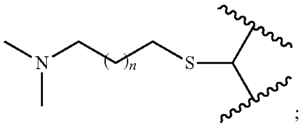
;
-continued
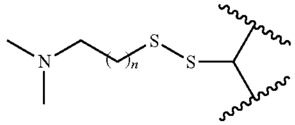
and
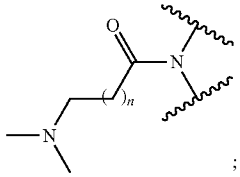
;
where n is 0-6.
Representative asymmetrical cationic lipids include:
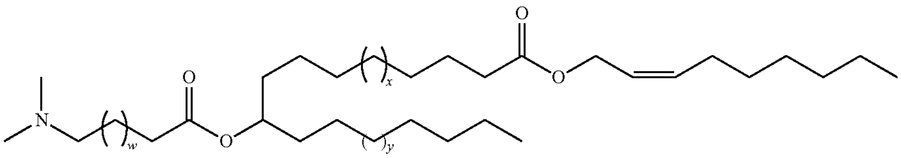
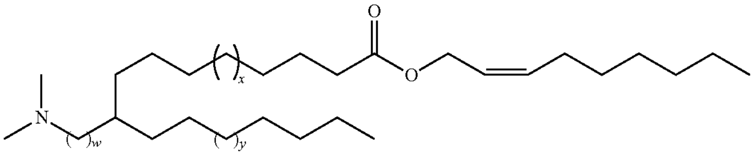
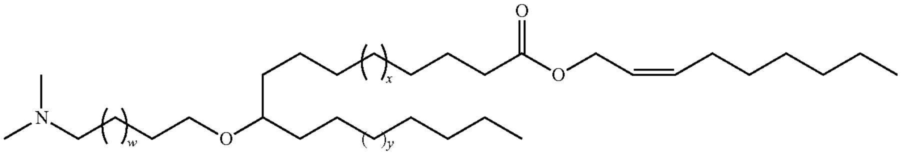
wherein w is 0, 1, 2, or 3; and x and y are each independently 1, 2, 3, 4, 5, 6, or 7.
In another embodiment, the biodegradable cationic lipid of the present invention is not one selected from:
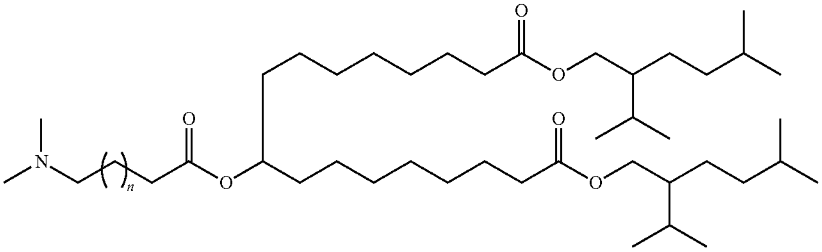
n = 0-2
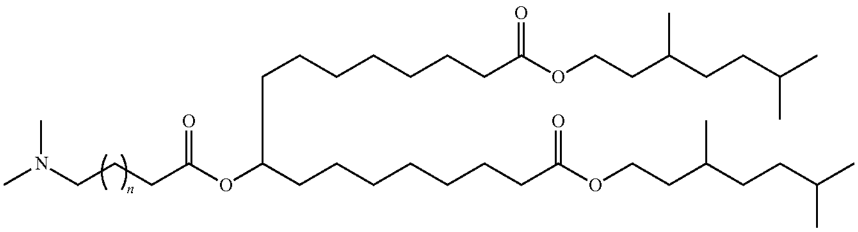
n = 0-2

-continued
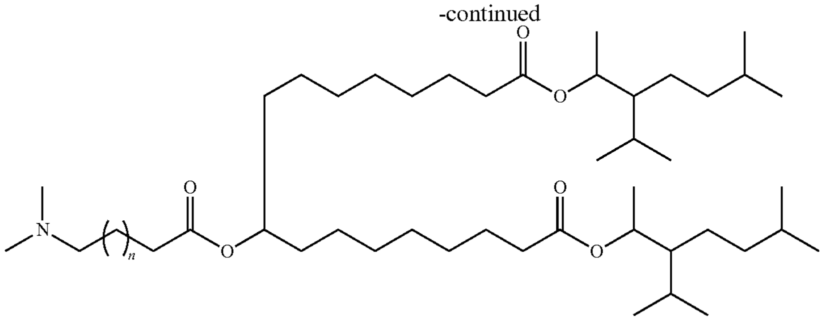
n = 0-2
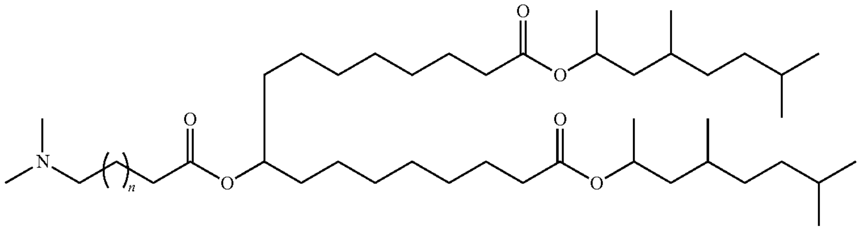
n = 0-2
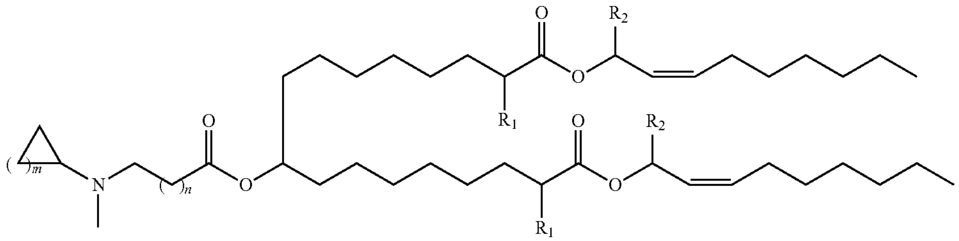
m = 1-6; n = 0-3
$R_1 = R_2$ = Me, Et, iPr etc.
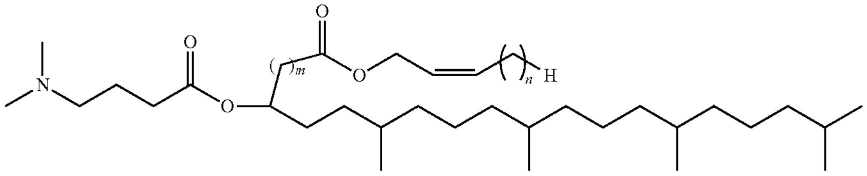
where m and n are integers, and m+n=13
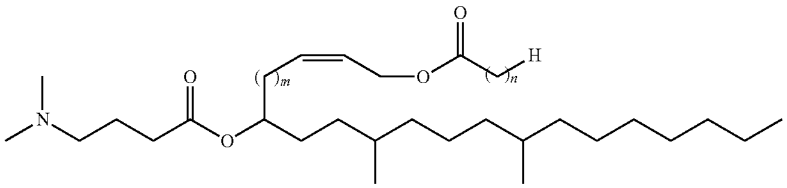
where m and n are integers, and m+n=13
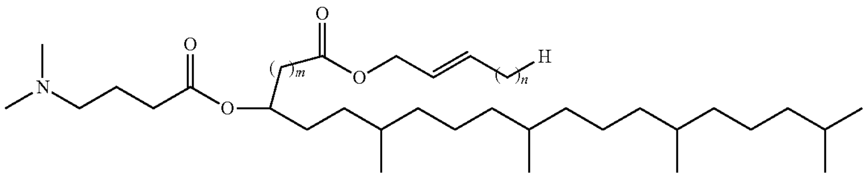
where m and n are integers, and m+n=13

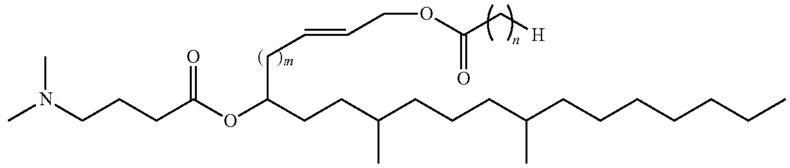

where m and n are integers, and m+n=13

In yet another embodiment, the biodegradable cationic lipid is not one selected from those disclosed in International Publication No. WO 2011/153493 and U.S. Patent Publication No. 2012/0027803, both of which are hereby incorporated by reference.

Yet another embodiment is a biodegradable cationic lipid having (i) a log P value of at least 10.1 and/or a $t_{lipid}$-$t_{chol}$, of at least 1.4, and (2) one or more biodegradable groups (such as an ester group) located in the mid- or distal section of a lipidic moiety (e.g., a hydrophobic chain) of the cationic lipid, with the proviso that the compound is not selected from

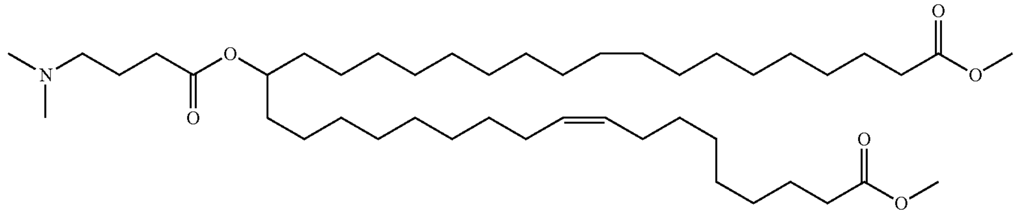

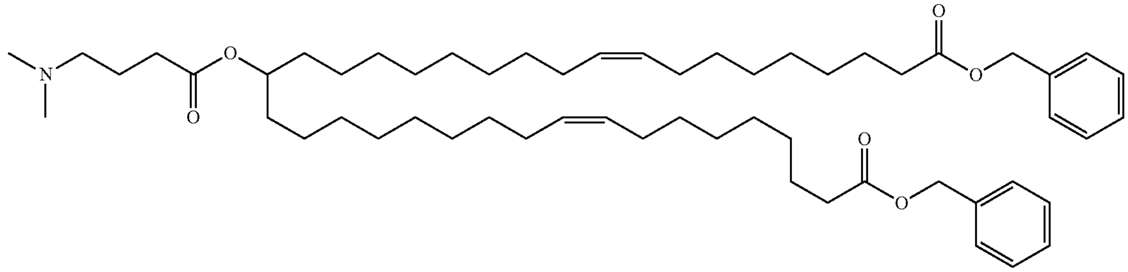

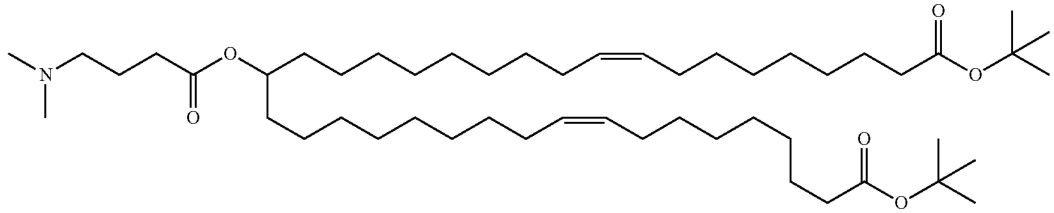

In another embodiment, the biodegradable cationic lipid is not one selected from those disclosed in International Publication No. WO 2011/153493 and U.S. Patent Publication No. 2012/0027803, both of which are hereby incorporated by reference.

In one embodiment, the cationic lipid having a log P value of at least 10.1 and/or a $t_{lipid}$-$t_{chol}$, of at least 1.4 comprises (a) a head group (preferably a nitrogen containing head group, such as the head groups described herein), (b) at least two hydrophobic tails, each of the formula -(hydrophobic chain)-(biodegradable group)-(hydrophobic chain), and (c) a linker group (for instance, a single central carbon atom) which is bound to the head group and the hydrophobic tails. The cationic lipid preferably has one, two, three, four or more of the properties listed below:

(i) a pKa of from about 4 to about 7 (such as 6.0 to 6.5);

(ii) in at least one hydrophobic tail (and preferably all hydrophobic tails), the biodegradable group is separated from the terminus of the hydrophobic tail by from about 6 to about 12 carbon atoms (for instance, 6 to 8 carbon atoms or 8 to 12 carbon atoms), (iii) for at least one hydrophobic tail (and preferably all hydrophobic tails), the chain length from the linker group to the terminus of the hydrophobic tail is at most 21 (e.g., at most 20, or from about 17 to about 21, from about 18 to about 20, or from about 16 to about 18) (The atom(s) in the linker group are not counted when calculating the chain length.);

(iv) for at least one hydrophobic tail (and preferably all hydrophobic tails), the total number of carbon atoms in the hydrophobic tail is from about 17 to about 26 (such as from about 19 to about 26, or from about 21 to about 26);

(v) for at least one hydrophobic tail (and preferably all hydrophobic tails), the number of carbon atoms between the linker group and the biodegradable group ranges from about 5 to about 10 (for example, 6 to 10, or 7 to 9);

(vi) for at least one hydrophobic tail (and preferably all hydrophobic tails), the total number of carbon atoms between the linker group and the terminus of the hydrophobic tail is from about 15 to about 20 (such as from 16 to 20, 16 to 18, or 18 to 20);

(vii) for at least one hydrophobic tail (and preferably all hydrophobic tails), the total number of carbon atoms between the biodegradable group and the terminus of the hydrophobic tail is from about 12 to about 18 (such as from 13 to 25);

(viii) for at least one hydrophobic tail (and preferably all hydrophobic tails), the terminal hydrophobic chain in the hydrophobic tail is a branched alkyl or alkenyl group, for example, where the branching occurs at the α, β, γ, or δ position on the hydrophobic chain relative to the biodegradable group;

(ix) when formulated as a lipid nanoparticle (such as in Example 35), the cationic lipid has an in vivo half life ($t_{1/2}$) in the liver of less than about 3 hours, such as less than about 2.5 hours, less than about 2 hours, less than about 1.5 hours, less than about 1 hour, less than about 0.5 hour or less than about 0.25 hours;

(x) when formulated as a lipid nanoparticle (such as in Example 35), the cationic lipid is eliminated from the liver in mice with a greater than 10-fold reduction in lipid levels relative to $C_{max}$ within the first 24 hours post-dose;

(xi) when formulated as a lipid nanoparticle (such as in Example 35), the cationic lipid is eliminated from the spleen in mice with an equal or greater than 10-fold reduction in lipid levels relative to $C_{max}$ within the first 168 hours post-dose; and (xii) when formulated as a lipid nanoparticle (such as in Example 35), the cationic lipid is eliminated from plasma with a terminal plasma half-life ($t\frac{1}{2}\beta$) in rodents and non-human primates of 48 hours or shorter.

The present invention embodies compounds having any combination of some or all of the aforementioned properties. These properties provide a cationic lipid which remains intact until delivery of an active agent, such as a nucleic acid, after which cleavage of the hydrophobic tail occurs in vivo. For instance, the compounds can have all of properties (i) to (viii) (in addition to the log P or $t_{lipid}-t_{chol}$ value). In another embodiment, the compounds have properties (i), (ii), (iii), and (viii). In yet another embodiment, the compounds have properties (i), (ii), (iii), (v), (vi), and (viii).

Another embodiment is a method of preparing a cationic lipid comprising: (a) designing a cationic lipid having a log P value of at least 10.1 and/or a $t_{lipid}-t_{chol}$, of at least 1.4, and optionally also having one, two, three, four, or more properties from the list above (i.e., properties (i)-(xii)); and (b) synthesizing the cationic lipid of step (a). The cationic lipid in step (a) may comprises (a) a head group (preferably a nitrogen containing head group, such as the head groups described herein), (b) at least two hydrophobic tails, each of the formula -(hydrophobic chain)-(biodegradable group)-(hydrophobic chain), and (c) a linker group (for instance, a single central carbon atom) which is bound to the head group and the hydrophobic tails. Step (a) may comprise:

(a)(i) preparing one or more cationic lipids having a log P value of at least 10.1 and/or a $t_{lipid}-t_{chol}$, of at least 1.4, and optionally also having one, two, three, four, or more properties from the list above (i.e., properties (i)-(xii);

(a)(ii) screening the cationic lipids to determine their efficacy and/or toxicity in lipid nanoparticles; and (a)(iii) selecting a cationic lipid for synthesis.

Yet another embodiment is a method of designing a cationic lipid comprising:

(a) selecting a cationic lipid having a log P value of at least 10.1 and/or a $t_{lipid}-t_{chol}$, of at least 1.4, and optionally also having one, two, three, four, or more properties from the list above (i.e., properties (i)-(xii)); and (b) optionally, (i) preparing one or more cationic lipids having a log P value of at least 10.1 and/or a $t_{lipid}-t_{chol}$, of at least 1.4, and optionally also having one, two, three, four, or more properties from the list above (i.e., properties (i)-(xii);

(ii) screening the cationic lipids to determine their efficacy and/or toxicity in lipid nanoparticles; and (iii) optionally, selecting a cationic lipid for further development or use.

In one embodiment, the PEG lipid has the formula:

Formula (IX)

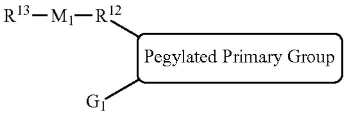

wherein $G_1$ is branched or unbranched $C_3$-$C_{15}$ alkyl, alkenyl or alkynyl (e.g., a n-$C_8$ alkyl n-$C_9$ alkyl, or n-$C_{10}$ alkyl); or $G_1$ is —$R^2$-$M_1$-$R^{13}$;

$R^{12}$ is a branched or unbranched alkylene or alkenylene (e.g., $C_6$-$C_{20}$ alkylene or $C_6$-$C_{20}$ alkenylene such as $C_{12}$-$C_{20}$ alkylene or $C_{12}$-$C_{20}$ alkenylene);

$M_1$ is a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)($NR^5$)—, —N($R^5$)C(O)—, —C(S)($NR^5$)—, —N($R^5$)C(O)—, —N($R^5$)C(O)N($R^5$)—, —OC(O)O—, —OSi($R^5$)$_2$O—, —C(O)($CR^3R^4$)C(O)O—, —OC(O)($CR^3R^4$)C(O)—, or

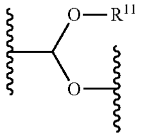

(wherein $R^{11}$ is a $C_2$-$C_8$ alkyl or alkenyl));

$R^3$ and $R^4$ are defined as in formula (I);

each occurrence of $R^5$ is, independently, H or alkyl (e.g., $C_1$-$C_4$ alkyl);

$R^{13}$ is branched or unbranched $C_3$-$C_{15}$ alkyl, alkenyl or alkynyl;

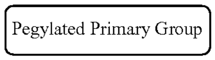

comprises a PEG moiety, such as

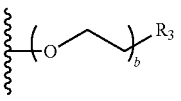

moiety wherein b is an integer from 10 to 1,000 (e.g., 5-100, 10-60, 15-50, or 20-45); $R^3$ is —H, —$R^c$, or —$OR^c$; and $R^c$ is —H, alkyl, acyl, cycloalkyl, alkenyl, alkynyl, aryl, heteroaryl, or heterocyclyl.

In one embodiment, the pegylated primary group includes (i) a head group having a PEG moiety, and (ii) a central moiety (e.g., a central carbon atom) to which both the hydrophobic tails are directly bonded. Representative central moieties include, but are not limited to, a central carbon atom, a central nitrogen atom, a central carbocyclic group, a central aryl group, a central hetrocyclic group (e.g., central tetrahydrofuranyl group or central pyrrolidinyl group) and a central heteroaryl group.

Representative

Pegylated Primary Group's include, but are not limited to,

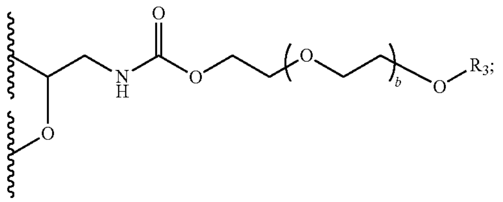

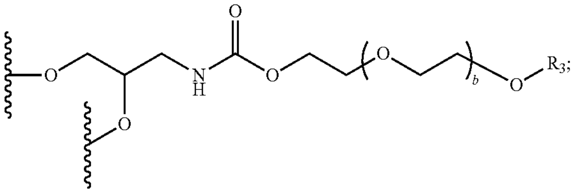

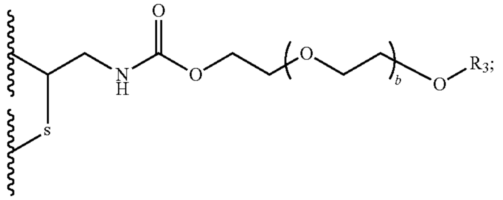

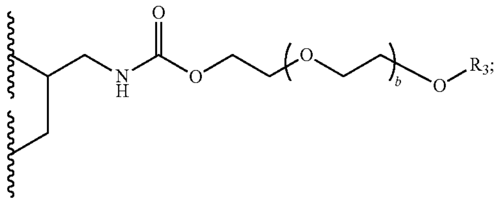

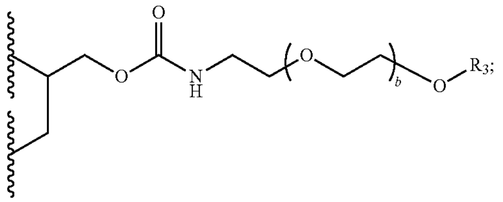

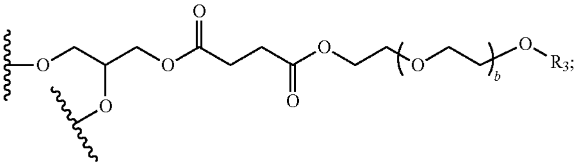

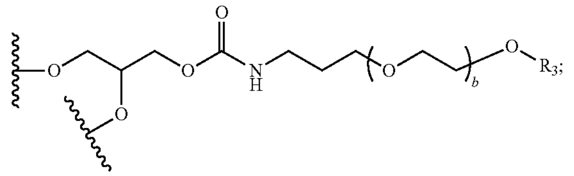

-continued

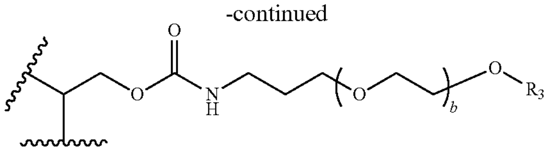

where b is 10-100 (e.g., 20-50 or 40-50)

Another embodiment of the present invention is a PEG lipid (or a salt thereof) having:

(i) a pegylated primary group including a head group which includes a PEG moiety (e.g., having from 10 to 1000 repeating units such as ethoxy units)), and (iii) one or more hydrophobic tails (preferably, two hydrophobic tails) directly bound to the pegylated primary group, wherein at least one hydrophobic tail is of the formula —$R^e$-M-$R^f$ where $R^e$ is a $C_4$-$C_{14}$ alkyl or alkenyl, M is a biodegradable group, and $R^f$ is a branched alkyl or alkenyl (e.g., a $C_{10}$-$C_{20}$ alkyl or $C_{10}$-$C_{20}$ alkenyl), such that (i) the chain length of —$R^e$-M-$R^f$ is at most 20 atoms (i.e. the total length of the tail from the first carbon atom after the central carbon atom to a terminus of the tail is at most 20), and (ii) the group —$R^e$-M-$R^f$ has at least 20 carbon atoms (e.g., at least 21 atoms). Optionally, the alkyl or alkenyl group in $R^e$ may be substituted with one or two fluorine atoms at the alpha position to the $M^1$ or $M^2$ group (e.g., 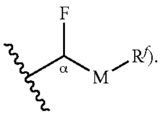).

Also, optionally, the alkenyl group in $R^f$ may be substituted with one or two fluorine atoms at the alpha position to a double bond which is between the double bond and the terminus of $R^f$ (e.g., 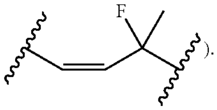).

In one embodiment, the pegylated primary group includes (i) a head group having a PEG moiety, and (ii) a central moiety (e.g., a central carbon atom) to which the hydrophobic tails are directly bound. The PEG moiety may have 5-100, 10-60, 15-50, or 20-45 repeating units. For example, the PEG moiety may have the formula

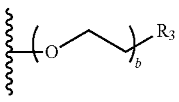

moiety wherein b is an integer from 10 to 1,000 (e.g., 5-100, 10-60, 15-50, or 20-45); $R^3$ is —H, —$R^c$, or —$OR^c$; and $R^c$ is —H, alkyl (e.g., $C_1$-$C_4$ alkyl), acyl, cycloalkyl, alkenyl, alkynyl, aryl, heteroaryl, or heterocyclyl.

In one embodiment, $M^1$ and $M^2$ are each, independently: —OC(O)—, —C(O)O—, —SC(O)—, —C(O)S—, —OC(S)—, —C(S)O—, —S—S—, —C($R^5$)═N—, —N═C($R^5$)—, —C($R^5$)═N—O—, —O—N═C($R^5$)—, —C(O)

$(NR^5)$—, —$N(R^5)C(O)$—, —$C(S)(NR^5)$—, —$N(R^5)C(O)$—, —$N(R^5)C(O)N(R^5)$—, —$OC(O)O$—, —$OSi(R^5)_2O$—, —$C(O)(CR^3R^4)C(O)O$—, —$OC(O)(CR^3R^4)C(O)$—, or

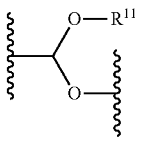

(wherein $R^{11}$ is a $C_2$-$C_8$ alkyl or alkenyl).

In another embodiment, $M^1$ and $M^2$ are each, independently:

—$OC(O)$—, —$C(O)$—$O$—, —$C(R^5)$═$N$—, —$N$═$C(R^5)$—, —$C(R^5)$═$N$—$O$—, —$O$—$N$═$C(R^5)$—, —$O$—$C(O)O$—, —$C(O)N(R^5)$—, —$N(R^5)C(O)$—, —$C(O)S$—, —$SC(O)$—, —$C(S)O$—, —$OC(S)$—, —$OSi(R^5)_2O$—, —$C(O)(CR^3R^4)C(O)O$—, or —$OC(O)(CR^3R^4)C(O)$—.

In yet another embodiment, $M^1$ and $M^2$ are each, independently:

—$C(O)$—$O$—, —$OC(O)$—, —$C(R^5)$═$N$—, —$C(R^5)$═$N$—$O$—, —$O$—$C(O)O$—, —$C(O)N(R^5)$—, —$C(O)S$—, —$C(S)O$—, —$OSi(R^5)_2O$—, —$C(O)(CR^3R^4)C(O)O$—, or —$OC(O)(CR^3R^4)C(O)$—.

In another embodiment, $M^1$ and $M^2$ are each —$C(O)O$—.

In one embodiment, $R^1$ and $R^2$ are each, individually, optionally substituted alkyl, cycloalkyl, cycloalkylalkyl, or heterocycle. In one embodiment, $R^1$ is alkyl and $R^2$ is alkyl, cycloalkyl or cycloalkylalkyl. In one embodiment, $R^1$ and $R^2$ are each, individually, alkyl (e.g., $C_1$-$C_4$ alkyl, such as methyl, ethyl, or isopropyl). In one embodiment, $R^1$ and $R^2$ are both methyl. In another embodiment, $R^1$ and $R^2$, together with the nitrogen atom to which they are attached, form an optionally substituted heterocylic ring (e.g., N-methylpiperazinyl). In another embodiment, one of $R^1$ and $R^2$ is

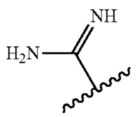 or 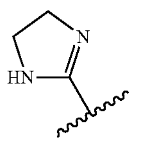

(e.g., $R^1$ is one of the two aforementioned groups and $R^2$ is hydrogen).

In one embodiment, R' is hydrogen or alkyl. In another embodiment, R' is hydrogen or methyl. In one embodiment, R' is absent. In one embodiment, R' is absent or methyl.

In one embodiment each R is, independently, —$(CR^3R^4)$—, wherein $R^3$ and $R^4$ are each, independently, H or alkyl (e.g., $C_1$-$C_4$ alkyl). For example, in one embodiment each R is, independently, —$(CHR^4)$—, wherein each $R^4$ is, independently H or alkyl (e.g., $C_1$-$C_4$ alkyl). In another embodiment, each R is, independently, —$CH_2$—, —$C(CH_3)_2$— or —CH(iPr)- (where iPr is isopropyl). In another embodiment, each R is —$CH_2$—.

In another embodiment $R^5$ is, in each case, hydrogen or methyl. For example, $R^5$ can be, in each case, hydrogen.

In one embodiment, Q is absent, —$C(O)O$—, —$OC(O)$—, —$C(O)N(R^5)$—, —$N(R^5)C(O)$—, —$S$—$S$—, —$OC(O)O$—, —$C(R^5)$═$N$—$O$—, —$OC(O)N(R^5)$—, —$N(R^5)C(O)N(R^5)$—, —$N(R^5)C(O)O$—, —$C(O)S$—, —$C(S)O$— or —$C(R^5)$═$N$—$O$—$C(O)$—. In one embodiment, Q is —$C(O)O$—.

In one embodiment, the dashed line to Q is absent, b is 0 and $R'R^1R^2N$—$(R)_a$-Q- and the tertiary carbon adjacent to it (C*) form the following group:

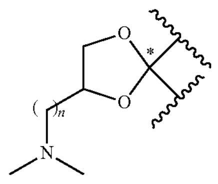

where n is 1 to 4 (e.g., n is 2).

In one embodiment, the dashed line to Q is absent, b is 0 and $R'R^1R^2N$—$(R)_a$-Q- and the tertiary carbon adjacent to it form the following group:

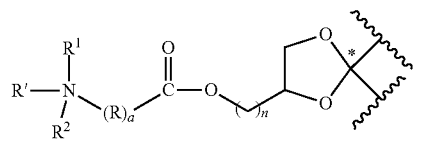

where n is 1 to 4 (e.g., n is 2), and $R^1$, $R^2$, R, a, and b are as defined with respect to formula (I). In one embodiment, a is 3.

In one embodiment, the dashed line to Q is absent, b is 0 and $R'R^1R^2N$—$(R)_a$-Q- and the tertiary carbon adjacent to it form the following group:

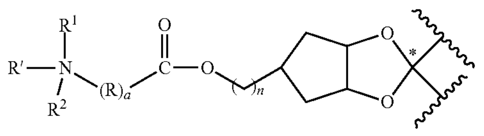

where n is 1 to 4 (e.g., n is 2), and $R^1$, $R^2$, R, a, and b are as defined with respect to formula (I). In one embodiment, a is 0. For example, the group can be:

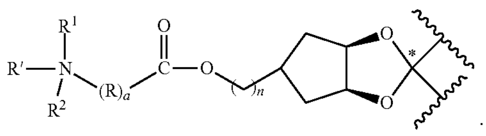

In one embodiment, b is 0. In another embodiment, a is 2, 3, or 4 and b is 0. For example, in one embodiment, a is 3 and b is 0. In another embodiment, a is 3, b is 0, and Q is —$C(O)O$—.

In certain embodiments, the biodegradable group present in the cationic lipid is selected from an ester (e.g., —$C(O)O$— or —$OC(O)$—), disulfide (—$S$—$S$—), oxime (e.g., —$C(H)$═$N$—$O$— or —$O$—$N$═$C(H)$—), —$C(O)$—$O$—, —$OC(O)$—, —$C(R^5)$═$N$—, —$N$═$C(R^5)$—, —$C(R^5)$═$N$—$O$—, —$O$—$N$═$C(R^5)$—, —$O$—$C(O)O$—, —$C(O)N(R^5)$, —$N(R^5)C(O)$—, —$C(S)(NR^5)$—, $(NR^5)C(S)$—, —$N(R^5)C(O)N(R^5)$—, —$C(O)S$—, —$SC(O)$—, —$C(S)O$—, —$OC(S)$—, —$OSi(R^5)_2O$—, —$C(O)(CR^3R^4)C(O)O$—, or —$OC(O)(CR^3R^4)C(O)$—.

Some suitable head groups include those depicted in Table 1A:

TABLE 1A
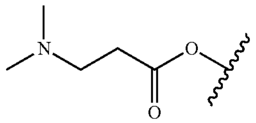 [SMILES: *OC(=O)CCN(C)C]
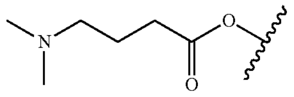 [SMILES: *OC(=O)CCCN(C)C]
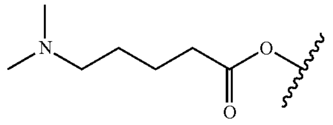 [SMILES: *OC(=O)CCCCN(C)C]
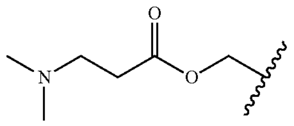 [SMILES: *COC(=O)CCN(C)C]
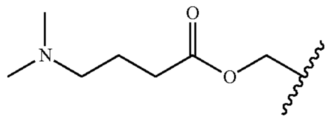 [SMILES: *COC(=O)CCCN(C)C]
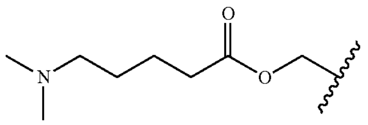 [SMILES: *COC(=O)CCCCN(C)C]
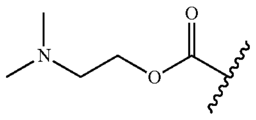 [SMILES: *C(=O)OCCN(C)C]
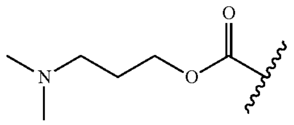 [SMILES: *C(=O)OCCCN(C)C]
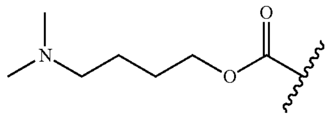 [SMILES: *C(=O)OCCCCN(C)C]
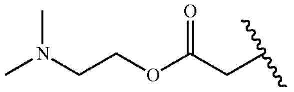 [SMILES: *CC(=O)OCCN(C)C]
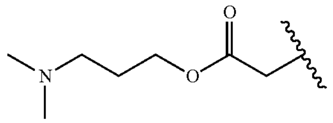 [SMILES: *CC(=O)OCCCN(C)C]
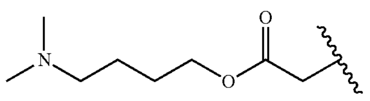 [SMILES: *CC(=O)OCCCCN(C)C]
TABLE 1A-continued
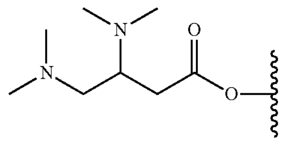 [SMILES: *OC(=O)CC(CN(C)C)N(C)C]
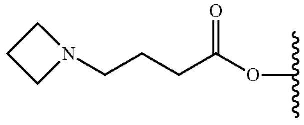 [SMILES: *OC(=O)CCCN1CCC1]
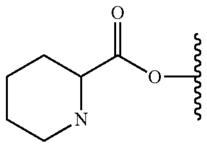 [SMILES: *OC(=O)C1CCCCN1]
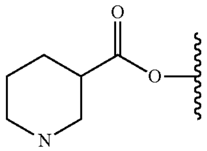 [SMILES: *OC(=O)C1CCCNC1]
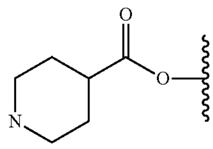 [SMILES: *OC(=O)C1CCNCC1]
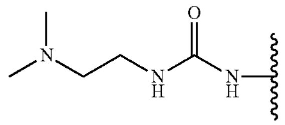 [SMILES: *NC(=O)NCCN(C)C]
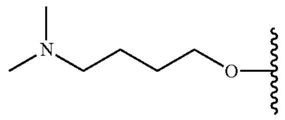 [SMILES: *OCCCCN(C)C]
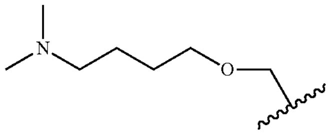 [SMILES: *COCCCCN(C)C]
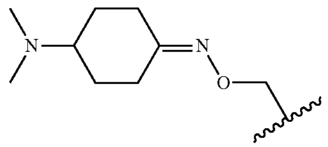 [SMILES: *CON=C1CCC(N(C)C)CC1]
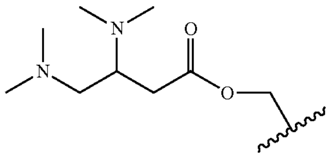 [SMILES: *COC(=O)CC(CN(C)C)N(C)C]

TABLE 1A-continued
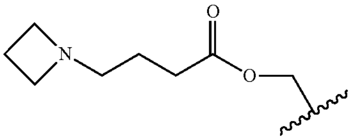 [SMILES: *COC(=O)CCCN1CCC1]
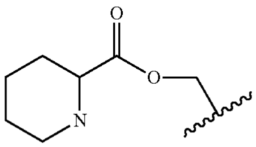 [SMILES: *COC(=O)C1CCCCN1]
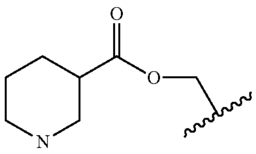 [SMILES: *COC(=O)C1CCCNC1]
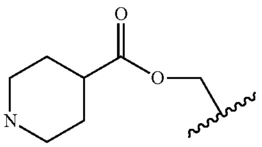 [SMILES: *COC(=O)C1CCNCC1]
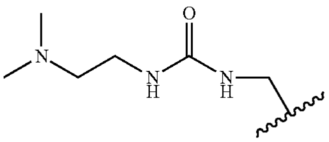 [SMILES: *CNC(=O)NCCN(C)C]
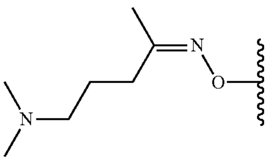 [SMILES: *O/N=C(/C)CCCN(C)C]
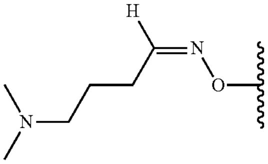 [SMILES: *O/N=C\CCCN(C)C]
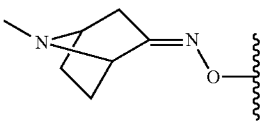 [SMILES: *O/N=C1/CC2CCC1N2C]
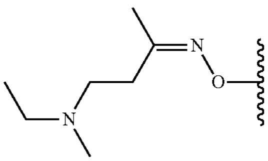 [SMILES: *O/N=C(/C)CCN(C)CC]
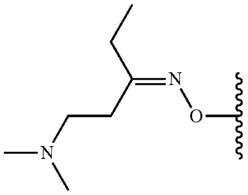 [SMILES: *O/N=C(/CC)CCN(C)C]
TABLE 1A-continued
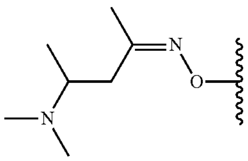 [SMILES: *O/N=C(/C)CC(C)N(C)C]
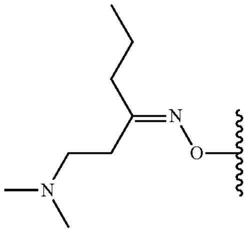 [SMILES: *O/N=C(/CCC)CCN(C)C]
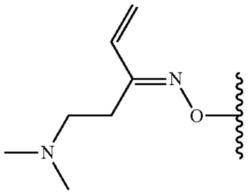 [SMILES: *O/N=C(/C=C)CCN(C)C]
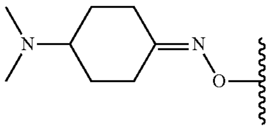 [SMILES: *ON=C1CCC(N(C)C)CC1]
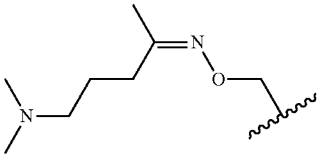 [SMILES: *CO/N=C(/C)CCCN(C)C]
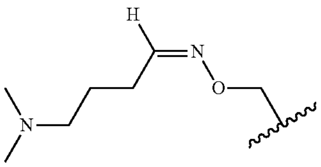 [SMILES: *CO/N=C\CCCN(C)C]
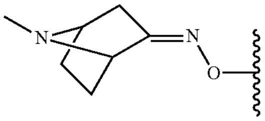 [SMILES: *O/N=C1/CC2CCC1N2C]
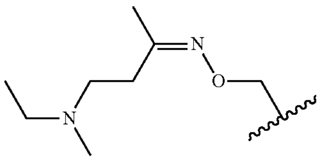 [SMILES: *CO/N=C(/C)CCN(C)CC]
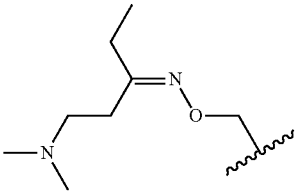 [SMILES: *CO/N=C(/CC)CCN(C)C]

TABLE 1A-continued

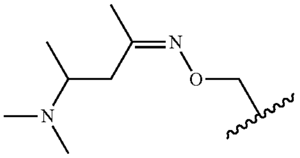 [SMILES: *CO/N=C(/C)CC(C)N(C)C]

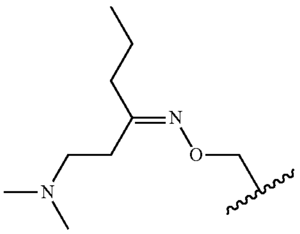 [SMILES: *CO/N=C(/CCC)CCN(C)C]

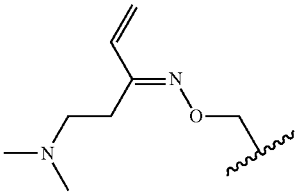 [SMILES: *CO/N=C(/C=C)CCN(C)C]

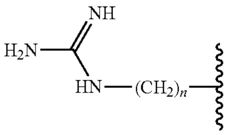

(where n is 0-5)

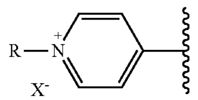

R = H, alkyl (e.g., methyl)
X = halogen (e.g., Cl)

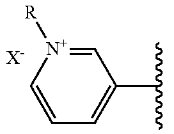

R = H, alkyl (e.g., methyl)
X = halogen (e.g., Cl)

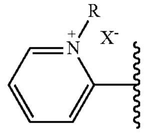

R = H, alkyl (e.g., methyl)
X = halogen (e.g., Cl)

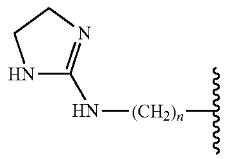

(where n is 0-5)

Suitable primary groups include, but are not limited to, those that are a combination of a head group from table 1A with a central carbon atom. Other suitable primary groups include those in table 1B below:

TABLE 1B

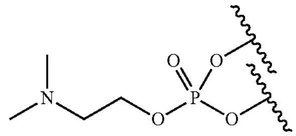 [SMILES: *OP(=O)(O*)OCCN(C)C]

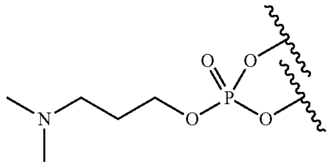 [SMILES: *OP(=O)(O*)OCCCN(C)C]

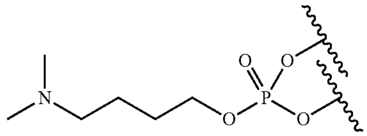 [SMILES: *OP(=O)(O*)OCCCCN(C)C]

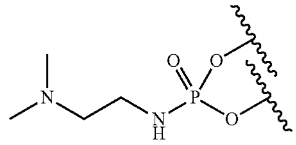 [SMILES: *OP(=O)(NCCN(C)C)O*]

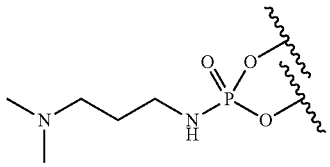 [SMILES: *OP(=O)(NCCCN(C)C)O*]

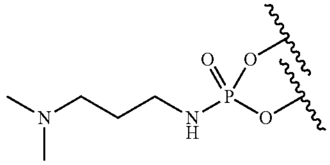 [SMILES: *OP(=O)(NCCCN(C)C)O*]

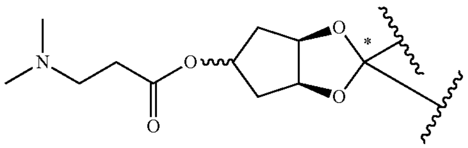

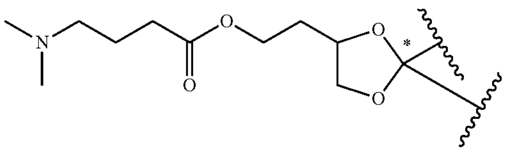

Some suitable hydrophobic tail groups include those depicted in Table 1C:

TABLE 1C
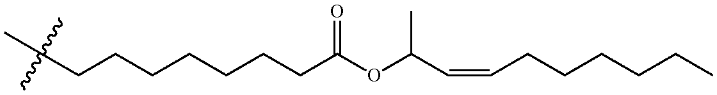 [SMILES: *CCCCCCCC(=O)OC(C)/C=C\CCCCCC]
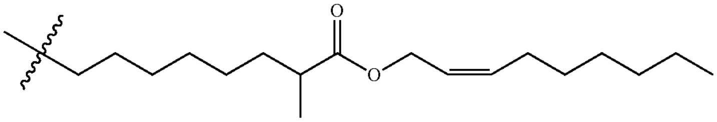 [SMILES: *CCCCCCC(C)C(=O)OC/C=C\CCCCCC]
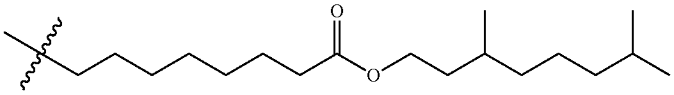 [SMILES: *CCCCCCCC(=O)OCCC(C)CCCC(C)C]
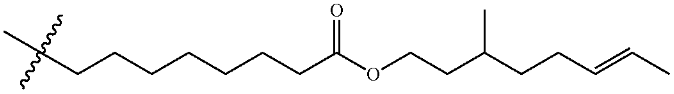 [SMILES: *CCCCCCCC(=O)OCCC(C)CC/C=C/C]
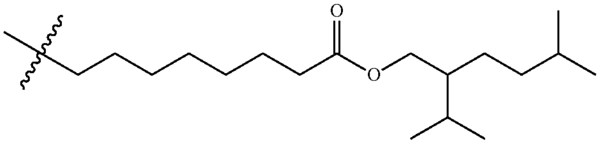 [SMILES: *CCCCCCCC(=O)OCC(CCC(C)C)C(C)C]
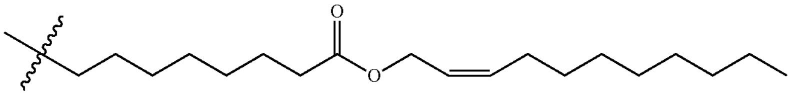 [SMILES: *CCCCCCCC(=O)OC/C=C\CCCCCCCC]
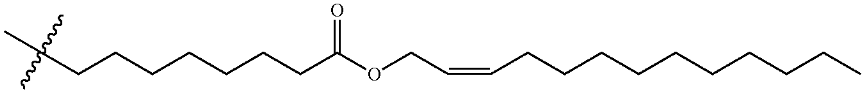 [SMILES: *CCCCCCCC(=O)OC/C=C\CCCCCCCCCC]
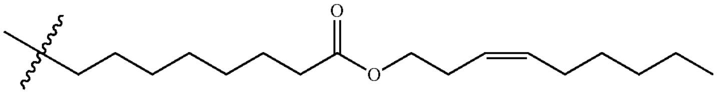 [SMILES: *CCCCCCCC(=O)OCC/C=C\CCCCC]
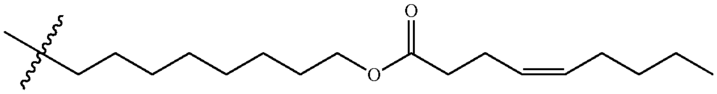 [SMILES: *CCCCCCCCOC(=O)CC/C=C\CCCC]
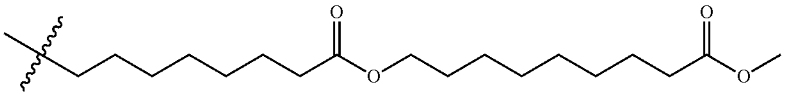 [SMILES: *CCCCCCCC(=O)OCCCCCCCCC(=O)OC]
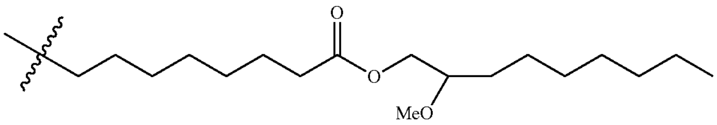 [SMILES: *CCCCCCCC(=O)OCC(CCCCCCC)OC]
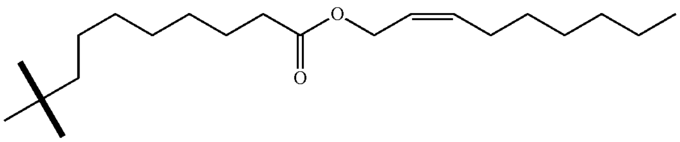
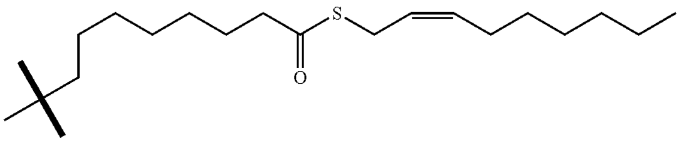

TABLE 1C-continued
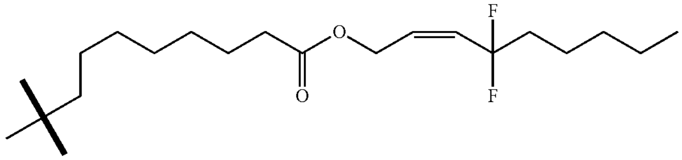
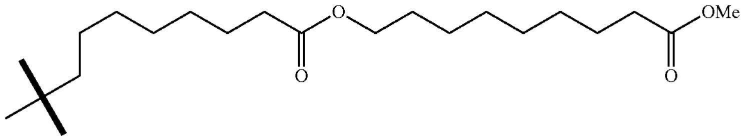
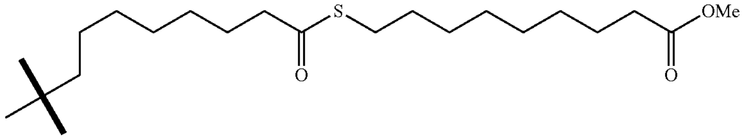
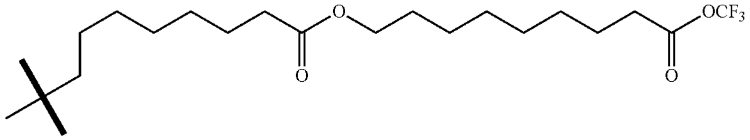
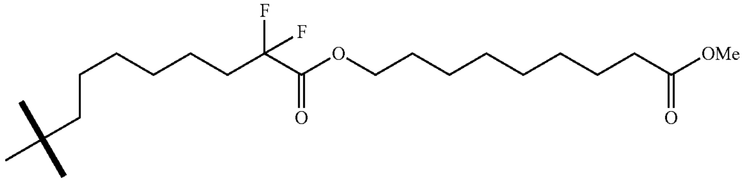
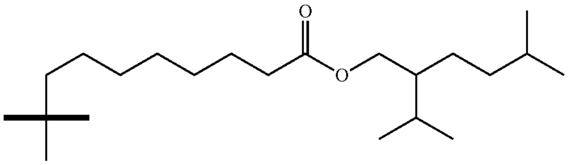
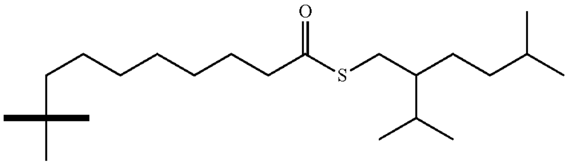
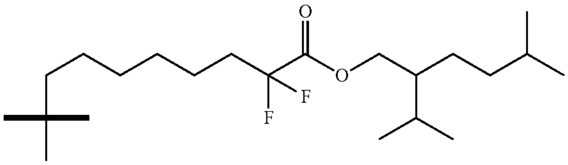
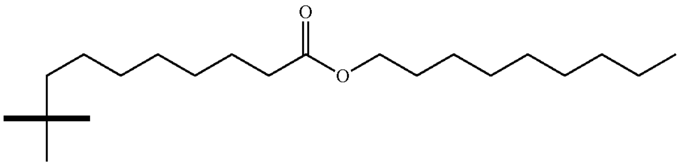

TABLE 1C-continued
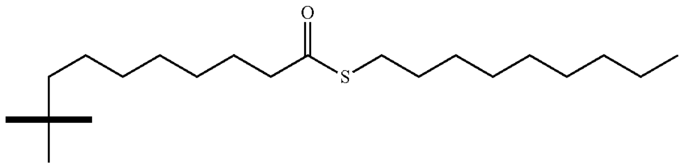
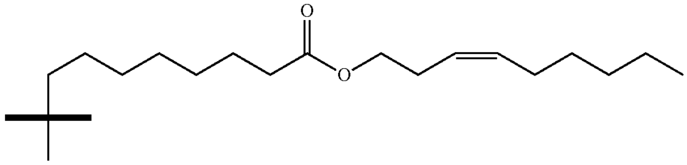
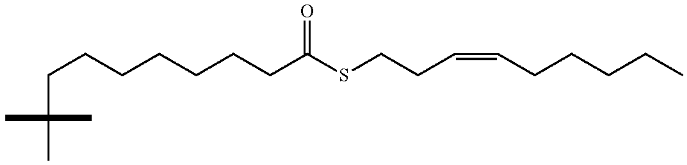
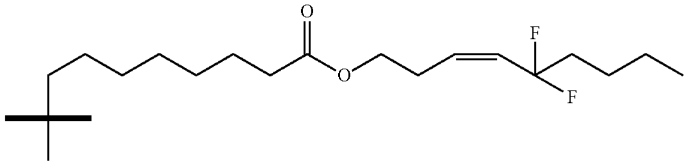
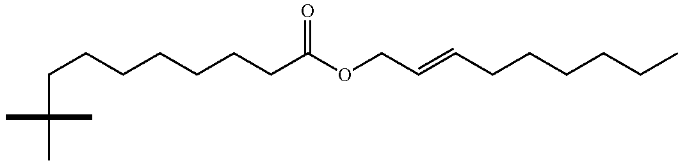
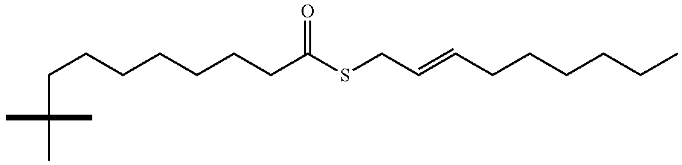
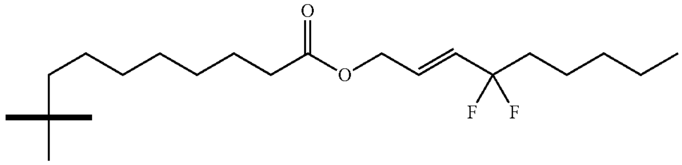
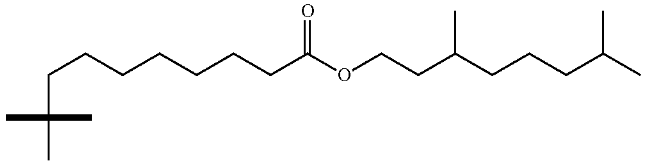
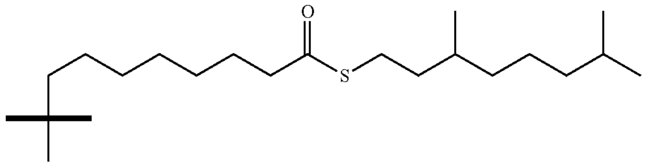

TABLE 1C-continued
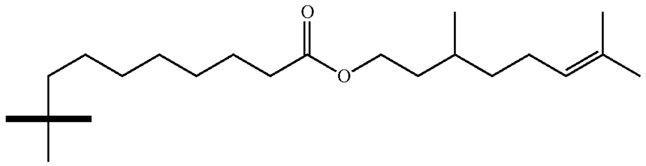
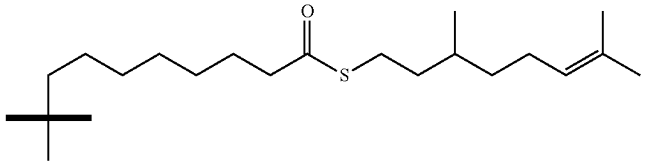
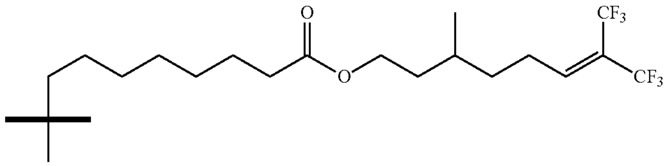
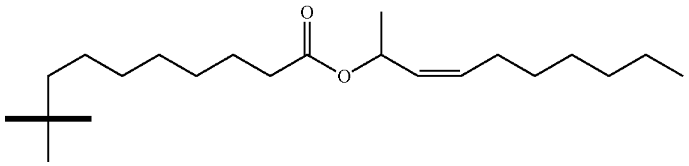
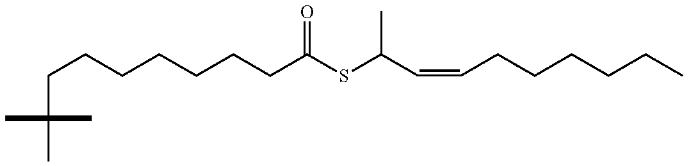
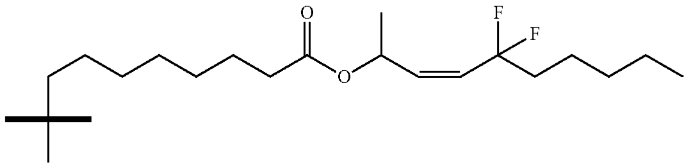
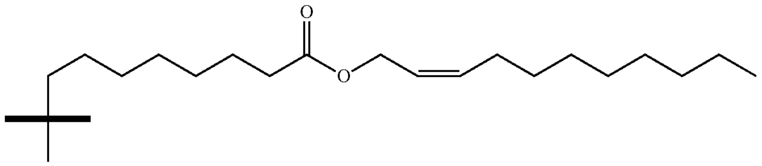
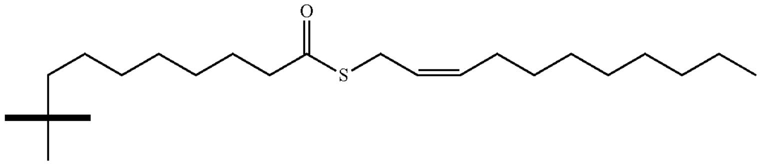
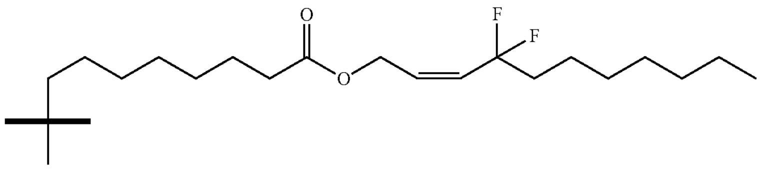

TABLE 1C-continued
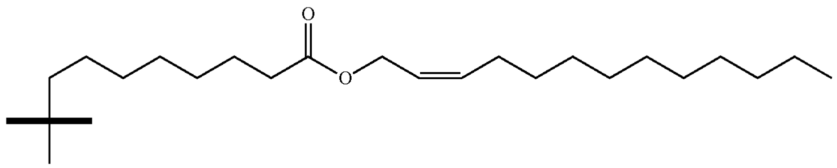
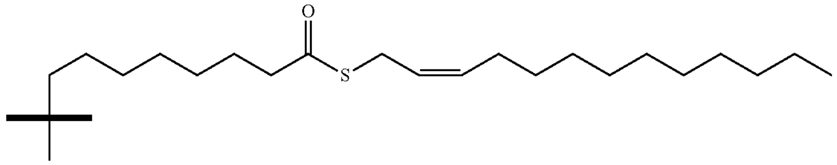
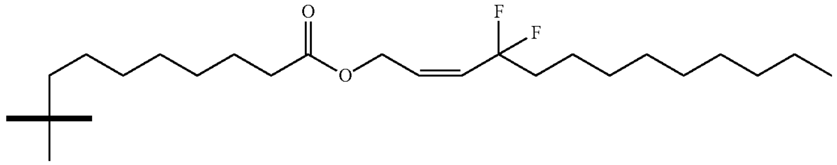
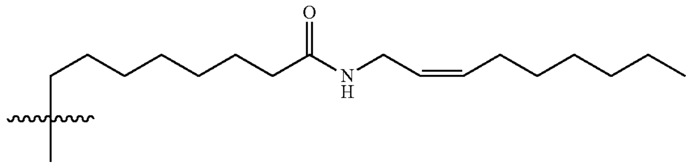 [SMILES: *CCCCCCCC(=O)NC/C=C\CCCCCC]
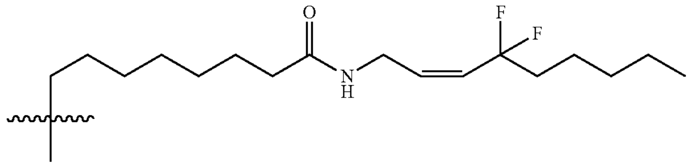 [SMILES: *CCCCCCCC(=O)NC/C=C\C(F)(F)CCCCC]
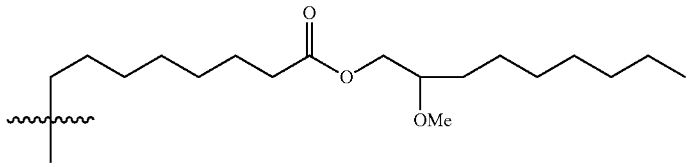 [SMILES: *CCCCCCCC(=O)OCC(CCCCCCC)OC]
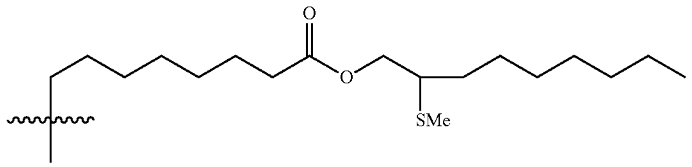 [SMILES: *CCCCCCCC(=O)OCC(CCCCCCC)SC]
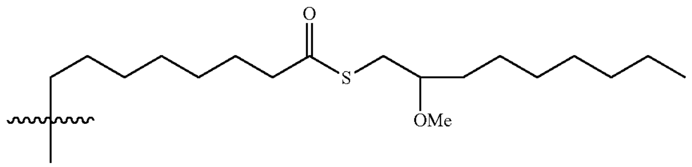
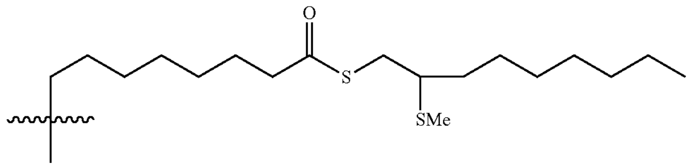 [SMILES: *CCCCCCCC(=O)SCC(CCCCCCC)SC]

TABLE 1C-continued

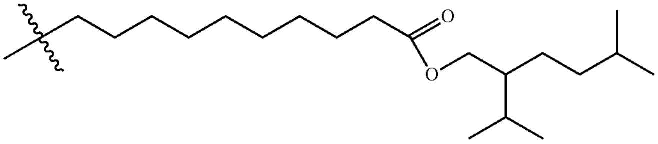 [SMILES: *CCCCCCCCCC(=O)OCC(CCC(C)C)C(C)C]

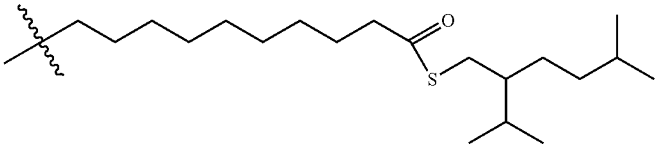 [SMILES: *CCCCCCCCCC(=O)SCC(CCC(C)C)C(C)C]

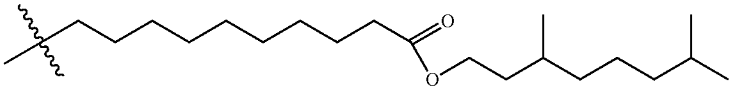

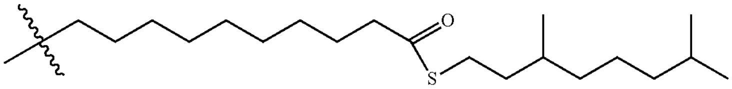 [SMILES: *CCCCCCCCCC(=O)OCCC(C)CCCC(C)C]

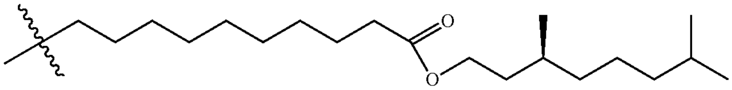 [SMILES: *CCCCCCCCCC(=O)OCC[C@@H](C)CCCC(C)C]

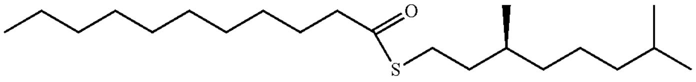 [SMILES: CCCCCCCCCCC(=O)SCC[C@@H](C)CCCC(C)C]

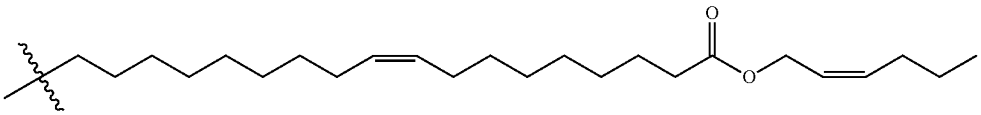 [SMILES: *CCCCCCCC/C=C\CCCCCCCC(=O)OC/C=C\CCC]

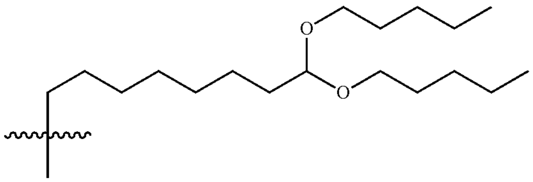 [SMILES: *CCCCCCCC(OCCCCC)OCCCCC]

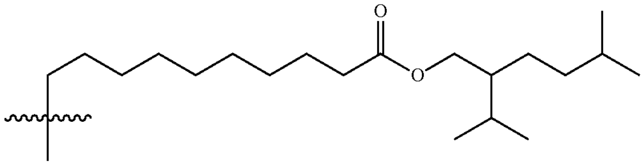 [SMILES: *CCCCCCCCCC(=O)OCC(CCC(C)C)C(C)C]

Other suitable tail groups includes those of the formula —$R^{12}$-$M^1$-$R^{13}$ where $R^{12}$ is a $C_4$-$C_{14}$ alkyl or $C_4$-$C_{14}$ alkenyl, $M^1$ is a biodegradable group as defined above, and $R^{13}$ is a branched alkyl or alkenyl (e.g., a $C_{10}$-$C_{20}$ alkyl or $C_{10}$-$C_{20}$ alkenyl), such that (i) the chain length of —$R^{12}$-$M^1$-$R^{13}$ is at most 21 atoms (i.e., the total length of the tail from the first carbon after the tertiary carbon (marked with an asterisk) to a terminus of the tail is at most 21), and (ii) the group —$R^{12}$-$M^1$-$R^{13}$ has at least 20 carbon atoms (e.g., at least 21 or 22 carbon atoms).

In one preferred embodiment, the chain length of —$R^{12}$-$M^1$-$R^{13}$ is at most 21 (e.g., at most 20). For example, the chain length can be from about 17 to about 24 or from about 18 to about 20.

In one embodiment, the total carbon atom content of each tail (—$R^{12}$-$M^1$-$R^{13}$) is from about 17 to about 26. For example, the total carbon atom content can be from about 19 to about 26 or from about 21 to about 26.

In one embodiment, the tail has the formula:

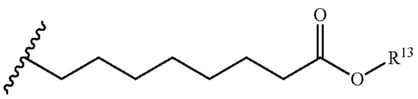

where $R^{13}$ is an alkyl or alkenyl group having from about 13 to about 17 carbon atoms, and the total carbon length of the tail from the first carbon (the leftmost carbon atom above) to a terminus of the tail is at most 20. Preferably, the tail has from about 22 to about 26 carbon atoms. In one embodiment, the maximum length of $R^{13}$ from its attachment point to the ester group of the compound is 12 carbon atoms (e.g., the maximum length can be 11 carbon atoms). In one preferred embodiment, the branch in the alkyl or alkenyl group is at the 6-position or later from the point of attachment of $R^{13}$ to the ester group. Suitable $R^{13}$ groups include, but are not limited to

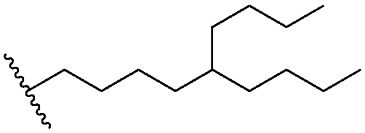

C13 (C21)
Length: C9 (18)

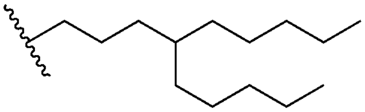

C14 (C22)
Length: C9 (18)

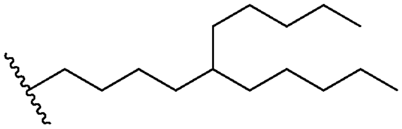

C15 (C23)
Length: C10 (19)

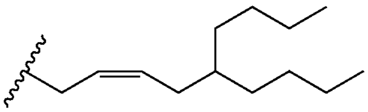

C13 (C21)
Length: C9 (18)

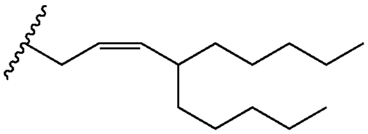

C14 (C22)
Length: C9 (18)

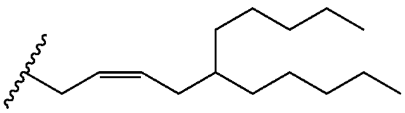

C15 (C23)
Length: C10 (19)

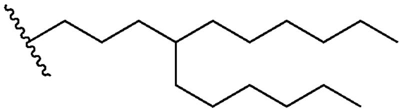

C16 (C24)
Length: C10 (19)

-continued

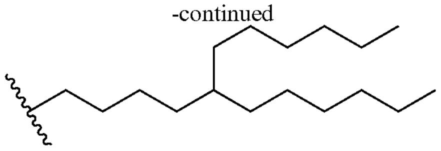

C17 (C25)
Length: C11 (20)

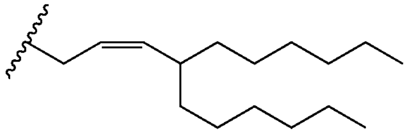

C16 (C24)
Length: C10 (19)

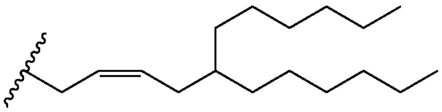

C17 (C25)
Length: C11 (20)

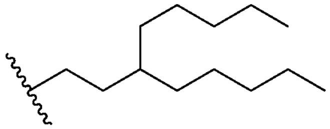

C13 (C21)
Length: C8 (17)

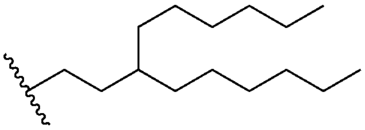

C15 (C23)
Length: C9 (18)

For example, the cationic lipid can be

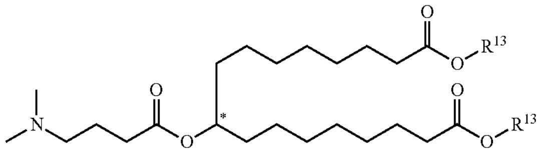

or a salt thereof (e.g., a pharmaceutically acceptable salt thereof), where $R^{13}$ is selected from the groups mentioned above.

Another example is a tail of the formula

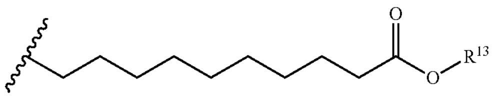

where $R^{13}$ is an alkyl or alkenyl group having from about 13 to about 15 carbon atoms, and the total carbon length of the tail from the first carbon (i.e., the leftmost carbon atom, which is attached to a tertiary carbon) to a terminus of the tail is at most 20. Preferably, the tail has from about 24 to about 26 carbon atoms. In one embodiment, the maximum length of $R^{13}$ from its attachment point to the ester group of the compound is 10 carbon atoms (e.g., the maximum length can be 9 carbon atoms). In one preferred embodiment, the branch in the alkyl or alkenyl group is at the δ-position or later from the point of attachment of $R^{13}$ to the ester group. Suitable $R^{13}$ groups include, but are not limited to

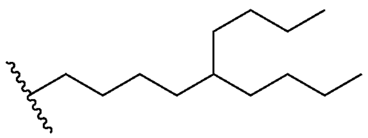

C13 (C23)
Length: C9 (20)

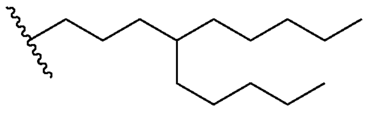

C14 (C24)
Length: C9 (20)

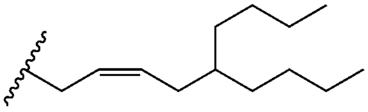

C13 (C23)
Length: C9 (20)

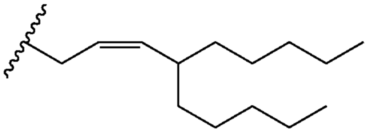

C14 (C24)
Length: C9 (20)

-continued

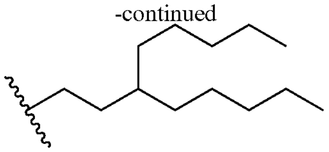

C13 (C24)
Length: C8 (19)

For example, the cationic lipid can be

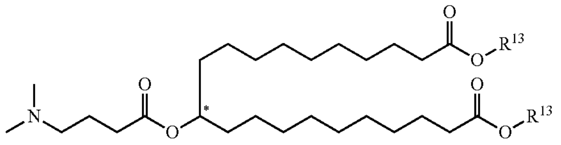

or a salt thereof (e.g., a pharmaceutically acceptable salt thereof), where $R^{13}$ is selected from the groups above.

The $R^{13}$ group may be derived from a natural product, such as dihydrocitgronellol, lavandulol, phytol, or dihydrophytol. In one embodiment, the $R^{13}$ group in the tails above is a dihydrocitronellol group (either as a racemic group or a chirally pure group):

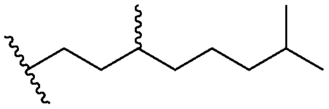 [SMILES: *CCC(C)CCCC(C)C]

For example, the cationic lipid having a dihydroitronellol group can be

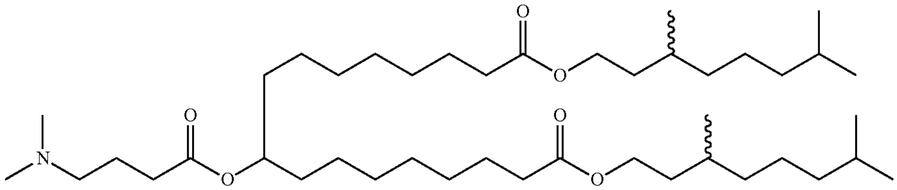

or

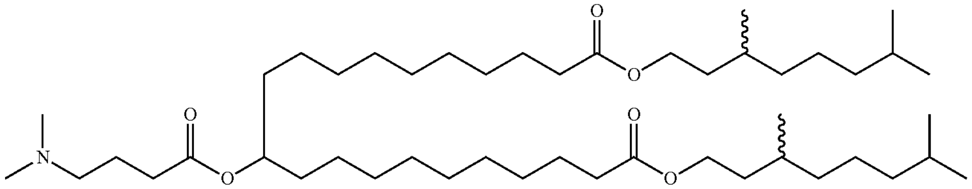

or a salt thereof.

In another embodiment, the $R^{13}$ group in the tails above is a lavandulol group or a homolog of it as shown below:

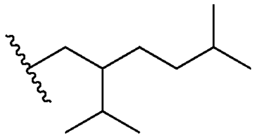

Lavandulol

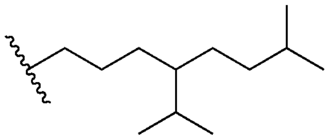

homolog

In another embodiment, the $R^{13}$ group in the tails above is a phytol or dihydrophytol group:

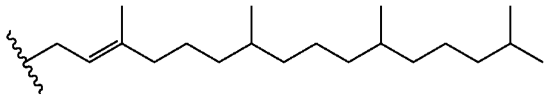

Phytol

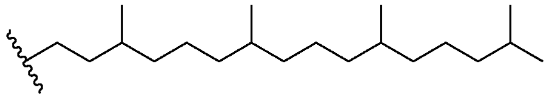

Dihydrophytol

For instance, the cationic lipid can be:

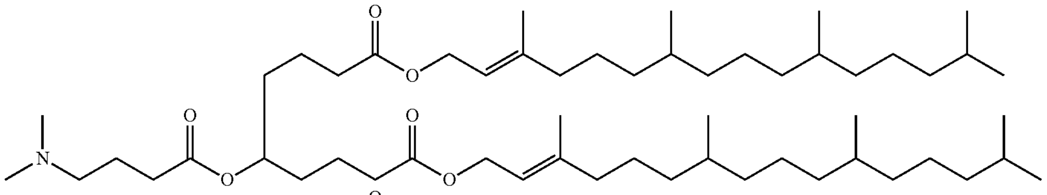

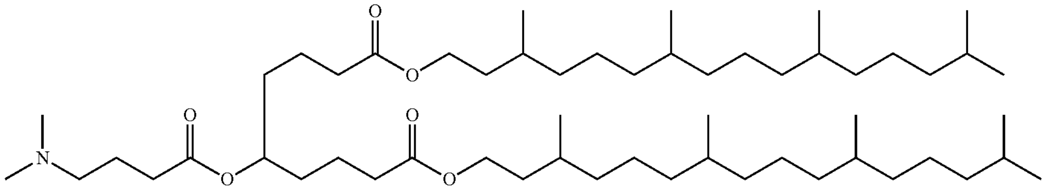

A cationic lipid of the formula:

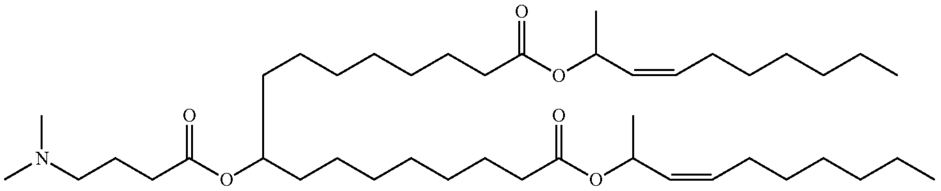 [SMILES: CCCCCC/C=C\C(C)OC(=O)CCCCCCCC(CCCCCCCC(=O)OC(C)/C=C\CCCCCC)OC(=O)CCCN(C)C]

can also be thought of as a combination of a headgroup, a linker moiety, and two parts of the hydrophobic chains as follows:

Hydrophobic chain I or Ia

Hydrophobic chain II or IIa

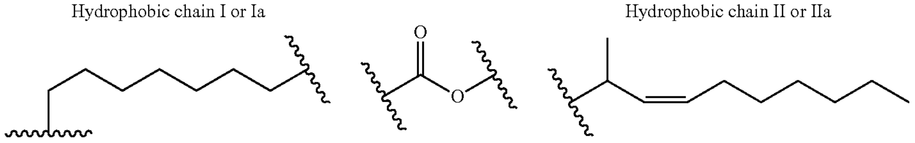

Biocleavable moiety I or Ia

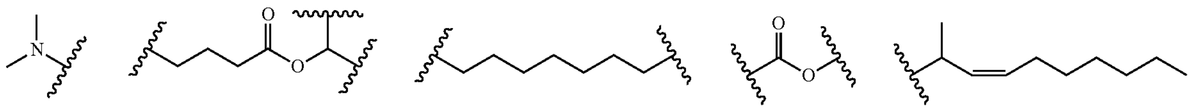

Head Group

Linker

Hydrophobic chain I

Hydrophobic chain II

-continued
Biocleavable moiety I
Various headgroups, linker moieties, and hydrophobic chains I and II are listed below. The present invention includes compounds composed of any combination of the head, linker, hydrophobic chain I, and hydrophobic chain II groups listed below.
TABLE 2A
| Representative headgroups |
| --- |
| 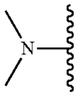 |
| 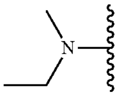 |
| 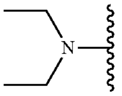 [SMILES: *N(CC)CC] |
| 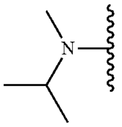 [SMILES: *N(C)C(C)C] |
| 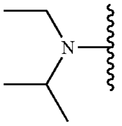 [SMILES: *N(CC)C(C)C] |
| 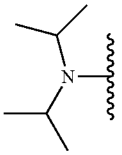 [SMILES: *N(C(C)C)C(C)C] |
| 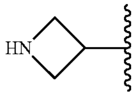 |
| 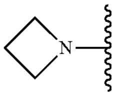 [SMILES: *N1CCC1] |
| 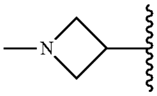 [SMILES: *C1CN(C)C1] |
| 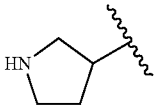 |
TABLE 2A-continued
| Representative headgroups |
| --- |
| 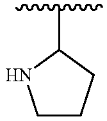 |
| 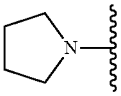 [SMILES: *N1CCCC1] |
| 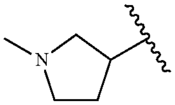 [SMILES: *C1CCN(C)C1] |
| 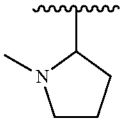 |
| 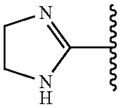 |
| 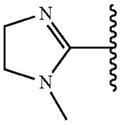 [SMILES: *C1=NCCN1C] |
| 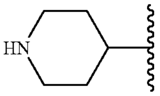 [SMILES: *C1CCNCC1] |
| 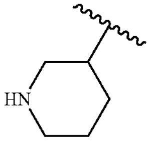 [SMILES: *C1CCCNC1] |
| 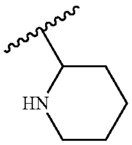 [SMILES: *C1CCCCN1] |
| 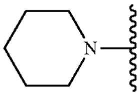 [SMILES: *N1CCCCC1] |
| 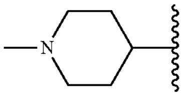 |

TABLE 2A-continued
Representative headgroups
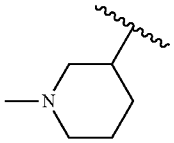 [SMILES: *C1CCCN(C)C1]
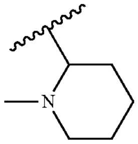 [SMILES: *C1CCCCN1C]
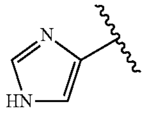
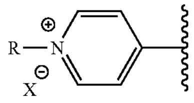
R = H, alkyl; X = halogen
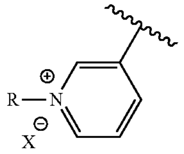
R = H, alkyl; X = halogen
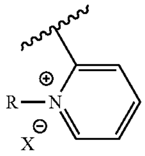
R = H, alkyl; X = halogen
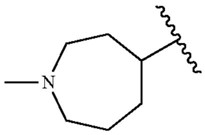 [SMILES: *C1CCCN(C)CC1]
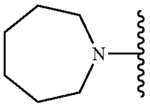 [SMILES: *N1CCCCCC1]
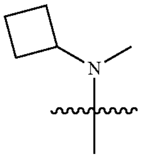 [SMILES: *N(C)C1CCC1]
TABLE 2A-continued
Representative headgroups
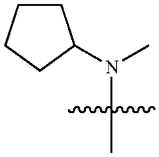 [SMILES: *N(C)C1CCCC1]
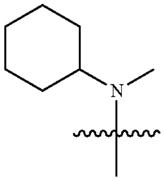 [SMILES: *N(C)C1CCCCC1]
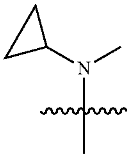 [SMILES: *N(C)C1CC1]
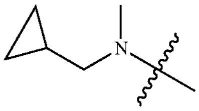 [SMILES: *N(C)CC1CC1]
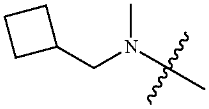 [SMILES: *N(C)CC1CCC1]
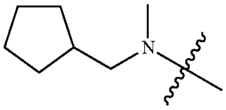 [SMILES: *N(C)CC1CCCC1]
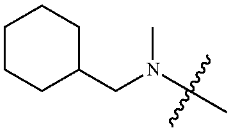 [SMILES: *N(C)CC1CCCCC1]
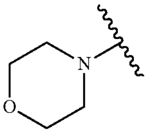 [SMILES: *N1CCOCC1]
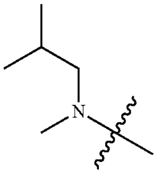 [SMILES: *N(C)CC(C)C]
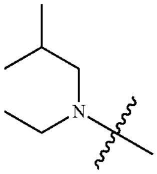 [SMILES: *N(CC)CC(C)C]

TABLE 2A-continued
| Representative headgroups |
| --- |
| 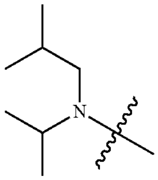 [SMILES: *N(CC(C)C)C(C)C] |
| 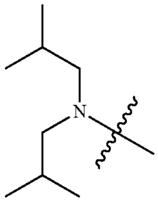 [SMILES: *N(CC(C)C)CC(C)C] |
| 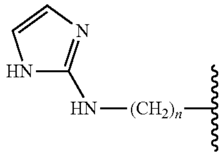 (where n is 0-5) |
| 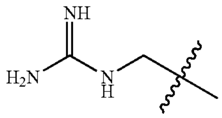 [SMILES: *CNC(=N)N] |
| 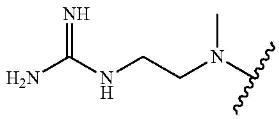 [SMILES: *N(C)CCNC(=N)N] |
| 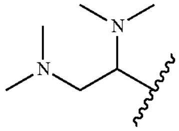 |
| 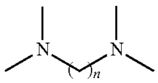 n = 0-6 |
| 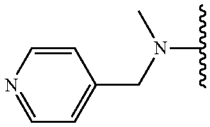 [SMILES: *N(C)Cc1ccncc1] |
| 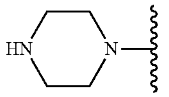 |
| 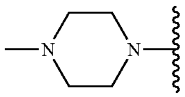 [SMILES: *N1CCN(C)CC1] |
TABLE 2A-continued
| Representative headgroups |
| --- |
| 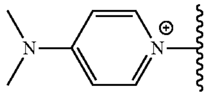 [SMILES: *[n+]1ccc(N(C)C)cc1] |
| 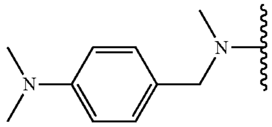 [SMILES: *N(C)Cc1ccc(N(C)C)cc1] |
| 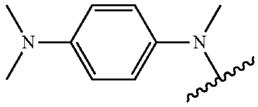 [SMILES: *N(C)c1ccc(N(C)C)cc1] |
| 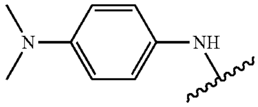 |
| 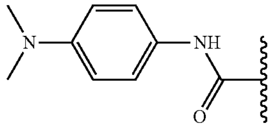 [SMILES: *C(=O)Nc1ccc(N(C)C)cc1] |
| 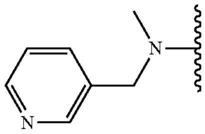 [SMILES: *N(C)Cc1cccnc1] |
| 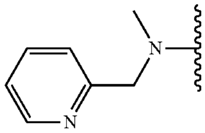 [SMILES: *N(C)Cc1ccccn1] |
| 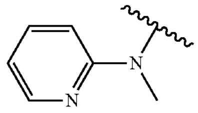 [SMILES: *N(C)c1ccccn1] |
| 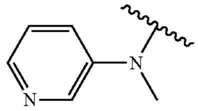 [SMILES: *N(C)c1cccnc1] |
| 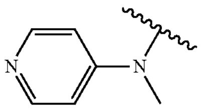 [SMILES: *N(C)c1ccncc1] |
TABLE 2B
| Representative linker groups |
| --- |
| 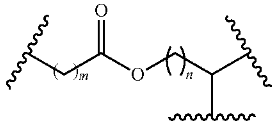 m = 1-5; n = 0-3 |

TABLE 2B-continued
Representative linker groups
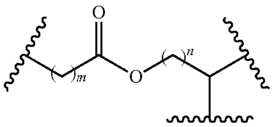
m = 1-5; n = 0-3
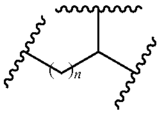
n = 0-5
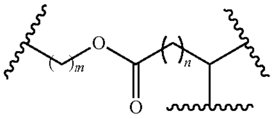
m = 0-5; n = 0-3
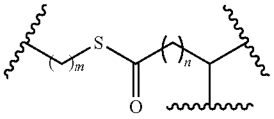
m = 0-5; n = 0-3
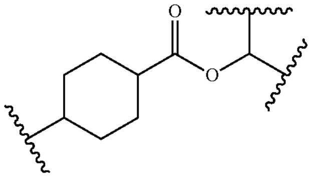 [SMILES: *C1CCC(C(=O)OC(*)*)CC1]
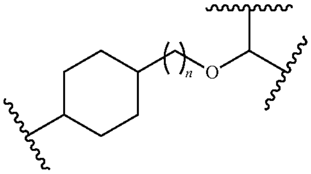
n = 0-3
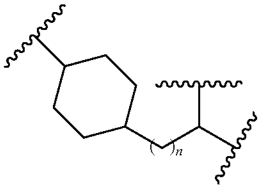
n = 0-3
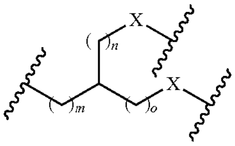
m = 1-4; n/o = 0-3
x = O or S
TABLE 2B-continued
Representative linker groups
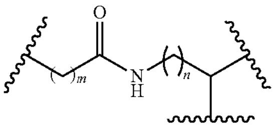
m = 0-5; n = 0-3
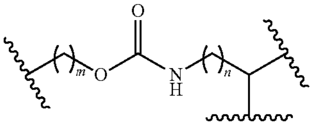
m = 0-5; n = 0-3
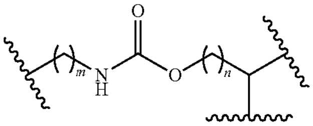
m = 0-5; n = 0-3
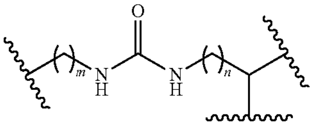
m = 0-5; n = 0-3
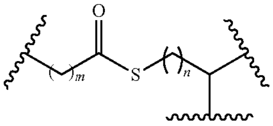
m = 0-5; n = 0-3
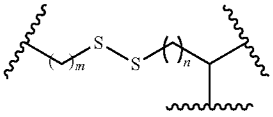
m = 0-5; n = 0-3
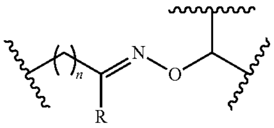
n = 0-5
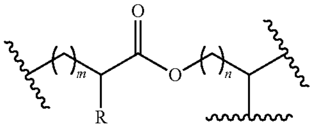
m = 1-4; N = 0-3
R = COOH, COOMe,
COOEt, CN, CONH2
CONHMe TABLE 2B-continued
| Representative linker groups |
| --- |
| 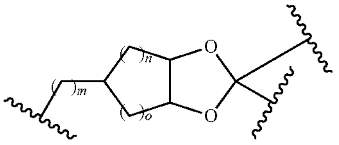<br>m = 1-4; n/o = 1-3 |
| 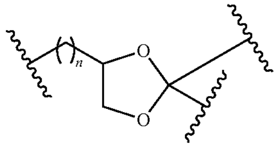<br>n = 1-5 |
| 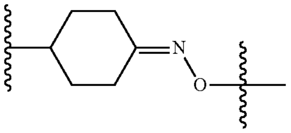 [SMILES: *ON=C1CCC(*)CC1] |
| 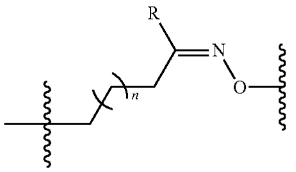<br>n = 0-5<br>R = H, Me, Et, Pr, allyl |
| 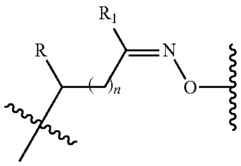<br>n = 0-5<br>R = Me, Et, Pr, allyl<br>R1 = Me, Et, Pr, allyl |
| 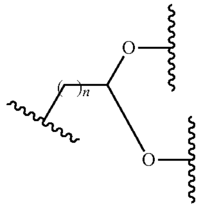<br>n = 0-6 |
| 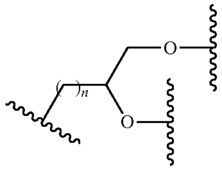<br>n = 0-6 |
TABLE 2B-continued
| Representative linker groups |
| --- |
| 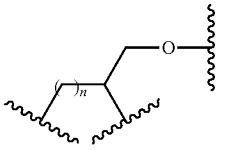<br>n = 0-6 |
| 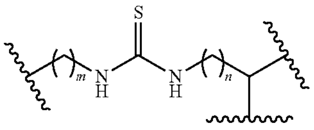<br>m = 0-5; n = 0-3 |
TABLE 2C
| Representative hydrophobic chain I and/or Ia, and combination thereof |
| --- |
| 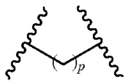<br>p = 0-15 |
| 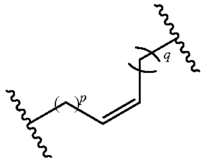<br>p = 0-15, q = 0-15 |
| 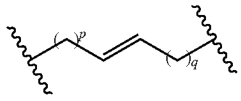<br>p = 0-15, q = 0-15 |
| 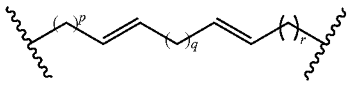<br>p = 0-15, q = 1-4, r = 0-15 |
| 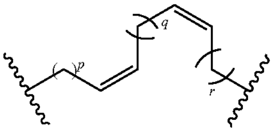<br>p = 0-15, q = 1-4, r = 0-15 |
| 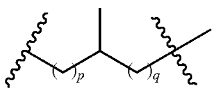<br>p = 0-15, q = 0-6 |

TABLE 2C-continued
Representative hydrophobic chain I and/or Ia, and combination thereof
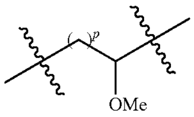
p = 0-15
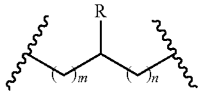
m = 0-4; n = 0-4;
R = Me, Et, Pr, iPr, Bu, iBu
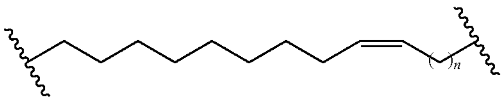
n = 1-7
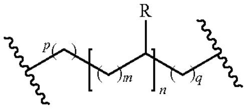
m = 1-4, n = 1-10, p = 0-15, q = 0-15
R = Me, Et, OMe
TABLE 2D
Representative biodegradable moieties I and/or Ia and combinations thereof
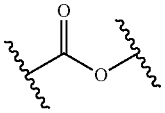 [SMILES: *OC(*)=O]
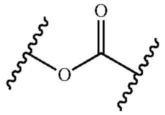 [SMILES: *OC(*)=O]
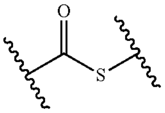 [SMILES: *SC(*)=O]
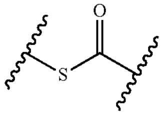 [SMILES: *SC(*)=O]
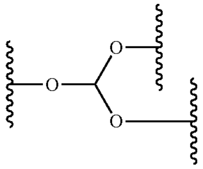 [SMILES: *OC(O*)O*]
TABLE 2D-continued
Representative biodegradable moieties I and/or Ia and combinations thereof
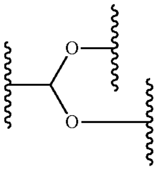 [SMILES: *OC(*)O*]
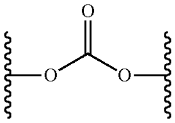 [SMILES: *OC(=O)O*]
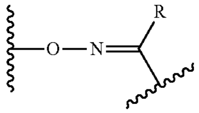
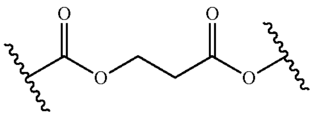 [SMILES: *OC(=O)CCOC(*)=O]
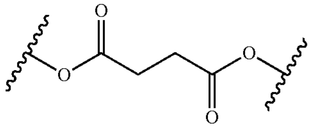 [SMILES: *OC(=O)CCC(=O)O*]
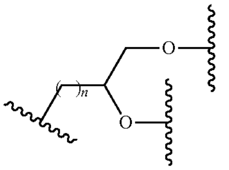
n = 0-6
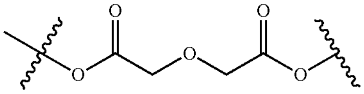 [SMILES: *OC(=O)CSCC(=O)O*]
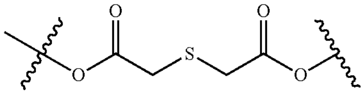
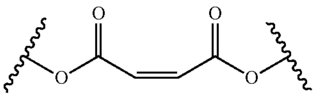 [SMILES: *OC(=O)/C=C\C(=O)O*]
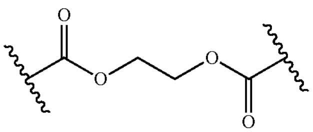 [SMILES: *C(=O)OCCOC(*)=O]
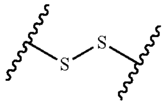 [SMILES: *SS*]

TABLE 2D-continued

| Representative biodegradable moieties I and/or Ia and combinations thereof |
|---|
| 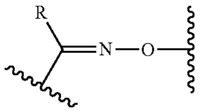 |
| 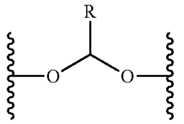 |
| R = H, Me, Et, cyclic alkyl, alicylic, aromatic |
| 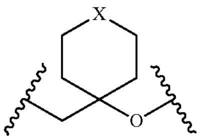 |
| X = $CH_2$, O. S |

TABLE 2E

| Representative hydrophobic chain II and/or IIa and combinations thereof |
|---|
| 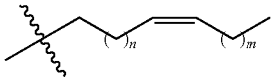 |
| n = 0-6; m = 0-16 |
| 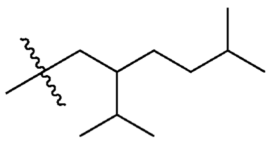 [SMILES: *CC(CCC(C)C)C(C)C] |
| 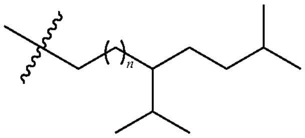 |
| n = 0-6 |
| 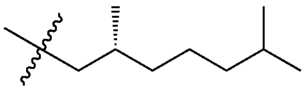 [SMILES: *C[C@H](C)CCCC(C)C] |
| 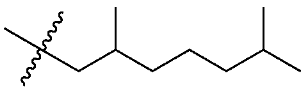 [SMILES: *CC(C)CCCC(C)C] |
| 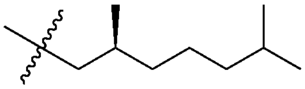 [SMILES: *C[C@@H](C)CCCC(C)C] |
| 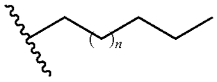 |
| n = 0-8 |

TABLE 2E-continued

| Representative hydrophobic chain II and/or IIa and combinations thereof |
|---|
| 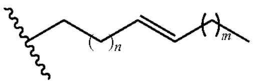 |
| n = 0-8; m = 0-6 |
| 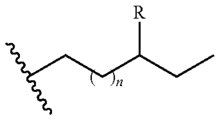 |
| n = 0-8<br>R = OMe, Me, Et, n-Pr, n-Bu |
| 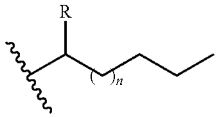 |
| n = 0-8<br>R = OMe, Me, Et, Pr |
| 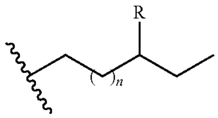 |
| n = 0-8<br>R = OMe, Me, Et, Pr |
| 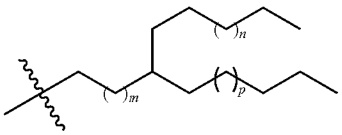 |
| m = 0-6; n = 0-6; p = 0-6 |
| 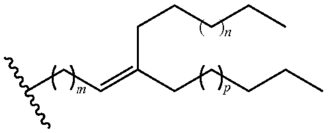 |
| m = 0-6; n = 0-6; p = 0-6 |
| 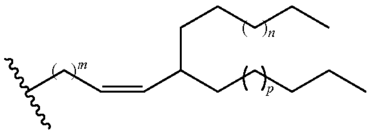 |
| m = 0-6; n = 0-6; p = 0-6 |
| 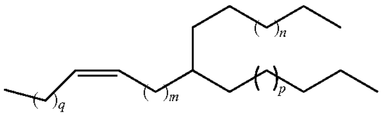 |
| m = 0-6; n = 0-6; p = 0-6; q = 0-6 |

Other cationic lipids of the present invention include those in Table 3 below. Each asymmetric carbon atom in the compounds below can be either chirally pure (R or S) or racemic. These cationic lipids as well as those in the working examples (such as Examples 36 and 37) are suitable for forming nucleic acid-lipid particles.

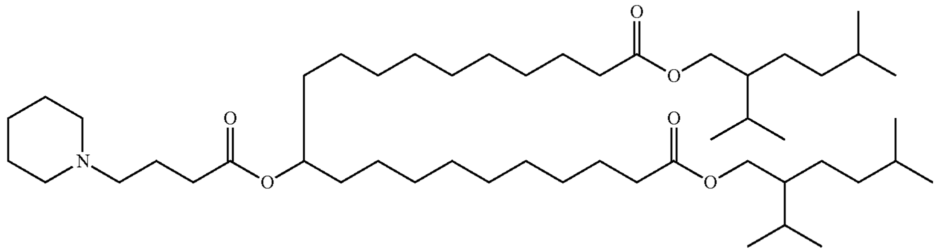 [SMILES: CC(C)CCC(COC(=O)CCCCCCCCCC(CCCCCCCCCC(=O)OCC(CCC(C)C)C(C)C)OC(=O)CCCN1CCCCC1)C(C)C]
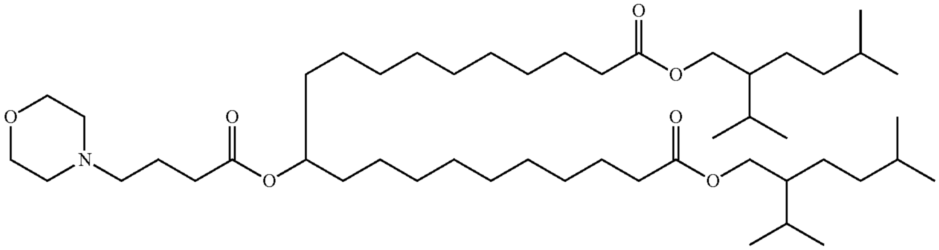 [SMILES: CC(C)CCC(COC(=O)CCCCCCCCCC(CCCCCCCCCC(=O)OCC(CCC(C)C)C(C)C)OC(=O)CCCN1CCOCC1)C(C)C]
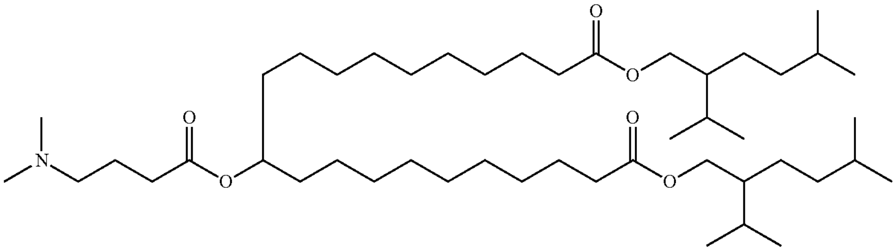 [SMILES: CC(C)CCC(COC(=O)CCCCCCCCCC(CCCCCCCCCC(=O)OCC(CCC(C)C)C(C)C)OC(=O)CCCN(C)C)C(C)C]
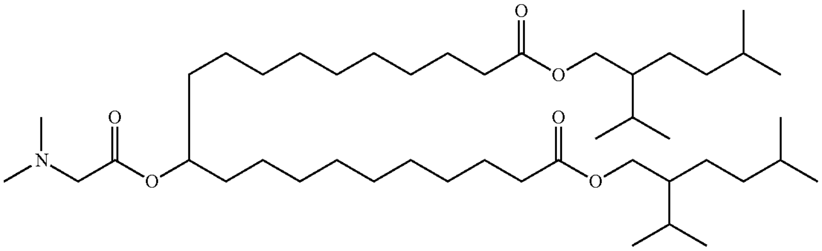 [SMILES: CC(C)CCC(COC(=O)CCCCCCCCCC(CCCCCCCCCC(=O)OCC(CCC(C)C)C(C)C)OC(=O)CN(C)C)C(C)C]
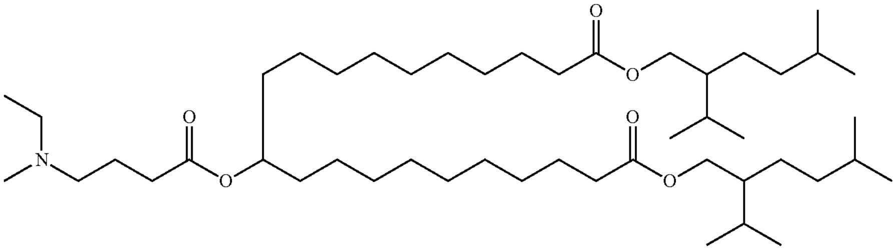 [SMILES: CCN(C)CCCC(=O)OC(CCCCCCCCCC(=O)OCC(CCC(C)C)C(C)C)CCCCCCCCCC(=O)OCC(CCC(C)C)C(C)C]
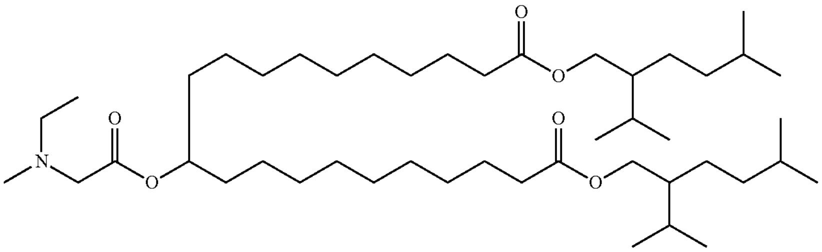 [SMILES: CCN(C)CC(=O)OC(CCCCCCCCCC(=O)OCC(CCC(C)C)C(C)C)CCCCCCCCCC(=O)OCC(CCC(C)C)C(C)C]

-continued
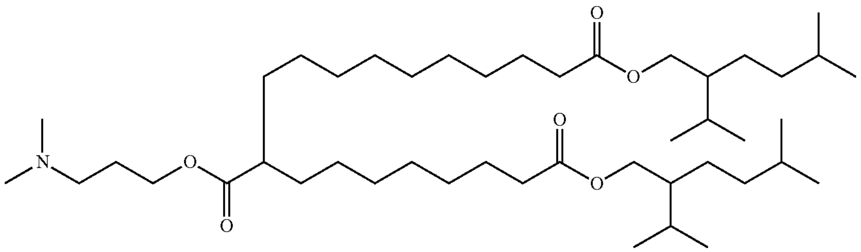 [SMILES: CC(C)CCC(COC(=O)CCCCCCCCCC(CCCCCCCC(=O)OCC(CCC(C)C)C(C)C)C(=O)OCCCN(C)C)C(C)C]
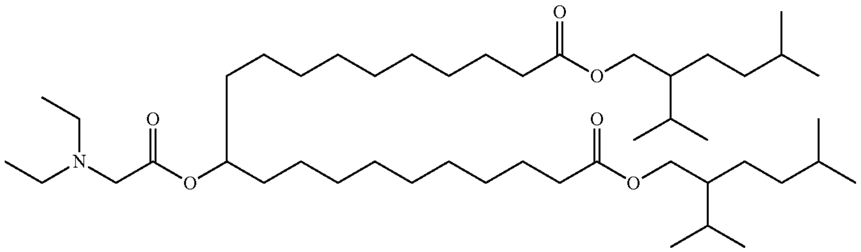 [SMILES: CCN(CC)CC(=O)OC(CCCCCCCCCC(=O)OCC(CCC(C)C)C(C)C)CCCCCCCCCC(=O)OCC(CCC(C)C)C(C)C]
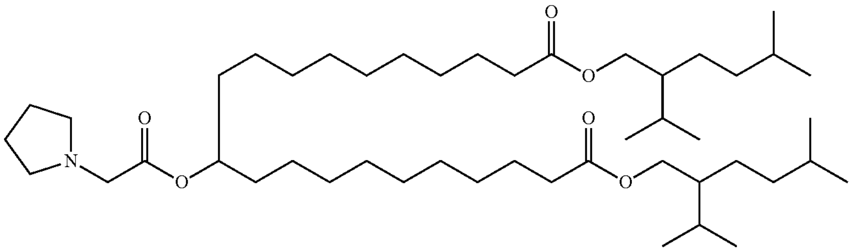 [SMILES: CC(C)CCC(COC(=O)CCCCCCCCCC(CCCCCCCCCC(=O)OCC(CCC(C)C)C(C)C)OC(=O)CN1CCCC1)C(C)C]
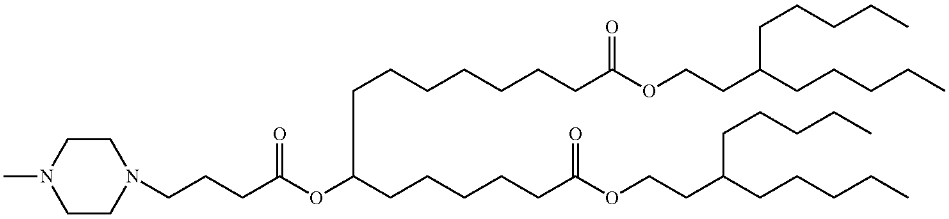 [SMILES: CCCCCC(CCCCC)CCOC(=O)CCCCCCCC(CCCCCC(=O)OCCC(CCCCC)CCCCC)OC(=O)CCCN1CCN(C)CC1]
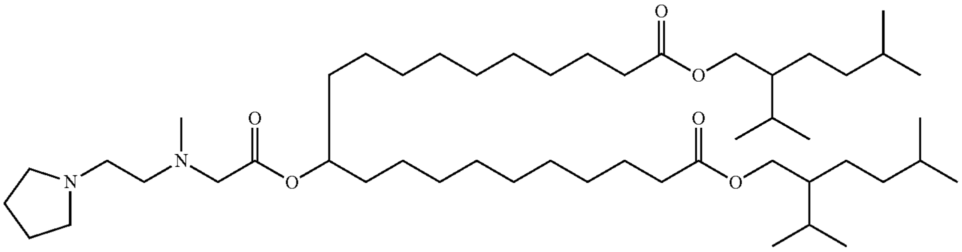 [SMILES: CC(C)CCC(COC(=O)CCCCCCCCCC(CCCCCCCCCC(=O)OCC(CCC(C)C)C(C)C)OC(=O)CN(C)CCN1CCCC1)C(C)C]
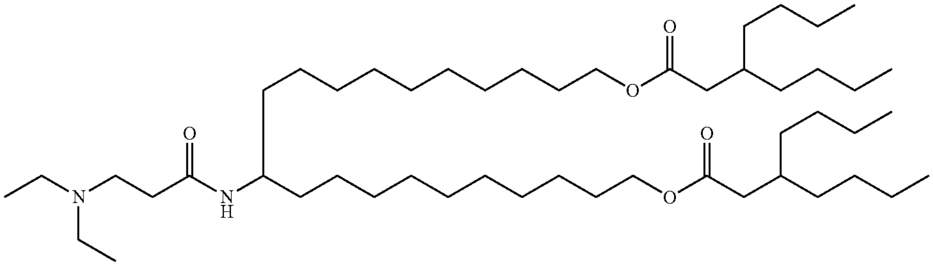 [SMILES: CCCCC(CCCC)CC(=O)OCCCCCCCCCCC(CCCCCCCCCCOC(=O)CC(CCCC)CCCC)NC(=O)CCN(CC)CC]

-continued
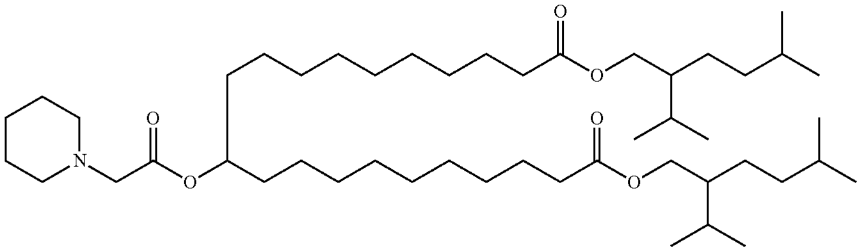 [SMILES: CC(C)CCC(COC(=O)CCCCCCCCCC(CCCCCCCCCC(=O)OCC(CCC(C)C)C(C)C)OC(=O)CN1CCCCC1)C(C)C]
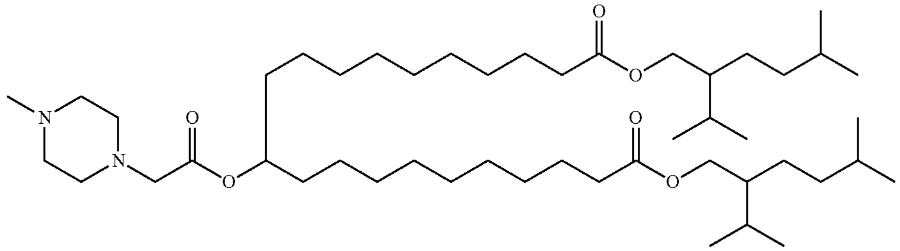 [SMILES: CC(C)CCC(COC(=O)CCCCCCCCCC(CCCCCCCCCC(=O)OCC(CCC(C)C)C(C)C)OC(=O)CN1CCN(C)CC1)C(C)C]
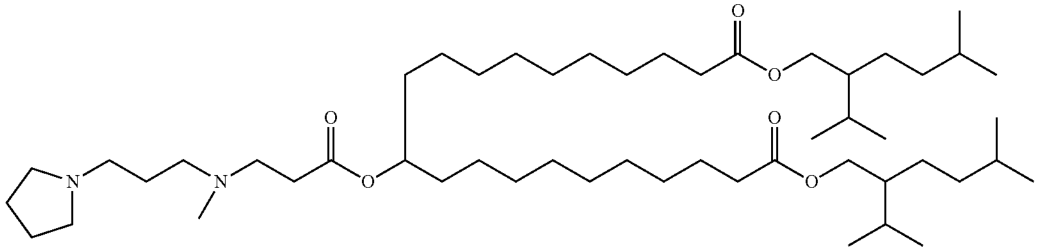 [SMILES: CC(C)CCC(COC(=O)CCCCCCCCCC(CCCCCCCCCC(=O)OCC(CCC(C)C)C(C)C)OC(=O)CCN(C)CCCN1CCCC1)C(C)C]
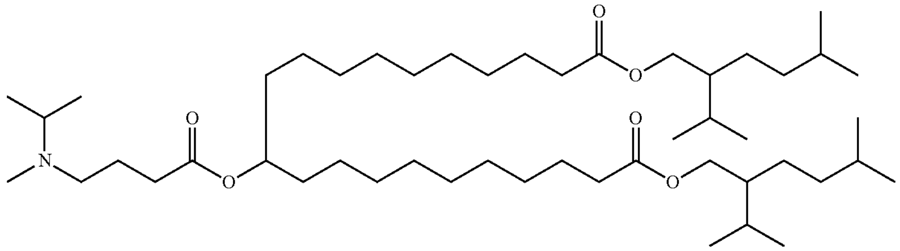 [SMILES: CC(C)CCC(COC(=O)CCCCCCCCCC(CCCCCCCCCC(=O)OCC(CCC(C)C)C(C)C)OC(=O)CCCN(C)C(C)C)C(C)C]
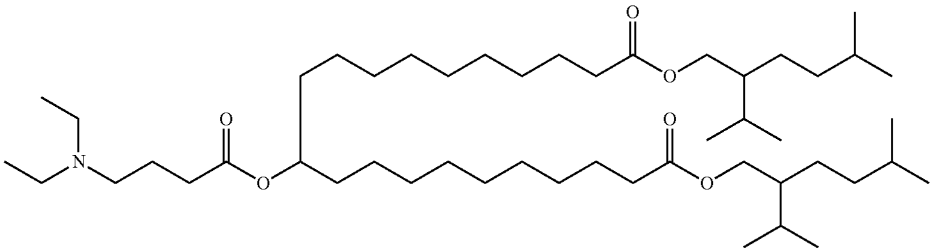 [SMILES: CCN(CC)CCCC(=O)OC(CCCCCCCCCC(=O)OCC(CCC(C)C)C(C)C)CCCCCCCCCC(=O)OCC(CCC(C)C)C(C)C]
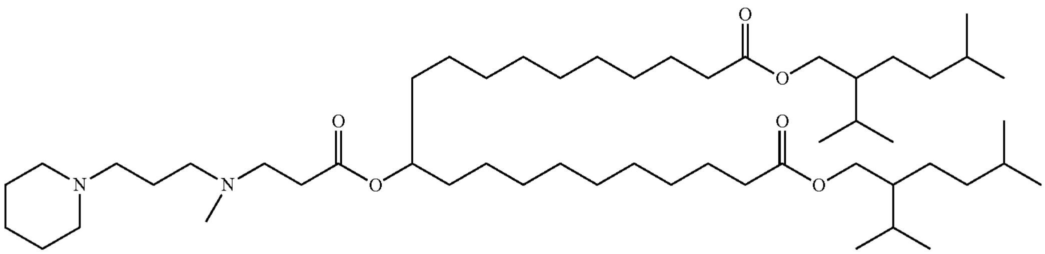 [SMILES: CC(C)CCC(COC(=O)CCCCCCCCCC(CCCCCCCCCC(=O)OCC(CCC(C)C)C(C)C)OC(=O)CCN(C)CCCN1CCCCC1)C(C)C]

-continued
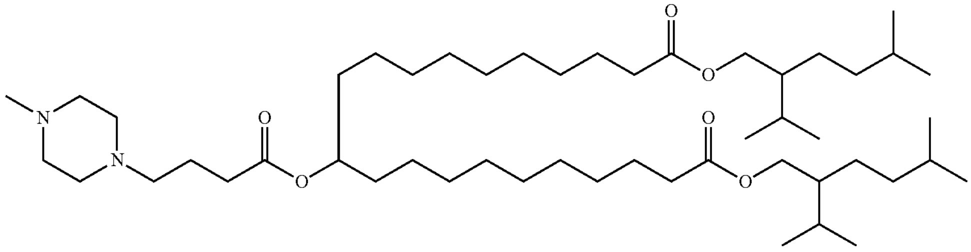 [SMILES: CC(C)CCC(COC(=O)CCCCCCCCCC(CCCCCCCCCC(=O)OCC(CCC(C)C)C(C)C)OC(=O)CCCN1CCN(C)CC1)C(C)C]
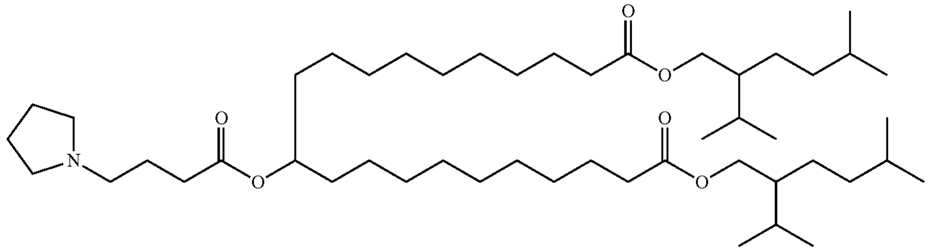 [SMILES: CC(C)CCC(COC(=O)CCCCCCCCCC(CCCCCCCCCC(=O)OCC(CCC(C)C)C(C)C)OC(=O)CCCN1CCCC1)C(C)C]
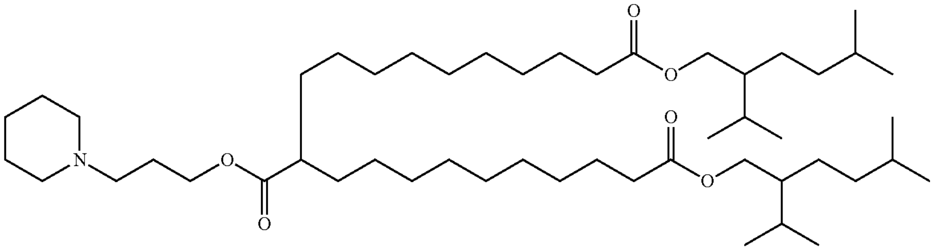 [SMILES: CC(C)CCC(COC(=O)CCCCCCCCCC(CCCCCCCCCC(=O)OCC(CCC(C)C)C(C)C)C(=O)OCCCN1CCCCC1)C(C)C]
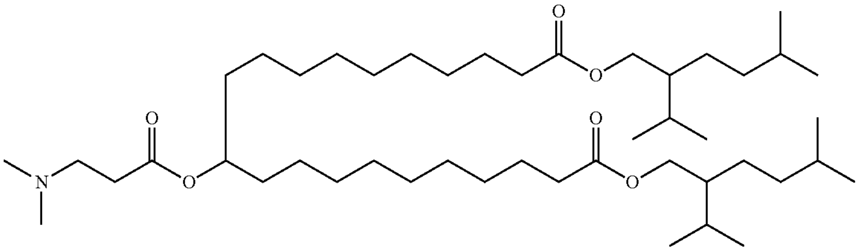 [SMILES: CC(C)CCC(COC(=O)CCCCCCCCCC(CCCCCCCCCC(=O)OCC(CCC(C)C)C(C)C)OC(=O)CCN(C)C)C(C)C]
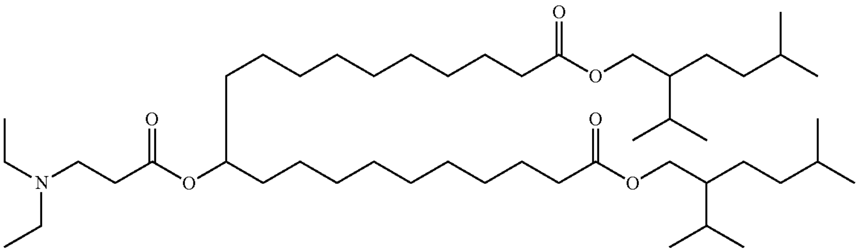 [SMILES: CCN(CC)CCC(=O)OC(CCCCCCCCCC(=O)OCC(CCC(C)C)C(C)C)CCCCCCCCCC(=O)OCC(CCC(C)C)C(C)C]
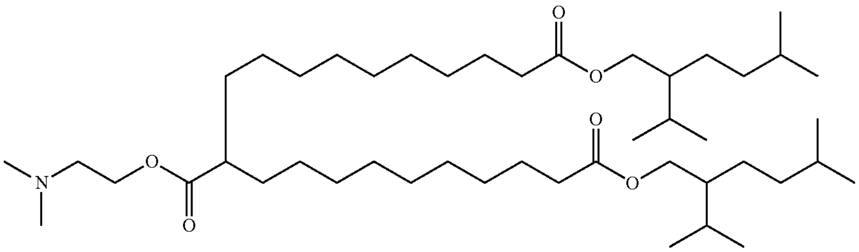 [SMILES: CC(C)CCC(COC(=O)CCCCCCCCCC(CCCCCCCCCC(=O)OCC(CCC(C)C)C(C)C)C(=O)OCCN(C)C)C(C)C]

-continued
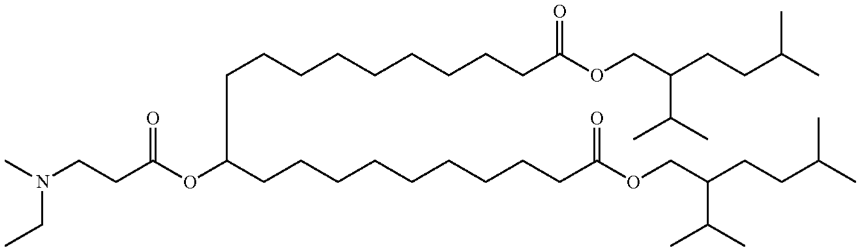 [SMILES: CCN(C)CCC(=O)OC(CCCCCCCCCC(=O)OCC(CCC(C)C)C(C)C)CCCCCCCCCC(=O)OCC(CCC(C)C)C(C)C]
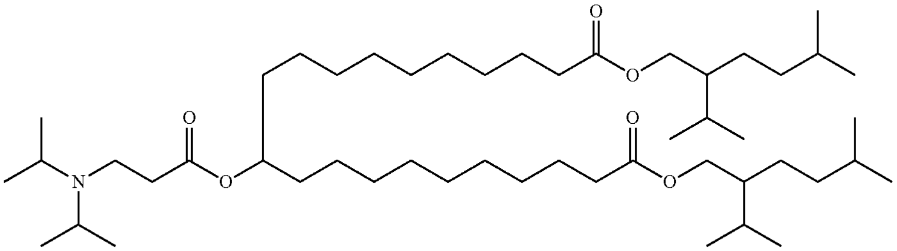 [SMILES: CC(C)CCC(COC(=O)CCCCCCCCCC(CCCCCCCCCC(=O)OCC(CCC(C)C)C(C)C)OC(=O)CCN(C(C)C)C(C)C)C(C)C]
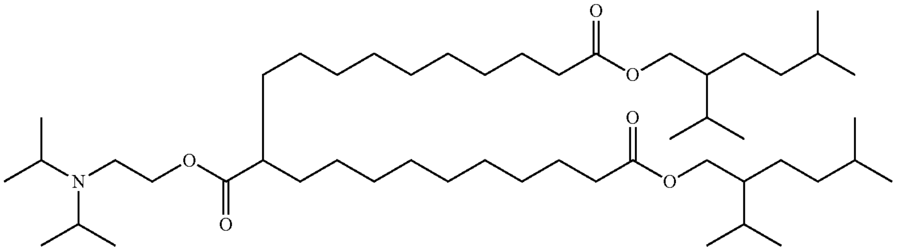 [SMILES: CC(C)CCC(COC(=O)CCCCCCCCCC(CCCCCCCCCC(=O)OCC(CCC(C)C)C(C)C)C(=O)OCCN(C(C)C)C(C)C)C(C)C]
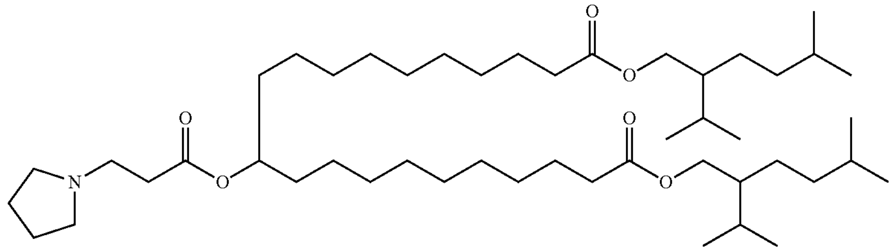 [SMILES: CC(C)CCC(COC(=O)CCCCCCCCCC(CCCCCCCCCC(=O)OCC(CCC(C)C)C(C)C)OC(=O)CCN1CCCC1)C(C)C]
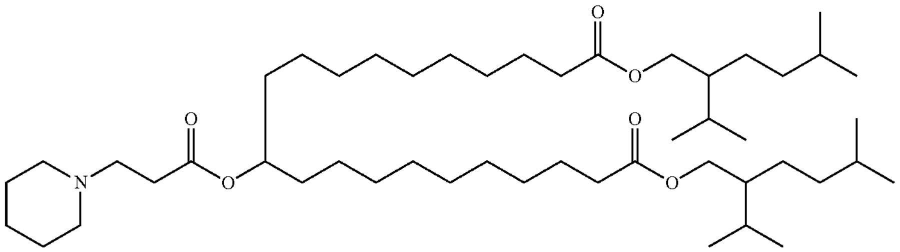 [SMILES: CC(C)CCC(COC(=O)CCCCCCCCCC(CCCCCCCCCC(=O)OCC(CCC(C)C)C(C)C)OC(=O)CCN1CCCCC1)C(C)C]
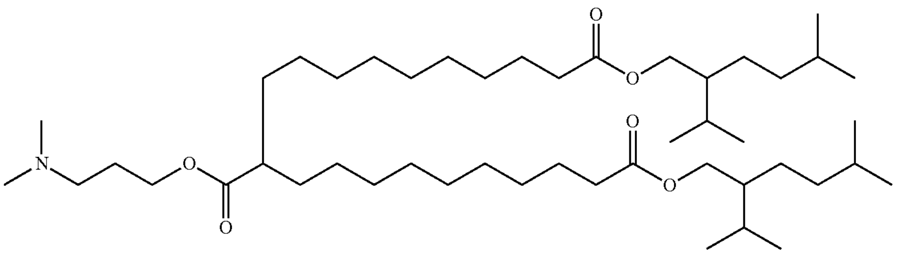 [SMILES: CC(C)CCC(COC(=O)CCCCCCCCCC(CCCCCCCCCC(=O)OCC(CCC(C)C)C(C)C)C(=O)OCCCN(C)C)C(C)C]

-continued
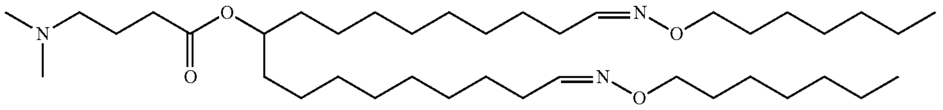 [SMILES: CCCCCCCO/N=C\CCCCCCCCC(CCCCCCCC/C=N\OCCCCCCC)OC(=O)CCCN(C)C]
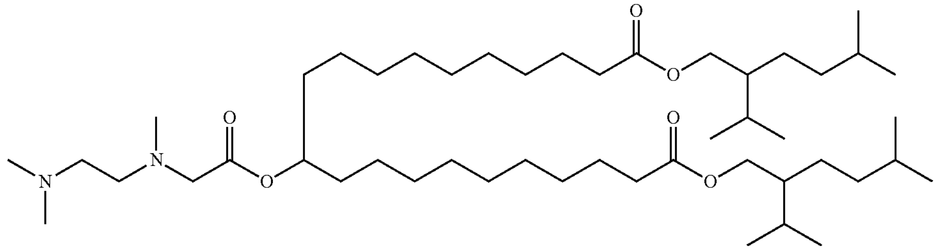 [SMILES: CC(C)CCC(COC(=O)CCCCCCCCCC(CCCCCCCCCC(=O)OCC(CCC(C)C)C(C)C)OC(=O)CN(C)CCN(C)C)C(C)C]
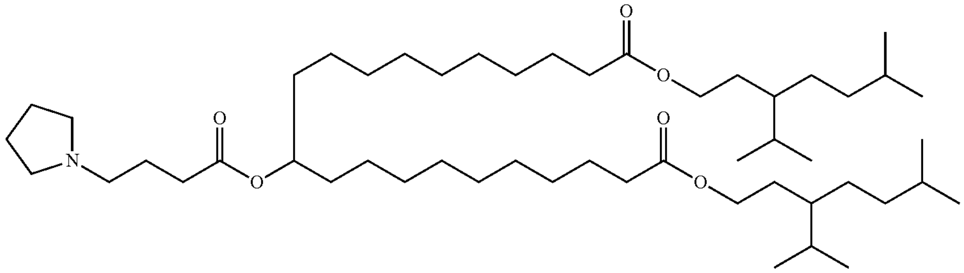 [SMILES: CC(C)CCC(CCOC(=O)CCCCCCCCCC(CCCCCCCCCC(=O)OCCC(CCC(C)C)C(C)C)OC(=O)CCCN1CCCC1)C(C)C]
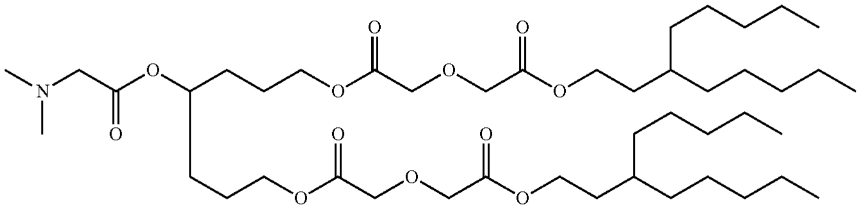 [SMILES: CCCCCC(CCCCC)CCOC(=O)COCC(=O)OCCCC(CCCOC(=O)COCC(=O)OCCC(CCCCC)CCCCC)OC(=O)CN(C)C]
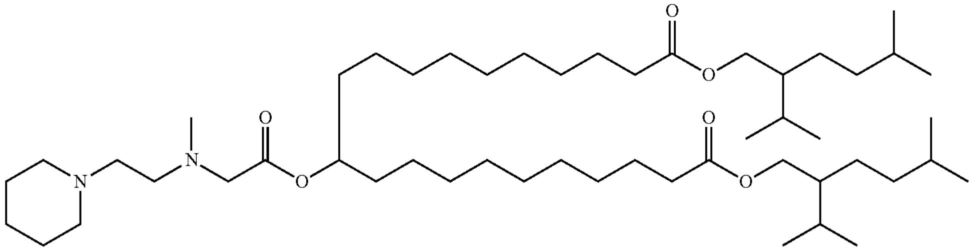 [SMILES: CC(C)CCC(COC(=O)CCCCCCCCCC(CCCCCCCCCC(=O)OCC(CCC(C)C)C(C)C)OC(=O)CN(C)CCN1CCCCC1)C(C)C]
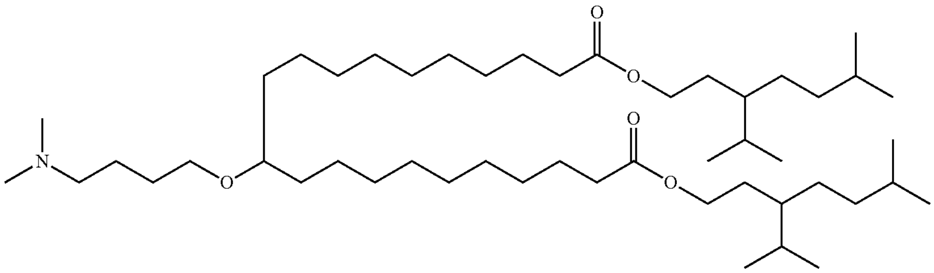 [SMILES: CC(C)CCC(CCOC(=O)CCCCCCCCCC(CCCCCCCCCC(=O)OCCC(CCC(C)C)C(C)C)OCCCCN(C)C)C(C)C]
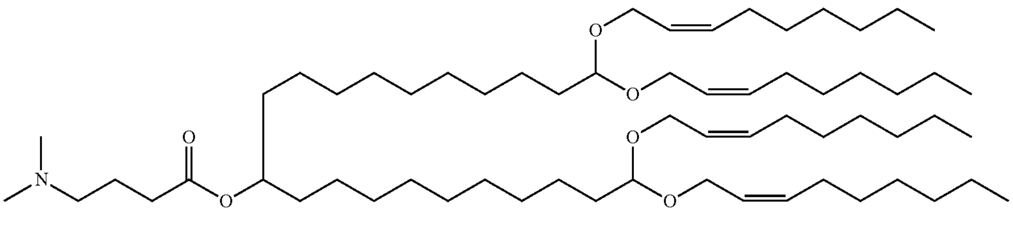 [SMILES: CCCCCC/C=C\COC(CCCCCCCCCC(CCCCCCCCCC(OC/C=C\CCCCCC)OC/C=C\CCCCCC)OC(=O)CCCN(C)C)OC/C=C\CCCCCC]

-continued
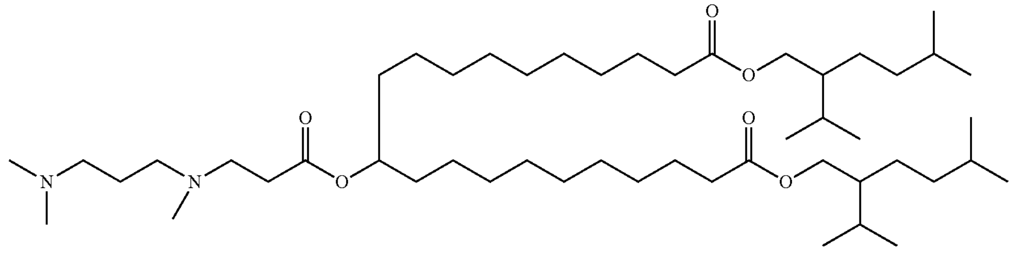 [SMILES: CC(C)CCC(COC(=O)CCCCCCCCCC(CCCCCCCCCC(=O)OCC(CCC(C)C)C(C)C)OC(=O)CCN(C)CCCN(C)C)C(C)C]
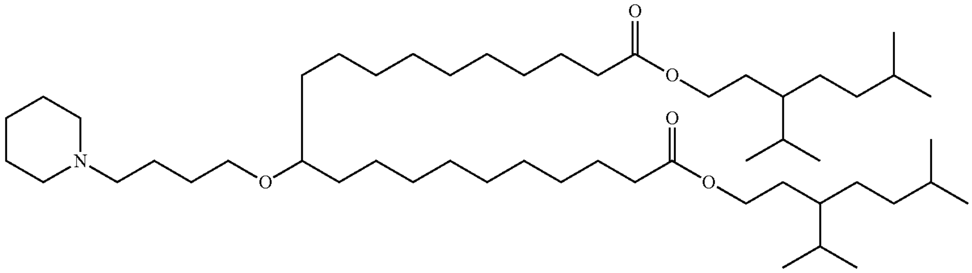 [SMILES: CC(C)CCC(CCOC(=O)CCCCCCCCCC(CCCCCCCCCC(=O)OCCC(CCC(C)C)C(C)C)OCCCCN1CCCCC1)C(C)C]
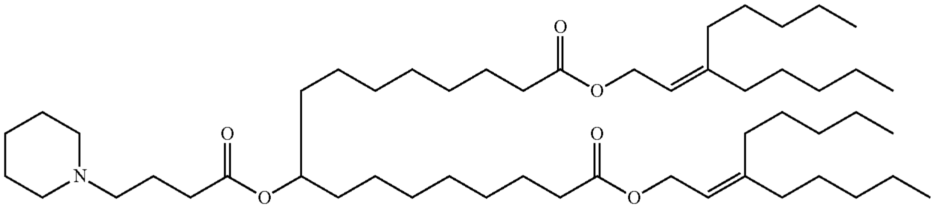 [SMILES: CCCCCC(=CCOC(=O)CCCCCCCC(CCCCCCCC(=O)OCC=C(CCCCC)CCCCC)OC(=O)CCCN1CCCCC1)CCCCC]
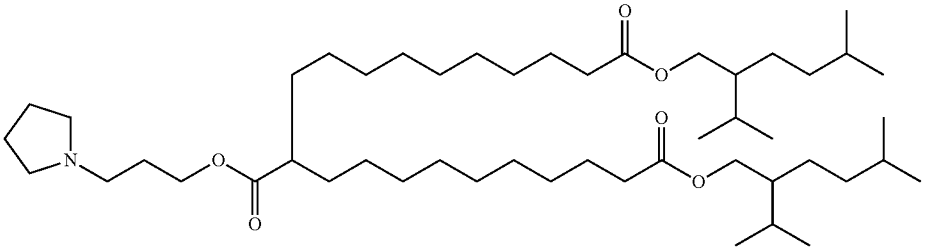 [SMILES: CC(C)CCC(COC(=O)CCCCCCCCCC(CCCCCCCCCC(=O)OCC(CCC(C)C)C(C)C)C(=O)OCCCN1CCCC1)C(C)C]
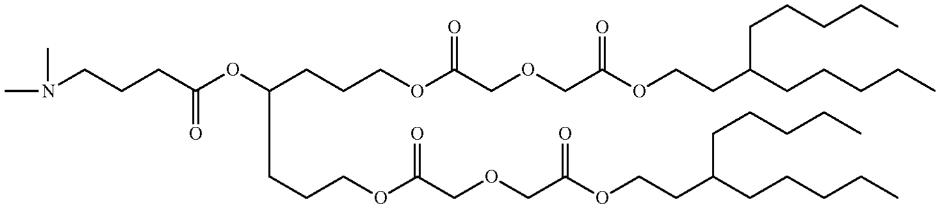 [SMILES: CCCCCC(CCCCC)CCOC(=O)COCC(=O)OCCCC(CCCOC(=O)COCC(=O)OCCC(CCCCC)CCCCC)OC(=O)CCCN(C)C]
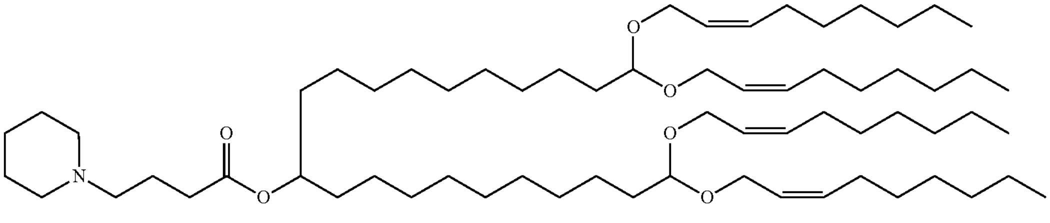 [SMILES: CCCCCC/C=C\COC(CCCCCCCCCC(CCCCCCCCCC(OC/C=C\CCCCCC)OC/C=C\CCCCCC)OC(=O)CCCN1CCCCC1)OC/C=C\CCCCCC]

-continued
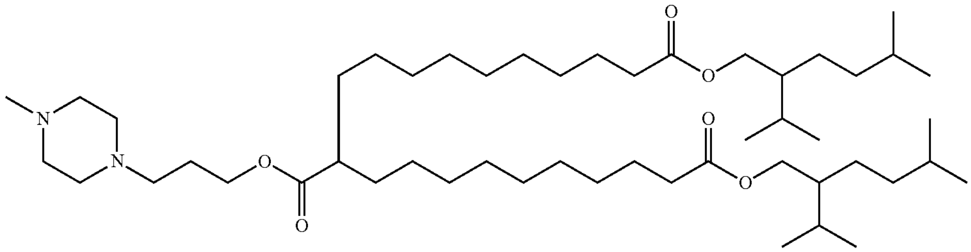 [SMILES: CC(C)CCC(COC(=O)CCCCCCCCCC(CCCCCCCCCC(=O)OCC(CCC(C)C)C(C)C)C(=O)OCCCN1CCN(C)CC1)C(C)C]
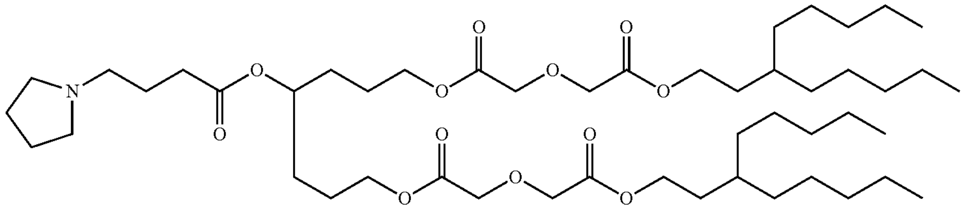 [SMILES: CCCCCC(CCCCC)CCOC(=O)COCC(=O)OCCCC(CCCOC(=O)COCC(=O)OCCC(CCCCC)CCCCC)OC(=O)CCCN1CCCC1]
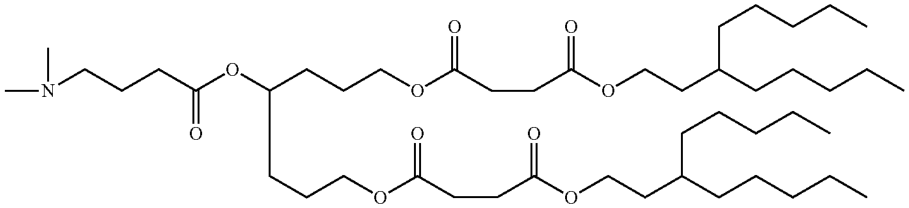 [SMILES: CCCCCC(CCCCC)CCOC(=O)CCC(=O)OCCCC(CCCOC(=O)CCC(=O)OCCC(CCCCC)CCCCC)OC(=O)CCCN(C)C]
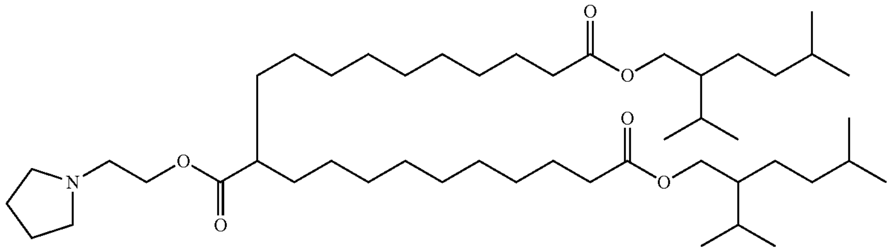 [SMILES: CC(C)CCC(COC(=O)CCCCCCCCCC(CCCCCCCCCC(=O)OCC(CCC(C)C)C(C)C)C(=O)OCCN1CCCC1)C(C)C]
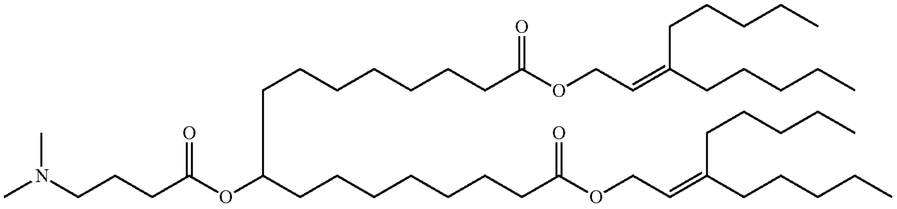 [SMILES: CCCCCC(=CCOC(=O)CCCCCCCC(CCCCCCCC(=O)OCC=C(CCCCC)CCCCC)OC(=O)CCCN(C)C)CCCCC]
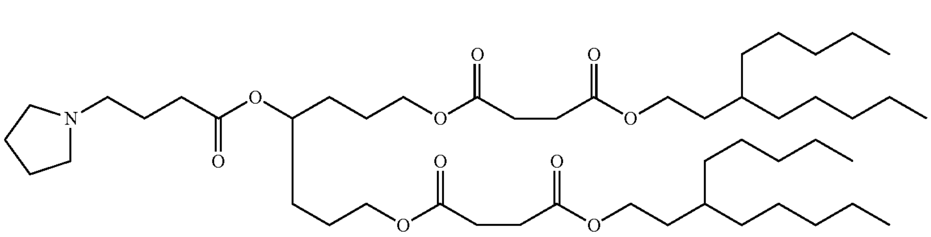 [SMILES: CCCCCC(CCCCC)CCOC(=O)CCC(=O)OCCCC(CCCOC(=O)CCC(=O)OCCC(CCCCC)CCCCC)OC(=O)CCCN1CCCC1]

-continued
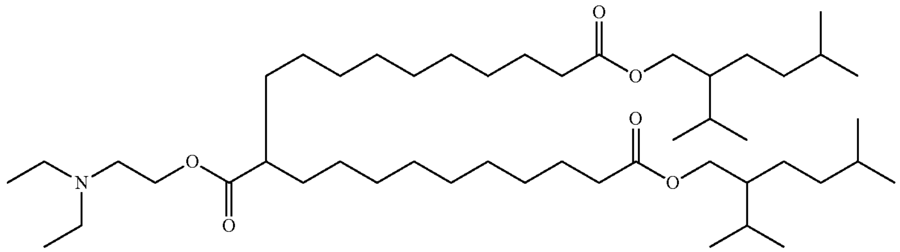 [SMILES: CCN(CC)CCOC(=O)C(CCCCCCCCCC(=O)OCC(CCC(C)C)C(C)C)CCCCCCCCCC(=O)OCC(CCC(C)C)C(C)C]
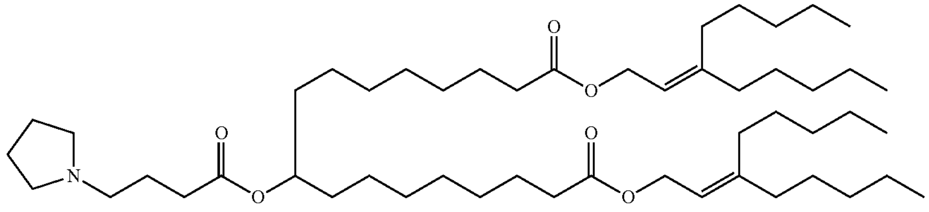 [SMILES: CCCCCC(=CCOC(=O)CCCCCCCC(CCCCCCCC(=O)OCC=C(CCCCC)CCCCC)OC(=O)CCCN1CCCC1)CCCCC]
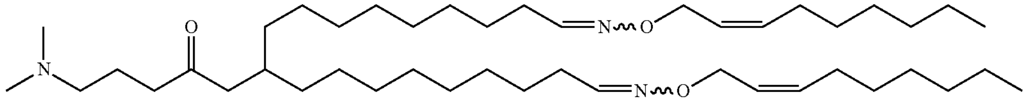 [SMILES: CCCCCC/C=C\CON=CCCCCCCCCC(CCCCCCCCC=NOC/C=C\CCCCCC)CC(=O)CCCN(C)C]
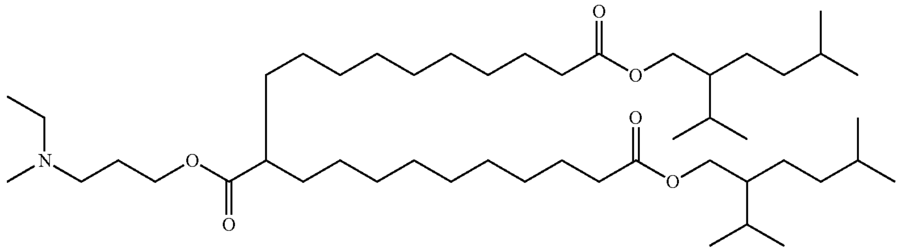 [SMILES: CCN(C)CCCOC(=O)C(CCCCCCCCCC(=O)OCC(CCC(C)C)C(C)C)CCCCCCCCCC(=O)OCC(CCC(C)C)C(C)C]
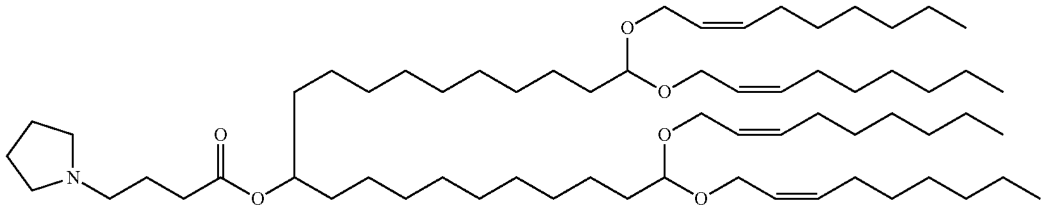 [SMILES: CCCCCC/C=C\COC(CCCCCCCCCC(CCCCCCCCCC(OC/C=C\CCCCCC)OC/C=C\CCCCCC)OC(=O)CCCN1CCCC1)OC/C=C\CCCCCC]
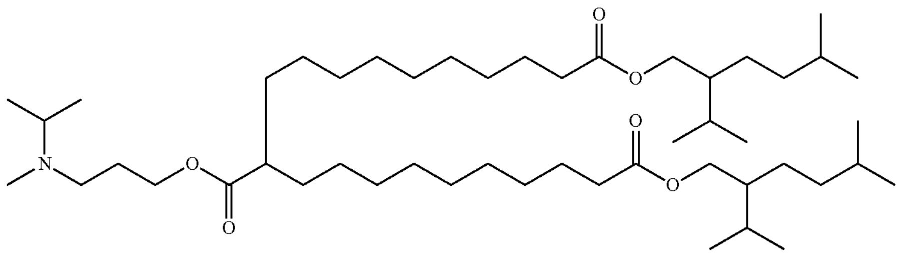 [SMILES: CC(C)CCC(COC(=O)CCCCCCCCCC(CCCCCCCCCC(=O)OCC(CCC(C)C)C(C)C)C(=O)OCCCN(C)C(C)C)C(C)C]
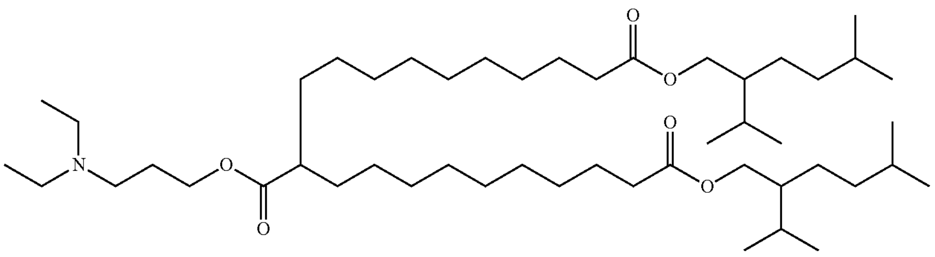 [SMILES: CCN(CC)CCCOC(=O)C(CCCCCCCCCC(=O)OCC(CCC(C)C)C(C)C)CCCCCCCCCC(=O)OCC(CCC(C)C)C(C)C]

-continued
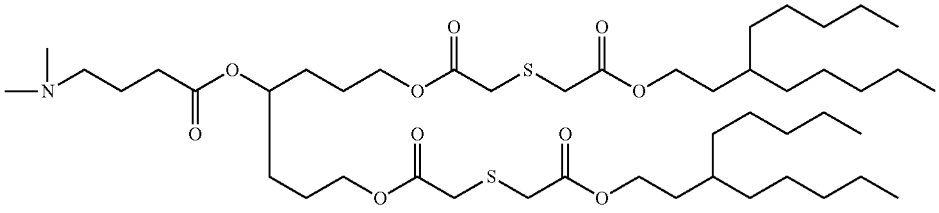
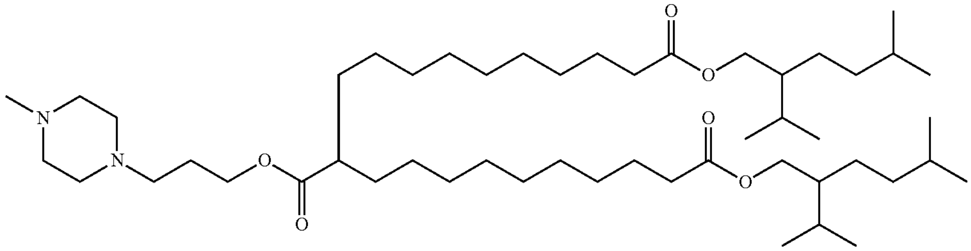 [SMILES: CC(C)CCC(COC(=O)CCCCCCCCCC(CCCCCCCCCC(=O)OCC(CCC(C)C)C(C)C)C(=O)OCCCN1CCN(C)CC1)C(C)C]
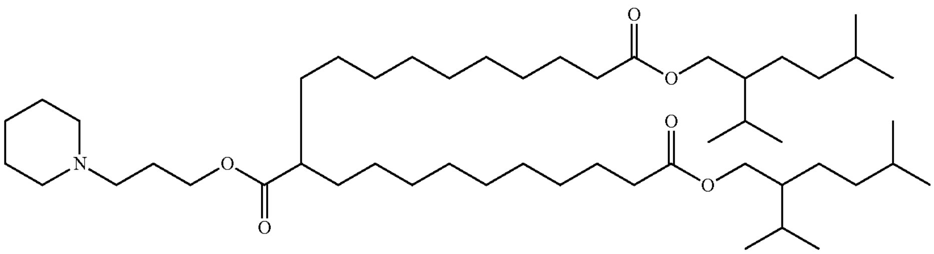 [SMILES: CC(C)CCC(COC(=O)CCCCCCCCCC(CCCCCCCCCC(=O)OCC(CCC(C)C)C(C)C)C(=O)OCCCN1CCCCC1)C(C)C]
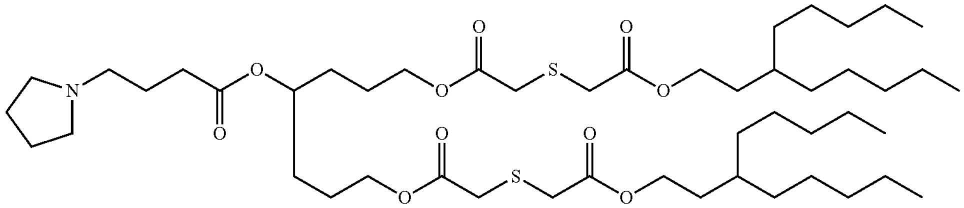 [SMILES: CCCCCC(CCCCC)CCOC(=O)CSCC(=O)OCCCC(CCCOC(=O)CSCC(=O)OCCC(CCCCC)CCCCC)OC(=O)CCCN1CCCC1]
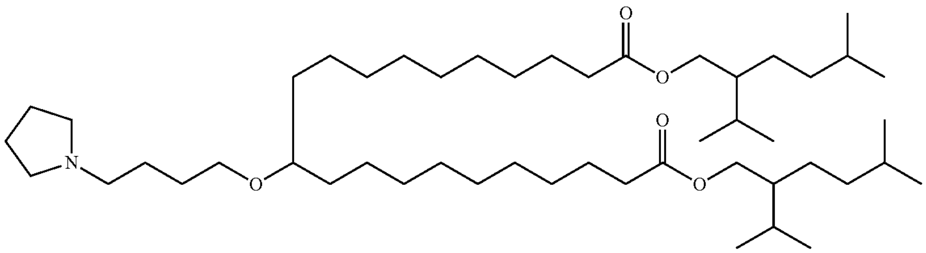 [SMILES: CC(C)CCC(COC(=O)CCCCCCCCCC(CCCCCCCCCC(=O)OCC(CCC(C)C)C(C)C)OCCCCN1CCCC1)C(C)C]
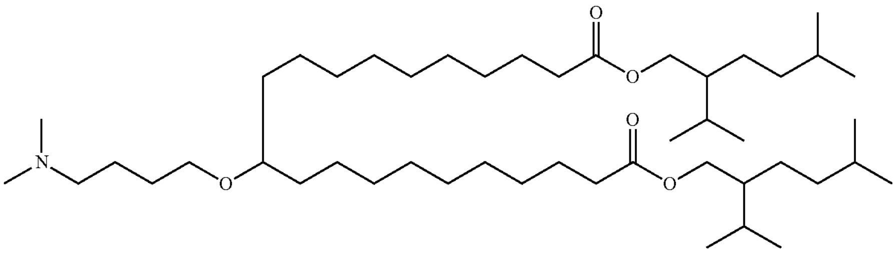 [SMILES: CC(C)CCC(COC(=O)CCCCCCCCCC(CCCCCCCCCC(=O)OCC(CCC(C)C)C(C)C)OCCCCN(C)C)C(C)C]

-continued
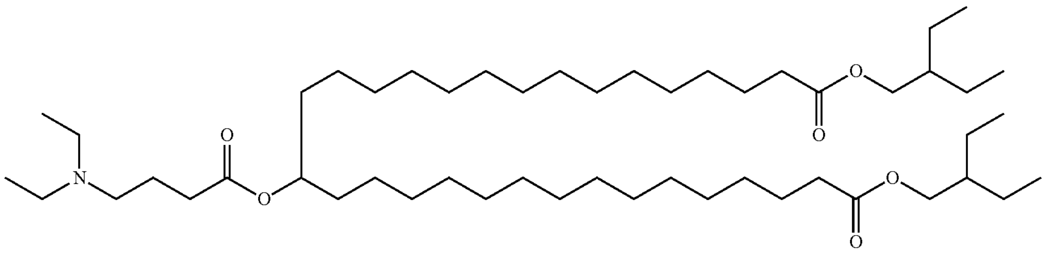 [SMILES: CCC(CC)COC(=O)CCCCCCCCCCCCCCC(CCCCCCCCCCCCCCC(=O)OCC(CC)CC)OC(=O)CCCN(CC)CC]
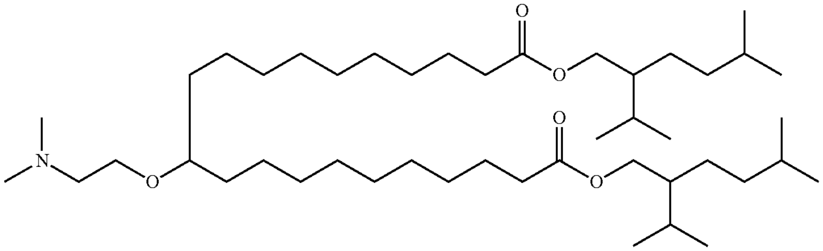 [SMILES: CC(C)CCC(COC(=O)CCCCCCCCCC(CCCCCCCCCC(=O)OCC(CCC(C)C)C(C)C)OCCN(C)C)C(C)C]
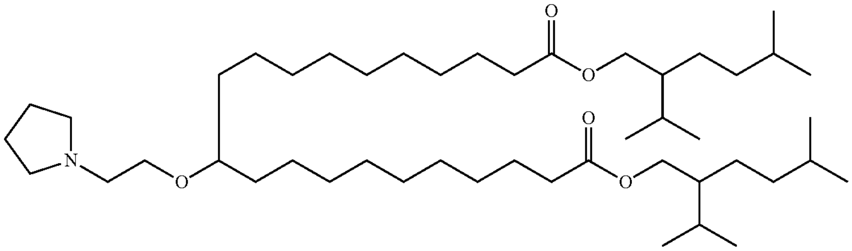 [SMILES: CC(C)CCC(COC(=O)CCCCCCCCCC(CCCCCCCCCC(=O)OCC(CCC(C)C)C(C)C)OCCN1CCCC1)C(C)C]
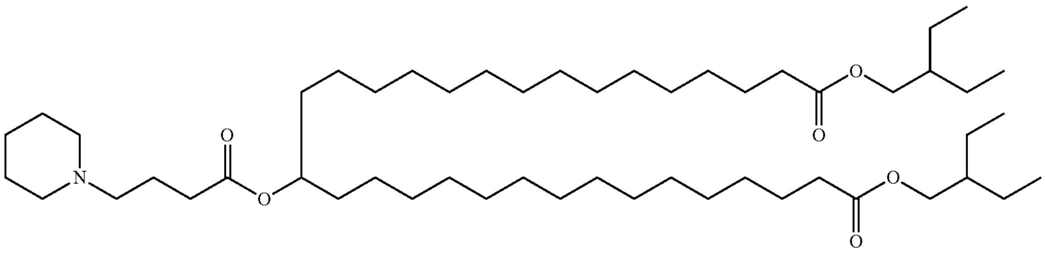 [SMILES: CCC(CC)COC(=O)CCCCCCCCCCCCCCC(CCCCCCCCCCCCCCC(=O)OCC(CC)CC)OC(=O)CCCN1CCCCC1]
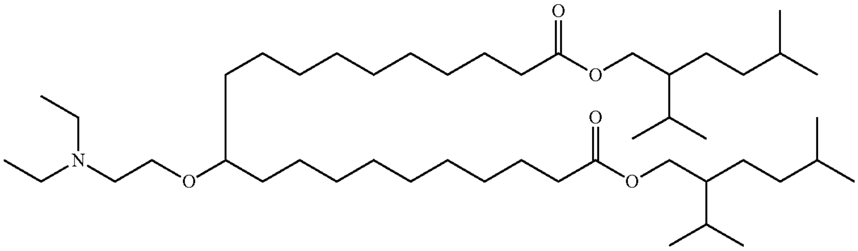 [SMILES: CCN(CC)CCOC(CCCCCCCCCC(=O)OCC(CCC(C)C)C(C)C)CCCCCCCCCC(=O)OCC(CCC(C)C)C(C)C]
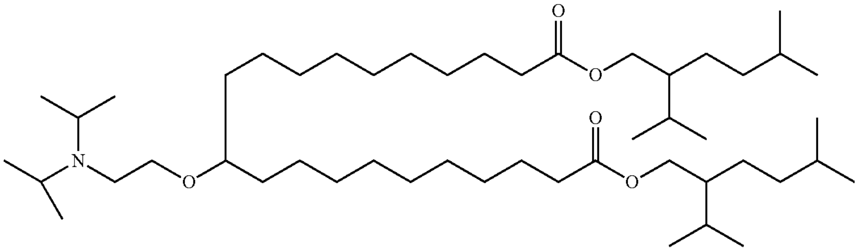 [SMILES: CC(C)CCC(COC(=O)CCCCCCCCCC(CCCCCCCCCC(=O)OCC(CCC(C)C)C(C)C)OCCN(C(C)C)C(C)C)C(C)C]

-continued
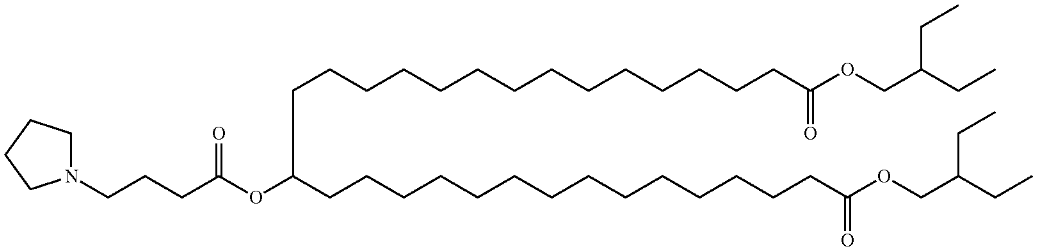 [SMILES: CCC(CC)COC(=O)CCCCCCCCCCCCCCC(CCCCCCCCCCCCCCC(=O)OCC(CC)CC)OC(=O)CCCN1CCCC1]
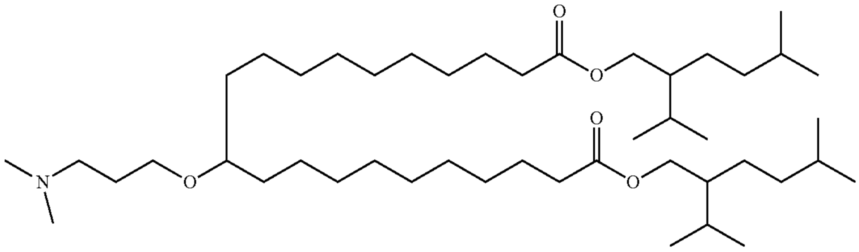 [SMILES: CC(C)CCC(COC(=O)CCCCCCCCCC(CCCCCCCCCC(=O)OCC(CCC(C)C)C(C)C)OCCCN(C)C)C(C)C]
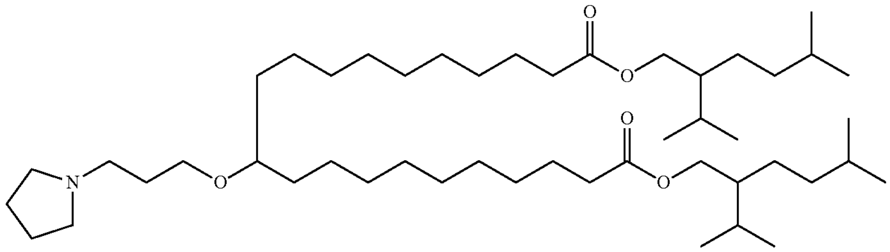 [SMILES: CC(C)CCC(COC(=O)CCCCCCCCCC(CCCCCCCCCC(=O)OCC(CCC(C)C)C(C)C)OCCCN1CCCC1)C(C)C]
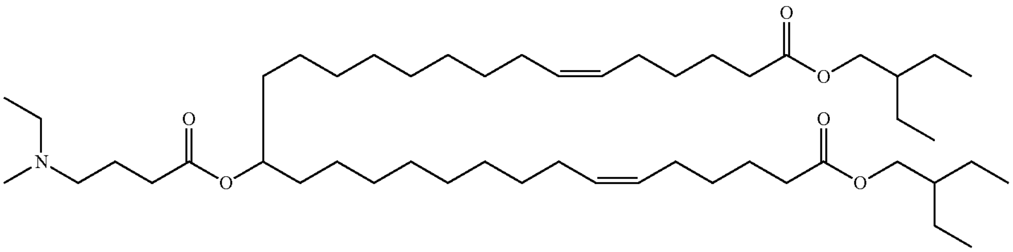 [SMILES: CCC(CC)COC(=O)CCCC/C=C\CCCCCCCCC(CCCCCCCC/C=C\CCCCC(=O)OCC(CC)CC)OC(=O)CCCN(C)CC]
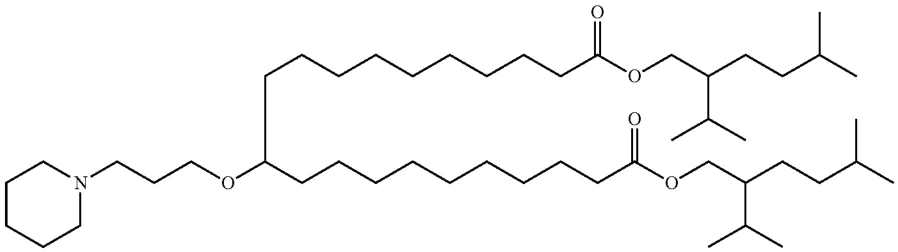 [SMILES: CC(C)CCC(COC(=O)CCCCCCCCCC(CCCCCCCCCC(=O)OCC(CCC(C)C)C(C)C)OCCCN1CCCCC1)C(C)C]
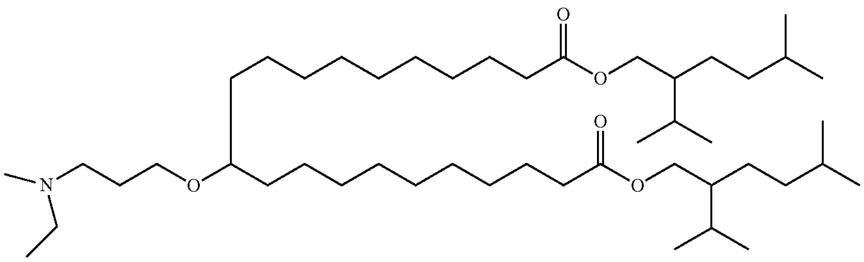 [SMILES: CCN(C)CCCOC(CCCCCCCCCC(=O)OCC(CCC(C)C)C(C)C)CCCCCCCCCC(=O)OCC(CCC(C)C)C(C)C]

-continued
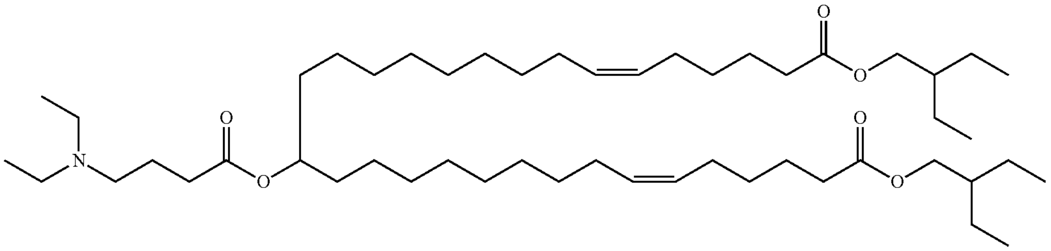 [SMILES: CCC(CC)COC(=O)CCCC/C=C\CCCCCCCCC(CCCCCCCC/C=C\CCCCC(=O)OCC(CC)CC)OC(=O)CCCN(CC)CC]
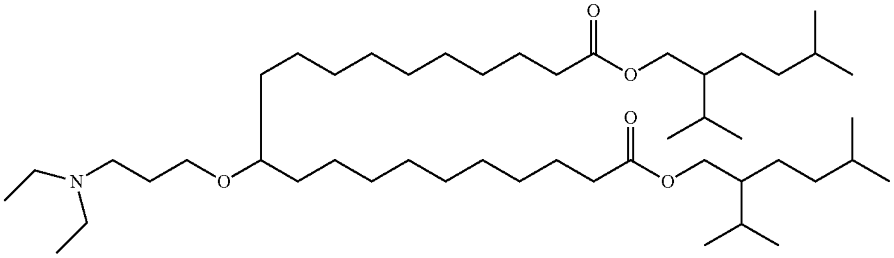 [SMILES: CCN(CC)CCCOC(CCCCCCCCCC(=O)OCC(CCC(C)C)C(C)C)CCCCCCCCCC(=O)OCC(CCC(C)C)C(C)C]
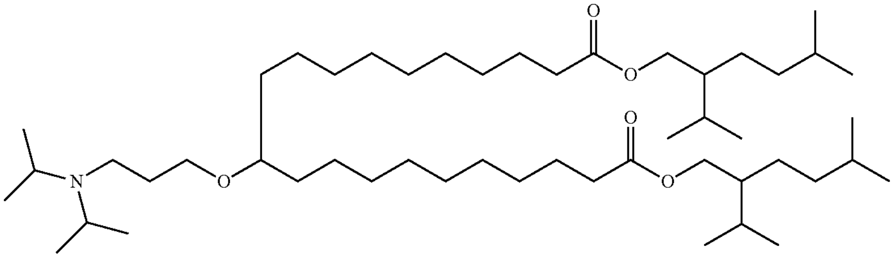 [SMILES: CC(C)CCC(COC(=O)CCCCCCCCCC(CCCCCCCCCC(=O)OCC(CCC(C)C)C(C)C)OCCCN(C(C)C)C(C)C)C(C)C]
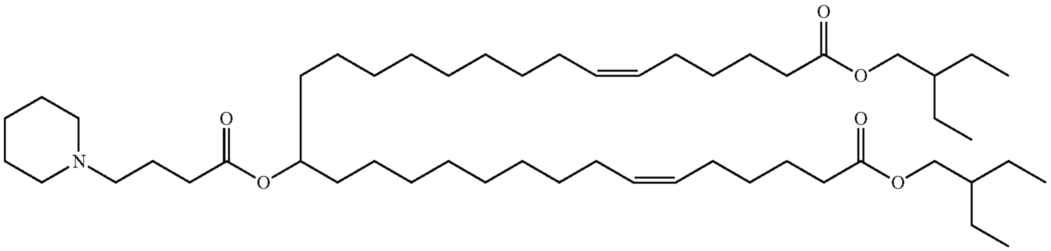 [SMILES: CCC(CC)COC(=O)CCCC/C=C\CCCCCCCCC(CCCCCCCC/C=C\CCCCC(=O)OCC(CC)CC)OC(=O)CCCN1CCCCC1]
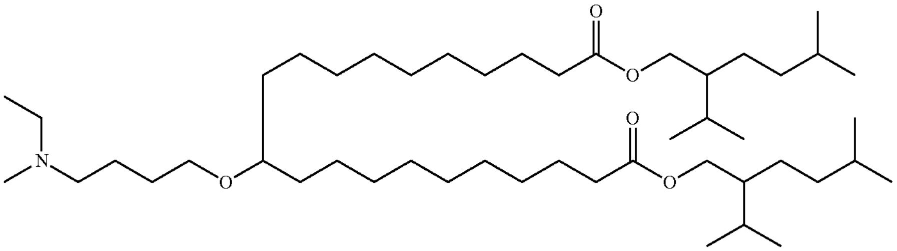 [SMILES: CCN(C)CCCCOC(CCCCCCCCCC(=O)OCC(CCC(C)C)C(C)C)CCCCCCCCCC(=O)OCC(CCC(C)C)C(C)C]
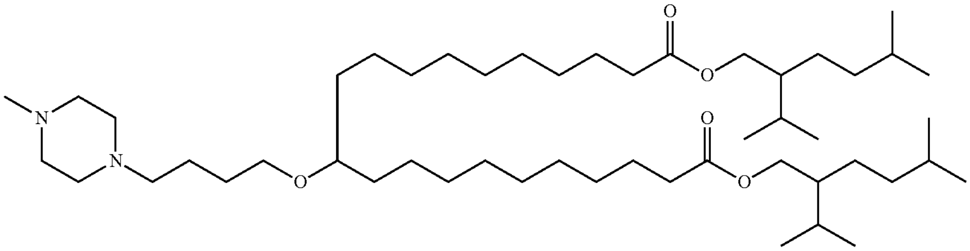 [SMILES: CC(C)CCC(COC(=O)CCCCCCCCCC(CCCCCCCCCC(=O)OCC(CCC(C)C)C(C)C)OCCCCN1CCN(C)CC1)C(C)C]

-continued
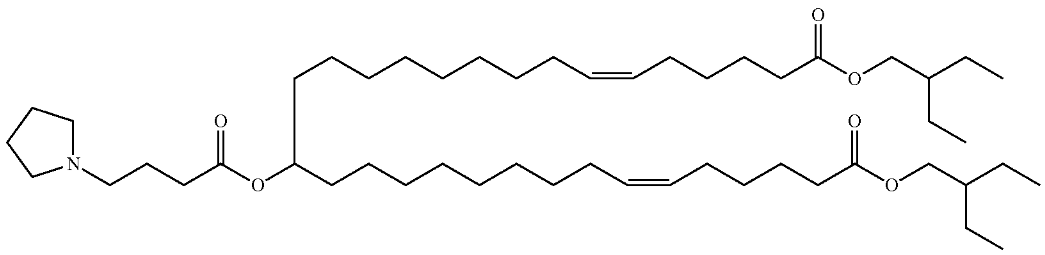 [SMILES: CCC(CC)COC(=O)CCCC/C=C\CCCCCCCCC(CCCCCCCC/C=C\CCCCC(=O)OCC(CC)CC)OC(=O)CCCN1CCCC1]
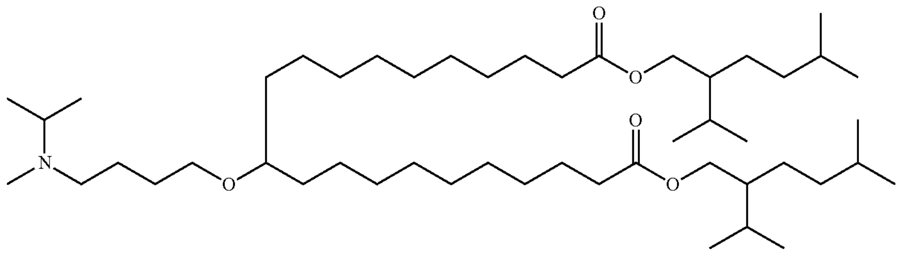 [SMILES: CC(C)CCC(COC(=O)CCCCCCCCCC(CCCCCCCCCC(=O)OCC(CCC(C)C)C(C)C)OCCCCN(C)C(C)C)C(C)C]
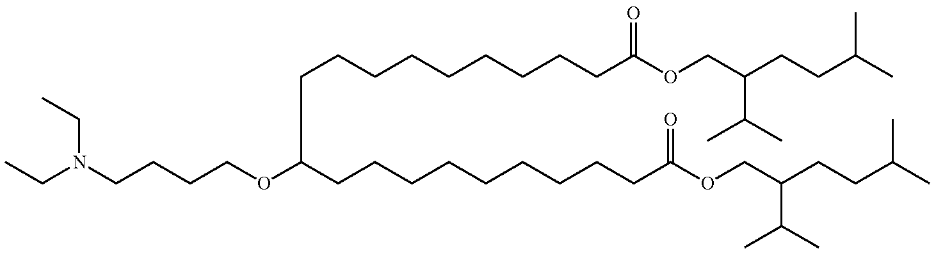 [SMILES: CCN(CC)CCCCOC(CCCCCCCCCC(=O)OCC(CCC(C)C)C(C)C)CCCCCCCCCC(=O)OCC(CCC(C)C)C(C)C]
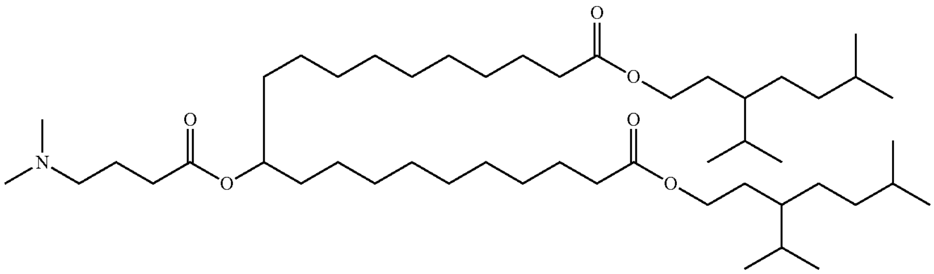 [SMILES: CC(C)CCC(CCOC(=O)CCCCCCCCCC(CCCCCCCCCC(=O)OCCC(CCC(C)C)C(C)C)OC(=O)CCCN(C)C)C(C)C]
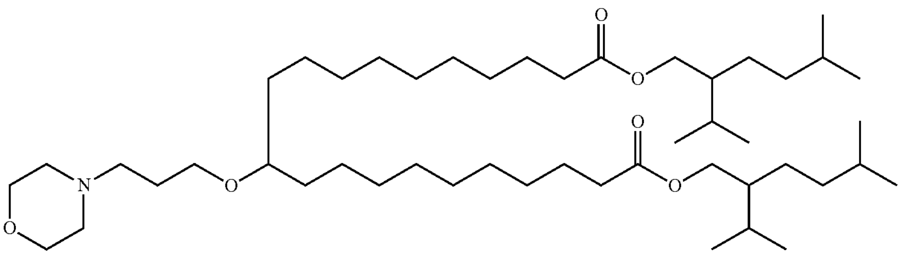 [SMILES: CC(C)CCC(COC(=O)CCCCCCCCCC(CCCCCCCCCC(=O)OCC(CCC(C)C)C(C)C)OCCCN1CCOCC1)C(C)C]
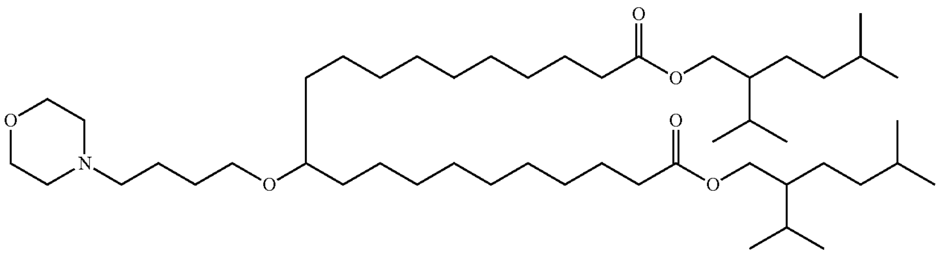 [SMILES: CC(C)CCC(COC(=O)CCCCCCCCCC(CCCCCCCCCC(=O)OCC(CCC(C)C)C(C)C)OCCCCN1CCOCC1)C(C)C]

-continued
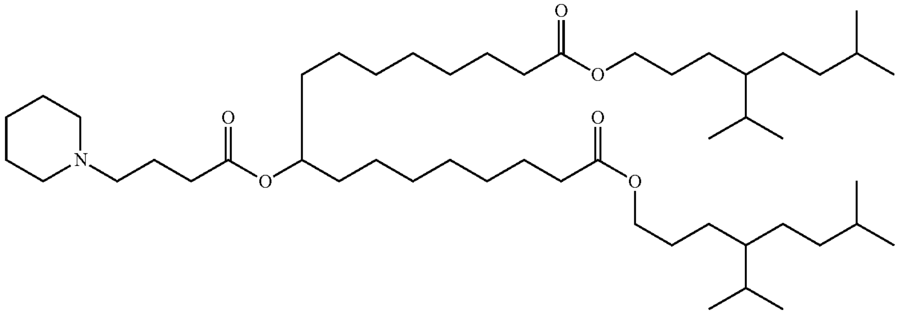 [SMILES: CC(C)CCC(CCCOC(=O)CCCCCCCC(CCCCCCCC(=O)OCCCC(CCC(C)C)C(C)C)OC(=O)CCCN1CCCCC1)C(C)C]
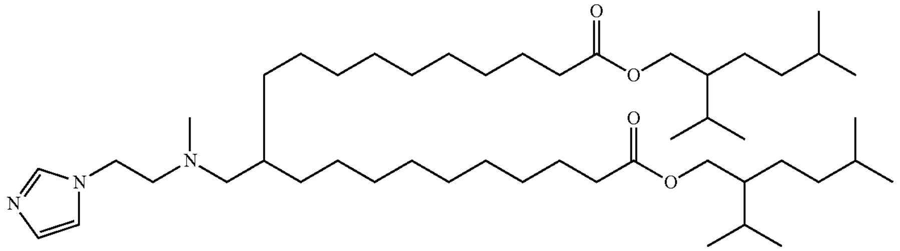 [SMILES: CC(C)CCC(COC(=O)CCCCCCCCCC(CCCCCCCCCC(=O)OCC(CCC(C)C)C(C)C)CN(C)CCn1ccnc1)C(C)C]
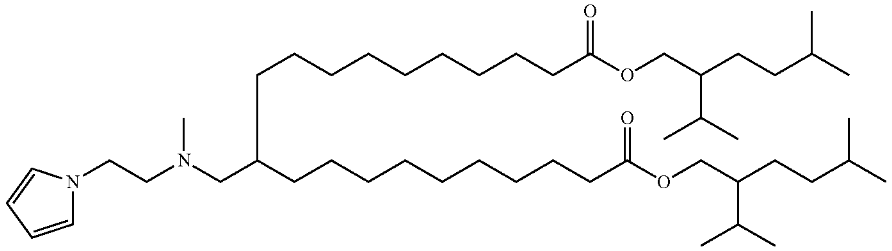 [SMILES: CC(C)CCC(COC(=O)CCCCCCCCCC(CCCCCCCCCC(=O)OCC(CCC(C)C)C(C)C)CN(C)CCn1cccc1)C(C)C]
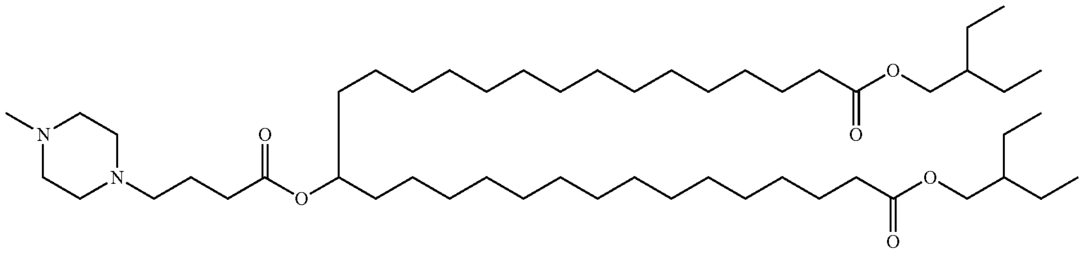 [SMILES: CCC(CC)COC(=O)CCCCCCCCCCCCCCC(CCCCCCCCCCCCCCC(=O)OCC(CC)CC)OC(=O)CCCN1CCN(C)CC1]
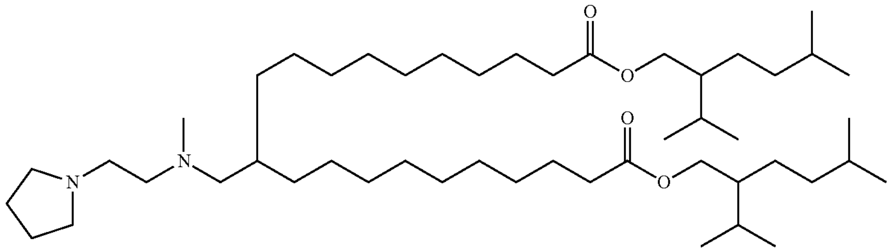 [SMILES: CC(C)CCC(COC(=O)CCCCCCCCCC(CCCCCCCCCC(=O)OCC(CCC(C)C)C(C)C)CN(C)CCN1CCCC1)C(C)C]
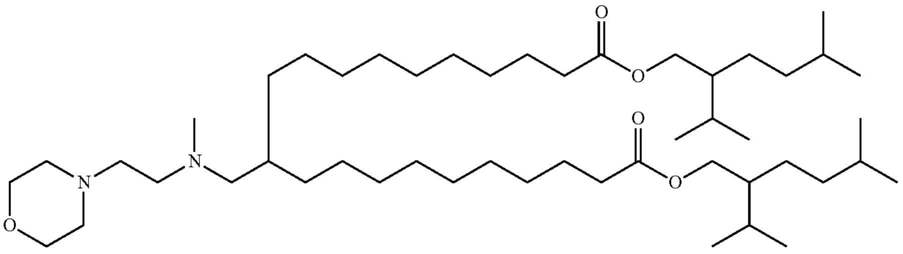 [SMILES: CC(C)CCC(COC(=O)CCCCCCCCCC(CCCCCCCCCC(=O)OCC(CCC(C)C)C(C)C)CN(C)CCN1CCOCC1)C(C)C]

-continued
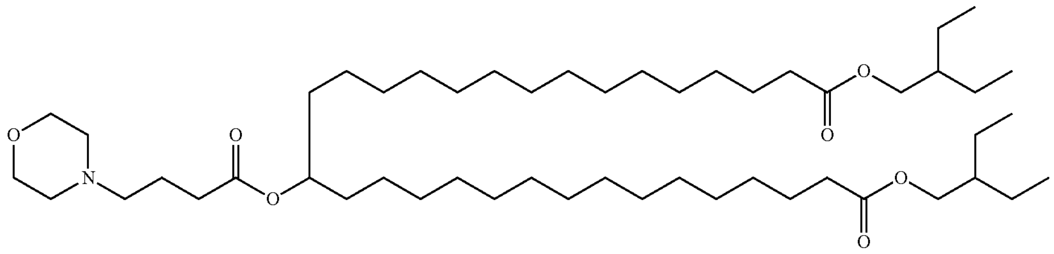 [SMILES: CCC(CC)COC(=O)CCCCCCCCCCCCCCC(CCCCCCCCCCCCCCC(=O)OCC(CC)CC)OC(=O)CCCN1CCOCC1]
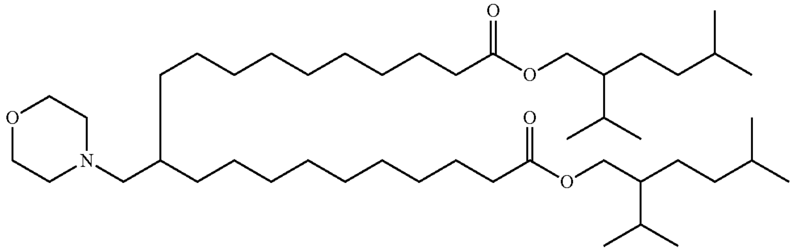 [SMILES: CC(C)CCC(COC(=O)CCCCCCCCCC(CCCCCCCCCC(=O)OCC(CCC(C)C)C(C)C)CN1CCOCC1)C(C)C]
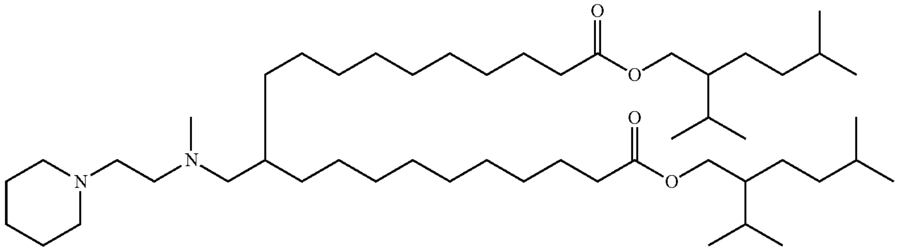 [SMILES: CC(C)CCC(COC(=O)CCCCCCCCCC(CCCCCCCCCC(=O)OCC(CCC(C)C)C(C)C)CN(C)CCN1CCCCC1)C(C)C]
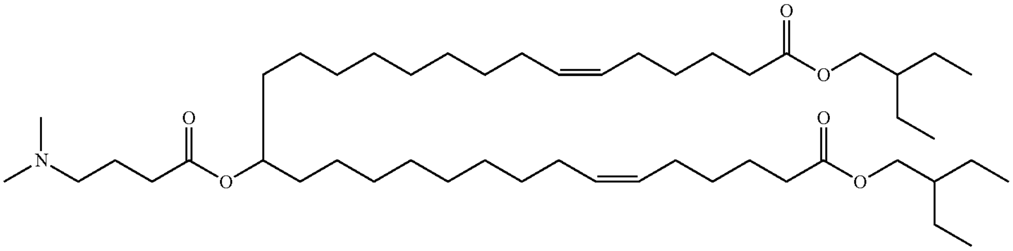 [SMILES: CCC(CC)COC(=O)CCCC/C=C\CCCCCCCCC(CCCCCCCC/C=C\CCCCC(=O)OCC(CC)CC)OC(=O)CCCN(C)C]
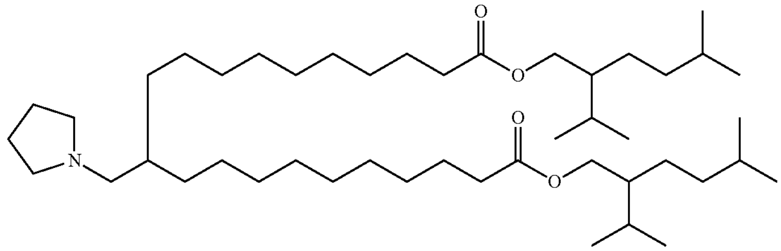 [SMILES: CC(C)CCC(COC(=O)CCCCCCCCCC(CCCCCCCCCC(=O)OCC(CCC(C)C)C(C)C)CN1CCCC1)C(C)C]
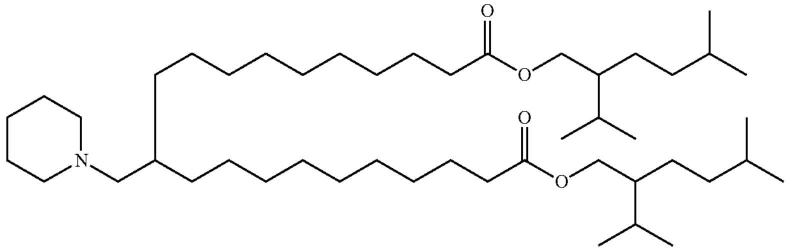 [SMILES: CC(C)CCC(COC(=O)CCCCCCCCCC(CCCCCCCCCC(=O)OCC(CCC(C)C)C(C)C)CN1CCCCC1)C(C)C]

-continued
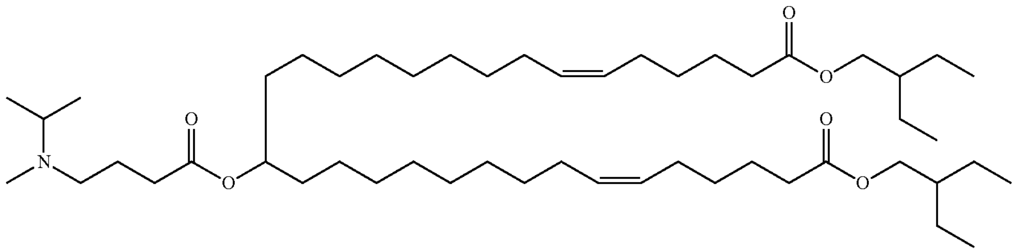 [SMILES: CCC(CC)COC(=O)CCCC/C=C\CCCCCCCCC(CCCCCCCC/C=C\CCCCC(=O)OCC(CC)CC)OC(=O)CCCN(C)C(C)C]
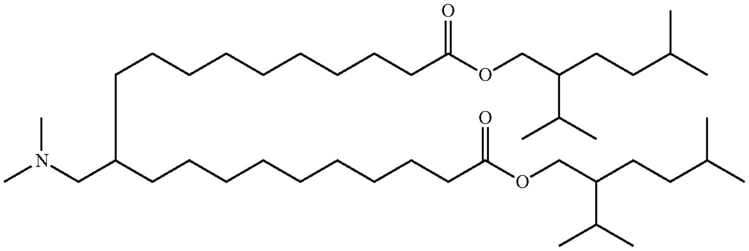 [SMILES: CC(C)CCC(COC(=O)CCCCCCCCCC(CCCCCCCCCC(=O)OCC(CCC(C)C)C(C)C)CN(C)C)C(C)C]
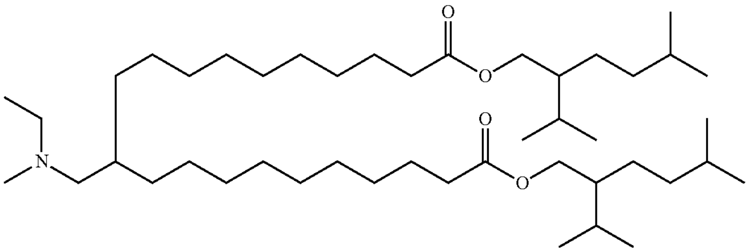 [SMILES: CCN(C)CC(CCCCCCCCCC(=O)OCC(CCC(C)C)C(C)C)CCCCCCCCCC(=O)OCC(CCC(C)C)C(C)C]
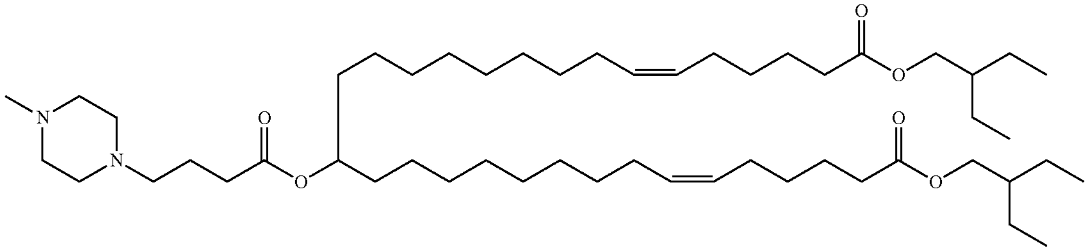 [SMILES: CCC(CC)COC(=O)CCCC/C=C\CCCCCCCCC(CCCCCCCC/C=C\CCCCC(=O)OCC(CC)CC)OC(=O)CCCN1CCN(C)CC1]
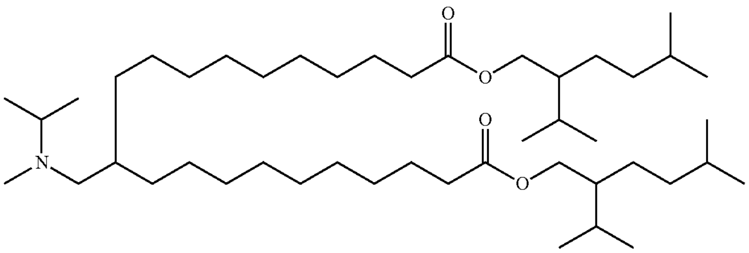 [SMILES: CC(C)CCC(COC(=O)CCCCCCCCCC(CCCCCCCCCC(=O)OCC(CCC(C)C)C(C)C)CN(C)C(C)C)C(C)C]
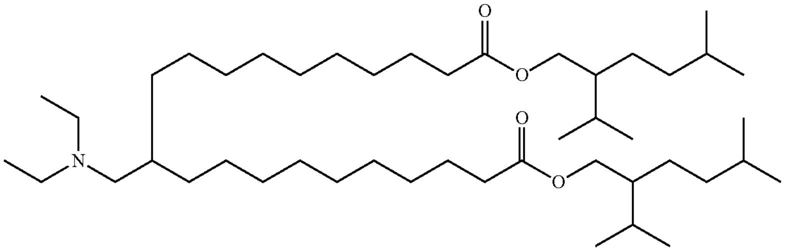 [SMILES: CCN(CC)CC(CCCCCCCCCC(=O)OCC(CCC(C)C)C(C)C)CCCCCCCCCC(=O)OCC(CCC(C)C)C(C)C]

-continued
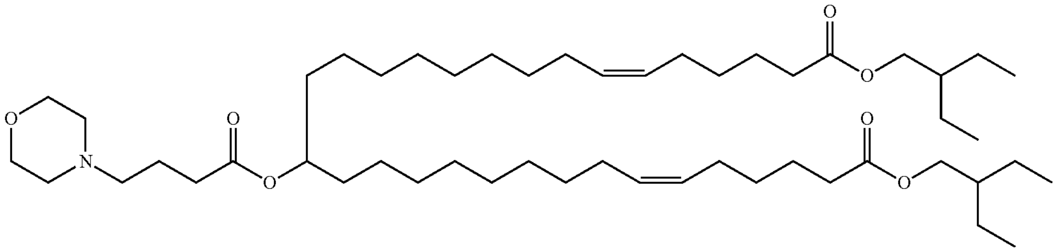 [SMILES: CCC(CC)COC(=O)CCCC/C=C\CCCCCCCCC(CCCCCCCC/C=C\CCCCC(=O)OCC(CC)CC)OC(=O)CCCN1CCOCC1]
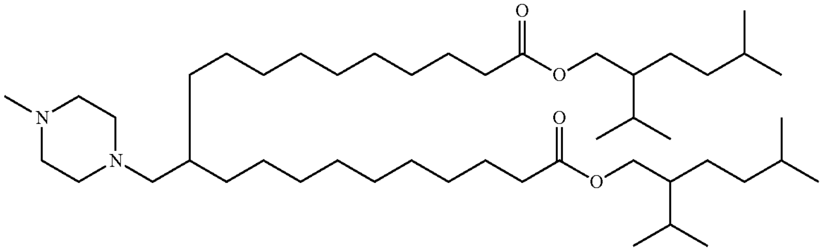 [SMILES: CC(C)CCC(COC(=O)CCCCCCCCCC(CCCCCCCCCC(=O)OCC(CCC(C)C)C(C)C)CN1CCN(C)CC1)C(C)C]
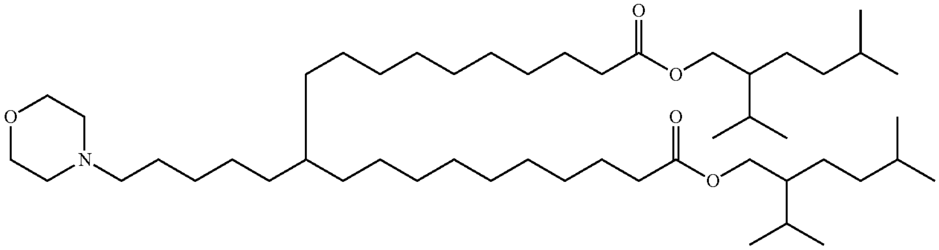 [SMILES: CC(C)CCC(COC(=O)CCCCCCCCCC(CCCCCCCCCC(=O)OCC(CCC(C)C)C(C)C)CCCCCN1CCOCC1)C(C)C]
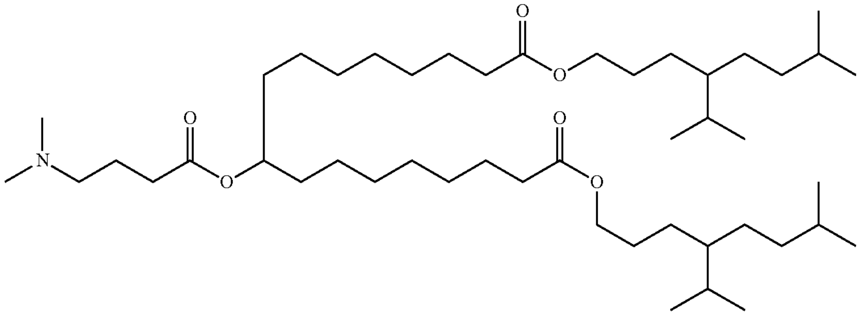 [SMILES: CC(C)CCC(CCCOC(=O)CCCCCCCC(CCCCCCCC(=O)OCCCC(CCC(C)C)C(C)C)OC(=O)CCCN(C)C)C(C)C]
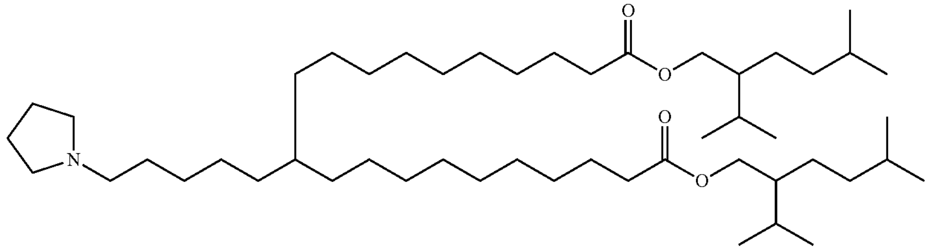 [SMILES: CC(C)CCC(COC(=O)CCCCCCCCCC(CCCCCCCCCC(=O)OCC(CCC(C)C)C(C)C)CCCCCN1CCCC1)C(C)C]
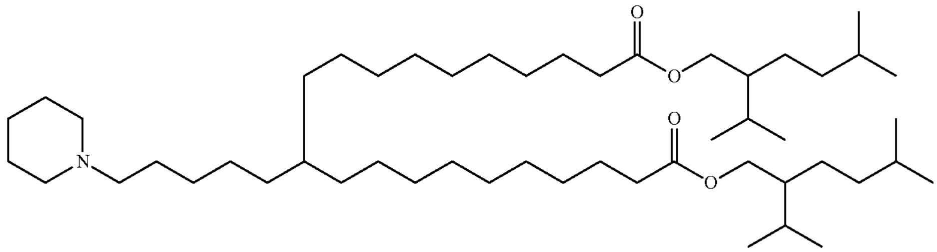 [SMILES: CC(C)CCC(COC(=O)CCCCCCCCCC(CCCCCCCCCC(=O)OCC(CCC(C)C)C(C)C)CCCCCN1CCCCC1)C(C)C]

-continued
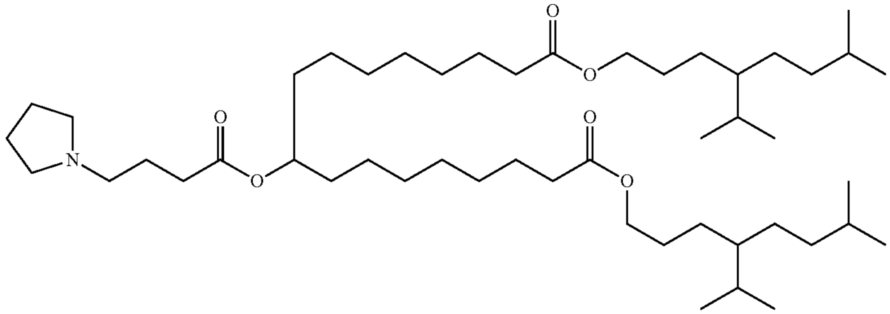 [SMILES: CC(C)CCC(CCCOC(=O)CCCCCCCC(CCCCCCCC(=O)OCCCC(CCC(C)C)C(C)C)OC(=O)CCCN1CCCC1)C(C)C]
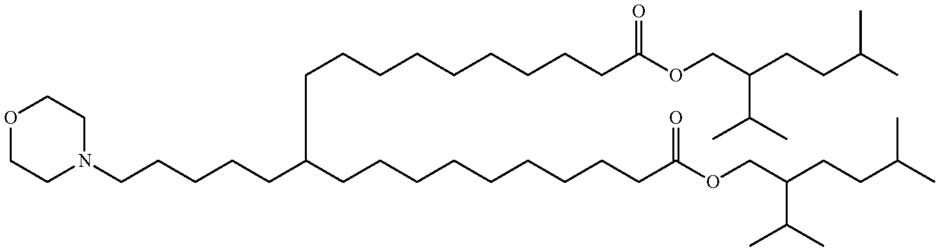 [SMILES: CC(C)CCC(COC(=O)CCCCCCCCCC(CCCCCCCCCC(=O)OCC(CCC(C)C)C(C)C)CCCCCN1CCOCC1)C(C)C]
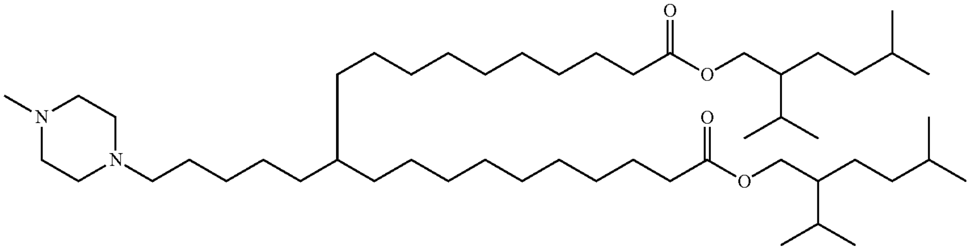 [SMILES: CC(C)CCC(COC(=O)CCCCCCCCCC(CCCCCCCCCC(=O)OCC(CCC(C)C)C(C)C)CCCCCN1CCN(C)CC1)C(C)C]
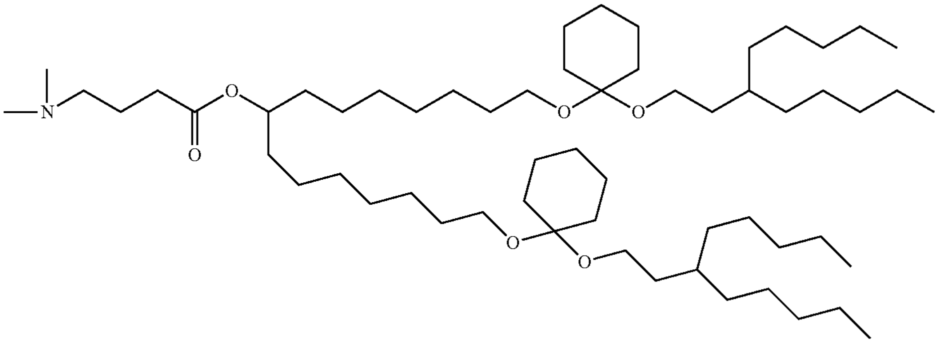 [SMILES: CCCCCC(CCCCC)CCOC1(OCCCCCCCC(CCCCCCCOC2(OCCC(CCCCC)CCCCC)CCCCC2)OC(=O)CCCN(C)C)CCCCC1]
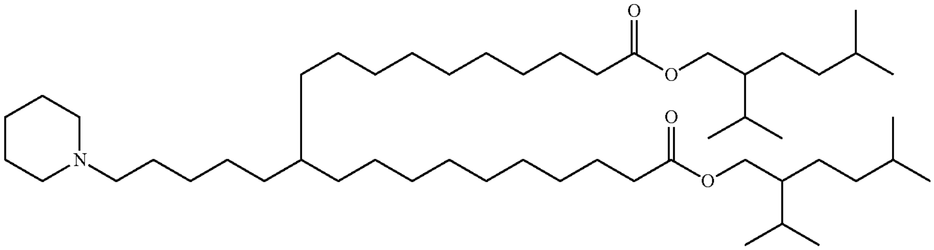 [SMILES: CC(C)CCC(COC(=O)CCCCCCCCCC(CCCCCCCCCC(=O)OCC(CCC(C)C)C(C)C)CCCCCN1CCCCC1)C(C)C]

-continued
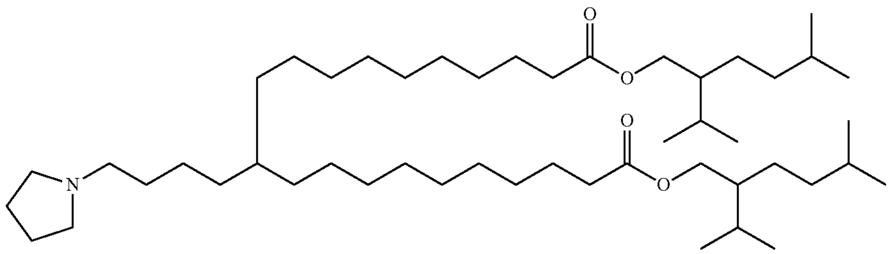 [SMILES: CC(C)CCC(COC(=O)CCCCCCCCCC(CCCCCCCCCC(=O)OCC(CCC(C)C)C(C)C)CCCCN1CCCC1)C(C)C]
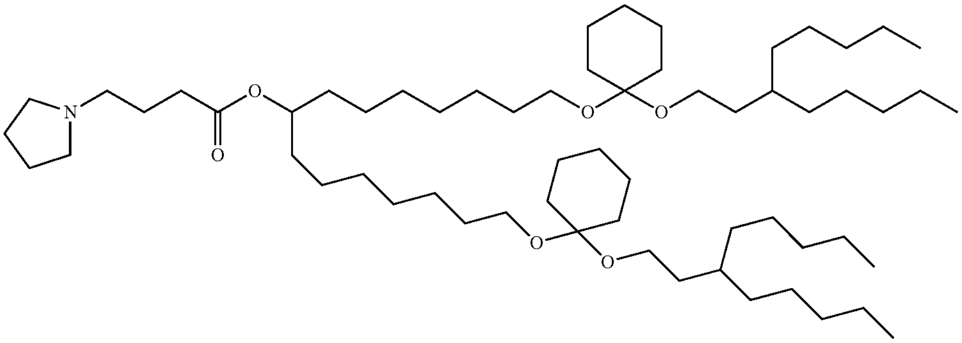 [SMILES: CCCCCC(CCCCC)CCOC1(OCCCCCCCC(CCCCCCCOC2(OCCC(CCCCC)CCCCC)CCCCC2)OC(=O)CCCN2CCCC2)CCCCC1]
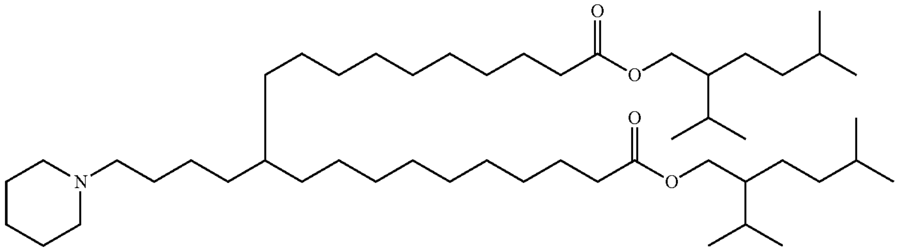 [SMILES: CC(C)CCC(COC(=O)CCCCCCCCCC(CCCCCCCCCC(=O)OCC(CCC(C)C)C(C)C)CCCCN1CCCCC1)C(C)C]
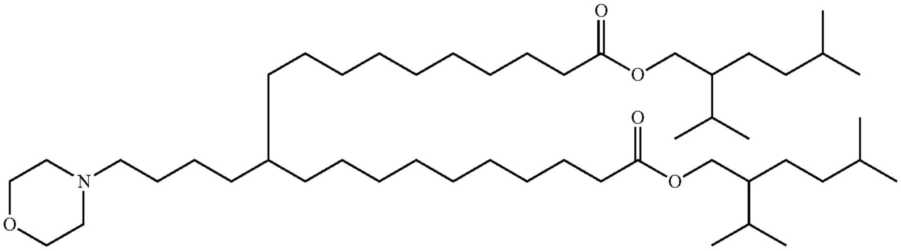 [SMILES: CC(C)CCC(COC(=O)CCCCCCCCCC(CCCCCCCCCC(=O)OCC(CCC(C)C)C(C)C)CCCCN1CCOCC1)C(C)C]
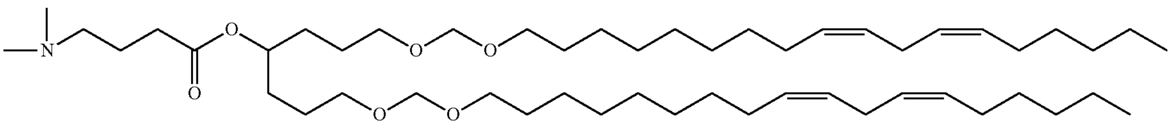 [SMILES: CCCCC/C=C\C/C=C\CCCCCCCCOCOCCCC(CCCOCOCCCCCCCC/C=C\C/C=C\CCCCC)OC(=O)CCCN(C)C]
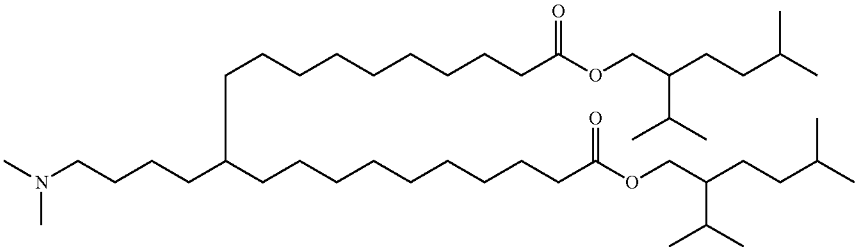 [SMILES: CC(C)CCC(COC(=O)CCCCCCCCCC(CCCCCCCCCC(=O)OCC(CCC(C)C)C(C)C)CCCCN(C)C)C(C)C]

-continued
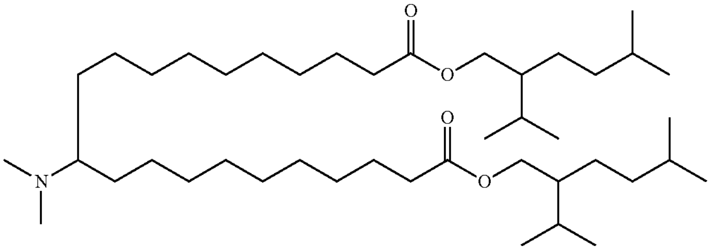 [SMILES: CC(C)CCC(COC(=O)CCCCCCCCCC(CCCCCCCCCC(=O)OCC(CCC(C)C)C(C)C)N(C)C)C(C)C]
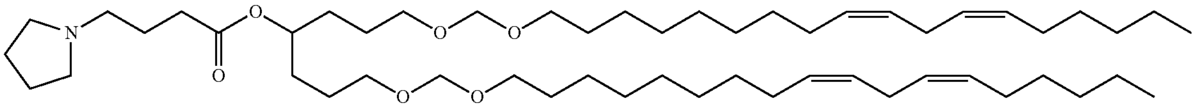 [SMILES: CCCCC/C=C\C/C=C\CCCCCCCCOCOCCCC(CCCOCOCCCCCCCC/C=C\C/C=C\CCCCC)OC(=O)CCCN1CCCC1]
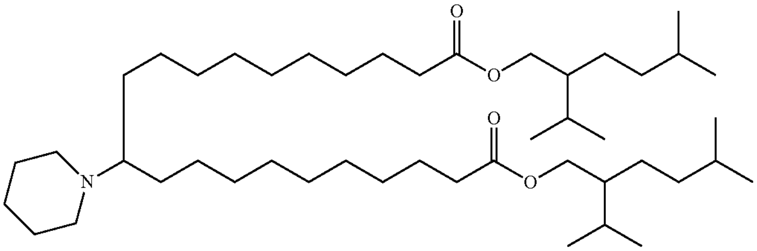 [SMILES: CC(C)CCC(COC(=O)CCCCCCCCCC(CCCCCCCCCC(=O)OCC(CCC(C)C)C(C)C)N1CCCCC1)C(C)C]
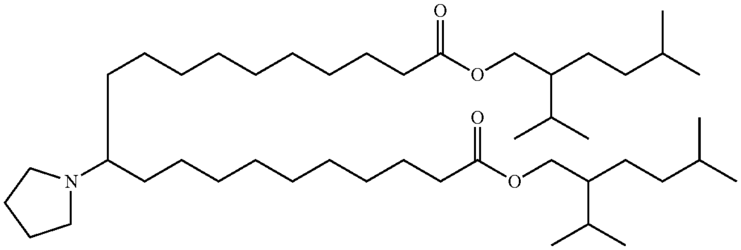 [SMILES: CC(C)CCC(COC(=O)CCCCCCCCCC(CCCCCCCCCC(=O)OCC(CCC(C)C)C(C)C)N1CCCC1)C(C)C]
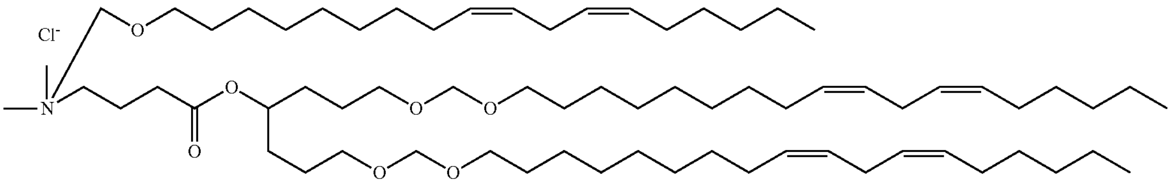
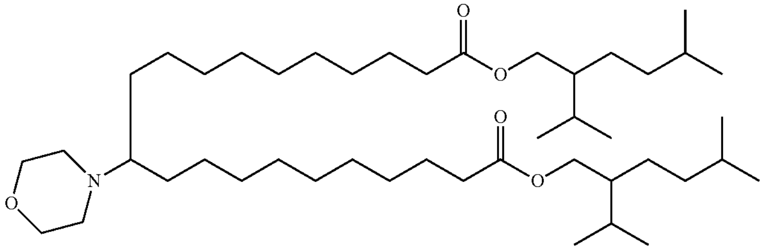 [SMILES: CC(C)CCC(COC(=O)CCCCCCCCCC(CCCCCCCCCC(=O)OCC(CCC(C)C)C(C)C)N1CCOCC1)C(C)C]
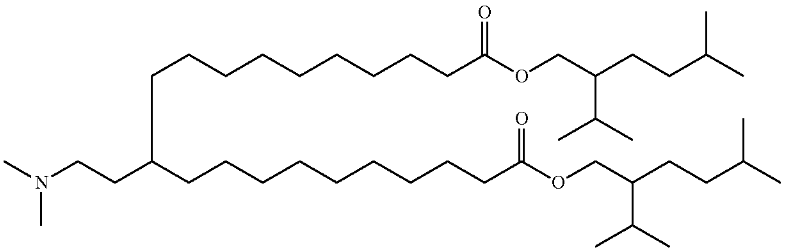 [SMILES: CC(C)CCC(COC(=O)CCCCCCCCCC(CCCCCCCCCC(=O)OCC(CCC(C)C)C(C)C)CCN(C)C)C(C)C]

-continued
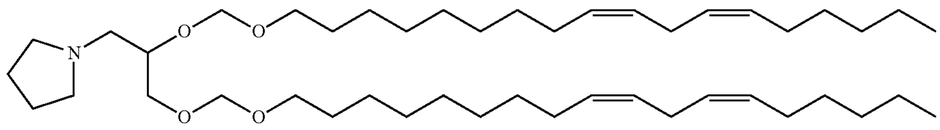 [SMILES: CCCCC/C=C\C/C=C\CCCCCCCCOCOCC(CN1CCCC1)OCOCCCCCCCC/C=C\C/C=C\CCCCC]
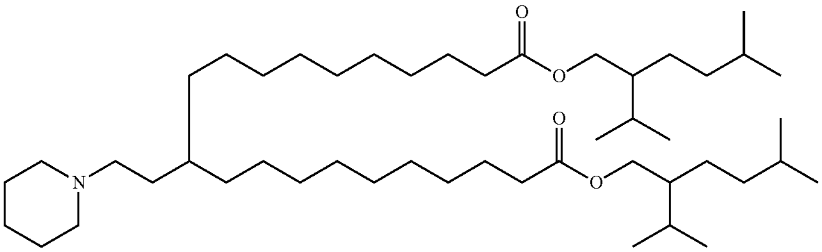 [SMILES: CC(C)CCC(COC(=O)CCCCCCCCCC(CCCCCCCCCC(=O)OCC(CCC(C)C)C(C)C)CCN1CCCCC1)C(C)C]
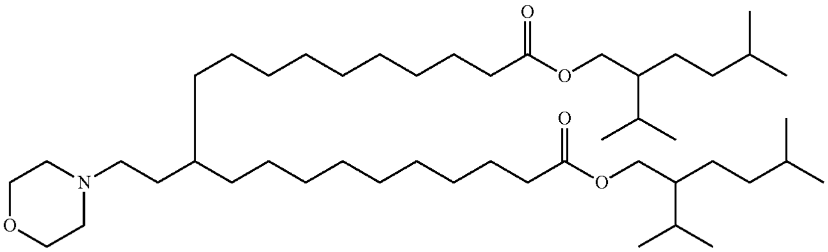 [SMILES: CC(C)CCC(COC(=O)CCCCCCCCCC(CCCCCCCCCC(=O)OCC(CCC(C)C)C(C)C)CCN1CCOCC1)C(C)C]
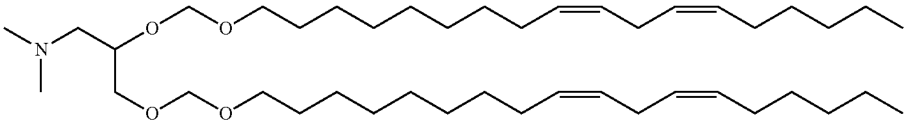 [SMILES: CCCCC/C=C\C/C=C\CCCCCCCCOCOCC(CN(C)C)OCOCCCCCCCC/C=C\C/C=C\CCCCC]
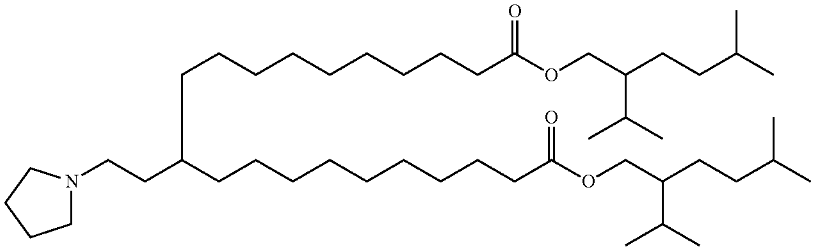 [SMILES: CC(C)CCC(COC(=O)CCCCCCCCCC(CCCCCCCCCC(=O)OCC(CCC(C)C)C(C)C)CCN1CCCC1)C(C)C]
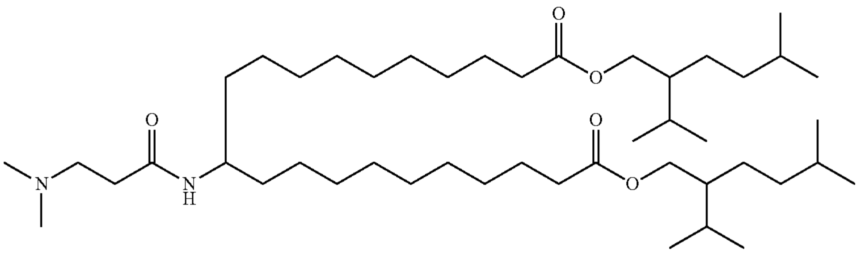
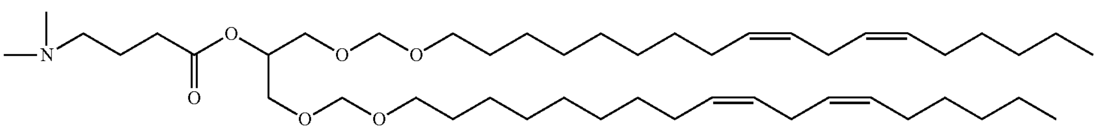 [SMILES: CCCCC/C=C\C/C=C\CCCCCCCCOCOCC(COCOCCCCCCCC/C=C\C/C=C\CCCCC)OC(=O)CCCN(C)C]

-continued
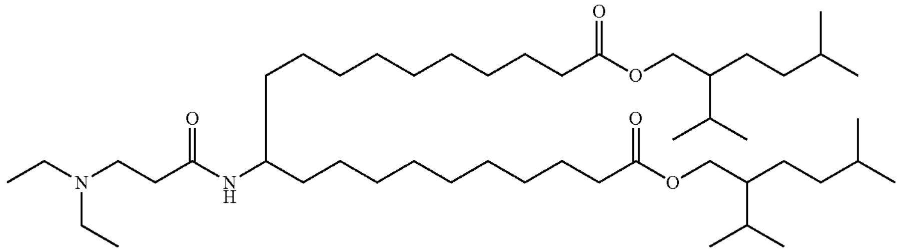 [SMILES: CCN(CC)CCC(=O)NC(CCCCCCCCCC(=O)OCC(CCC(C)C)C(C)C)CCCCCCCCCC(=O)OCC(CCC(C)C)C(C)C]
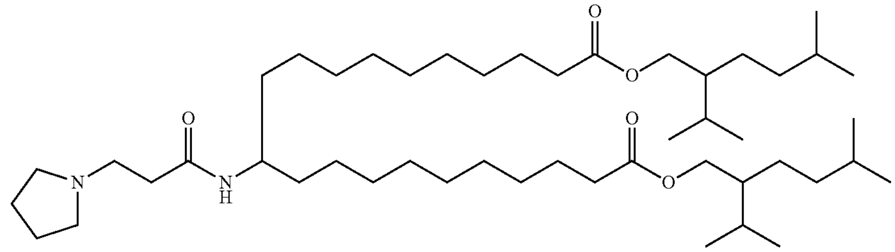 [SMILES: CC(C)CCC(COC(=O)CCCCCCCCCC(CCCCCCCCCC(=O)OCC(CCC(C)C)C(C)C)NC(=O)CCN1CCCC1)C(C)C]
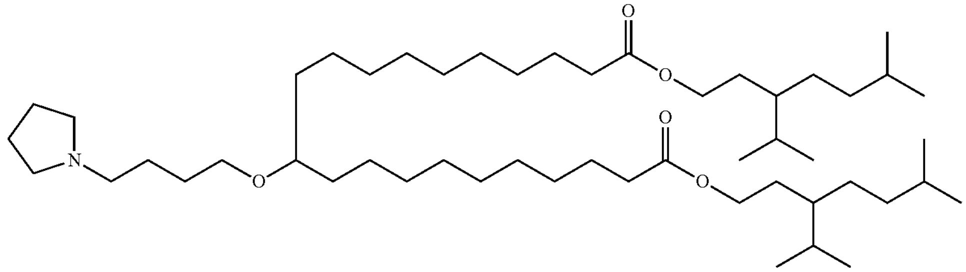 [SMILES: CC(C)CCC(CCOC(=O)CCCCCCCCCC(CCCCCCCCCC(=O)OCCC(CCC(C)C)C(C)C)OCCCCN1CCCC1)C(C)C]
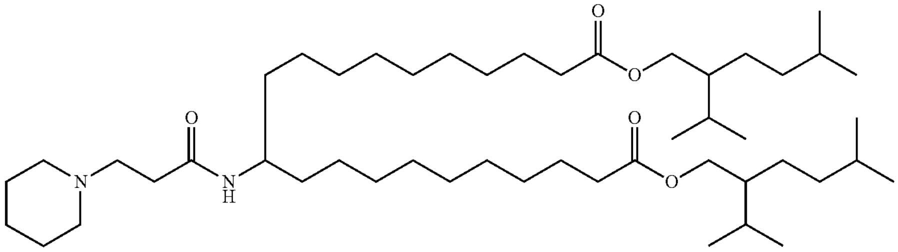 [SMILES: CC(C)CCC(COC(=O)CCCCCCCCCC(CCCCCCCCCC(=O)OCC(CCC(C)C)C(C)C)NC(=O)CCN1CCCCC1)C(C)C]
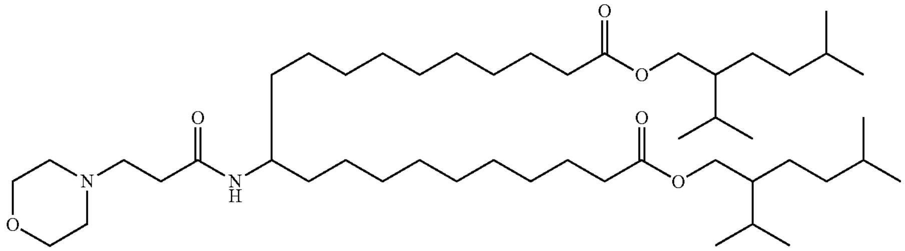 [SMILES: CC(C)CCC(COC(=O)CCCCCCCCCC(CCCCCCCCCC(=O)OCC(CCC(C)C)C(C)C)NC(=O)CCN1CCOCC1)C(C)C]
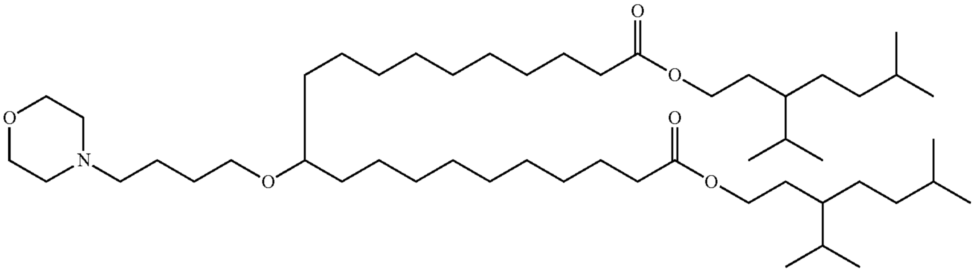 [SMILES: CC(C)CCC(CCOC(=O)CCCCCCCCCC(CCCCCCCCCC(=O)OCCC(CCC(C)C)C(C)C)OCCCCN1CCOCC1)C(C)C]

-continued
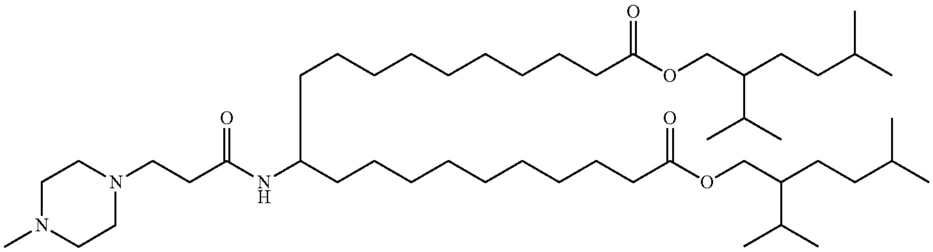 [SMILES: CC(C)CCC(COC(=O)CCCCCCCCCC(CCCCCCCCCC(=O)OCC(CCC(C)C)C(C)C)NC(=O)CCN1CCN(C)CC1)C(C)C]
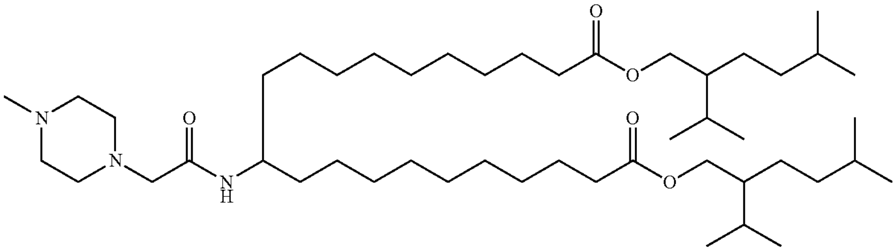 [SMILES: CC(C)CCC(COC(=O)CCCCCCCCCC(CCCCCCCCCC(=O)OCC(CCC(C)C)C(C)C)NC(=O)CN1CCN(C)CC1)C(C)C]
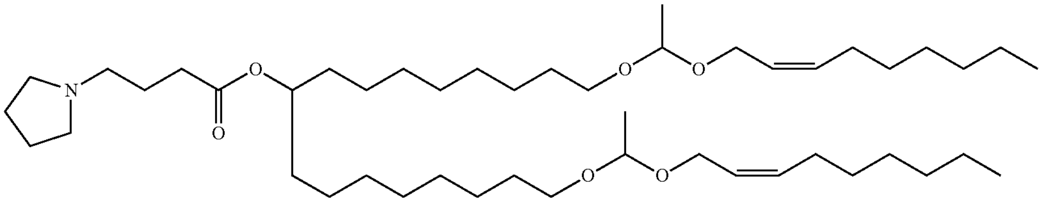 [SMILES: CCCCCC/C=C\COC(C)OCCCCCCCCC(CCCCCCCCOC(C)OC/C=C\CCCCCC)OC(=O)CCCN1CCCC1]
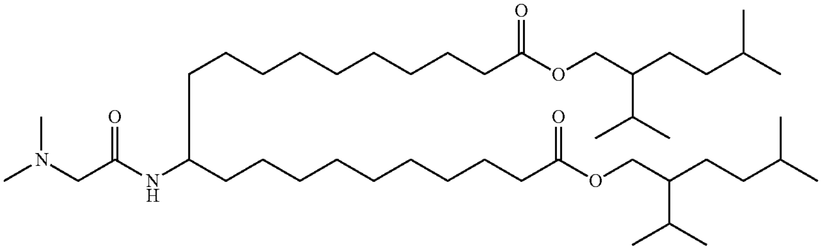
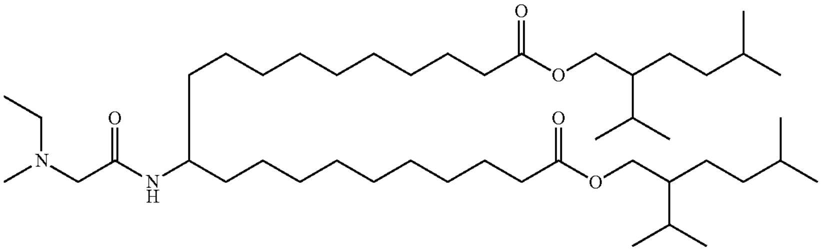 [SMILES: CCN(C)CC(=O)NC(CCCCCCCCCC(=O)OCC(CCC(C)C)C(C)C)CCCCCCCCCC(=O)OCC(CCC(C)C)C(C)C]
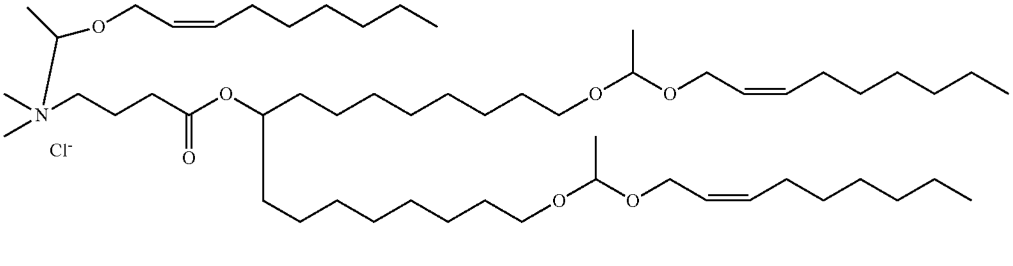

-continued
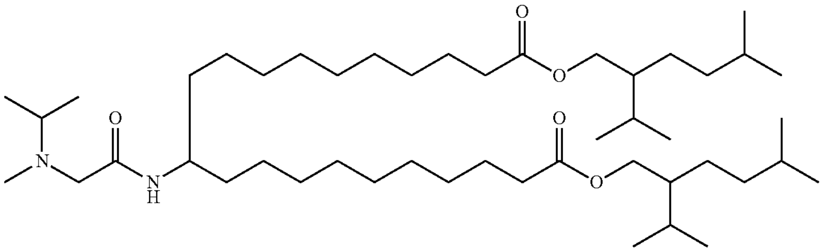 [SMILES: CC(C)CCC(COC(=O)CCCCCCCCCC(CCCCCCCCCC(=O)OCC(CCC(C)C)C(C)C)NC(=O)CN(C)C(C)C)C(C)C]
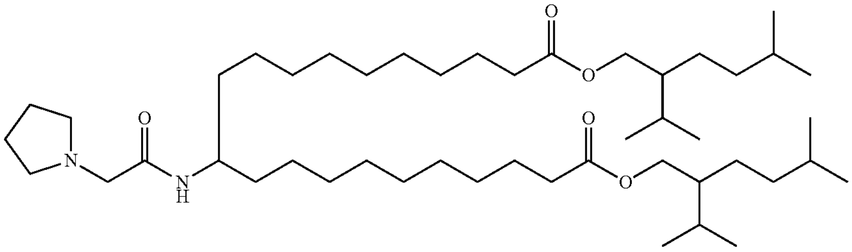 [SMILES: CC(C)CCC(COC(=O)CCCCCCCCCC(CCCCCCCCCC(=O)OCC(CCC(C)C)C(C)C)NC(=O)CN1CCCC1)C(C)C]
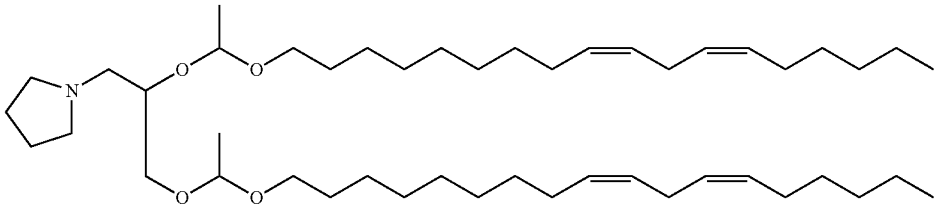 [SMILES: CCCCC/C=C\C/C=C\CCCCCCCCOC(C)OCC(CN1CCCC1)OC(C)OCCCCCCCC/C=C\C/C=C\CCCCC]
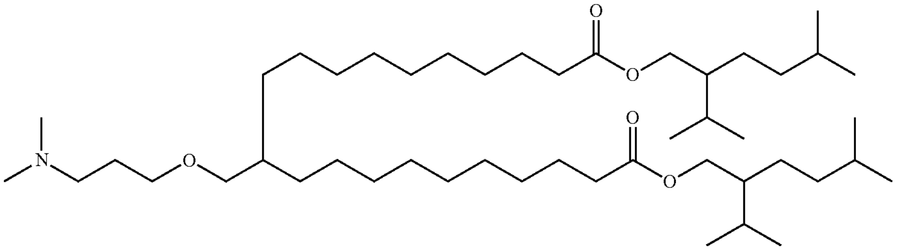 [SMILES: CC(C)CCC(COC(=O)CCCCCCCCCC(CCCCCCCCCC(=O)OCC(CCC(C)C)C(C)C)COCCCN(C)C)C(C)C]
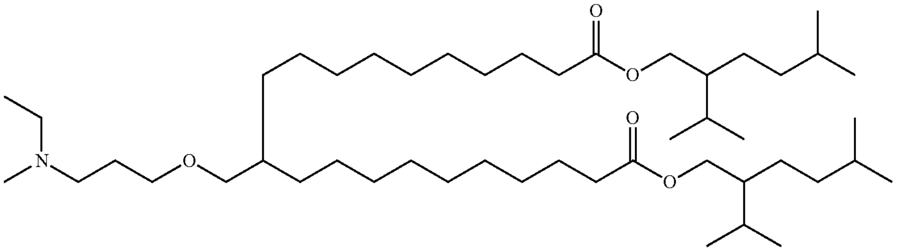 [SMILES: CCN(C)CCCOCC(CCCCCCCCCC(=O)OCC(CCC(C)C)C(C)C)CCCCCCCCCC(=O)OCC(CCC(C)C)C(C)C]
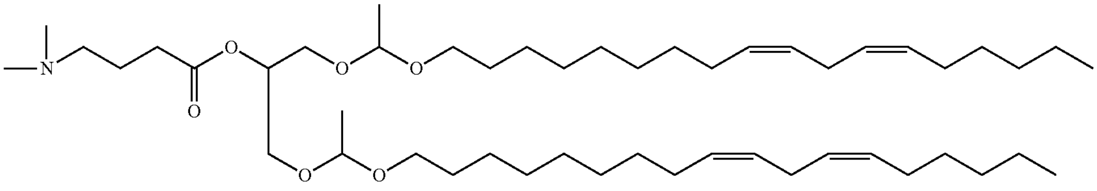 [SMILES: CCCCC/C=C\C/C=C\CCCCCCCCOC(C)OCC(COC(C)OCCCCCCCC/C=C\C/C=C\CCCCC)OC(=O)CCCN(C)C]

-continued
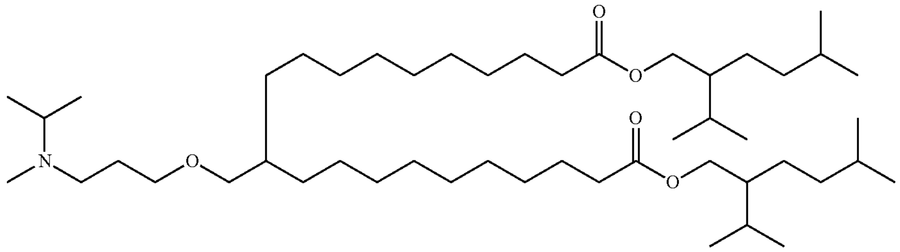
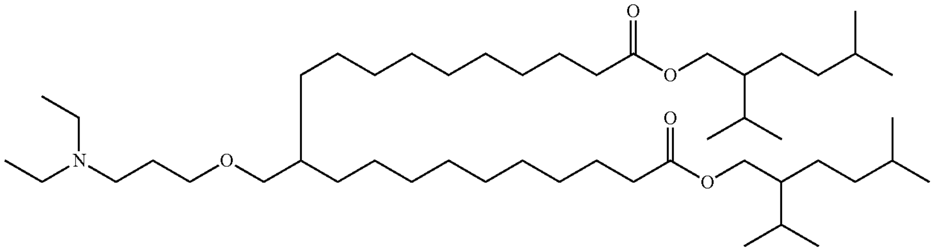
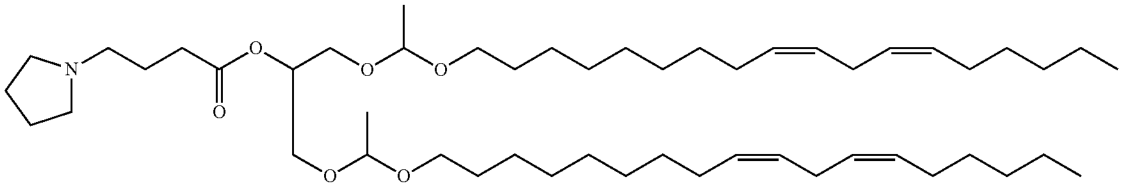 [SMILES: CCCCC/C=C\C/C=C\CCCCCCCCOC(C)OCC(COC(C)OCCCCCCCC/C=C\C/C=C\CCCCC)OC(=O)CCCN1CCCC1]
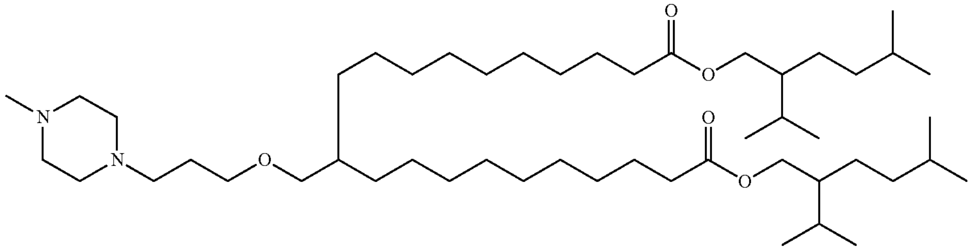 [SMILES: CC(C)CCC(COC(=O)CCCCCCCCCC(CCCCCCCCCC(=O)OCC(CCC(C)C)C(C)C)COCCCN1CCN(C)CC1)C(C)C]
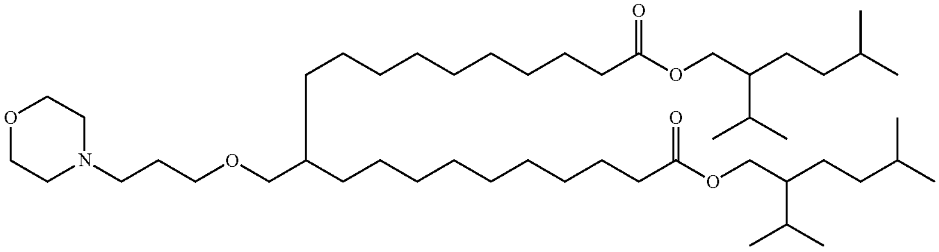 [SMILES: CC(C)CCC(COC(=O)CCCCCCCCCC(CCCCCCCCCC(=O)OCC(CCC(C)C)C(C)C)COCCCN1CCOCC1)C(C)C]
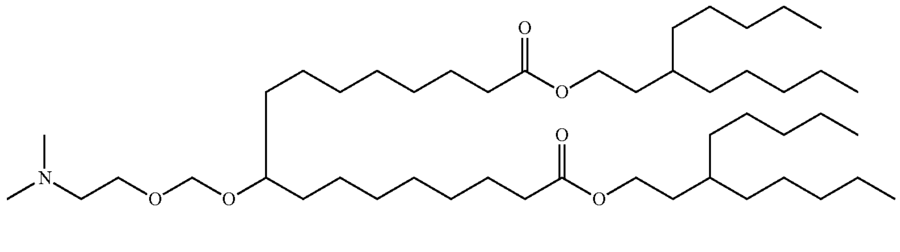 [SMILES: CCCCCC(CCCCC)CCOC(=O)CCCCCCCC(CCCCCCCC(=O)OCCC(CCCCC)CCCCC)OCOCCN(C)C]

-continued
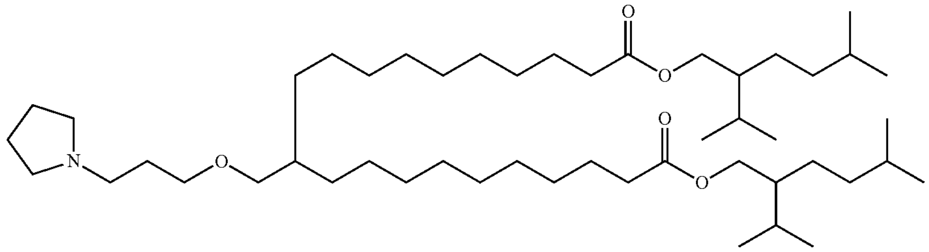
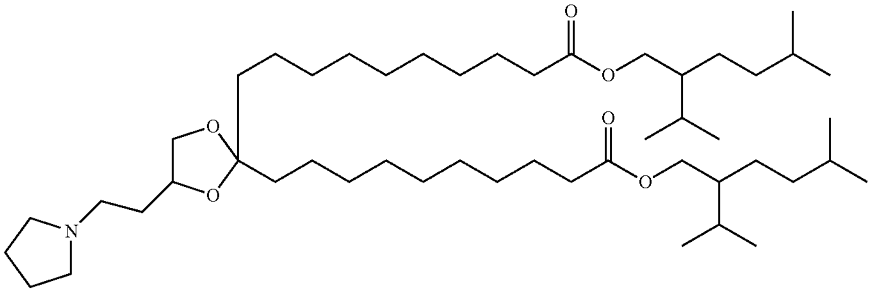 [SMILES: CC(C)CCC(COC(=O)CCCCCCCCCC1(CCCCCCCCCC(=O)OCC(CCC(C)C)C(C)C)OCC(CCN2CCCC2)O1)C(C)C]
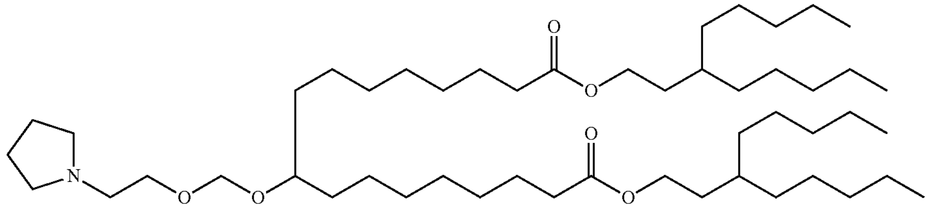 [SMILES: CCCCCC(CCCCC)CCOC(=O)CCCCCCCC(CCCCCCCC(=O)OCCC(CCCCC)CCCCC)OCOCCN1CCCC1]
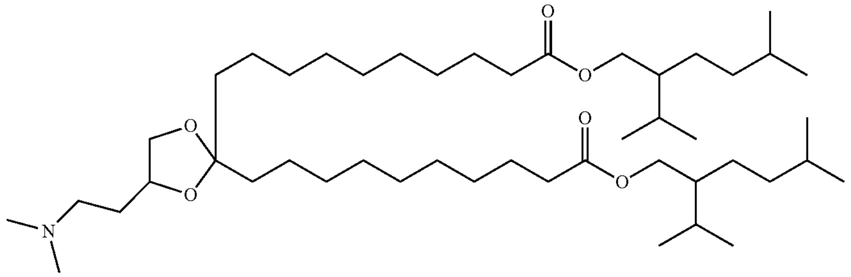 [SMILES: CC(C)CCC(COC(=O)CCCCCCCCCC1(CCCCCCCCCC(=O)OCC(CCC(C)C)C(C)C)OCC(CCN(C)C)O1)C(C)C]
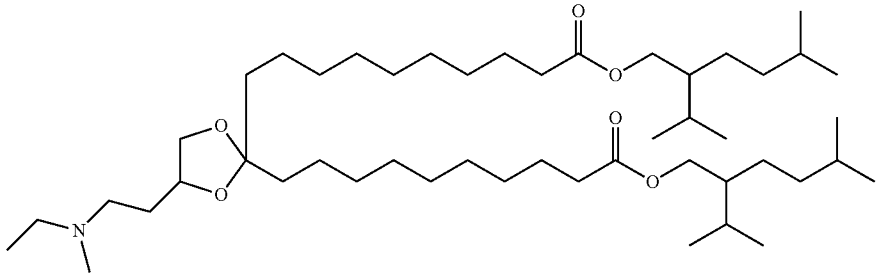 [SMILES: CCN(C)CCC1COC(CCCCCCCCCC(=O)OCC(CCC(C)C)C(C)C)(CCCCCCCCCC(=O)OCC(CCC(C)C)C(C)C)O1]
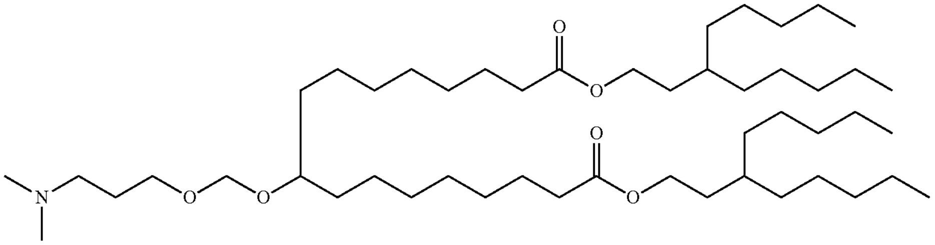 [SMILES: CCCCCC(CCCCC)CCOC(=O)CCCCCCCC(CCCCCCCC(=O)OCCC(CCCCC)CCCCC)OCOCCCN(C)C]

-continued
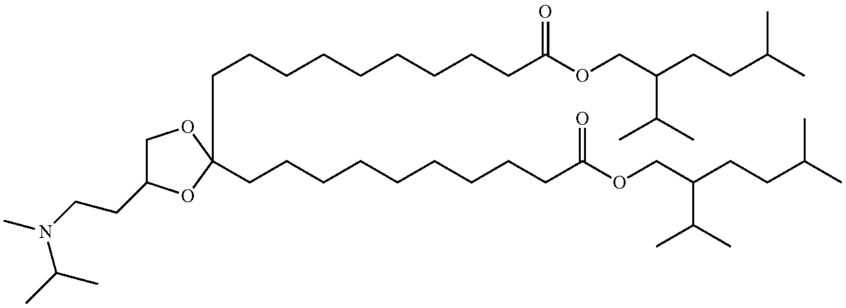 [SMILES: CC(C)CCC(COC(=O)CCCCCCCCCC1(CCCCCCCCCC(=O)OCC(CCC(C)C)C(C)C)OCC(CCN(C)C(C)C)O1)C(C)C]
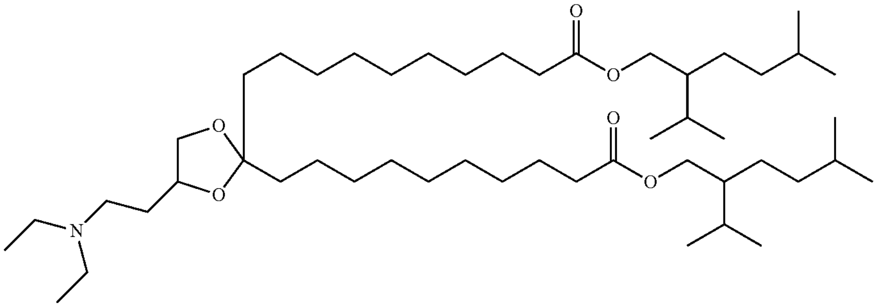 [SMILES: CCN(CC)CCC1COC(CCCCCCCCCC(=O)OCC(CCC(C)C)C(C)C)(CCCCCCCCCC(=O)OCC(CCC(C)C)C(C)C)O1]
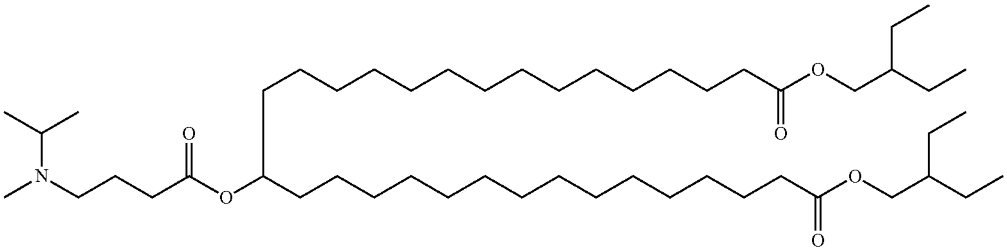 [SMILES: CCC(CC)COC(=O)CCCCCCCCCCCCCCC(CCCCCCCCCCCCCCC(=O)OCC(CC)CC)OC(=O)CCCN(C)C(C)C]
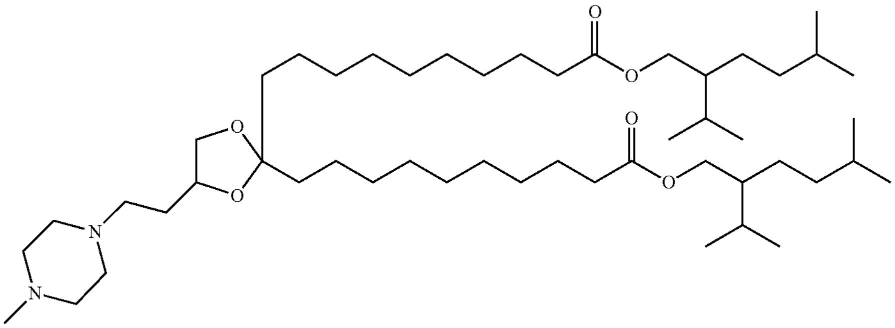 [SMILES: CC(C)CCC(COC(=O)CCCCCCCCCC1(CCCCCCCCCC(=O)OCC(CCC(C)C)C(C)C)OCC(CCN2CCN(C)CC2)O1)C(C)C]
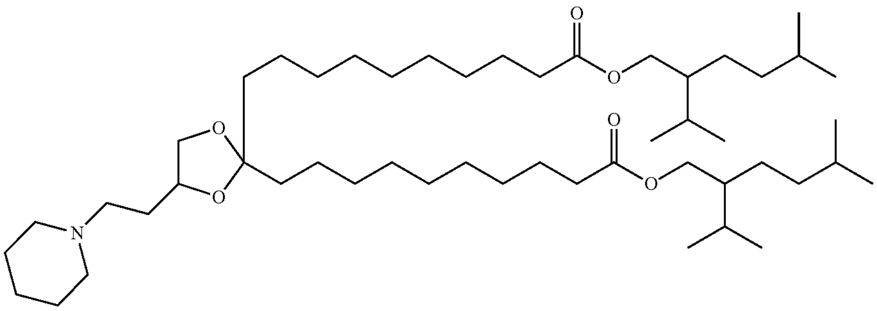 [SMILES: CC(C)CCC(COC(=O)CCCCCCCCCC1(CCCCCCCCCC(=O)OCC(CCC(C)C)C(C)C)OCC(CCN2CCCCC2)O1)C(C)C]

-continued
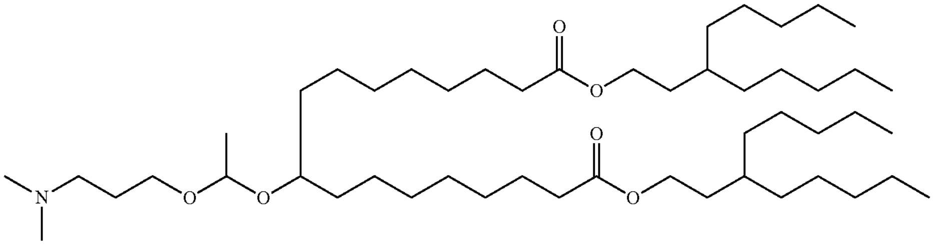 [SMILES: CCCCCC(CCCCC)CCOC(=O)CCCCCCCC(CCCCCCCC(=O)OCCC(CCCCC)CCCCC)OC(C)OCCCN(C)C]
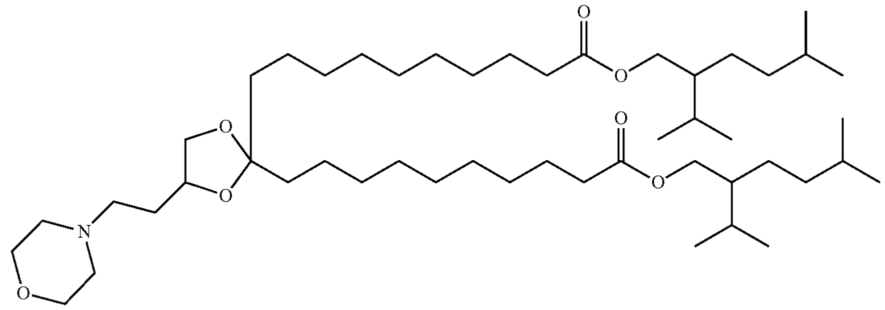 [SMILES: CC(C)CCC(COC(=O)CCCCCCCCCC1(CCCCCCCCCC(=O)OCC(CCC(C)C)C(C)C)OCC(CCN2CCOCC2)O1)C(C)C]
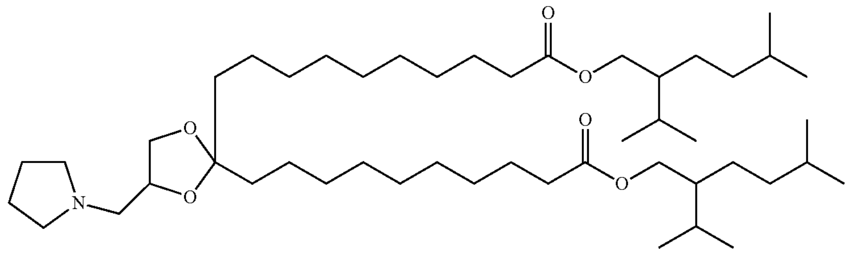 [SMILES: CC(C)CCC(COC(=O)CCCCCCCCCC1(CCCCCCCCCC(=O)OCC(CCC(C)C)C(C)C)OCC(CN2CCCC2)O1)C(C)C]
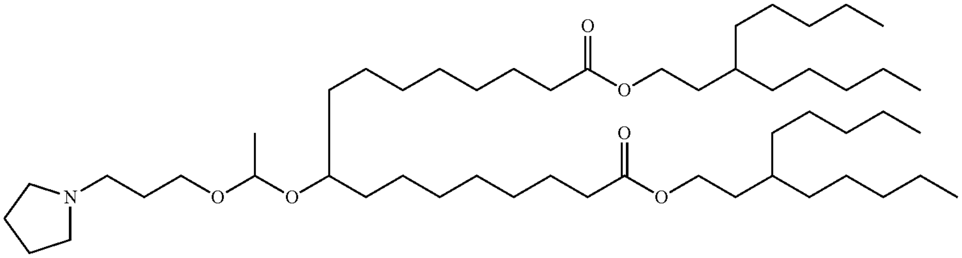 [SMILES: CCCCCC(CCCCC)CCOC(=O)CCCCCCCC(CCCCCCCC(=O)OCCC(CCCCC)CCCCC)OC(C)OCCCN1CCCC1]
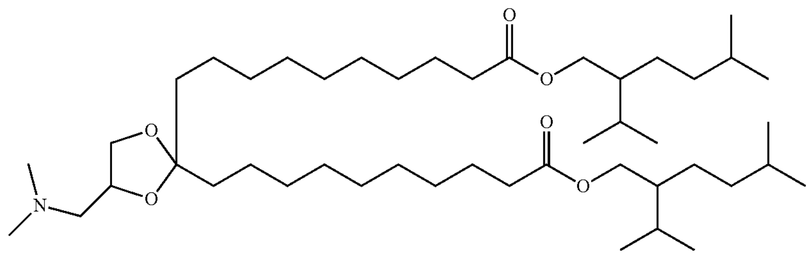 [SMILES: CC(C)CCC(COC(=O)CCCCCCCCCC1(CCCCCCCCCC(=O)OCC(CCC(C)C)C(C)C)OCC(CN(C)C)O1)C(C)C]
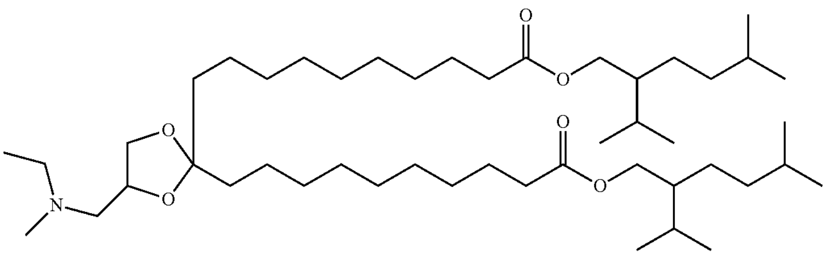 [SMILES: CCN(C)CC1COC(CCCCCCCCCC(=O)OCC(CCC(C)C)C(C)C)(CCCCCCCCCC(=O)OCC(CCC(C)C)C(C)C)O1]

-continued
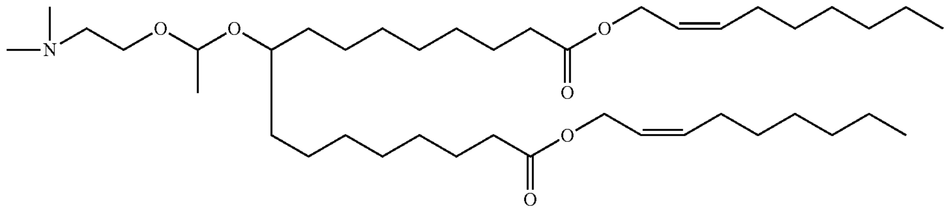 [SMILES: CCCCCC/C=C\COC(=O)CCCCCCCC(CCCCCCCC(=O)OC/C=C\CCCCCC)OC(C)OCCN(C)C]
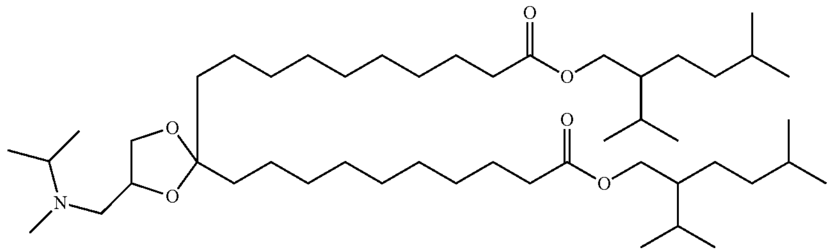 [SMILES: CC(C)CCC(COC(=O)CCCCCCCCCC1(CCCCCCCCCC(=O)OCC(CCC(C)C)C(C)C)OCC(CN(C)C(C)C)O1)C(C)C]
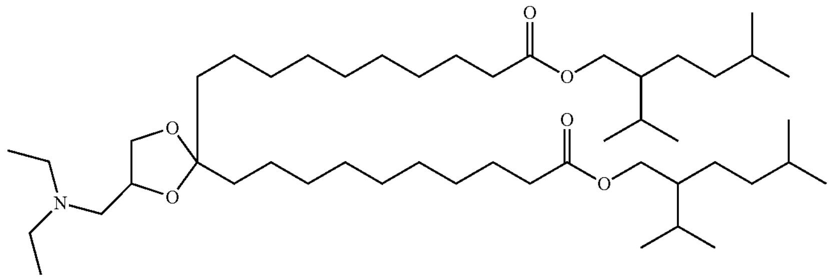 [SMILES: CCN(CC)CC1COC(CCCCCCCCCC(=O)OCC(CCC(C)C)C(C)C)(CCCCCCCCCC(=O)OCC(CCC(C)C)C(C)C)O1]
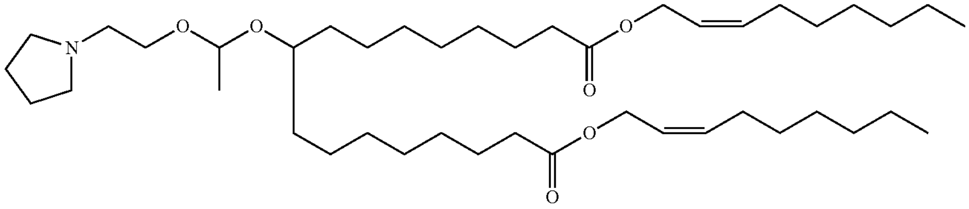 [SMILES: CCCCCC/C=C\COC(=O)CCCCCCCC(CCCCCCCC(=O)OC/C=C\CCCCCC)OC(C)OCCN1CCCC1]
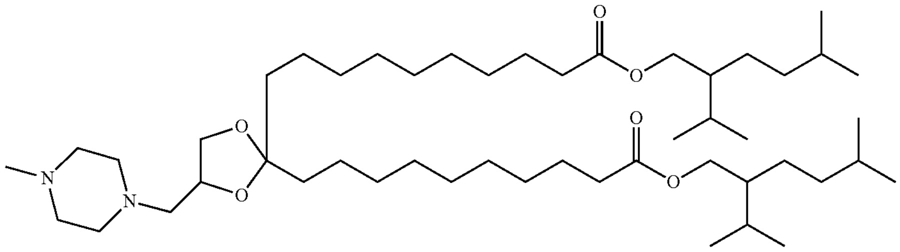 [SMILES: CC(C)CCC(COC(=O)CCCCCCCCCC1(CCCCCCCCCC(=O)OCC(CCC(C)C)C(C)C)OCC(CN2CCN(C)CC2)O1)C(C)C]
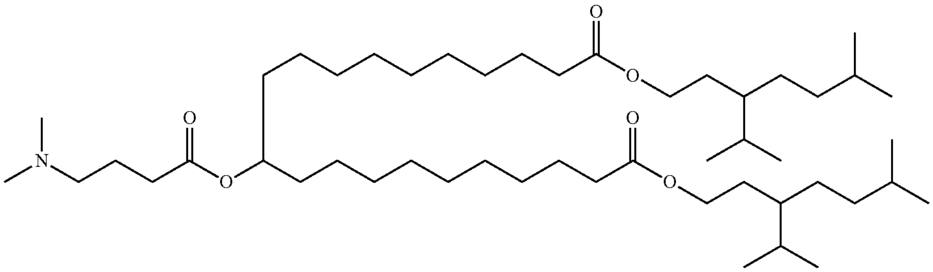 [SMILES: CC(C)CCC(CCOC(=O)CCCCCCCCCC(CCCCCCCCCC(=O)OCCC(CCC(C)C)C(C)C)OC(=O)CCCN(C)C)C(C)C]

-continued
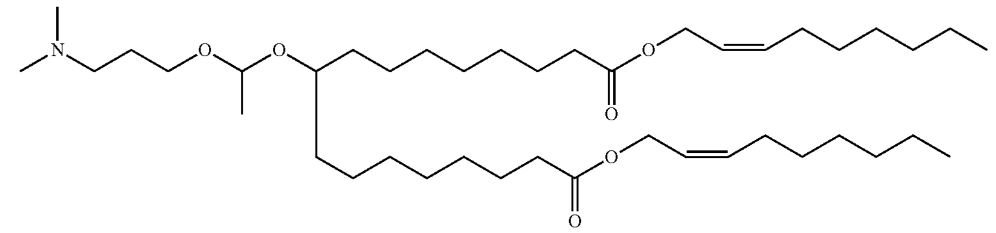 [SMILES: CCCCCC/C=C\COC(=O)CCCCCCCC(CCCCCCCC(=O)OC/C=C\CCCCCC)OC(C)OCCCN(C)C]
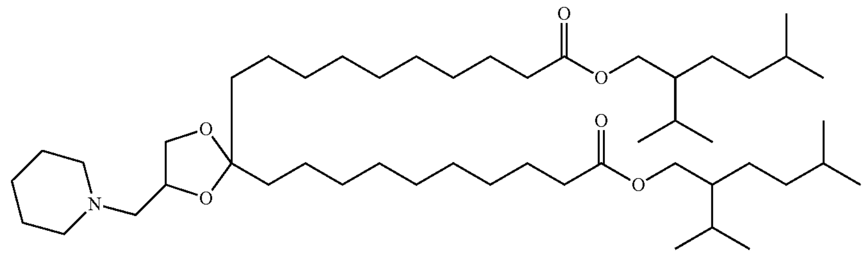 [SMILES: CC(C)CCC(COC(=O)CCCCCCCCCC1(CCCCCCCCCC(=O)OCC(CCC(C)C)C(C)C)OCC(CN2CCCCC2)O1)C(C)C]
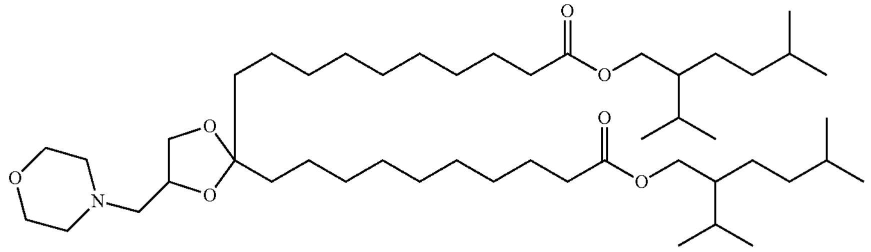 [SMILES: CC(C)CCC(COC(=O)CCCCCCCCCC1(CCCCCCCCCC(=O)OCC(CCC(C)C)C(C)C)OCC(CN2CCOCC2)O1)C(C)C]
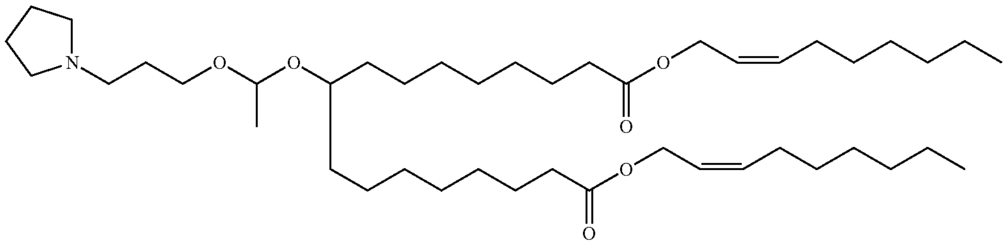 [SMILES: CCCCCC/C=C\COC(=O)CCCCCCCC(CCCCCCCC(=O)OC/C=C\CCCCCC)OC(C)OCCCN1CCCC1]
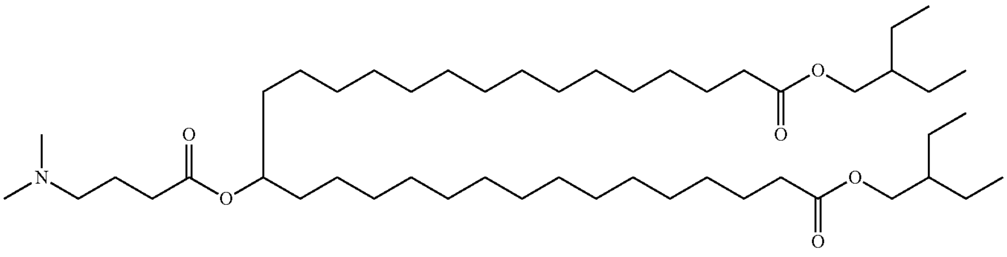 [SMILES: CCC(CC)COC(=O)CCCCCCCCCCCCCCC(CCCCCCCCCCCCCCC(=O)OCC(CC)CC)OC(=O)CCCN(C)C]
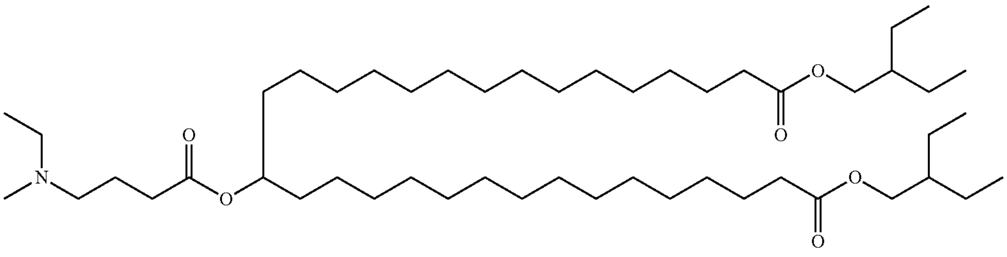 [SMILES: CCC(CC)COC(=O)CCCCCCCCCCCCCCC(CCCCCCCCCCCCCCC(=O)OCC(CC)CC)OC(=O)CCCN(C)CC]

-continued
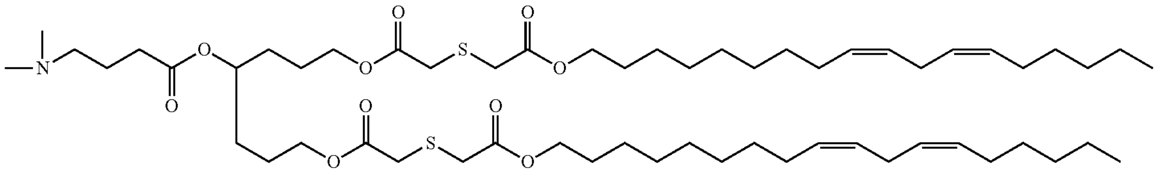 [SMILES: CCCCC/C=C\C/C=C\CCCCCCCCOC(=O)CSCC(=O)OCCCC(CCCOC(=O)CSCC(=O)OCCCCCCCC/C=C\C/C=C\CCCCC)OC(=O)CCCN(C)C]
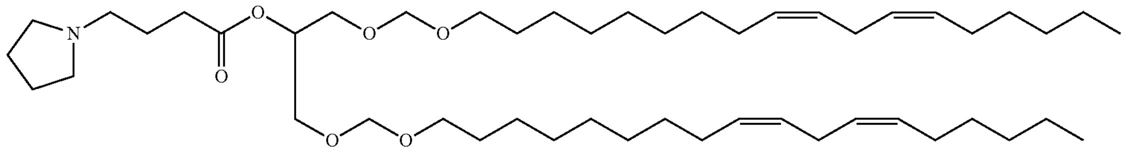 [SMILES: CCCCC/C=C\C/C=C\CCCCCCCCOCOCC(COCOCCCCCCCC/C=C\C/C=C\CCCCC)OC(=O)CCCN1CCCC1]
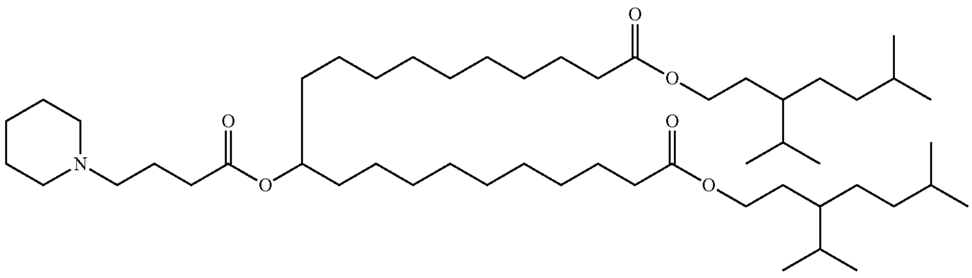 [SMILES: CC(C)CCC(CCOC(=O)CCCCCCCCCC(CCCCCCCCCC(=O)OCCC(CCC(C)C)C(C)C)OC(=O)CCCN1CCCCC1)C(C)C]
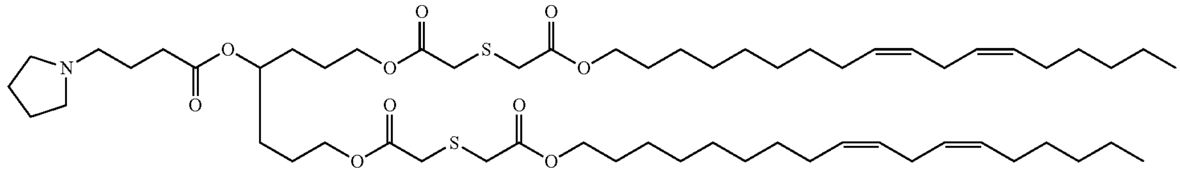 [SMILES: CCCCC/C=C\C/C=C\CCCCCCCCOC(=O)CSCC(=O)OCCCC(CCCOC(=O)CSCC(=O)OCCCCCCCC/C=C\C/C=C\CCCCC)OC(=O)CCCN1CCCC1]
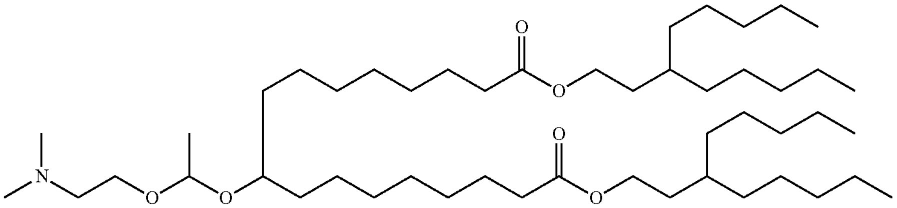 [SMILES: CCCCCC(CCCCC)CCOC(=O)CCCCCCCC(CCCCCCCC(=O)OCCC(CCCCC)CCCCC)OC(C)OCCN(C)C]
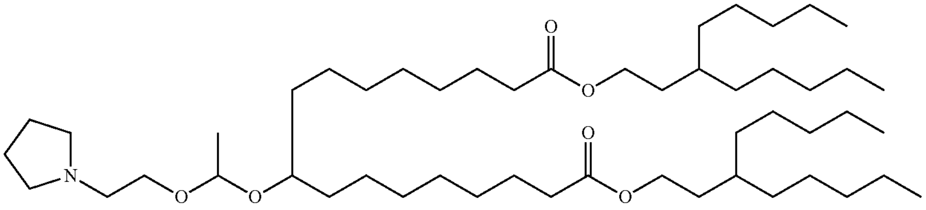 [SMILES: CCCCCC(CCCCC)CCOC(=O)CCCCCCCC(CCCCCCCC(=O)OCCC(CCCCC)CCCCC)OC(C)OCCN1CCCC1]
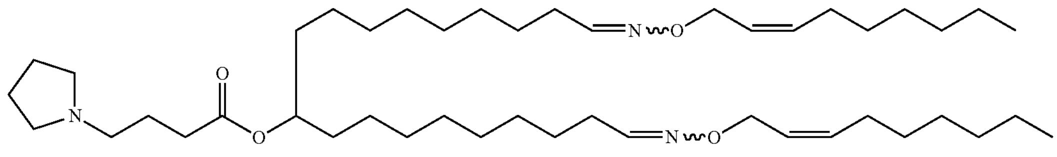 [SMILES: CCCCCC/C=C\CON=CCCCCCCCCC(CCCCCCCCC=NOC/C=C\CCCCCC)OC(=O)CCCN1CCCC1]
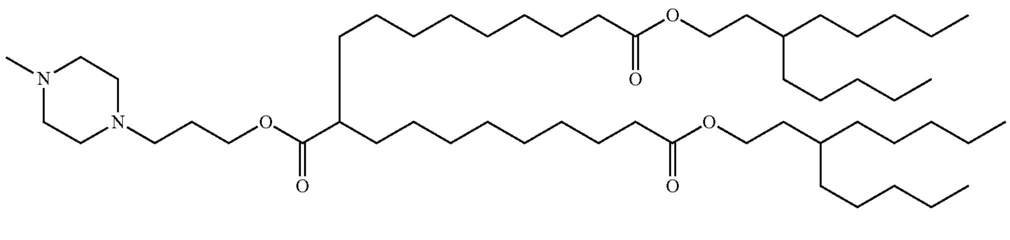 [SMILES: CCCCCC(CCCCC)CCOC(=O)CCCCCCCCC(CCCCCCCCC(=O)OCCC(CCCCC)CCCCC)C(=O)OCCCN1CCN(C)CC1]

-continued
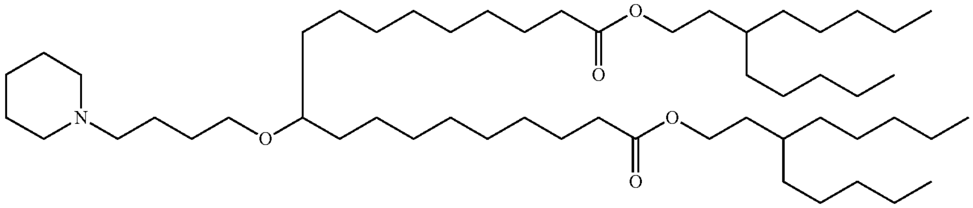 [SMILES: CCCCCC(CCCCC)CCOC(=O)CCCCCCCCC(CCCCCCCCC(=O)OCCC(CCCCC)CCCCC)OCCCCN1CCCCC1]
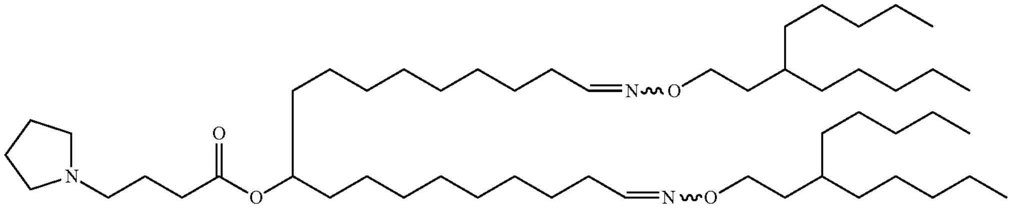 [SMILES: CCCCCC(CCCCC)CCON=CCCCCCCCCC(CCCCCCCCC=NOCCC(CCCCC)CCCCC)OC(=O)CCCN1CCCC1]
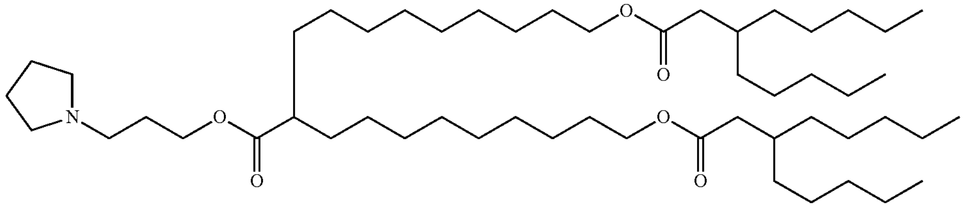 [SMILES: CCCCCC(CCCCC)CC(=O)OCCCCCCCCCC(CCCCCCCCCOC(=O)CC(CCCCC)CCCCC)C(=O)OCCCN1CCCC1]
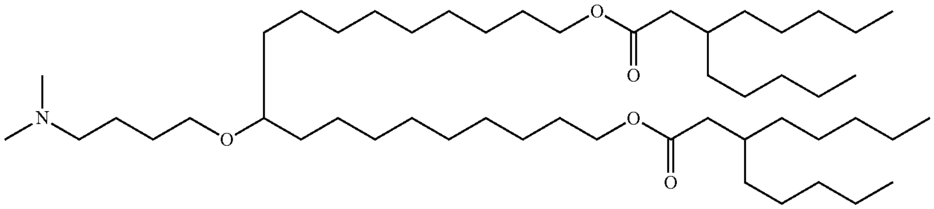 [SMILES: CCCCCC(CCCCC)CC(=O)OCCCCCCCCCC(CCCCCCCCCOC(=O)CC(CCCCC)CCCCC)OCCCCN(C)C]
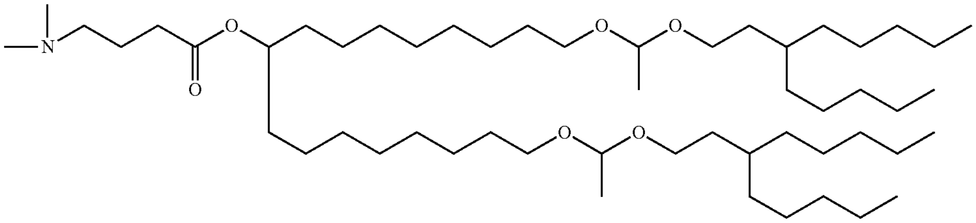 [SMILES: CCCCCC(CCCCC)CCOC(C)OCCCCCCCCC(CCCCCCCCOC(C)OCCC(CCCCC)CCCCC)OC(=O)CCCN(C)C]
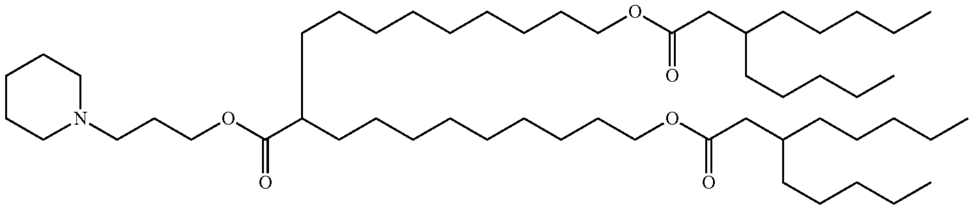 [SMILES: CCCCCC(CCCCC)CC(=O)OCCCCCCCCCC(CCCCCCCCCOC(=O)CC(CCCCC)CCCCC)C(=O)OCCCN1CCCCC1]
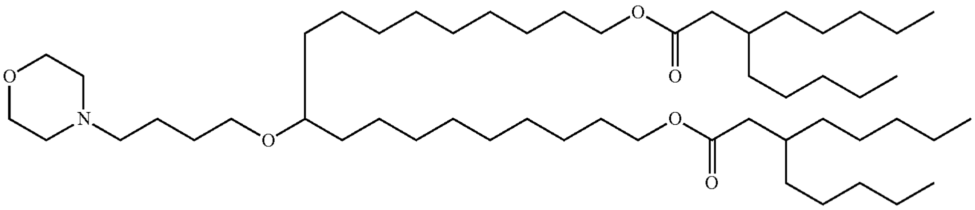 [SMILES: CCCCCC(CCCCC)CC(=O)OCCCCCCCCCC(CCCCCCCCCOC(=O)CC(CCCCC)CCCCC)OCCCCN1CCOCC1]

-continued
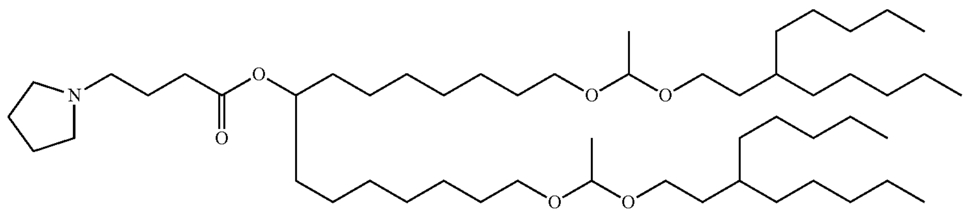 [SMILES: CCCCCC(CCCCC)CCOC(C)OCCCCCCCC(CCCCCCCOC(C)OCCC(CCCCC)CCCCC)OC(=O)CCCN1CCCC1]
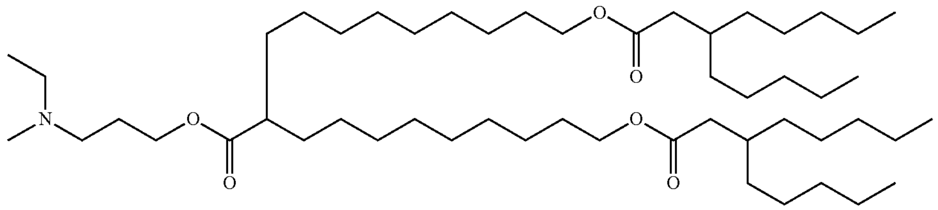 [SMILES: CCCCCC(CCCCC)CC(=O)OCCCCCCCCCC(CCCCCCCCCOC(=O)CC(CCCCC)CCCCC)C(=O)OCCCN(C)CC]
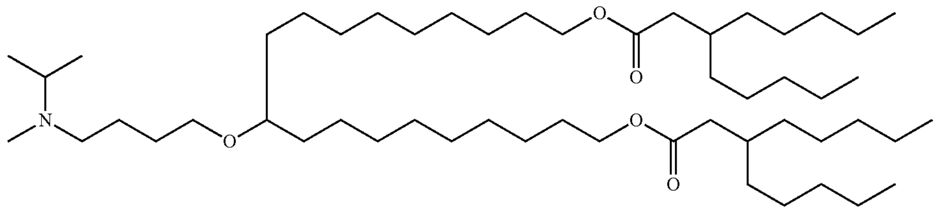 [SMILES: CCCCCC(CCCCC)CC(=O)OCCCCCCCCCC(CCCCCCCCCOC(=O)CC(CCCCC)CCCCC)OCCCCN(C)C(C)C]
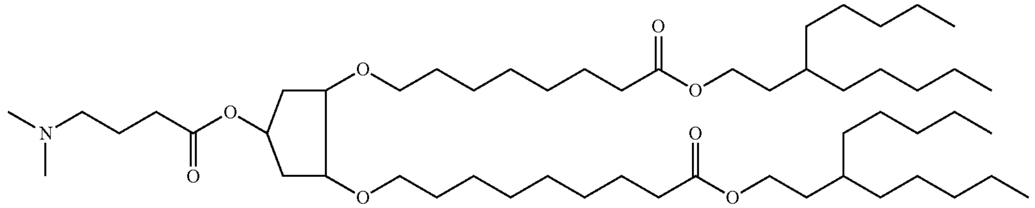 [SMILES: CCCCCC(CCCCC)CCOC(=O)CCCCCCCCOC1CC(OC(=O)CCCN(C)C)CC1OCCCCCCCC(=O)OCCC(CCCCC)CCCCC]
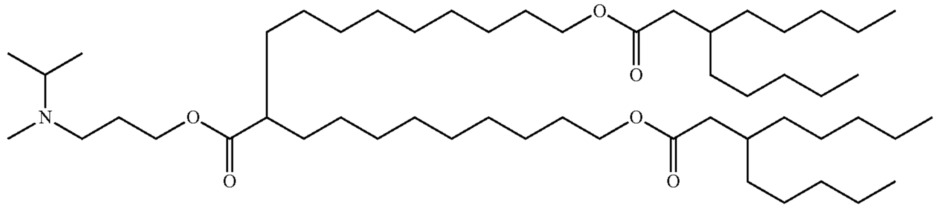 [SMILES: CCCCCC(CCCCC)CC(=O)OCCCCCCCCCC(CCCCCCCCCOC(=O)CC(CCCCC)CCCCC)C(=O)OCCCN(C)C(C)C]
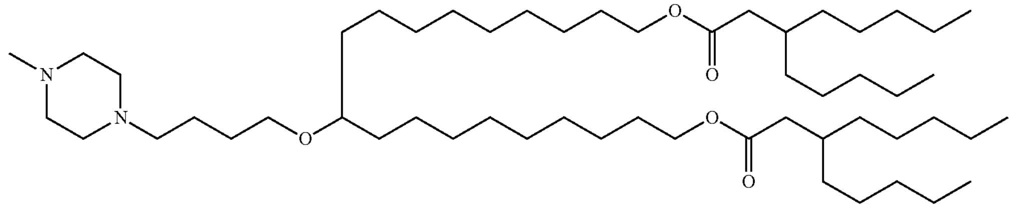 [SMILES: CCCCCC(CCCCC)CC(=O)OCCCCCCCCCC(CCCCCCCCCOC(=O)CC(CCCCC)CCCCC)OCCCCN1CCN(C)CC1]
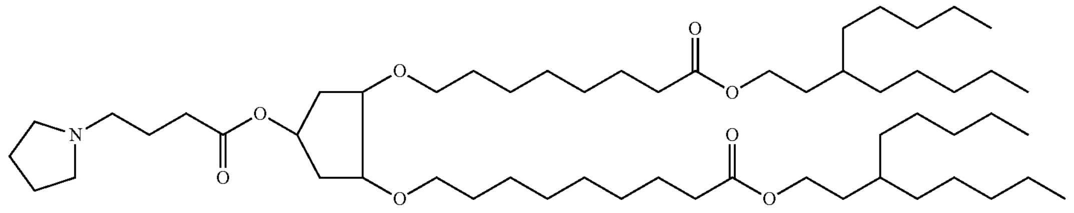 [SMILES: CCCCCC(CCCCC)CCOC(=O)CCCCCCCCOC1CC(OC(=O)CCCN2CCCC2)CC1OCCCCCCCC(=O)OCCC(CCCCC)CCCCC]

-continued
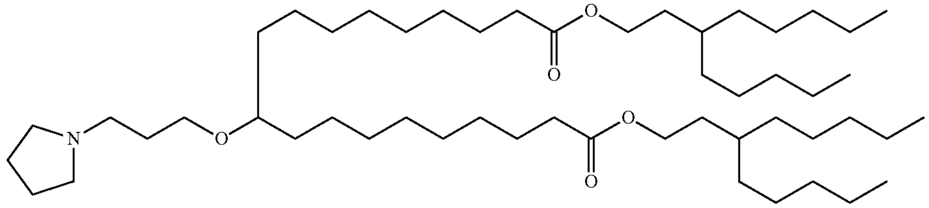 [SMILES: CCCCCC(CCCCC)CCOC(=O)CCCCCCCCC(CCCCCCCCC(=O)OCCC(CCCCC)CCCCC)OCCCN1CCCC1]
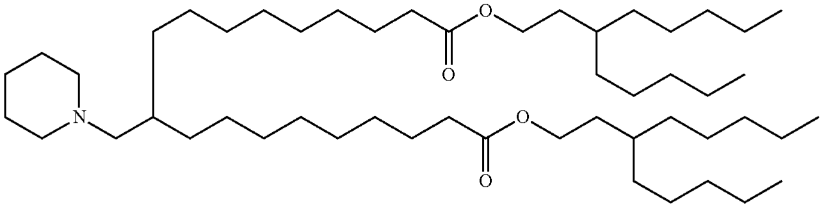 [SMILES: CCCCCC(CCCCC)CCOC(=O)CCCCCCCCC(CCCCCCCCC(=O)OCCC(CCCCC)CCCCC)CN1CCCCC1]
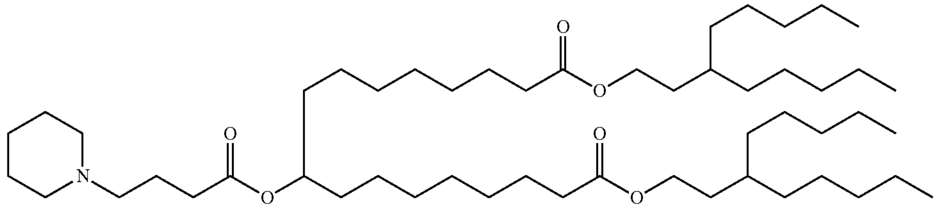 [SMILES: CCCCCC(CCCCC)CCOC(=O)CCCCCCCC(CCCCCCCC(=O)OCCC(CCCCC)CCCCC)OC(=O)CCCN1CCCCC1]
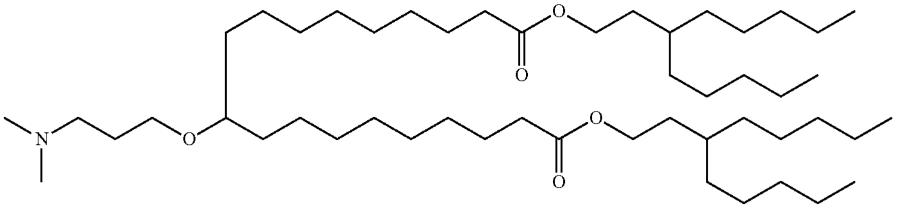 [SMILES: CCCCCC(CCCCC)CCOC(=O)CCCCCCCCC(CCCCCCCCC(=O)OCCC(CCCCC)CCCCC)OCCCN(C)C]
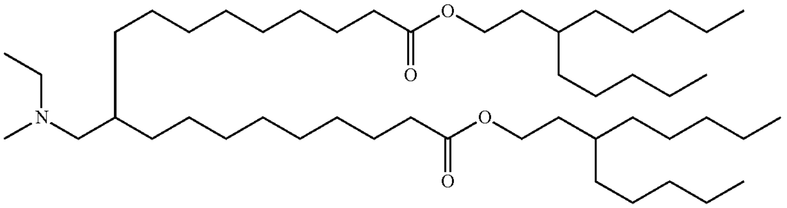 [SMILES: CCCCCC(CCCCC)CCOC(=O)CCCCCCCCC(CCCCCCCCC(=O)OCCC(CCCCC)CCCCC)CN(C)CC]
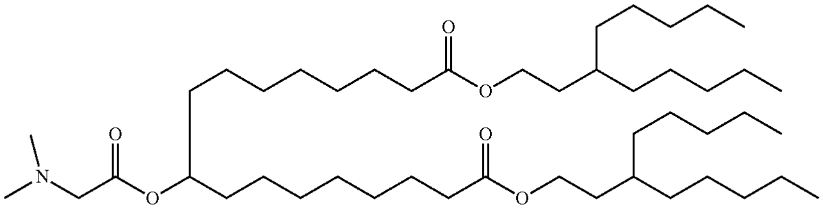 [SMILES: CCCCCC(CCCCC)CCOC(=O)CCCCCCCC(CCCCCCCC(=O)OCCC(CCCCC)CCCCC)OC(=O)CN(C)C]
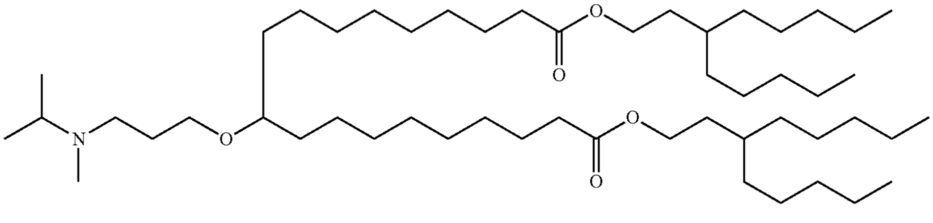 [SMILES: CCCCCC(CCCCC)CCOC(=O)CCCCCCCCC(CCCCCCCCC(=O)OCCC(CCCCC)CCCCC)OCCCN(C)C(C)C]

-continued
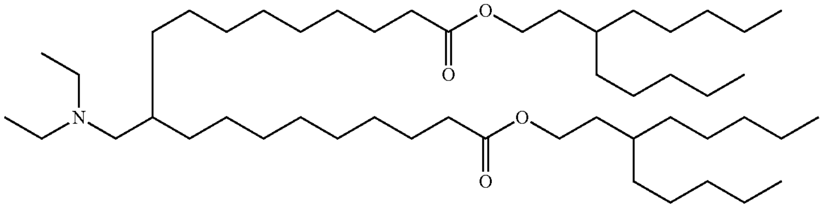 [SMILES: CCCCCC(CCCCC)CCOC(=O)CCCCCCCCC(CCCCCCCCC(=O)OCCC(CCCCC)CCCCC)CN(CC)CC]
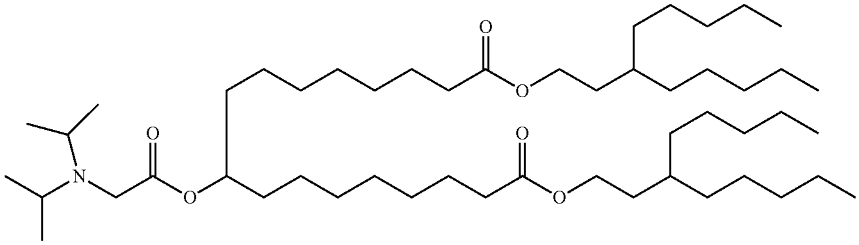 [SMILES: CCCCCC(CCCCC)CCOC(=O)CCCCCCCC(CCCCCCCC(=O)OCCC(CCCCC)CCCCC)OC(=O)CN(C(C)C)C(C)C]
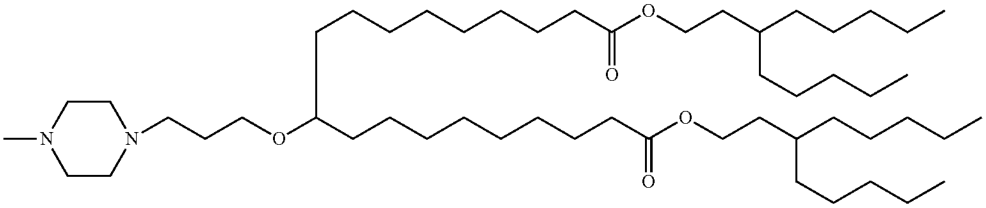 [SMILES: CCCCCC(CCCCC)CCOC(=O)CCCCCCCCC(CCCCCCCCC(=O)OCCC(CCCCC)CCCCC)OCCCN1CCN(C)CC1]
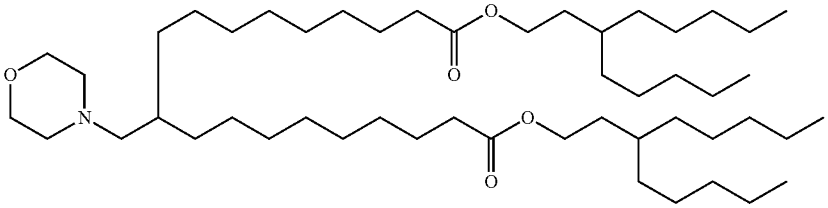 [SMILES: CCCCCC(CCCCC)CCOC(=O)CCCCCCCCC(CCCCCCCCC(=O)OCCC(CCCCC)CCCCC)CN1CCOCC1]
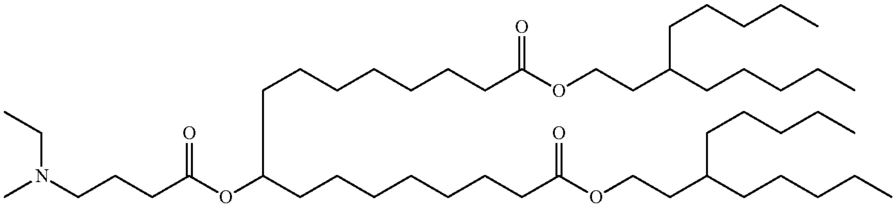 [SMILES: CCCCCC(CCCCC)CCOC(=O)CCCCCCCC(CCCCCCCC(=O)OCCC(CCCCC)CCCCC)OC(=O)CCCN(C)CC]
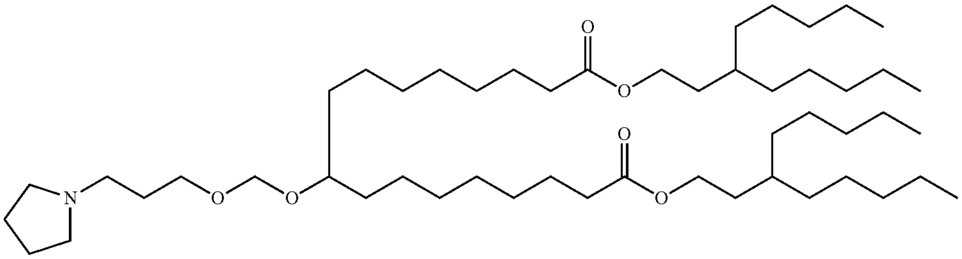 [SMILES: CCCCCC(CCCCC)CCOC(=O)CCCCCCCC(CCCCCCCC(=O)OCCC(CCCCC)CCCCC)OCOCCCN1CCCC1]
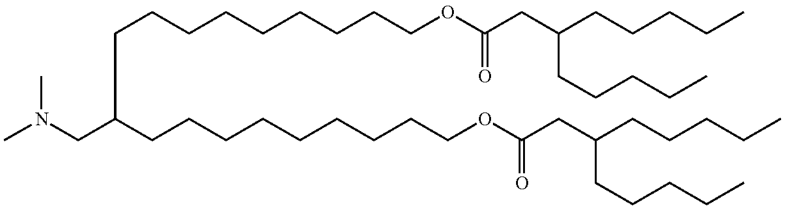 [SMILES: CCCCCC(CCCCC)CC(=O)OCCCCCCCCCC(CCCCCCCCCOC(=O)CC(CCCCC)CCCCC)CN(C)C]

-continued
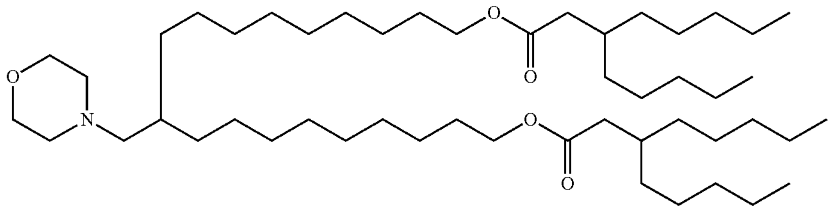 [SMILES: CCCCCC(CCCCC)CC(=O)OCCCCCCCCCC(CCCCCCCCCOC(=O)CC(CCCCC)CCCCC)CN1CCOCC1]
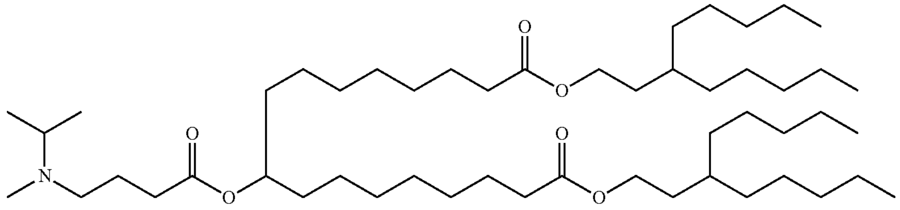 [SMILES: CCCCCC(CCCCC)CCOC(=O)CCCCCCCC(CCCCCCCC(=O)OCCC(CCCCC)CCCCC)OC(=O)CCCN(C)C(C)C]
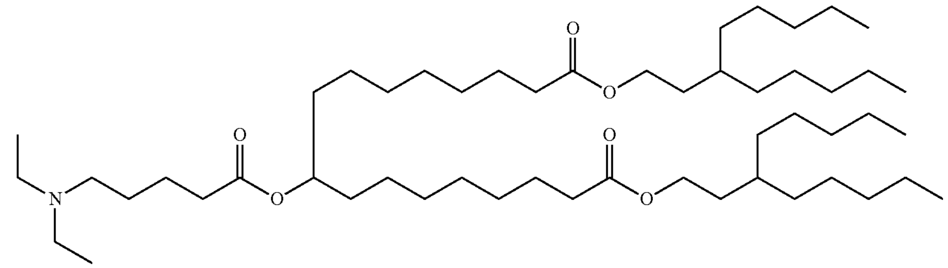 [SMILES: CCCCCC(CCCCC)CCOC(=O)CCCCCCCC(CCCCCCCC(=O)OCCC(CCCCC)CCCCC)OC(=O)CCCCN(CC)CC]
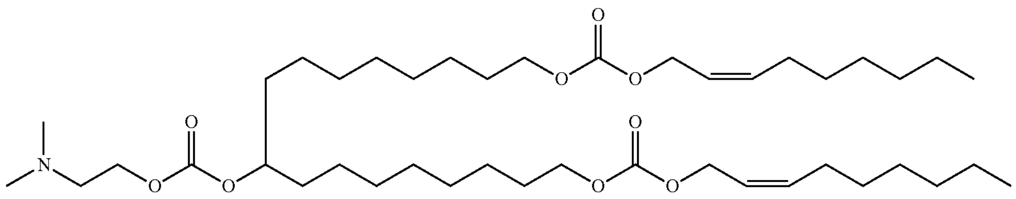 [SMILES: CCCCCC/C=C\COC(=O)OCCCCCCCCC(CCCCCCCCOC(=O)OC/C=C\CCCCCC)OC(=O)OCCN(C)C]
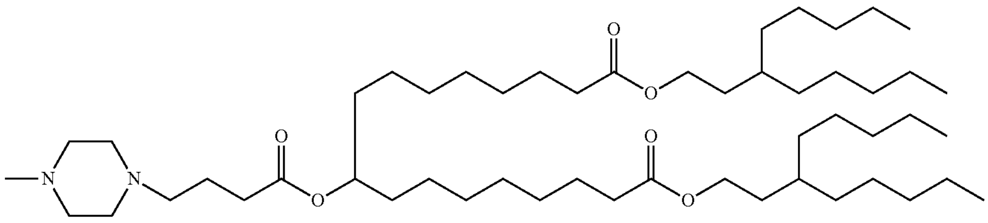 [SMILES: CCCCCC(CCCCC)CCOC(=O)CCCCCCCC(CCCCCCCC(=O)OCCC(CCCCC)CCCCC)OC(=O)CCCN1CCN(C)CC1]
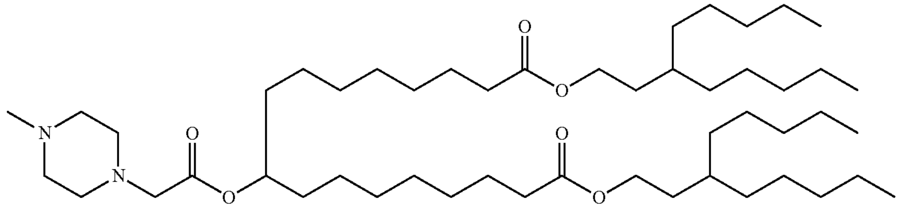 [SMILES: CCCCCC(CCCCC)CCOC(=O)CCCCCCCC(CCCCCCCC(=O)OCCC(CCCCC)CCCCC)OC(=O)CN1CCN(C)CC1]
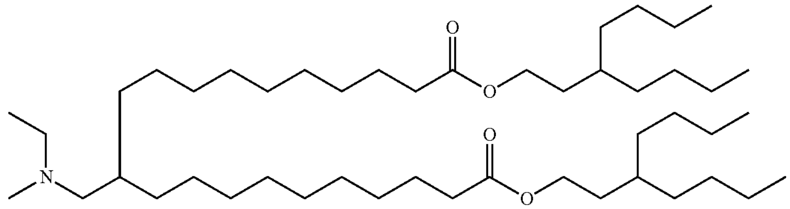 [SMILES: CCCCC(CCCC)CCOC(=O)CCCCCCCCCC(CCCCCCCCCC(=O)OCCC(CCCC)CCCC)CN(C)CC]

-continued
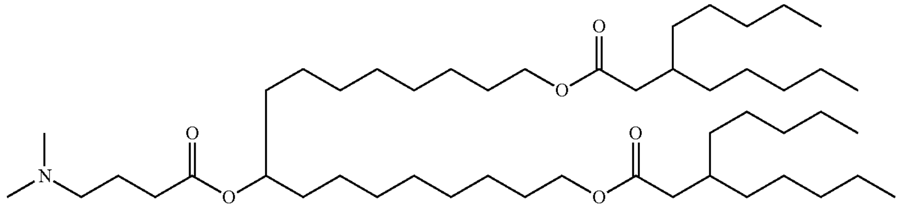 [SMILES: CCCCCC(CCCCC)CC(=O)OCCCCCCCCC(CCCCCCCCOC(=O)CC(CCCCC)CCCCC)OC(=O)CCCN(C)C]
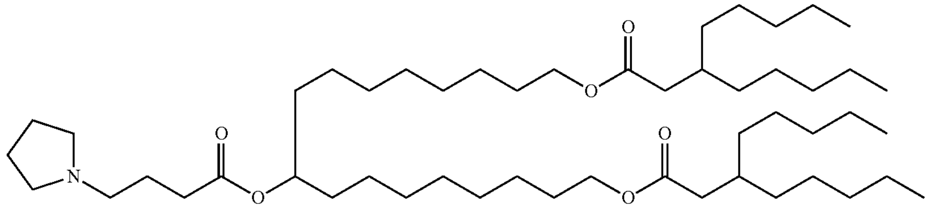 [SMILES: CCCCCC(CCCCC)CC(=O)OCCCCCCCCC(CCCCCCCCOC(=O)CC(CCCCC)CCCCC)OC(=O)CCCN1CCCC1]
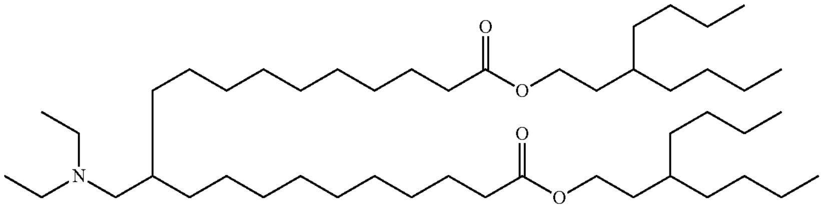 [SMILES: CCCCC(CCCC)CCOC(=O)CCCCCCCCCC(CCCCCCCCCC(=O)OCCC(CCCC)CCCC)CN(CC)CC]
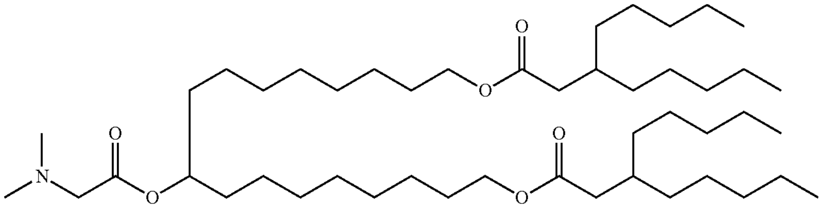 [SMILES: CCCCCC(CCCCC)CC(=O)OCCCCCCCCC(CCCCCCCCOC(=O)CC(CCCCC)CCCCC)OC(=O)CN(C)C]
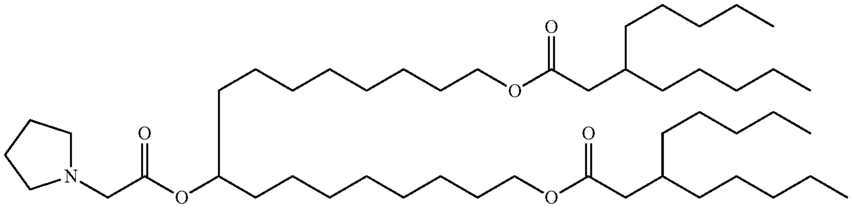 [SMILES: CCCCCC(CCCCC)CC(=O)OCCCCCCCCC(CCCCCCCCOC(=O)CC(CCCCC)CCCCC)OC(=O)CN1CCCC1]
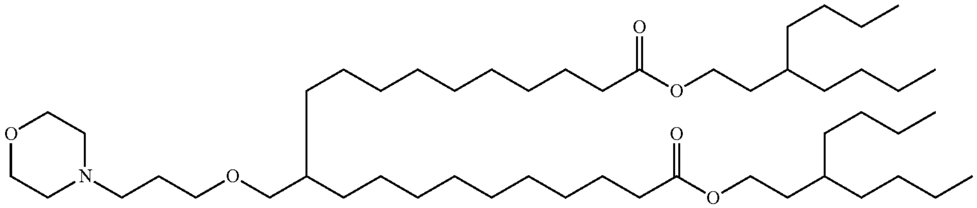 [SMILES: CCCCC(CCCC)CCOC(=O)CCCCCCCCCC(CCCCCCCCCC(=O)OCCC(CCCC)CCCC)COCCCN1CCOCC1]
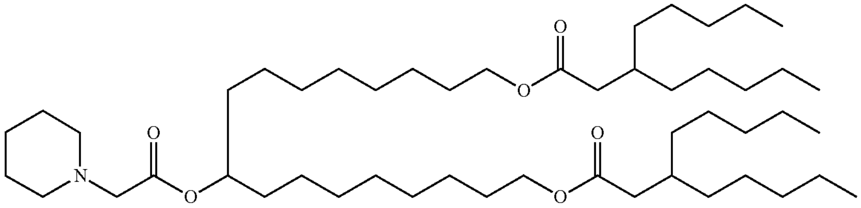 [SMILES: CCCCCC(CCCCC)CC(=O)OCCCCCCCCC(CCCCCCCCOC(=O)CC(CCCCC)CCCCC)OC(=O)CN1CCCCC1]

-continued
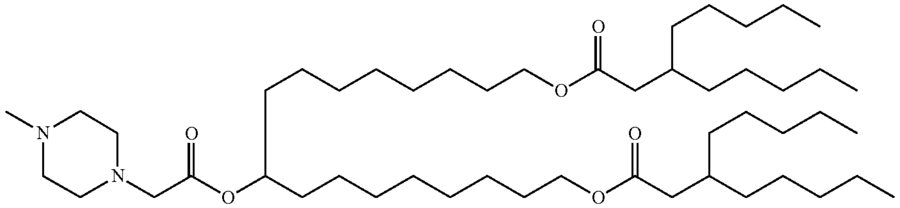 [SMILES: CCCCCC(CCCCC)CC(=O)OCCCCCCCCC(CCCCCCCCOC(=O)CC(CCCCC)CCCCC)OC(=O)CN1CCN(C)CC1]
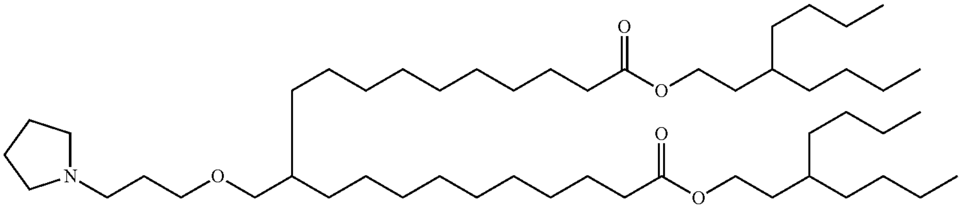 [SMILES: CCCCC(CCCC)CCOC(=O)CCCCCCCCCC(CCCCCCCCCC(=O)OCCC(CCCC)CCCC)COCCCN1CCCC1]
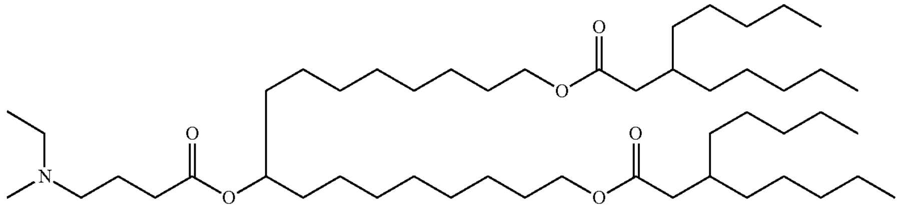 [SMILES: CCCCCC(CCCCC)CC(=O)OCCCCCCCCC(CCCCCCCCOC(=O)CC(CCCCC)CCCCC)OC(=O)CCCN(C)CC]
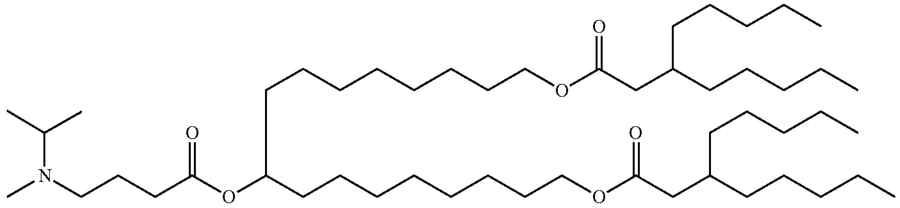 [SMILES: CCCCCC(CCCCC)CC(=O)OCCCCCCCCC(CCCCCCCCOC(=O)CC(CCCCC)CCCCC)OC(=O)CCCN(C)C(C)C]
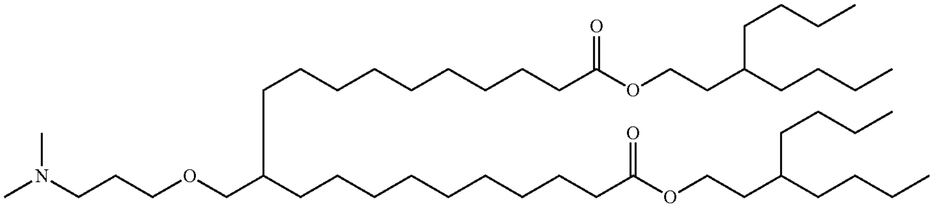 [SMILES: CCCCC(CCCC)CCOC(=O)CCCCCCCCCC(CCCCCCCCCC(=O)OCCC(CCCC)CCCC)COCCCN(C)C]
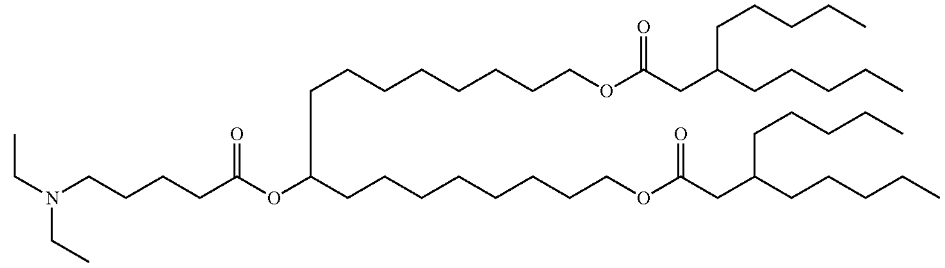 [SMILES: CCCCCC(CCCCC)CC(=O)OCCCCCCCCC(CCCCCCCCOC(=O)CC(CCCCC)CCCCC)OC(=O)CCCCN(CC)CC]
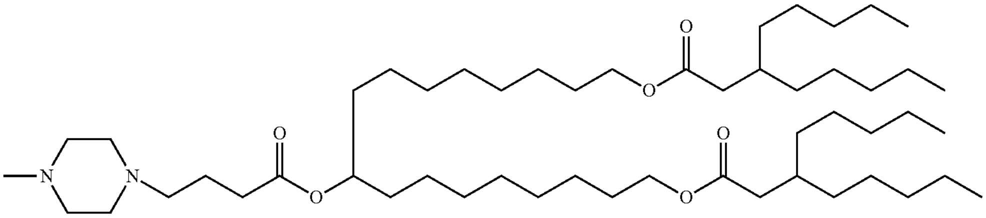 [SMILES: CCCCCC(CCCCC)CC(=O)OCCCCCCCCC(CCCCCCCCOC(=O)CC(CCCCC)CCCCC)OC(=O)CCCN1CCN(C)CC1]

-continued
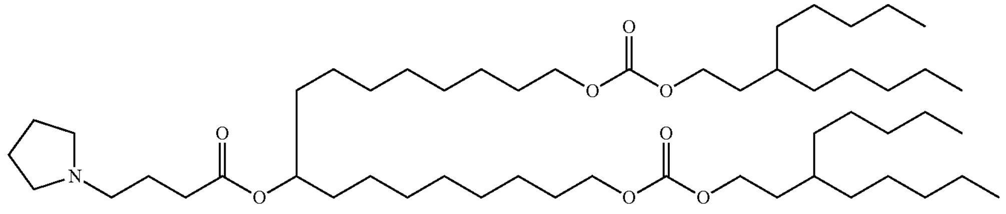 [SMILES: CCCCCC(CCCCC)CCOC(=O)OCCCCCCCCC(CCCCCCCCOC(=O)OCCC(CCCCC)CCCCC)OC(=O)CCCN1CCCC1]
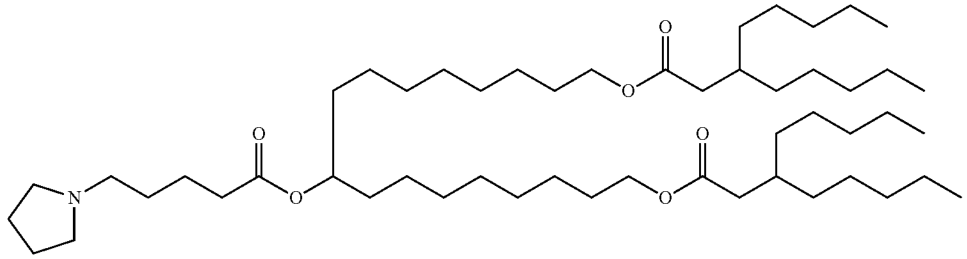 [SMILES: CCCCCC(CCCCC)CC(=O)OCCCCCCCCC(CCCCCCCCOC(=O)CC(CCCCC)CCCCC)OC(=O)CCCCN1CCCC1]
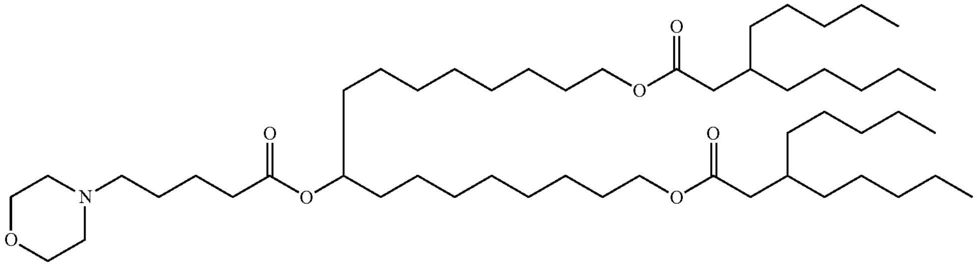 [SMILES: CCCCCC(CCCCC)CC(=O)OCCCCCCCCC(CCCCCCCCOC(=O)CC(CCCCC)CCCCC)OC(=O)CCCCN1CCOCC1]
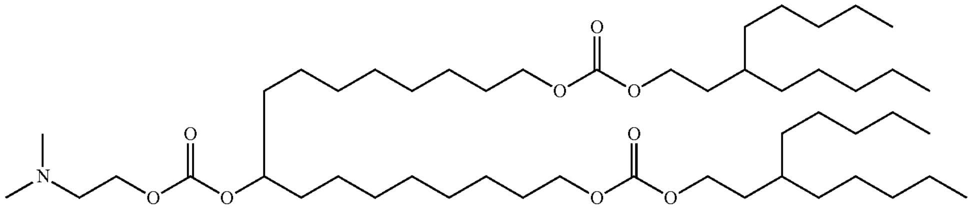 [SMILES: CCCCCC(CCCCC)CCOC(=O)OCCCCCCCCC(CCCCCCCCOC(=O)OCCC(CCCCC)CCCCC)OC(=O)OCCN(C)C]
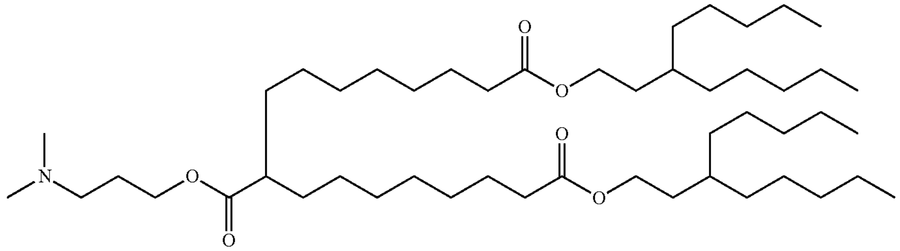 [SMILES: CCCCCC(CCCCC)CCOC(=O)CCCCCCCC(CCCCCCCC(=O)OCCC(CCCCC)CCCCC)C(=O)OCCCN(C)C]
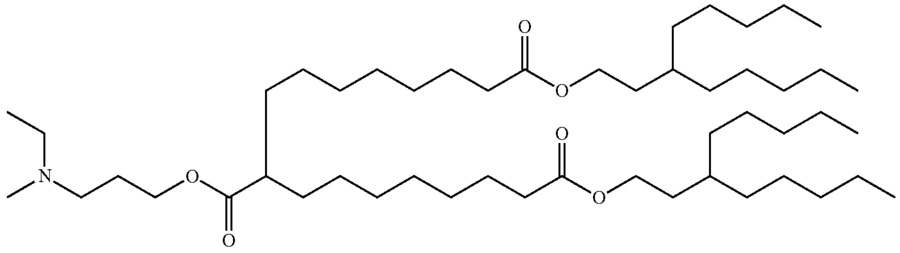 [SMILES: CCCCCC(CCCCC)CCOC(=O)CCCCCCCC(CCCCCCCC(=O)OCCC(CCCCC)CCCCC)C(=O)OCCCN(C)CC]

-continued
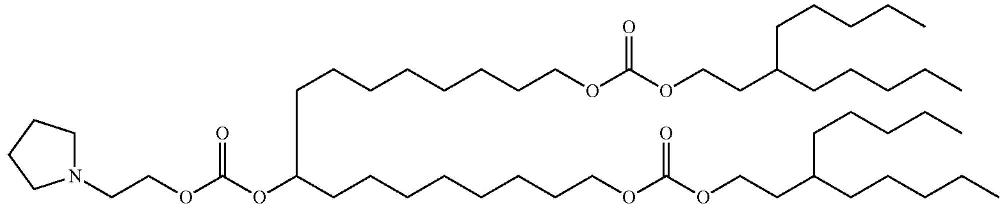 [SMILES: CCCCCC(CCCCC)CCOC(=O)OCCCCCCCCC(CCCCCCCCOC(=O)OCCC(CCCCC)CCCCC)OC(=O)OCCN1CCCC1]
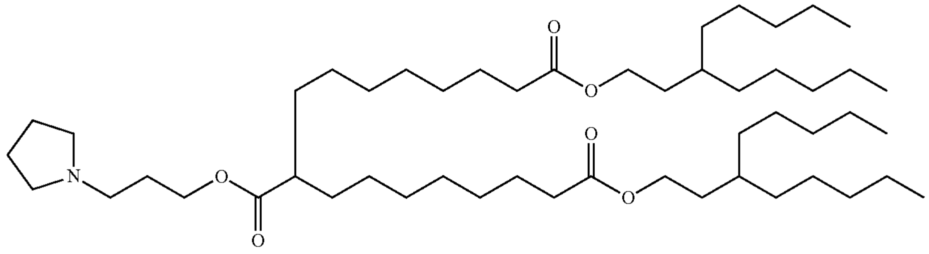 [SMILES: CCCCCC(CCCCC)CCOC(=O)CCCCCCCC(CCCCCCCC(=O)OCCC(CCCCC)CCCCC)C(=O)OCCCN1CCCC1]
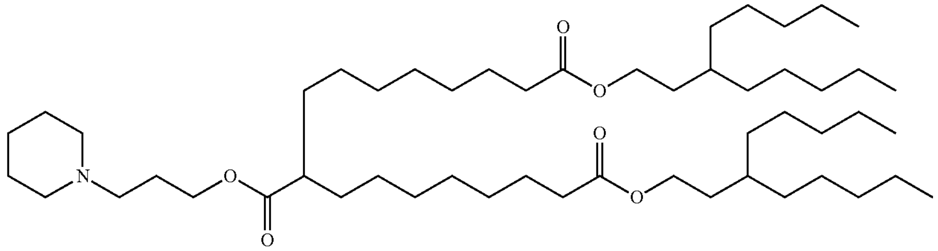 [SMILES: CCCCCC(CCCCC)CCOC(=O)CCCCCCCC(CCCCCCCC(=O)OCCC(CCCCC)CCCCC)C(=O)OCCCN1CCCCC1]
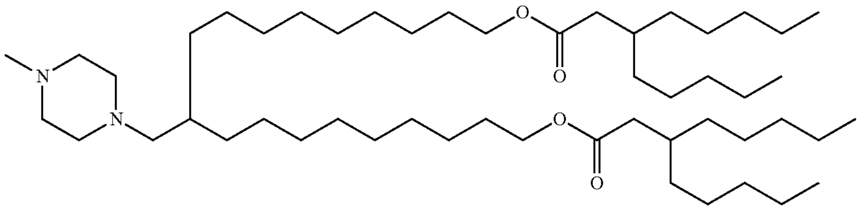 [SMILES: CCCCCC(CCCCC)CC(=O)OCCCCCCCCCC(CCCCCCCCCOC(=O)CC(CCCCC)CCCCC)CN1CCN(C)CC1]
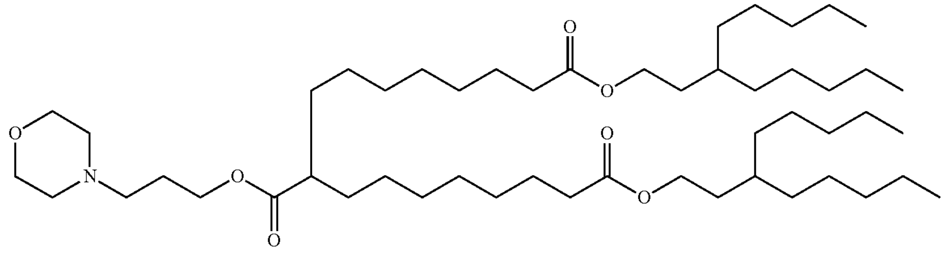 [SMILES: CCCCCC(CCCCC)CCOC(=O)CCCCCCCC(CCCCCCCC(=O)OCCC(CCCCC)CCCCC)C(=O)OCCCN1CCOCC1]
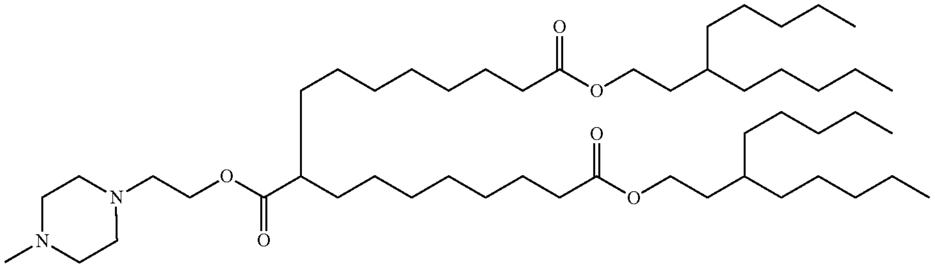 [SMILES: CCCCCC(CCCCC)CCOC(=O)CCCCCCCC(CCCCCCCC(=O)OCCC(CCCCC)CCCCC)C(=O)OCCN1CCN(C)CC1]

-continued
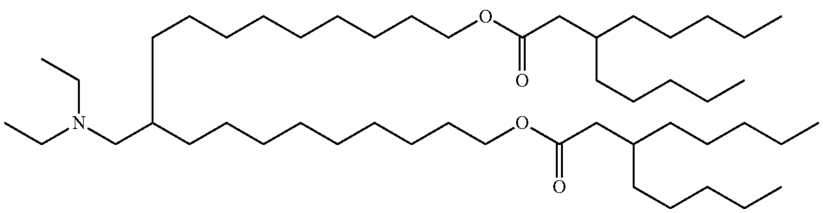 [SMILES: CCCCCC(CCCCC)CC(=O)OCCCCCCCCCC(CCCCCCCCCOC(=O)CC(CCCCC)CCCCC)CN(CC)CC]
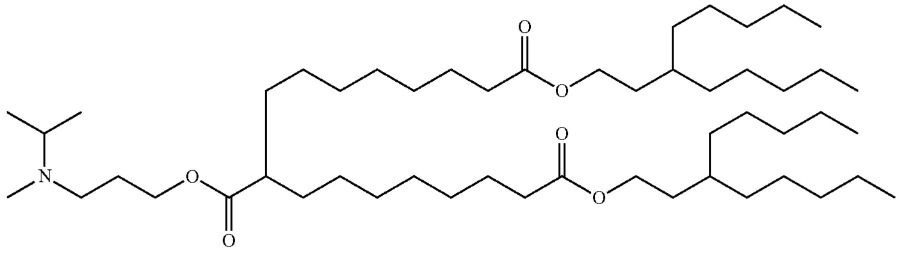 [SMILES: CCCCCC(CCCCC)CCOC(=O)CCCCCCCC(CCCCCCCC(=O)OCCC(CCCCC)CCCCC)C(=O)OCCCN(C)C(C)C]
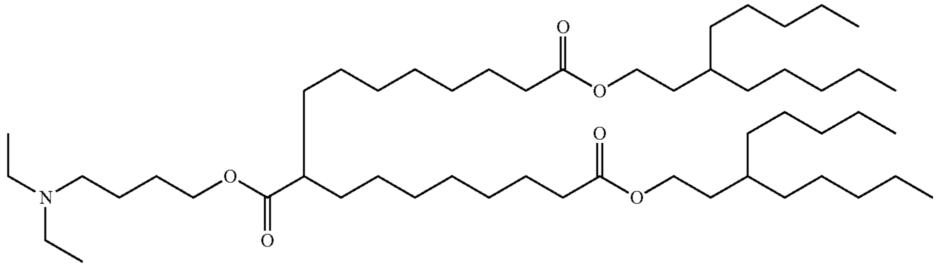 [SMILES: CCCCCC(CCCCC)CCOC(=O)CCCCCCCC(CCCCCCCC(=O)OCCC(CCCCC)CCCCC)C(=O)OCCCCN(CC)CC]
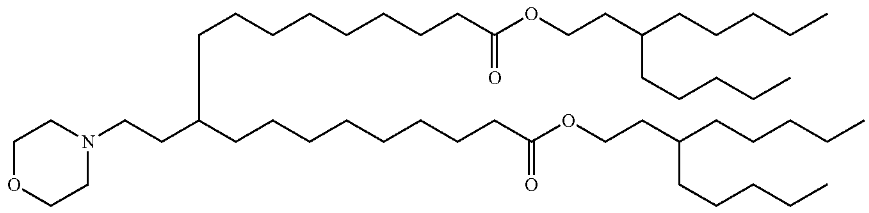 [SMILES: CCCCCC(CCCCC)CCOC(=O)CCCCCCCCC(CCCCCCCCC(=O)OCCC(CCCCC)CCCCC)CCN1CCOCC1]
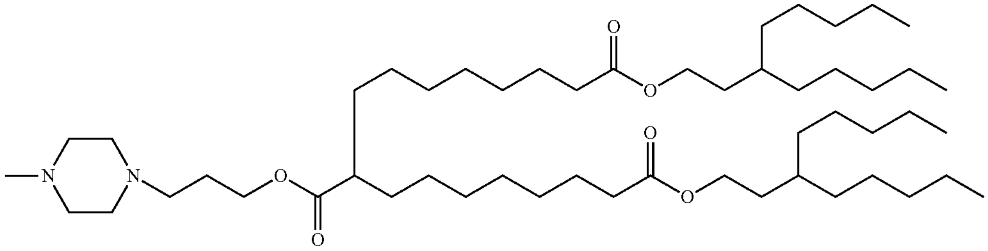 [SMILES: CCCCCC(CCCCC)CCOC(=O)CCCCCCCC(CCCCCCCC(=O)OCCC(CCCCC)CCCCC)C(=O)OCCCN1CCN(C)CC1]
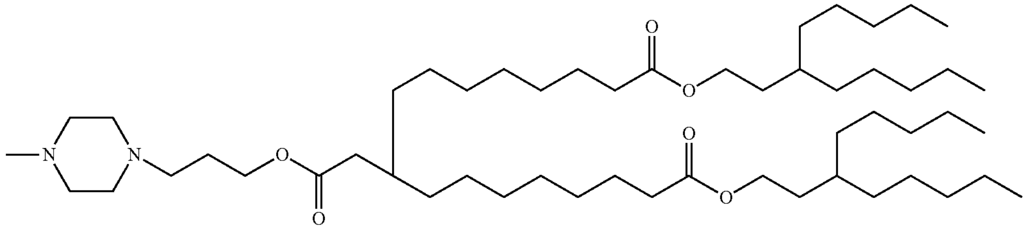 [SMILES: CCCCCC(CCCCC)CCOC(=O)CCCCCCCC(CCCCCCCC(=O)OCCC(CCCCC)CCCCC)CC(=O)OCCCN1CCN(C)CC1]

-continued
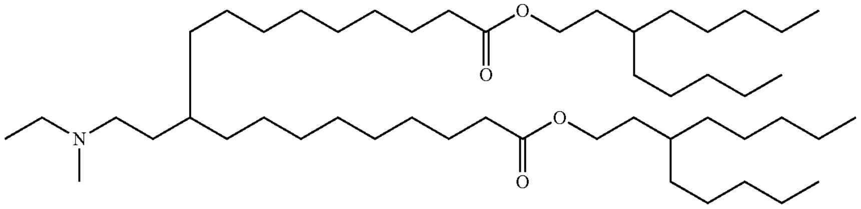 [SMILES: CCCCCC(CCCCC)CCOC(=O)CCCCCCCCC(CCCCCCCCC(=O)OCCC(CCCCC)CCCCC)CCN(C)CC]
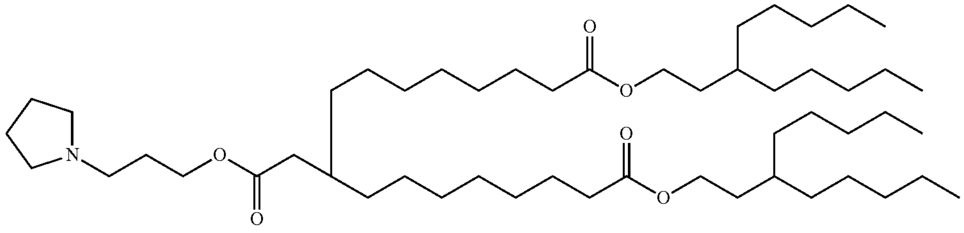 [SMILES: CCCCCC(CCCCC)CCOC(=O)CCCCCCCC(CCCCCCCC(=O)OCCC(CCCCC)CCCCC)CC(=O)OCCCN1CCCC1]
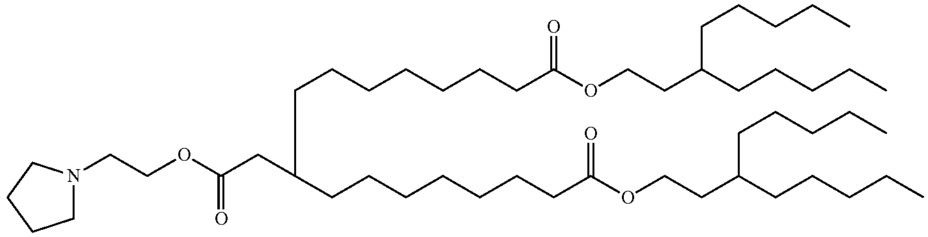 [SMILES: CCCCCC(CCCCC)CCOC(=O)CCCCCCCC(CCCCCCCC(=O)OCCC(CCCCC)CCCCC)CC(=O)OCCN1CCCC1]
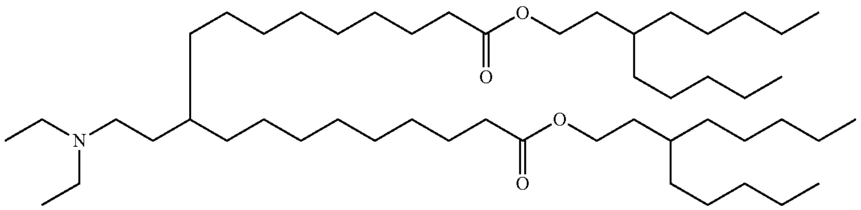 [SMILES: CCCCCC(CCCCC)CCOC(=O)CCCCCCCCC(CCCCCCCCC(=O)OCCC(CCCCC)CCCCC)CCN(CC)CC]
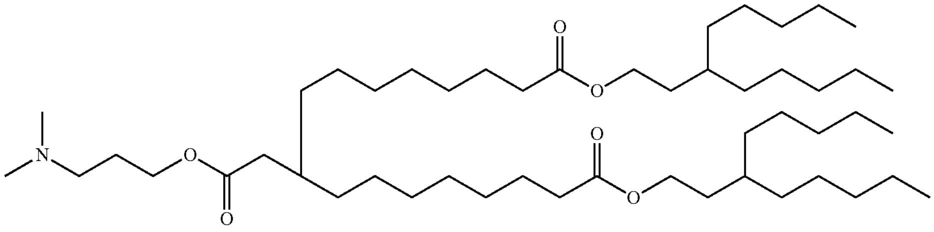 [SMILES: CCCCCC(CCCCC)CCOC(=O)CCCCCCCC(CCCCCCCC(=O)OCCC(CCCCC)CCCCC)CC(=O)OCCCN(C)C]
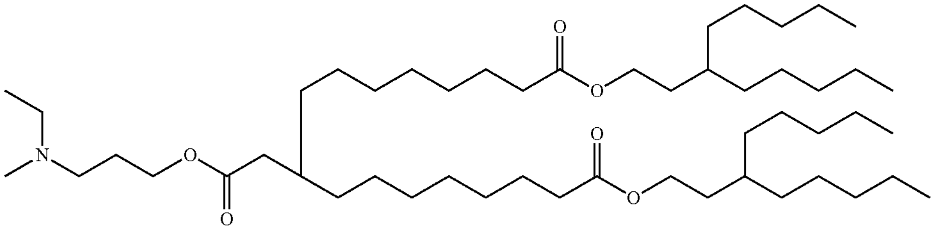 [SMILES: CCCCCC(CCCCC)CCOC(=O)CCCCCCCC(CCCCCCCC(=O)OCCC(CCCCC)CCCCC)CC(=O)OCCCN(C)CC]
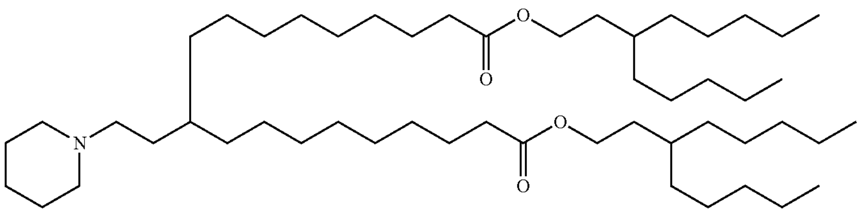 [SMILES: CCCCCC(CCCCC)CCOC(=O)CCCCCCCCC(CCCCCCCCC(=O)OCCC(CCCCC)CCCCC)CCN1CCCCC1]

-continued
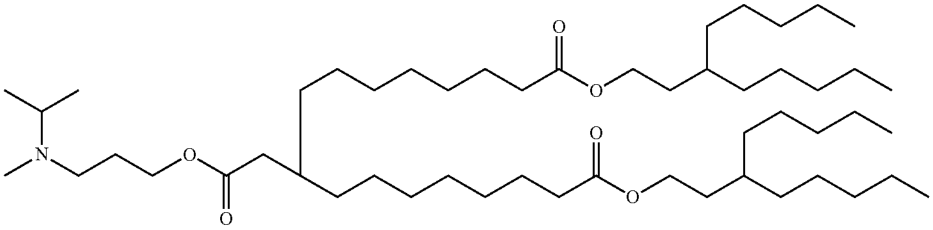 [SMILES: CCCCCC(CCCCC)CCOC(=O)CCCCCCCC(CCCCCCCC(=O)OCCC(CCCCC)CCCCC)CC(=O)OCCCN(C)C(C)C]
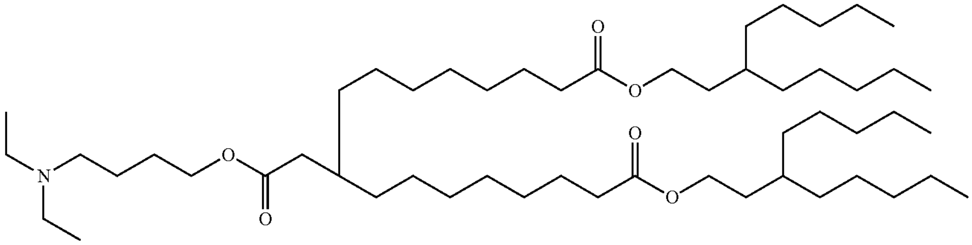 [SMILES: CCCCCC(CCCCC)CCOC(=O)CCCCCCCC(CCCCCCCC(=O)OCCC(CCCCC)CCCCC)CC(=O)OCCCCN(CC)CC]
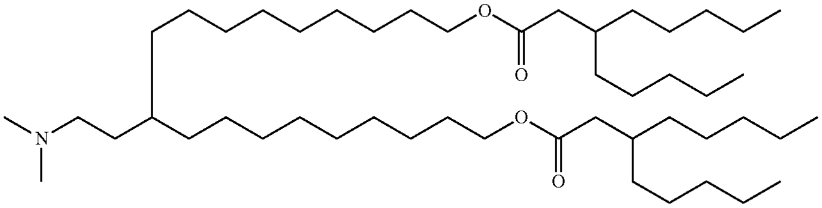 [SMILES: CCCCCC(CCCCC)CC(=O)OCCCCCCCCCC(CCCCCCCCCOC(=O)CC(CCCCC)CCCCC)CCN(C)C]
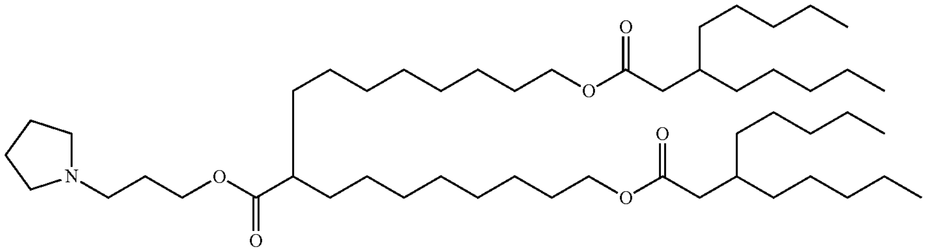 [SMILES: CCCCCC(CCCCC)CC(=O)OCCCCCCCCC(CCCCCCCCOC(=O)CC(CCCCC)CCCCC)C(=O)OCCCN1CCCC1]
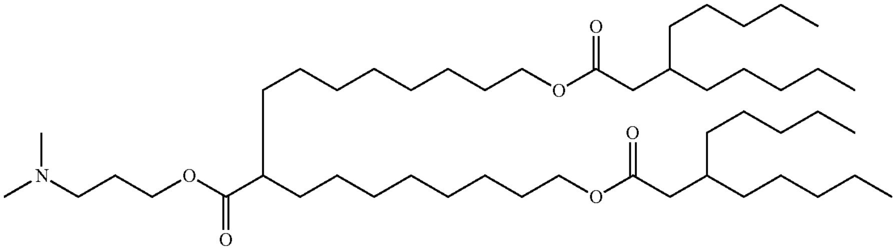 [SMILES: CCCCCC(CCCCC)CC(=O)OCCCCCCCCC(CCCCCCCCOC(=O)CC(CCCCC)CCCCC)C(=O)OCCCN(C)C]
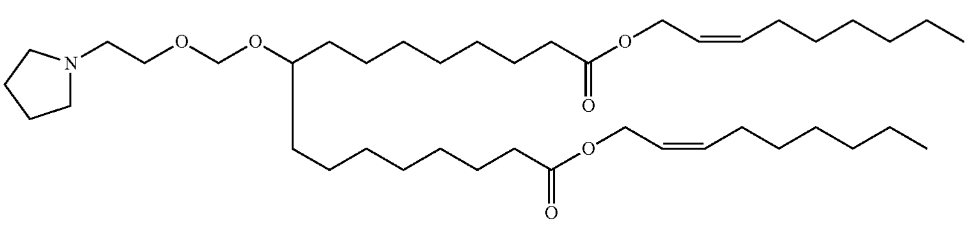 [SMILES: CCCCCC/C=C\COC(=O)CCCCCCCC(CCCCCCCC(=O)OC/C=C\CCCCCC)OCOCCN1CCCC1]

-continued
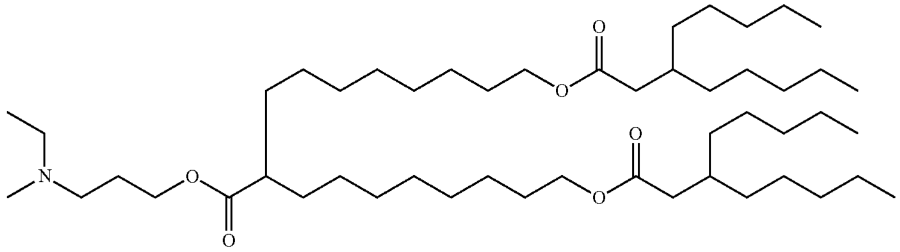 [SMILES: CCCCCC(CCCCC)CC(=O)OCCCCCCCCC(CCCCCCCCOC(=O)CC(CCCCC)CCCCC)C(=O)OCCCN(C)CC]
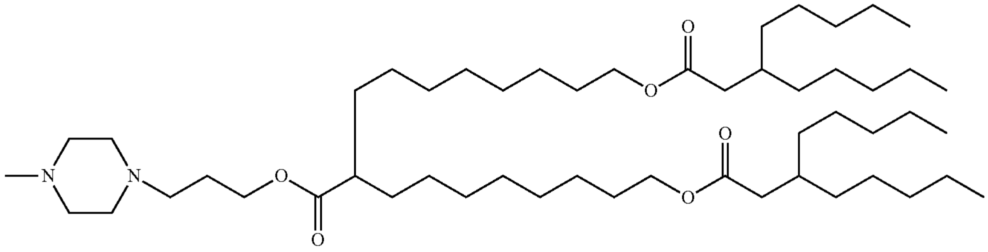 [SMILES: CCCCCC(CCCCC)CC(=O)OCCCCCCCCC(CCCCCCCCOC(=O)CC(CCCCC)CCCCC)C(=O)OCCCN1CCN(C)CC1]
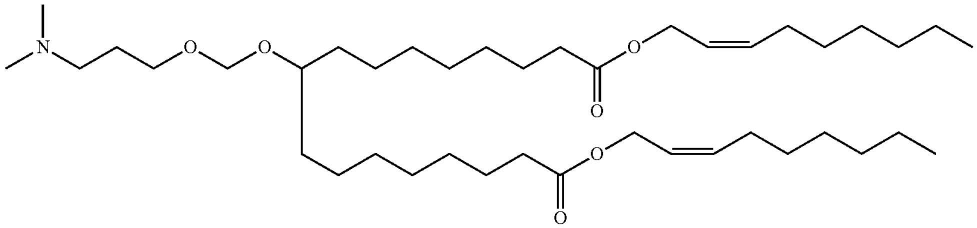 [SMILES: CCCCCC/C=C\COC(=O)CCCCCCCC(CCCCCCCC(=O)OC/C=C\CCCCCC)OCOCCCN(C)C]
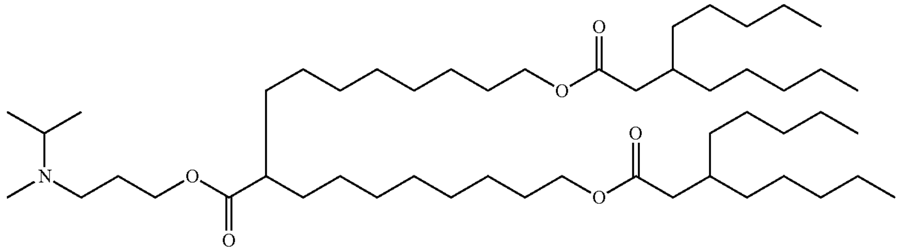 [SMILES: CCCCCC(CCCCC)CC(=O)OCCCCCCCCC(CCCCCCCCOC(=O)CC(CCCCC)CCCCC)C(=O)OCCCN(C)C(C)C]
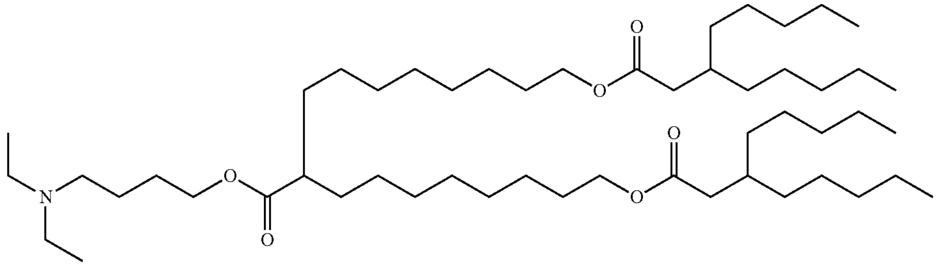 [SMILES: CCCCCC(CCCCC)CC(=O)OCCCCCCCCC(CCCCCCCCOC(=O)CC(CCCCC)CCCCC)C(=O)OCCCCN(CC)CC]
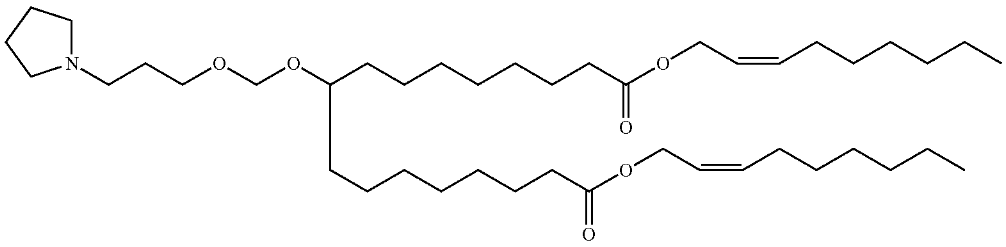 [SMILES: CCCCCC/C=C\COC(=O)CCCCCCCC(CCCCCCCC(=O)OC/C=C\CCCCCC)OCOCCCN1CCCC1]

-continued
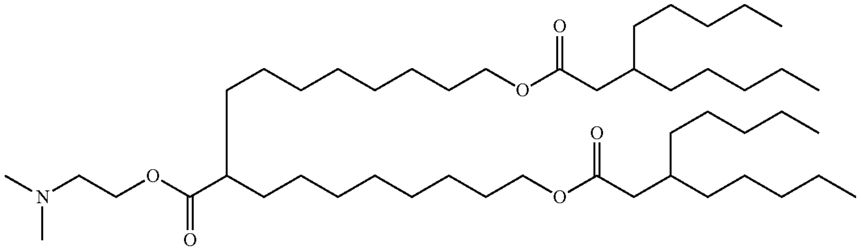 [SMILES: CCCCCC(CCCCC)CC(=O)OCCCCCCCCC(CCCCCCCCOC(=O)CC(CCCCC)CCCCC)C(=O)OCCN(C)C]
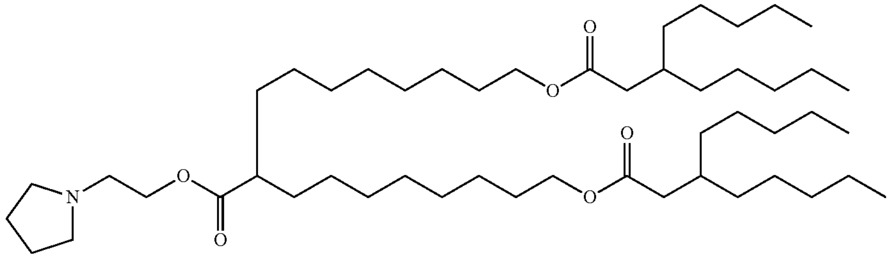 [SMILES: CCCCCC(CCCCC)CC(=O)OCCCCCCCCC(CCCCCCCCOC(=O)CC(CCCCC)CCCCC)C(=O)OCCN1CCCC1]
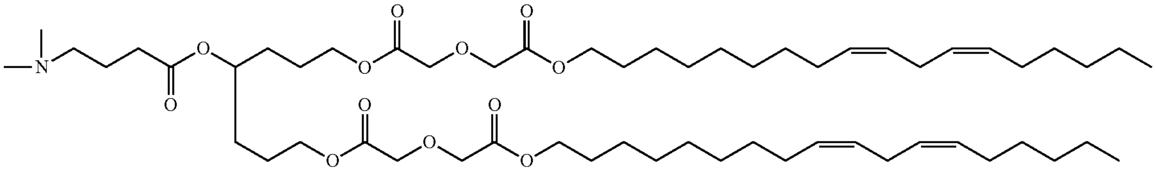
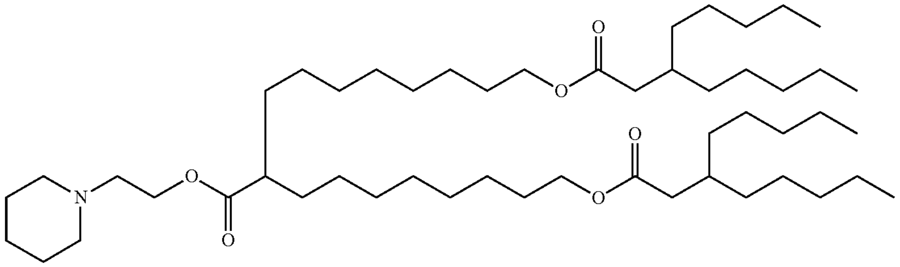 [SMILES: CCCCCC(CCCCC)CC(=O)OCCCCCCCCC(CCCCCCCCOC(=O)CC(CCCCC)CCCCC)C(=O)OCCN1CCCCC1]
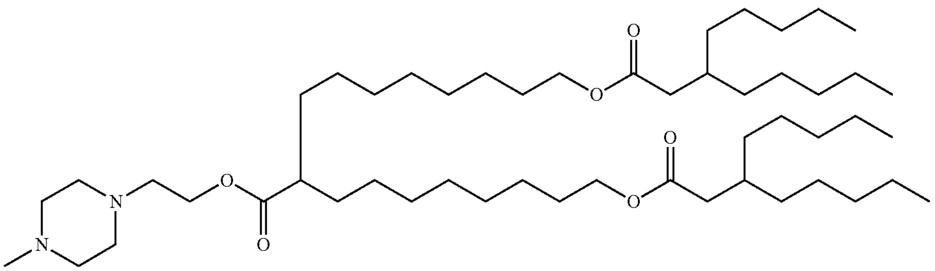 [SMILES: CCCCCC(CCCCC)CC(=O)OCCCCCCCCC(CCCCCCCCOC(=O)CC(CCCCC)CCCCC)C(=O)OCCN1CCN(C)CC1]
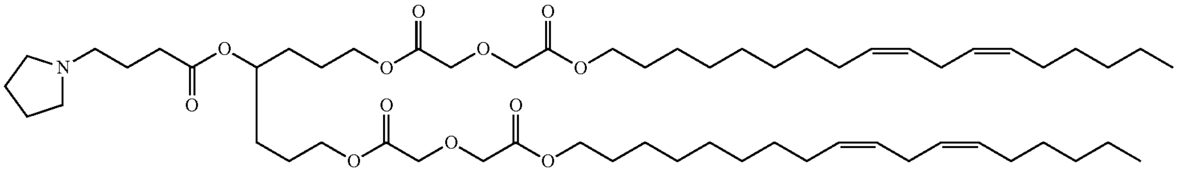

-continued
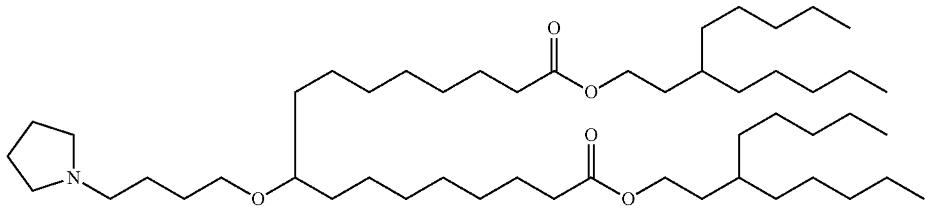 [SMILES: CCCCCC(CCCCC)CCOC(=O)CCCCCCCC(CCCCCCCC(=O)OCCC(CCCCC)CCCCC)OCCCCN1CCCC1]
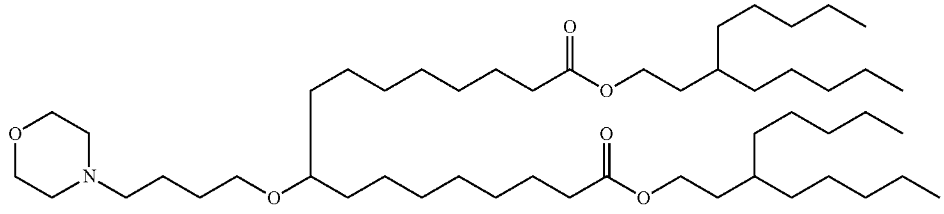 [SMILES: CCCCCC(CCCCC)CCOC(=O)CCCCCCCC(CCCCCCCC(=O)OCCC(CCCCC)CCCCC)OCCCCN1CCOCC1]
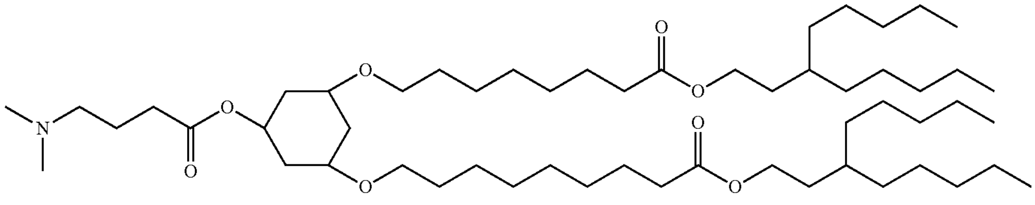 [SMILES: CCCCCC(CCCCC)CCOC(=O)CCCCCCCCOC1CC(OCCCCCCCC(=O)OCCC(CCCCC)CCCCC)CC(OC(=O)CCCN(C)C)C1]
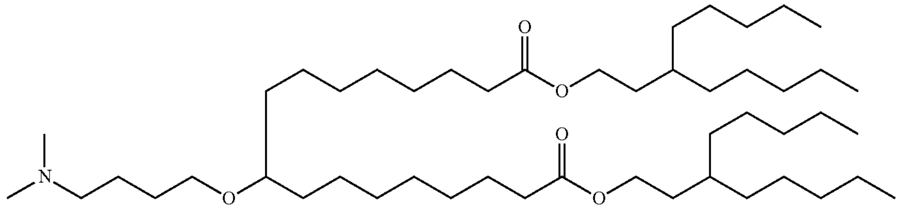 [SMILES: CCCCCC(CCCCC)CCOC(=O)CCCCCCCC(CCCCCCCC(=O)OCCC(CCCCC)CCCCC)OCCCCN(C)C]
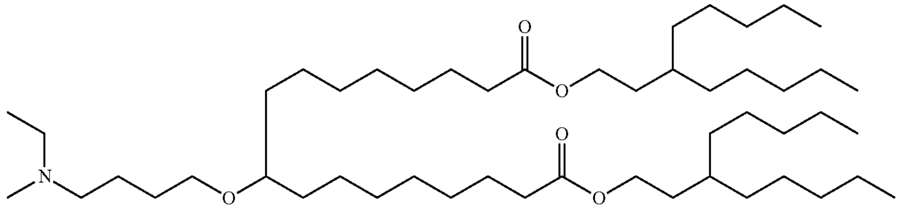 [SMILES: CCCCCC(CCCCC)CCOC(=O)CCCCCCCC(CCCCCCCC(=O)OCCC(CCCCC)CCCCC)OCCCCN(C)CC]
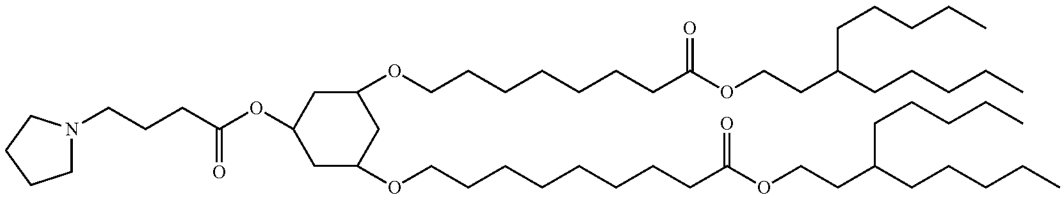 [SMILES: CCCCCC(CCCCC)CCOC(=O)CCCCCCCCOC1CC(OCCCCCCCC(=O)OCCC(CCCCC)CCCCC)CC(OC(=O)CCCN2CCCC2)C1]
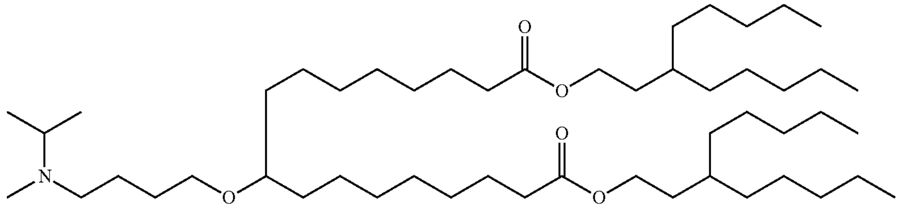 [SMILES: CCCCCC(CCCCC)CCOC(=O)CCCCCCCC(CCCCCCCC(=O)OCCC(CCCCC)CCCCC)OCCCCN(C)C(C)C]

-continued
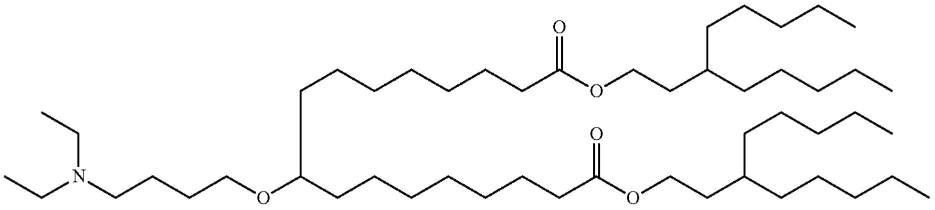 [SMILES: CCCCCC(CCCCC)CCOC(=O)CCCCCCCC(CCCCCCCC(=O)OCCC(CCCCC)CCCCC)OCCCCN(CC)CC]
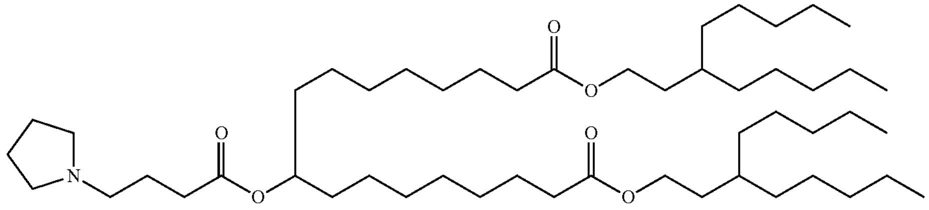 [SMILES: CCCCCC(CCCCC)CCOC(=O)CCCCCCCC(CCCCCCCC(=O)OCCC(CCCCC)CCCCC)OC(=O)CCCN1CCCC1]
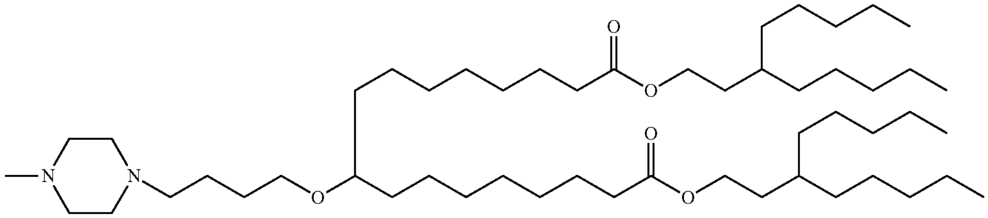 [SMILES: CCCCCC(CCCCC)CCOC(=O)CCCCCCCC(CCCCCCCC(=O)OCCC(CCCCC)CCCCC)OCCCCN1CCN(C)CC1]
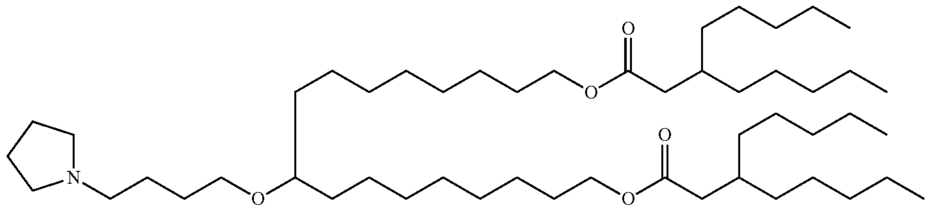 [SMILES: CCCCCC(CCCCC)CC(=O)OCCCCCCCCC(CCCCCCCCOC(=O)CC(CCCCC)CCCCC)OCCCCN1CCCC1]
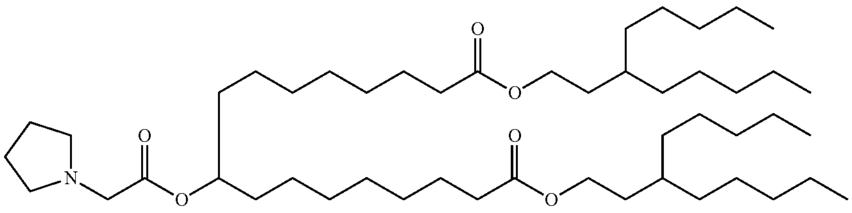 [SMILES: CCCCCC(CCCCC)CCOC(=O)CCCCCCCC(CCCCCCCC(=O)OCCC(CCCCC)CCCCC)OC(=O)CN1CCCC1]
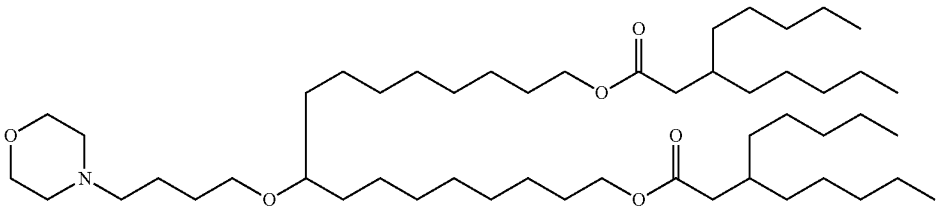 [SMILES: CCCCCC(CCCCC)CC(=O)OCCCCCCCCC(CCCCCCCCOC(=O)CC(CCCCC)CCCCC)OCCCCN1CCOCC1]
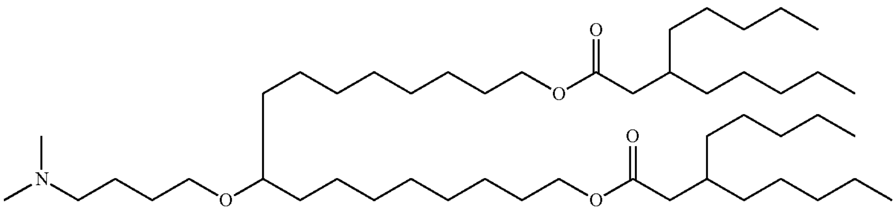 [SMILES: CCCCCC(CCCCC)CC(=O)OCCCCCCCCC(CCCCCCCCOC(=O)CC(CCCCC)CCCCC)OCCCCN(C)C]

-continued
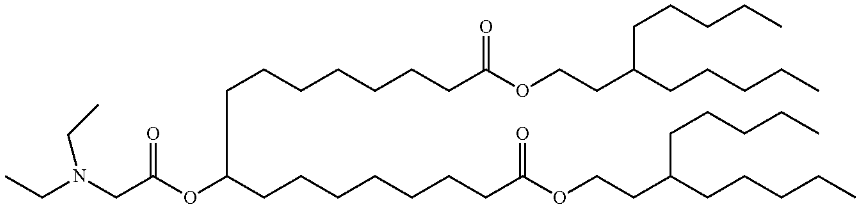 [SMILES: CCCCCC(CCCCC)CCOC(=O)CCCCCCCC(CCCCCCCC(=O)OCCC(CCCCC)CCCCC)OC(=O)CN(CC)CC]
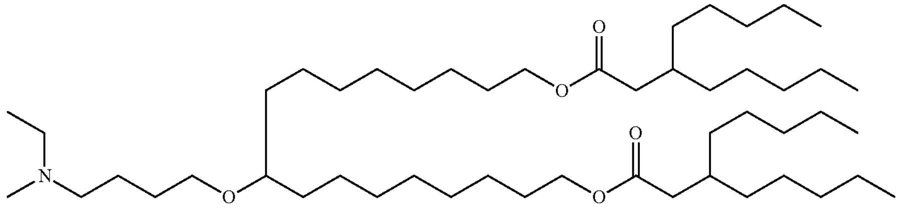 [SMILES: CCCCCC(CCCCC)CC(=O)OCCCCCCCCC(CCCCCCCCOC(=O)CC(CCCCC)CCCCC)OCCCCN(C)CC]
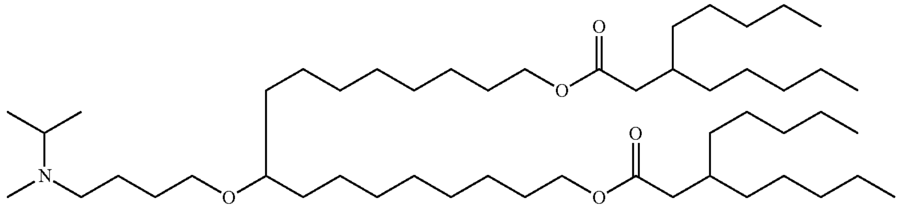 [SMILES: CCCCCC(CCCCC)CC(=O)OCCCCCCCCC(CCCCCCCCOC(=O)CC(CCCCC)CCCCC)OCCCCN(C)C(C)C]
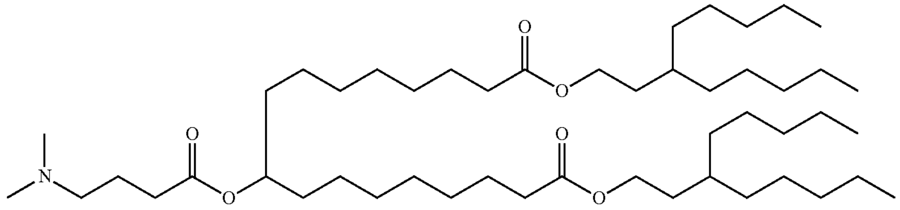 [SMILES: CCCCCC(CCCCC)CCOC(=O)CCCCCCCC(CCCCCCCC(=O)OCCC(CCCCC)CCCCC)OC(=O)CCCN(C)C]
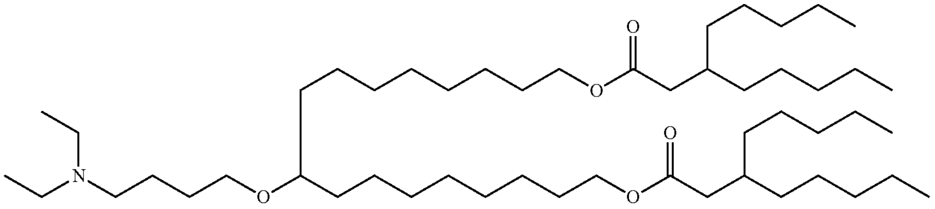 [SMILES: CCCCCC(CCCCC)CC(=O)OCCCCCCCCC(CCCCCCCCOC(=O)CC(CCCCC)CCCCC)OCCCCN(CC)CC]
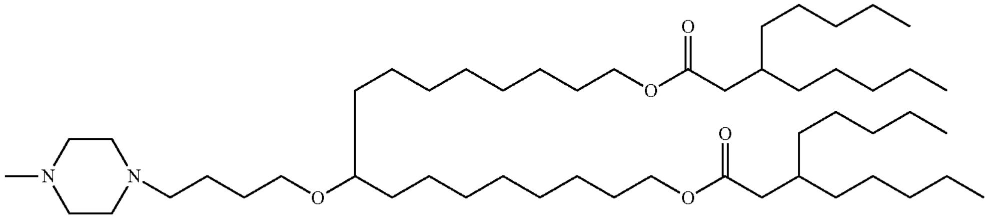 [SMILES: CCCCCC(CCCCC)CC(=O)OCCCCCCCCC(CCCCCCCCOC(=O)CC(CCCCC)CCCCC)OCCCCN1CCN(C)CC1]
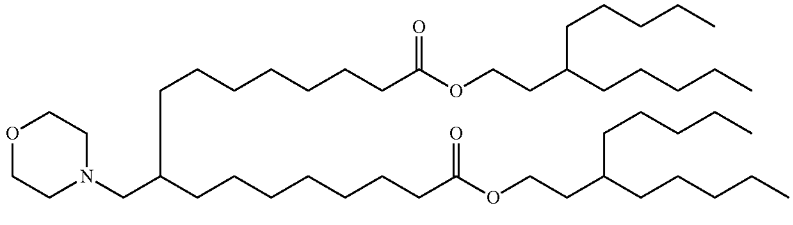 [SMILES: CCCCCC(CCCCC)CCOC(=O)CCCCCCCC(CCCCCCCC(=O)OCCC(CCCCC)CCCCC)CN1CCOCC1]

-continued
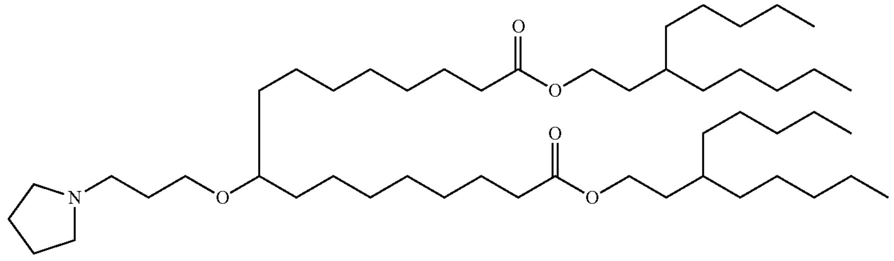 [SMILES: CCCCCC(CCCCC)CCOC(=O)CCCCCCCC(CCCCCCCC(=O)OCCC(CCCCC)CCCCC)OCCCN1CCCC1]
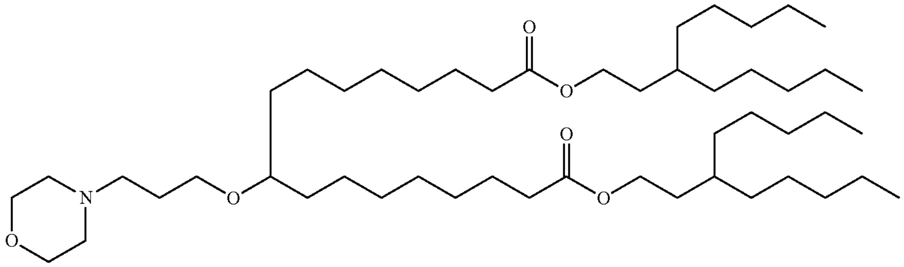 [SMILES: CCCCCC(CCCCC)CCOC(=O)CCCCCCCC(CCCCCCCC(=O)OCCC(CCCCC)CCCCC)OCCCN1CCOCC1]
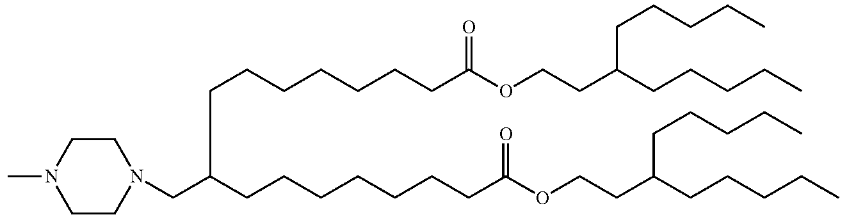 [SMILES: CCCCCC(CCCCC)CCOC(=O)CCCCCCCC(CCCCCCCC(=O)OCCC(CCCCC)CCCCC)CN1CCN(C)CC1]
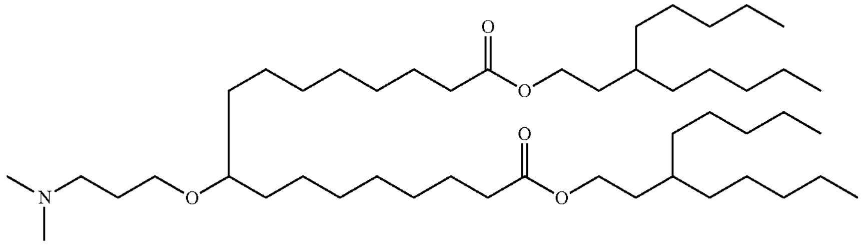 [SMILES: CCCCCC(CCCCC)CCOC(=O)CCCCCCCC(CCCCCCCC(=O)OCCC(CCCCC)CCCCC)OCCCN(C)C]
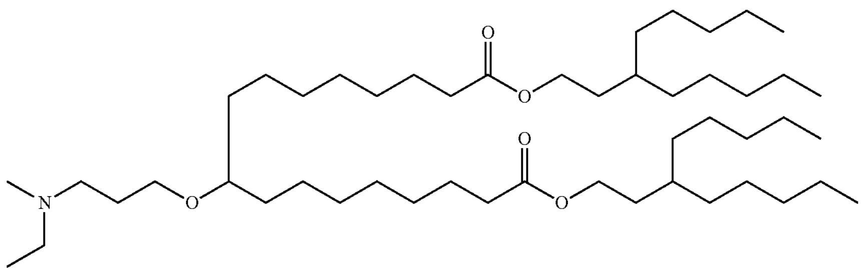 [SMILES: CCCCCC(CCCCC)CCOC(=O)CCCCCCCC(CCCCCCCC(=O)OCCC(CCCCC)CCCCC)OCCCN(C)CC]
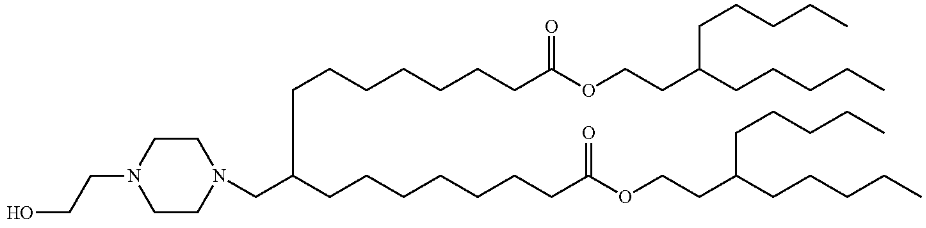 [SMILES: CCCCCC(CCCCC)CCOC(=O)CCCCCCCC(CCCCCCCC(=O)OCCC(CCCCC)CCCCC)CN1CCN(CCO)CC1]

-continued
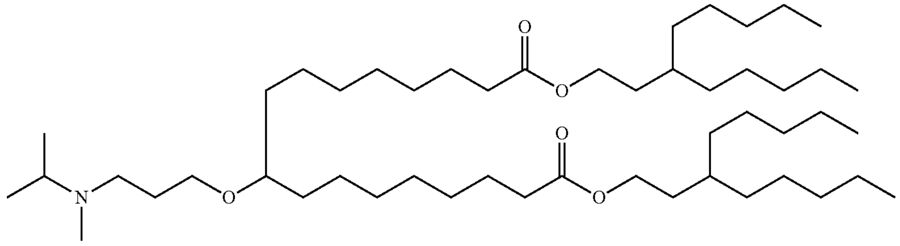 [SMILES: CCCCCC(CCCCC)CCOC(=O)CCCCCCCC(CCCCCCCC(=O)OCCC(CCCCC)CCCCC)OCCCN(C)C(C)C]
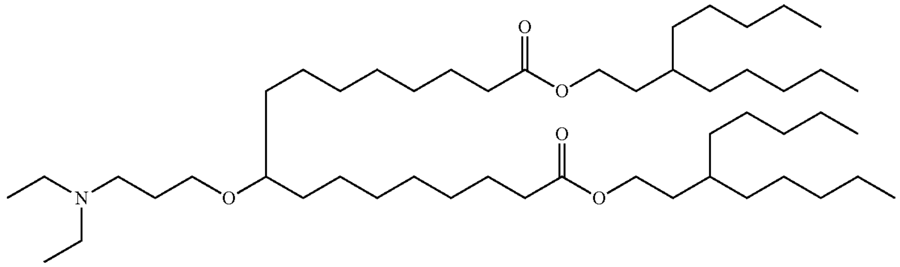 [SMILES: CCCCCC(CCCCC)CCOC(=O)CCCCCCCC(CCCCCCCC(=O)OCCC(CCCCC)CCCCC)OCCCN(CC)CC]
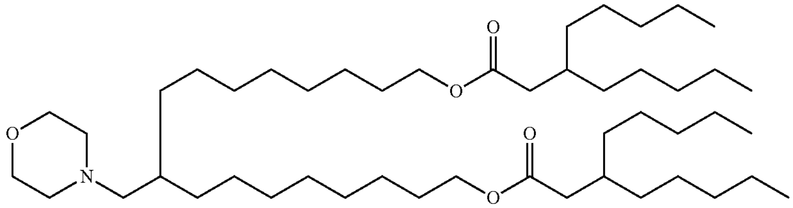 [SMILES: CCCCCC(CCCCC)CC(=O)OCCCCCCCCC(CCCCCCCCOC(=O)CC(CCCCC)CCCCC)CN1CCOCC1]
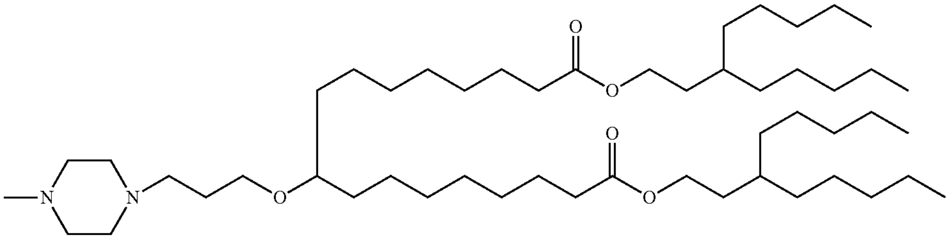 [SMILES: CCCCCC(CCCCC)CCOC(=O)CCCCCCCC(CCCCCCCC(=O)OCCC(CCCCC)CCCCC)OCCCN1CCN(C)CC1]
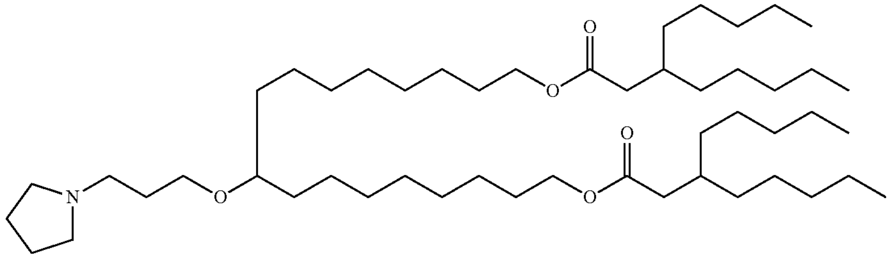 [SMILES: CCCCCC(CCCCC)CC(=O)OCCCCCCCCC(CCCCCCCCOC(=O)CC(CCCCC)CCCCC)OCCCN1CCCC1]
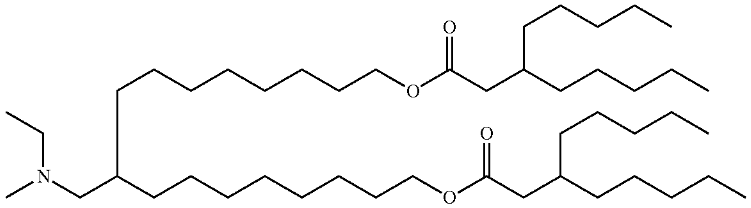 [SMILES: CCCCCC(CCCCC)CC(=O)OCCCCCCCCC(CCCCCCCCOC(=O)CC(CCCCC)CCCCC)CN(C)CC]

-continued
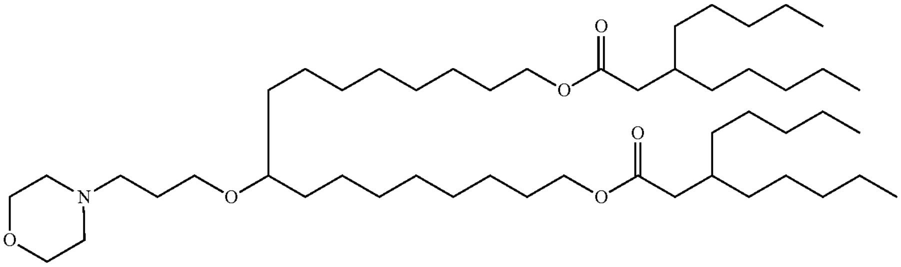 [SMILES: CCCCCC(CCCCC)CC(=O)OCCCCCCCCC(CCCCCCCCOC(=O)CC(CCCCC)CCCCC)OCCCN1CCOCC1]
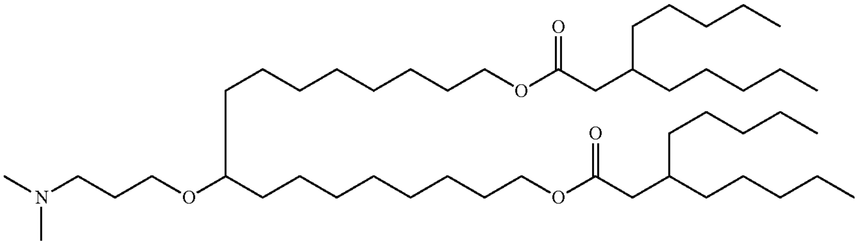 [SMILES: CCCCCC(CCCCC)CC(=O)OCCCCCCCCC(CCCCCCCCOC(=O)CC(CCCCC)CCCCC)OCCCN(C)C]
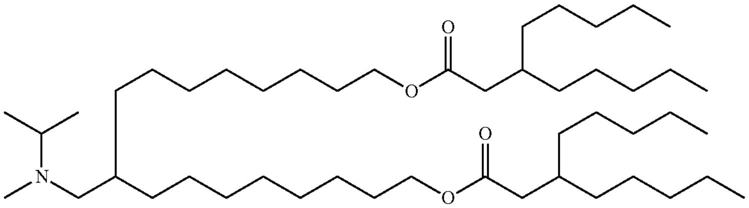 [SMILES: CCCCCC(CCCCC)CC(=O)OCCCCCCCCC(CCCCCCCCOC(=O)CC(CCCCC)CCCCC)CN(C)C(C)C]
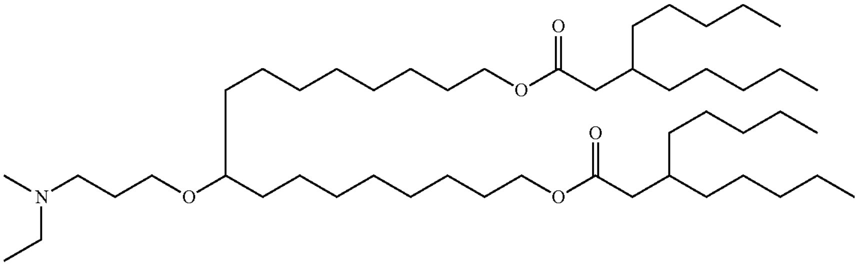 [SMILES: CCCCCC(CCCCC)CC(=O)OCCCCCCCCC(CCCCCCCCOC(=O)CC(CCCCC)CCCCC)OCCCN(C)CC]
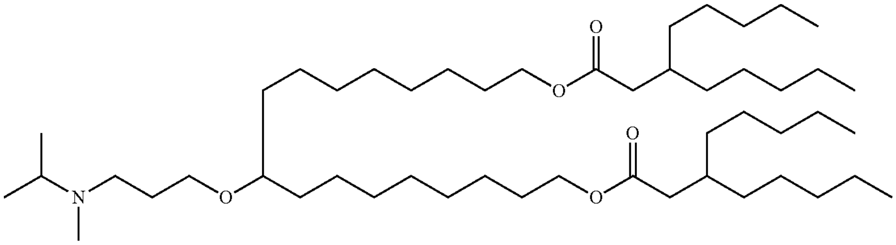 [SMILES: CCCCCC(CCCCC)CC(=O)OCCCCCCCCC(CCCCCCCCOC(=O)CC(CCCCC)CCCCC)OCCCN(C)C(C)C]
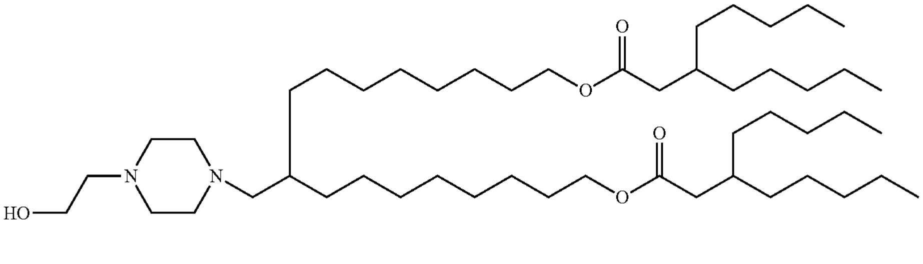 [SMILES: CCCCCC(CCCCC)CC(=O)OCCCCCCCCC(CCCCCCCCOC(=O)CC(CCCCC)CCCCC)CN1CCN(CCO)CC1]

-continued
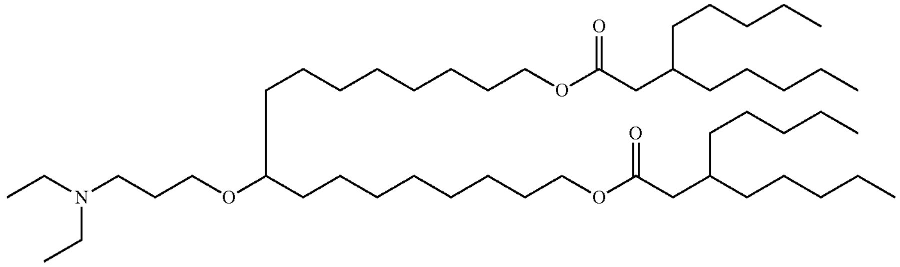 [SMILES: CCCCCC(CCCCC)CC(=O)OCCCCCCCCC(CCCCCCCCOC(=O)CC(CCCCC)CCCCC)OCCCN(CC)CC]
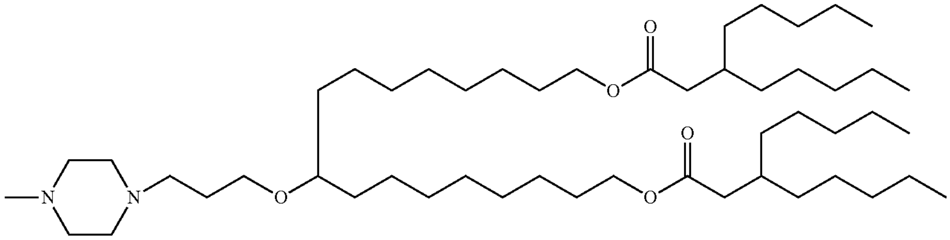 [SMILES: CCCCCC(CCCCC)CC(=O)OCCCCCCCCC(CCCCCCCCOC(=O)CC(CCCCC)CCCCC)OCCCN1CCN(C)CC1]
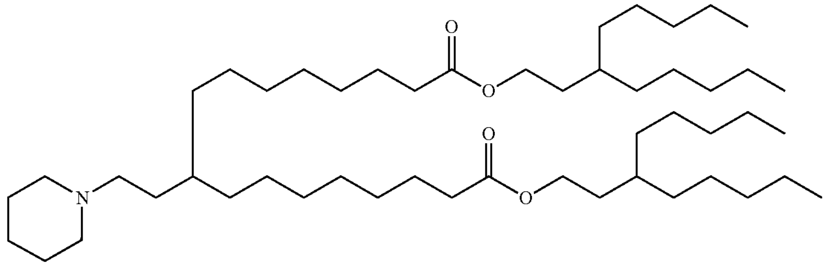 [SMILES: CCCCCC(CCCCC)CCOC(=O)CCCCCCCC(CCCCCCCC(=O)OCCC(CCCCC)CCCCC)CCN1CCCCC1]
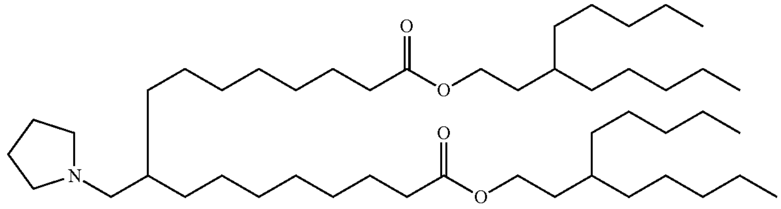 [SMILES: CCCCCC(CCCCC)CCOC(=O)CCCCCCCC(CCCCCCCC(=O)OCCC(CCCCC)CCCCC)CN1CCCC1]
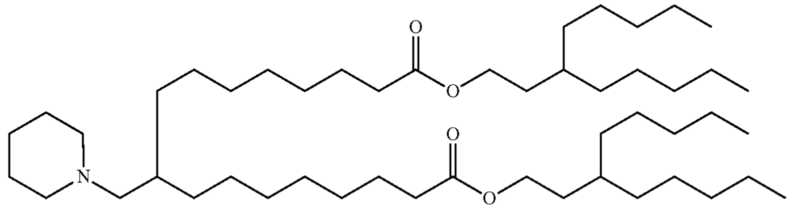 [SMILES: CCCCCC(CCCCC)CCOC(=O)CCCCCCCC(CCCCCCCC(=O)OCCC(CCCCC)CCCCC)CN1CCCCC1]
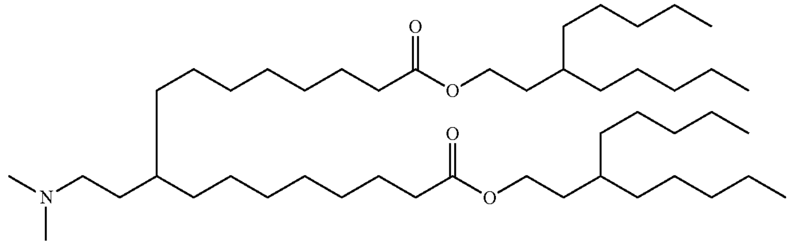 [SMILES: CCCCCC(CCCCC)CCOC(=O)CCCCCCCC(CCCCCCCC(=O)OCCC(CCCCC)CCCCC)CCN(C)C]

-continued
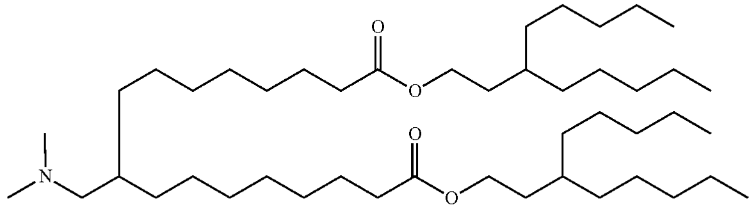 [SMILES: CCCCCC(CCCCC)CCOC(=O)CCCCCCCC(CCCCCCCC(=O)OCCC(CCCCC)CCCCC)CN(C)C]
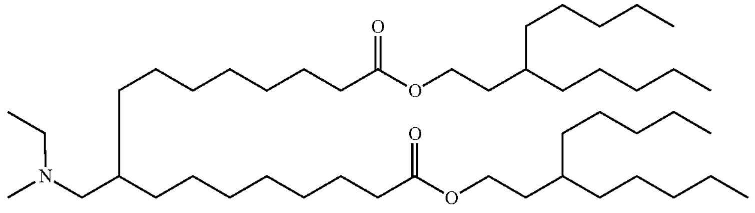 [SMILES: CCCCCC(CCCCC)CCOC(=O)CCCCCCCC(CCCCCCCC(=O)OCCC(CCCCC)CCCCC)CN(C)CC]
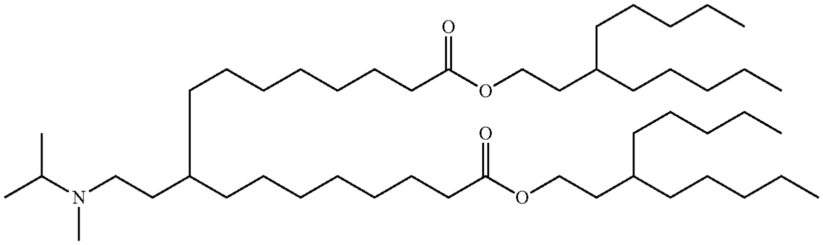 [SMILES: CCCCCC(CCCCC)CCOC(=O)CCCCCCCC(CCCCCCCC(=O)OCCC(CCCCC)CCCCC)CCN(C)C(C)C]
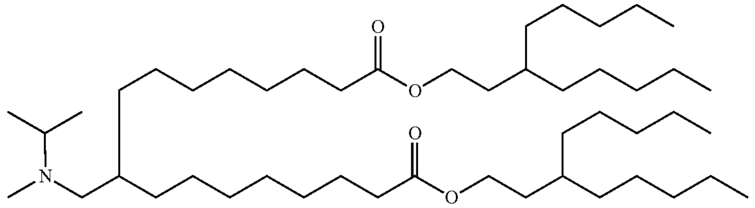 [SMILES: CCCCCC(CCCCC)CCOC(=O)CCCCCCCC(CCCCCCCC(=O)OCCC(CCCCC)CCCCC)CN(C)C(C)C]
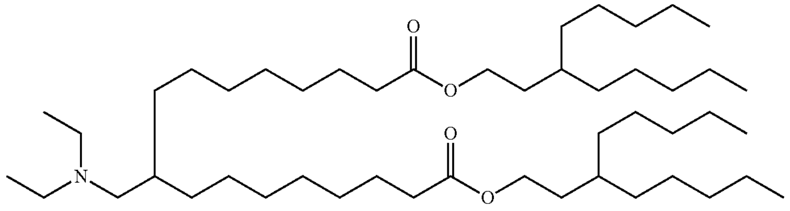 [SMILES: CCCCCC(CCCCC)CCOC(=O)CCCCCCCC(CCCCCCCC(=O)OCCC(CCCCC)CCCCC)CN(CC)CC]
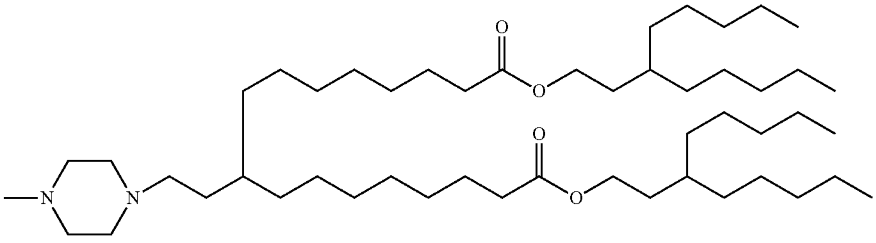 [SMILES: CCCCCC(CCCCC)CCOC(=O)CCCCCCCC(CCCCCCCC(=O)OCCC(CCCCC)CCCCC)CCN1CCN(C)CC1]
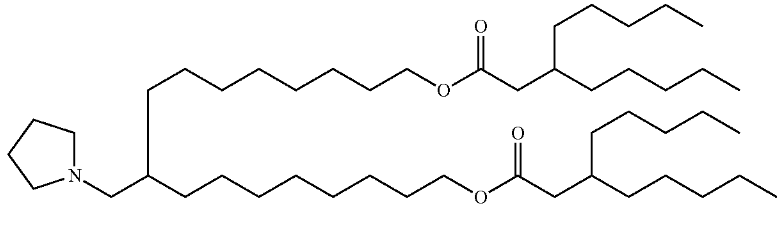 [SMILES: CCCCCC(CCCCC)CC(=O)OCCCCCCCCC(CCCCCCCCOC(=O)CC(CCCCC)CCCCC)CN1CCCC1]

-continued
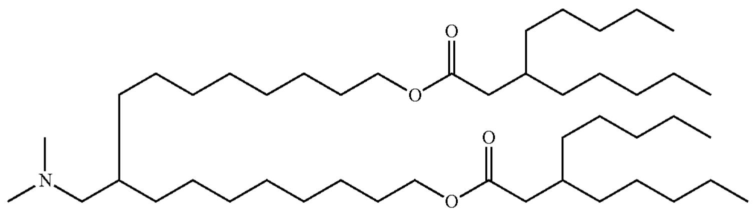 [SMILES: CCCCCC(CCCCC)CC(=O)OCCCCCCCCC(CCCCCCCCOC(=O)CC(CCCCC)CCCCC)CN(C)C]
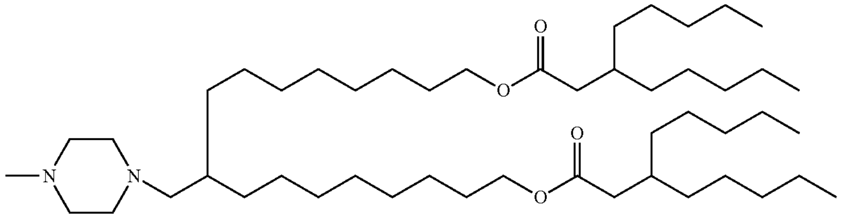 [SMILES: CCCCCC(CCCCC)CC(=O)OCCCCCCCCC(CCCCCCCCOC(=O)CC(CCCCC)CCCCC)CN1CCN(C)CC1]
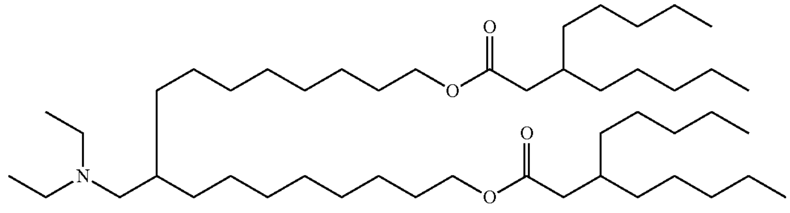 [SMILES: CCCCCC(CCCCC)CC(=O)OCCCCCCCCC(CCCCCCCCOC(=O)CC(CCCCC)CCCCC)CN(CC)CC]
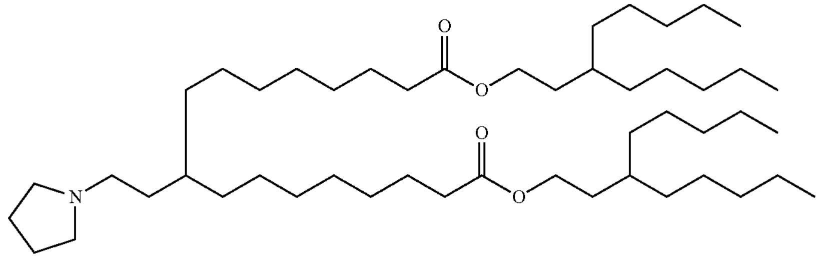 [SMILES: CCCCCC(CCCCC)CCOC(=O)CCCCCCCC(CCCCCCCC(=O)OCCC(CCCCC)CCCCC)CCN1CCCC1]
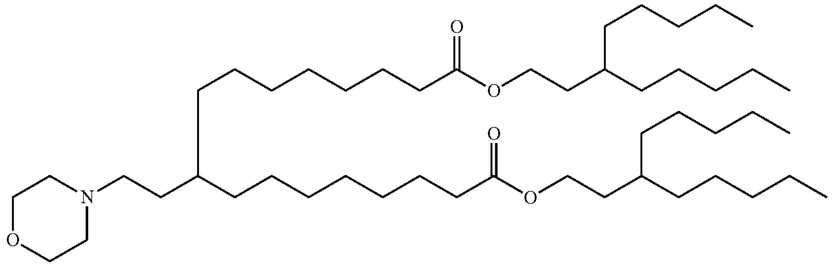 [SMILES: CCCCCC(CCCCC)CCOC(=O)CCCCCCCC(CCCCCCCC(=O)OCCC(CCCCC)CCCCC)CCN1CCOCC1]
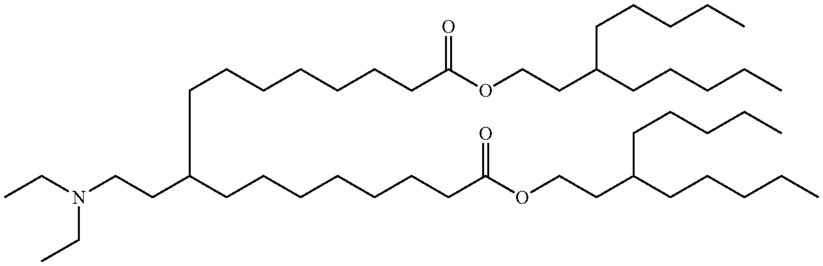 [SMILES: CCCCCC(CCCCC)CCOC(=O)CCCCCCCC(CCCCCCCC(=O)OCCC(CCCCC)CCCCC)CCN(CC)CC]

-continued
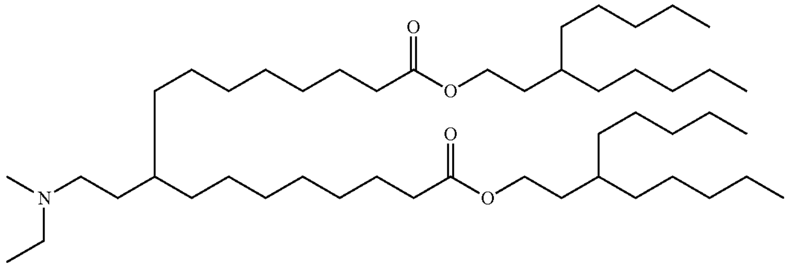 [SMILES: CCCCCC(CCCCC)CCOC(=O)CCCCCCCC(CCCCCCCC(=O)OCCC(CCCCC)CCCCC)CCN(C)CC]
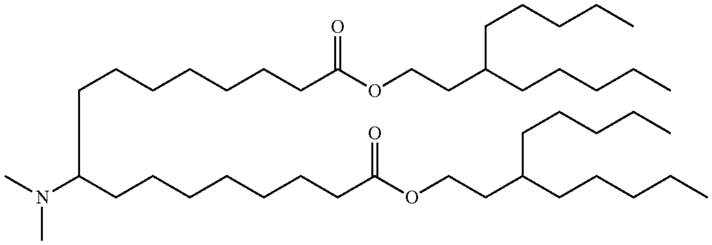 [SMILES: CCCCCC(CCCCC)CCOC(=O)CCCCCCCC(CCCCCCCC(=O)OCCC(CCCCC)CCCCC)N(C)C]
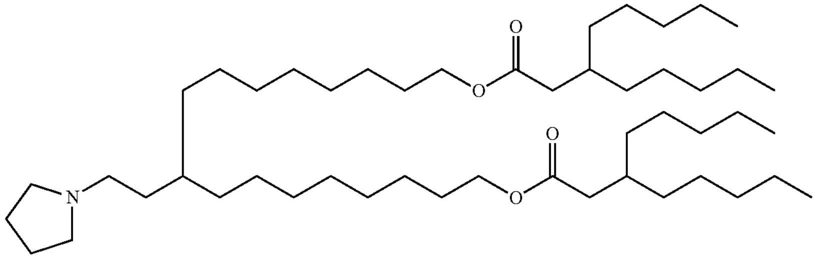 [SMILES: CCCCCC(CCCCC)CC(=O)OCCCCCCCCC(CCCCCCCCOC(=O)CC(CCCCC)CCCCC)CCN1CCCC1]
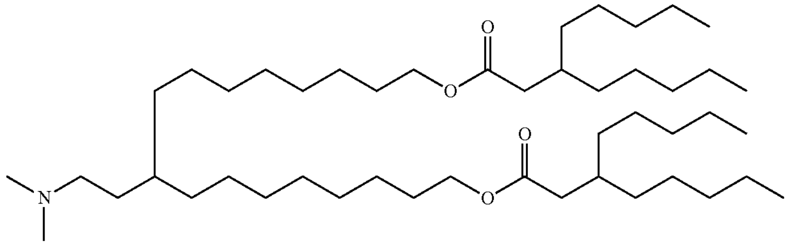 [SMILES: CCCCCC(CCCCC)CC(=O)OCCCCCCCCC(CCCCCCCCOC(=O)CC(CCCCC)CCCCC)CCN(C)C]
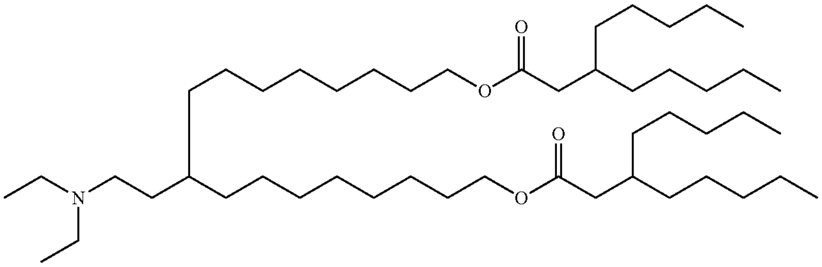 [SMILES: CCCCCC(CCCCC)CC(=O)OCCCCCCCCC(CCCCCCCCOC(=O)CC(CCCCC)CCCCC)CCN(CC)CC]
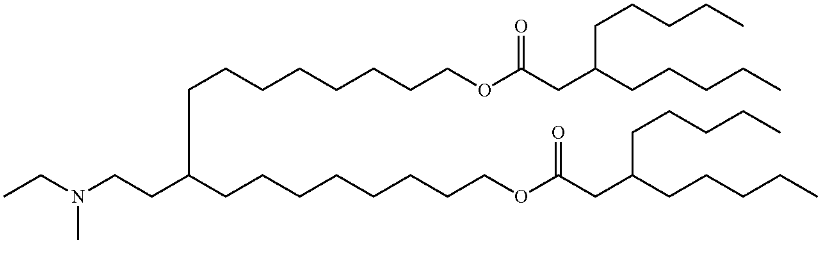 [SMILES: CCCCCC(CCCCC)CC(=O)OCCCCCCCCC(CCCCCCCCOC(=O)CC(CCCCC)CCCCC)CCN(C)CC]

-continued
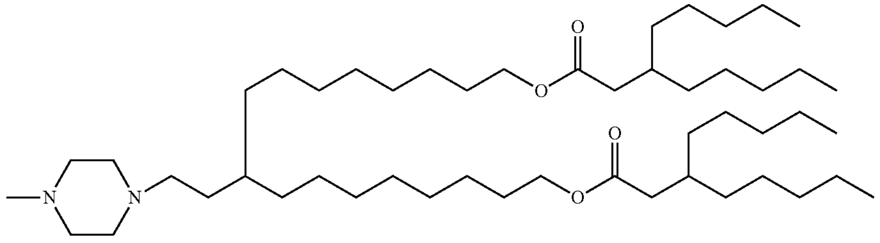 [SMILES: CCCCCC(CCCCC)CC(=O)OCCCCCCCCC(CCCCCCCCOC(=O)CC(CCCCC)CCCCC)CCN1CCN(C)CC1]
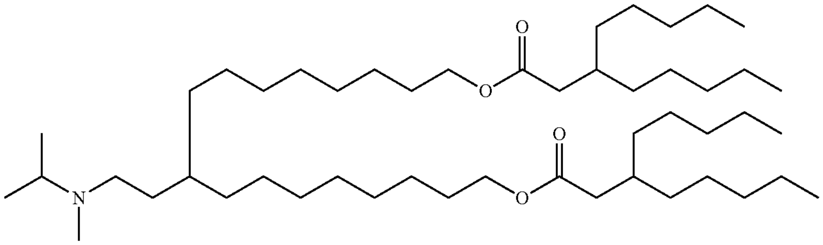 [SMILES: CCCCCC(CCCCC)CC(=O)OCCCCCCCCC(CCCCCCCCOC(=O)CC(CCCCC)CCCCC)CCN(C)C(C)C]
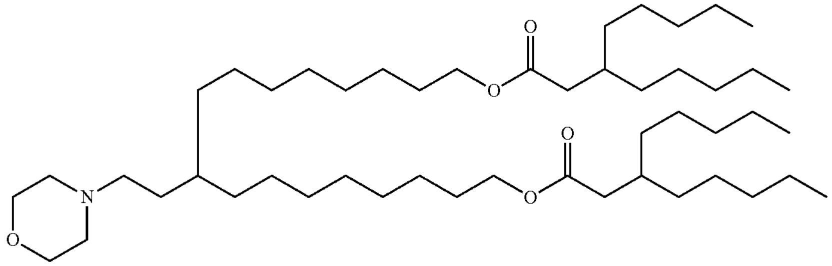 [SMILES: CCCCCC(CCCCC)CC(=O)OCCCCCCCCC(CCCCCCCCOC(=O)CC(CCCCC)CCCCC)CCN1CCOCC1]
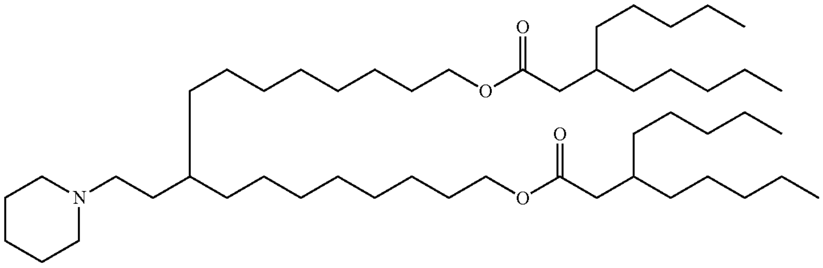 [SMILES: CCCCCC(CCCCC)CC(=O)OCCCCCCCCC(CCCCCCCCOC(=O)CC(CCCCC)CCCCC)CCN1CCCCC1]
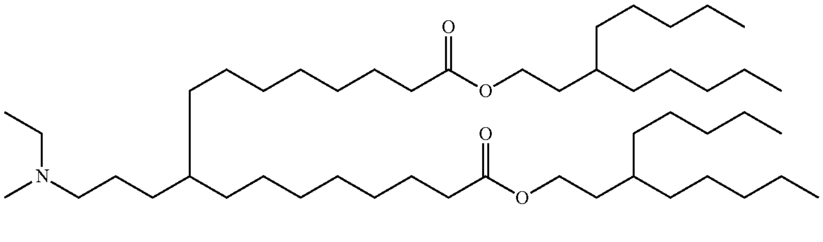 [SMILES: CCCCCC(CCCCC)CCOC(=O)CCCCCCCC(CCCCCCCC(=O)OCCC(CCCCC)CCCCC)CCCN(C)CC]
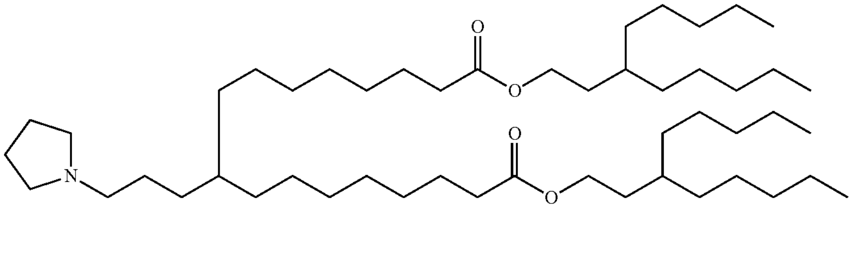 [SMILES: CCCCCC(CCCCC)CCOC(=O)CCCCCCCC(CCCCCCCC(=O)OCCC(CCCCC)CCCCC)CCCN1CCCC1]

-continued
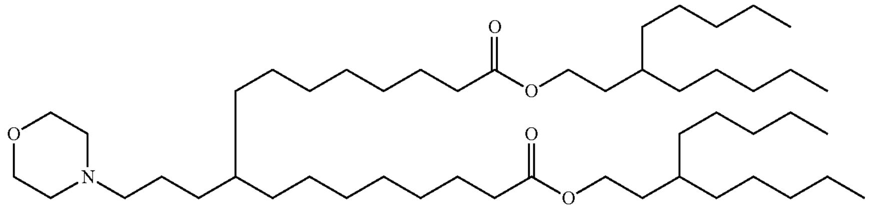 [SMILES: CCCCCC(CCCCC)CCOC(=O)CCCCCCCC(CCCCCCCC(=O)OCCC(CCCCC)CCCCC)CCCN1CCOCC1]
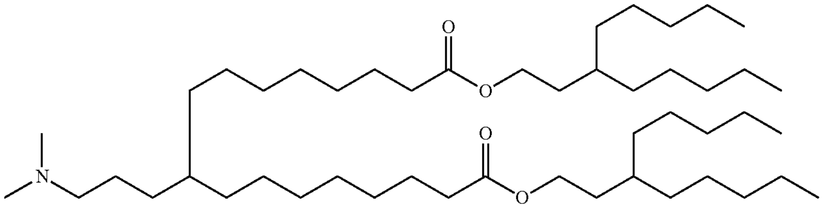 [SMILES: CCCCCC(CCCCC)CCOC(=O)CCCCCCCC(CCCCCCCC(=O)OCCC(CCCCC)CCCCC)CCCN(C)C]
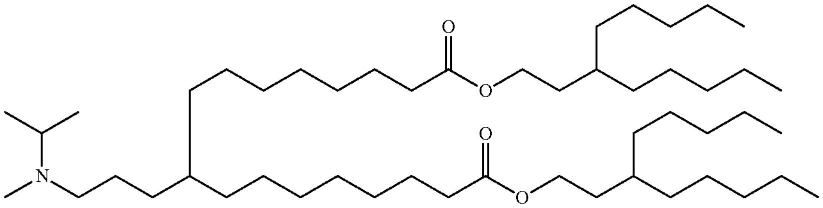 [SMILES: CCCCCC(CCCCC)CCOC(=O)CCCCCCCC(CCCCCCCC(=O)OCCC(CCCCC)CCCCC)CCCN(C)C(C)C]
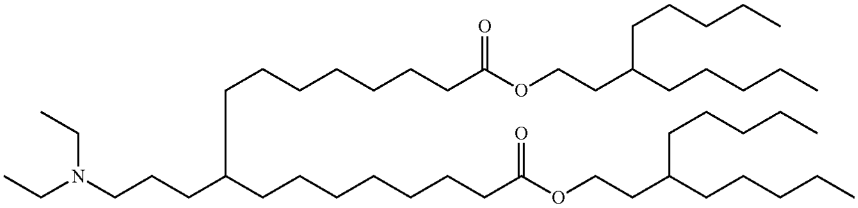 [SMILES: CCCCCC(CCCCC)CCOC(=O)CCCCCCCC(CCCCCCCC(=O)OCCC(CCCCC)CCCCC)CCCN(CC)CC]
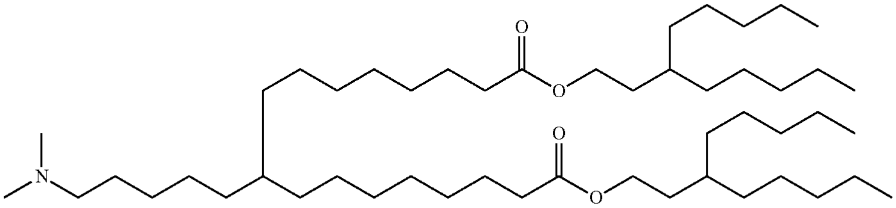 [SMILES: CCCCCC(CCCCC)CCOC(=O)CCCCCCCC(CCCCCCCC(=O)OCCC(CCCCC)CCCCC)CCCCCN(C)C]
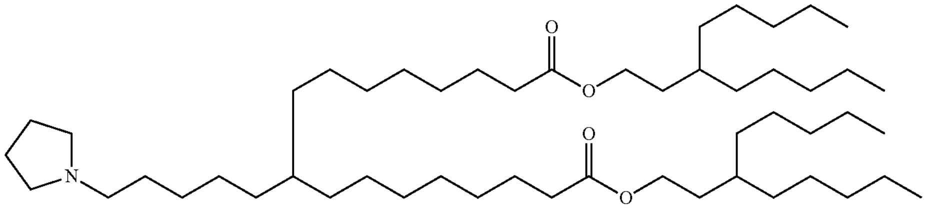 [SMILES: CCCCCC(CCCCC)CCOC(=O)CCCCCCCC(CCCCCCCC(=O)OCCC(CCCCC)CCCCC)CCCCCN1CCCC1]
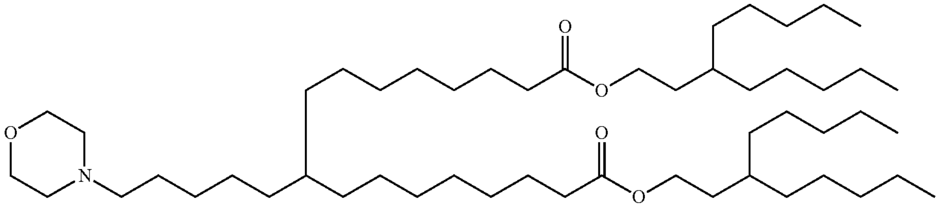 [SMILES: CCCCCC(CCCCC)CCOC(=O)CCCCCCCC(CCCCCCCC(=O)OCCC(CCCCC)CCCCC)CCCCCN1CCOCC1]

-continued
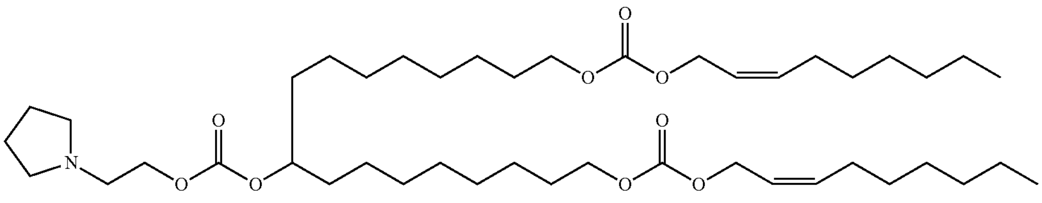
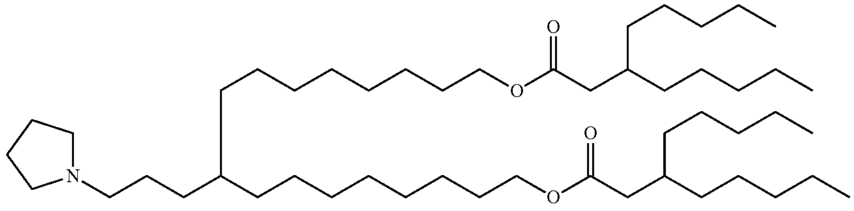 [SMILES: CCCCCC(CCCCC)CC(=O)OCCCCCCCCC(CCCCCCCCOC(=O)CC(CCCCC)CCCCC)CCCN1CCCC1]
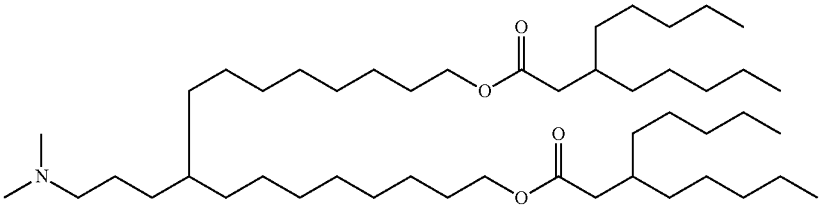 [SMILES: CCCCCC(CCCCC)CC(=O)OCCCCCCCCC(CCCCCCCCOC(=O)CC(CCCCC)CCCCC)CCCN(C)C]
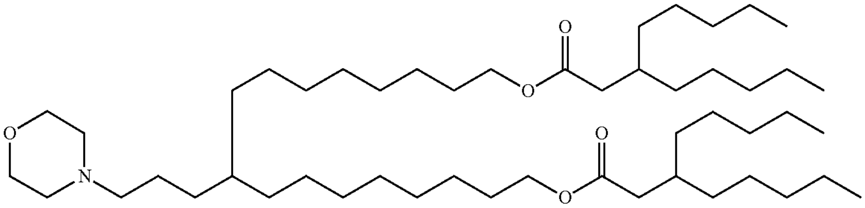 [SMILES: CCCCCC(CCCCC)CC(=O)OCCCCCCCCC(CCCCCCCCOC(=O)CC(CCCCC)CCCCC)CCCN1CCOCC1]
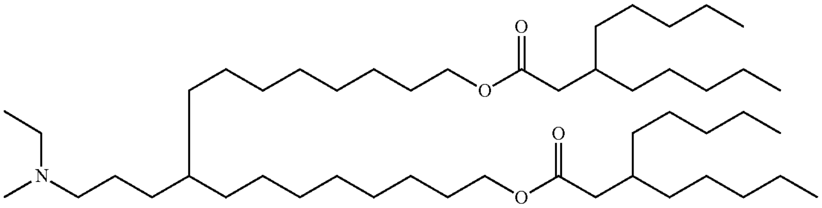 [SMILES: CCCCCC(CCCCC)CC(=O)OCCCCCCCCC(CCCCCCCCOC(=O)CC(CCCCC)CCCCC)CCCN(C)CC]
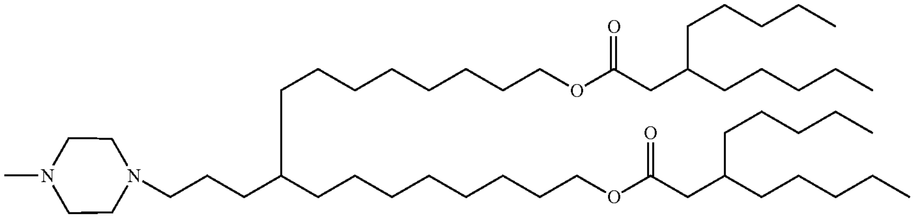 [SMILES: CCCCCC(CCCCC)CC(=O)OCCCCCCCCC(CCCCCCCCOC(=O)CC(CCCCC)CCCCC)CCCN1CCN(C)CC1]
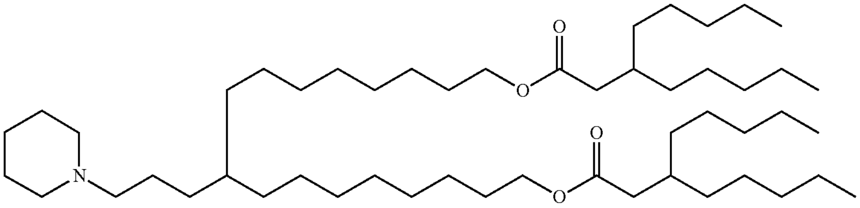 [SMILES: CCCCCC(CCCCC)CC(=O)OCCCCCCCCC(CCCCCCCCOC(=O)CC(CCCCC)CCCCC)CCCN1CCCCC1]

-continued
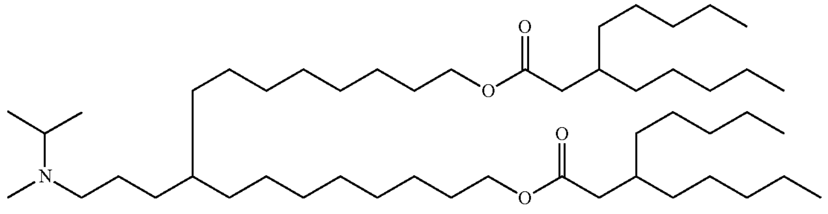 [SMILES: CCCCCC(CCCCC)CC(=O)OCCCCCCCCC(CCCCCCCCOC(=O)CC(CCCCC)CCCCC)CCCN(C)C(C)C]
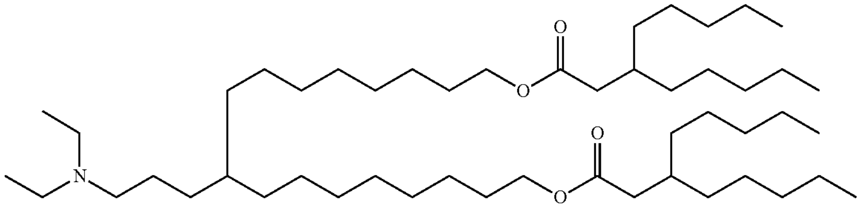 [SMILES: CCCCCC(CCCCC)CC(=O)OCCCCCCCCC(CCCCCCCCOC(=O)CC(CCCCC)CCCCC)CCCN(CC)CC]
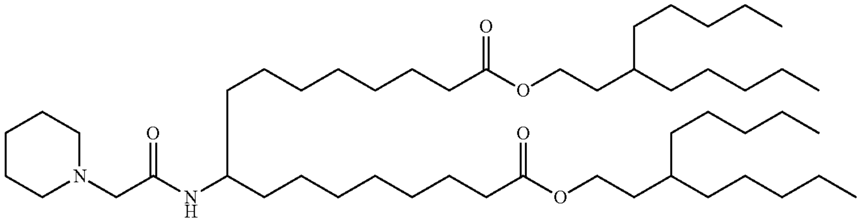 [SMILES: CCCCCC(CCCCC)CCOC(=O)CCCCCCCC(CCCCCCCC(=O)OCCC(CCCCC)CCCCC)NC(=O)CN1CCCCC1]
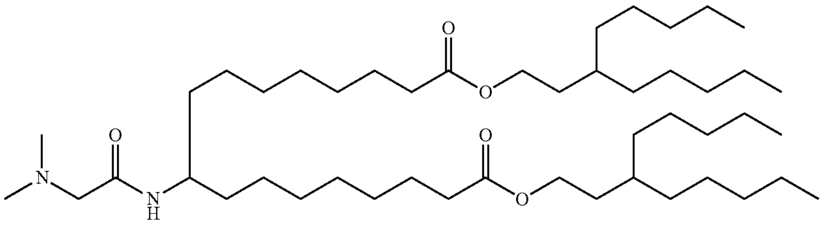 [SMILES: CCCCCC(CCCCC)CCOC(=O)CCCCCCCC(CCCCCCCC(=O)OCCC(CCCCC)CCCCC)NC(=O)CN(C)C]
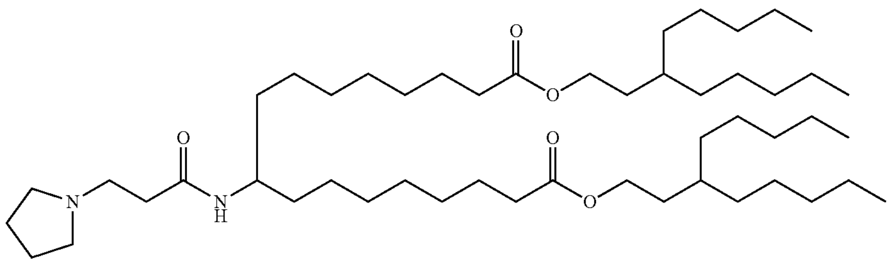 [SMILES: CCCCCC(CCCCC)CCOC(=O)CCCCCCCC(CCCCCCCC(=O)OCCC(CCCCC)CCCCC)NC(=O)CCN1CCCC1]
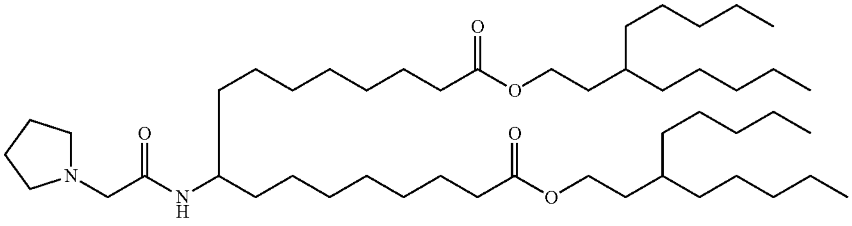 [SMILES: CCCCCC(CCCCC)CCOC(=O)CCCCCCCC(CCCCCCCC(=O)OCCC(CCCCC)CCCCC)NC(=O)CN1CCCC1]
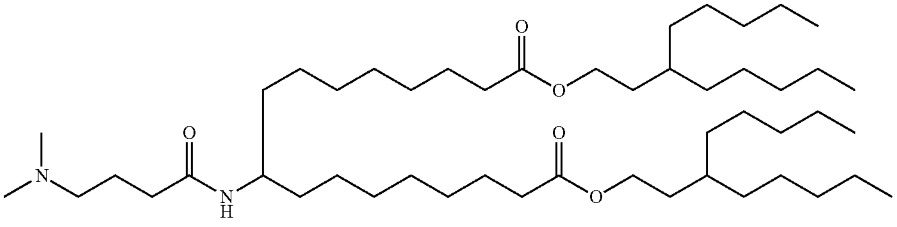 [SMILES: CCCCCC(CCCCC)CCOC(=O)CCCCCCCC(CCCCCCCC(=O)OCCC(CCCCC)CCCCC)NC(=O)CCCN(C)C]

-continued
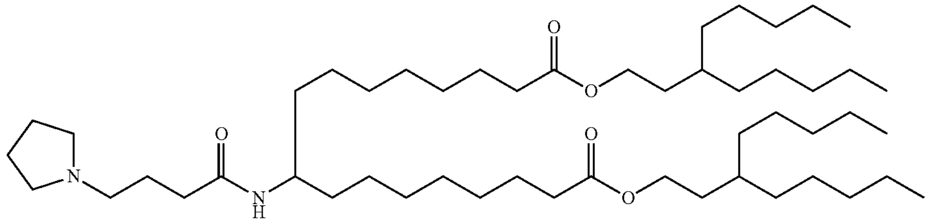 [SMILES: CCCCCC(CCCCC)CCOC(=O)CCCCCCCC(CCCCCCCC(=O)OCCC(CCCCC)CCCCC)NC(=O)CCCN1CCCC1]
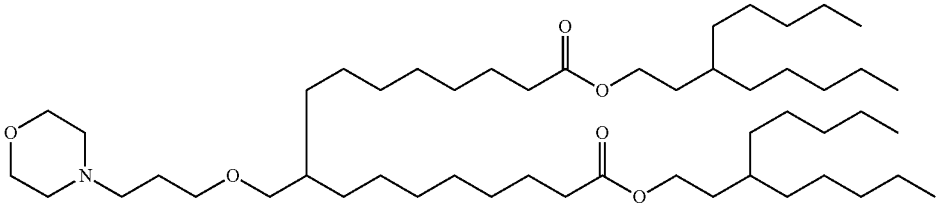 [SMILES: CCCCCC(CCCCC)CCOC(=O)CCCCCCCC(CCCCCCCC(=O)OCCC(CCCCC)CCCCC)COCCCN1CCOCC1]
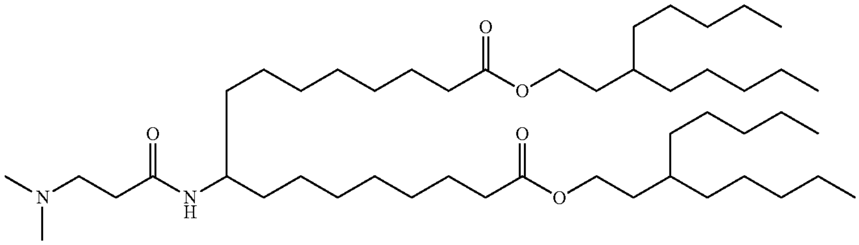 [SMILES: CCCCCC(CCCCC)CCOC(=O)CCCCCCCC(CCCCCCCC(=O)OCCC(CCCCC)CCCCC)NC(=O)CCN(C)C]
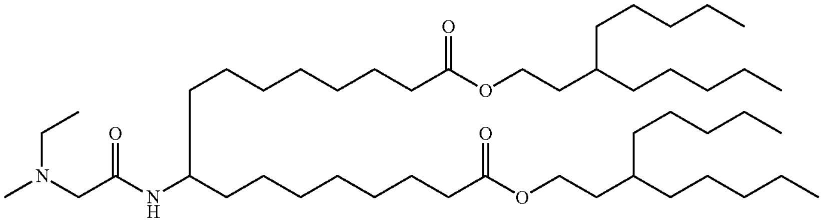 [SMILES: CCCCCC(CCCCC)CCOC(=O)CCCCCCCC(CCCCCCCC(=O)OCCC(CCCCC)CCCCC)NC(=O)CN(C)CC]
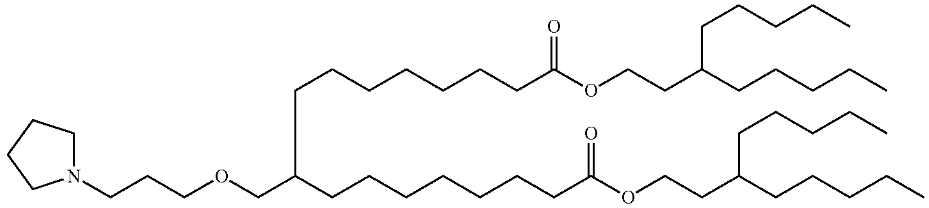 [SMILES: CCCCCC(CCCCC)CCOC(=O)CCCCCCCC(CCCCCCCC(=O)OCCC(CCCCC)CCCCC)COCCCN1CCCC1]
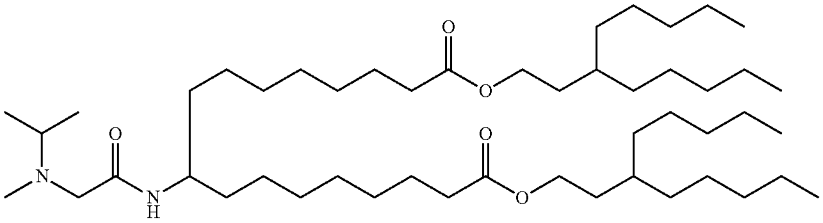 [SMILES: CCCCCC(CCCCC)CCOC(=O)CCCCCCCC(CCCCCCCC(=O)OCCC(CCCCC)CCCCC)NC(=O)CN(C)C(C)C]
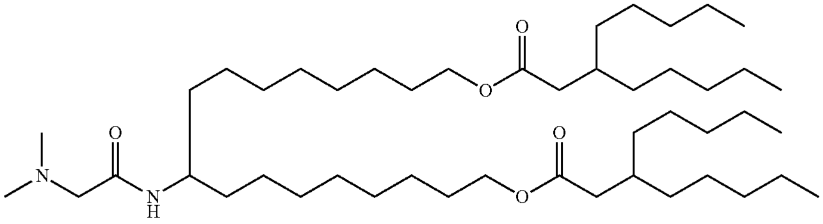 [SMILES: CCCCCC(CCCCC)CC(=O)OCCCCCCCCC(CCCCCCCCOC(=O)CC(CCCCC)CCCCC)NC(=O)CN(C)C]

-continued
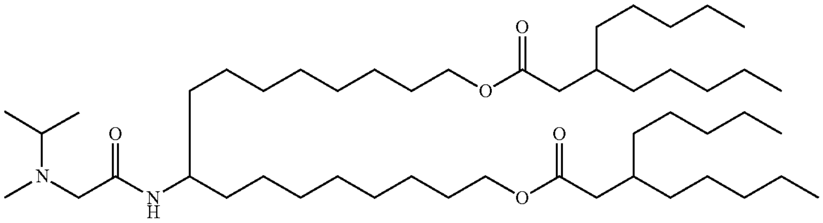 [SMILES: CCCCCC(CCCCC)CC(=O)OCCCCCCCCC(CCCCCCCCOC(=O)CC(CCCCC)CCCCC)NC(=O)CN(C)C(C)C]
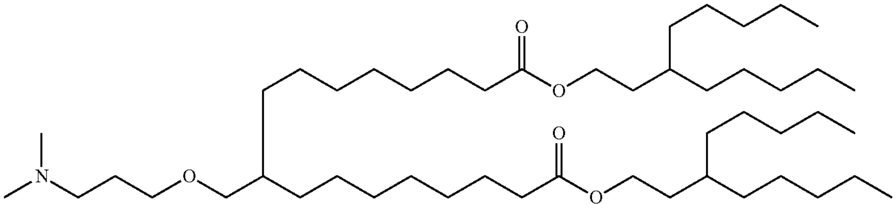 [SMILES: CCCCCC(CCCCC)CCOC(=O)CCCCCCCC(CCCCCCCC(=O)OCCC(CCCCC)CCCCC)COCCCN(C)C]
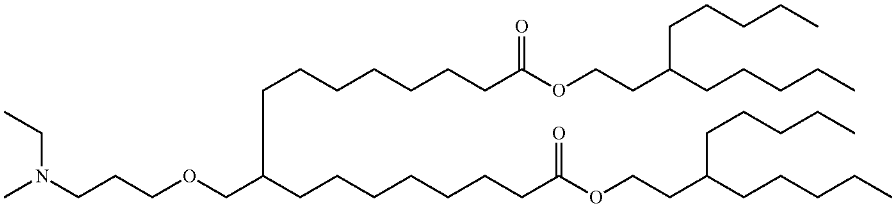 [SMILES: CCCCCC(CCCCC)CCOC(=O)CCCCCCCC(CCCCCCCC(=O)OCCC(CCCCC)CCCCC)COCCCN(C)CC]
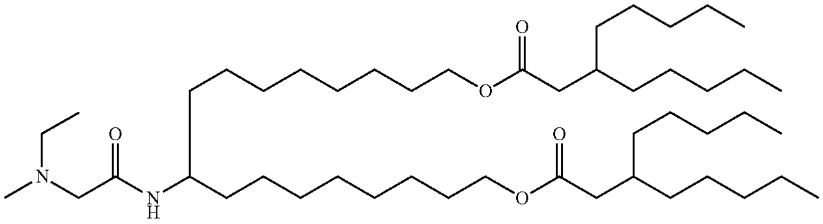 [SMILES: CCCCCC(CCCCC)CC(=O)OCCCCCCCCC(CCCCCCCCOC(=O)CC(CCCCC)CCCCC)NC(=O)CN(C)CC]
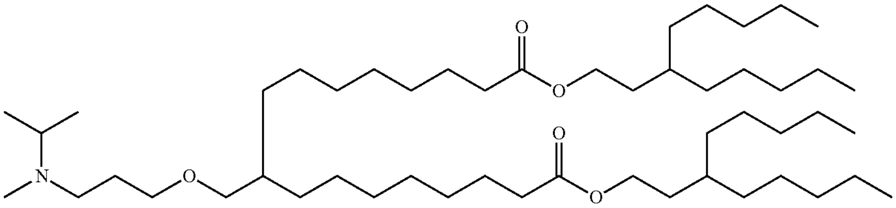 [SMILES: CCCCCC(CCCCC)CCOC(=O)CCCCCCCC(CCCCCCCC(=O)OCCC(CCCCC)CCCCC)COCCCN(C)C(C)C]
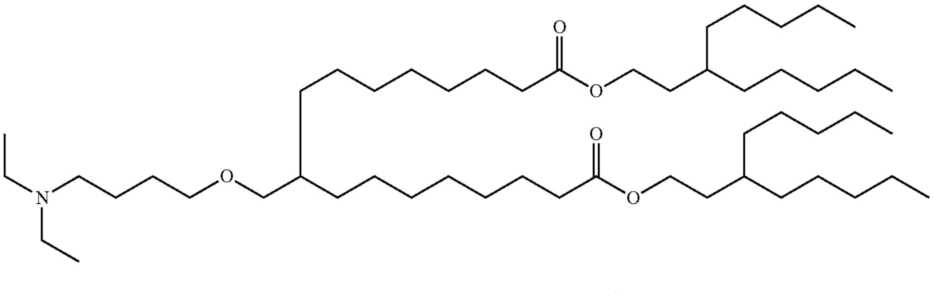 [SMILES: CCCCCC(CCCCC)CCOC(=O)CCCCCCCC(CCCCCCCC(=O)OCCC(CCCCC)CCCCC)COCCCCN(CC)CC]
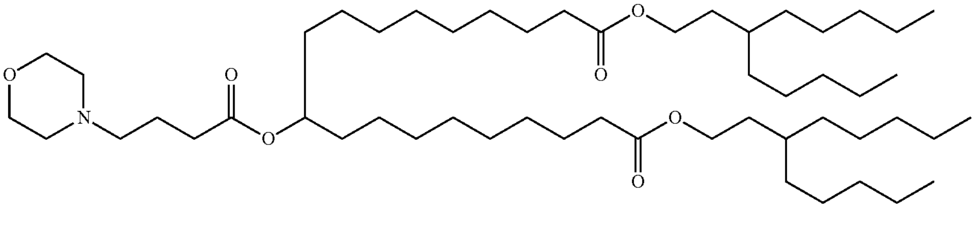 [SMILES: CCCCCC(CCCCC)CCOC(=O)CCCCCCCCC(CCCCCCCCC(=O)OCCC(CCCCC)CCCCC)OC(=O)CCCN1CCOCC1]

-continued
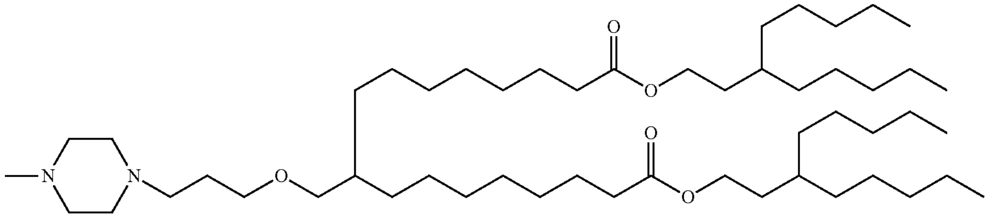 [SMILES: CCCCCC(CCCCC)CCOC(=O)CCCCCCCC(CCCCCCCC(=O)OCCC(CCCCC)CCCCC)COCCCN1CCN(C)CC1]
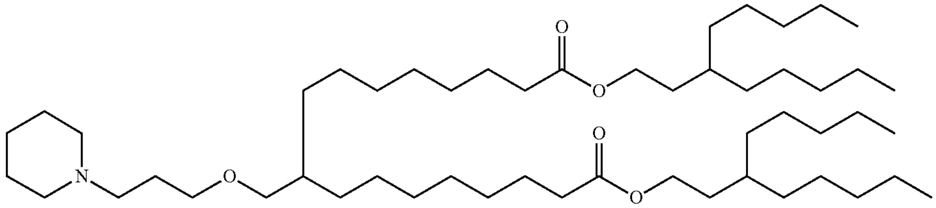 [SMILES: CCCCCC(CCCCC)CCOC(=O)CCCCCCCC(CCCCCCCC(=O)OCCC(CCCCC)CCCCC)COCCCN1CCCCC1]
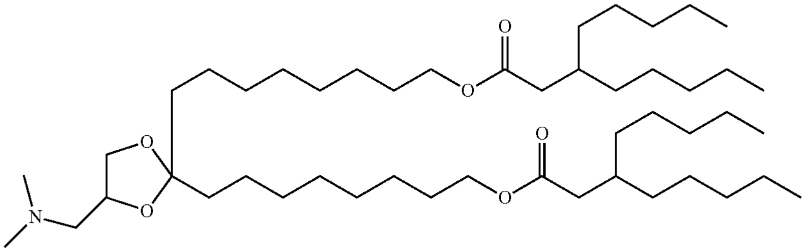 [SMILES: CCCCCC(CCCCC)CC(=O)OCCCCCCCCC1(CCCCCCCCOC(=O)CC(CCCCC)CCCCC)OCC(CN(C)C)O1]
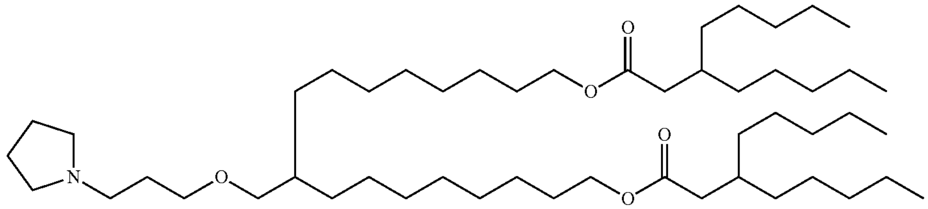 [SMILES: CCCCCC(CCCCC)CC(=O)OCCCCCCCCC(CCCCCCCCOC(=O)CC(CCCCC)CCCCC)COCCCN1CCCC1]
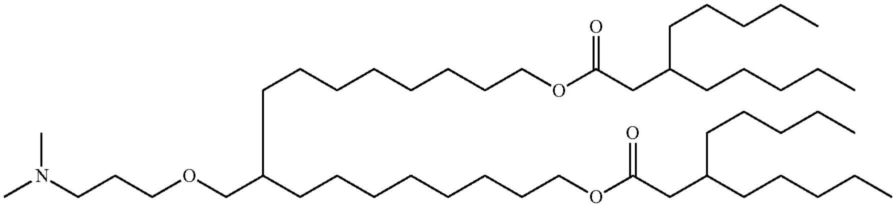 [SMILES: CCCCCC(CCCCC)CC(=O)OCCCCCCCCC(CCCCCCCCOC(=O)CC(CCCCC)CCCCC)COCCCN(C)C]
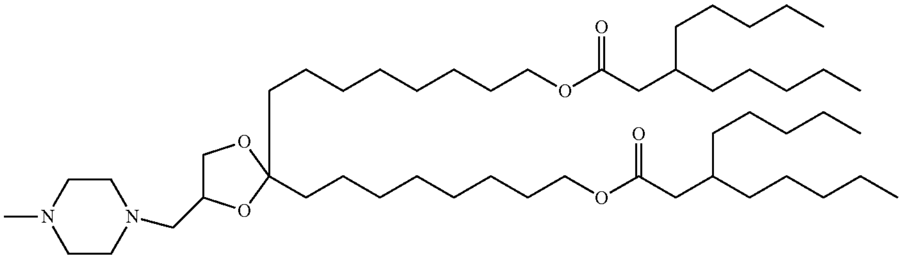 [SMILES: CCCCCC(CCCCC)CC(=O)OCCCCCCCCC1(CCCCCCCCOC(=O)CC(CCCCC)CCCCC)OCC(CN2CCN(C)CC2)O1]

-continued
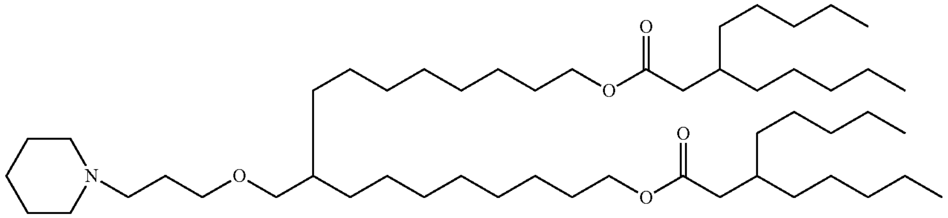 [SMILES: CCCCCC(CCCCC)CC(=O)OCCCCCCCCC(CCCCCCCCOC(=O)CC(CCCCC)CCCCC)COCCCN1CCCCC1]
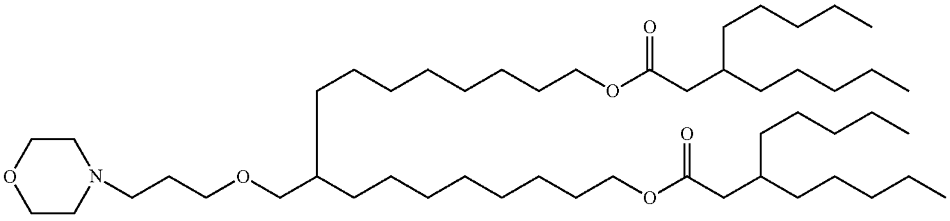 [SMILES: CCCCCC(CCCCC)CC(=O)OCCCCCCCCC(CCCCCCCCOC(=O)CC(CCCCC)CCCCC)COCCCN1CCOCC1]
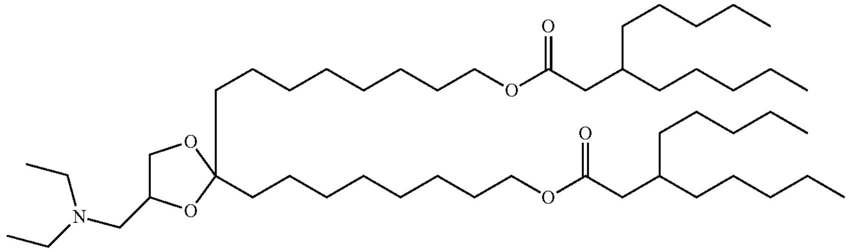 [SMILES: CCCCCC(CCCCC)CC(=O)OCCCCCCCCC1(CCCCCCCCOC(=O)CC(CCCCC)CCCCC)OCC(CN(CC)CC)O1]
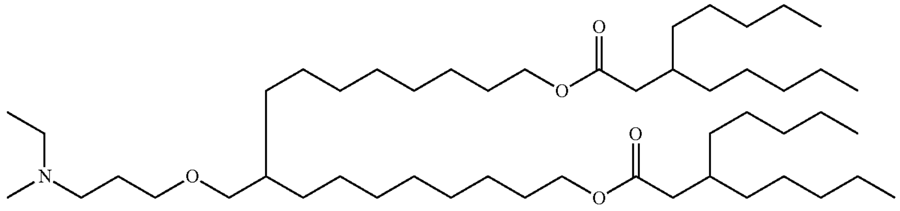 [SMILES: CCCCCC(CCCCC)CC(=O)OCCCCCCCCC(CCCCCCCCOC(=O)CC(CCCCC)CCCCC)COCCCN(C)CC]
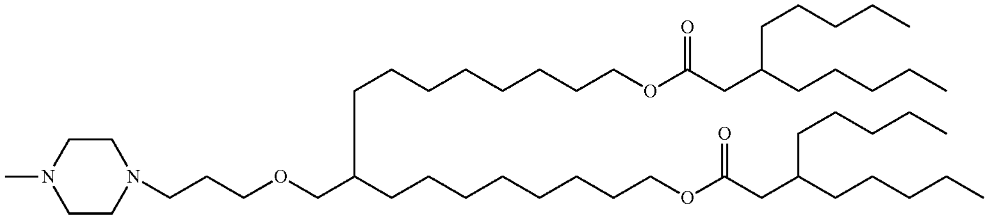 [SMILES: CCCCCC(CCCCC)CC(=O)OCCCCCCCCC(CCCCCCCCOC(=O)CC(CCCCC)CCCCC)COCCCN1CCN(C)CC1]
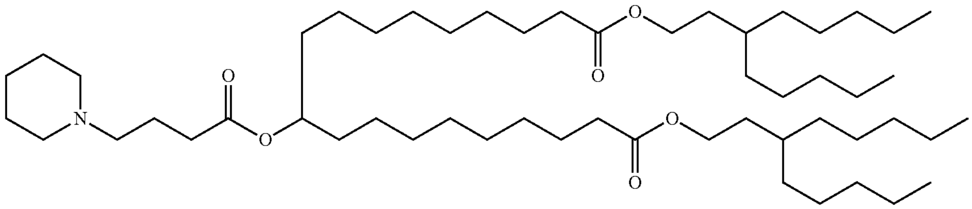 [SMILES: CCCCCC(CCCCC)CCOC(=O)CCCCCCCCC(CCCCCCCCC(=O)OCCC(CCCCC)CCCCC)OC(=O)CCCN1CCCCC1]
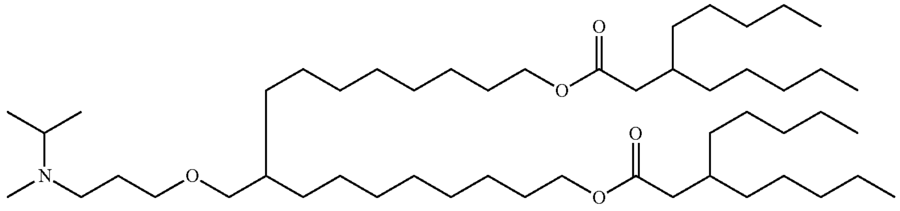 [SMILES: CCCCCC(CCCCC)CC(=O)OCCCCCCCCC(CCCCCCCCOC(=O)CC(CCCCC)CCCCC)COCCCN(C)C(C)C]

-continued
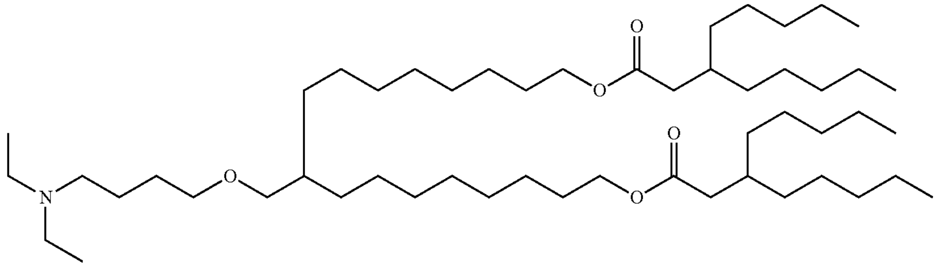 [SMILES: CCCCCC(CCCCC)CC(=O)OCCCCCCCCC(CCCCCCCCOC(=O)CC(CCCCC)CCCCC)COCCCCN(CC)CC]
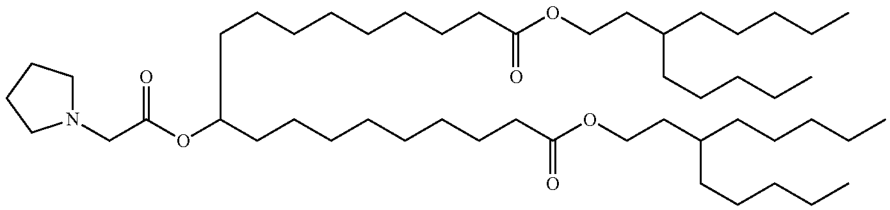 [SMILES: CCCCCC(CCCCC)CCOC(=O)CCCCCCCCC(CCCCCCCCC(=O)OCCC(CCCCC)CCCCC)OC(=O)CN1CCCC1]
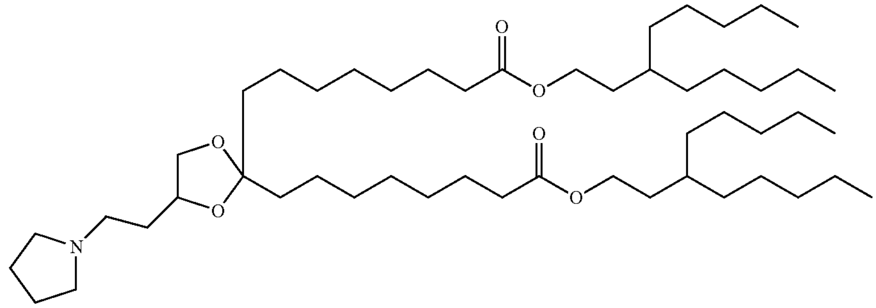 [SMILES: CCCCCC(CCCCC)CCOC(=O)CCCCCCCC1(CCCCCCCC(=O)OCCC(CCCCC)CCCCC)OCC(CCN2CCCC2)O1]
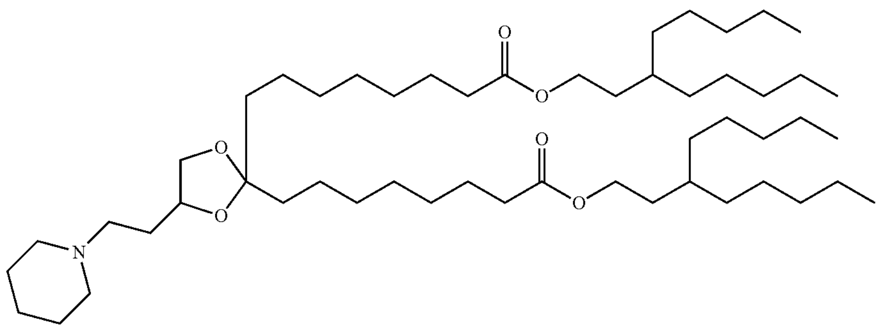 [SMILES: CCCCCC(CCCCC)CCOC(=O)CCCCCCCC1(CCCCCCCC(=O)OCCC(CCCCC)CCCCC)OCC(CCN2CCCCC2)O1]
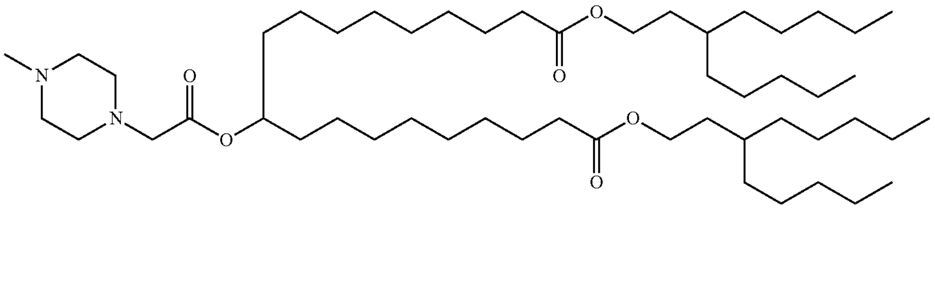 [SMILES: CCCCCC(CCCCC)CCOC(=O)CCCCCCCCC(CCCCCCCCC(=O)OCCC(CCCCC)CCCCC)OC(=O)CN1CCN(C)CC1]

-continued
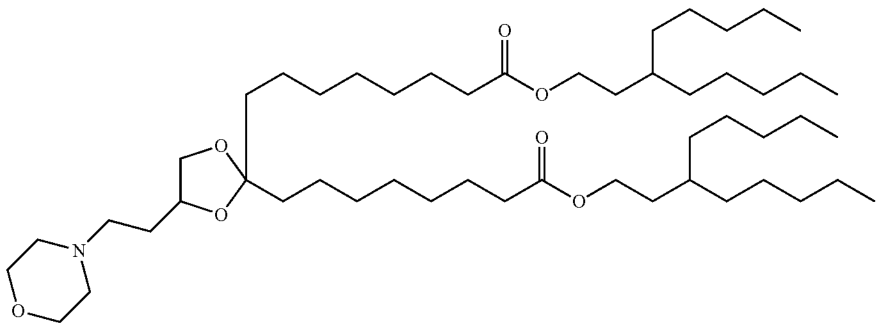 [SMILES: CCCCCC(CCCCC)CCOC(=O)CCCCCCCC1(CCCCCCCC(=O)OCCC(CCCCC)CCCCC)OCC(CCN2CCOCC2)O1]
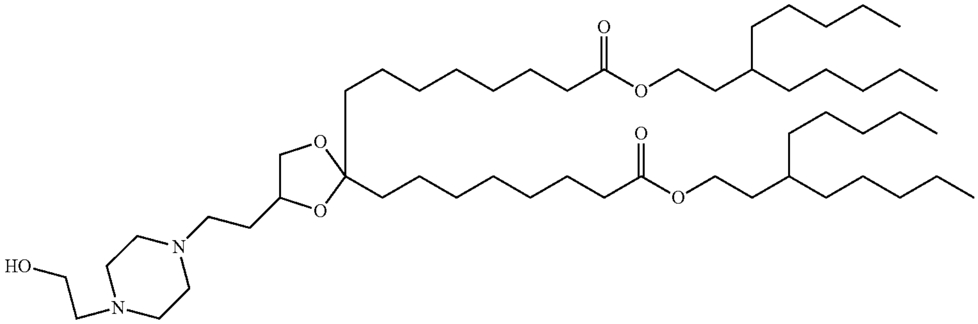 [SMILES: CCCCCC(CCCCC)CCOC(=O)CCCCCCCC1(CCCCCCCC(=O)OCCC(CCCCC)CCCCC)OCC(CCN2CCN(CCO)CC2)O1]
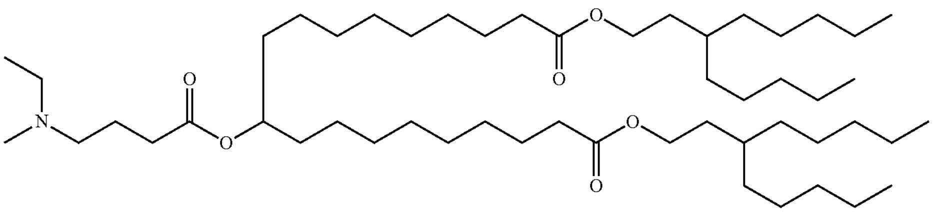 [SMILES: CCCCCC(CCCCC)CCOC(=O)CCCCCCCCC(CCCCCCCCC(=O)OCCC(CCCCC)CCCCC)OC(=O)CCCN(C)CC]
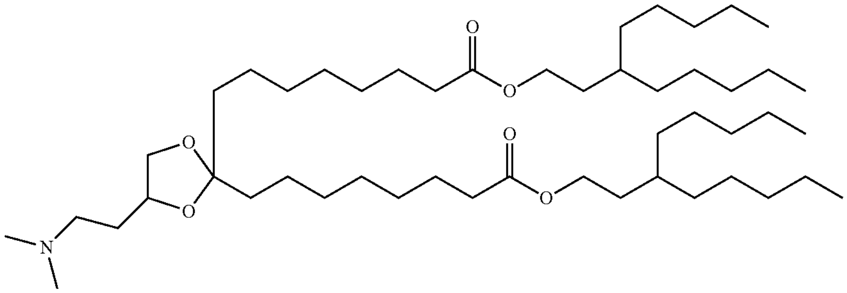 [SMILES: CCCCCC(CCCCC)CCOC(=O)CCCCCCCC1(CCCCCCCC(=O)OCCC(CCCCC)CCCCC)OCC(CCN(C)C)O1]
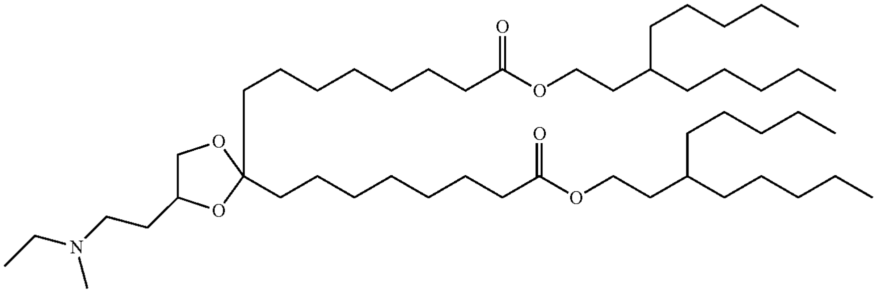 [SMILES: CCCCCC(CCCCC)CCOC(=O)CCCCCCCC1(CCCCCCCC(=O)OCCC(CCCCC)CCCCC)OCC(CCN(C)CC)O1]

-continued
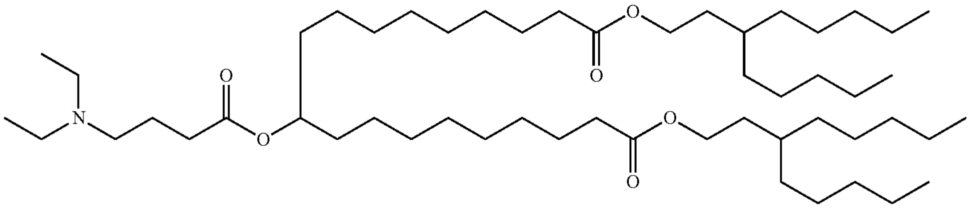 [SMILES: CCCCCC(CCCCC)CCOC(=O)CCCCCCCCC(CCCCCCCCC(=O)OCCC(CCCCC)CCCCC)OC(=O)CCCN(CC)CC]
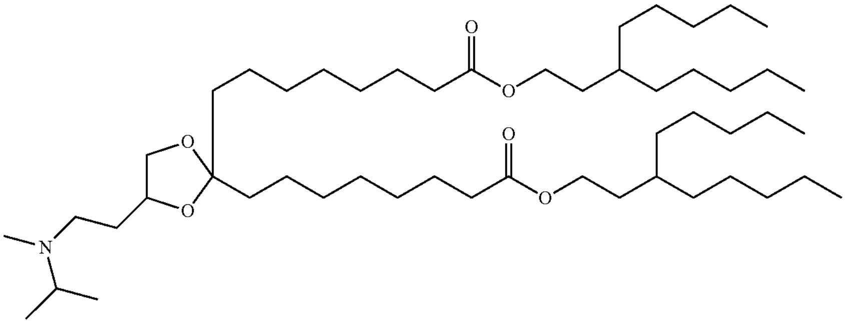 [SMILES: CCCCCC(CCCCC)CCOC(=O)CCCCCCCC1(CCCCCCCC(=O)OCCC(CCCCC)CCCCC)OCC(CCN(C)C(C)C)O1]
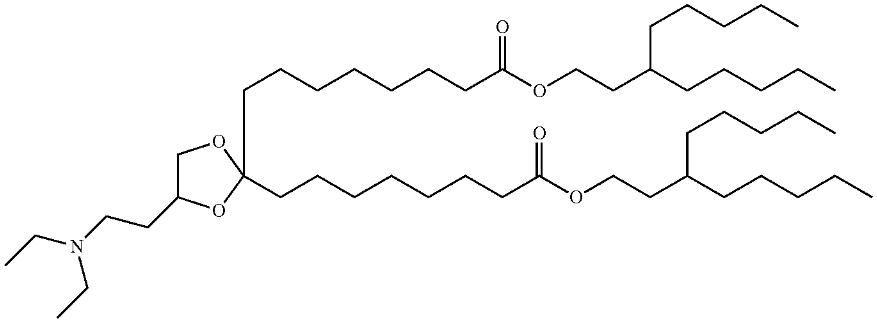 [SMILES: CCCCCC(CCCCC)CCOC(=O)CCCCCCCC1(CCCCCCCC(=O)OCCC(CCCCC)CCCCC)OCC(CCN(CC)CC)O1]
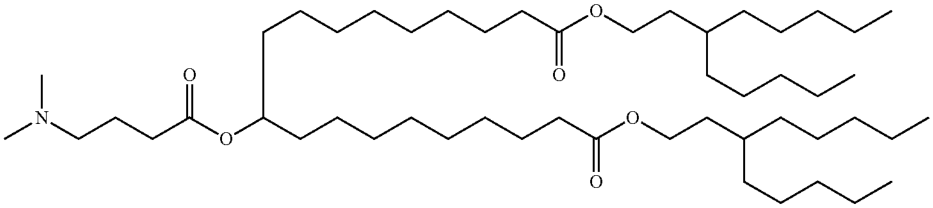 [SMILES: CCCCCC(CCCCC)CCOC(=O)CCCCCCCCC(CCCCCCCCC(=O)OCCC(CCCCC)CCCCC)OC(=O)CCCN(C)C]
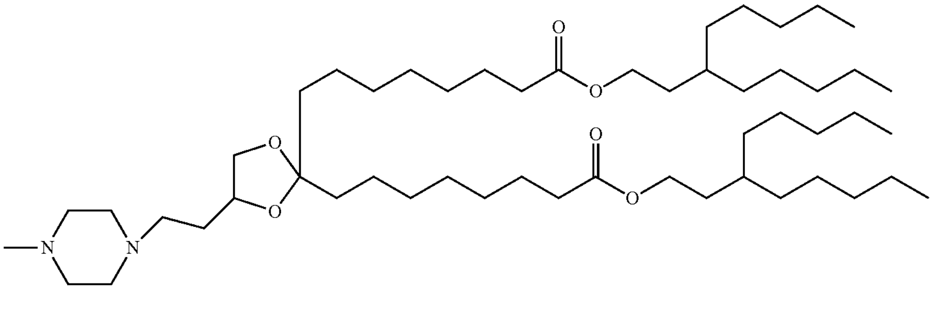 [SMILES: CCCCCC(CCCCC)CCOC(=O)CCCCCCCC1(CCCCCCCC(=O)OCCC(CCCCC)CCCCC)OCC(CCN2CCN(C)CC2)O1]

-continued
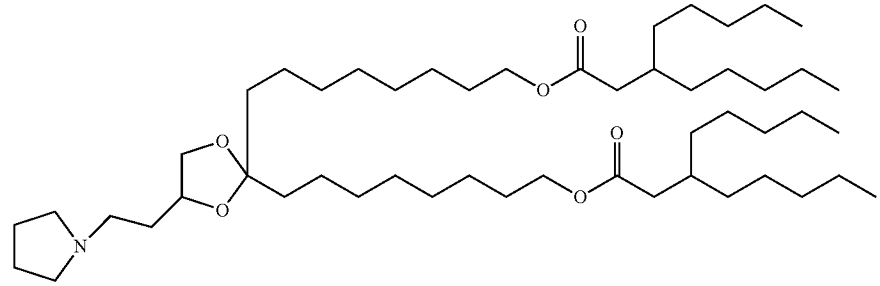 [SMILES: CCCCCC(CCCCC)CC(=O)OCCCCCCCCC1(CCCCCCCCOC(=O)CC(CCCCC)CCCCC)OCC(CCN2CCCC2)O1]
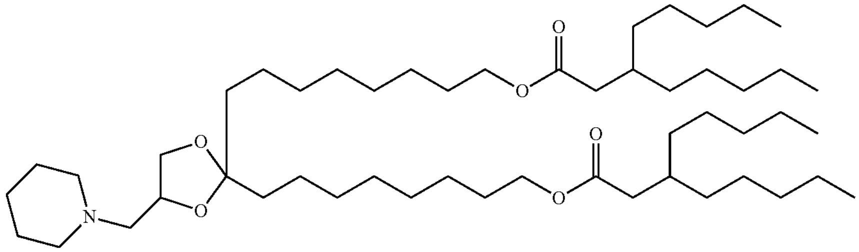 [SMILES: CCCCCC(CCCCC)CC(=O)OCCCCCCCCC1(CCCCCCCCOC(=O)CC(CCCCC)CCCCC)OCC(CN2CCCCC2)O1]
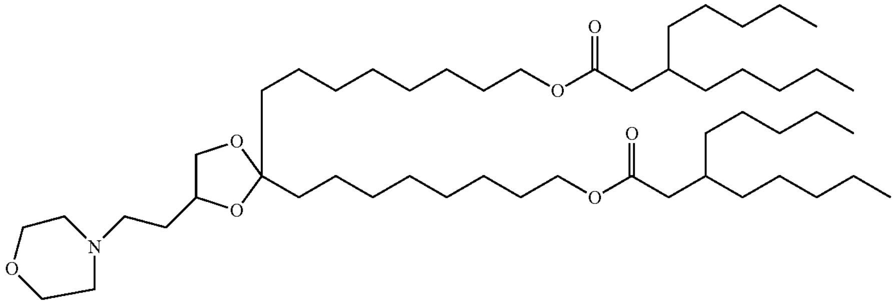 [SMILES: CCCCCC(CCCCC)CC(=O)OCCCCCCCCC1(CCCCCCCCOC(=O)CC(CCCCC)CCCCC)OCC(CCN2CCOCC2)O1]
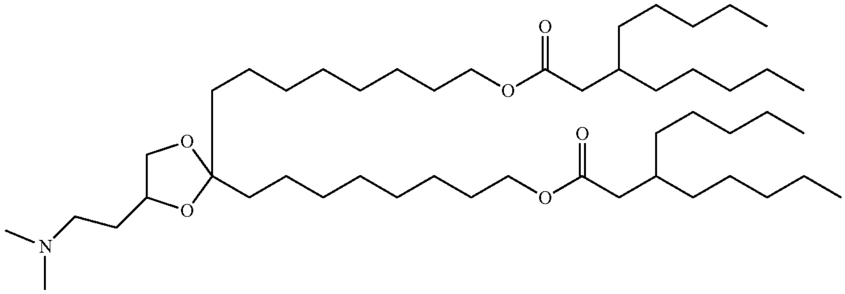 [SMILES: CCCCCC(CCCCC)CC(=O)OCCCCCCCCC1(CCCCCCCCOC(=O)CC(CCCCC)CCCCC)OCC(CCN(C)C)O1]
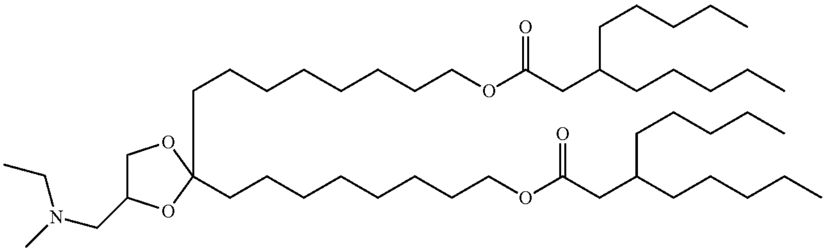 [SMILES: CCCCCC(CCCCC)CC(=O)OCCCCCCCCC1(CCCCCCCCOC(=O)CC(CCCCC)CCCCC)OCC(CN(C)CC)O1]

-continued
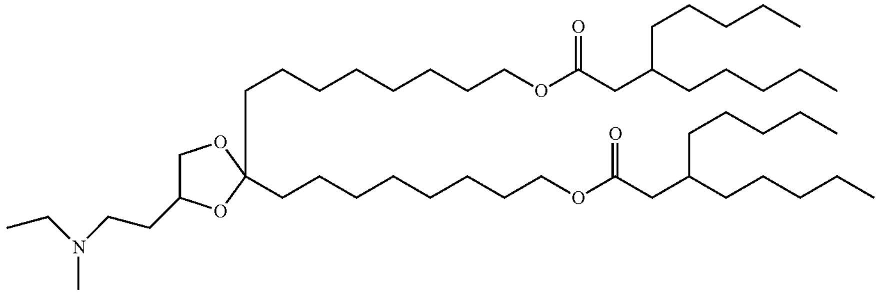 [SMILES: CCCCCC(CCCCC)CC(=O)OCCCCCCCCC1(CCCCCCCCOC(=O)CC(CCCCC)CCCCC)OCC(CCN(C)CC)O1]
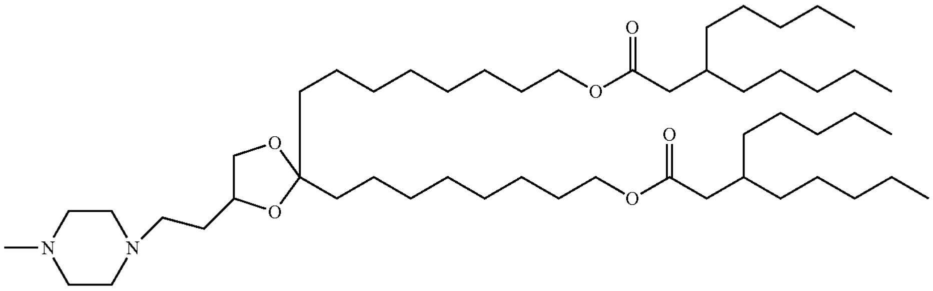 [SMILES: CCCCCC(CCCCC)CC(=O)OCCCCCCCCC1(CCCCCCCCOC(=O)CC(CCCCC)CCCCC)OCC(CCN2CCN(C)CC2)O1]
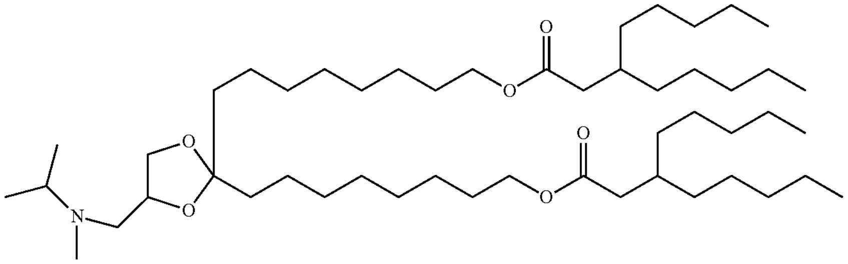 [SMILES: CCCCCC(CCCCC)CC(=O)OCCCCCCCCC1(CCCCCCCCOC(=O)CC(CCCCC)CCCCC)OCC(CN(C)C(C)C)O1]
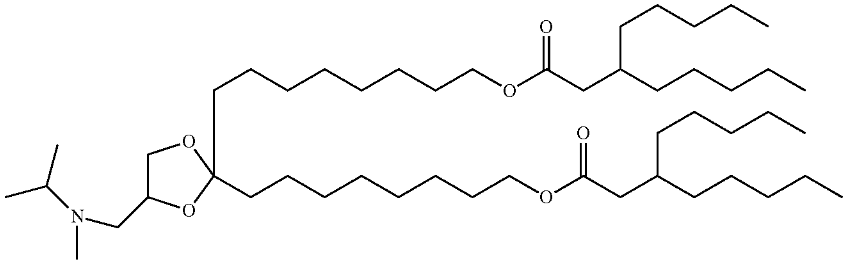 [SMILES: CCCCCC(CCCCC)CC(=O)OCCCCCCCCC1(CCCCCCCCOC(=O)CC(CCCCC)CCCCC)OCC(CN(C)C(C)C)O1]
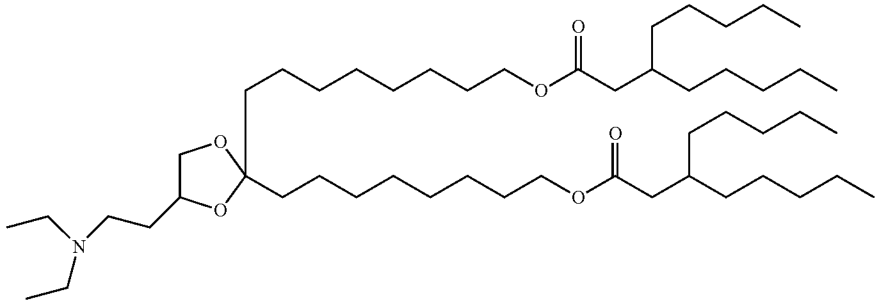 [SMILES: CCCCCC(CCCCC)CC(=O)OCCCCCCCCC1(CCCCCCCCOC(=O)CC(CCCCC)CCCCC)OCC(CCN(CC)CC)O1]

-continued
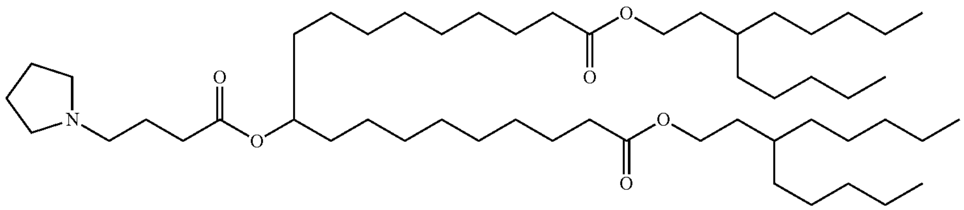 [SMILES: CCCCCC(CCCCC)CCOC(=O)CCCCCCCCC(CCCCCCCCC(=O)OCCC(CCCCC)CCCCC)OC(=O)CCCN1CCCC1]
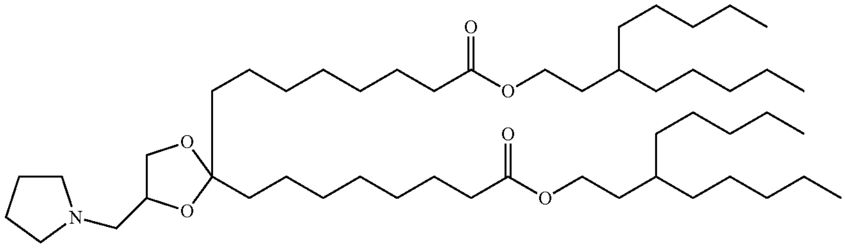 [SMILES: CCCCCC(CCCCC)CCOC(=O)CCCCCCCC1(CCCCCCCC(=O)OCCC(CCCCC)CCCCC)OCC(CN2CCCC2)O1]
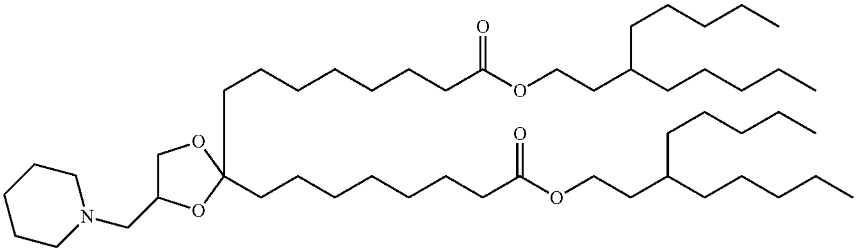 [SMILES: CCCCCC(CCCCC)CCOC(=O)CCCCCCCC1(CCCCCCCC(=O)OCCC(CCCCC)CCCCC)OCC(CN2CCCCC2)O1]
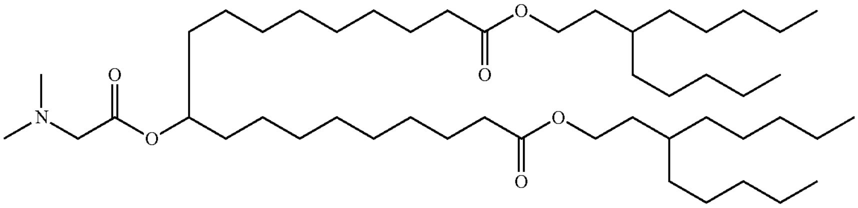 [SMILES: CCCCCC(CCCCC)CCOC(=O)CCCCCCCCC(CCCCCCCCC(=O)OCCC(CCCCC)CCCCC)OC(=O)CN(C)C]
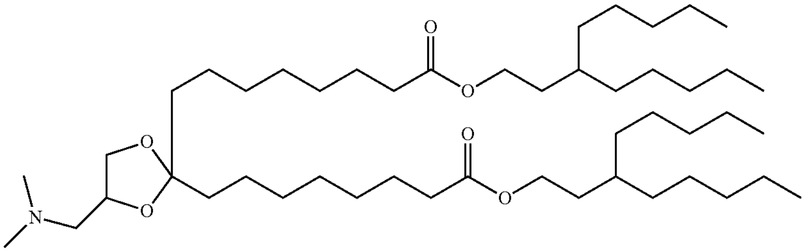 [SMILES: CCCCCC(CCCCC)CCOC(=O)CCCCCCCC1(CCCCCCCC(=O)OCCC(CCCCC)CCCCC)OCC(CN(C)C)O1]
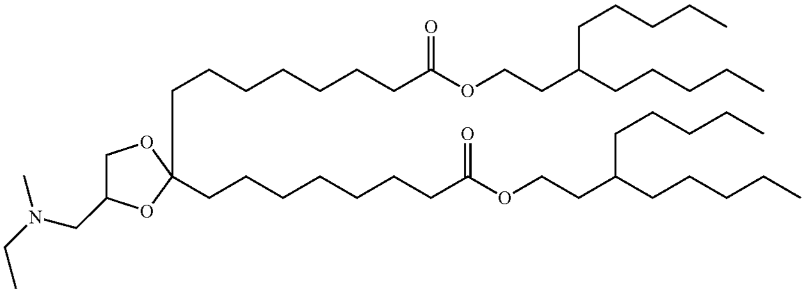 [SMILES: CCCCCC(CCCCC)CCOC(=O)CCCCCCCC1(CCCCCCCC(=O)OCCC(CCCCC)CCCCC)OCC(CN(C)CC)O1]

-continued
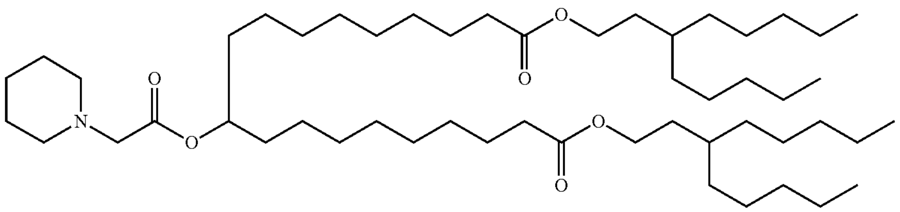 [SMILES: CCCCCC(CCCCC)CCOC(=O)CCCCCCCCC(CCCCCCCCC(=O)OCCC(CCCCC)CCCCC)OC(=O)CN1CCCCC1]
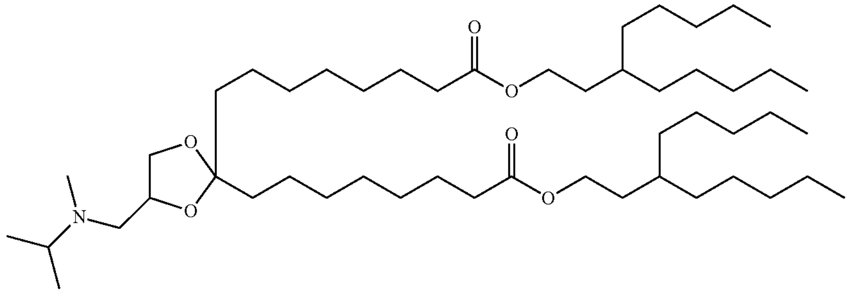 [SMILES: CCCCCC(CCCCC)CCOC(=O)CCCCCCCC1(CCCCCCCC(=O)OCCC(CCCCC)CCCCC)OCC(CN(C)C(C)C)O1]
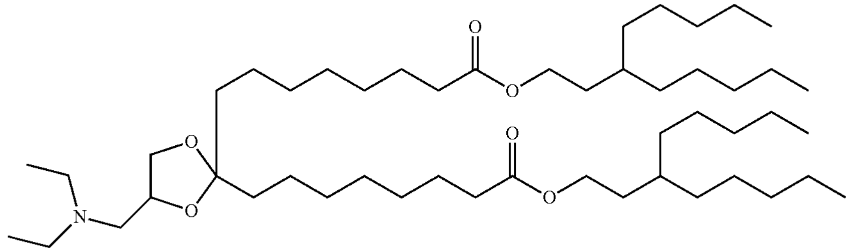 [SMILES: CCCCCC(CCCCC)CCOC(=O)CCCCCCCC1(CCCCCCCC(=O)OCCC(CCCCC)CCCCC)OCC(CN(CC)CC)O1]
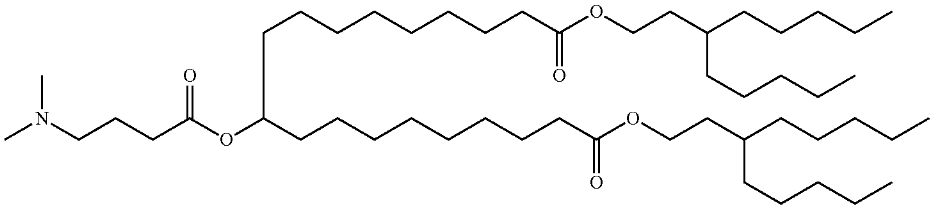 [SMILES: CCCCCC(CCCCC)CCOC(=O)CCCCCCCCC(CCCCCCCCC(=O)OCCC(CCCCC)CCCCC)OC(=O)CCCN(C)C]
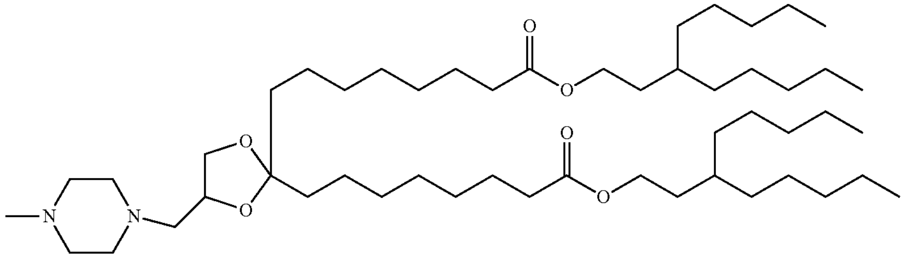 [SMILES: CCCCCC(CCCCC)CCOC(=O)CCCCCCCC1(CCCCCCCC(=O)OCCC(CCCCC)CCCCC)OCC(CN2CCN(C)CC2)O1]
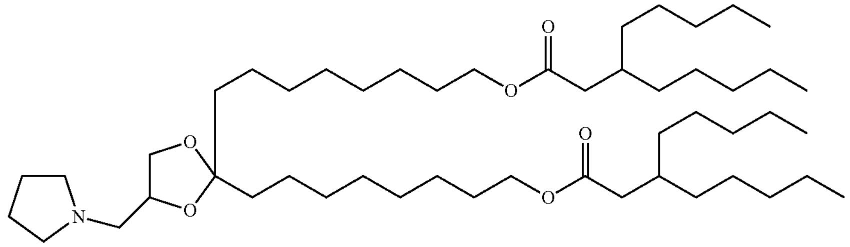 [SMILES: CCCCCC(CCCCC)CC(=O)OCCCCCCCCC1(CCCCCCCCOC(=O)CC(CCCCC)CCCCC)OCC(CN2CCCC2)O1]

-continued
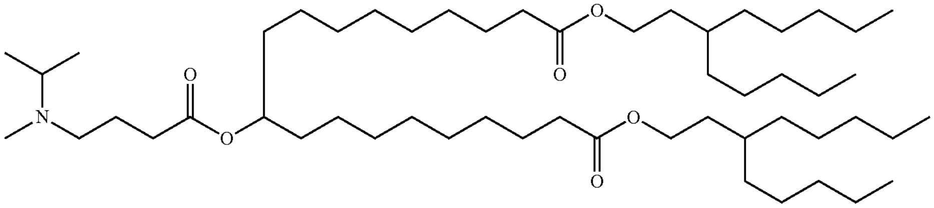 [SMILES: CCCCCC(CCCCC)CCOC(=O)CCCCCCCCC(CCCCCCCCC(=O)OCCC(CCCCC)CCCCC)OC(=O)CCCN(C)C(C)C]
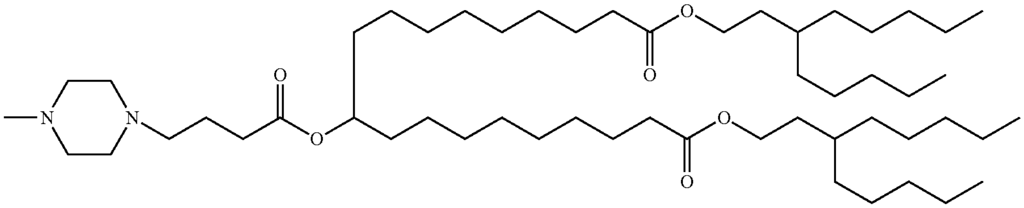 [SMILES: CCCCCC(CCCCC)CCOC(=O)CCCCCCCCC(CCCCCCCCC(=O)OCCC(CCCCC)CCCCC)OC(=O)CCCN1CCN(C)CC1]
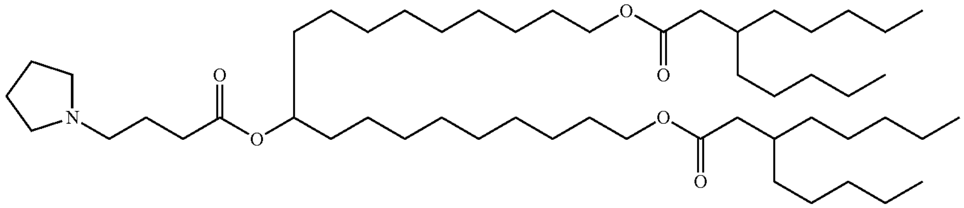 [SMILES: CCCCCC(CCCCC)CC(=O)OCCCCCCCCCC(CCCCCCCCCOC(=O)CC(CCCCC)CCCCC)OC(=O)CCCN1CCCC1]
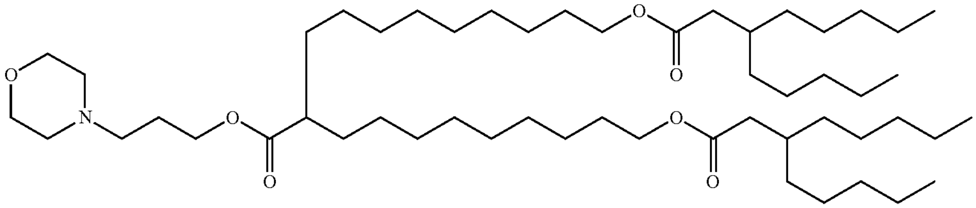 [SMILES: CCCCCC(CCCCC)CC(=O)OCCCCCCCCCC(CCCCCCCCCOC(=O)CC(CCCCC)CCCCC)C(=O)OCCCN1CCOCC1]
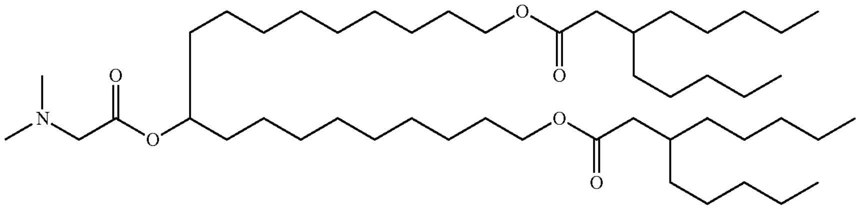 [SMILES: CCCCCC(CCCCC)CC(=O)OCCCCCCCCCC(CCCCCCCCCOC(=O)CC(CCCCC)CCCCC)OC(=O)CN(C)C]
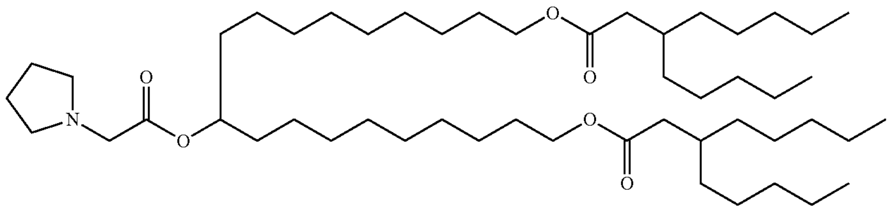 [SMILES: CCCCCC(CCCCC)CC(=O)OCCCCCCCCCC(CCCCCCCCCOC(=O)CC(CCCCC)CCCCC)OC(=O)CN1CCCC1]
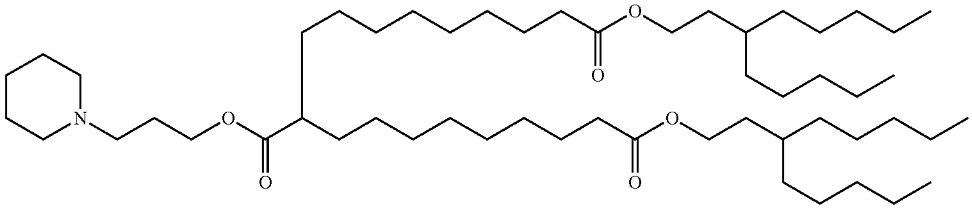 [SMILES: CCCCCC(CCCCC)CCOC(=O)CCCCCCCCC(CCCCCCCCC(=O)OCCC(CCCCC)CCCCC)C(=O)OCCCN1CCCCC1]

-continued
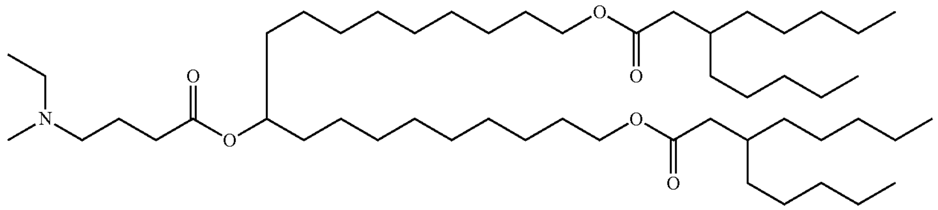 [SMILES: CCCCCC(CCCCC)CC(=O)OCCCCCCCCCC(CCCCCCCCCOC(=O)CC(CCCCC)CCCCC)OC(=O)CCCN(C)CC]
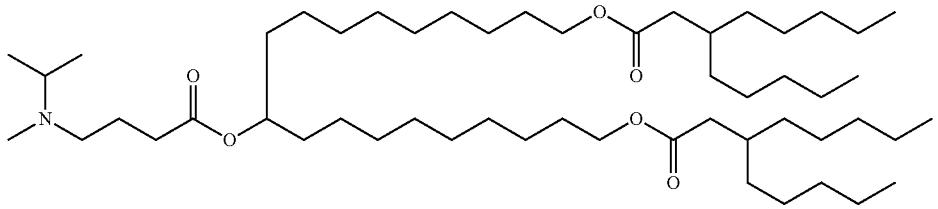 [SMILES: CCCCCC(CCCCC)CC(=O)OCCCCCCCCCC(CCCCCCCCCOC(=O)CC(CCCCC)CCCCC)OC(=O)CCCN(C)C(C)C]
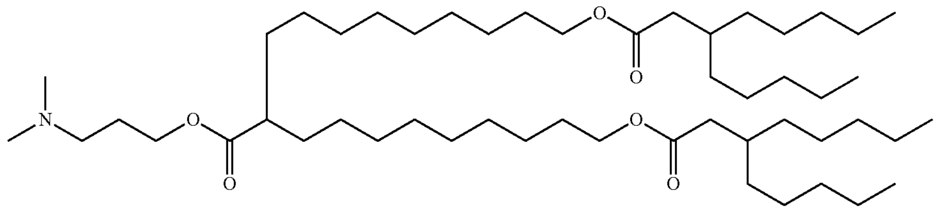 [SMILES: CCCCCC(CCCCC)CC(=O)OCCCCCCCCCC(CCCCCCCCCOC(=O)CC(CCCCC)CCCCC)C(=O)OCCCN(C)C]
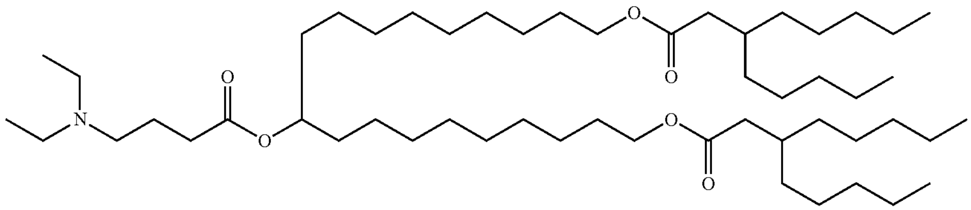 [SMILES: CCCCCC(CCCCC)CC(=O)OCCCCCCCCCC(CCCCCCCCCOC(=O)CC(CCCCC)CCCCC)OC(=O)CCCN(CC)CC]
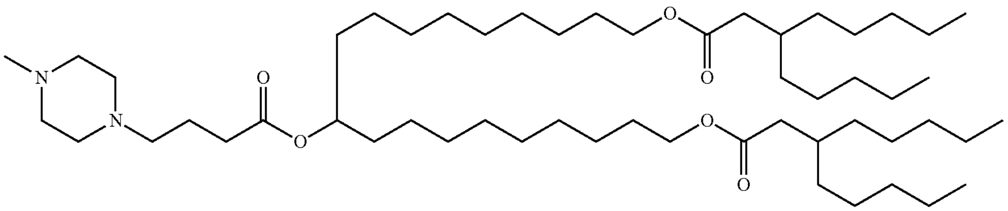 [SMILES: CCCCCC(CCCCC)CC(=O)OCCCCCCCCCC(CCCCCCCCCOC(=O)CC(CCCCC)CCCCC)OC(=O)CCCN1CCN(C)CC1]
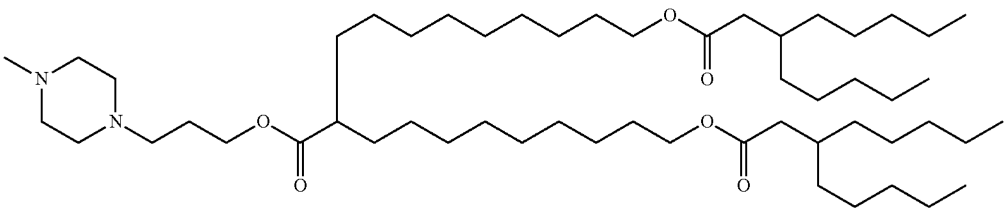 [SMILES: CCCCCC(CCCCC)CC(=O)OCCCCCCCCCC(CCCCCCCCCOC(=O)CC(CCCCC)CCCCC)C(=O)OCCCN1CCN(C)CC1]
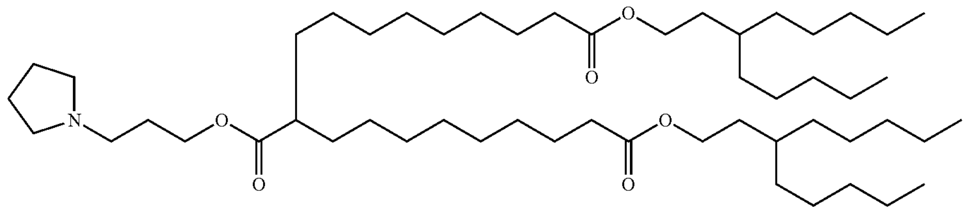 [SMILES: CCCCCC(CCCCC)CCOC(=O)CCCCCCCCC(CCCCCCCCC(=O)OCCC(CCCCC)CCCCC)C(=O)OCCCN1CCCC1]

-continued
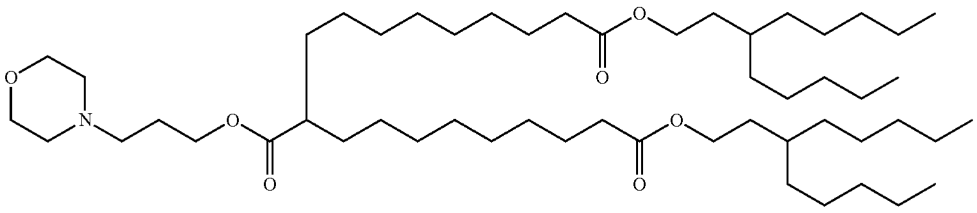 [SMILES: CCCCCC(CCCCC)CCOC(=O)CCCCCCCCC(CCCCCCCCC(=O)OCCC(CCCCC)CCCCC)C(=O)OCCCN1CCOCC1]
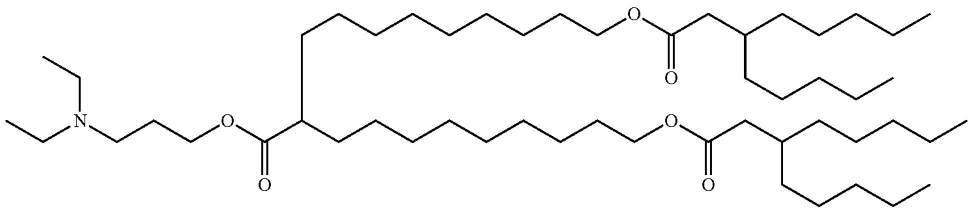 [SMILES: CCCCCC(CCCCC)CC(=O)OCCCCCCCCCC(CCCCCCCCCOC(=O)CC(CCCCC)CCCCC)C(=O)OCCCN(CC)CC]
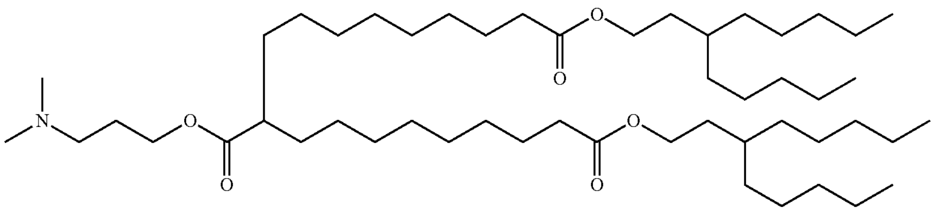 [SMILES: CCCCCC(CCCCC)CCOC(=O)CCCCCCCCC(CCCCCCCCC(=O)OCCC(CCCCC)CCCCC)C(=O)OCCCN(C)C]
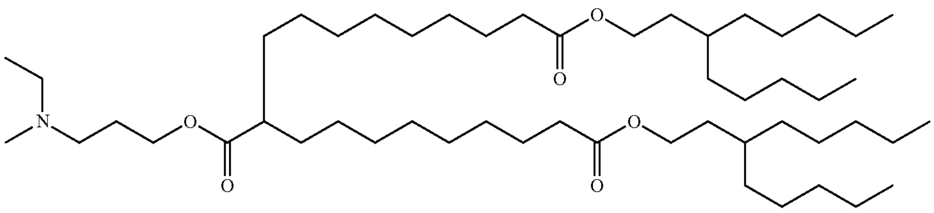 [SMILES: CCCCCC(CCCCC)CCOC(=O)CCCCCCCCC(CCCCCCCCC(=O)OCCC(CCCCC)CCCCC)C(=O)OCCCN(C)CC]
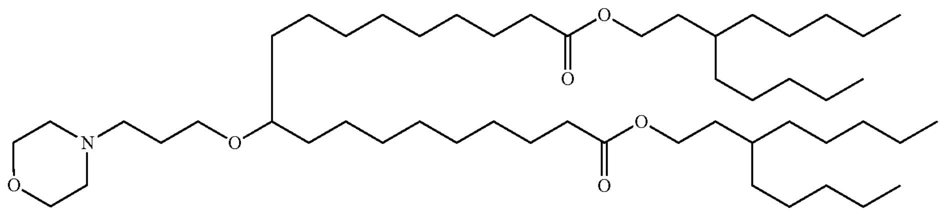 [SMILES: CCCCCC(CCCCC)CCOC(=O)CCCCCCCCC(CCCCCCCCC(=O)OCCC(CCCCC)CCCCC)OCCCN1CCOCC1]
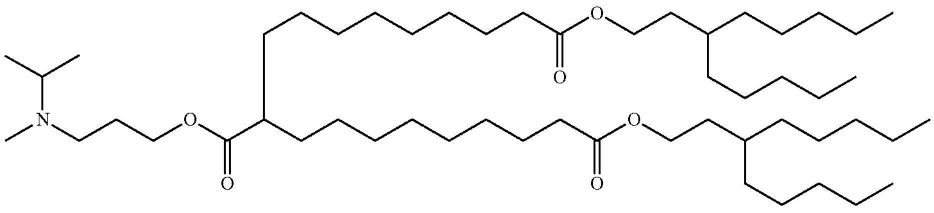 [SMILES: CCCCCC(CCCCC)CCOC(=O)CCCCCCCCC(CCCCCCCCC(=O)OCCC(CCCCC)CCCCC)C(=O)OCCCN(C)C(C)C]
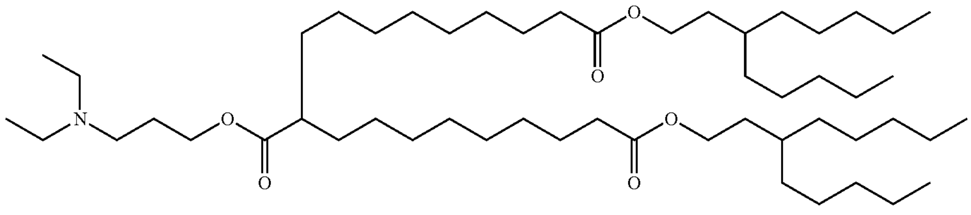 [SMILES: CCCCCC(CCCCC)CCOC(=O)CCCCCCCCC(CCCCCCCCC(=O)OCCC(CCCCC)CCCCC)C(=O)OCCCN(CC)CC]

-continued
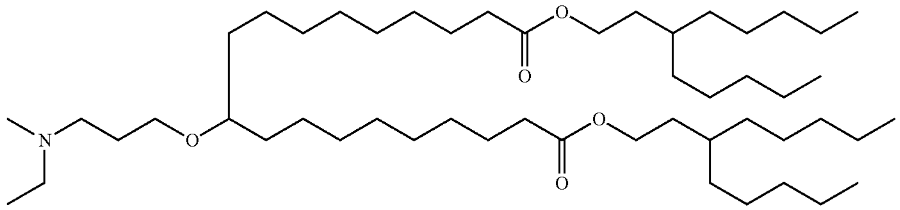 [SMILES: CCCCCC(CCCCC)CCOC(=O)CCCCCCCCC(CCCCCCCCC(=O)OCCC(CCCCC)CCCCC)OCCCN(C)CC]
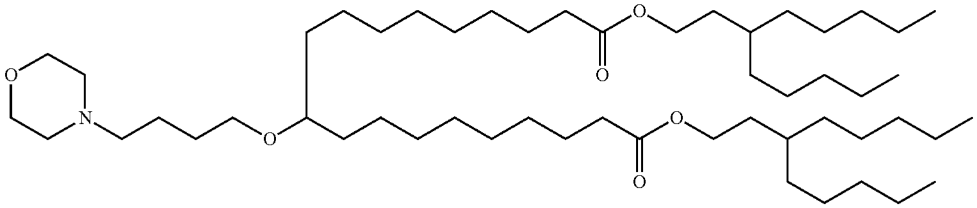 [SMILES: CCCCCC(CCCCC)CCOC(=O)CCCCCCCCC(CCCCCCCCC(=O)OCCC(CCCCC)CCCCC)OCCCCN1CCOCC1]
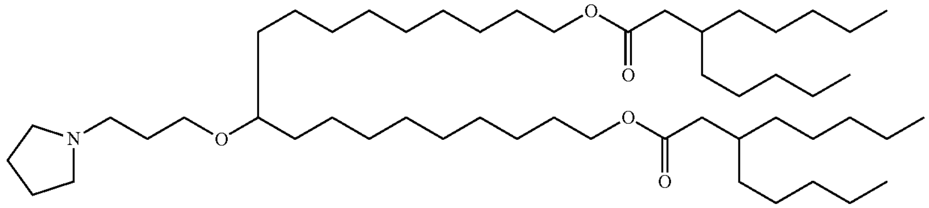 [SMILES: CCCCCC(CCCCC)CC(=O)OCCCCCCCCCC(CCCCCCCCCOC(=O)CC(CCCCC)CCCCC)OCCCN1CCCC1]
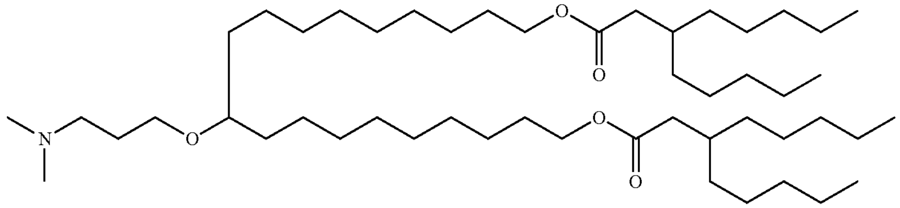 [SMILES: CCCCCC(CCCCC)CC(=O)OCCCCCCCCCC(CCCCCCCCCOC(=O)CC(CCCCC)CCCCC)OCCCN(C)C]
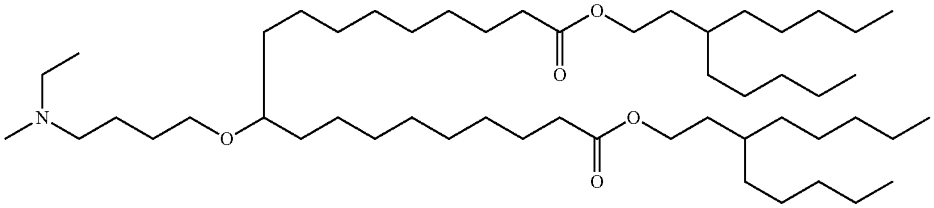
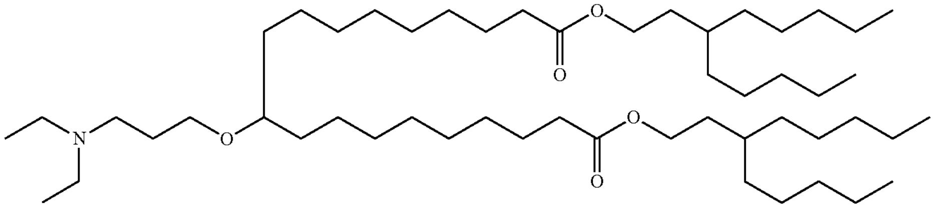 [SMILES: CCCCCC(CCCCC)CCOC(=O)CCCCCCCCC(CCCCCCCCC(=O)OCCC(CCCCC)CCCCC)OCCCN(CC)CC]
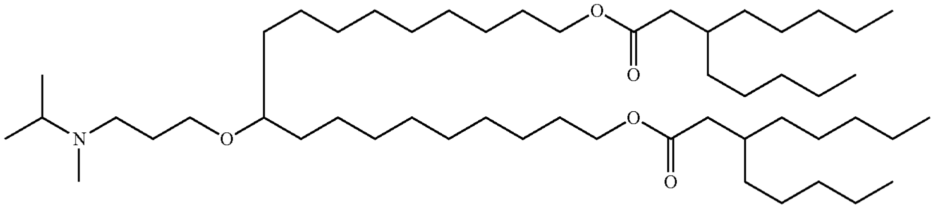 [SMILES: CCCCCC(CCCCC)CC(=O)OCCCCCCCCCC(CCCCCCCCCOC(=O)CC(CCCCC)CCCCC)OCCCN(C)C(C)C]

-continued
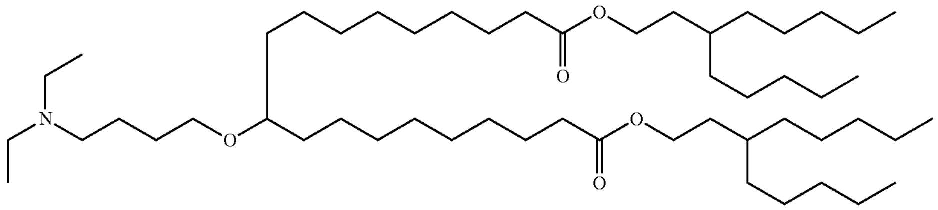 [SMILES: CCCCCC(CCCCC)CCOC(=O)CCCCCCCCC(CCCCCCCCC(=O)OCCC(CCCCC)CCCCC)OCCCCN(CC)CC]
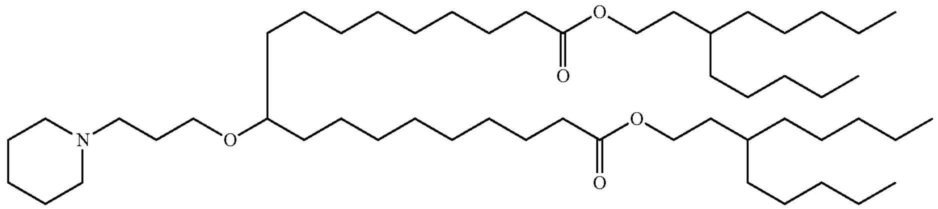 [SMILES: CCCCCC(CCCCC)CCOC(=O)CCCCCCCCC(CCCCCCCCC(=O)OCCC(CCCCC)CCCCC)OCCCN1CCCCC1]
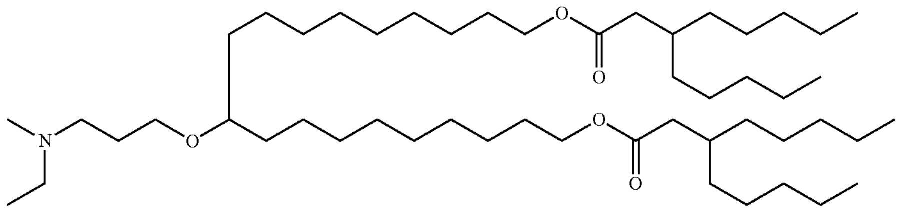 [SMILES: CCCCCC(CCCCC)CC(=O)OCCCCCCCCCC(CCCCCCCCCOC(=O)CC(CCCCC)CCCCC)OCCCN(C)CC]
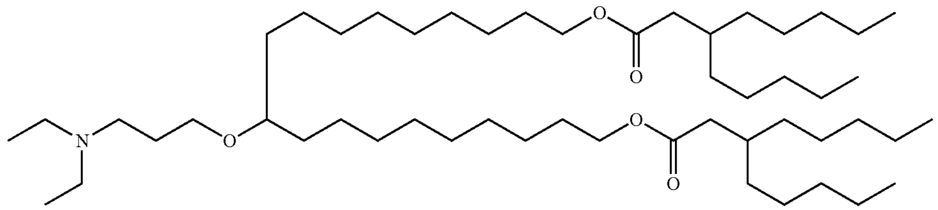 [SMILES: CCCCCC(CCCCC)CC(=O)OCCCCCCCCCC(CCCCCCCCCOC(=O)CC(CCCCC)CCCCC)OCCCN(CC)CC]
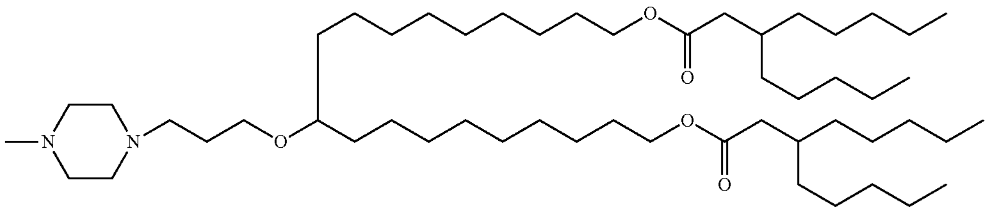 [SMILES: CCCCCC(CCCCC)CC(=O)OCCCCCCCCCC(CCCCCCCCCOC(=O)CC(CCCCC)CCCCC)OCCCN1CCN(C)CC1]
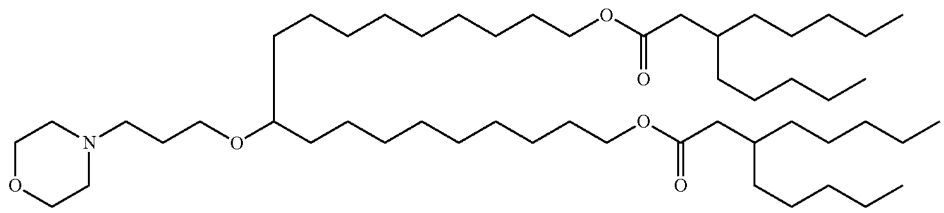 [SMILES: CCCCCC(CCCCC)CC(=O)OCCCCCCCCCC(CCCCCCCCCOC(=O)CC(CCCCC)CCCCC)OCCCN1CCOCC1]
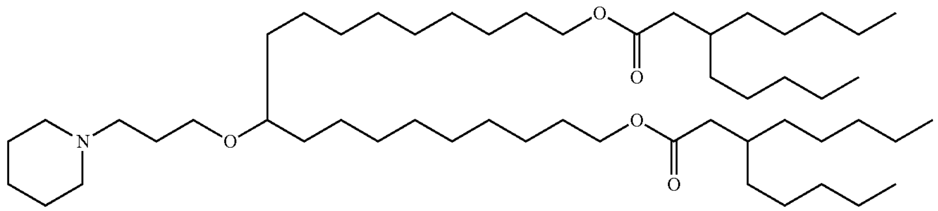 [SMILES: CCCCCC(CCCCC)CC(=O)OCCCCCCCCCC(CCCCCCCCCOC(=O)CC(CCCCC)CCCCC)OCCCN1CCCCC1]

-continued
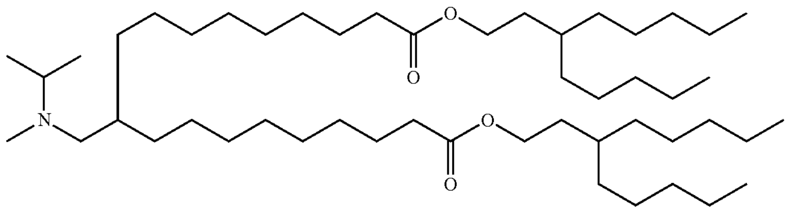 [SMILES: CCCCCC(CCCCC)CCOC(=O)CCCCCCCCC(CCCCCCCCC(=O)OCCC(CCCCC)CCCCC)CN(C)C(C)C]
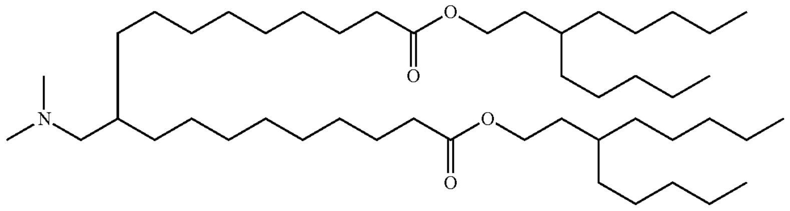 [SMILES: CCCCCC(CCCCC)CCOC(=O)CCCCCCCCC(CCCCCCCCC(=O)OCCC(CCCCC)CCCCC)CN(C)C]
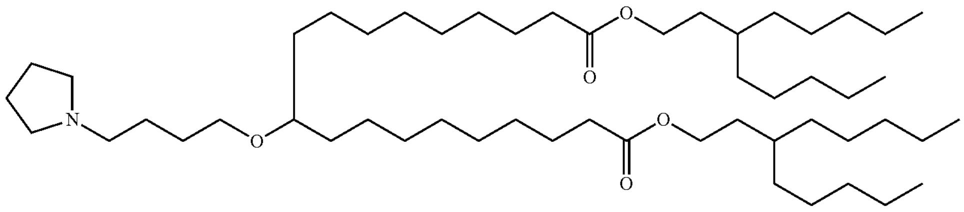 [SMILES: CCCCCC(CCCCC)CCOC(=O)CCCCCCCCC(CCCCCCCCC(=O)OCCC(CCCCC)CCCCC)OCCCCN1CCCC1]
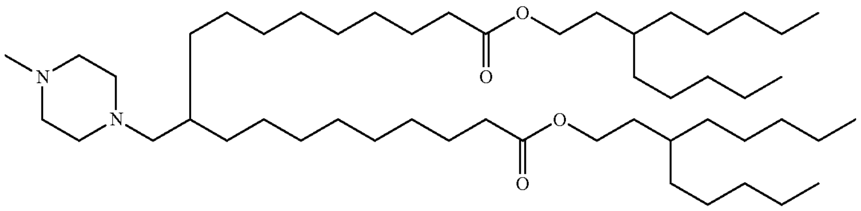 [SMILES: CCCCCC(CCCCC)CCOC(=O)CCCCCCCCC(CCCCCCCCC(=O)OCCC(CCCCC)CCCCC)CN1CCN(C)CC1]
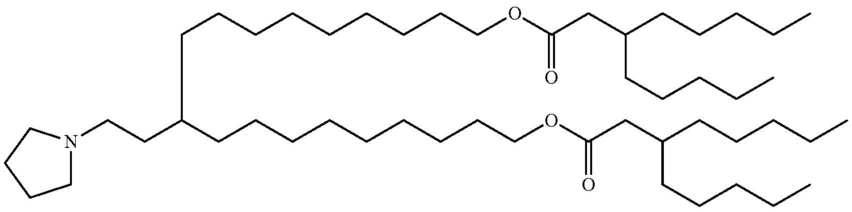 [SMILES: CCCCCC(CCCCC)CC(=O)OCCCCCCCCCC(CCCCCCCCCOC(=O)CC(CCCCC)CCCCC)CCN1CCCC1]
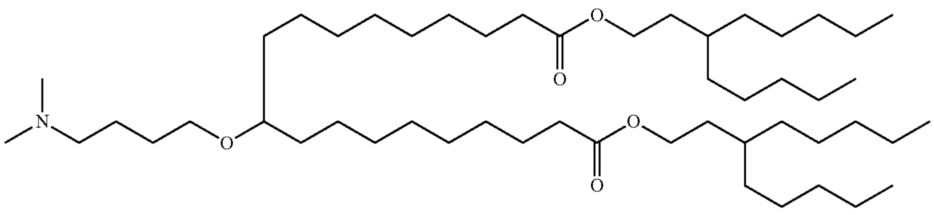 [SMILES: CCCCCC(CCCCC)CCOC(=O)CCCCCCCCC(CCCCCCCCC(=O)OCCC(CCCCC)CCCCC)OCCCCN(C)C]
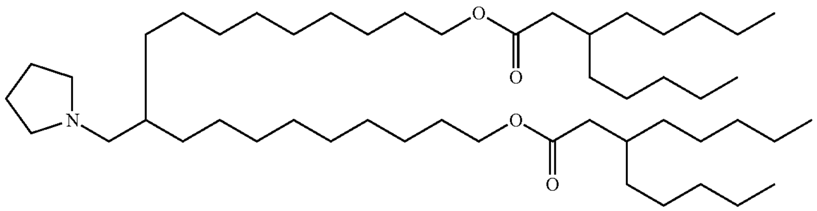 [SMILES: CCCCCC(CCCCC)CC(=O)OCCCCCCCCCC(CCCCCCCCCOC(=O)CC(CCCCC)CCCCC)CN1CCCC1]

-continued
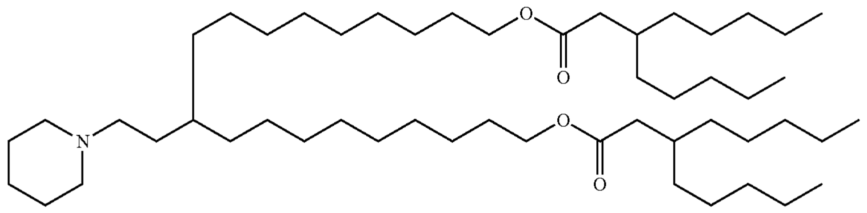 [SMILES: CCCCCC(CCCCC)CC(=O)OCCCCCCCCCC(CCCCCCCCCOC(=O)CC(CCCCC)CCCCC)CCN1CCCCC1]
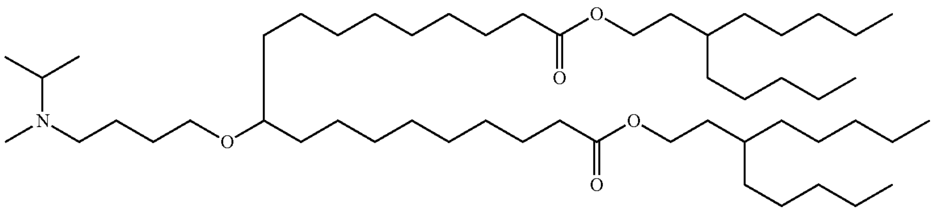 [SMILES: CCCCCC(CCCCC)CCOC(=O)CCCCCCCCC(CCCCCCCCC(=O)OCCC(CCCCC)CCCCC)OCCCCN(C)C(C)C]
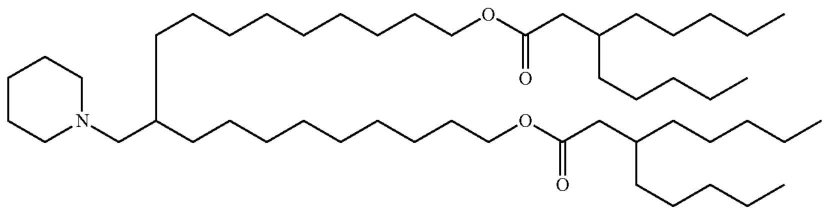 [SMILES: CCCCCC(CCCCC)CC(=O)OCCCCCCCCCC(CCCCCCCCCOC(=O)CC(CCCCC)CCCCC)CN1CCCCC1]
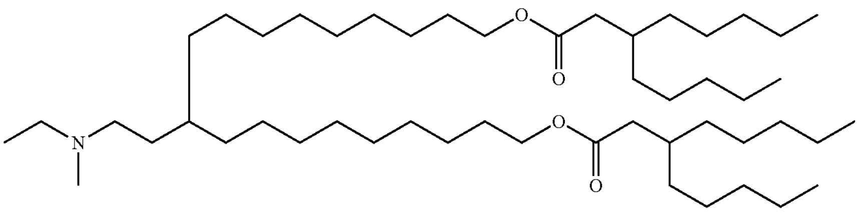 [SMILES: CCCCCC(CCCCC)CC(=O)OCCCCCCCCCC(CCCCCCCCCOC(=O)CC(CCCCC)CCCCC)CCN(C)CC]
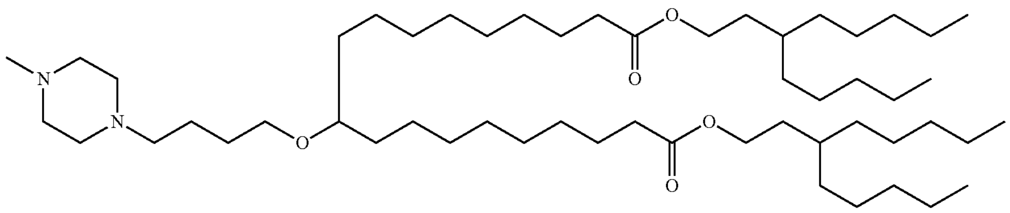 [SMILES: CCCCCC(CCCCC)CCOC(=O)CCCCCCCCC(CCCCCCCCC(=O)OCCC(CCCCC)CCCCC)OCCCCN1CCN(C)CC1]
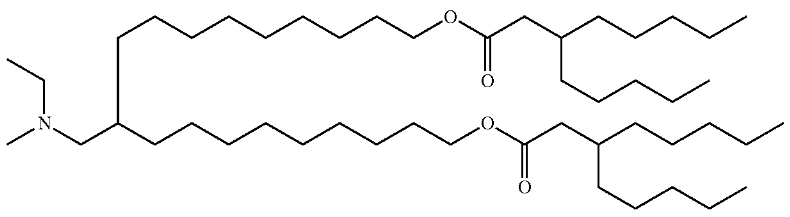 [SMILES: CCCCCC(CCCCC)CC(=O)OCCCCCCCCCC(CCCCCCCCCOC(=O)CC(CCCCC)CCCCC)CN(C)CC]
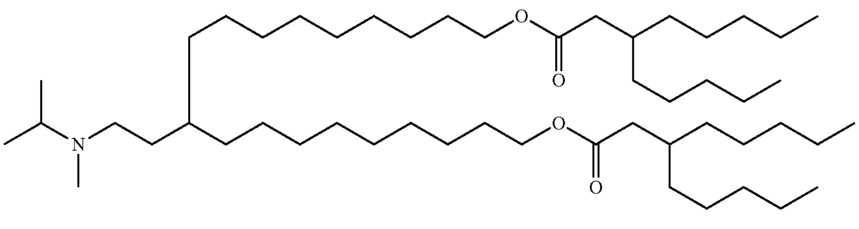 [SMILES: CCCCCC(CCCCC)CC(=O)OCCCCCCCCCC(CCCCCCCCCOC(=O)CC(CCCCC)CCCCC)CCN(C)C(C)C]

-continued
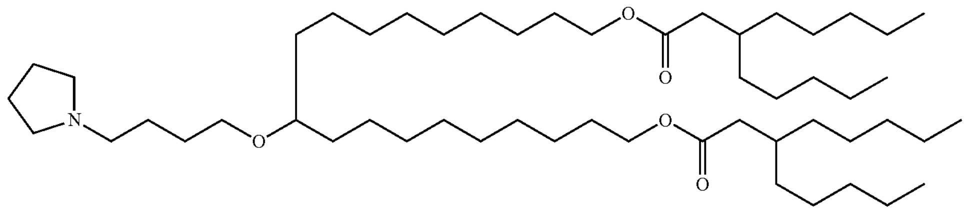 [SMILES: CCCCCC(CCCCC)CC(=O)OCCCCCCCCCC(CCCCCCCCCOC(=O)CC(CCCCC)CCCCC)OCCCCN1CCCC1]
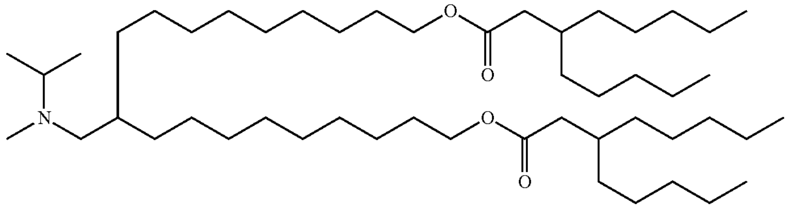 [SMILES: CCCCCC(CCCCC)CC(=O)OCCCCCCCCCC(CCCCCCCCCOC(=O)CC(CCCCC)CCCCC)CN(C)C(C)C]
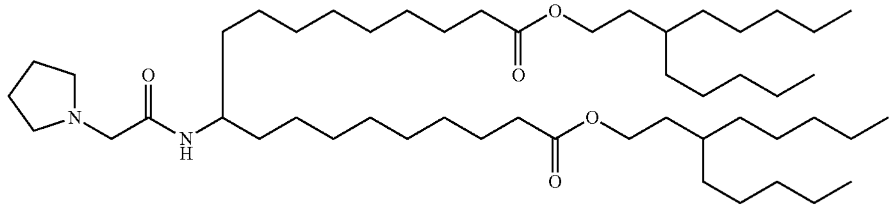 [SMILES: CCCCCC(CCCCC)CCOC(=O)CCCCCCCCC(CCCCCCCCC(=O)OCCC(CCCCC)CCCCC)NC(=O)CN1CCCC1]
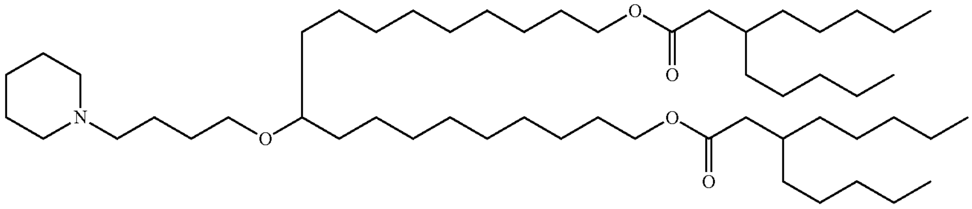 [SMILES: CCCCCC(CCCCC)CC(=O)OCCCCCCCCCC(CCCCCCCCCOC(=O)CC(CCCCC)CCCCC)OCCCCN1CCCCC1]
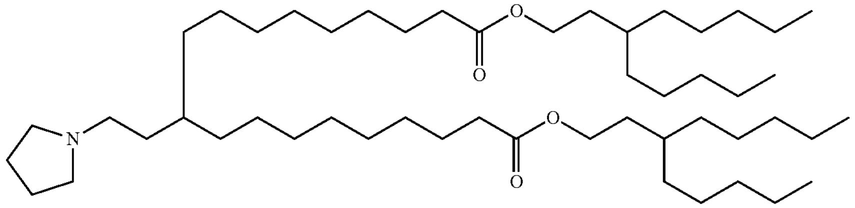 [SMILES: CCCCCC(CCCCC)CCOC(=O)CCCCCCCCC(CCCCCCCCC(=O)OCCC(CCCCC)CCCCC)CCN1CCCC1]
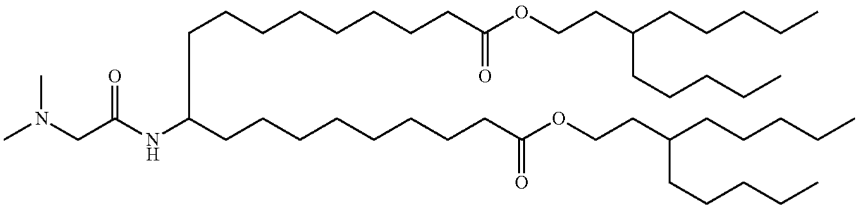 [SMILES: CCCCCC(CCCCC)CCOC(=O)CCCCCCCCC(CCCCCCCCC(=O)OCCC(CCCCC)CCCCC)NC(=O)CN(C)C]
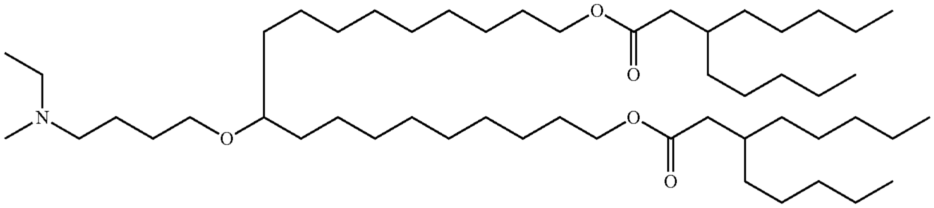 [SMILES: CCCCCC(CCCCC)CC(=O)OCCCCCCCCCC(CCCCCCCCCOC(=O)CC(CCCCC)CCCCC)OCCCCN(C)CC]

-continued
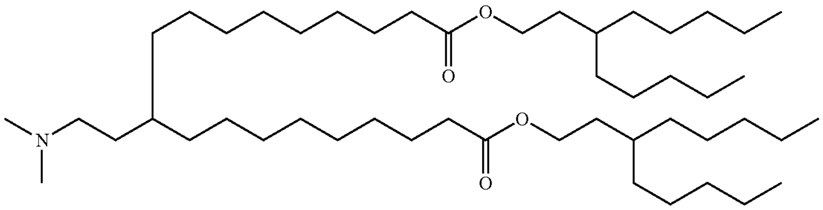 [SMILES: CCCCCC(CCCCC)CCOC(=O)CCCCCCCCC(CCCCCCCCC(=O)OCCC(CCCCC)CCCCC)CCN(C)C]
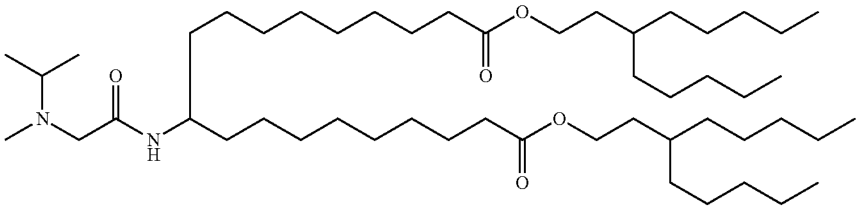 [SMILES: CCCCCC(CCCCC)CCOC(=O)CCCCCCCCC(CCCCCCCCC(=O)OCCC(CCCCC)CCCCC)NC(=O)CN(C)C(C)C]
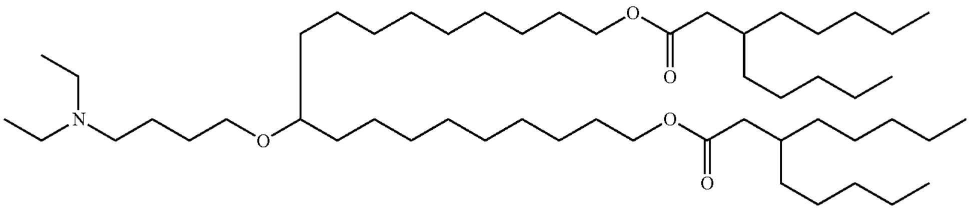 [SMILES: CCCCCC(CCCCC)CC(=O)OCCCCCCCCCC(CCCCCCCCCOC(=O)CC(CCCCC)CCCCC)OCCCCN(CC)CC]
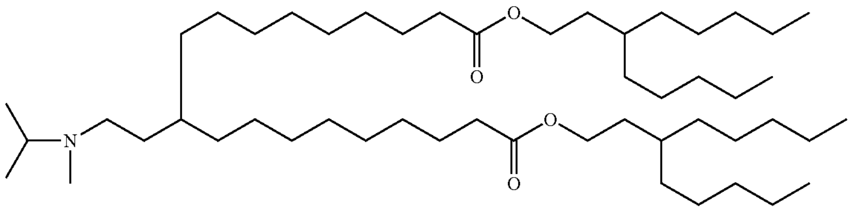 [SMILES: CCCCCC(CCCCC)CCOC(=O)CCCCCCCCC(CCCCCCCCC(=O)OCCC(CCCCC)CCCCC)CCN(C)C(C)C]
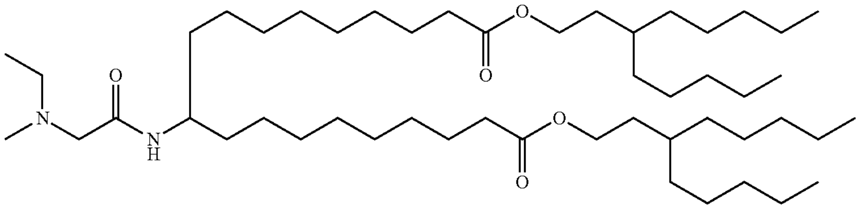 [SMILES: CCCCCC(CCCCC)CCOC(=O)CCCCCCCCC(CCCCCCCCC(=O)OCCC(CCCCC)CCCCC)NC(=O)CN(C)CC]
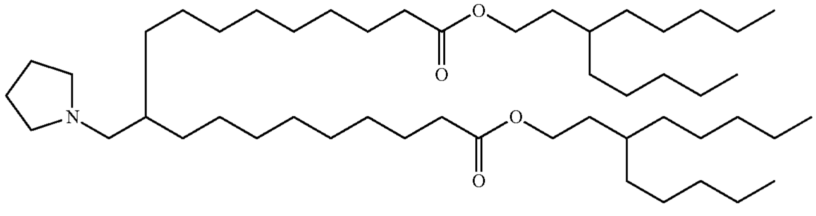 [SMILES: CCCCCC(CCCCC)CCOC(=O)CCCCCCCCC(CCCCCCCCC(=O)OCCC(CCCCC)CCCCC)CN1CCCC1]
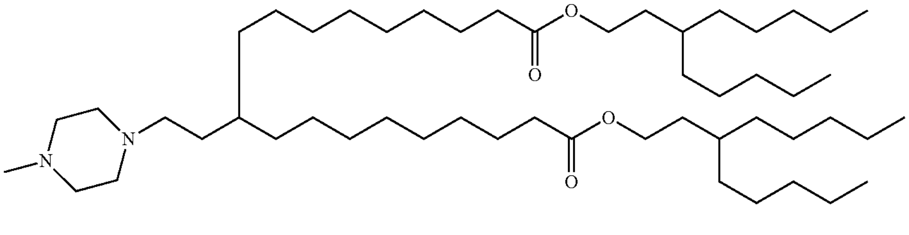 [SMILES: CCCCCC(CCCCC)CCOC(=O)CCCCCCCCC(CCCCCCCCC(=O)OCCC(CCCCC)CCCCC)CCN1CCN(C)CC1]

-continued
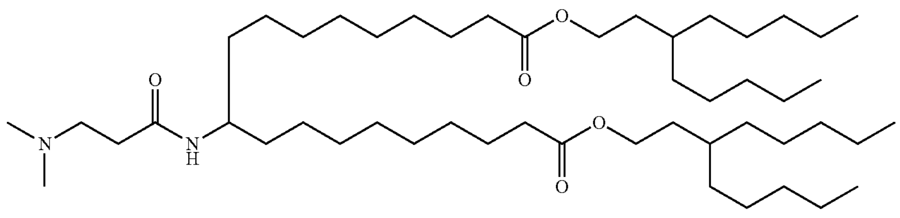 [SMILES: CCCCCC(CCCCC)CCOC(=O)CCCCCCCCC(CCCCCCCCC(=O)OCCC(CCCCC)CCCCC)NC(=O)CCN(C)C]
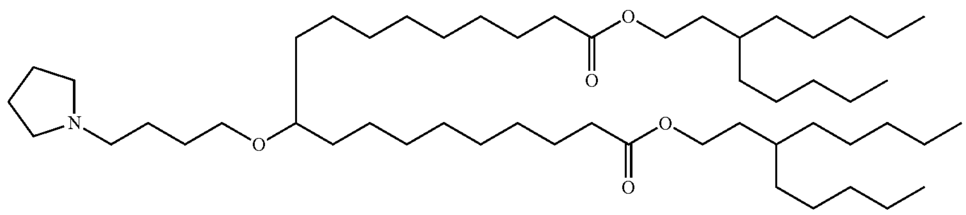 [SMILES: CCCCCC(CCCCC)CCOC(=O)CCCCCCCCC(CCCCCCCCC(=O)OCCC(CCCCC)CCCCC)OCCCCN1CCCC1]
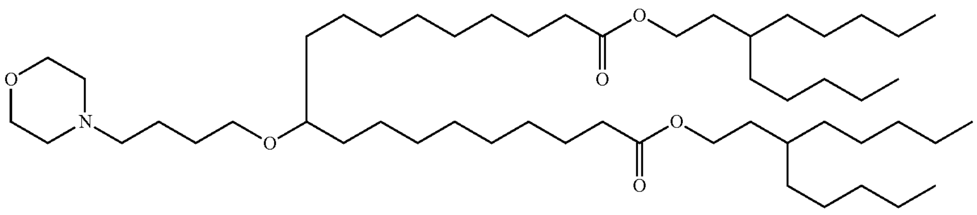 [SMILES: CCCCCC(CCCCC)CCOC(=O)CCCCCCCCC(CCCCCCCCC(=O)OCCC(CCCCC)CCCCC)OCCCCN1CCOCC1]
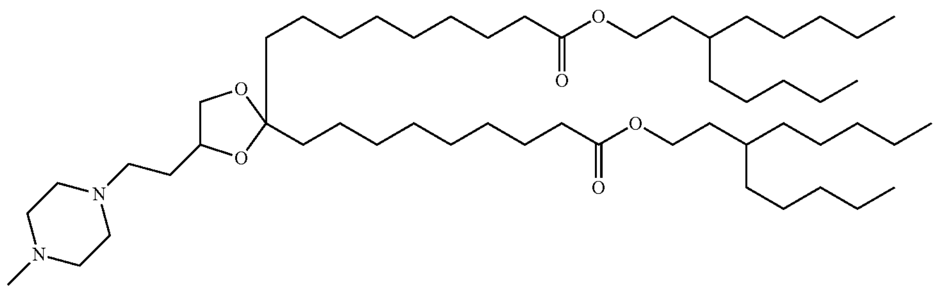 [SMILES: CCCCCC(CCCCC)CCOC(=O)CCCCCCCCC1(CCCCCCCCC(=O)OCCC(CCCCC)CCCCC)OCC(CCN2CCN(C)CC2)O1]
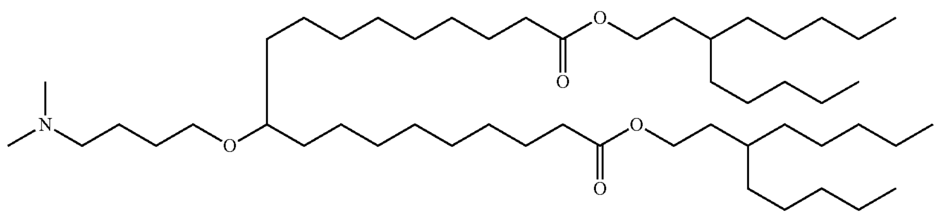 [SMILES: CCCCCC(CCCCC)CCOC(=O)CCCCCCCCC(CCCCCCCCC(=O)OCCC(CCCCC)CCCCC)OCCCCN(C)C]
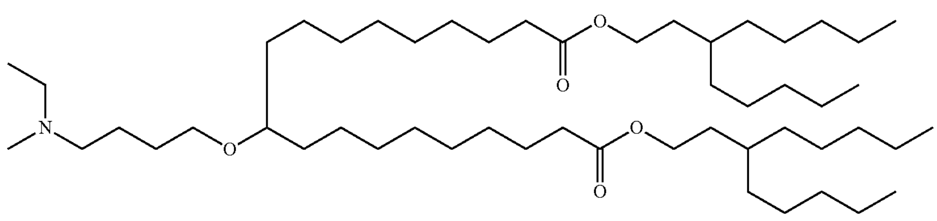

-continued
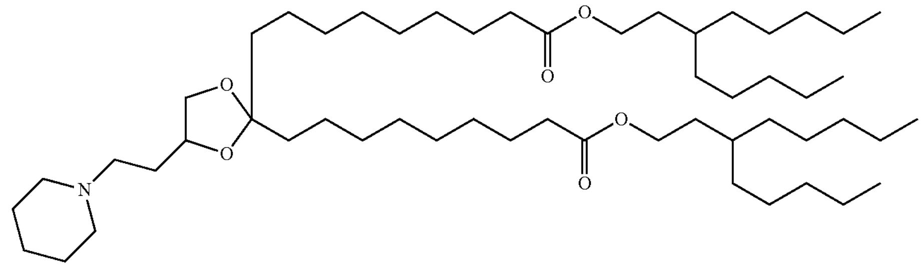 [SMILES: CCCCCC(CCCCC)CCOC(=O)CCCCCCCCC1(CCCCCCCCC(=O)OCCC(CCCCC)CCCCC)OCC(CCN2CCCCC2)O1]
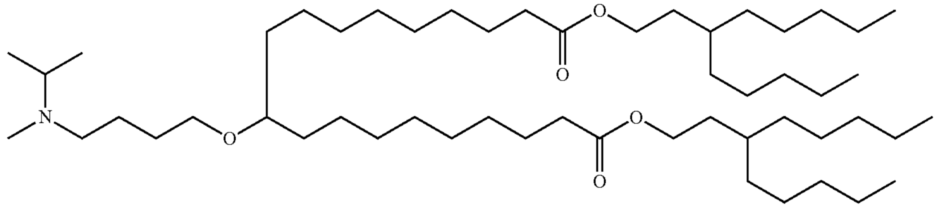 [SMILES: CCCCCC(CCCCC)CCOC(=O)CCCCCCCCC(CCCCCCCCC(=O)OCCC(CCCCC)CCCCC)OCCCCN(C)C(C)C]
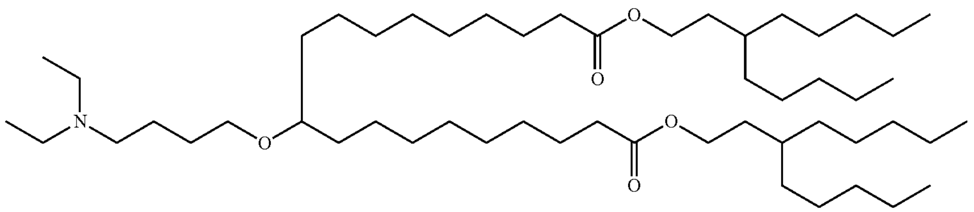 [SMILES: CCCCCC(CCCCC)CCOC(=O)CCCCCCCCC(CCCCCCCCC(=O)OCCC(CCCCC)CCCCC)OCCCCN(CC)CC]
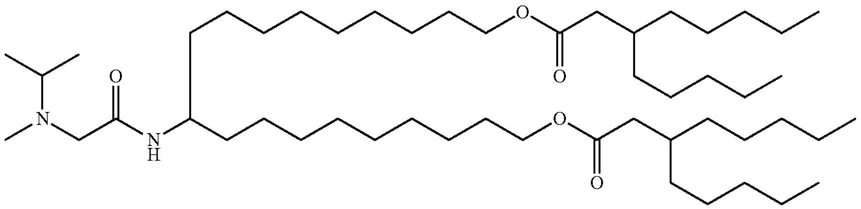 [SMILES: CCCCCC(CCCCC)CC(=O)OCCCCCCCCCC(CCCCCCCCCOC(=O)CC(CCCCC)CCCCC)NC(=O)CN(C)C(C)C]
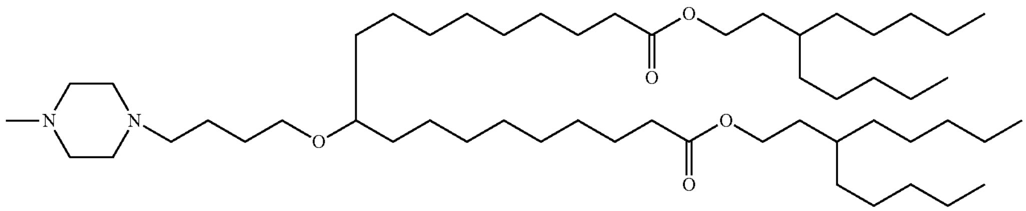 [SMILES: CCCCCC(CCCCC)CCOC(=O)CCCCCCCCC(CCCCCCCCC(=O)OCCC(CCCCC)CCCCC)OCCCCN1CCN(C)CC1]
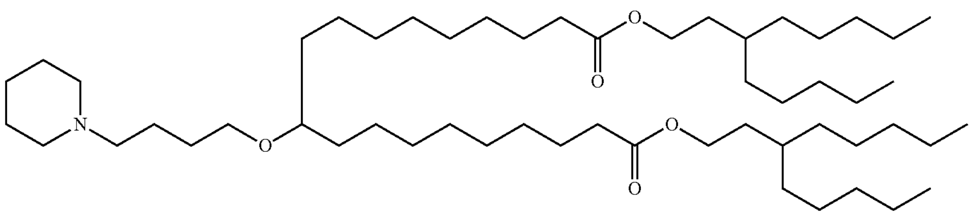 [SMILES: CCCCCC(CCCCC)CCOC(=O)CCCCCCCCC(CCCCCCCCC(=O)OCCC(CCCCC)CCCCC)OCCCCN1CCCCC1]
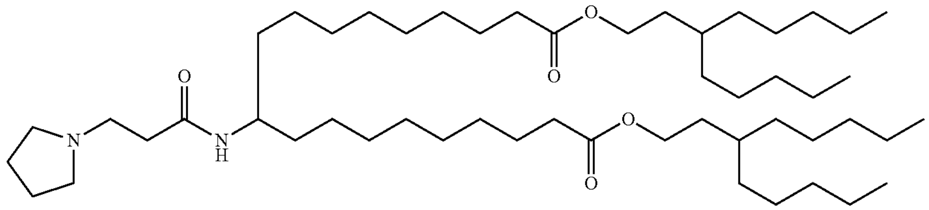 [SMILES: CCCCCC(CCCCC)CCOC(=O)CCCCCCCCC(CCCCCCCCC(=O)OCCC(CCCCC)CCCCC)NC(=O)CCN1CCCC1]

-continued
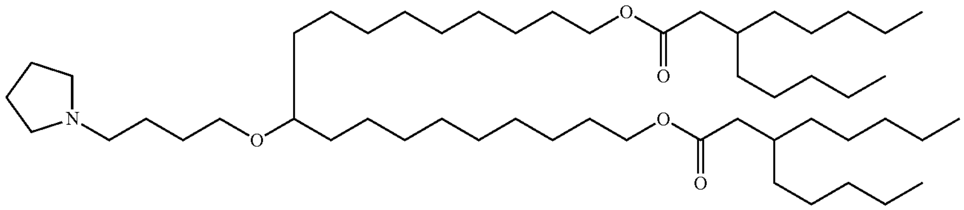 [SMILES: CCCCCC(CCCCC)CC(=O)OCCCCCCCCCC(CCCCCCCCCOC(=O)CC(CCCCC)CCCCC)OCCCCN1CCCC1]
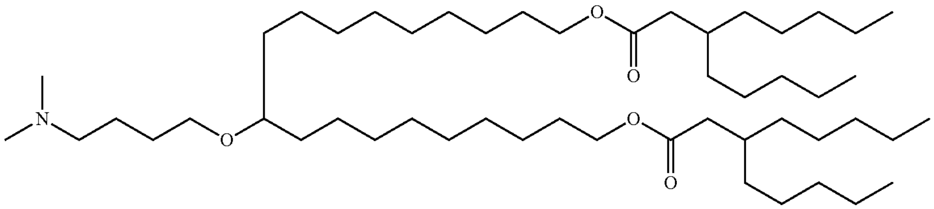 [SMILES: CCCCCC(CCCCC)CC(=O)OCCCCCCCCCC(CCCCCCCCCOC(=O)CC(CCCCC)CCCCC)OCCCCN(C)C]
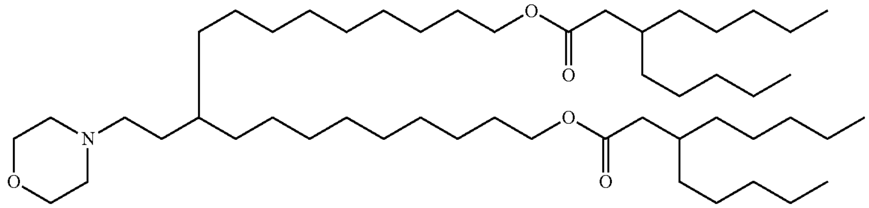 [SMILES: CCCCCC(CCCCC)CC(=O)OCCCCCCCCCC(CCCCCCCCCOC(=O)CC(CCCCC)CCCCC)CCN1CCOCC1]
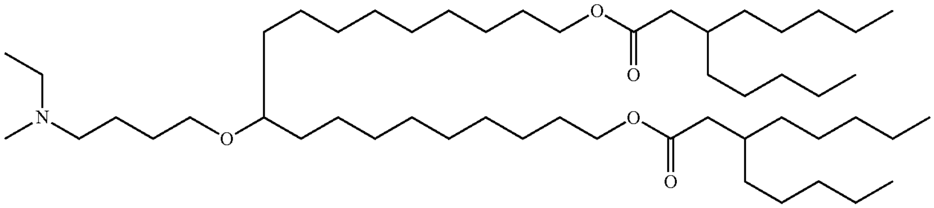 [SMILES: CCCCCC(CCCCC)CC(=O)OCCCCCCCCCC(CCCCCCCCCOC(=O)CC(CCCCC)CCCCC)OCCCCN(C)CC]
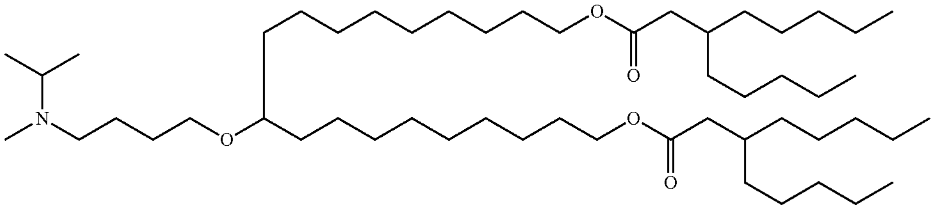 [SMILES: CCCCCC(CCCCC)CC(=O)OCCCCCCCCCC(CCCCCCCCCOC(=O)CC(CCCCC)CCCCC)OCCCCN(C)C(C)C]
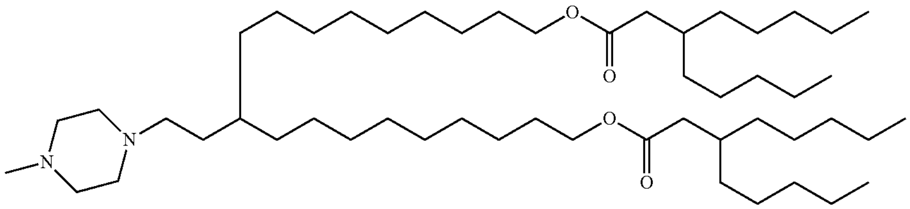 [SMILES: CCCCCC(CCCCC)CC(=O)OCCCCCCCCCC(CCCCCCCCCOC(=O)CC(CCCCC)CCCCC)CCN1CCN(C)CC1]
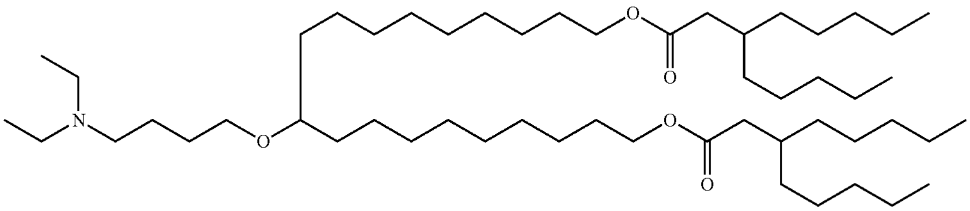 [SMILES: CCCCCC(CCCCC)CC(=O)OCCCCCCCCCC(CCCCCCCCCOC(=O)CC(CCCCC)CCCCC)OCCCCN(CC)CC]

-continued
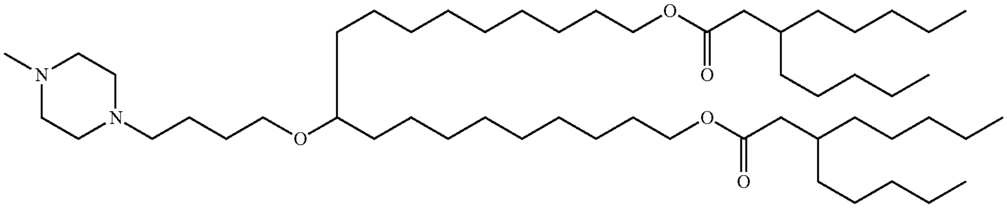 [SMILES: CCCCCC(CCCCC)CC(=O)OCCCCCCCCCC(CCCCCCCCCOC(=O)CC(CCCCC)CCCCC)OCCCCN1CCN(C)CC1]
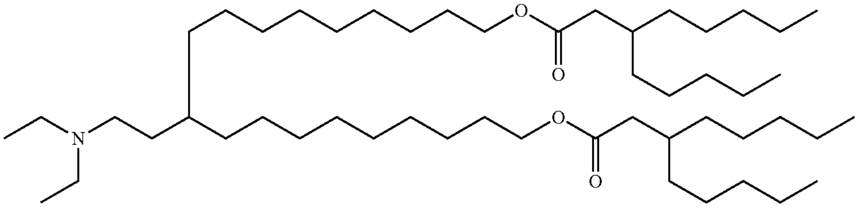 [SMILES: CCCCCC(CCCCC)CC(=O)OCCCCCCCCCC(CCCCCCCCCOC(=O)CC(CCCCC)CCCCC)CCN(CC)CC]
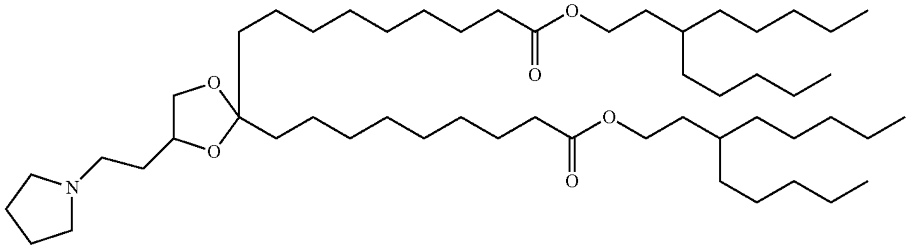 [SMILES: CCCCCC(CCCCC)CCOC(=O)CCCCCCCCC1(CCCCCCCCC(=O)OCCC(CCCCC)CCCCC)OCC(CCN2CCCC2)O1]
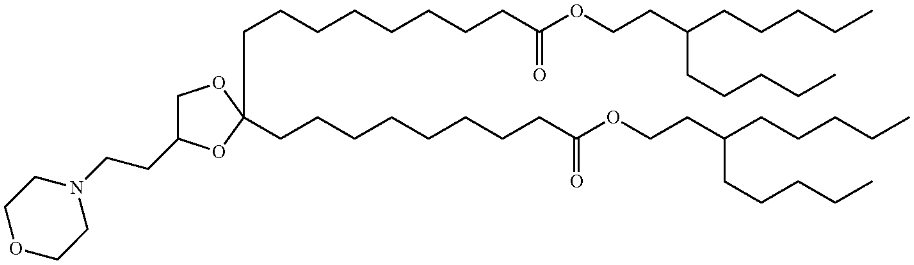 [SMILES: CCCCCC(CCCCC)CCOC(=O)CCCCCCCCC1(CCCCCCCCC(=O)OCCC(CCCCC)CCCCC)OCC(CCN2CCOCC2)O1]
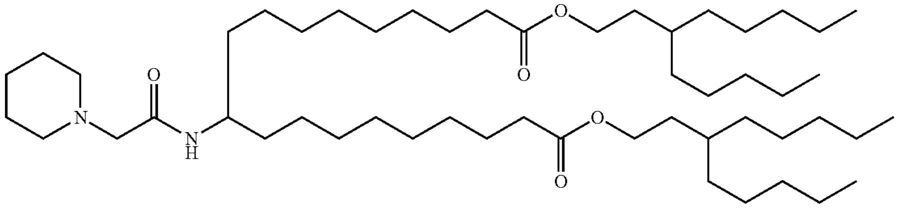 [SMILES: CCCCCC(CCCCC)CCOC(=O)CCCCCCCCC(CCCCCCCCC(=O)OCCC(CCCCC)CCCCC)NC(=O)CN1CCCCC1]
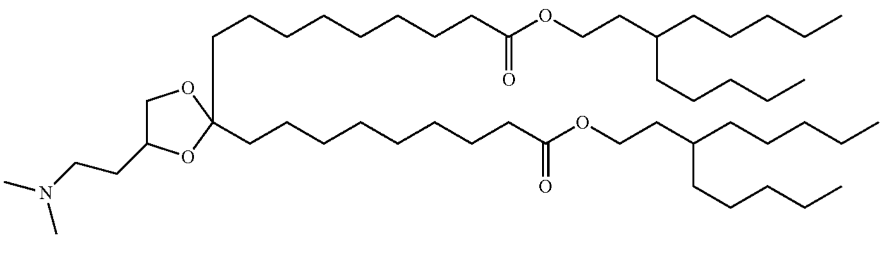 [SMILES: CCCCCC(CCCCC)CCOC(=O)CCCCCCCCC1(CCCCCCCCC(=O)OCCC(CCCCC)CCCCC)OCC(CCN(C)C)O1]

-continued
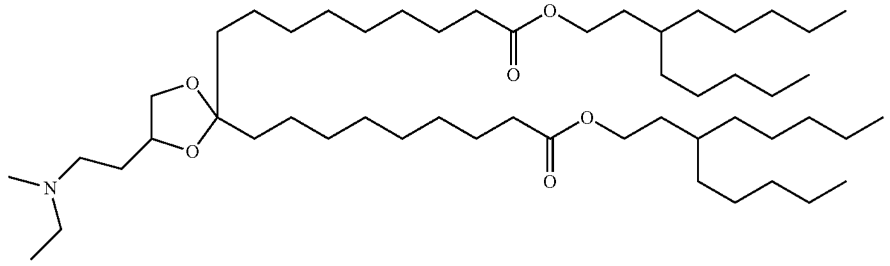 [SMILES: CCCCCC(CCCCC)CCOC(=O)CCCCCCCCC1(CCCCCCCCC(=O)OCCC(CCCCC)CCCCC)OCC(CCN(C)CC)O1]
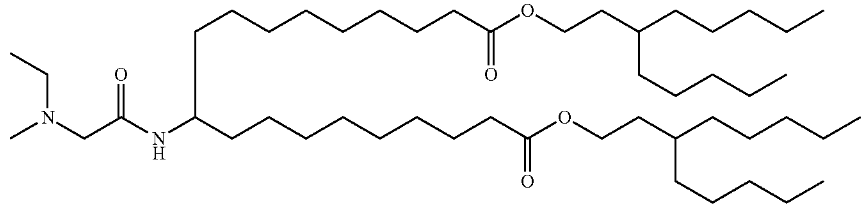 [SMILES: CCCCCC(CCCCC)CCOC(=O)CCCCCCCCC(CCCCCCCCC(=O)OCCC(CCCCC)CCCCC)NC(=O)CN(C)CC]
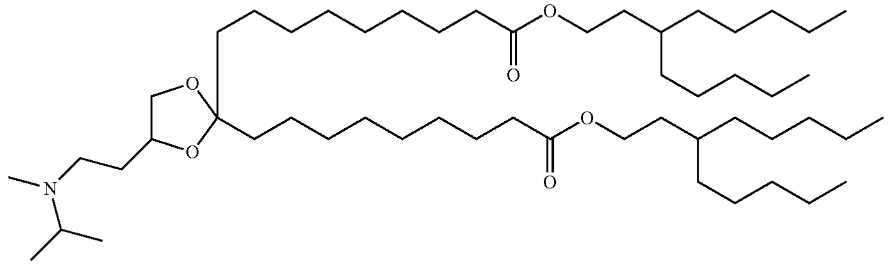 [SMILES: CCCCCC(CCCCC)CCOC(=O)CCCCCCCCC1(CCCCCCCCC(=O)OCCC(CCCCC)CCCCC)OCC(CCN(C)C(C)C)O1]
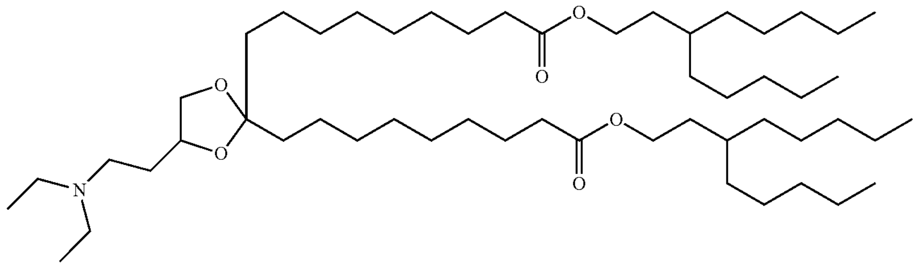 [SMILES: CCCCCC(CCCCC)CCOC(=O)CCCCCCCCC1(CCCCCCCCC(=O)OCCC(CCCCC)CCCCC)OCC(CCN(CC)CC)O1]
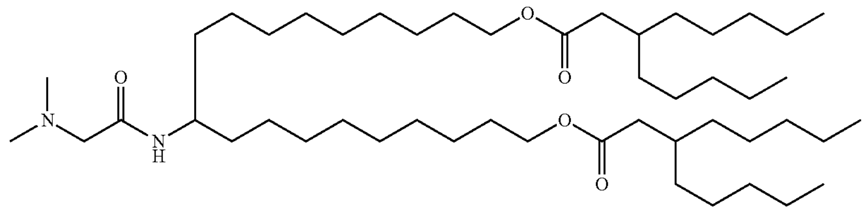 [SMILES: CCCCCC(CCCCC)CC(=O)OCCCCCCCCCC(CCCCCCCCCOC(=O)CC(CCCCC)CCCCC)NC(=O)CN(C)C]
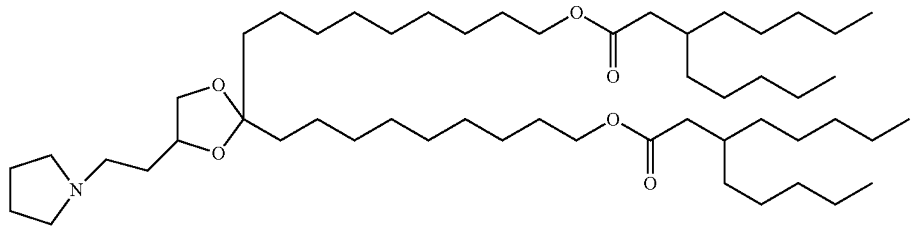 [SMILES: CCCCCC(CCCCC)CC(=O)OCCCCCCCCCC1(CCCCCCCCCOC(=O)CC(CCCCC)CCCCC)OCC(CCN2CCCC2)O1]

-continued
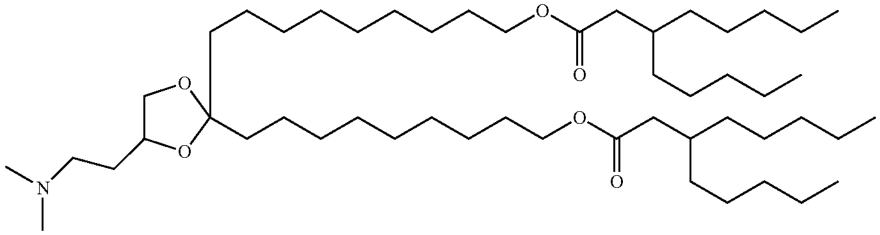 [SMILES: CCCCCC(CCCCC)CC(=O)OCCCCCCCCCC1(CCCCCCCCCOC(=O)CC(CCCCC)CCCCC)OCC(CCN(C)C)O1]
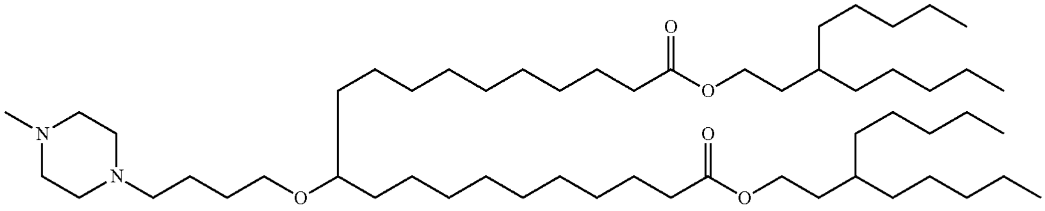 [SMILES: CCCCCC(CCCCC)CCOC(=O)CCCCCCCCCC(CCCCCCCCCC(=O)OCCC(CCCCC)CCCCC)OCCCCN1CCN(C)CC1]
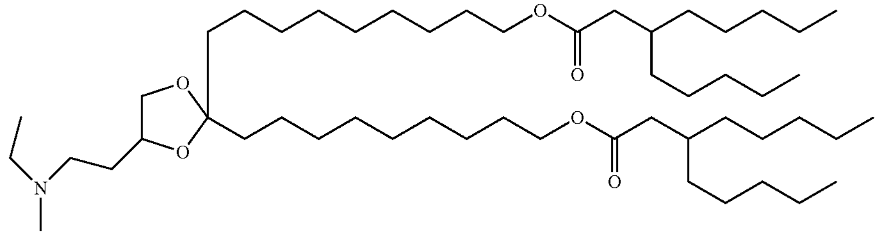 [SMILES: CCCCCC(CCCCC)CC(=O)OCCCCCCCCCC1(CCCCCCCCCOC(=O)CC(CCCCC)CCCCC)OCC(CCN(C)CC)O1]
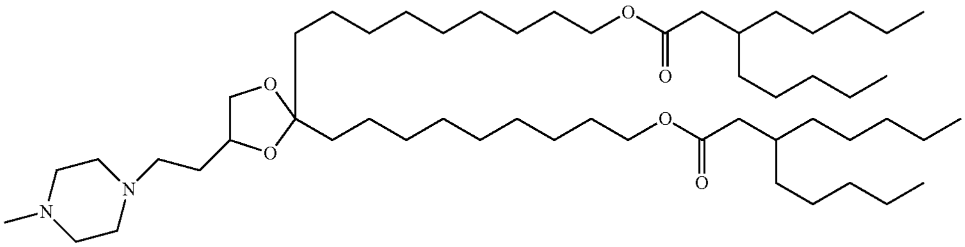 [SMILES: CCCCCC(CCCCC)CC(=O)OCCCCCCCCCC1(CCCCCCCCCOC(=O)CC(CCCCC)CCCCC)OCC(CCN2CCN(C)CC2)O1]
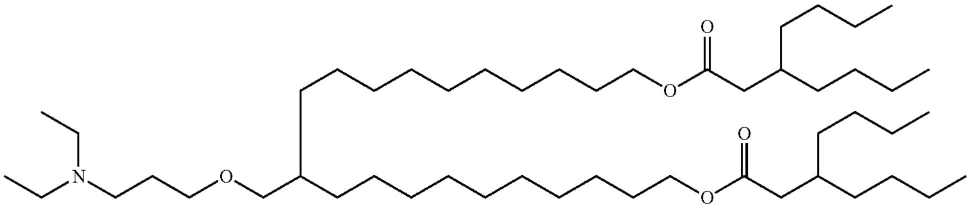 [SMILES: CCCCC(CCCC)CC(=O)OCCCCCCCCCCC(CCCCCCCCCCOC(=O)CC(CCCC)CCCC)COCCCN(CC)CC]
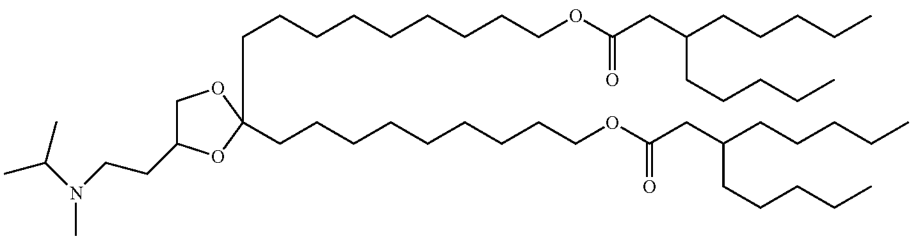 [SMILES: CCCCCC(CCCCC)CC(=O)OCCCCCCCCCC1(CCCCCCCCCOC(=O)CC(CCCCC)CCCCC)OCC(CCN(C)C(C)C)O1]

-continued
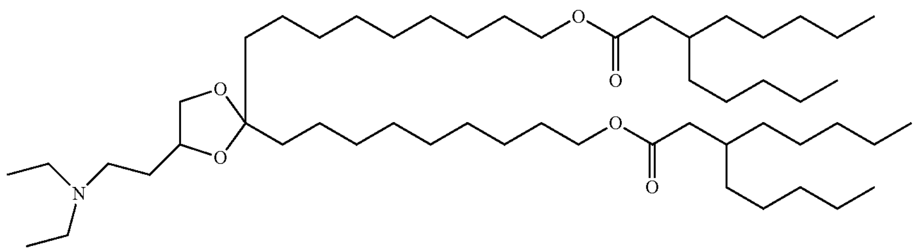 [SMILES: CCCCCC(CCCCC)CC(=O)OCCCCCCCCCC1(CCCCCCCCCOC(=O)CC(CCCCC)CCCCC)OCC(CCN(CC)CC)O1]
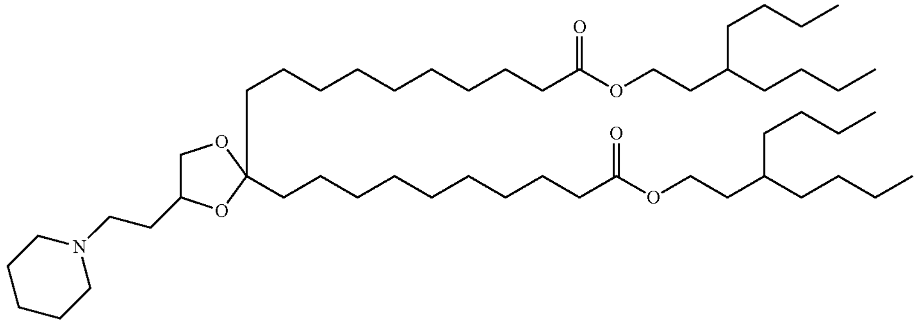 [SMILES: CCCCC(CCCC)CCOC(=O)CCCCCCCCCC1(CCCCCCCCCC(=O)OCCC(CCCC)CCCC)OCC(CCN2CCCCC2)O1]
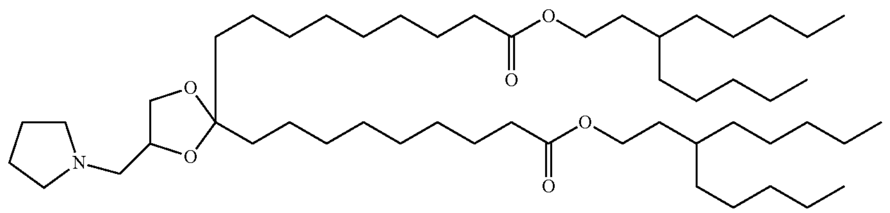 [SMILES: CCCCCC(CCCCC)CCOC(=O)CCCCCCCCC1(CCCCCCCCC(=O)OCCC(CCCCC)CCCCC)OCC(CN2CCCC2)O1]
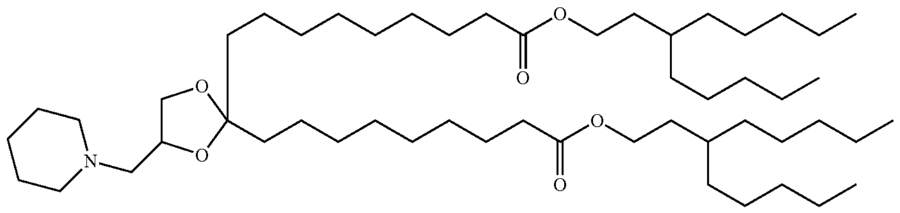 [SMILES: CCCCCC(CCCCC)CCOC(=O)CCCCCCCCC1(CCCCCCCCC(=O)OCCC(CCCCC)CCCCC)OCC(CN2CCCCC2)O1]
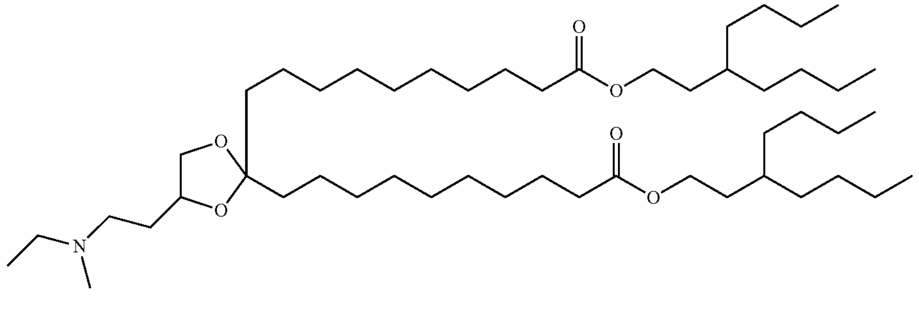 [SMILES: CCCCC(CCCC)CCOC(=O)CCCCCCCCCC1(CCCCCCCCCC(=O)OCCC(CCCC)CCCC)OCC(CCN(C)CC)O1]
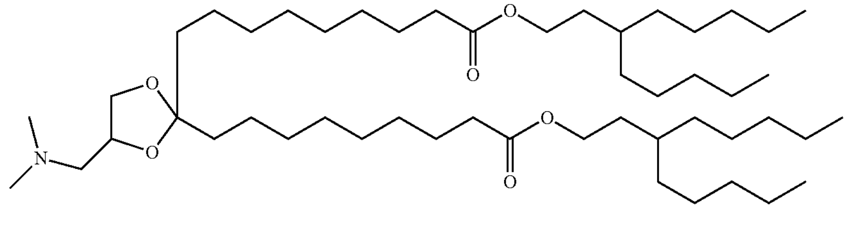 [SMILES: CCCCCC(CCCCC)CCOC(=O)CCCCCCCCC1(CCCCCCCCC(=O)OCCC(CCCCC)CCCCC)OCC(CN(C)C)O1]

-continued
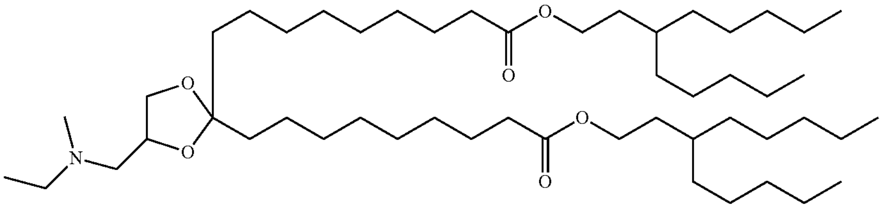 [SMILES: CCCCCC(CCCCC)CCOC(=O)CCCCCCCCC1(CCCCCCCCC(=O)OCCC(CCCCC)CCCCC)OCC(CN(C)CC)O1]
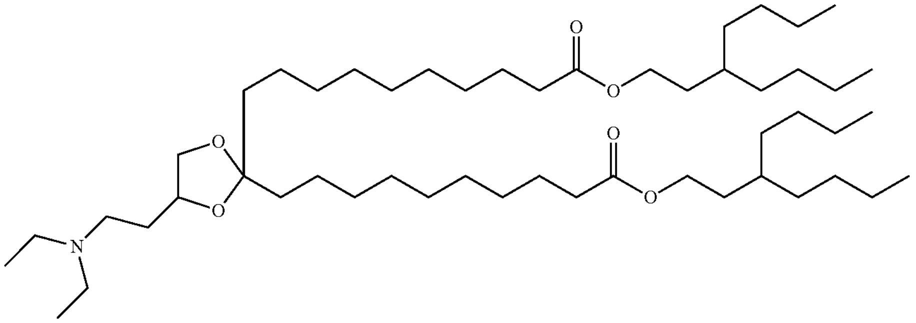 [SMILES: CCCCC(CCCC)CCOC(=O)CCCCCCCCCC1(CCCCCCCCCC(=O)OCCC(CCCC)CCCC)OCC(CCN(CC)CC)O1]
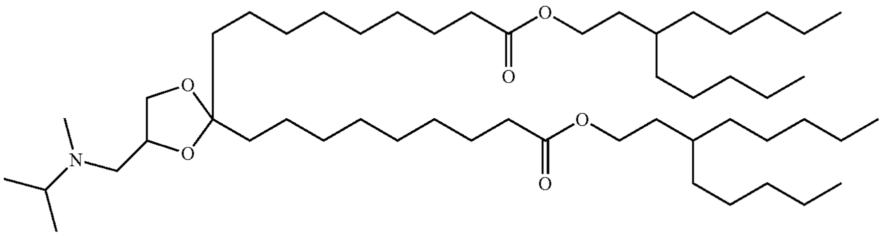 [SMILES: CCCCCC(CCCCC)CCOC(=O)CCCCCCCCC1(CCCCCCCCC(=O)OCCC(CCCCC)CCCCC)OCC(CN(C)C(C)C)O1]
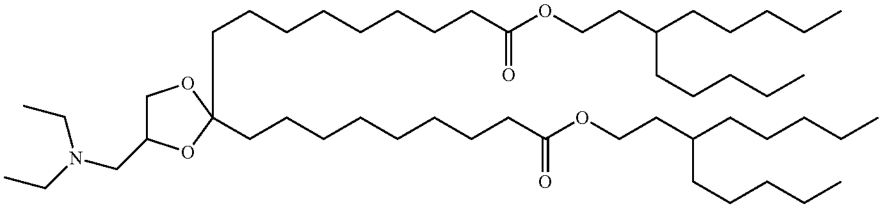 [SMILES: CCCCCC(CCCCC)CCOC(=O)CCCCCCCCC1(CCCCCCCCC(=O)OCCC(CCCCC)CCCCC)OCC(CN(CC)CC)O1]
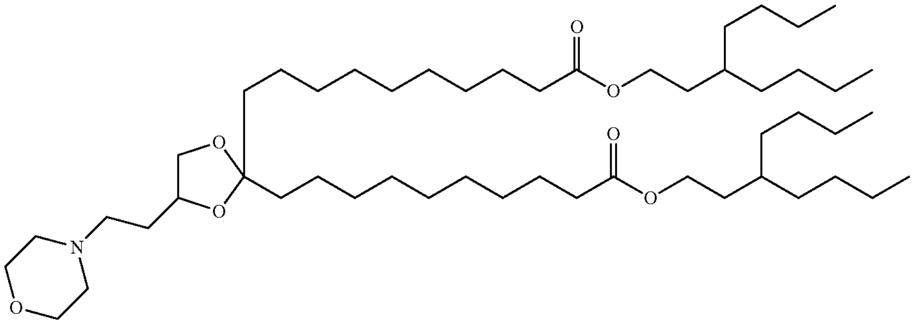 [SMILES: CCCCC(CCCC)CCOC(=O)CCCCCCCCCC1(CCCCCCCCCC(=O)OCCC(CCCC)CCCC)OCC(CCN2CCOCC2)O1]
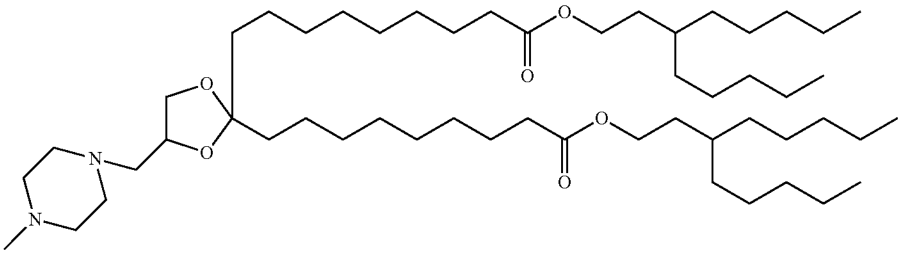 [SMILES: CCCCCC(CCCCC)CCOC(=O)CCCCCCCCC1(CCCCCCCCC(=O)OCCC(CCCCC)CCCCC)OCC(CN2CCN(C)CC2)O1]

-continued
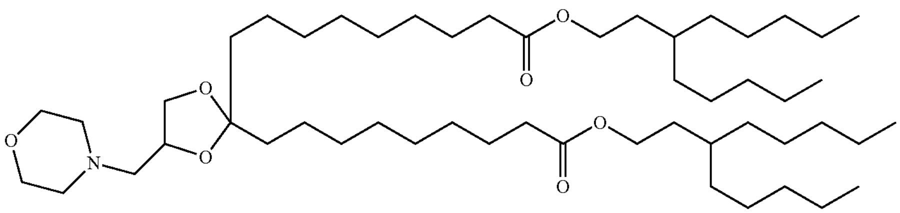 [SMILES: CCCCCC(CCCCC)CCOC(=O)CCCCCCCCC1(CCCCCCCCC(=O)OCCC(CCCCC)CCCCC)OCC(CN2CCOCC2)O1]
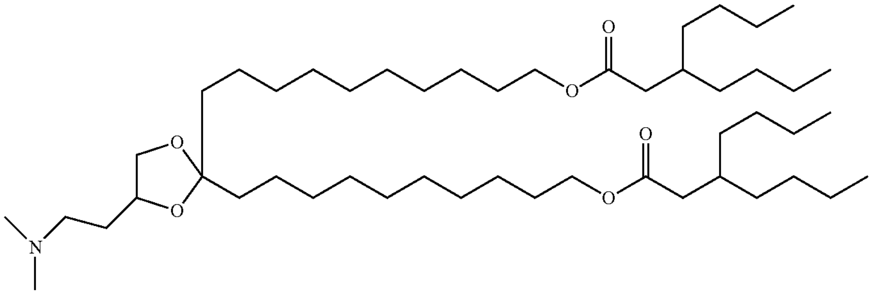 [SMILES: CCCCC(CCCC)CC(=O)OCCCCCCCCCCC1(CCCCCCCCCCOC(=O)CC(CCCC)CCCC)OCC(CCN(C)C)O1]
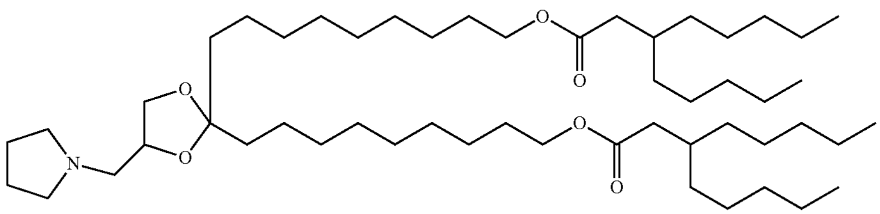 [SMILES: CCCCCC(CCCCC)CC(=O)OCCCCCCCCCC1(CCCCCCCCCOC(=O)CC(CCCCC)CCCCC)OCC(CN2CCCC2)O1]
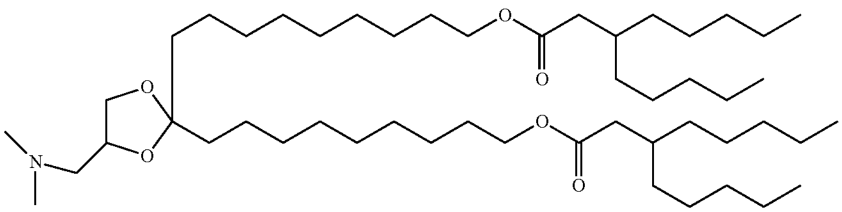 [SMILES: CCCCCC(CCCCC)CC(=O)OCCCCCCCCCC1(CCCCCCCCCOC(=O)CC(CCCCC)CCCCC)OCC(CN(C)C)O1]
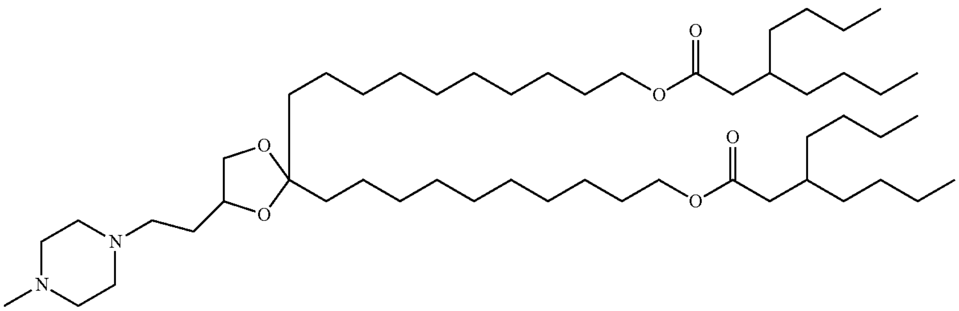 [SMILES: CCCCC(CCCC)CC(=O)OCCCCCCCCCCC1(CCCCCCCCCCOC(=O)CC(CCCC)CCCC)OCC(CCN2CCN(C)CC2)O1]
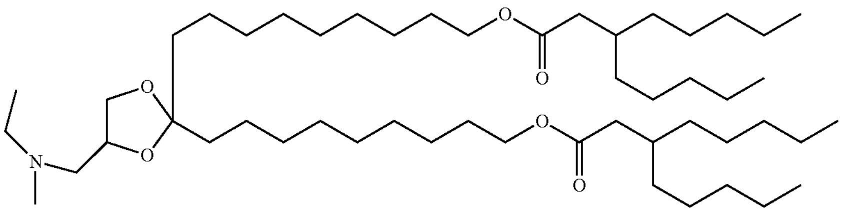 [SMILES: CCCCCC(CCCCC)CC(=O)OCCCCCCCCCC1(CCCCCCCCCOC(=O)CC(CCCCC)CCCCC)OCC(CN(C)CC)O1]

-continued
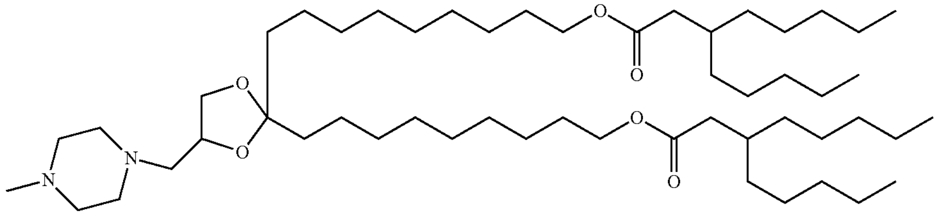 [SMILES: CCCCCC(CCCCC)CC(=O)OCCCCCCCCCC1(CCCCCCCCCOC(=O)CC(CCCCC)CCCCC)OCC(CN2CCN(C)CC2)O1]
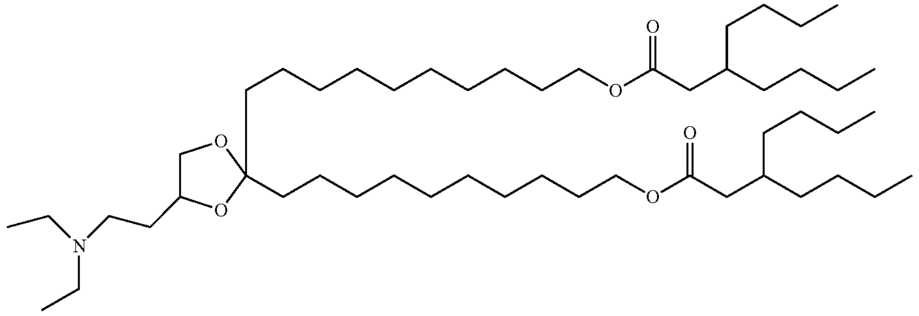 [SMILES: CCCCC(CCCC)CC(=O)OCCCCCCCCCCC1(CCCCCCCCCCOC(=O)CC(CCCC)CCCC)OCC(CCN(CC)CC)O1]
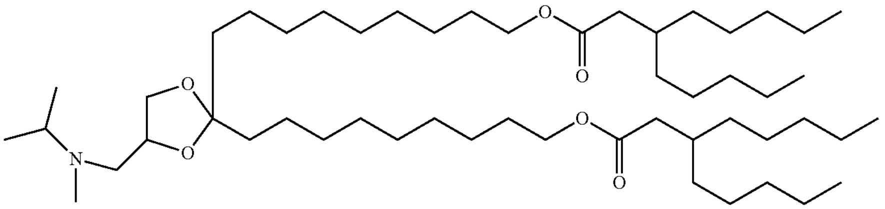 [SMILES: CCCCCC(CCCCC)CC(=O)OCCCCCCCCCC1(CCCCCCCCCOC(=O)CC(CCCCC)CCCCC)OCC(CN(C)C(C)C)O1]
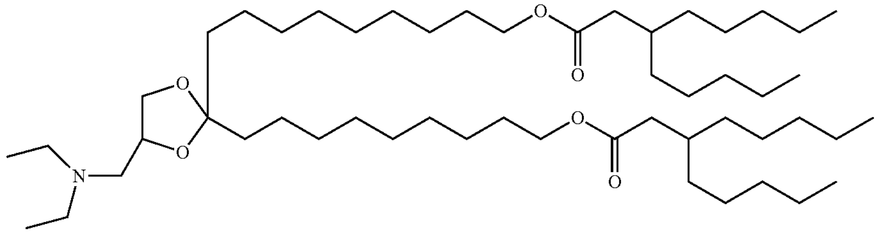 [SMILES: CCCCCC(CCCCC)CC(=O)OCCCCCCCCCC1(CCCCCCCCCOC(=O)CC(CCCCC)CCCCC)OCC(CN(CC)CC)O1]
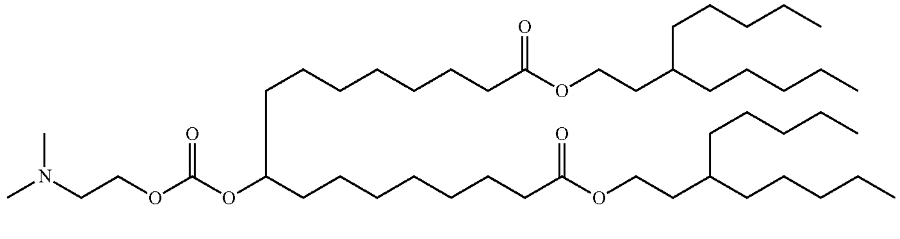
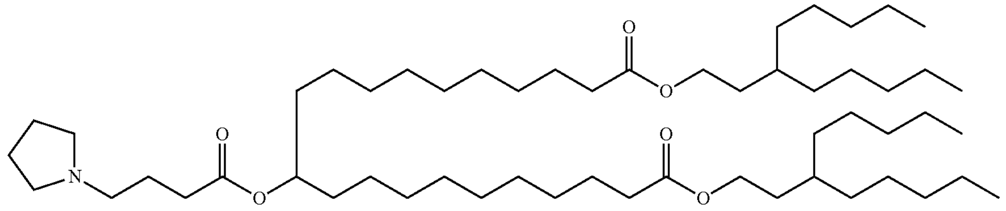 [SMILES: CCCCCC(CCCCC)CCOC(=O)CCCCCCCCCC(CCCCCCCCCC(=O)OCCC(CCCCC)CCCCC)OC(=O)CCCN1CCCC1]

-continued
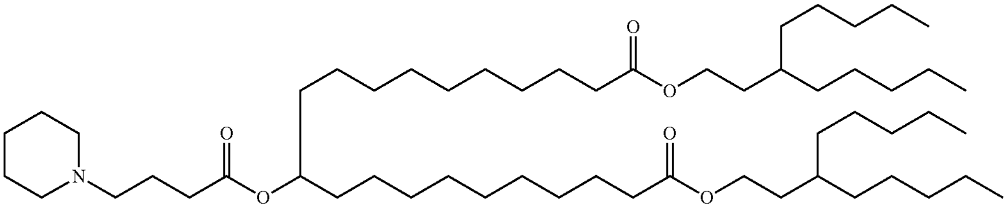 [SMILES: CCCCCC(CCCCC)CCOC(=O)CCCCCCCCCC(CCCCCCCCCC(=O)OCCC(CCCCC)CCCCC)OC(=O)CCCN1CCCCC1]
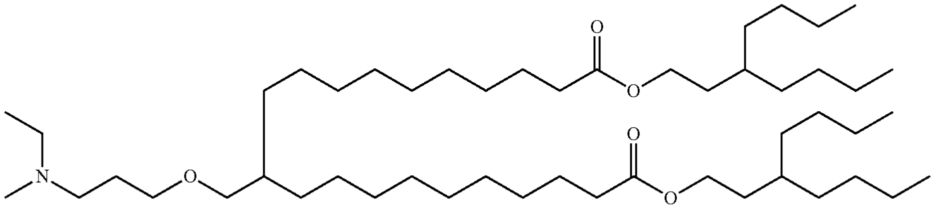 [SMILES: CCCCC(CCCC)CCOC(=O)CCCCCCCCCC(CCCCCCCCCC(=O)OCCC(CCCC)CCCC)COCCCN(C)CC]
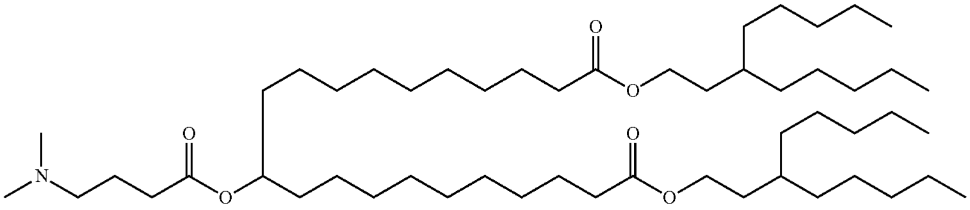 [SMILES: CCCCCC(CCCCC)CCOC(=O)CCCCCCCCCC(CCCCCCCCCC(=O)OCCC(CCCCC)CCCCC)OC(=O)CCCN(C)C]
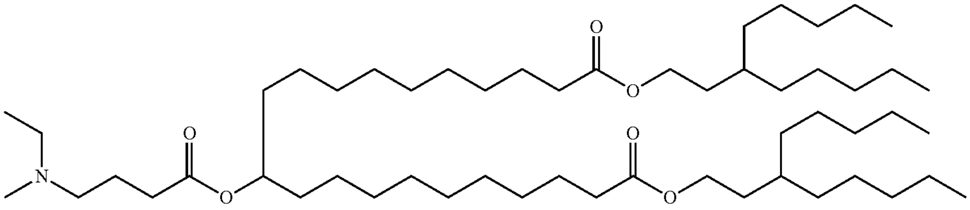 [SMILES: CCCCCC(CCCCC)CCOC(=O)CCCCCCCCCC(CCCCCCCCCC(=O)OCCC(CCCCC)CCCCC)OC(=O)CCCN(C)CC]
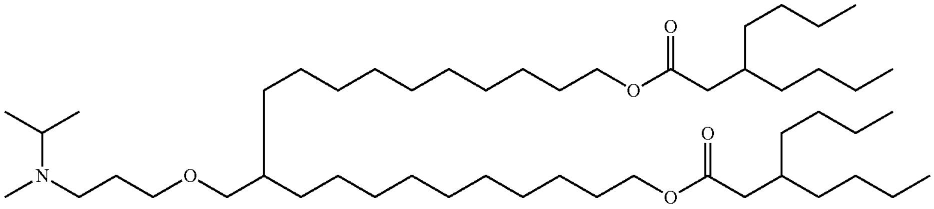 [SMILES: CCCCC(CCCC)CC(=O)OCCCCCCCCCCC(CCCCCCCCCCOC(=O)CC(CCCC)CCCC)COCCCN(C)C(C)C]
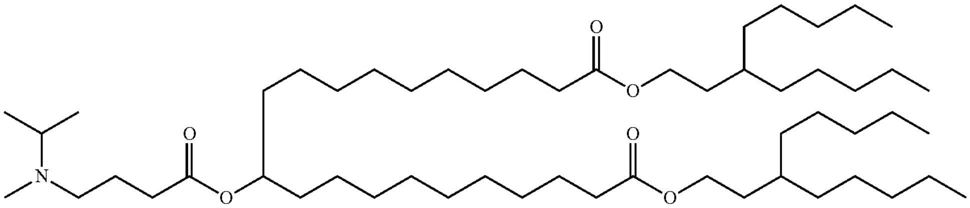 [SMILES: CCCCCC(CCCCC)CCOC(=O)CCCCCCCCCC(CCCCCCCCCC(=O)OCCC(CCCCC)CCCCC)OC(=O)CCCN(C)C(C)C]
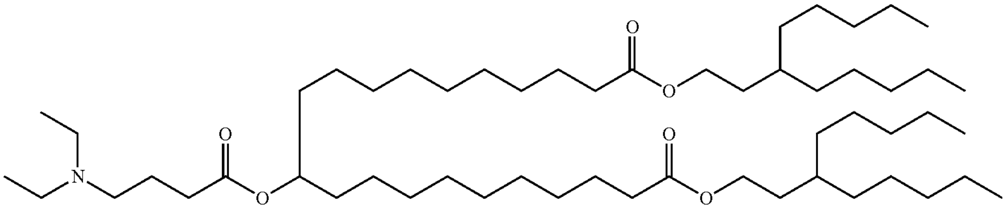 [SMILES: CCCCCC(CCCCC)CCOC(=O)CCCCCCCCCC(CCCCCCCCCC(=O)OCCC(CCCCC)CCCCC)OC(=O)CCCN(CC)CC]

-continued
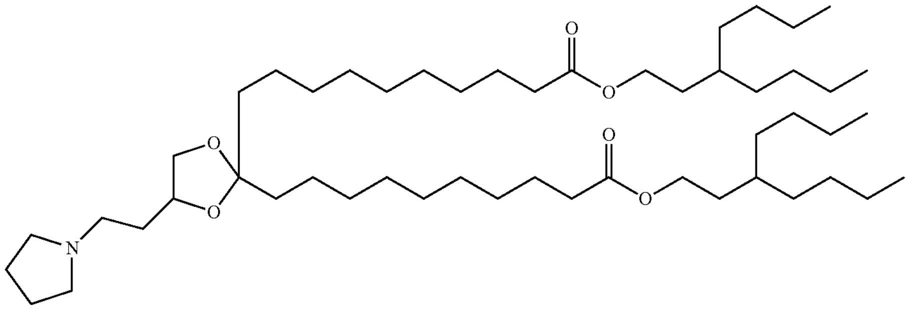 [SMILES: CCCCC(CCCC)CCOC(=O)CCCCCCCCCC1(CCCCCCCCCC(=O)OCCC(CCCC)CCCC)OCC(CCN2CCCC2)O1]
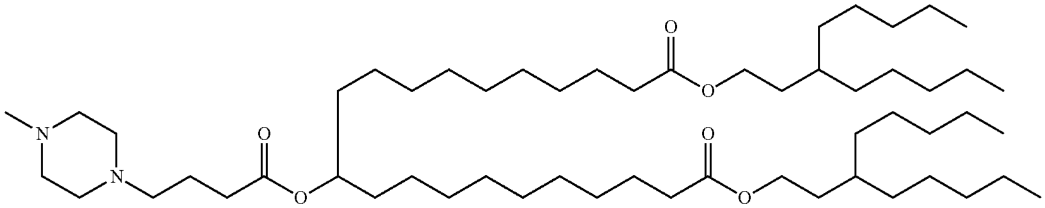 [SMILES: CCCCCC(CCCCC)CCOC(=O)CCCCCCCCCC(CCCCCCCCCC(=O)OCCC(CCCCC)CCCCC)OC(=O)CCCN1CCN(C)CC1]
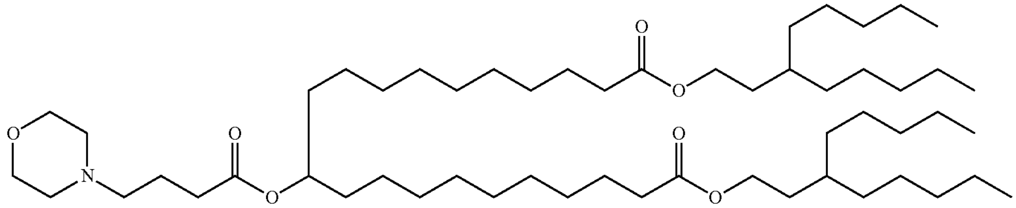 [SMILES: CCCCCC(CCCCC)CCOC(=O)CCCCCCCCCC(CCCCCCCCCC(=O)OCCC(CCCCC)CCCCC)OC(=O)CCCN1CCOCC1]
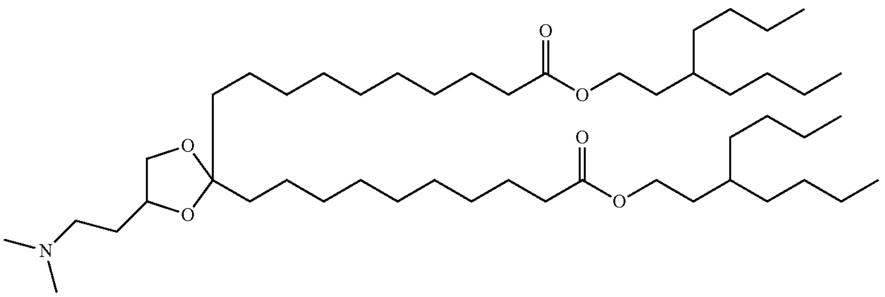 [SMILES: CCCCC(CCCC)CCOC(=O)CCCCCCCCCC1(CCCCCCCCCC(=O)OCCC(CCCC)CCCC)OCC(CCN(C)C)O1]
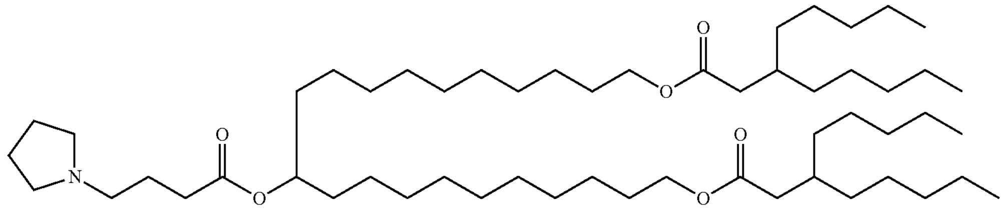 [SMILES: CCCCCC(CCCCC)CC(=O)OCCCCCCCCCCC(CCCCCCCCCCOC(=O)CC(CCCCC)CCCCC)OC(=O)CCCN1CCCC1]
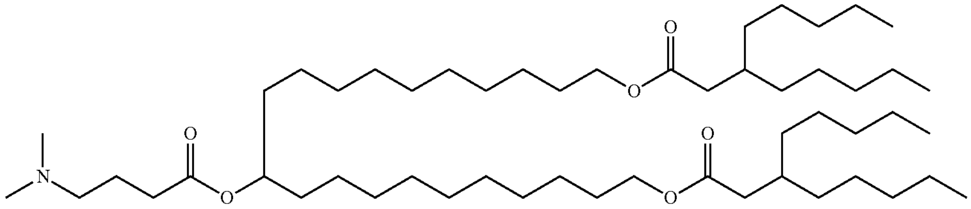 [SMILES: CCCCCC(CCCCC)CC(=O)OCCCCCCCCCCC(CCCCCCCCCCOC(=O)CC(CCCCC)CCCCC)OC(=O)CCCN(C)C]

-continued
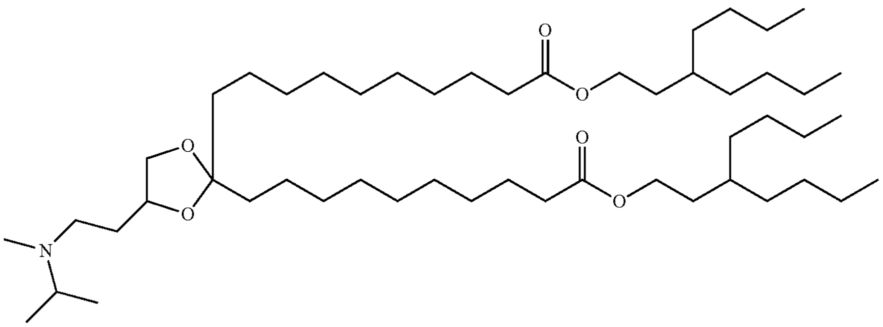 [SMILES: CCCCC(CCCC)CCOC(=O)CCCCCCCCCC1(CCCCCCCCCC(=O)OCCC(CCCC)CCCC)OCC(CCN(C)C(C)C)O1]
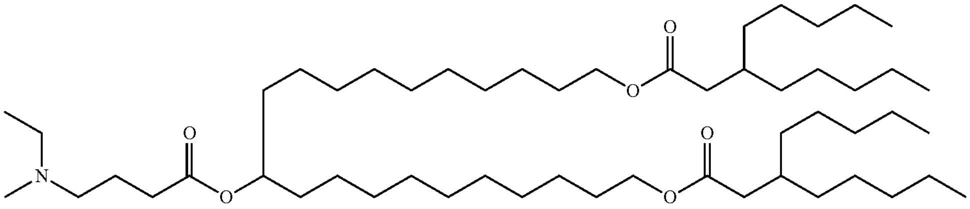 [SMILES: CCCCCC(CCCCC)CC(=O)OCCCCCCCCCCC(CCCCCCCCCCOC(=O)CC(CCCCC)CCCCC)OC(=O)CCCN(C)CC]
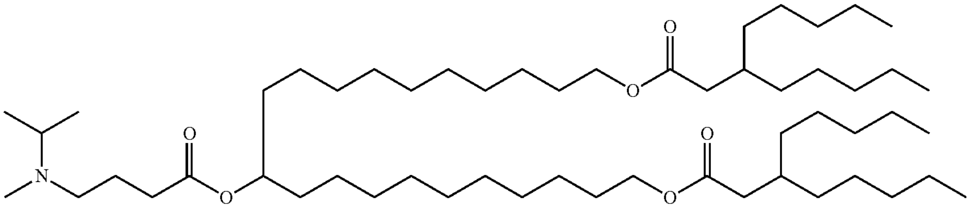 [SMILES: CCCCCC(CCCCC)CC(=O)OCCCCCCCCCCC(CCCCCCCCCCOC(=O)CC(CCCCC)CCCCC)OC(=O)CCCN(C)C(C)C]
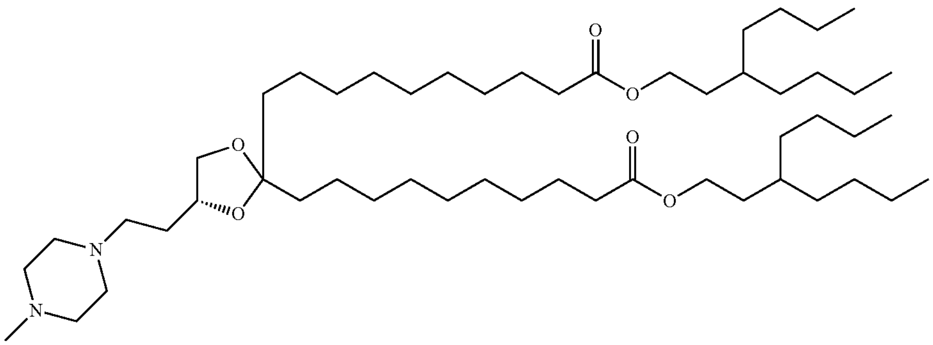 [SMILES: CCCCC(CCCC)CCOC(=O)CCCCCCCCCC1(CCCCCCCCCC(=O)OCCC(CCCC)CCCC)OC[C@@H](CCN2CCN(C)CC2)O1]
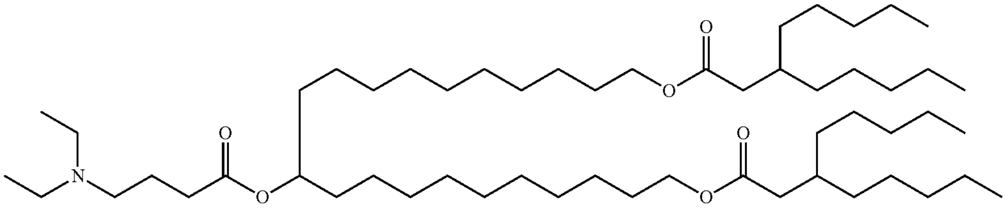 [SMILES: CCCCCC(CCCCC)CC(=O)OCCCCCCCCCCC(CCCCCCCCCCOC(=O)CC(CCCCC)CCCCC)OC(=O)CCCN(CC)CC]
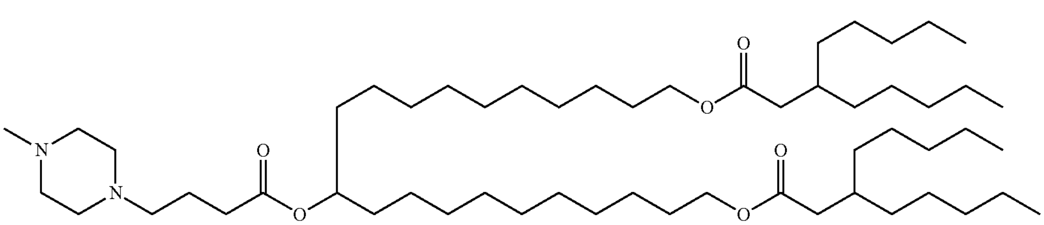 [SMILES: CCCCCC(CCCCC)CC(=O)OCCCCCCCCCCC(CCCCCCCCCCOC(=O)CC(CCCCC)CCCCC)OC(=O)CCCN1CCN(C)CC1]

-continued
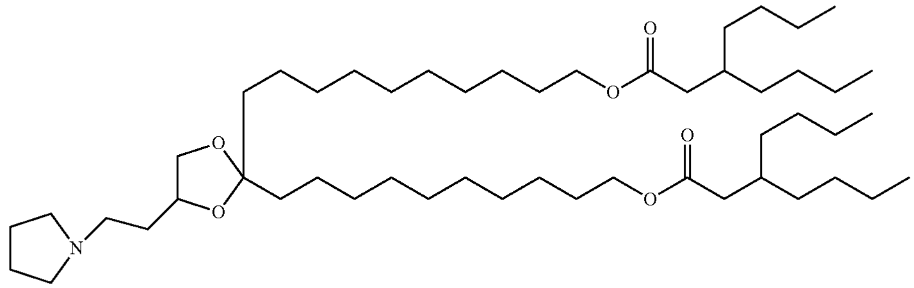 [SMILES: CCCCC(CCCC)CC(=O)OCCCCCCCCCCC1(CCCCCCCCCCOC(=O)CC(CCCC)CCCC)OCC(CCN2CCCC2)O1]
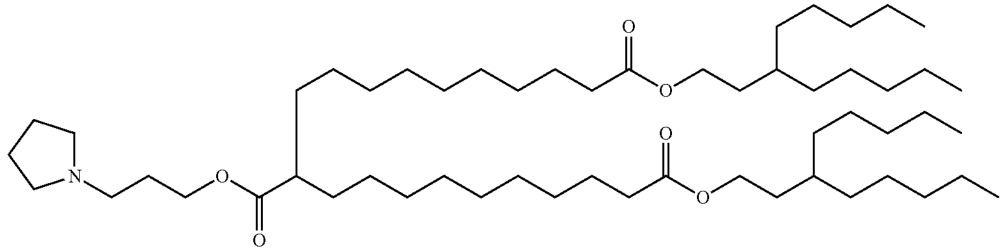 [SMILES: CCCCCC(CCCCC)CCOC(=O)CCCCCCCCCC(CCCCCCCCCC(=O)OCCC(CCCCC)CCCCC)C(=O)OCCCN1CCCC1]
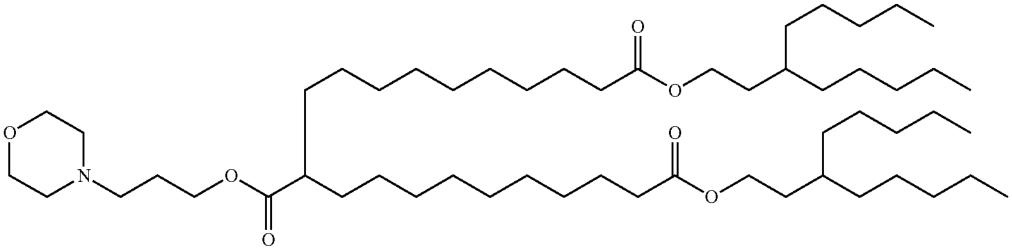 [SMILES: CCCCCC(CCCCC)CCOC(=O)CCCCCCCCCC(CCCCCCCCCC(=O)OCCC(CCCCC)CCCCC)C(=O)OCCCN1CCOCC1]
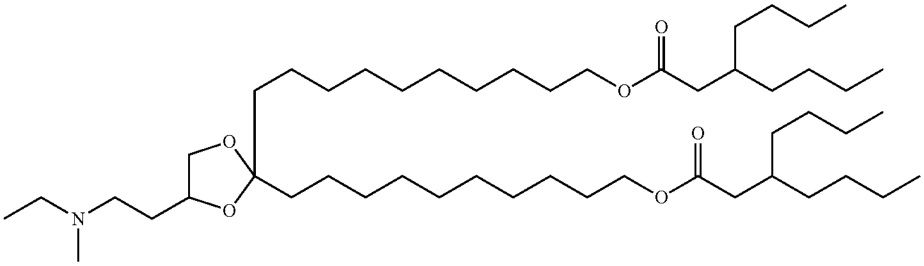 [SMILES: CCCCC(CCCC)CC(=O)OCCCCCCCCCCC1(CCCCCCCCCCOC(=O)CC(CCCC)CCCC)OCC(CCN(C)CC)O1]
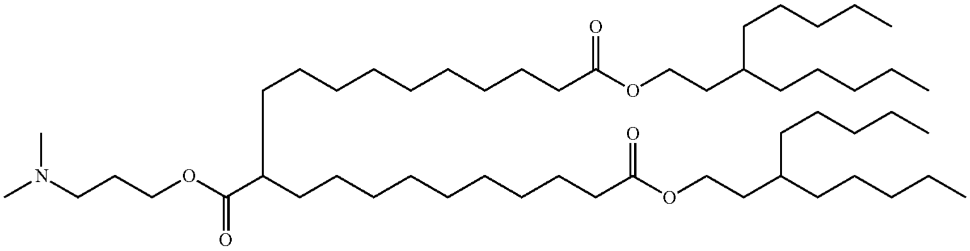 [SMILES: CCCCCC(CCCCC)CCOC(=O)CCCCCCCCCC(CCCCCCCCCC(=O)OCCC(CCCCC)CCCCC)C(=O)OCCCN(C)C]
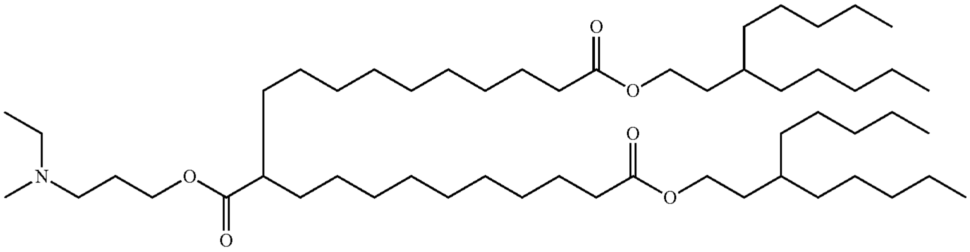 [SMILES: CCCCCC(CCCCC)CCOC(=O)CCCCCCCCCC(CCCCCCCCCC(=O)OCCC(CCCCC)CCCCC)C(=O)OCCCN(C)CC]

-continued
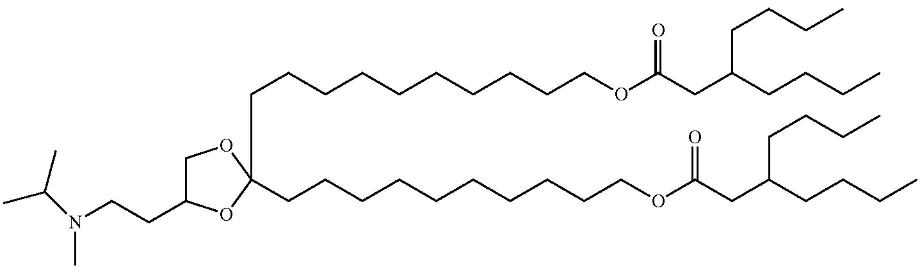 [SMILES: CCCCC(CCCC)CC(=O)OCCCCCCCCCCC1(CCCCCCCCCCOC(=O)CC(CCCC)CCCC)OCC(CCN(C)C(C)C)O1]
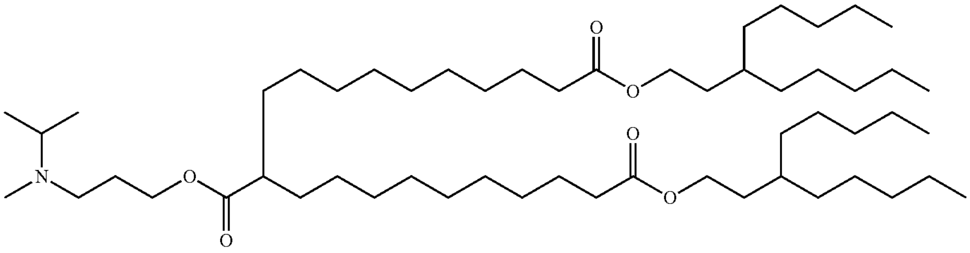 [SMILES: CCCCCC(CCCCC)CCOC(=O)CCCCCCCCCC(CCCCCCCCCC(=O)OCCC(CCCCC)CCCCC)C(=O)OCCCN(C)C(C)C]
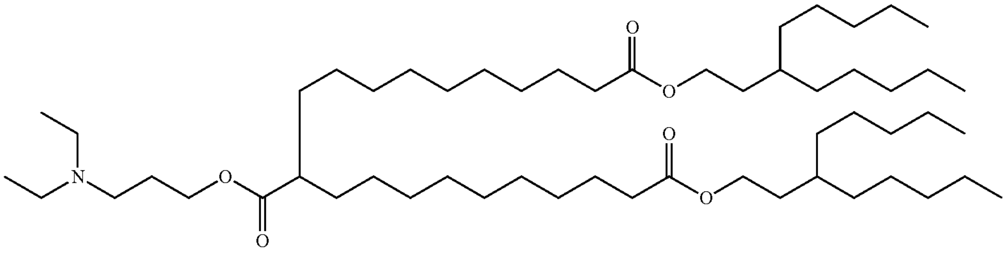 [SMILES: CCCCCC(CCCCC)CCOC(=O)CCCCCCCCCC(CCCCCCCCCC(=O)OCCC(CCCCC)CCCCC)C(=O)OCCCN(CC)CC]
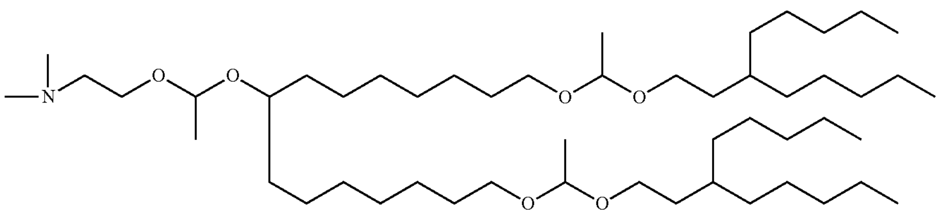 [SMILES: CCCCCC(CCCCC)CCOC(C)OCCCCCCCC(CCCCCCCOC(C)OCCC(CCCCC)CCCCC)OC(C)OCCN(C)C]
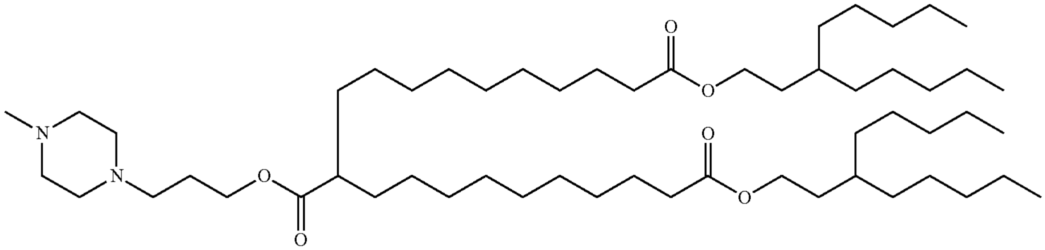 [SMILES: CCCCCC(CCCCC)CCOC(=O)CCCCCCCCCC(CCCCCCCCCC(=O)OCCC(CCCCC)CCCCC)C(=O)OCCCN1CCN(C)CC1]
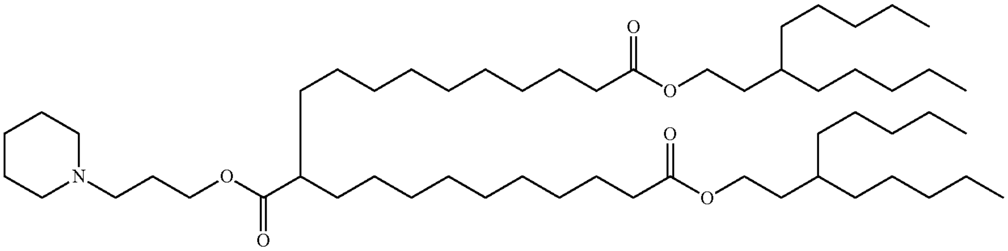 [SMILES: CCCCCC(CCCCC)CCOC(=O)CCCCCCCCCC(CCCCCCCCCC(=O)OCCC(CCCCC)CCCCC)C(=O)OCCCN1CCCCC1]

-continued
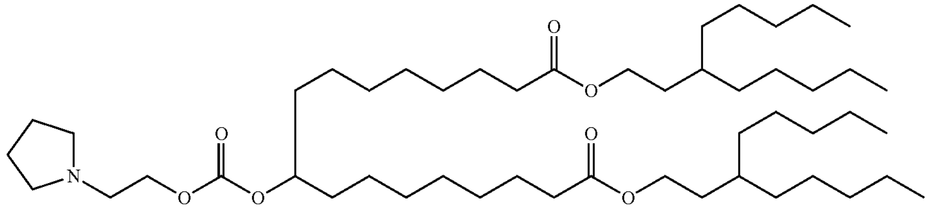
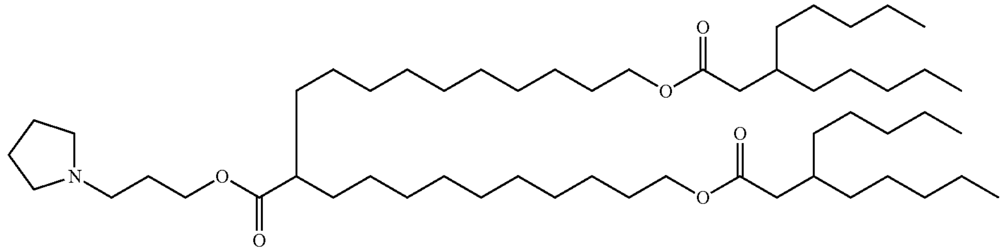 [SMILES: CCCCCC(CCCCC)CC(=O)OCCCCCCCCCCC(CCCCCCCCCCOC(=O)CC(CCCCC)CCCCC)C(=O)OCCCN1CCCC1]
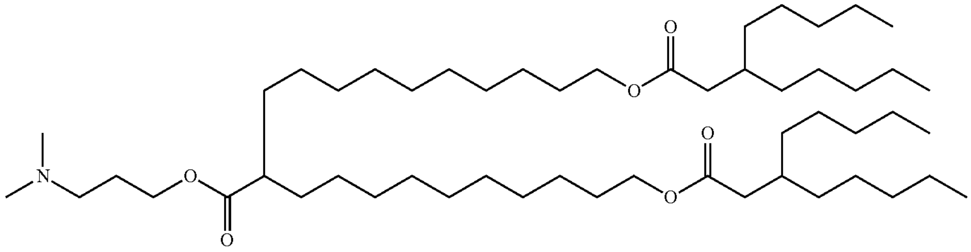 [SMILES: CCCCCC(CCCCC)CC(=O)OCCCCCCCCCCC(CCCCCCCCCCOC(=O)CC(CCCCC)CCCCC)C(=O)OCCCN(C)C]
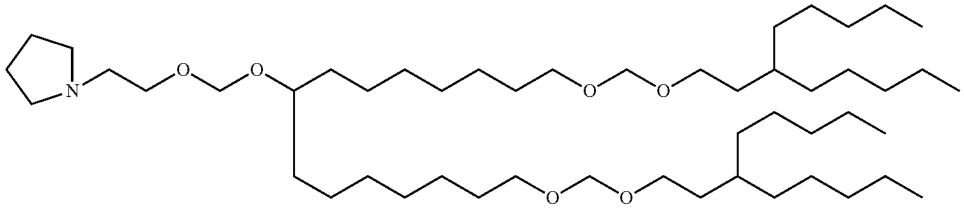 [SMILES: CCCCCC(CCCCC)CCOCOCCCCCCCC(CCCCCCCOCOCCC(CCCCC)CCCCC)OCOCCN1CCCC1]
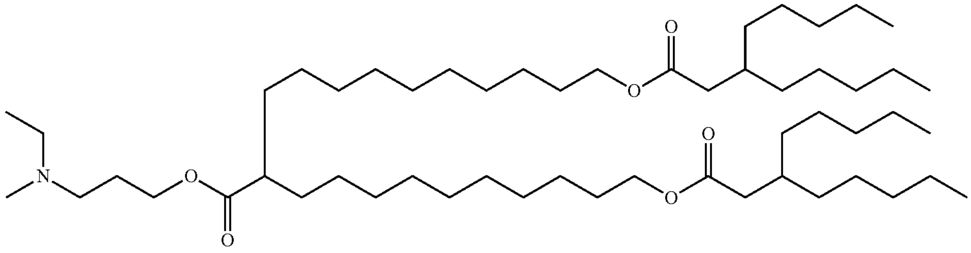 [SMILES: CCCCCC(CCCCC)CC(=O)OCCCCCCCCCCC(CCCCCCCCCCOC(=O)CC(CCCCC)CCCCC)C(=O)OCCCN(C)CC]
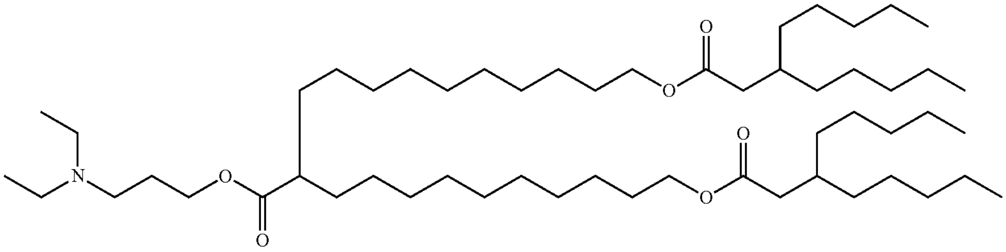 [SMILES: CCCCCC(CCCCC)CC(=O)OCCCCCCCCCCC(CCCCCCCCCCOC(=O)CC(CCCCC)CCCCC)C(=O)OCCCN(CC)CC]

-continued
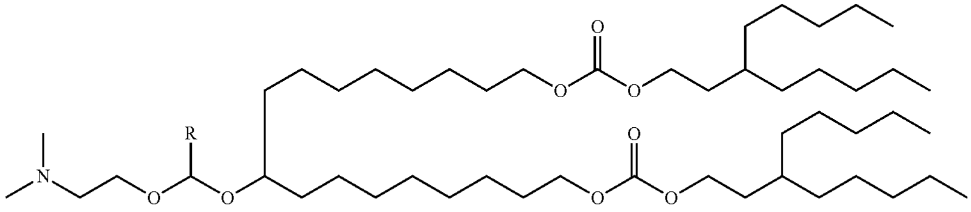
R = H, Me
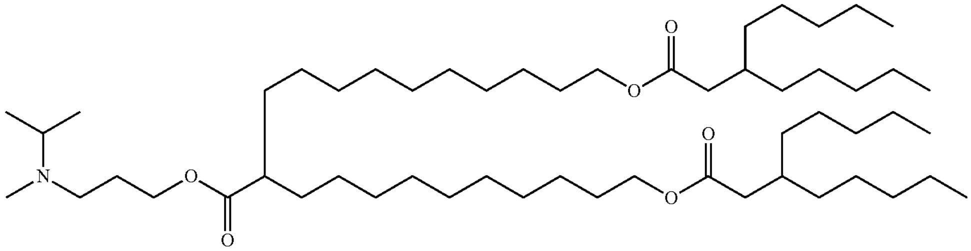 [SMILES: CCCCCC(CCCCC)CC(=O)OCCCCCCCCCCC(CCCCCCCCCCOC(=O)CC(CCCCC)CCCCC)C(=O)OCCCN(C)C(C)C]
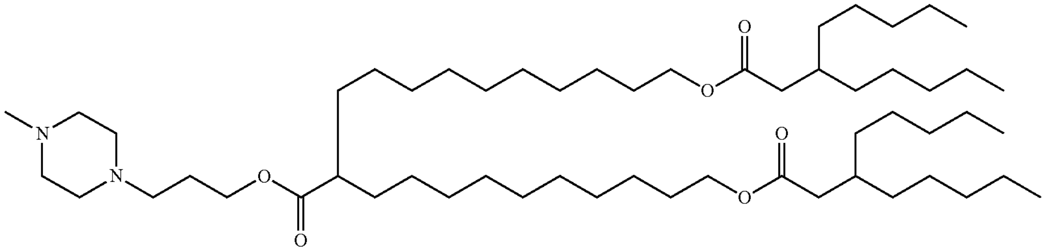 [SMILES: CCCCCC(CCCCC)CC(=O)OCCCCCCCCCCC(CCCCCCCCCCOC(=O)CC(CCCCC)CCCCC)C(=O)OCCCN1CCN(C)CC1]
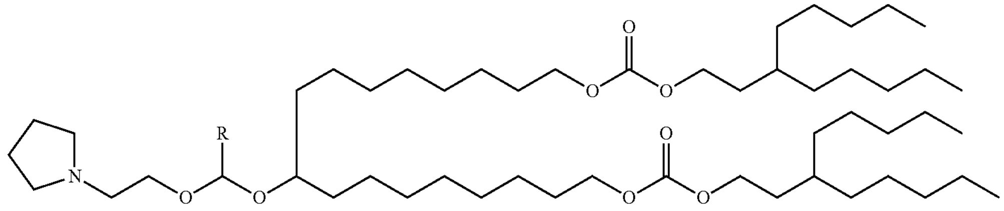
R = H, Me
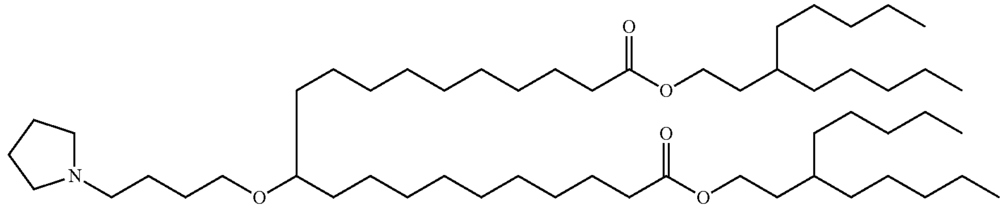 [SMILES: CCCCCC(CCCCC)CCOC(=O)CCCCCCCCCC(CCCCCCCCCC(=O)OCCC(CCCCC)CCCCC)OCCCCN1CCCC1]
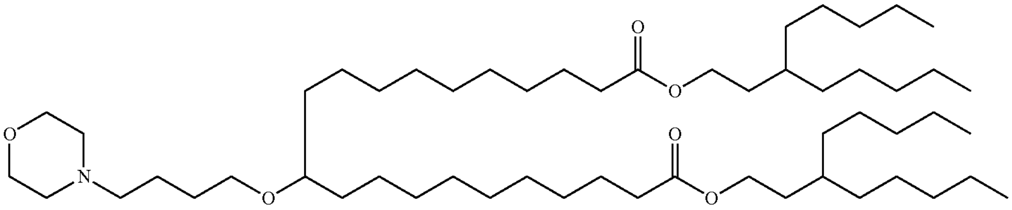 [SMILES: CCCCCC(CCCCC)CCOC(=O)CCCCCCCCCC(CCCCCCCCCC(=O)OCCC(CCCCC)CCCCC)OCCCCN1CCOCC1]

-continued
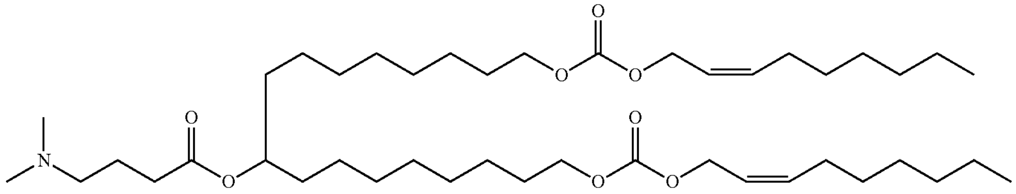
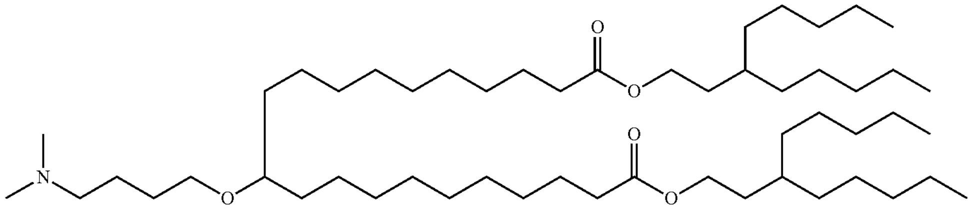 [SMILES: CCCCCC(CCCCC)CCOC(=O)CCCCCCCCCC(CCCCCCCCCC(=O)OCCC(CCCCC)CCCCC)OCCCCN(C)C]
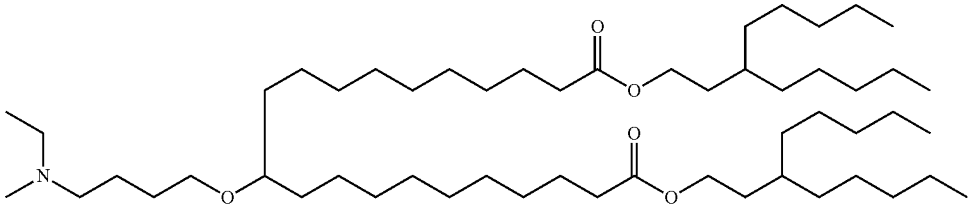 [SMILES: CCCCCC(CCCCC)CCOC(=O)CCCCCCCCCC(CCCCCCCCCC(=O)OCCC(CCCCC)CCCCC)OCCCCN(C)CC]
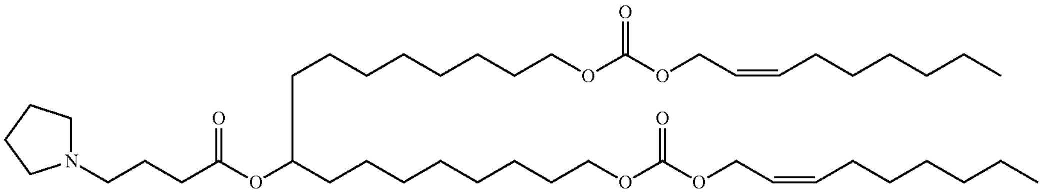 [SMILES: CCCCCC/C=C\COC(=O)OCCCCCCCCC(CCCCCCCCOC(=O)OC/C=C\CCCCCC)OC(=O)CCCN1CCCC1]
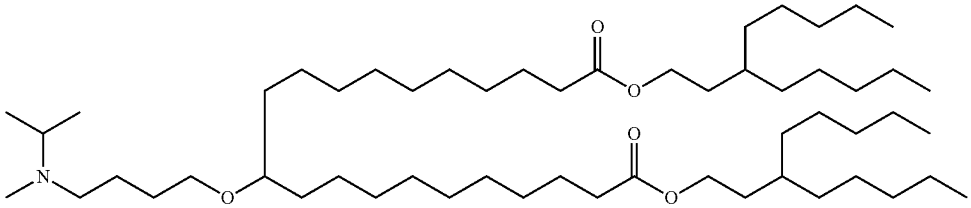 [SMILES: CCCCCC(CCCCC)CCOC(=O)CCCCCCCCCC(CCCCCCCCCC(=O)OCCC(CCCCC)CCCCC)OCCCCN(C)C(C)C]
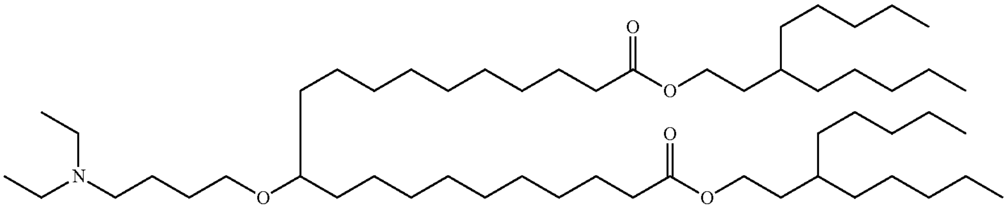 [SMILES: CCCCCC(CCCCC)CCOC(=O)CCCCCCCCCC(CCCCCCCCCC(=O)OCCC(CCCCC)CCCCC)OCCCCN(CC)CC]
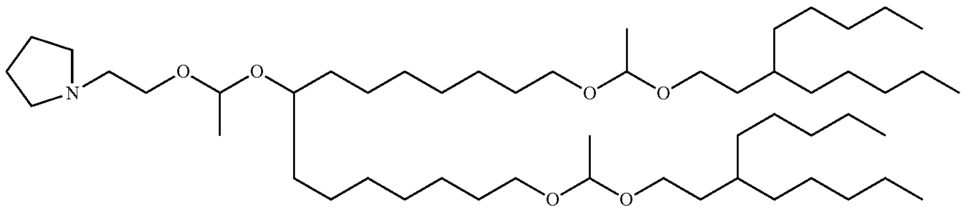 [SMILES: CCCCCC(CCCCC)CCOC(C)OCCCCCCCC(CCCCCCCOC(C)OCCC(CCCCC)CCCCC)OC(C)OCCN1CCCC1]

-continued
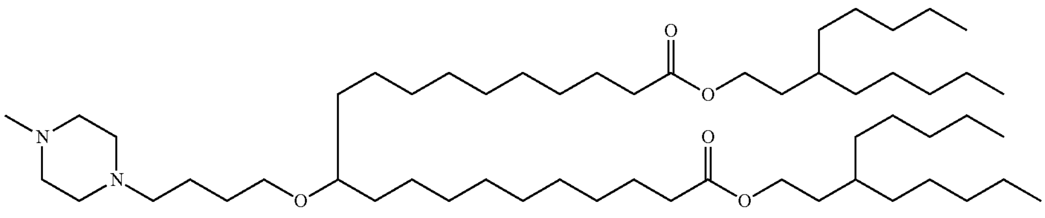 [SMILES: CCCCCC(CCCCC)CCOC(=O)CCCCCCCCCC(CCCCCCCCCC(=O)OCCC(CCCCC)CCCCC)OCCCCN1CCN(C)CC1]
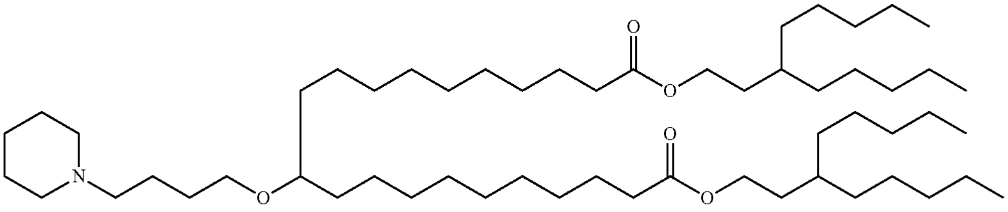 [SMILES: CCCCCC(CCCCC)CCOC(=O)CCCCCCCCCC(CCCCCCCCCC(=O)OCCC(CCCCC)CCCCC)OCCCCN1CCCCC1]
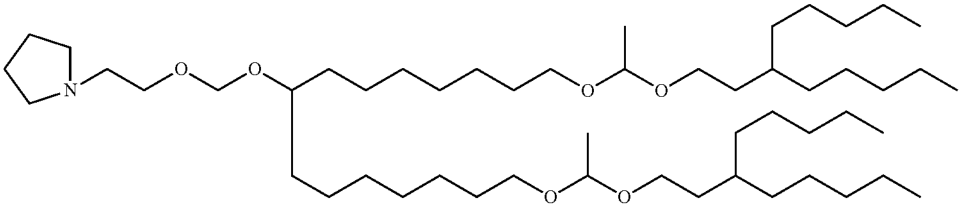 [SMILES: CCCCCC(CCCCC)CCOC(C)OCCCCCCCC(CCCCCCCOC(C)OCCC(CCCCC)CCCCC)OCOCCN1CCCC1]
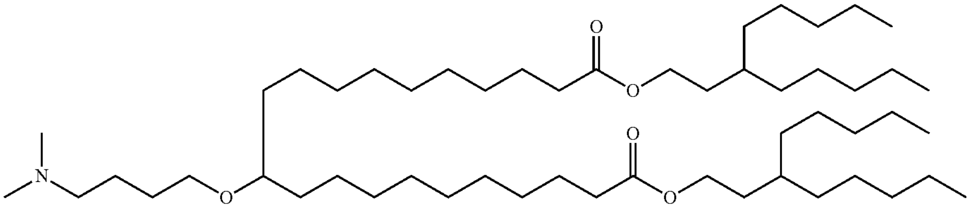 [SMILES: CCCCCC(CCCCC)CCOC(=O)CCCCCCCCCC(CCCCCCCCCC(=O)OCCC(CCCCC)CCCCC)OCCCCN(C)C]
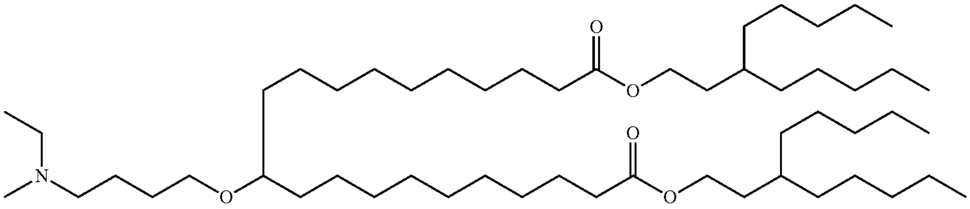 [SMILES: CCCCCC(CCCCC)CCOC(=O)CCCCCCCCCC(CCCCCCCCCC(=O)OCCC(CCCCC)CCCCC)OCCCCN(C)CC]
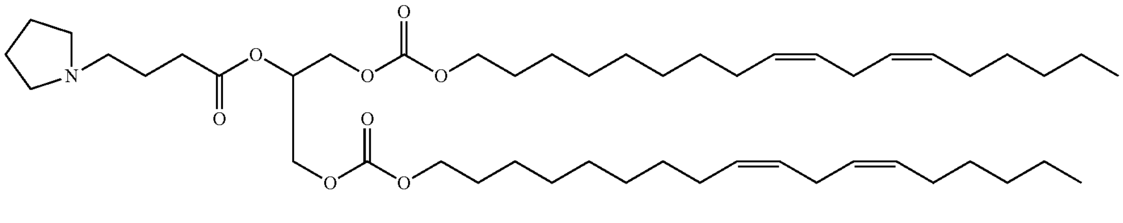 [SMILES: CCCCC/C=C\C/C=C\CCCCCCCCOC(=O)OCC(COC(=O)OCCCCCCCC/C=C\C/C=C\CCCCC)OC(=O)CCCN1CCCC1]
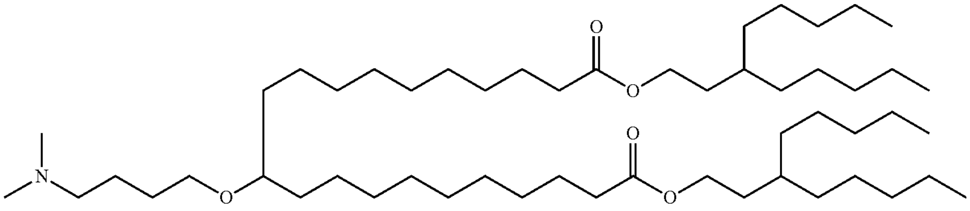 [SMILES: CCCCCC(CCCCC)CCOC(=O)CCCCCCCCCC(CCCCCCCCCC(=O)OCCC(CCCCC)CCCCC)OCCCCN(C)C]

-continued
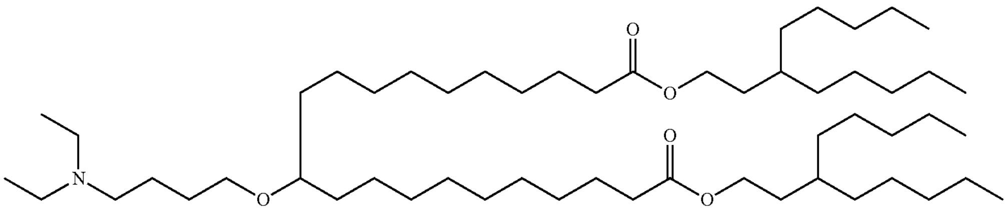 [SMILES: CCCCCC(CCCCC)CCOC(=O)CCCCCCCCCC(CCCCCCCCCC(=O)OCCC(CCCCC)CCCCC)OCCCCN(CC)CC]
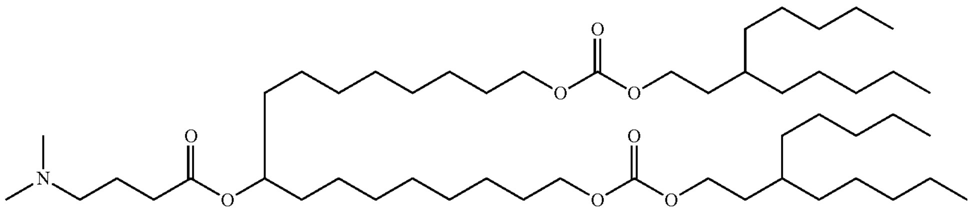 [SMILES: CCCCCC(CCCCC)CCOC(=O)OCCCCCCCCC(CCCCCCCCOC(=O)OCCC(CCCCC)CCCCC)OC(=O)CCCN(C)C]
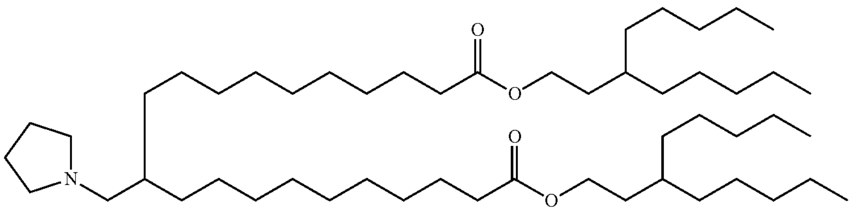 [SMILES: CCCCCC(CCCCC)CCOC(=O)CCCCCCCCCC(CCCCCCCCCC(=O)OCCC(CCCCC)CCCCC)CN1CCCC1]
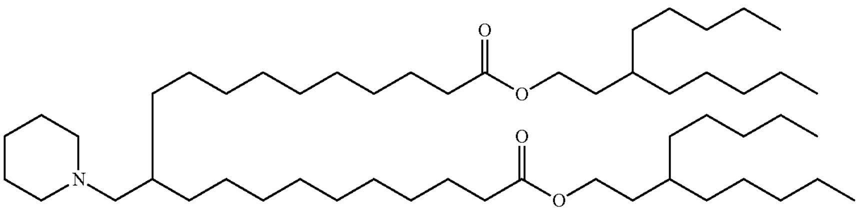 [SMILES: CCCCCC(CCCCC)CCOC(=O)CCCCCCCCCC(CCCCCCCCCC(=O)OCCC(CCCCC)CCCCC)CN1CCCCC1]
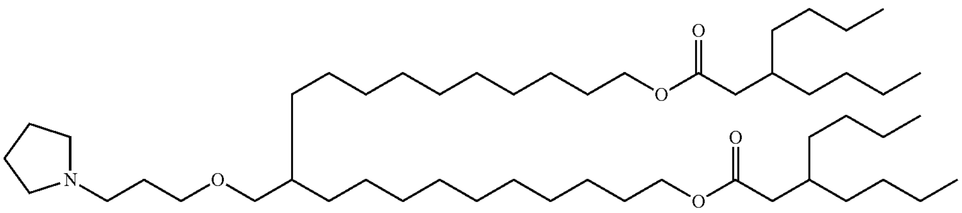 [SMILES: CCCCC(CCCC)CC(=O)OCCCCCCCCCCC(CCCCCCCCCCOC(=O)CC(CCCC)CCCC)COCCCN1CCCC1]
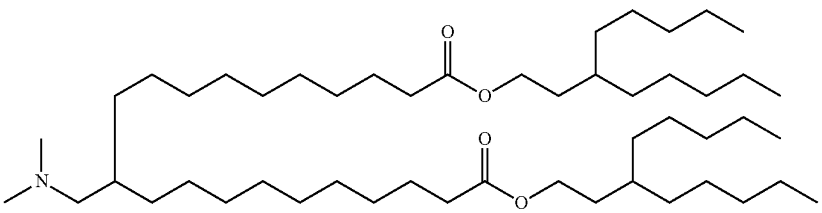 [SMILES: CCCCCC(CCCCC)CCOC(=O)CCCCCCCCCC(CCCCCCCCCC(=O)OCCC(CCCCC)CCCCC)CN(C)C]
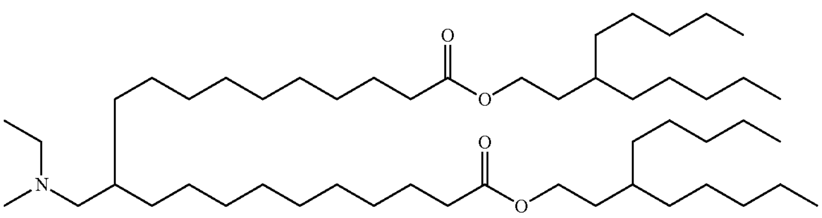 [SMILES: CCCCCC(CCCCC)CCOC(=O)CCCCCCCCCC(CCCCCCCCCC(=O)OCCC(CCCCC)CCCCC)CN(C)CC]

-continued
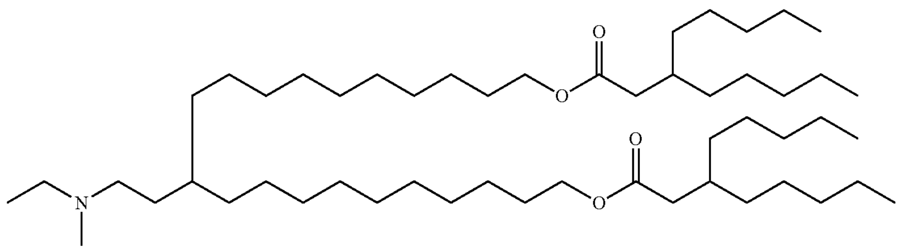 [SMILES: CCCCCC(CCCCC)CC(=O)OCCCCCCCCCCC(CCCCCCCCCCOC(=O)CC(CCCCC)CCCCC)CCN(C)CC]
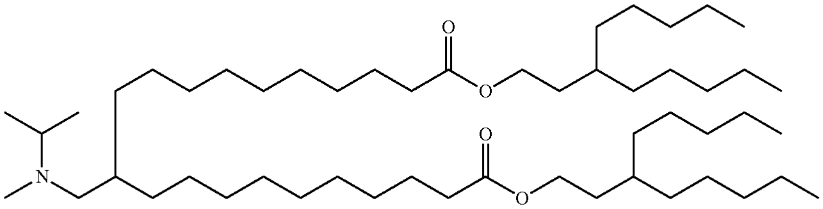 [SMILES: CCCCCC(CCCCC)CCOC(=O)CCCCCCCCCC(CCCCCCCCCC(=O)OCCC(CCCCC)CCCCC)CN(C)C(C)C]
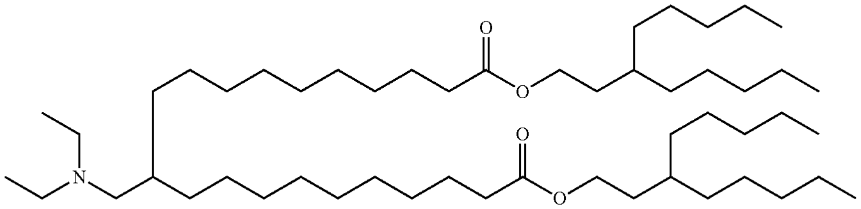 [SMILES: CCCCCC(CCCCC)CCOC(=O)CCCCCCCCCC(CCCCCCCCCC(=O)OCCC(CCCCC)CCCCC)CN(CC)CC]
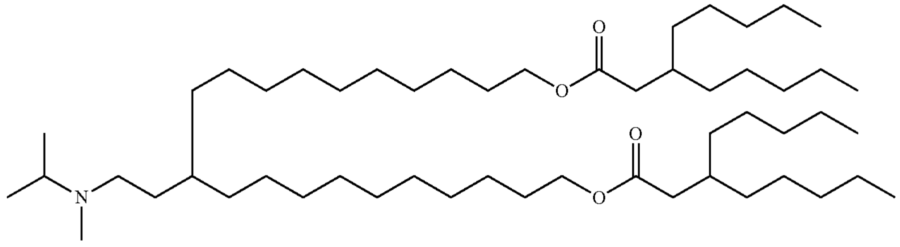 [SMILES: CCCCCC(CCCCC)CC(=O)OCCCCCCCCCCC(CCCCCCCCCCOC(=O)CC(CCCCC)CCCCC)CCN(C)C(C)C]
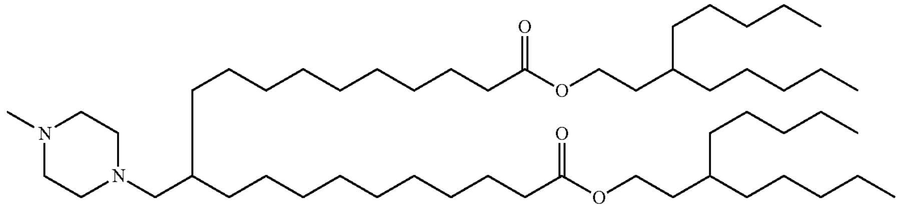 [SMILES: CCCCCC(CCCCC)CCOC(=O)CCCCCCCCCC(CCCCCCCCCC(=O)OCCC(CCCCC)CCCCC)CN1CCN(C)CC1]
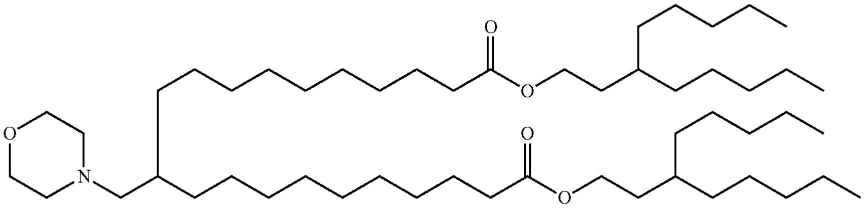 [SMILES: CCCCCC(CCCCC)CCOC(=O)CCCCCCCCCC(CCCCCCCCCC(=O)OCCC(CCCCC)CCCCC)CN1CCOCC1]
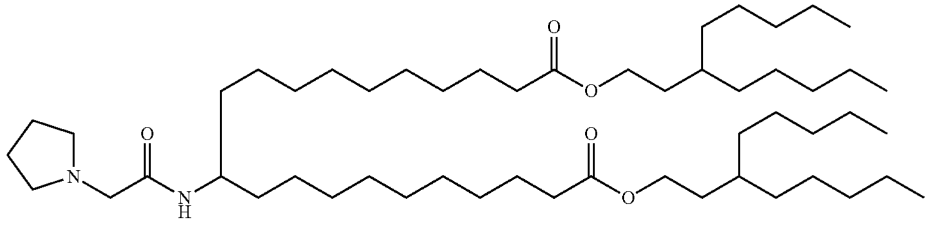 [SMILES: CCCCCC(CCCCC)CCOC(=O)CCCCCCCCCC(CCCCCCCCCC(=O)OCCC(CCCCC)CCCCC)NC(=O)CN1CCCC1]

-continued
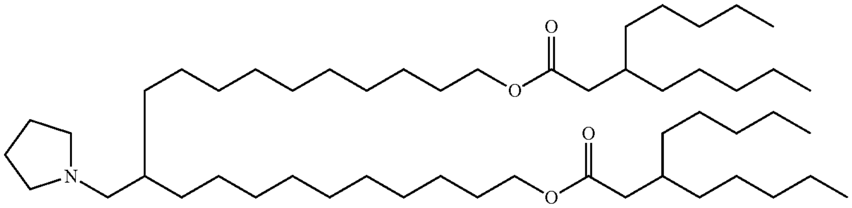 [SMILES: CCCCCC(CCCCC)CC(=O)OCCCCCCCCCCC(CCCCCCCCCCOC(=O)CC(CCCCC)CCCCC)CN1CCCC1]
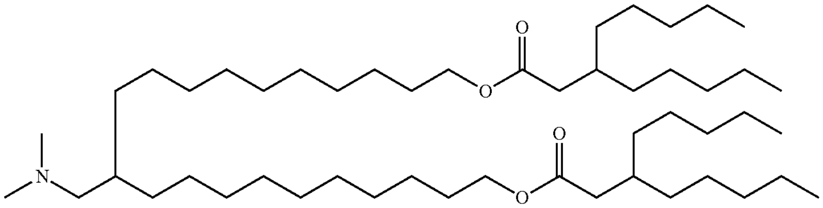 [SMILES: CCCCCC(CCCCC)CC(=O)OCCCCCCCCCCC(CCCCCCCCCCOC(=O)CC(CCCCC)CCCCC)CN(C)C]
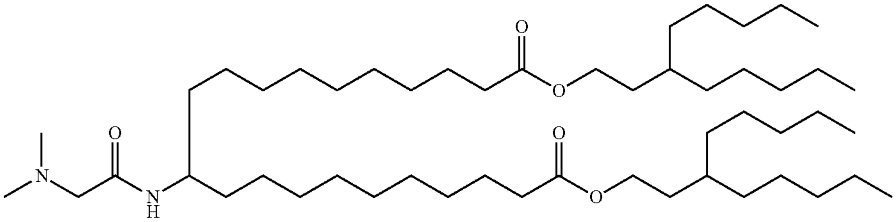 [SMILES: CCCCCC(CCCCC)CCOC(=O)CCCCCCCCCC(CCCCCCCCCC(=O)OCCC(CCCCC)CCCCC)NC(=O)CN(C)C]
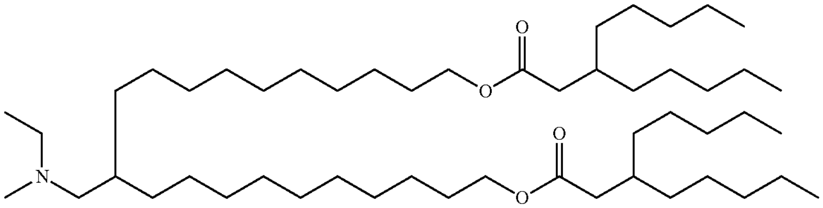 [SMILES: CCCCCC(CCCCC)CC(=O)OCCCCCCCCCCC(CCCCCCCCCCOC(=O)CC(CCCCC)CCCCC)CN(C)CC]
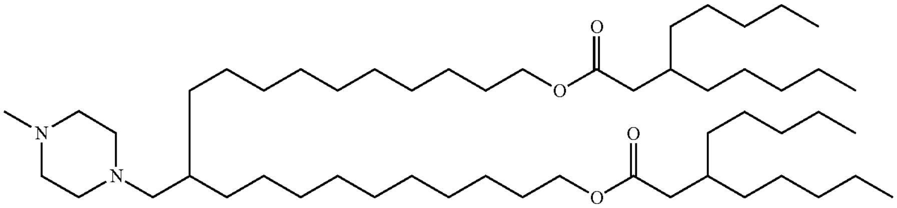 [SMILES: CCCCCC(CCCCC)CC(=O)OCCCCCCCCCCC(CCCCCCCCCCOC(=O)CC(CCCCC)CCCCC)CN1CCN(C)CC1]
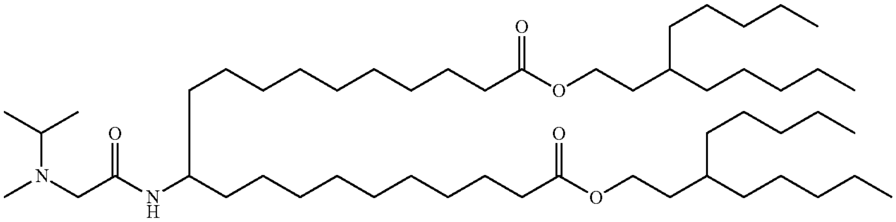 [SMILES: CCCCCC(CCCCC)CCOC(=O)CCCCCCCCCC(CCCCCCCCCC(=O)OCCC(CCCCC)CCCCC)NC(=O)CN(C)C(C)C]
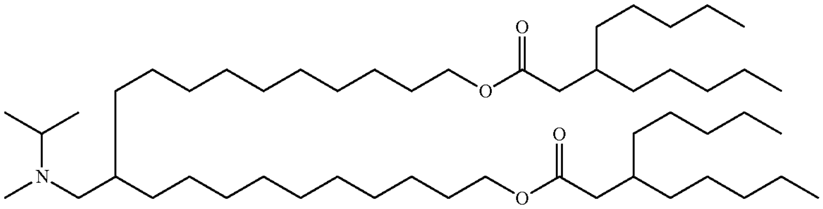 [SMILES: CCCCCC(CCCCC)CC(=O)OCCCCCCCCCCC(CCCCCCCCCCOC(=O)CC(CCCCC)CCCCC)CN(C)C(C)C]

-continued
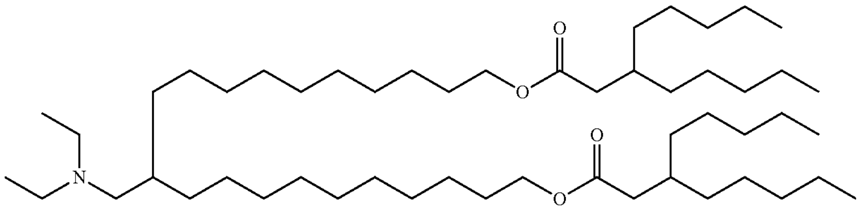 [SMILES: CCCCCC(CCCCC)CC(=O)OCCCCCCCCCCC(CCCCCCCCCCOC(=O)CC(CCCCC)CCCCC)CN(CC)CC]
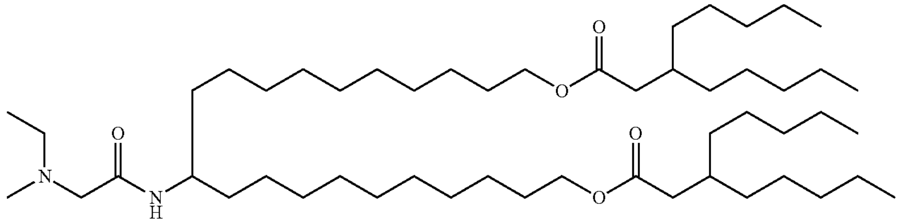 [SMILES: CCCCCC(CCCCC)CC(=O)OCCCCCCCCCCC(CCCCCCCCCCOC(=O)CC(CCCCC)CCCCC)NC(=O)CN(C)CC]
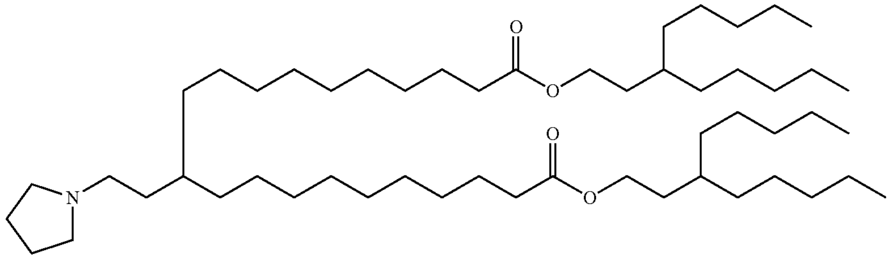 [SMILES: CCCCCC(CCCCC)CCOC(=O)CCCCCCCCCC(CCCCCCCCCC(=O)OCCC(CCCCC)CCCCC)CCN1CCCC1]
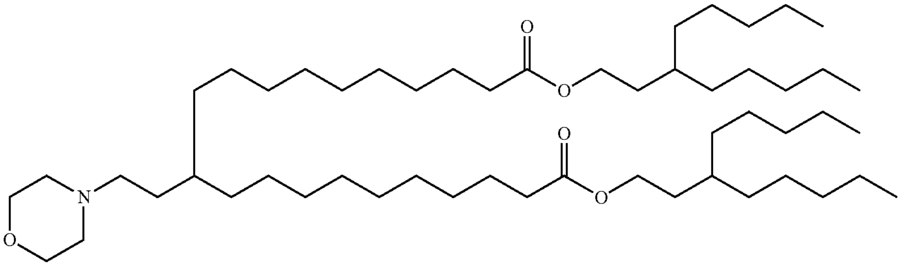 [SMILES: CCCCCC(CCCCC)CCOC(=O)CCCCCCCCCC(CCCCCCCCCC(=O)OCCC(CCCCC)CCCCC)CCN1CCOCC1]
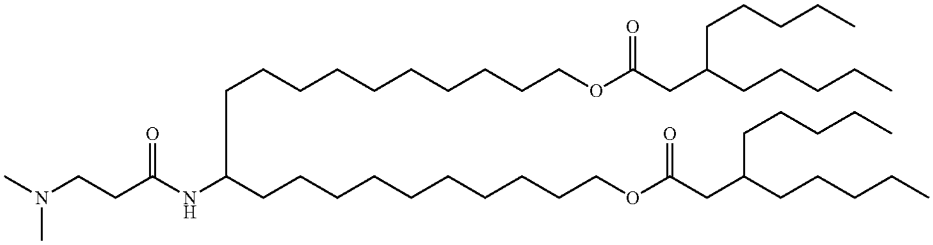 [SMILES: CCCCCC(CCCCC)CC(=O)OCCCCCCCCCCC(CCCCCCCCCCOC(=O)CC(CCCCC)CCCCC)NC(=O)CCN(C)C]
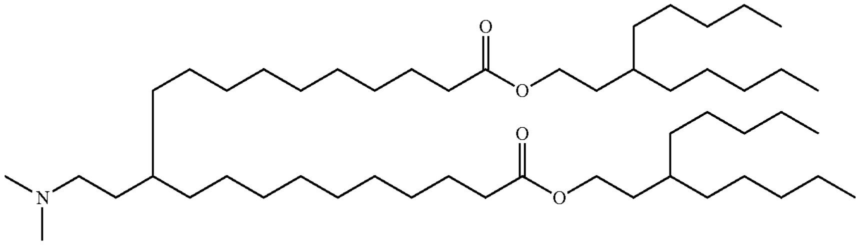 [SMILES: CCCCCC(CCCCC)CCOC(=O)CCCCCCCCCC(CCCCCCCCCC(=O)OCCC(CCCCC)CCCCC)CCN(C)C]

-continued
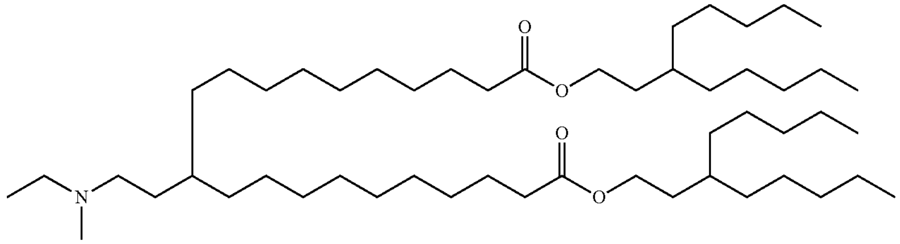 [SMILES: CCCCCC(CCCCC)CCOC(=O)CCCCCCCCCC(CCCCCCCCCC(=O)OCCC(CCCCC)CCCCC)CCN(C)CC]
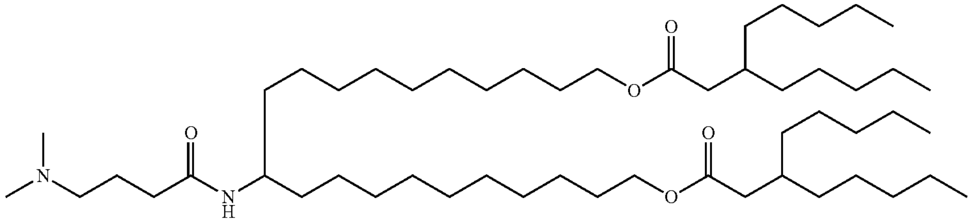 [SMILES: CCCCCC(CCCCC)CC(=O)OCCCCCCCCCCC(CCCCCCCCCCOC(=O)CC(CCCCC)CCCCC)NC(=O)CCCN(C)C]
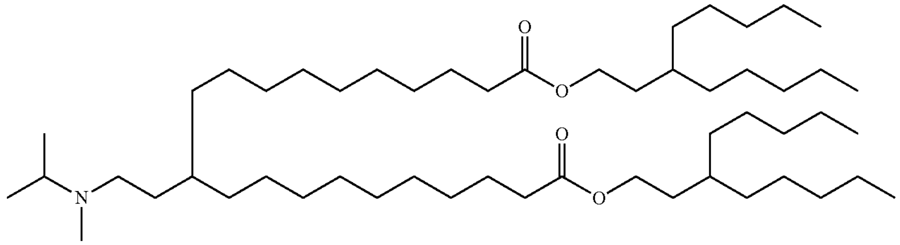 [SMILES: CCCCCC(CCCCC)CCOC(=O)CCCCCCCCCC(CCCCCCCCCC(=O)OCCC(CCCCC)CCCCC)CCN(C)C(C)C]
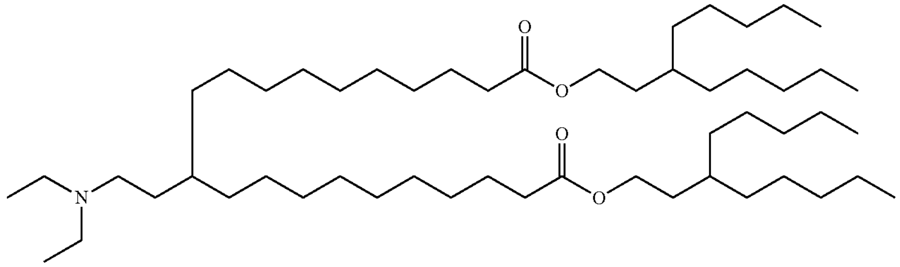 [SMILES: CCCCCC(CCCCC)CCOC(=O)CCCCCCCCCC(CCCCCCCCCC(=O)OCCC(CCCCC)CCCCC)CCN(CC)CC]
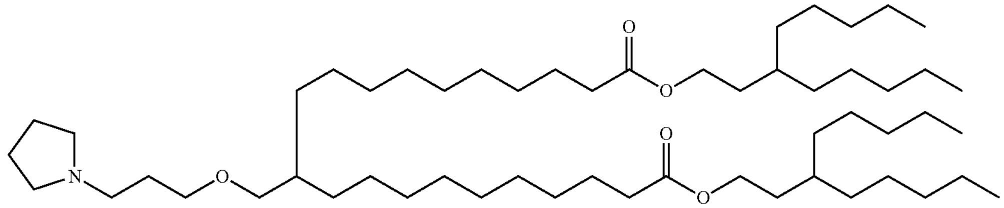 [SMILES: CCCCCC(CCCCC)CCOC(=O)CCCCCCCCCC(CCCCCCCCCC(=O)OCCC(CCCCC)CCCCC)COCCCN1CCCC1]
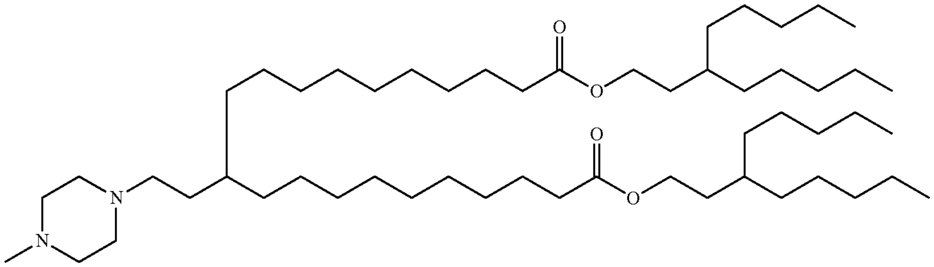 [SMILES: CCCCCC(CCCCC)CCOC(=O)CCCCCCCCCC(CCCCCCCCCC(=O)OCCC(CCCCC)CCCCC)CCN1CCN(C)CC1]

-continued
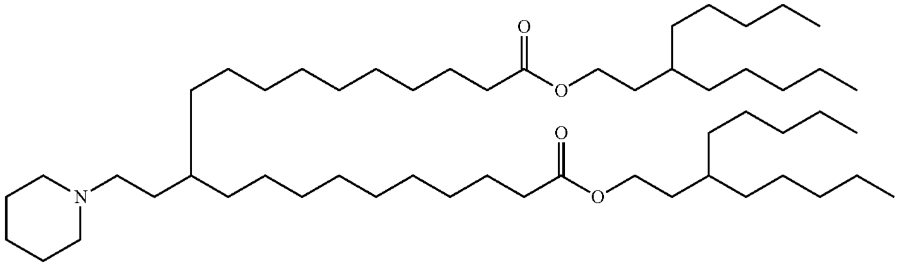 [SMILES: CCCCCC(CCCCC)CCOC(=O)CCCCCCCCCC(CCCCCCCCCC(=O)OCCC(CCCCC)CCCCC)CCN1CCCCC1]
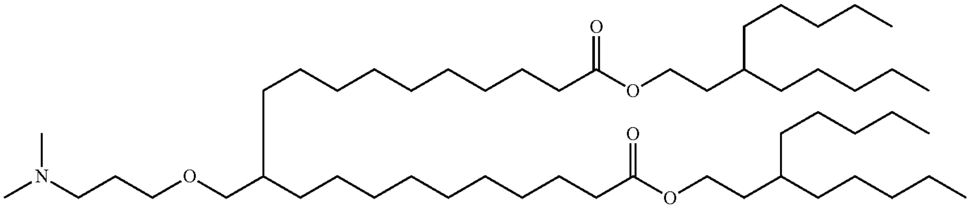 [SMILES: CCCCCC(CCCCC)CCOC(=O)CCCCCCCCCC(CCCCCCCCCC(=O)OCCC(CCCCC)CCCCC)COCCCN(C)C]
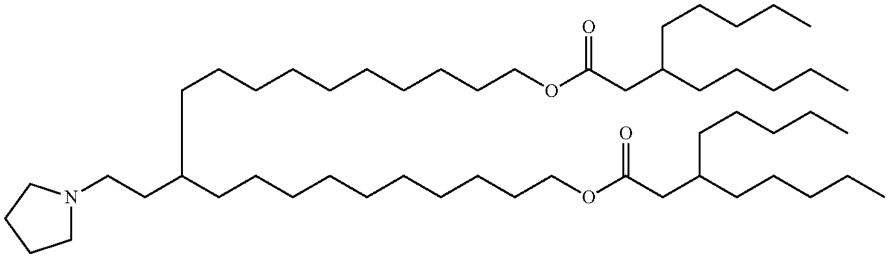 [SMILES: CCCCCC(CCCCC)CC(=O)OCCCCCCCCCCC(CCCCCCCCCCOC(=O)CC(CCCCC)CCCCC)CCN1CCCC1]
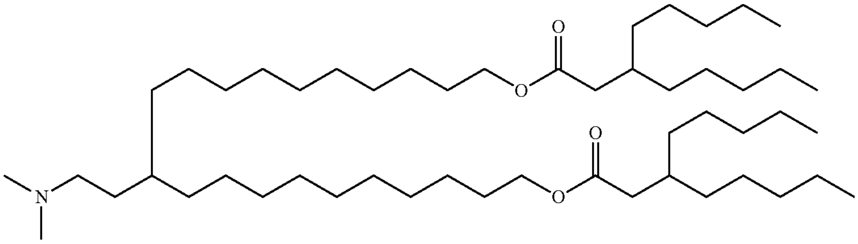 [SMILES: CCCCCC(CCCCC)CC(=O)OCCCCCCCCCCC(CCCCCCCCCCOC(=O)CC(CCCCC)CCCCC)CCN(C)C]
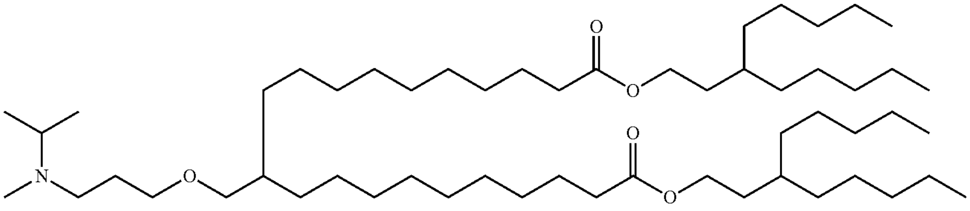 [SMILES: CCCCCC(CCCCC)CCOC(=O)CCCCCCCCCC(CCCCCCCCCC(=O)OCCC(CCCCC)CCCCC)COCCCN(C)C(C)C]
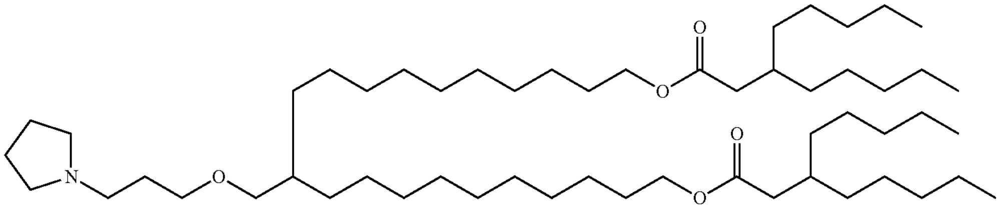 [SMILES: CCCCCC(CCCCC)CC(=O)OCCCCCCCCCCC(CCCCCCCCCCOC(=O)CC(CCCCC)CCCCC)COCCCN1CCCC1]

-continued
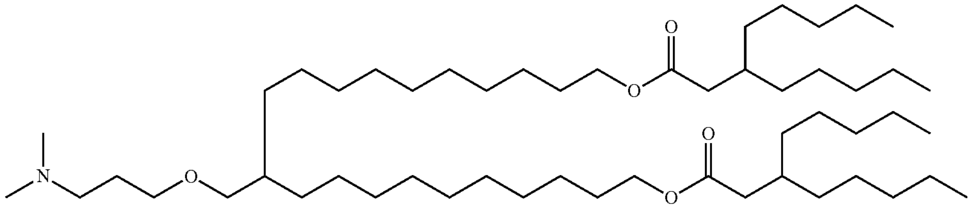 [SMILES: CCCCCC(CCCCC)CC(=O)OCCCCCCCCCCC(CCCCCCCCCCOC(=O)CC(CCCCC)CCCCC)COCCCN(C)C]
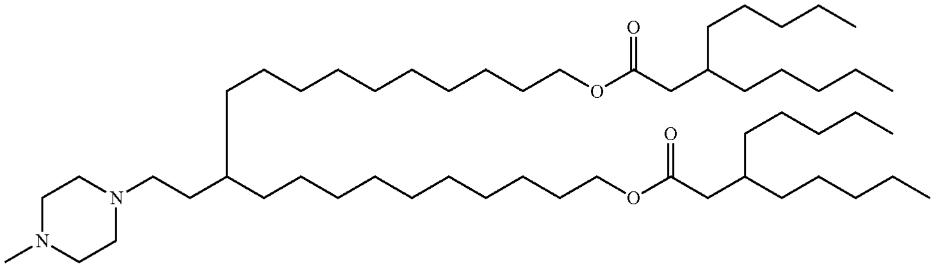 [SMILES: CCCCCC(CCCCC)CC(=O)OCCCCCCCCCCC(CCCCCCCCCCOC(=O)CC(CCCCC)CCCCC)CCN1CCN(C)CC1]
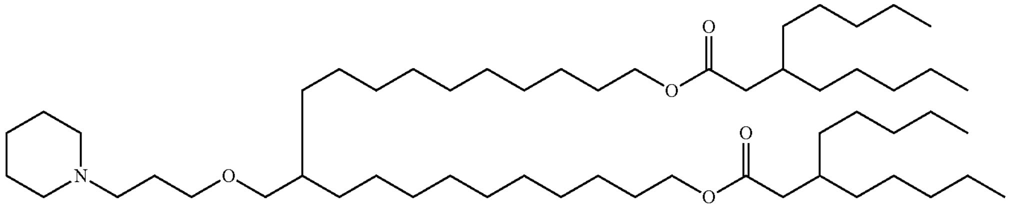 [SMILES: CCCCCC(CCCCC)CC(=O)OCCCCCCCCCCC(CCCCCCCCCCOC(=O)CC(CCCCC)CCCCC)COCCCN1CCCCC1]
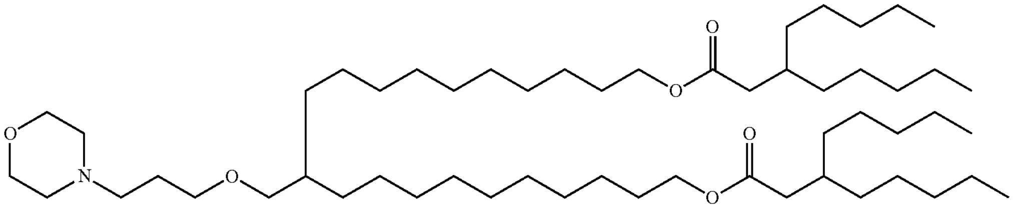 [SMILES: CCCCCC(CCCCC)CC(=O)OCCCCCCCCCCC(CCCCCCCCCCOC(=O)CC(CCCCC)CCCCC)COCCCN1CCOCC1]
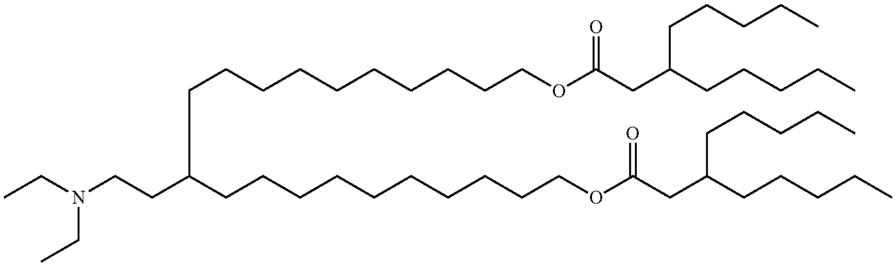 [SMILES: CCCCCC(CCCCC)CC(=O)OCCCCCCCCCCC(CCCCCCCCCCOC(=O)CC(CCCCC)CCCCC)CCN(CC)CC]
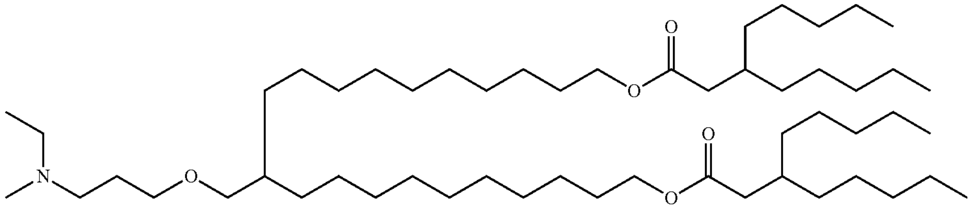 [SMILES: CCCCCC(CCCCC)CC(=O)OCCCCCCCCCCC(CCCCCCCCCCOC(=O)CC(CCCCC)CCCCC)COCCCN(C)CC]
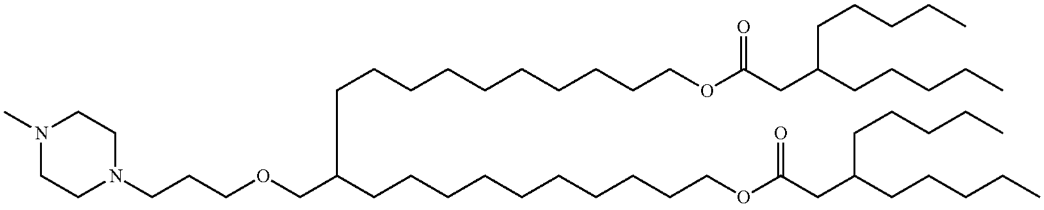 [SMILES: CCCCCC(CCCCC)CC(=O)OCCCCCCCCCCC(CCCCCCCCCCOC(=O)CC(CCCCC)CCCCC)COCCCN1CCN(C)CC1]

-continued
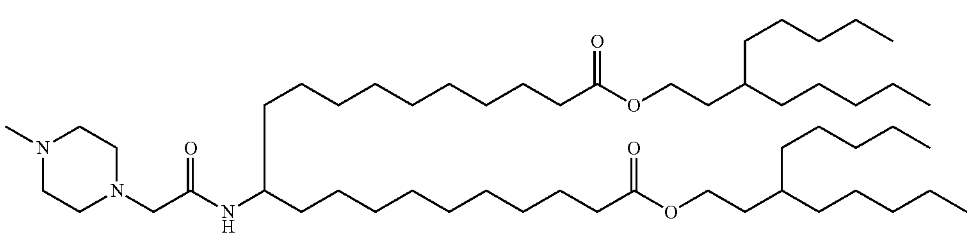 [SMILES: CCCCCC(CCCCC)CCOC(=O)CCCCCCCCCC(CCCCCCCCCC(=O)OCCC(CCCCC)CCCCC)NC(=O)CN1CCN(C)CC1]
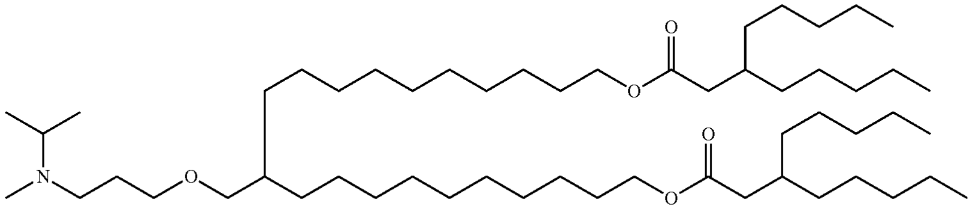 [SMILES: CCCCCC(CCCCC)CC(=O)OCCCCCCCCCCC(CCCCCCCCCCOC(=O)CC(CCCCC)CCCCC)COCCCN(C)C(C)C]
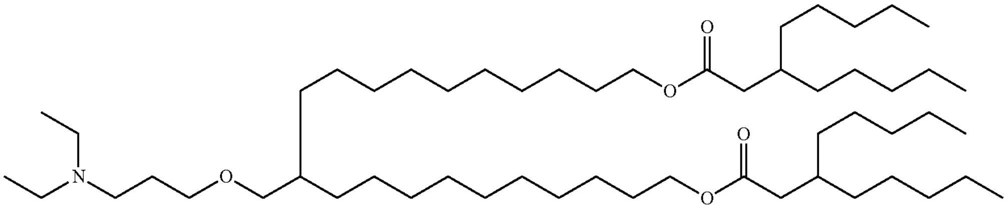 [SMILES: CCCCCC(CCCCC)CC(=O)OCCCCCCCCCCC(CCCCCCCCCCOC(=O)CC(CCCCC)CCCCC)COCCCN(CC)CC]
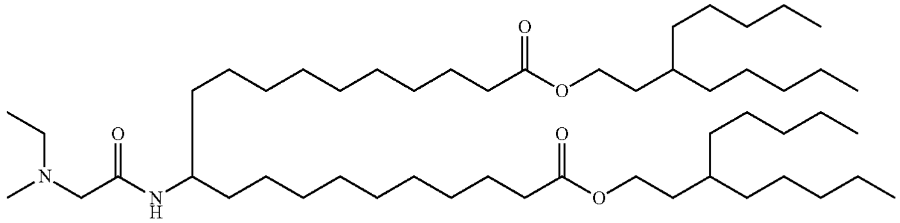 [SMILES: CCCCCC(CCCCC)CCOC(=O)CCCCCCCCCC(CCCCCCCCCC(=O)OCCC(CCCCC)CCCCC)NC(=O)CN(C)CC]
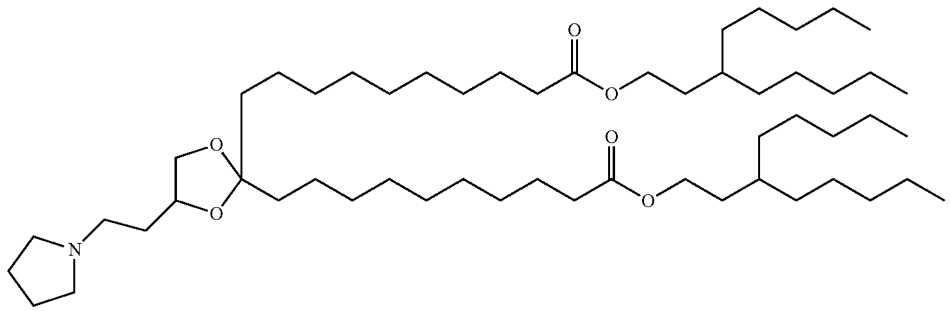 [SMILES: CCCCCC(CCCCC)CCOC(=O)CCCCCCCCCC1(CCCCCCCCCC(=O)OCCC(CCCCC)CCCCC)OCC(CCN2CCCC2)O1]
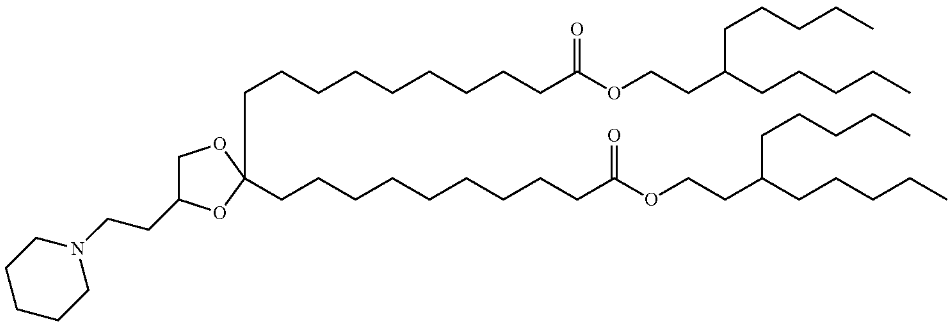

-continued
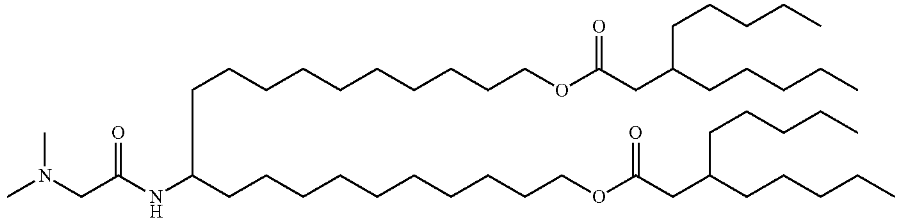 [SMILES: CCCCCC(CCCCC)CC(=O)OCCCCCCCCCCC(CCCCCCCCCCOC(=O)CC(CCCCC)CCCCC)NC(=O)CN(C)C]
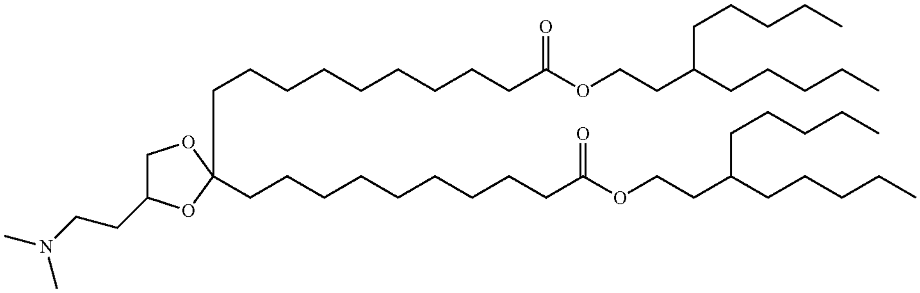 [SMILES: CCCCCC(CCCCC)CCOC(=O)CCCCCCCCCC1(CCCCCCCCCC(=O)OCCC(CCCCC)CCCCC)OCC(CCN(C)C)O1]
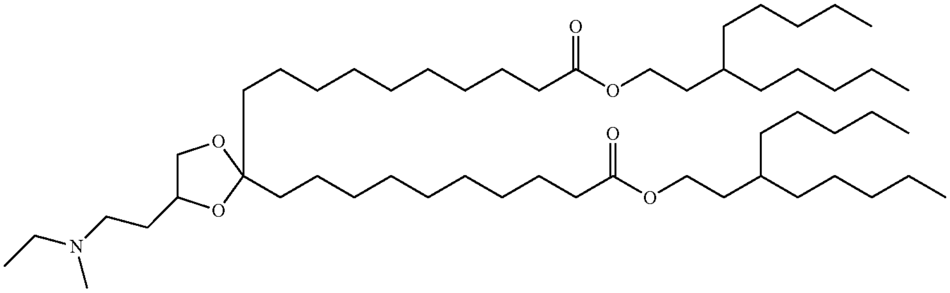 [SMILES: CCCCCC(CCCCC)CCOC(=O)CCCCCCCCCC1(CCCCCCCCCC(=O)OCCC(CCCCC)CCCCC)OCC(CCN(C)CC)O1]
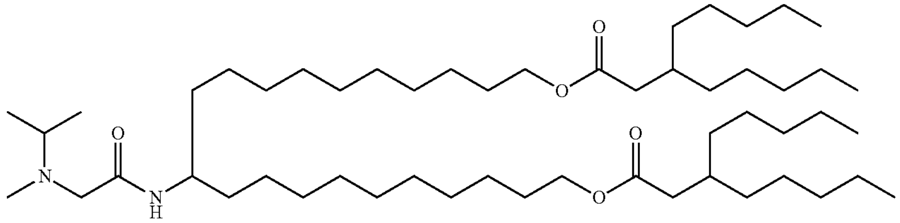 [SMILES: CCCCCC(CCCCC)CC(=O)OCCCCCCCCCCC(CCCCCCCCCCOC(=O)CC(CCCCC)CCCCC)NC(=O)CN(C)C(C)C]
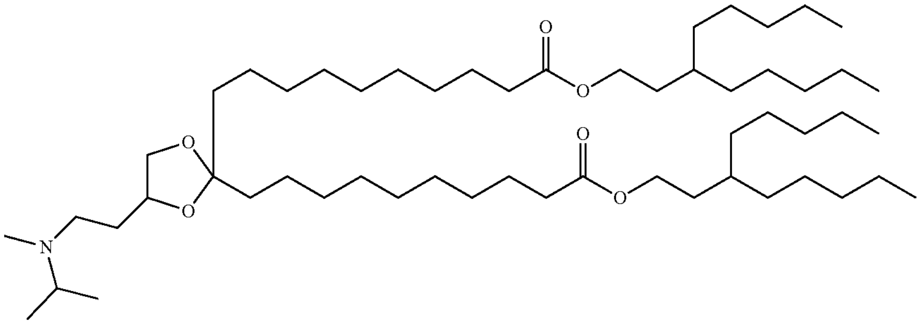 [SMILES: CCCCCC(CCCCC)CCOC(=O)CCCCCCCCCC1(CCCCCCCCCC(=O)OCCC(CCCCC)CCCCC)OCC(CCN(C)C(C)C)O1]

-continued
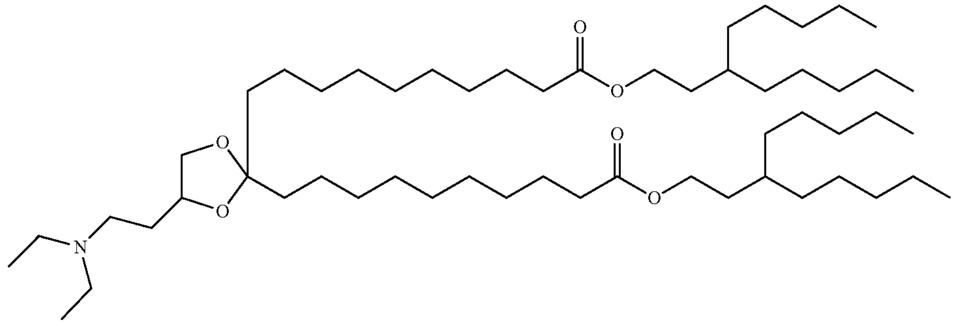 [SMILES: CCCCCC(CCCCC)CCOC(=O)CCCCCCCCCC1(CCCCCCCCCC(=O)OCCC(CCCCC)CCCCC)OCC(CCN(CC)CC)O1]
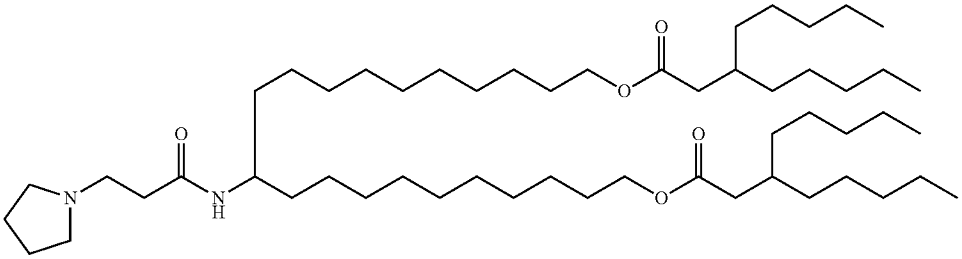 [SMILES: CCCCCC(CCCCC)CC(=O)OCCCCCCCCCCC(CCCCCCCCCCOC(=O)CC(CCCCC)CCCCC)NC(=O)CCN1CCCC1]
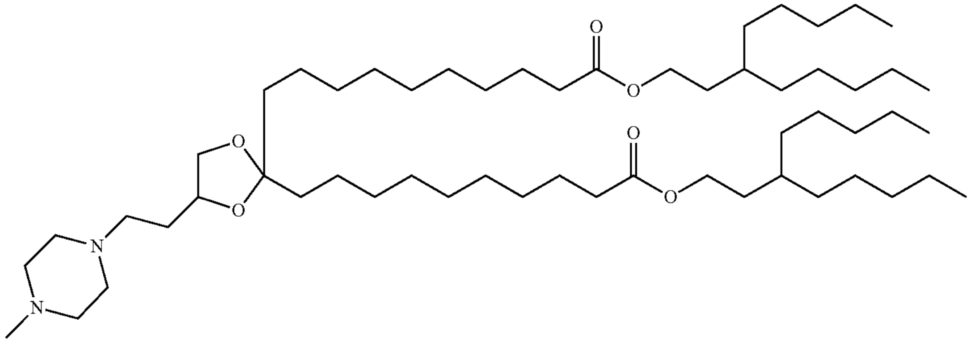 [SMILES: CCCCCC(CCCCC)CCOC(=O)CCCCCCCCCC1(CCCCCCCCCC(=O)OCCC(CCCCC)CCCCC)OCC(CCN2CCN(C)CC2)O1]
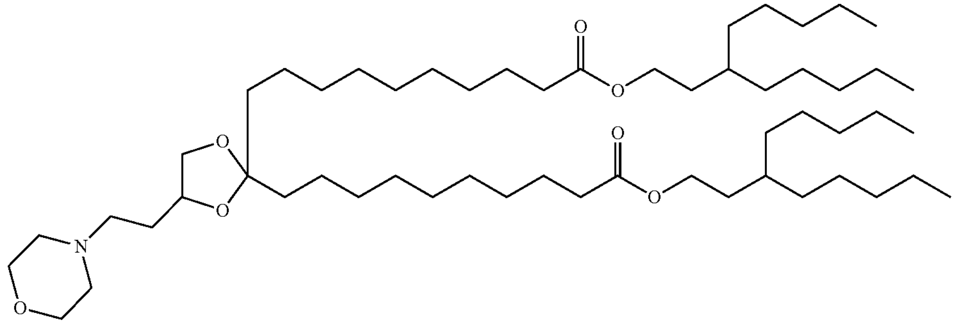 [SMILES: CCCCCC(CCCCC)CCOC(=O)CCCCCCCCCC1(CCCCCCCCCC(=O)OCCC(CCCCC)CCCCC)OCC(CCN2CCOCC2)O1]
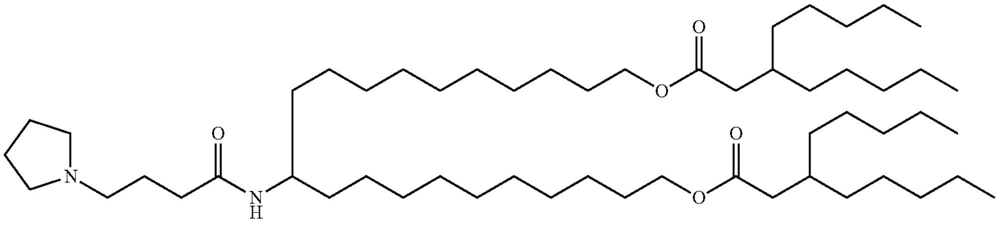 [SMILES: CCCCCC(CCCCC)CC(=O)OCCCCCCCCCCC(CCCCCCCCCCOC(=O)CC(CCCCC)CCCCC)NC(=O)CCCN1CCCC1]

-continued
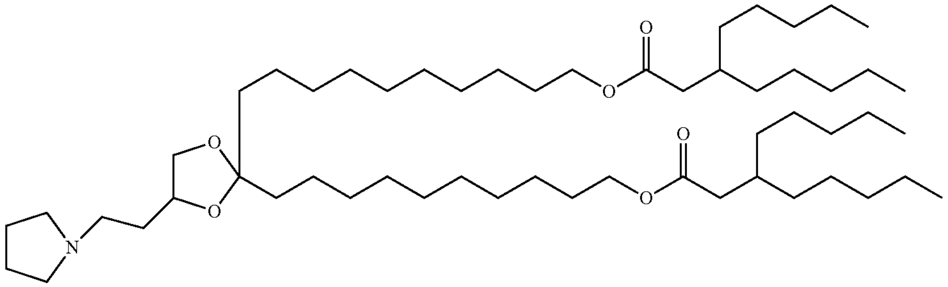 [SMILES: CCCCCC(CCCCC)CC(=O)OCCCCCCCCCCC1(CCCCCCCCCCOC(=O)CC(CCCCC)CCCCC)OCC(CCN2CCCC2)O1]
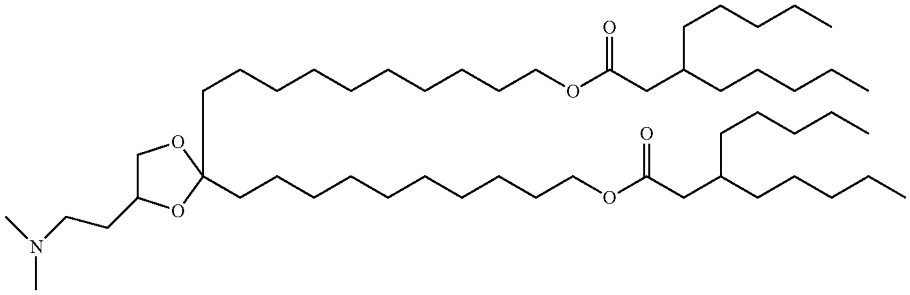 [SMILES: CCCCCC(CCCCC)CC(=O)OCCCCCCCCCCC1(CCCCCCCCCCOC(=O)CC(CCCCC)CCCCC)OCC(CCN(C)C)O1]
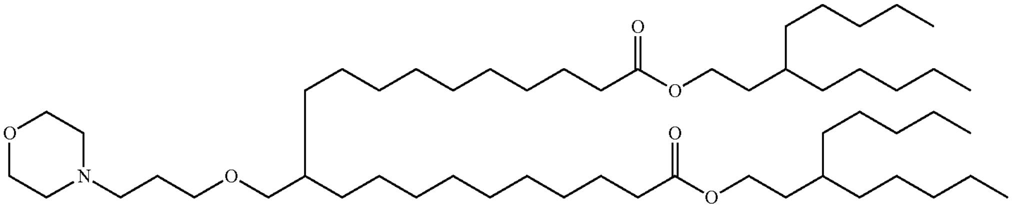 [SMILES: CCCCCC(CCCCC)CCOC(=O)CCCCCCCCCC(CCCCCCCCCC(=O)OCCC(CCCCC)CCCCC)COCCCN1CCOCC1]
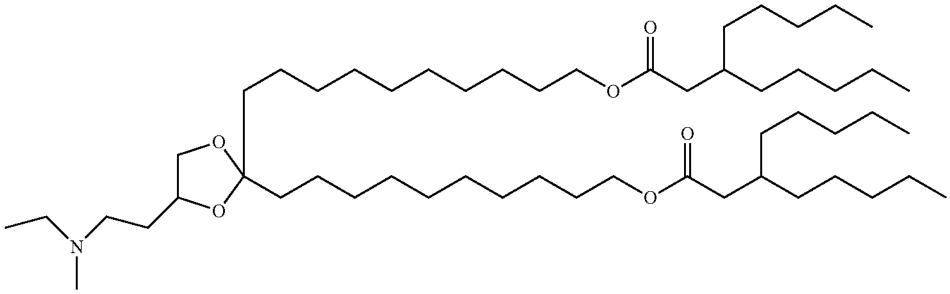 [SMILES: CCCCCC(CCCCC)CC(=O)OCCCCCCCCCCC1(CCCCCCCCCCOC(=O)CC(CCCCC)CCCCC)OCC(CCN(C)CC)O1]
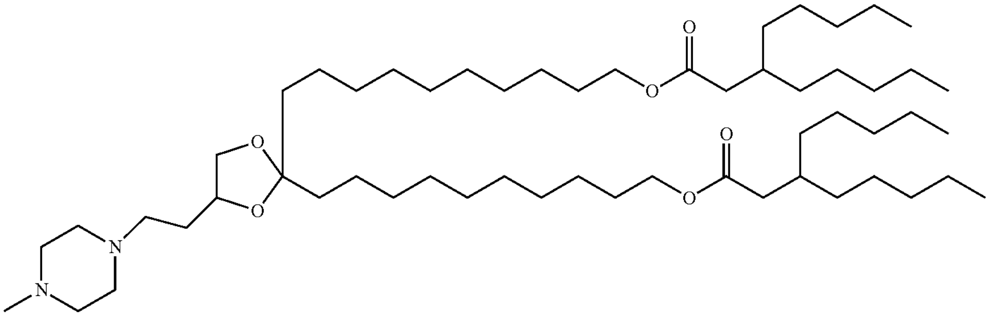 [SMILES: CCCCCC(CCCCC)CC(=O)OCCCCCCCCCCC1(CCCCCCCCCCOC(=O)CC(CCCCC)CCCCC)OCC(CCN2CCN(C)CC2)O1]

-continued
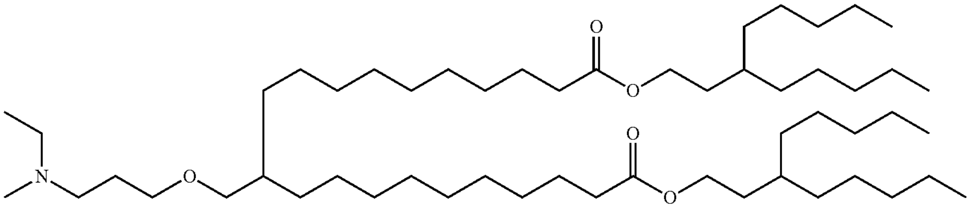 [SMILES: CCCCCC(CCCCC)CCOC(=O)CCCCCCCCCC(CCCCCCCCCC(=O)OCCC(CCCCC)CCCCC)COCCCN(C)CC]
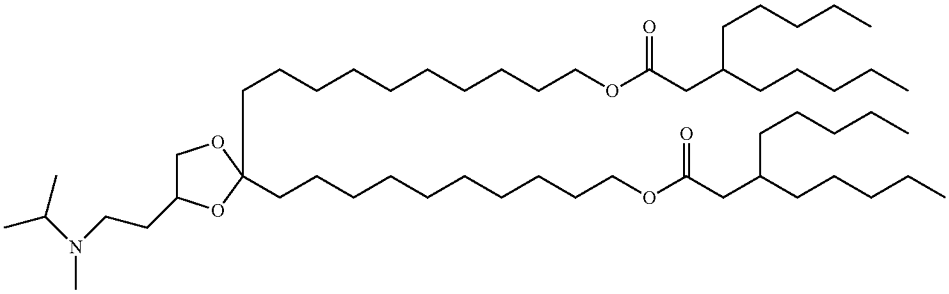 [SMILES: CCCCCC(CCCCC)CC(=O)OCCCCCCCCCCC1(CCCCCCCCCCOC(=O)CC(CCCCC)CCCCC)OCC(CCN(C)C(C)C)O1]
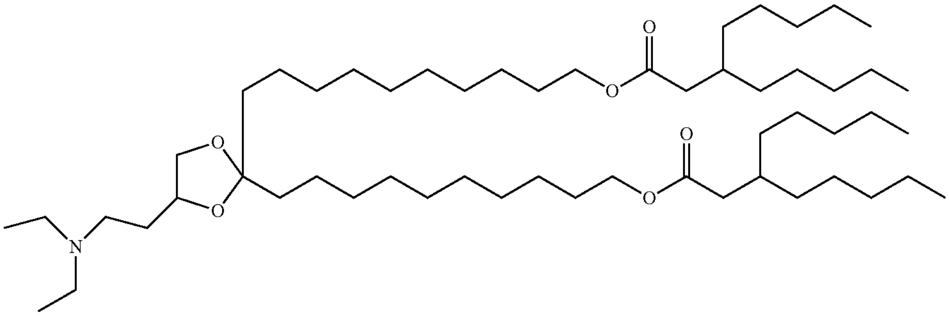 [SMILES: CCCCCC(CCCCC)CC(=O)OCCCCCCCCCCC1(CCCCCCCCCCOC(=O)CC(CCCCC)CCCCC)OCC(CCN(CC)CC)O1]
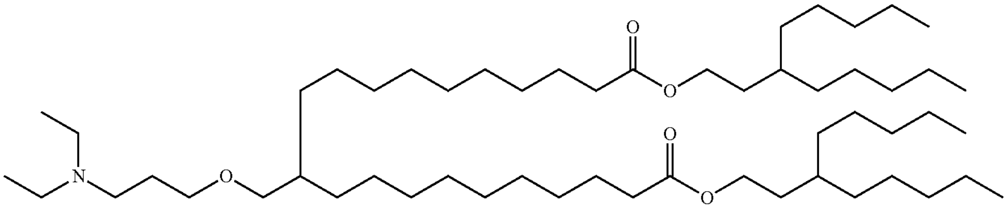 [SMILES: CCCCCC(CCCCC)CCOC(=O)CCCCCCCCCC(CCCCCCCCCC(=O)OCCC(CCCCC)CCCCC)COCCCN(CC)CC]
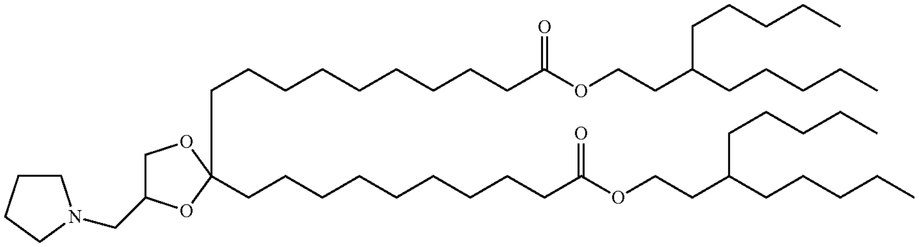 [SMILES: CCCCCC(CCCCC)CCOC(=O)CCCCCCCCCC1(CCCCCCCCCC(=O)OCCC(CCCCC)CCCCC)OCC(CN2CCCC2)O1]
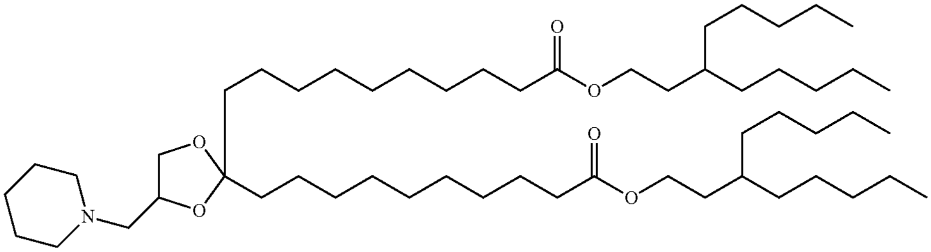 [SMILES: CCCCCC(CCCCC)CCOC(=O)CCCCCCCCCC1(CCCCCCCCCC(=O)OCCC(CCCCC)CCCCC)OCC(CN2CCCCC2)O1]

-continued
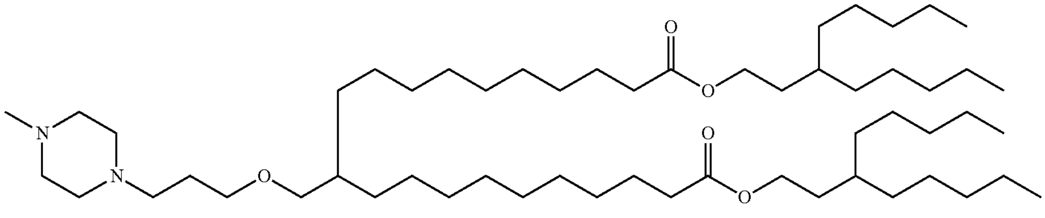 [SMILES: CCCCCC(CCCCC)CCOC(=O)CCCCCCCCCC(CCCCCCCCCC(=O)OCCC(CCCCC)CCCCC)COCCCN1CCN(C)CC1]
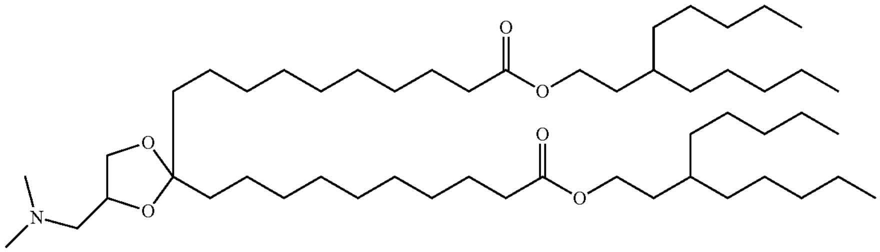 [SMILES: CCCCCC(CCCCC)CCOC(=O)CCCCCCCCCC1(CCCCCCCCCC(=O)OCCC(CCCCC)CCCCC)OCC(CN(C)C)O1]
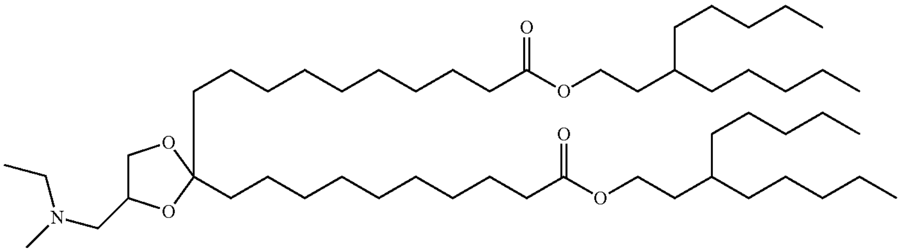 [SMILES: CCCCCC(CCCCC)CCOC(=O)CCCCCCCCCC1(CCCCCCCCCC(=O)OCCC(CCCCC)CCCCC)OCC(CN(C)CC)O1]
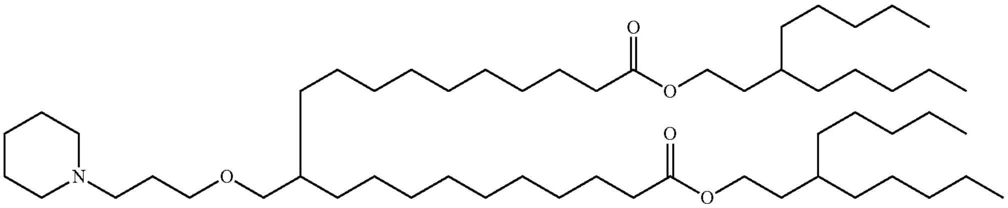 [SMILES: CCCCCC(CCCCC)CCOC(=O)CCCCCCCCCC(CCCCCCCCCC(=O)OCCC(CCCCC)CCCCC)COCCCN1CCCCC1]
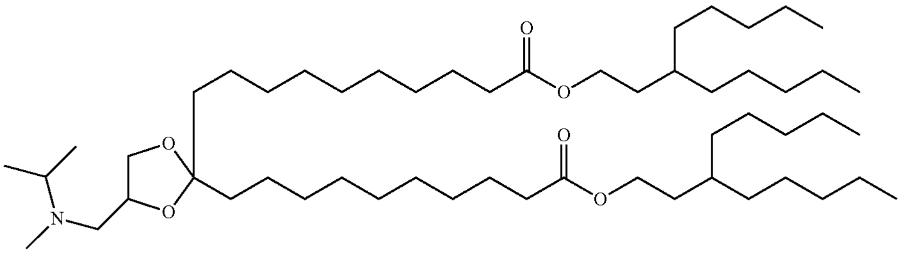 [SMILES: CCCCCC(CCCCC)CCOC(=O)CCCCCCCCCC1(CCCCCCCCCC(=O)OCCC(CCCCC)CCCCC)OCC(CN(C)C(C)C)O1]
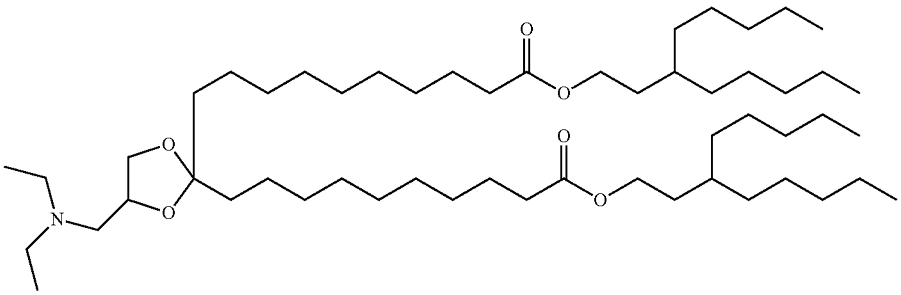 [SMILES: CCCCCC(CCCCC)CCOC(=O)CCCCCCCCCC1(CCCCCCCCCC(=O)OCCC(CCCCC)CCCCC)OCC(CN(CC)CC)O1]

-continued
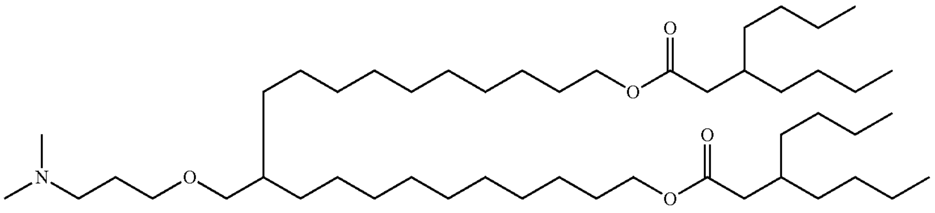 [SMILES: CCCCC(CCCC)CC(=O)OCCCCCCCCCCC(CCCCCCCCCCOC(=O)CC(CCCC)CCCC)COCCCN(C)C]
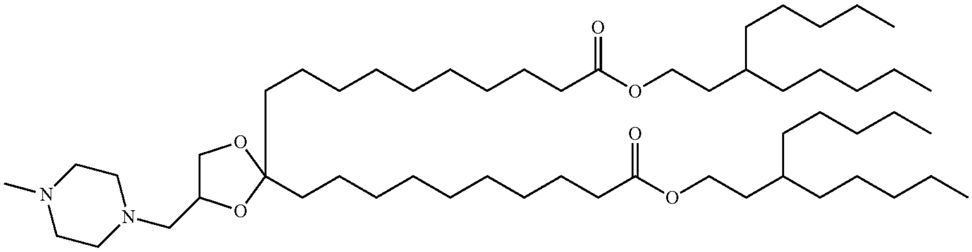 [SMILES: CCCCCC(CCCCC)CCOC(=O)CCCCCCCCCC1(CCCCCCCCCC(=O)OCCC(CCCCC)CCCCC)OCC(CN2CCN(C)CC2)O1]
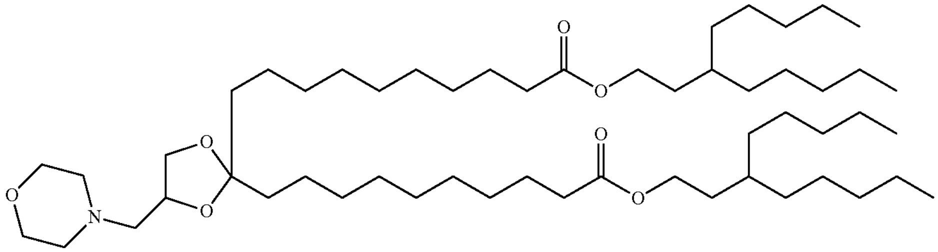 [SMILES: CCCCCC(CCCCC)CCOC(=O)CCCCCCCCCC1(CCCCCCCCCC(=O)OCCC(CCCCC)CCCCC)OCC(CN2CCOCC2)O1]
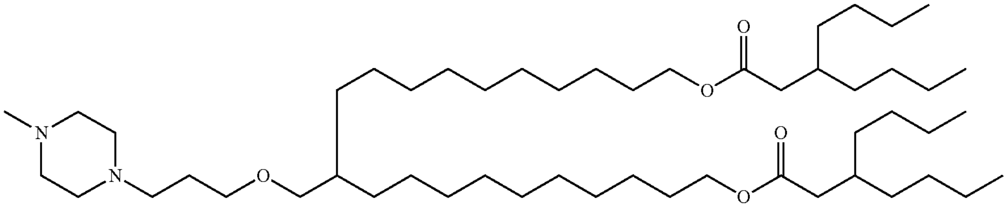 [SMILES: CCCCC(CCCC)CC(=O)OCCCCCCCCCCC(CCCCCCCCCCOC(=O)CC(CCCC)CCCC)COCCCN1CCN(C)CC1]
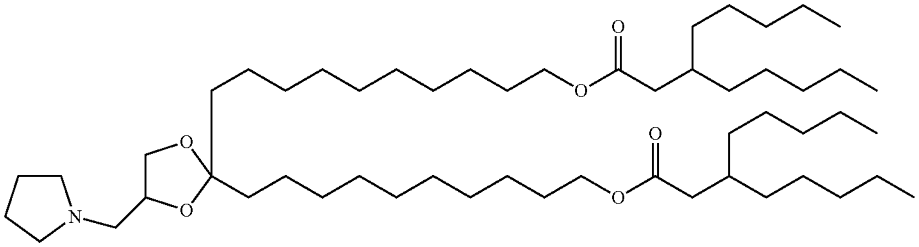 [SMILES: CCCCCC(CCCCC)CC(=O)OCCCCCCCCCCC1(CCCCCCCCCCOC(=O)CC(CCCCC)CCCCC)OCC(CN2CCCC2)O1]
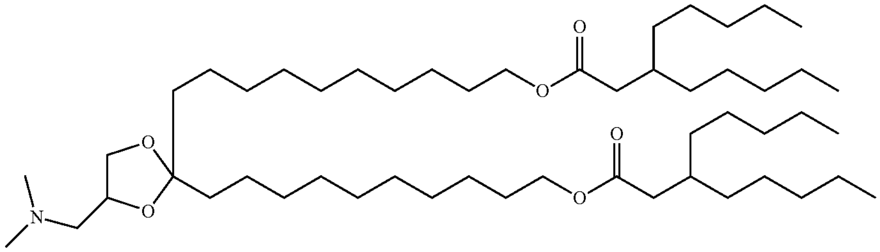 [SMILES: CCCCCC(CCCCC)CC(=O)OCCCCCCCCCCC1(CCCCCCCCCCOC(=O)CC(CCCCC)CCCCC)OCC(CN(C)C)O1]

-continued
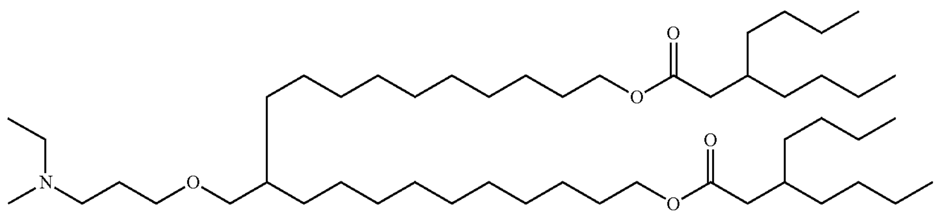 [SMILES: CCCCC(CCCC)CC(=O)OCCCCCCCCCCC(CCCCCCCCCCOC(=O)CC(CCCC)CCCC)COCCCN(C)CC]
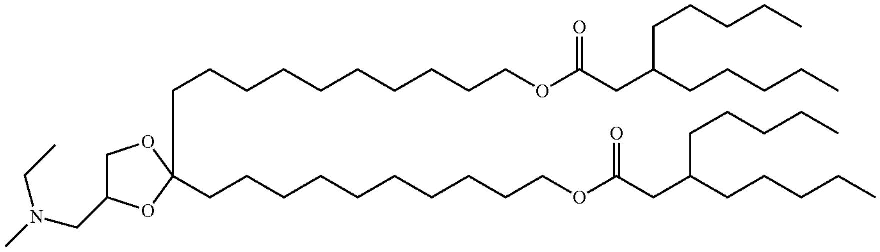 [SMILES: CCCCCC(CCCCC)CC(=O)OCCCCCCCCCCC1(CCCCCCCCCCOC(=O)CC(CCCCC)CCCCC)OCC(CN(C)CC)O1]
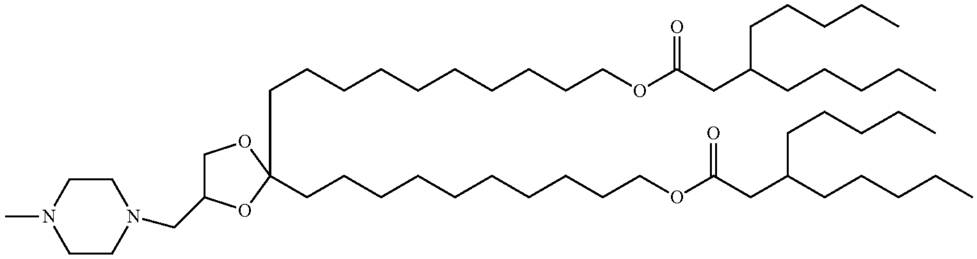 [SMILES: CCCCCC(CCCCC)CC(=O)OCCCCCCCCCCC1(CCCCCCCCCCOC(=O)CC(CCCCC)CCCCC)OCC(CN2CCN(C)CC2)O1]
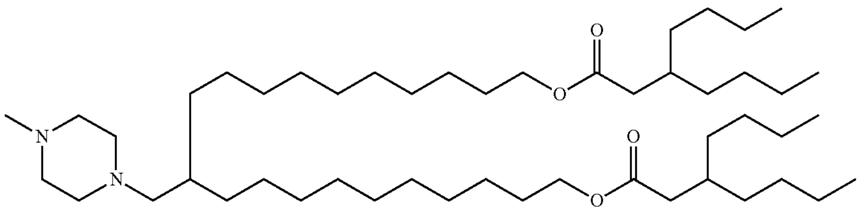 [SMILES: CCCCC(CCCC)CC(=O)OCCCCCCCCCCC(CCCCCCCCCCOC(=O)CC(CCCC)CCCC)CN1CCN(C)CC1]
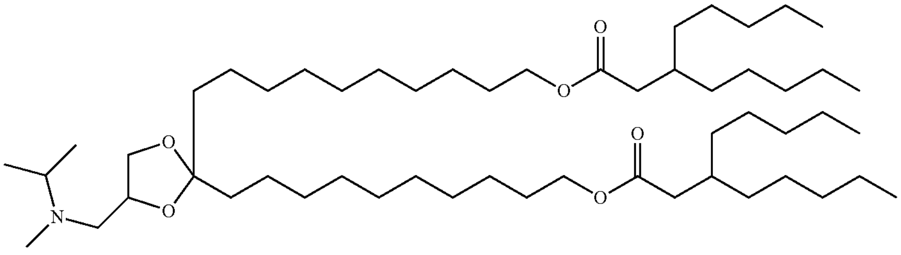 [SMILES: CCCCCC(CCCCC)CC(=O)OCCCCCCCCCCC1(CCCCCCCCCCOC(=O)CC(CCCCC)CCCCC)OCC(CN(C)C(C)C)O1]
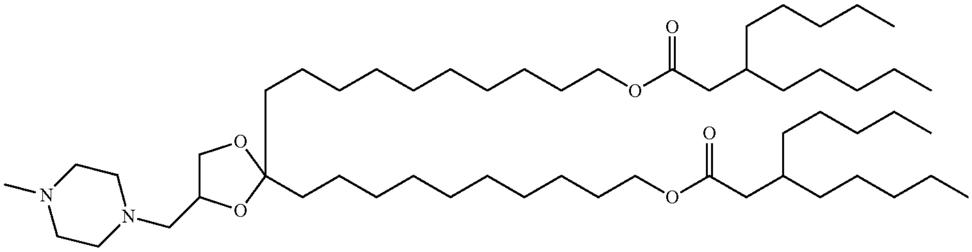 [SMILES: CCCCCC(CCCCC)CC(=O)OCCCCCCCCCCC1(CCCCCCCCCCOC(=O)CC(CCCCC)CCCCC)OCC(CN2CCN(C)CC2)O1]

-continued
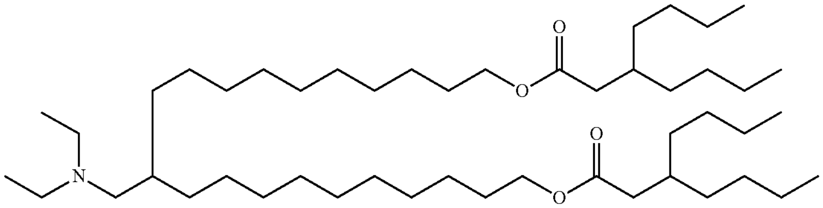 [SMILES: CCCCC(CCCC)CC(=O)OCCCCCCCCCCC(CCCCCCCCCCOC(=O)CC(CCCC)CCCC)CN(CC)CC]
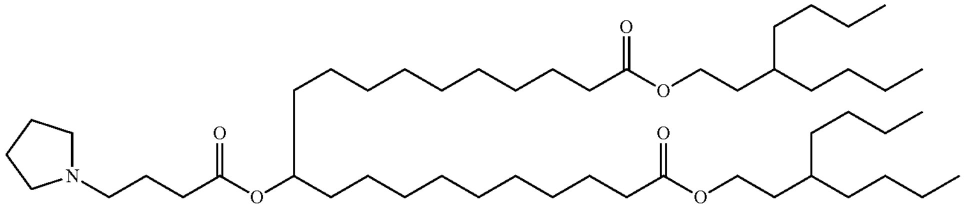 [SMILES: CCCCC(CCCC)CCOC(=O)CCCCCCCCCC(CCCCCCCCCC(=O)OCCC(CCCC)CCCC)OC(=O)CCCN1CCCC1]
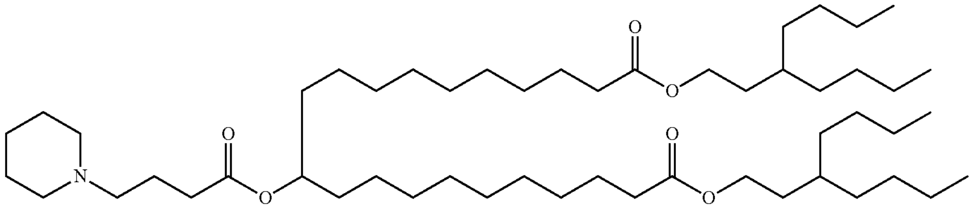 [SMILES: CCCCC(CCCC)CCOC(=O)CCCCCCCCCC(CCCCCCCCCC(=O)OCCC(CCCC)CCCC)OC(=O)CCCN1CCCCC1]
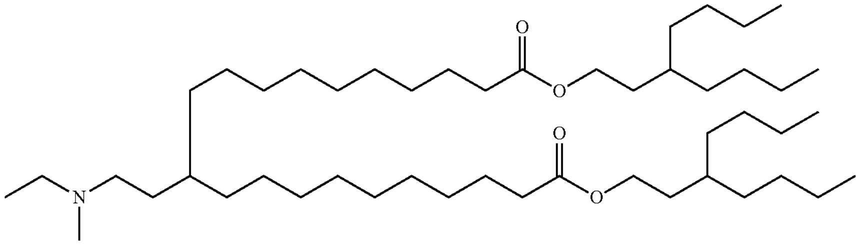 [SMILES: CCCCC(CCCC)CCOC(=O)CCCCCCCCCC(CCCCCCCCCC(=O)OCCC(CCCC)CCCC)CCN(C)CC]
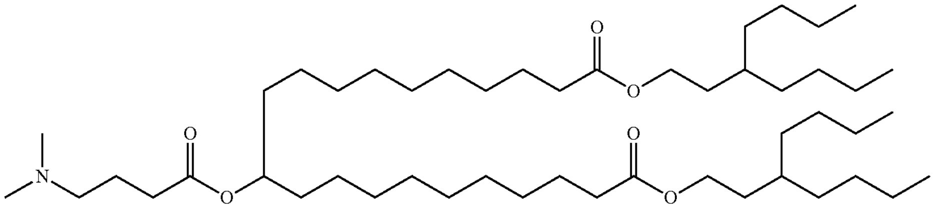 [SMILES: CCCCC(CCCC)CCOC(=O)CCCCCCCCCC(CCCCCCCCCC(=O)OCCC(CCCC)CCCC)OC(=O)CCCN(C)C]
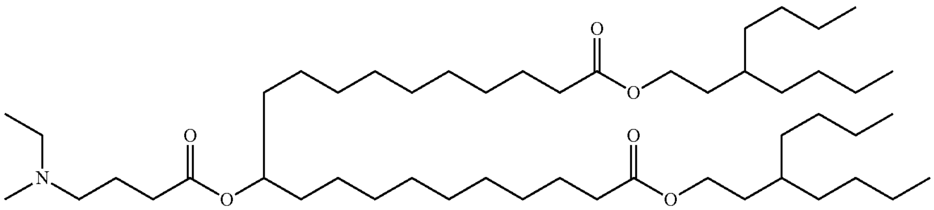 [SMILES: CCCCC(CCCC)CCOC(=O)CCCCCCCCCC(CCCCCCCCCC(=O)OCCC(CCCC)CCCC)OC(=O)CCCN(C)CC]
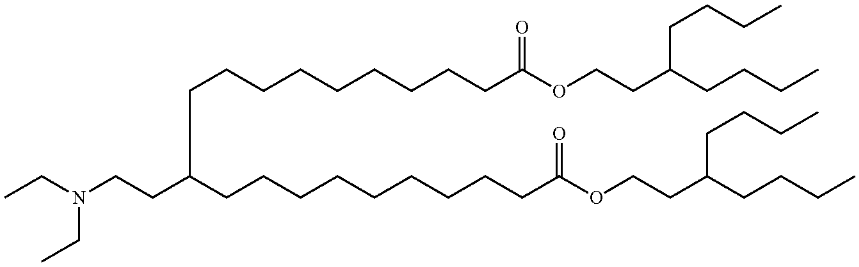 [SMILES: CCCCC(CCCC)CCOC(=O)CCCCCCCCCC(CCCCCCCCCC(=O)OCCC(CCCC)CCCC)CCN(CC)CC]

-continued
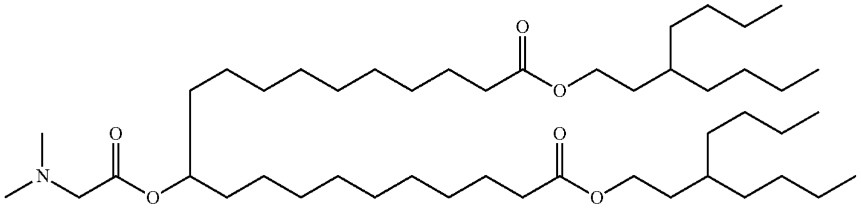 [SMILES: CCCCC(CCCC)CCOC(=O)CCCCCCCCCC(CCCCCCCCCC(=O)OCCC(CCCC)CCCC)OC(=O)CN(C)C]
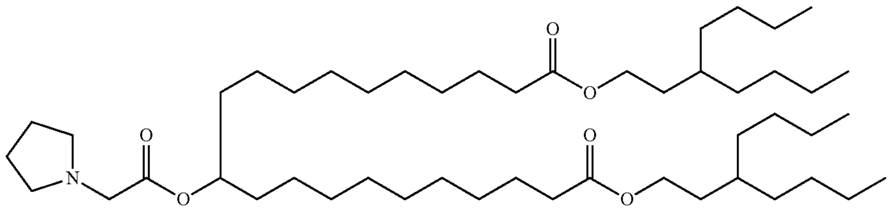 [SMILES: CCCCC(CCCC)CCOC(=O)CCCCCCCCCC(CCCCCCCCCC(=O)OCCC(CCCC)CCCC)OC(=O)CN1CCCC1]
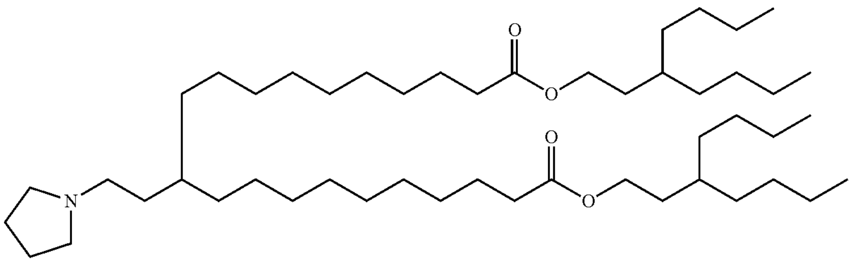 [SMILES: CCCCC(CCCC)CCOC(=O)CCCCCCCCCC(CCCCCCCCCC(=O)OCCC(CCCC)CCCC)CCN1CCCC1]
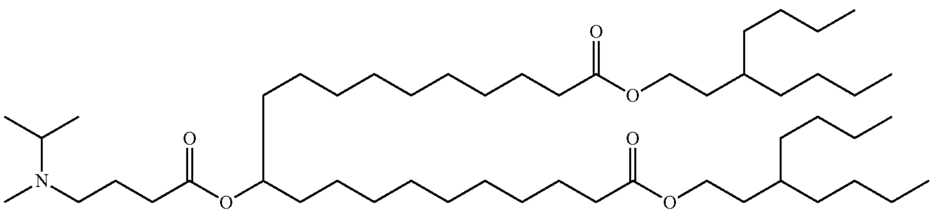 [SMILES: CCCCC(CCCC)CCOC(=O)CCCCCCCCCC(CCCCCCCCCC(=O)OCCC(CCCC)CCCC)OC(=O)CCCN(C)C(C)C]
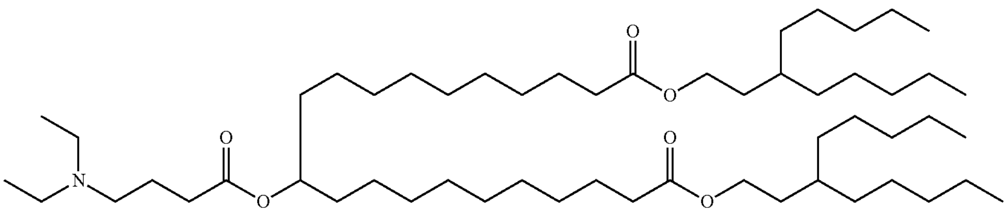 [SMILES: CCCCCC(CCCCC)CCOC(=O)CCCCCCCCCC(CCCCCCCCCC(=O)OCCC(CCCCC)CCCCC)OC(=O)CCCN(CC)CC]
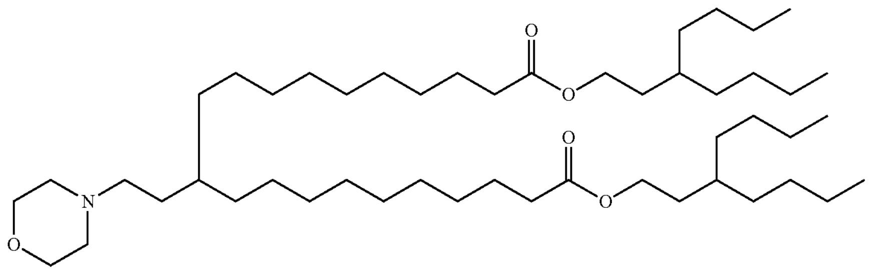 [SMILES: CCCCC(CCCC)CCOC(=O)CCCCCCCCCC(CCCCCCCCCC(=O)OCCC(CCCC)CCCC)CCN1CCOCC1]
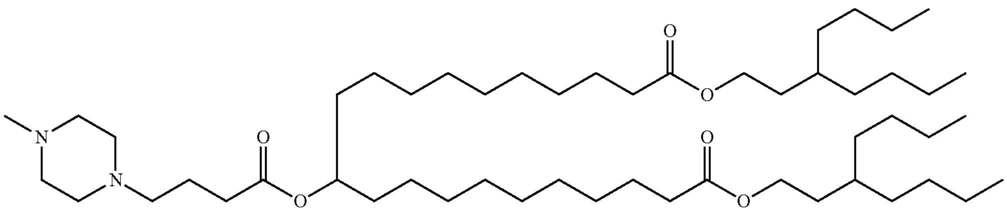 [SMILES: CCCCC(CCCC)CCOC(=O)CCCCCCCCCC(CCCCCCCCCC(=O)OCCC(CCCC)CCCC)OC(=O)CCCN1CCN(C)CC1]

-continued
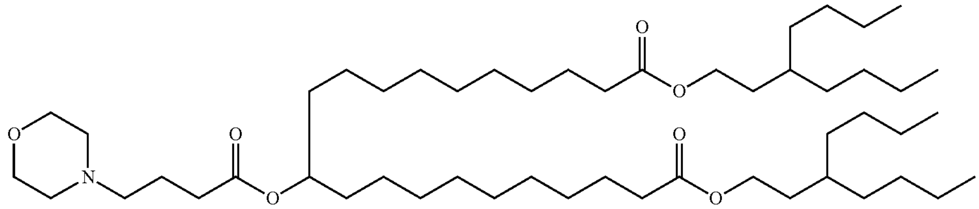 [SMILES: CCCCC(CCCC)CCOC(=O)CCCCCCCCCC(CCCCCCCCCC(=O)OCCC(CCCC)CCCC)OC(=O)CCCN1CCOCC1]
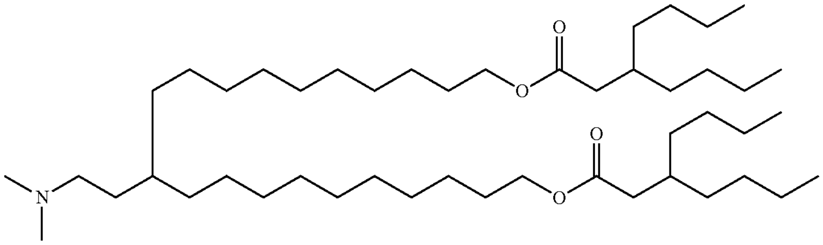 [SMILES: CCCCC(CCCC)CC(=O)OCCCCCCCCCCC(CCCCCCCCCCOC(=O)CC(CCCC)CCCC)CCN(C)C]
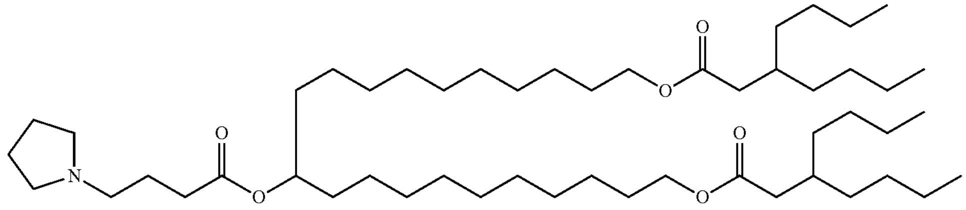 [SMILES: CCCCC(CCCC)CC(=O)OCCCCCCCCCCC(CCCCCCCCCCOC(=O)CC(CCCC)CCCC)OC(=O)CCCN1CCCC1]
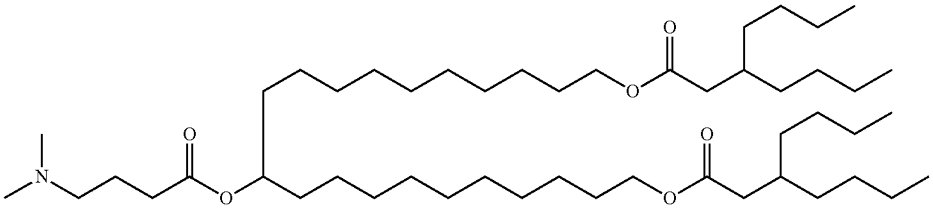 [SMILES: CCCCC(CCCC)CC(=O)OCCCCCCCCCCC(CCCCCCCCCCOC(=O)CC(CCCC)CCCC)OC(=O)CCCN(C)C]
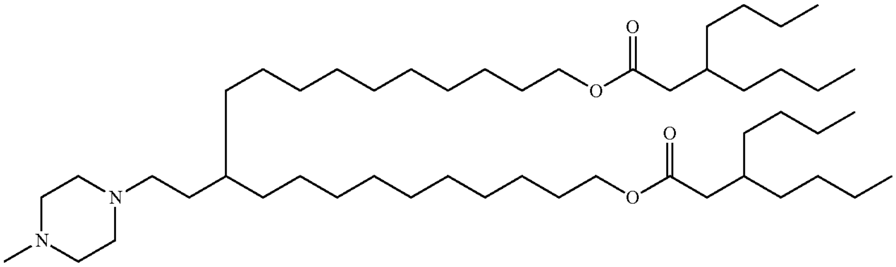 [SMILES: CCCCC(CCCC)CC(=O)OCCCCCCCCCCC(CCCCCCCCCCOC(=O)CC(CCCC)CCCC)CCN1CCN(C)CC1]
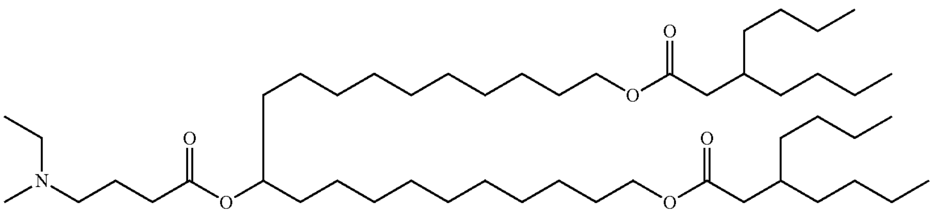 [SMILES: CCCCC(CCCC)CC(=O)OCCCCCCCCCCC(CCCCCCCCCCOC(=O)CC(CCCC)CCCC)OC(=O)CCCN(C)CC]
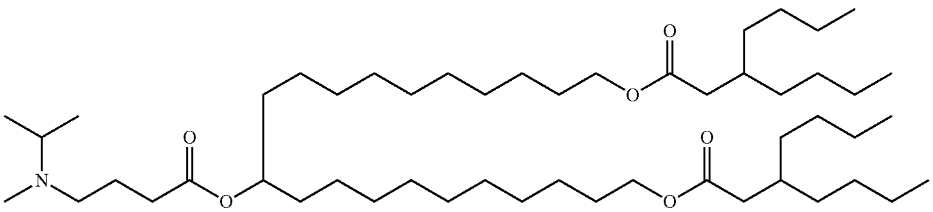 [SMILES: CCCCC(CCCC)CC(=O)OCCCCCCCCCCC(CCCCCCCCCCOC(=O)CC(CCCC)CCCC)OC(=O)CCCN(C)C(C)C]

-continued
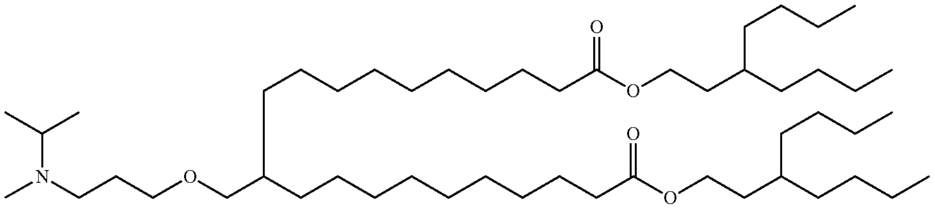 [SMILES: CCCCC(CCCC)CCOC(=O)CCCCCCCCCC(CCCCCCCCCC(=O)OCCC(CCCC)CCCC)COCCCN(C)C(C)C]
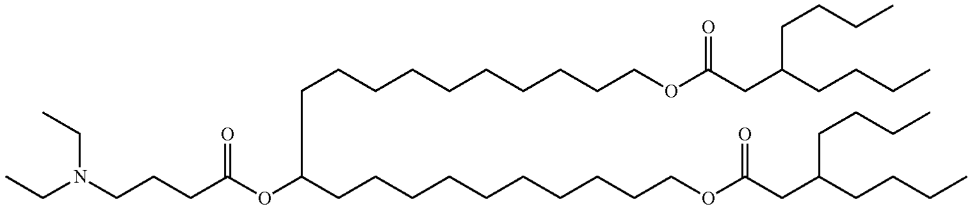 [SMILES: CCCCC(CCCC)CC(=O)OCCCCCCCCCCC(CCCCCCCCCCOC(=O)CC(CCCC)CCCC)OC(=O)CCCN(CC)CC]
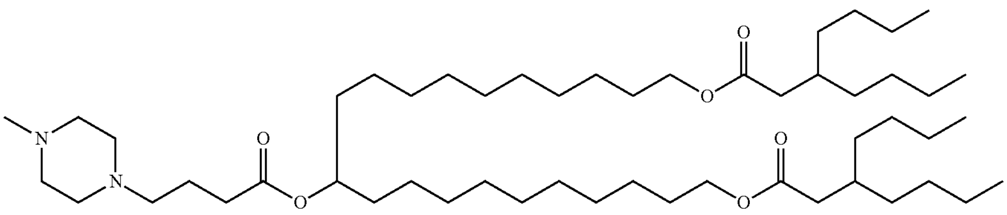 [SMILES: CCCCC(CCCC)CC(=O)OCCCCCCCCCCC(CCCCCCCCCCOC(=O)CC(CCCC)CCCC)OC(=O)CCCN1CCN(C)CC1]
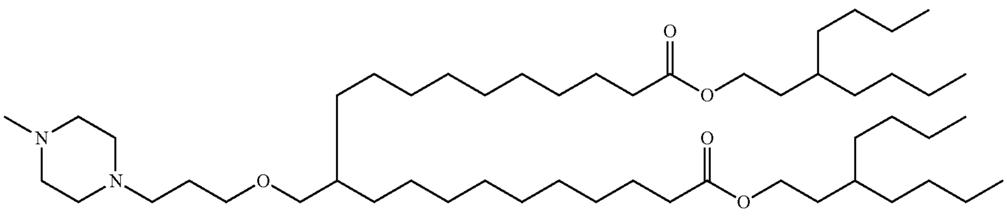 [SMILES: CCCCC(CCCC)CCOC(=O)CCCCCCCCCC(CCCCCCCCCC(=O)OCCC(CCCC)CCCC)COCCCN1CCN(C)CC1]
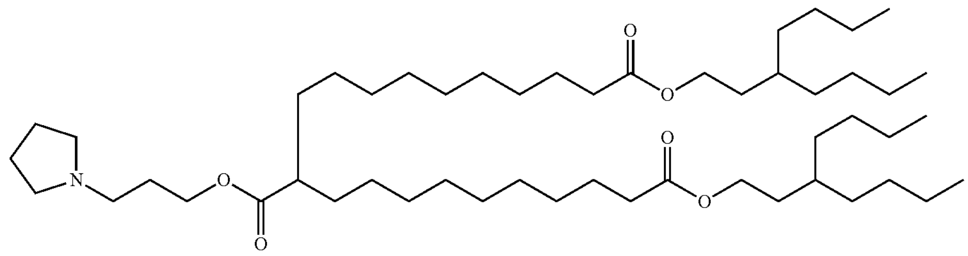 [SMILES: CCCCC(CCCC)CCOC(=O)CCCCCCCCCC(CCCCCCCCCC(=O)OCCC(CCCC)CCCC)C(=O)OCCCN1CCCC1]
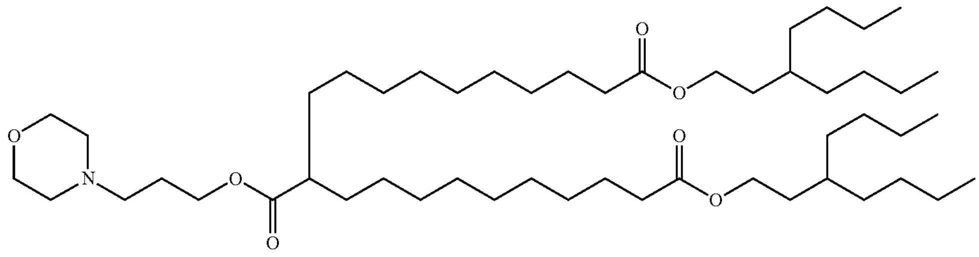 [SMILES: CCCCC(CCCC)CCOC(=O)CCCCCCCCCC(CCCCCCCCCC(=O)OCCC(CCCC)CCCC)C(=O)OCCCN1CCOCC1]
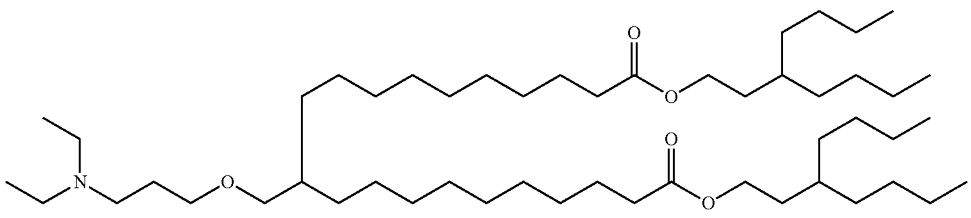 [SMILES: CCCCC(CCCC)CCOC(=O)CCCCCCCCCC(CCCCCCCCCC(=O)OCCC(CCCC)CCCC)COCCCN(CC)CC]

-continued
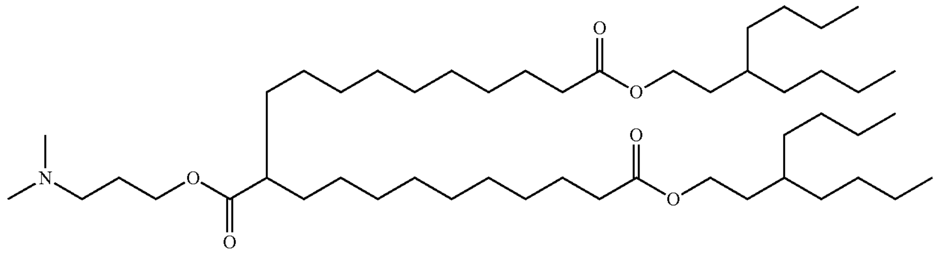 [SMILES: CCCCC(CCCC)CCOC(=O)CCCCCCCCCC(CCCCCCCCCC(=O)OCCC(CCCC)CCCC)C(=O)OCCCN(C)C]
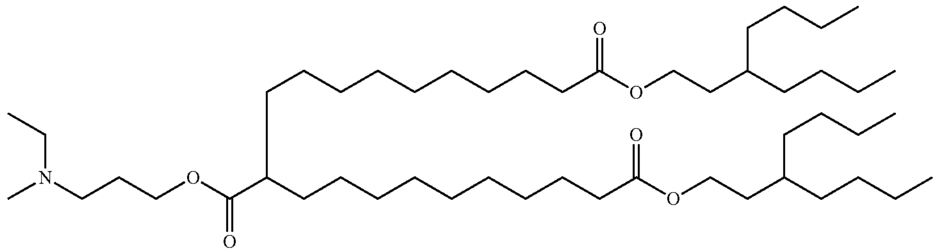 [SMILES: CCCCC(CCCC)CCOC(=O)CCCCCCCCCC(CCCCCCCCCC(=O)OCCC(CCCC)CCCC)C(=O)OCCCN(C)CC]
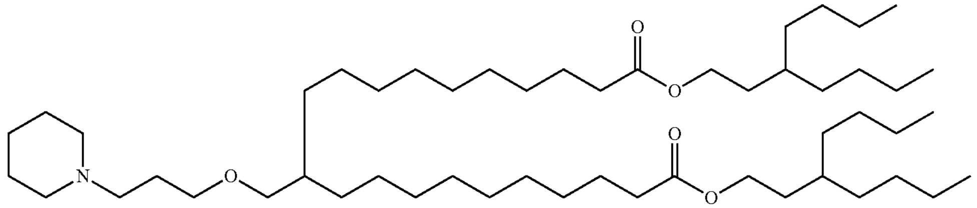 [SMILES: CCCCC(CCCC)CCOC(=O)CCCCCCCCCC(CCCCCCCCCC(=O)OCCC(CCCC)CCCC)COCCCN1CCCCC1]
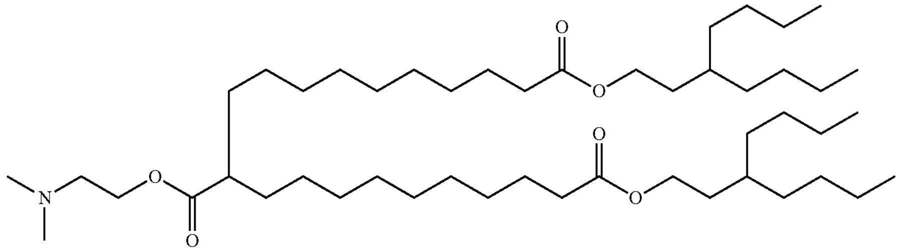 [SMILES: CCCCC(CCCC)CCOC(=O)CCCCCCCCCC(CCCCCCCCCC(=O)OCCC(CCCC)CCCC)C(=O)OCCN(C)C]
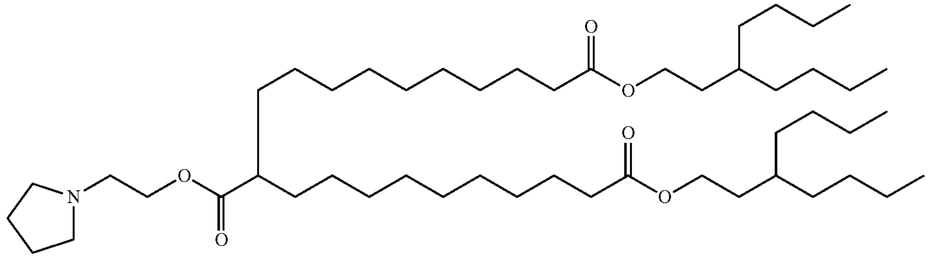 [SMILES: CCCCC(CCCC)CCOC(=O)CCCCCCCCCC(CCCCCCCCCC(=O)OCCC(CCCC)CCCC)C(=O)OCCN1CCCC1]
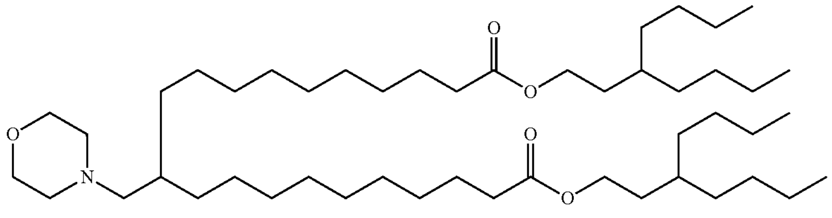 [SMILES: CCCCC(CCCC)CCOC(=O)CCCCCCCCCC(CCCCCCCCCC(=O)OCCC(CCCC)CCCC)CN1CCOCC1]

-continued
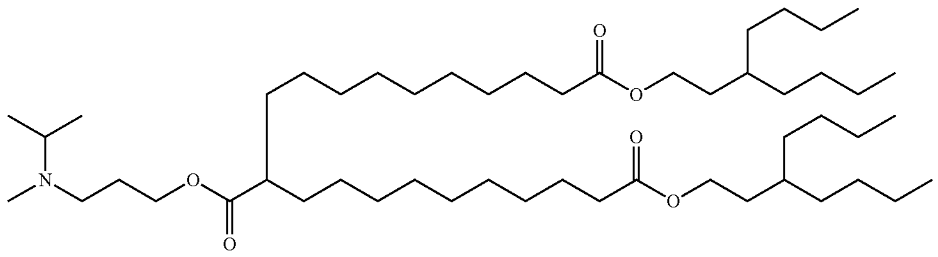 [SMILES: CCCCC(CCCC)CCOC(=O)CCCCCCCCCC(CCCCCCCCCC(=O)OCCC(CCCC)CCCC)C(=O)OCCCN(C)C(C)C]
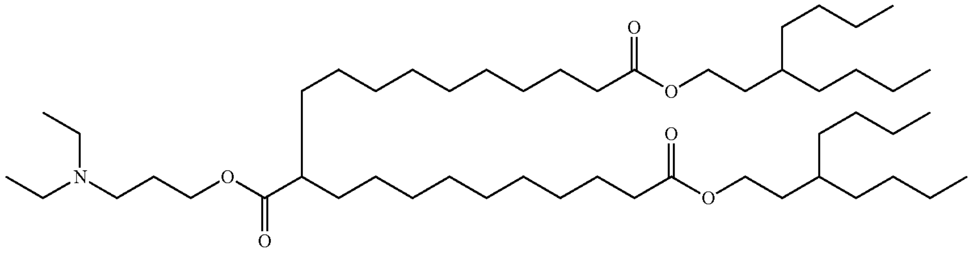 [SMILES: CCCCC(CCCC)CCOC(=O)CCCCCCCCCC(CCCCCCCCCC(=O)OCCC(CCCC)CCCC)C(=O)OCCCN(CC)CC]
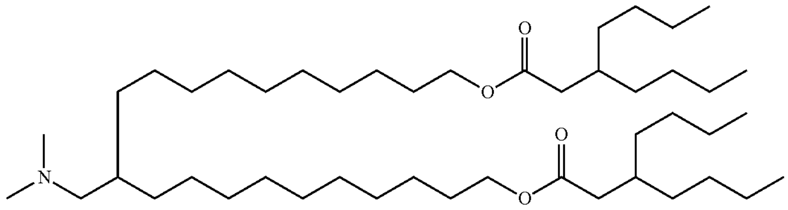 [SMILES: CCCCC(CCCC)CC(=O)OCCCCCCCCCCC(CCCCCCCCCCOC(=O)CC(CCCC)CCCC)CN(C)C]
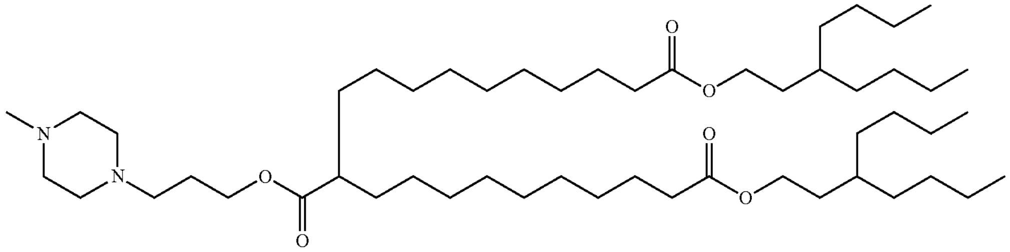 [SMILES: CCCCC(CCCC)CCOC(=O)CCCCCCCCCC(CCCCCCCCCC(=O)OCCC(CCCC)CCCC)C(=O)OCCCN1CCN(C)CC1]
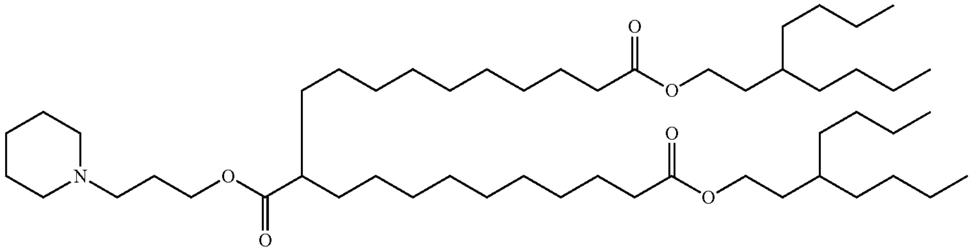 [SMILES: CCCCC(CCCC)CCOC(=O)CCCCCCCCCC(CCCCCCCCCC(=O)OCCC(CCCC)CCCC)C(=O)OCCCN1CCCCC1]
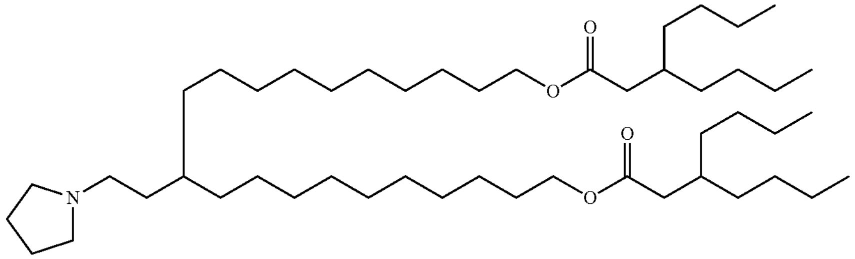 [SMILES: CCCCC(CCCC)CC(=O)OCCCCCCCCCCC(CCCCCCCCCCOC(=O)CC(CCCC)CCCC)CCN1CCCC1]

-continued
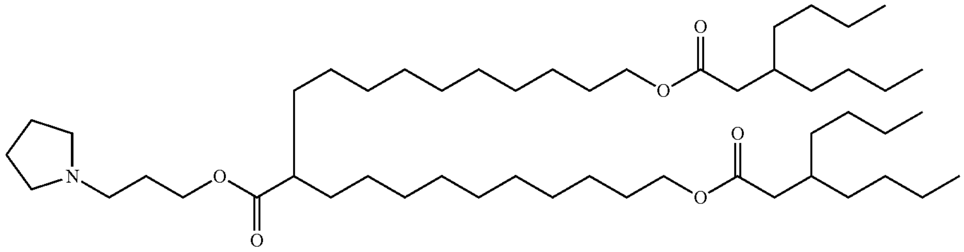 [SMILES: CCCCC(CCCC)CC(=O)OCCCCCCCCCCC(CCCCCCCCCCOC(=O)CC(CCCC)CCCC)C(=O)OCCCN1CCCC1]
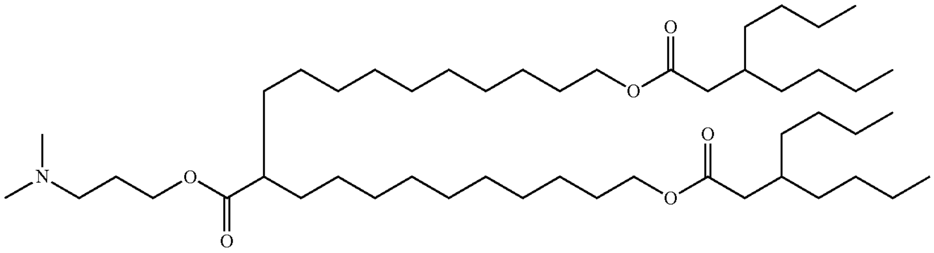 [SMILES: CCCCC(CCCC)CC(=O)OCCCCCCCCCCC(CCCCCCCCCCOC(=O)CC(CCCC)CCCC)C(=O)OCCCN(C)C]
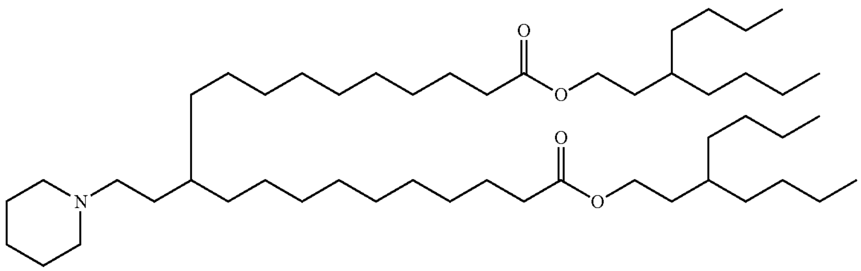 [SMILES: CCCCC(CCCC)CCOC(=O)CCCCCCCCCC(CCCCCCCCCC(=O)OCCC(CCCC)CCCC)CCN1CCCCC1]
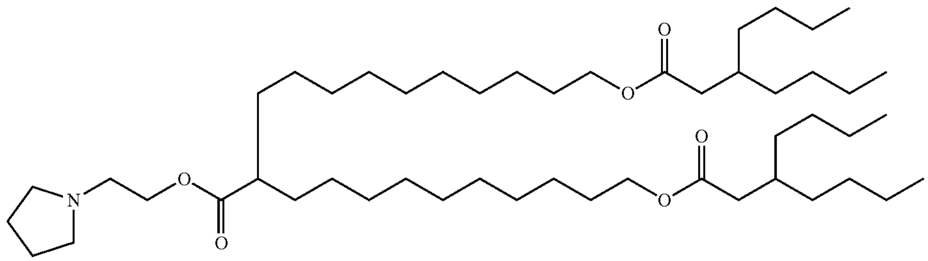 [SMILES: CCCCC(CCCC)CC(=O)OCCCCCCCCCCC(CCCCCCCCCCOC(=O)CC(CCCC)CCCC)C(=O)OCCN1CCCC1]
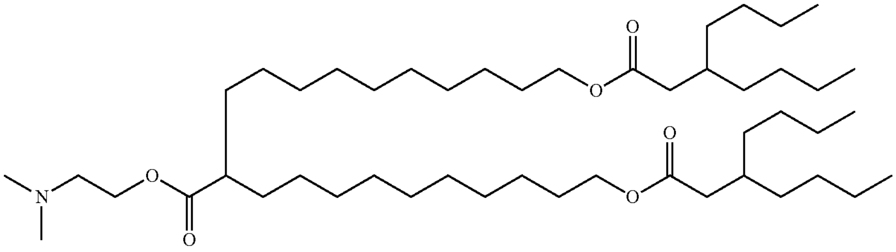 [SMILES: CCCCC(CCCC)CC(=O)OCCCCCCCCCCC(CCCCCCCCCCOC(=O)CC(CCCC)CCCC)C(=O)OCCN(C)C]
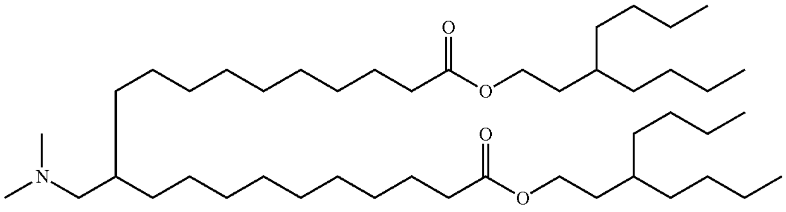 [SMILES: CCCCC(CCCC)CCOC(=O)CCCCCCCCCC(CCCCCCCCCC(=O)OCCC(CCCC)CCCC)CN(C)C]

-continued
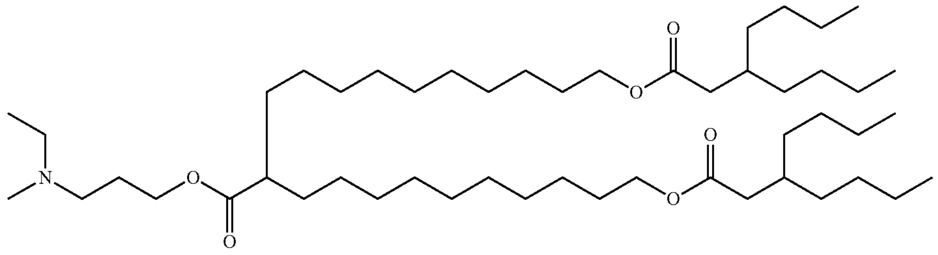 [SMILES: CCCCC(CCCC)CC(=O)OCCCCCCCCCCC(CCCCCCCCCCOC(=O)CC(CCCC)CCCC)C(=O)OCCCN(C)CC]
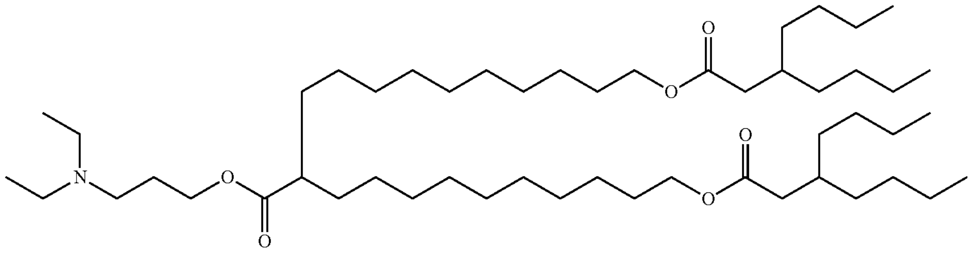 [SMILES: CCCCC(CCCC)CC(=O)OCCCCCCCCCCC(CCCCCCCCCCOC(=O)CC(CCCC)CCCC)C(=O)OCCCN(CC)CC]
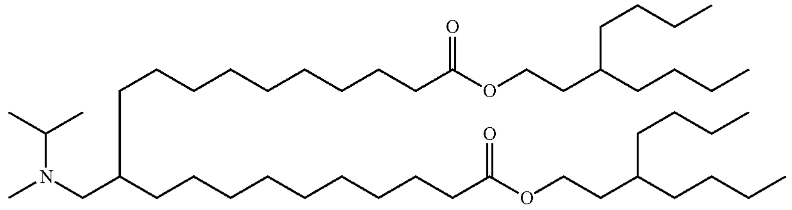 [SMILES: CCCCC(CCCC)CCOC(=O)CCCCCCCCCC(CCCCCCCCCC(=O)OCCC(CCCC)CCCC)CN(C)C(C)C]
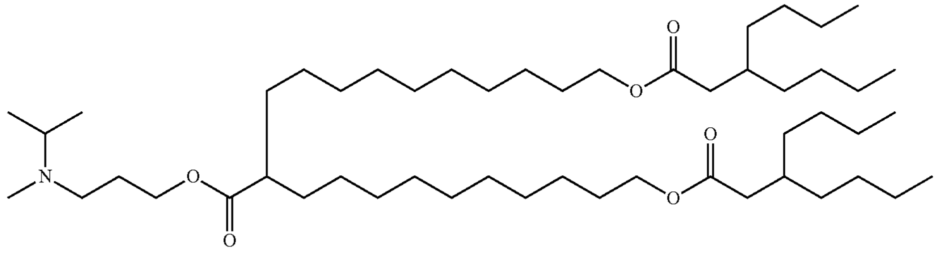 [SMILES: CCCCC(CCCC)CC(=O)OCCCCCCCCCCC(CCCCCCCCCCOC(=O)CC(CCCC)CCCC)C(=O)OCCCN(C)C(C)C]
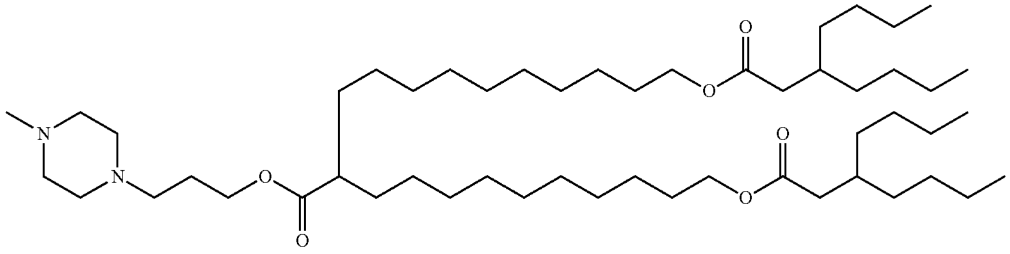 [SMILES: CCCCC(CCCC)CC(=O)OCCCCCCCCCCC(CCCCCCCCCCOC(=O)CC(CCCC)CCCC)C(=O)OCCCN1CCN(C)CC1]
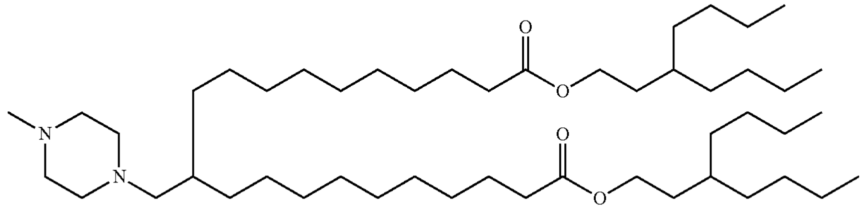 [SMILES: CCCCC(CCCC)CCOC(=O)CCCCCCCCCC(CCCCCCCCCC(=O)OCCC(CCCC)CCCC)CN1CCN(C)CC1]

-continued
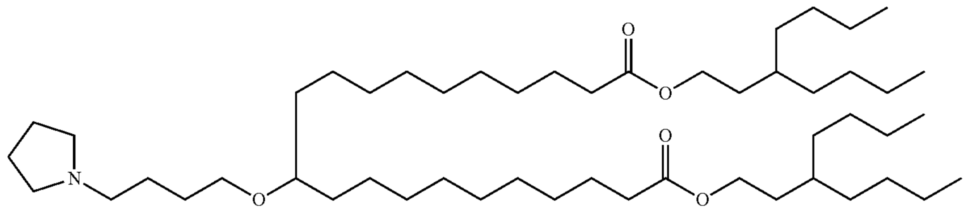 [SMILES: CCCCC(CCCC)CCOC(=O)CCCCCCCCCC(CCCCCCCCCC(=O)OCCC(CCCC)CCCC)OCCCCN1CCCC1]
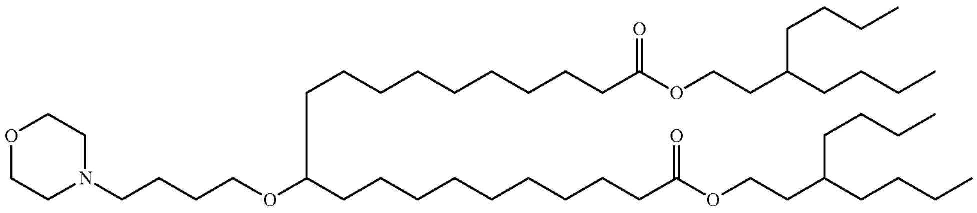
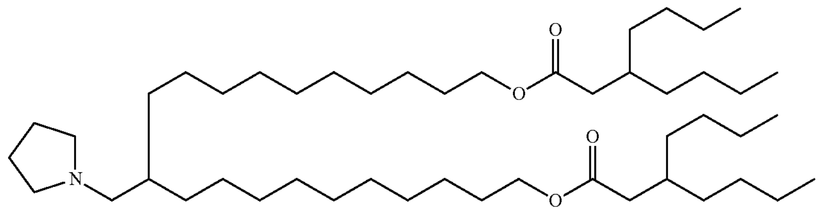 [SMILES: CCCCC(CCCC)CC(=O)OCCCCCCCCCCC(CCCCCCCCCCOC(=O)CC(CCCC)CCCC)CN1CCCC1]
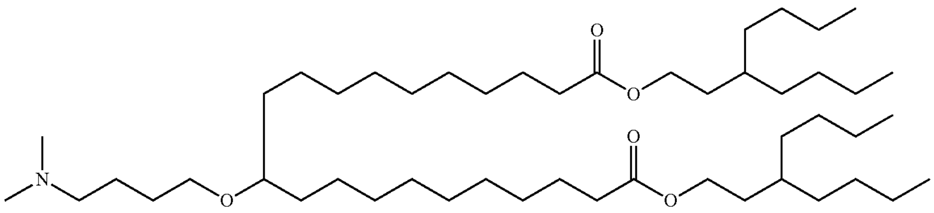 [SMILES: CCCCC(CCCC)CCOC(=O)CCCCCCCCCC(CCCCCCCCCC(=O)OCCC(CCCC)CCCC)OCCCCN(C)C]
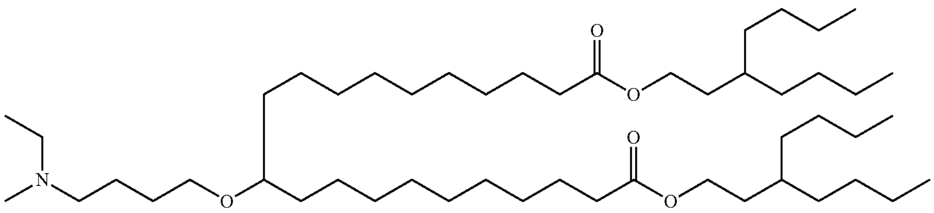 [SMILES: CCCCC(CCCC)CCOC(=O)CCCCCCCCCC(CCCCCCCCCC(=O)OCCC(CCCC)CCCC)OCCCCN(C)CC]
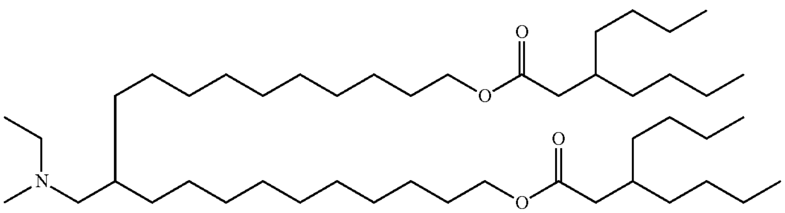 [SMILES: CCCCC(CCCC)CC(=O)OCCCCCCCCCCC(CCCCCCCCCCOC(=O)CC(CCCC)CCCC)CN(C)CC]
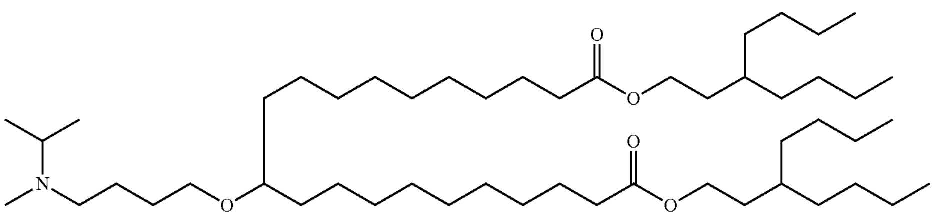 [SMILES: CCCCC(CCCC)CCOC(=O)CCCCCCCCCC(CCCCCCCCCC(=O)OCCC(CCCC)CCCC)OCCCCN(C)C(C)C]

-continued
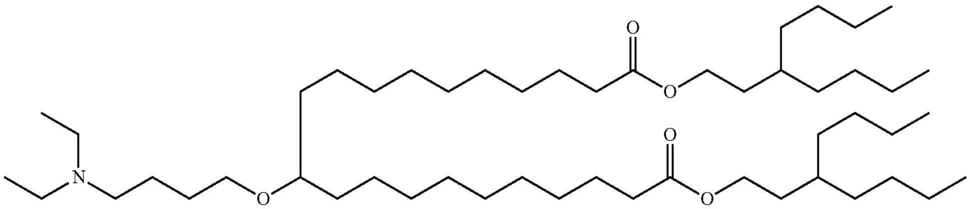 [SMILES: CCCCC(CCCC)CCOC(=O)CCCCCCCCCC(CCCCCCCCCC(=O)OCCC(CCCC)CCCC)OCCCCN(CC)CC]
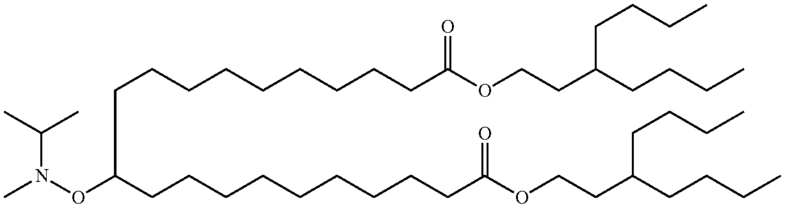 [SMILES: CCCCC(CCCC)CCOC(=O)CCCCCCCCCC(CCCCCCCCCC(=O)OCCC(CCCC)CCCC)ON(C)C(C)C]
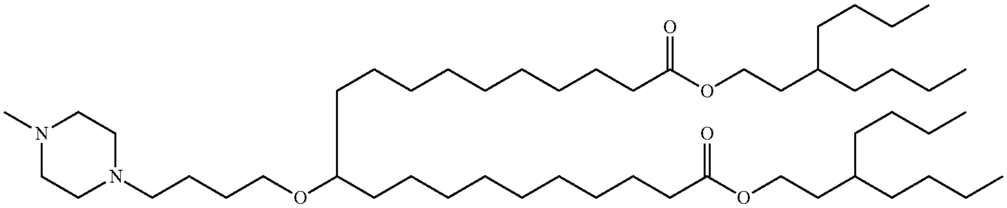 [SMILES: CCCCC(CCCC)CCOC(=O)CCCCCCCCCC(CCCCCCCCCC(=O)OCCC(CCCC)CCCC)OCCCCN1CCN(C)CC1]
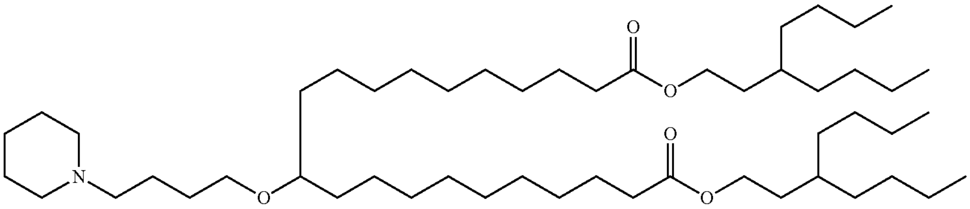 [SMILES: CCCCC(CCCC)CCOC(=O)CCCCCCCCCC(CCCCCCCCCC(=O)OCCC(CCCC)CCCC)OCCCCN1CCCCC1]
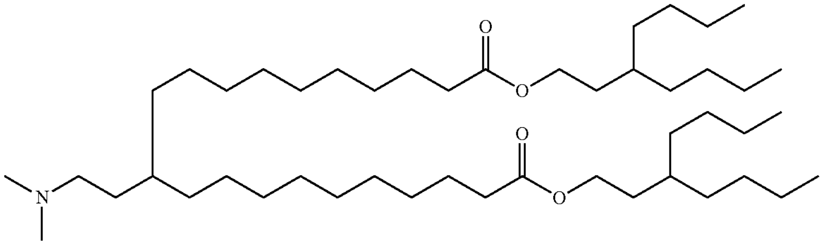 [SMILES: CCCCC(CCCC)CCOC(=O)CCCCCCCCCC(CCCCCCCCCC(=O)OCCC(CCCC)CCCC)CCN(C)C]
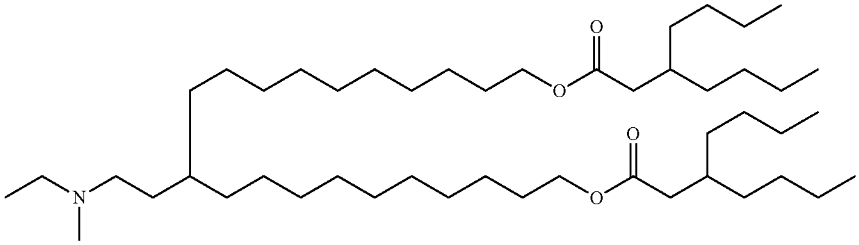 [SMILES: CCCCC(CCCC)CC(=O)OCCCCCCCCCCC(CCCCCCCCCCOC(=O)CC(CCCC)CCCC)CCN(C)CC]
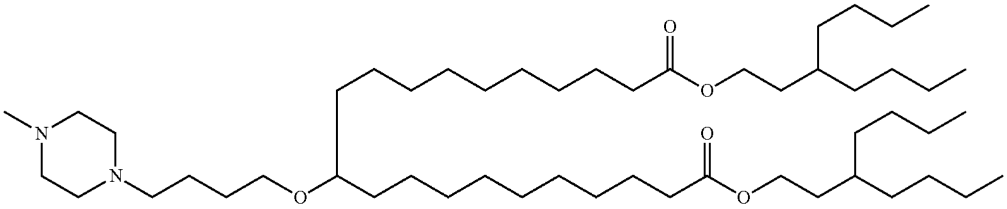 [SMILES: CCCCC(CCCC)CCOC(=O)CCCCCCCCCC(CCCCCCCCCC(=O)OCCC(CCCC)CCCC)OCCCCN1CCN(C)CC1]

-continued
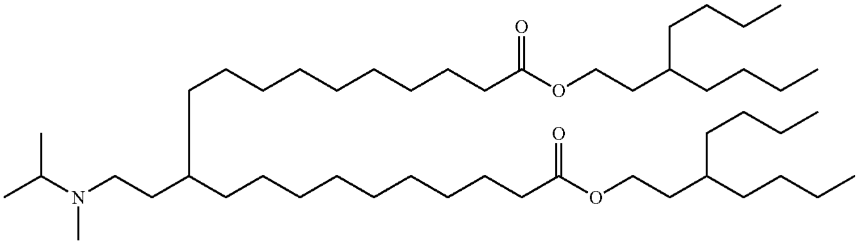 [SMILES: CCCCC(CCCC)CCOC(=O)CCCCCCCCCC(CCCCCCCCCC(=O)OCCC(CCCC)CCCC)CCN(C)C(C)C]
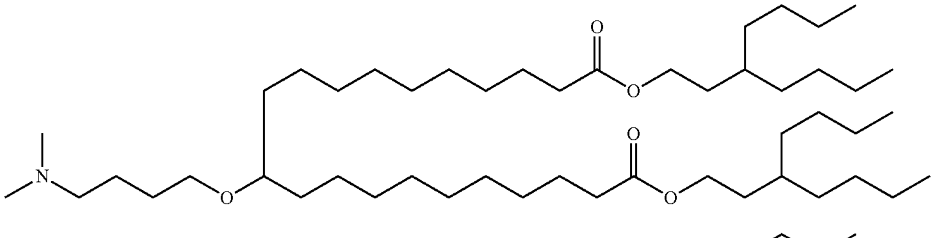
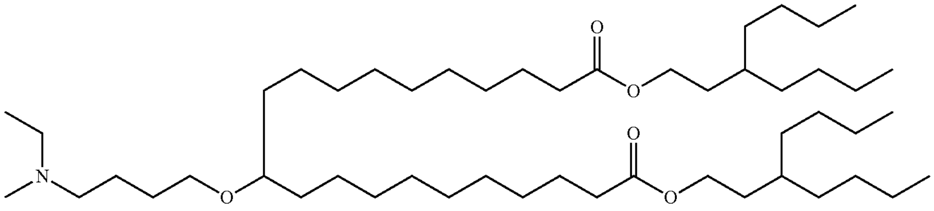 [SMILES: CCCCC(CCCC)CCOC(=O)CCCCCCCCCC(CCCCCCCCCC(=O)OCCC(CCCC)CCCC)OCCCCN(C)CC]
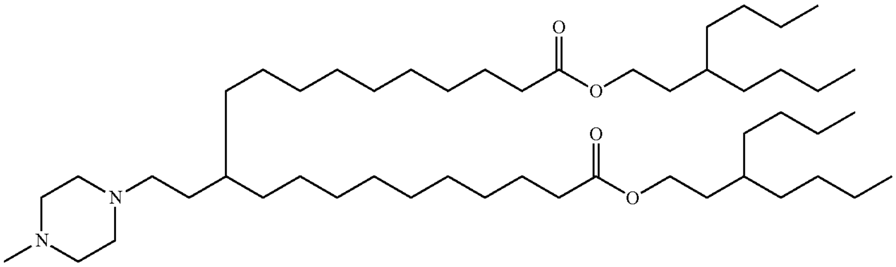 [SMILES: CCCCC(CCCC)CCOC(=O)CCCCCCCCCC(CCCCCCCCCC(=O)OCCC(CCCC)CCCC)CCN1CCN(C)CC1]
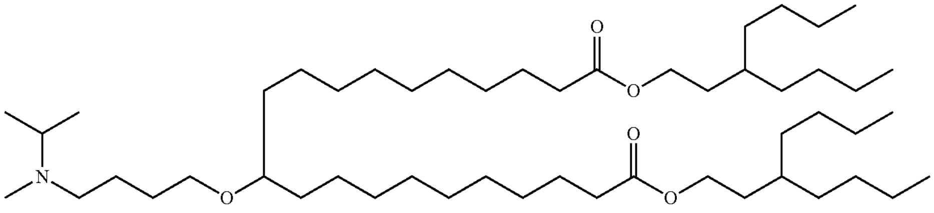 [SMILES: CCCCC(CCCC)CCOC(=O)CCCCCCCCCC(CCCCCCCCCC(=O)OCCC(CCCC)CCCC)OCCCCN(C)C(C)C]
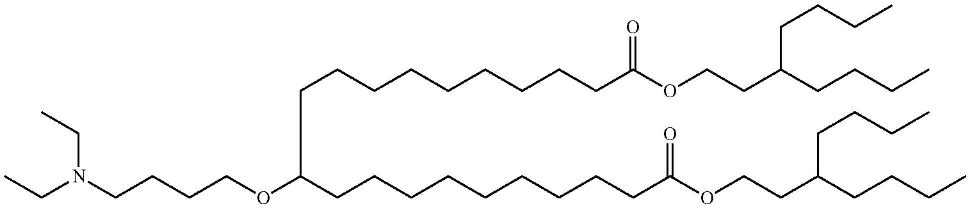 [SMILES: CCCCC(CCCC)CCOC(=O)CCCCCCCCCC(CCCCCCCCCC(=O)OCCC(CCCC)CCCC)OCCCCN(CC)CC]
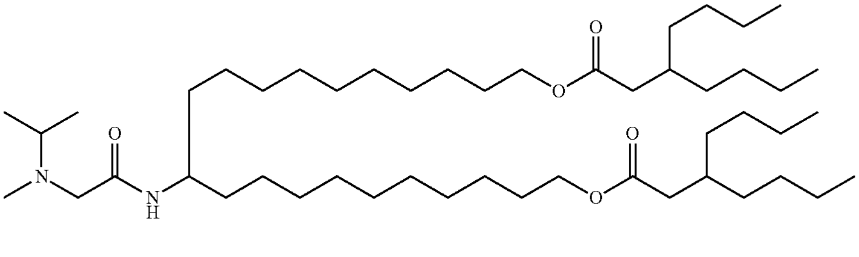 [SMILES: CCCCC(CCCC)CC(=O)OCCCCCCCCCCC(CCCCCCCCCCOC(=O)CC(CCCC)CCCC)NC(=O)CN(C)C(C)C]

-continued
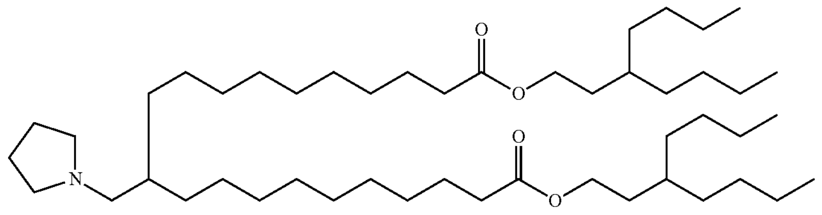 [SMILES: CCCCC(CCCC)CCOC(=O)CCCCCCCCCC(CCCCCCCCCC(=O)OCCC(CCCC)CCCC)CN1CCCC1]
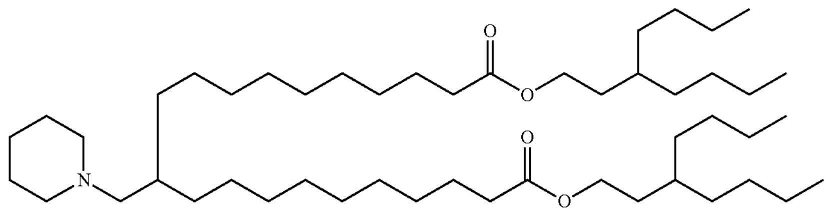 [SMILES: CCCCC(CCCC)CCOC(=O)CCCCCCCCCC(CCCCCCCCCC(=O)OCCC(CCCC)CCCC)CN1CCCCC1]
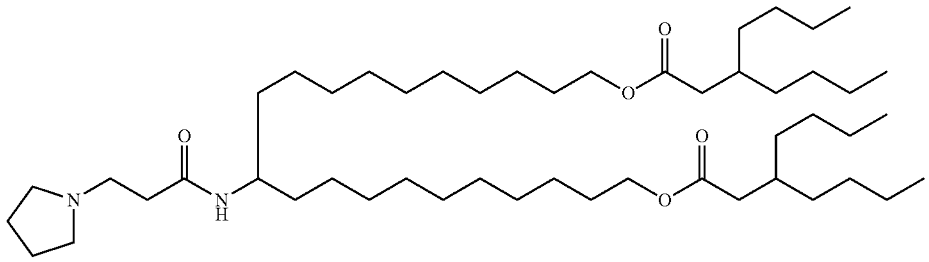 [SMILES: CCCCC(CCCC)CC(=O)OCCCCCCCCCCC(CCCCCCCCCCOC(=O)CC(CCCC)CCCC)NC(=O)CCN1CCCC1]
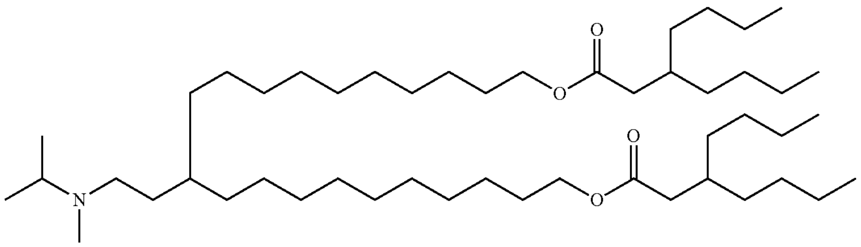 [SMILES: CCCCC(CCCC)CC(=O)OCCCCCCCCCCC(CCCCCCCCCCOC(=O)CC(CCCC)CCCC)CCN(C)C(C)C]
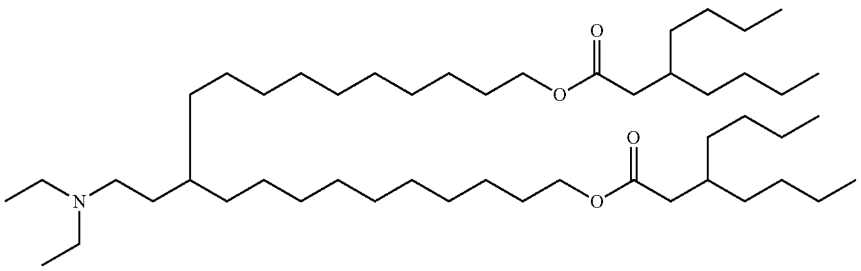 [SMILES: CCCCC(CCCC)CC(=O)OCCCCCCCCCCC(CCCCCCCCCCOC(=O)CC(CCCC)CCCC)CCN(CC)CC]
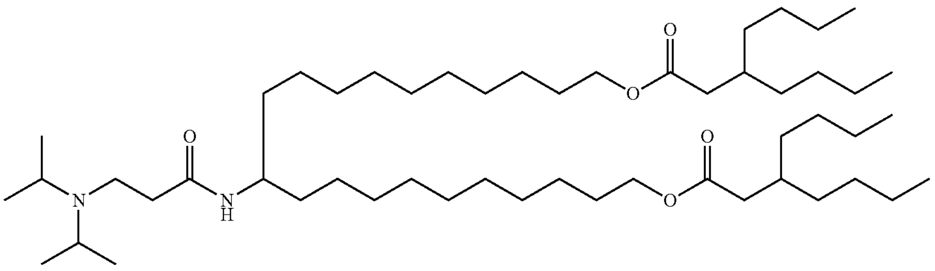 [SMILES: CCCCC(CCCC)CC(=O)OCCCCCCCCCCC(CCCCCCCCCCOC(=O)CC(CCCC)CCCC)NC(=O)CCN(C(C)C)C(C)C]

-continued
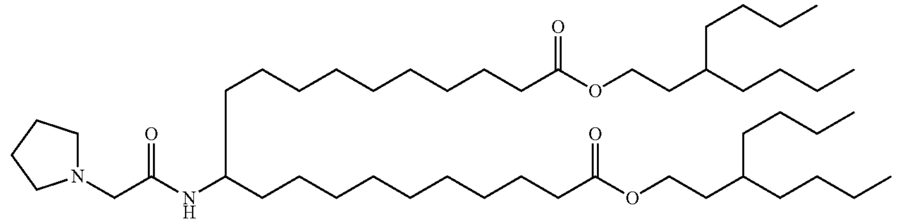 [SMILES: CCCCC(CCCC)CCOC(=O)CCCCCCCCCC(CCCCCCCCCC(=O)OCCC(CCCC)CCCC)NC(=O)CN1CCCC1]
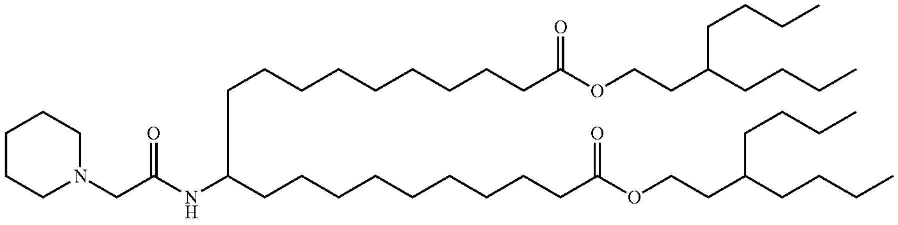 [SMILES: CCCCC(CCCC)CCOC(=O)CCCCCCCCCC(CCCCCCCCCC(=O)OCCC(CCCC)CCCC)NC(=O)CN1CCCCC1]
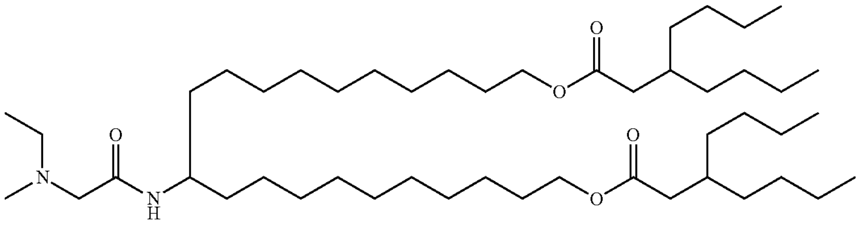 [SMILES: CCCCC(CCCC)CC(=O)OCCCCCCCCCCC(CCCCCCCCCCOC(=O)CC(CCCC)CCCC)NC(=O)CN(C)CC]
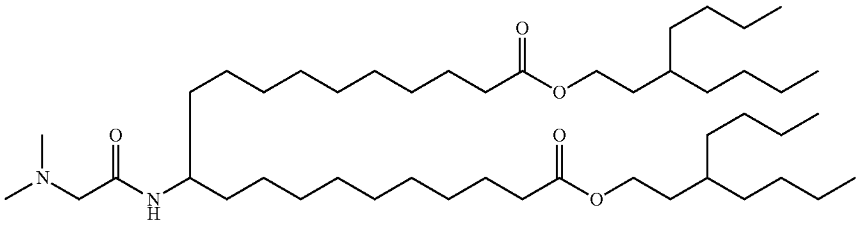 [SMILES: CCCCC(CCCC)CCOC(=O)CCCCCCCCCC(CCCCCCCCCC(=O)OCCC(CCCC)CCCC)NC(=O)CN(C)C]
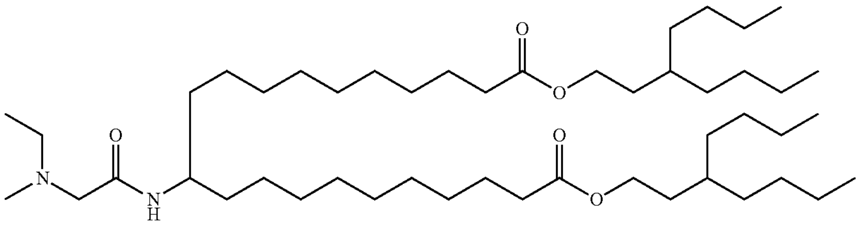 [SMILES: CCCCC(CCCC)CCOC(=O)CCCCCCCCCC(CCCCCCCCCC(=O)OCCC(CCCC)CCCC)NC(=O)CN(C)CC]
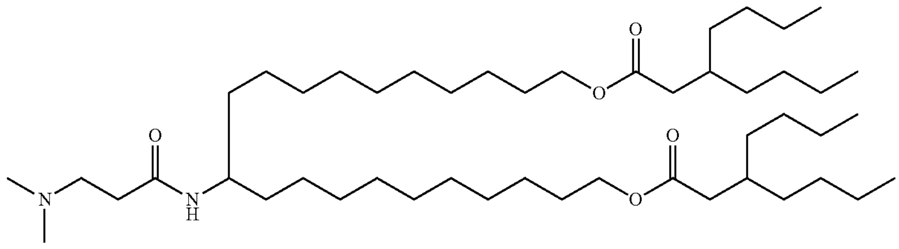 [SMILES: CCCCC(CCCC)CC(=O)OCCCCCCCCCCC(CCCCCCCCCCOC(=O)CC(CCCC)CCCC)NC(=O)CCN(C)C]
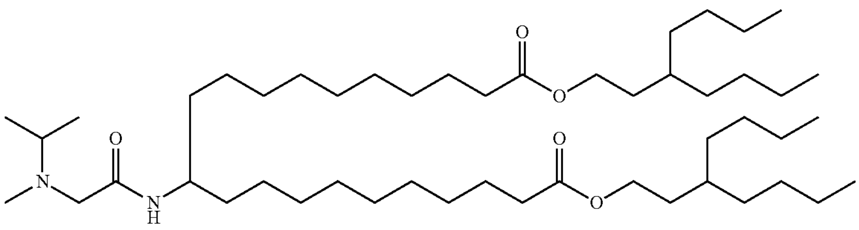 [SMILES: CCCCC(CCCC)CCOC(=O)CCCCCCCCCC(CCCCCCCCCC(=O)OCCC(CCCC)CCCC)NC(=O)CN(C)C(C)C]

-continued
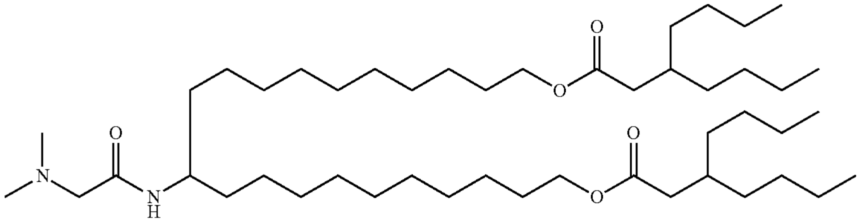 [SMILES: CCCCC(CCCC)CC(=O)OCCCCCCCCCCC(CCCCCCCCCCOC(=O)CC(CCCC)CCCC)NC(=O)CN(C)C]
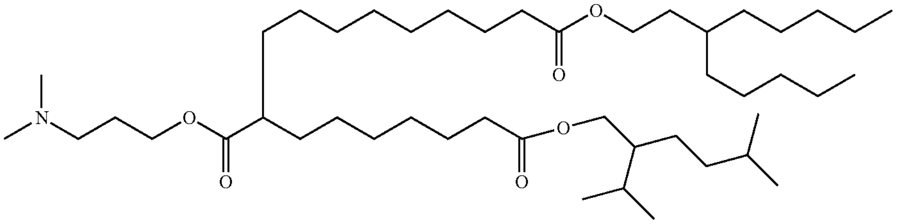 [SMILES: CCCCCC(CCCCC)CCOC(=O)CCCCCCCCC(CCCCCCC(=O)OCC(CCC(C)C)C(C)C)C(=O)OCCCN(C)C]
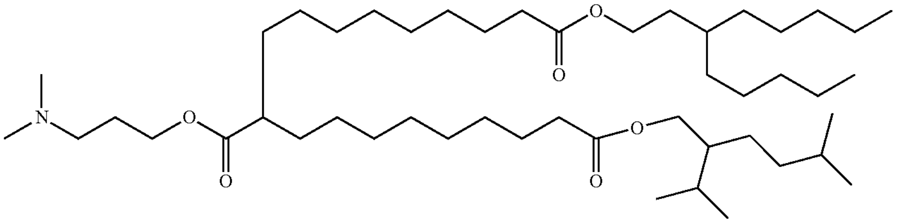 [SMILES: CCCCCC(CCCCC)CCOC(=O)CCCCCCCCC(CCCCCCCCC(=O)OCC(CCC(C)C)C(C)C)C(=O)OCCCN(C)C]
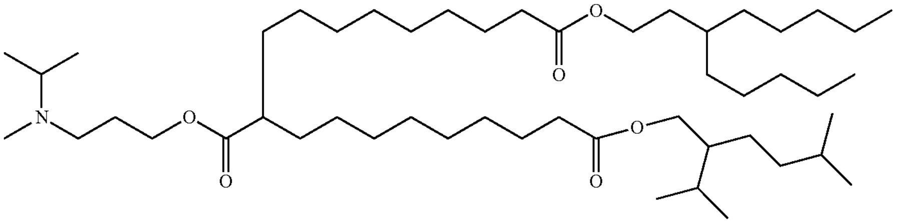 [SMILES: CCCCCC(CCCCC)CCOC(=O)CCCCCCCCC(CCCCCCCCC(=O)OCC(CCC(C)C)C(C)C)C(=O)OCCCN(C)C(C)C]
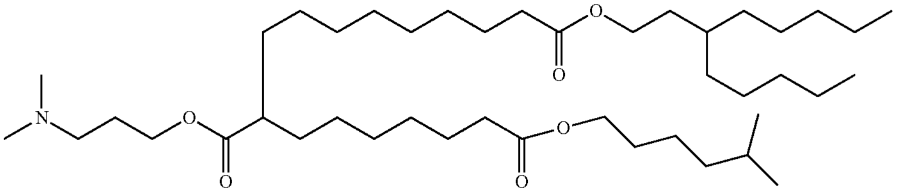 [SMILES: CCCCCC(CCCCC)CCOC(=O)CCCCCCCCC(CCCCCCC(=O)OCCCCC(C)C)C(=O)OCCCN(C)C]
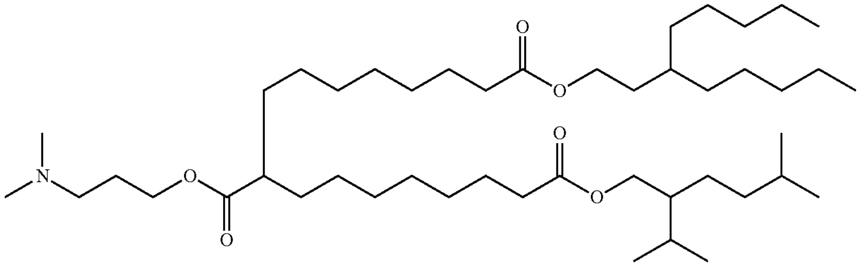 [SMILES: CCCCCC(CCCCC)CCOC(=O)CCCCCCCC(CCCCCCCC(=O)OCC(CCC(C)C)C(C)C)C(=O)OCCCN(C)C]

-continued

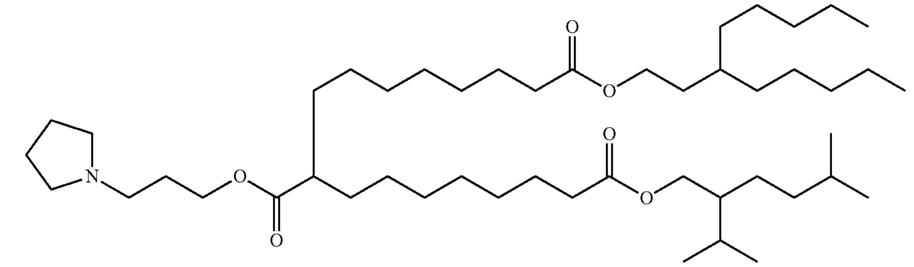 [SMILES: CCCCCC(CCCCC)CCOC(=O)CCCCCCCC(CCCCCCCC(=O)OCC(CCC(C)C)C(C)C)C(=O)OCCCN1CCCC1]

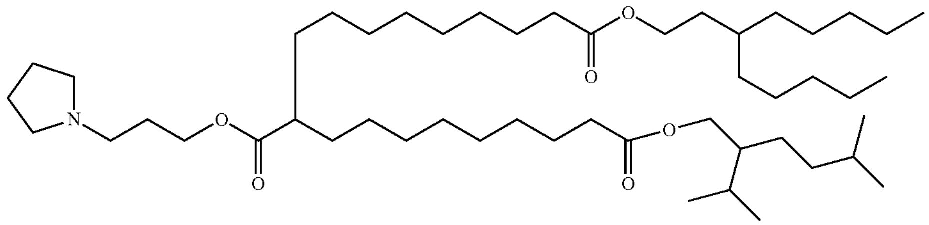 [SMILES: CCCCCC(CCCCC)CCOC(=O)CCCCCCCCC(CCCCCCCCC(=O)OCC(CCC(C)C)C(C)C)C(=O)OCCCN1CCCC1]

In certain embodiments, the cationic lipid in the formulation has at least one protonatable or deprotonatable group, such that the lipid is positively charged at a pH at or below physiological pH (e.g. pH 7.4), and neutral at a second pH, preferably at or above physiological pH. Such lipids are also referred to as cationic lipids. It will, of course, be understood that the addition or removal of protons as a function of pH is an equilibrium process, and that the reference to a charged or a neutral lipid refers to the nature of the predominant species and does not require that all of the lipid be present in the charged or neutral form. The lipids can have more than one protonatable or deprotonatable group, or can be zwiterrionic.

In certain embodiments, protonatable lipids (i.e., cationic lipids) have a $pK_a$ of the protonatable group in the range of about 4 to about 11. Typically, lipids will have a $pK_a$ of about 4 to about 7, e.g., between about 5 and 7, such as between about 5.5 and 6.8, when incorporated into lipid particles. Such lipids will be cationic at a lower pH formulation stage, while particles will be largely (though not completely) surface neutralized at physiological pH around pH 7.4. One of the benefits of a $pK_a$ in the range of between about 4 and 7 is that at least some nucleic acid associated with the outside surface of the particle will lose its electrostatic interaction at physiological pH and be removed by simple dialysis; thus greatly reducing the particle's susceptibility to clearance. $pK_a$ measurements of lipids within lipid particles can be performed, for example, by using the fluorescent probe 2-(p-toluidino)-6-napthalene sulfonic acid (TNS), using methods described in Cullis et al., (1986) *Chem Phys Lipids* 40, 127-144, which is incorporated by reference in its entirety.

In particular embodiments, the lipids are charged lipids. As used herein, the term "charged lipid" is meant to include those lipids having one or two fatty acyl or fatty alkyl chains and a quaternary amino head group. The quaternary amine carries a permanent positive charge. The head group can optionally include an ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine).

Lipid particles can include two or more cationic lipids. The cationic lipids can be selected to contribute different advantageous properties. For example, cationic lipids that differ in properties such as amine $pK_a$, chemical stability, half-life in circulation, half-life in tissue, net accumulation in tissue, or toxicity can be used in the lipid nanoparticle. In particular, the cationic lipids can be chosen so that the properties of the mixed-lipid particle are more desirable than the properties of a single-lipid particle of individual lipids.

Net tissue accumulation and long term toxicity (if any) from the cationic lipids can be modulated in a favorable way by choosing mixtures of cationic lipids instead of selecting a single cationic lipid in a given formulation. Such mixtures can also provide better encapsulation and/or release of the active pharmaceutical ingredient.

In one example, a series of structurally similar compounds can have varying $pK_a$ values that span a range, e.g. of less than 1 $pK_a$ unit, from 1 to 2 $pK_a$ units, or a range of more than 2 $pK_a$ units. Within the series, it may be found that a $pK_a$ in the middle of the range is associated with an enhancement of advantageous properties (greater effectiveness) or a decrease in disadvantageous properties (e.g., reduced toxicity), compared to compounds having $pK_a$ values toward the ends of the range. In such a case, two (or more) different compounds having $pK_a$ values toward opposing ends of the range can be selected for use together in a lipid nanoparticle. In this way, the net properties of the lipid nanoparticle (for instance, charge as a function of local pH) can be closer to that of a particle including a single lipid from the middle of the range. Cationic lipids that are structurally dissimilar (for example, not part of the series of structurally similar compounds mentioned above) can also be used in a mixed-lipid nanoparticle.

In some cases, two or more different cationic lipids may have widely differing $pK_a$ values, e.g., differing by 3 or more $pK_a$ units. In this case, the net behavior of a mixed lipid nanoparticle will not necessarily mimic that of a single-lipid particle having an intermediate $pK_a$. Rather, the net behavior may be that of a particle having two distinct protonatable (or deprotonatable, as the case may be) site with different $pK_a$ values. In the case of a single lipid, the fraction of protonatable sites that are in fact protonated varies sharply as the pH moves from below the $pK_a$ to above the $pK_a$ (when the pH is equal to the $pK_a$ value, 50% of the sites are protonated). When two or more different cationic lipids may have widely differing $pK_a$ values (e.g., differing by 3 or more $pK_a$ units) are combined in a lipid nanoparticle, the lipid nanoparticle can show a more gradual transition from non-protonated to protonated as the pH is varied.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle).

In one embodiment, the ratio of cationic lipid to nucleic acid is from about 3 to about 15, such as from about 5 to about 13 or from about 7 to about 11.

Non-Cationic Lipids

The non-cationic lipid can be a neutral lipid, an anionic lipid, or an amphipathic lipid. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., lipid particle size and stability of the lipid particle in the bloodstream. Preferably, the neutral lipid is a lipid having two acyl groups (e.g., diacylphosphatidylcholine and diacylphosphatidylethanolamine). In one embodiment, the neutral lipids contain saturated fatty acids with carbon chain lengths in the range of $C_{10}$ to $C_{20}$. In another embodiment, neutral lipids with mono or diunsaturated fatty acids with carbon chain lengths in the range of $C_{10}$ to $C_{20}$ are used. Additionally, neutral lipids having mixtures of saturated and unsaturated fatty acid chains can be used.

Suitable neutral lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), dimyristoyl phosphatidylcholine (DMPC), distearoyl-phosphatidyl-ethanolamine (DSPE), SM, 16-O-monomethyl PE, 16-O-dimethyl PE, 18-1-trans PE, 1-stearoyl-2-oleoyl-phosphatidyethanolamine (SOPE), cholesterol, or a mixture thereof.

Anionic lipids suitable for use in lipid particles of the invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphipathic lipids refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used.

The non-cationic lipid can be from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the particle. In one embodiment, the lipid nanoparticles include from about 0% to about 15 or 45% on a molar basis of neutral lipid, e.g., from about 3 to about 12% or from about 5 to about 10%. For instance, the lipid nanoparticles may include about 15%, about 10%, about 7.5%, or about 7.1% of neutral lipid on a molar basis (based upon 100% total moles of lipid in the lipid nanoparticle).

Sterols

A preferred sterol is cholesterol.

The sterol can be about 10 to about 60 mol % or about 25 to about 40 mol % of the lipid particle. In one embodiment, the sterol is about 10, 15, 20, 25, 30, 35, 40, 45, 50, 55, or about 60 mol % of the total lipid present in the lipid particle. In another embodiment, the lipid nanoparticles include from about 5% to about 50% on a molar basis of the sterol, e.g., about 15 to about 45%, about 20 to about 40%, about 48%, about 40%, about 38.5%, about 35%, about 34.4%, about 31.5% or about 31% on a molar basis (based upon 100% total moles of lipid in the lipid nanoparticle).

PEG-DPG and Other Aggregation Reducing Agents

The concentration of the PEG-DPG may range from about 0.1 to about 15 mol %, based upon the 100% total moles of lipid in the lipid particles. In one embodiment, the formulation includes from about 0.1 to about 3, about 2, about 1.5, about 1 or about 0.5 mole percent of PEG-DPG, based upon the total moles of lipid in the lipid particles.

In another embodiment, the lipid nanoparticles include from about 0.1% to about 20% on a molar basis of PEG-DPG, e.g., about 0.5 to about 10%, about 0.5 to about 5%, about 10%, about 5%, about 3.5%, about 1.5%, about 0.5%, or about 0.3% on a molar basis (based on 100% total moles of lipids in the lipid nanoparticles).

In one embodiment, the lipid nanoparticles contain an aggregation reducing agent in addition to PEG-DPG.

The aggregation reducing agent can be a lipid capable of reducing aggregation. Examples of such lipids include, but are not limited to, polyethylene glycol (PEG)-modified lipids, monosialoganglioside Gm1, and polyamide oligomers (PAO) such as those described in U.S. Pat. No. 6,320,017, which is incorporated by reference in its entirety. Other compounds with uncharged, hydrophilic, steric-barrier moieties, which prevent aggregation during formulation, like PEG, Gm1 or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613, each of which is incorporated by reference in its entirety.

The aggregation reducing agent may be, for example, a polyethyleneglycol (PEG)-lipid including, without limitation, a PEG-diacylglycerol (DAG), a PEG-dialkylglycerol, a PEG-dialkyloxypropyl (DAA), a PEG-phospholipid, a PEG-ceramide (Cer), or a mixture thereof (such as PEG-Cer14 or PEG-Cer20). The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). Other pegylated-lipids include, but are not limited to, polyethylene glycol-di-dimyristoyl glycerol (C14-PEG or PEG-C14, where PEG has an average molecular weight of 2000 Da) (PEG-DMG); (R)-2,3-bis(octadecyloxy)propyl-1-(methoxy poly(ethylene glycol)2000)propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy)propyl-1-(methoxy poly(ethylene glycol)2000)propylcarbamate)) (GalNAc-PEG-DSG); and mPEG (mw2000)-diastearoyl-phosphatidylethanolamine (PEG-DSPE). In one embodiment, the aggregation reducing agent is PEG-DMG. In another embodiment, the aggregation reducing agent is PEG-c-DMA.

The average molecular weight of the PEG moiety in the PEG-modified lipids (including PEG-DPG) can range from about 500 to about 8,000 Daltons (e.g., from about 1,000 to about 4,000 Daltons). In one preferred embodiment, the average molecular weight of the PEG moiety is about 2,000 Daltons.

The total concentration of the PEG-DPG and additional aggregation reducing agent(s) may range from about 0.1 to about 15 mol %, based upon the 100% total moles of lipid in the lipid particle. In one embodiment, the formulation includes less than about 3, 2, or 1 mole percent of PEG-modified lipids, based upon the total moles of lipid in the lipid particle.

In another embodiment, the lipid nanoparticles include from about 0.1% to about 20% on a molar basis of the PEG-modified lipids, e.g., about 0.5 to about 10%, about 0.5 to about 5%, about 10%, about 5%, about 3.5%, about 1.5%, about 0.5%, or about 0.3% on a molar basis (based on 100% total moles of lipids in the lipid nanoparticle).

Lipid Nanoparticles (LNPs)

The lipid nanoparticles may have the structure of a liposome. A liposome is a structure having lipid-containing membranes enclosing an aqueous interior. Liposomes may have one or more lipid membranes. Liposomes can be single-layered, referred to as unilamellar, or multi-layered, referred to as multilamellar. When complexed with nucleic acids, lipid particles may also be lipoplexes, which are composed of cationic lipid bilayers sandwiched between DNA layers.

The formulation is preferably substantially free of aggregates of lipid nanoparticles. For instance, the formulation may have a $d_{90}$ (i.e., 90% of the particles have a particle size) less than about 1, about 0.9, about 0.8, about 0.7, or about 0.6 μm. In one preferred embodiment, the formulation includes less than about 5, about 4, about 3, about 2, or about 1% by volume of aggregates greater than about 2, about 1.5, about 1, or about 0.8 Mm.

In certain embodiments, the lipid nanoparticles in the formulation have a $d_{98}$ of less than 1 micron, such as less than about 500 nm, less than about 400 nm, less than about 300 nm, less than about 250 nm, less than about 200 nm, less than about 150 nm or less than about 100 nm. For example, the lipid nanoparticles have a $d_{99}$ of less than 1 micron, such as less than about 500 nm, less than about 400 nm, less than about 300 nm, less than about 250 nm, less than about 200 nm, less than about 150 nm or less than about 100 nm. In additional embodiments, the particle has a $d_{50}$ of less than about 100 nm, such as less than about 75 nm, less than about 50 nm, less than about 40 nm, less than about 30 nm, less than about 20 nm or less than about 10 nm. For instance, the lipid nanoparticles may have a $d_{99}$ ranging from about 50 to about 200 nm, or from about 75 to about 150 nm. The lipid nanoparticles may have a $d_{50}$ ranging from about 5 to about 50 nm, such as from about 10 to about 40 nm or from about 20 to about 30 nm.

In another embodiment, the lipid nanoparticles have a median diameter size of from about 50 nm to about 300 nm, such as from about 50 nm to about 250 nm, for example, from about 50 nm to about 200 nm.

In one preferred embodiment, the $d_{50}$, $d_{98}$ or $d_{99}$ of the lipid nanoparticles in the formulation does not vary by more than 40, 30, 20, 10, or 5% after 1, 3, 6, 9, 12, and 24 months of storage at 4° C. In one embodiment, after 1 month of storage at 4° C., the lipid nanoparticles in the formulation have $d_{50}$, $d_{98}$ and/or $d_{99}$ values as set forth above. For instance, after 1 month storage at 4° C., the lipid nanoparticles in the formulation have $d_{98}$ or $d_{99}$ of less than 1 micron, such as less than about 500 nm, less than about 400 nm, less than about 300 nm, less than about 250 nm, less than about 200 nm, less than about 150 nm or less than about 100 nm.

In yet another embodiment, the lipid nanoparticles in the formulation of the present invention have a single mode particle size distribution (i.e., they are not bi- or poly-modal).

The lipid nanoparticles may further comprise one or more lipids and/or other components in addition to those mentioned above. Other lipids may be included in the liposome compositions for a variety of purposes, such as to prevent lipid oxidation or to attach ligands onto the liposome surface. Any of a number of lipids may be present in lipid particles, including amphipathic, neutral, cationic, and anionic lipids. Such lipids can be used alone or in combination.

Additional components that may be present in a lipid particle include bilayer stabilizing components such as polyamide oligomers (see, e.g., U.S. Pat. No. 6,320,017, which is incorporated by reference in its entirety), peptides, proteins, and detergents.

Different lipid nanoparticles having varying molar ratios of cationic lipid, non-cationic (or neutral) lipid, sterol (e.g., cholesterol), and aggregation reducing agent (such as a PEG-modified lipid) on a molar basis (based upon the total moles of lipid in the lipid nanoparticles) are provided in Table 1 below.

TABLE 1

| | Molar Ratio of Lipids (Based upon 100% total moles of lipid in the lipid nanoparticle) | | | |
|---|---|---|---|---|
| Formulation No. | Cationic Lipid | Non-Cationic (or Neutral) Lipid | Sterol | Aggregation Reducing Agent (e.g., PEG-lipid) |
| 1 | from about 35 to about 65% | from about 3 to about 12 or 15% | from about 15 to about 45% | from about 0.1 to about 10% (preferably from about 0.5 to about 2 or |

TABLE 1-continued

| | Molar Ratio of Lipids (Based upon 100% total moles of lipid in the lipid nanoparticle) | | | |
|---|---|---|---|---|
| Formulation No. | Cationic Lipid | Non-Cationic (or Neutral) Lipid | Sterol | Aggregation Reducing Agent (e.g., PEG-lipid) |
| | | | | 3%) |
| 2 | from about 20 to about 70% | from about 5 to about 45% | from about 20 to about 55% | from about 0.1 to about 10% (preferably from about 0.5 to about 2 or 3%) |
| 3 | from about 45 to about 65% | from about 5 to about 10% | from about 25 to about 40% | from about 0.1 to about 3% |
| 4 | from about 20 to about 60% | from about 5 to about 25% | from about 25 to about 55% | from about 0.1 to about 5% (preferably from about 0.1 to about 3%) |
| 5 | about 40% | about 10% | about 40% | about 10% |
| 6 | about 35% | about 15% | about 40% | about 10% |
| 7 | about 52% | about 13% | about 30% | about 5% |
| 8 | about 50% | about 10% | about 38.5% | about 1.5% |

In one embodiment, the weight ratio of lipid to siRNA is at least about 0.5:1, at least about 1:1, at least about 2:1, at least about 3:1, at least about 4:1, at least about 5:1, at least about 6:1, at least about 7:1, at least about 11:1 or at least about 33:1. In one embodiment, the weight ratio of lipid to siRNA is from about 1:1 to about 35:1, about 3:1 to about 15:1, about 4:1 to about 15:1, or about 5:1 to about 13:1. In one embodiment, the weight ratio of lipid to siRNA is from about 0.5:1 to about 12:1.

In one embodiment, the lipid nanoparticles have an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

The Medium

The medium containing the lipid nanoparticles preferably is substantially free of negative counter-ions (i.e., anions). Without wishing to be bound by any particular theory, the inventors believe that the presence of negative counter-ions in an LNP formulation at least partially neutralizes the positively charged surface of the LNPs, thereby eliminating the aggregation reducing effect of charge repulsion.

The medium may comprise a non-ionic or substantially non-ionic diluent, and preferably includes a non-ionic or substantially non-ionic diluent that does not destabilize the formulation. In one embodiment, the non-ionic or substantially non-ionic diluent increases the stability of the lipid nanoparticles, such as against mechanical disturbances, and/or inhibits the aggregation of the lipid nanoparticles. The medium may comprise water. In a preferred embodiment, the medium is deionized (e.g., deionized water). The water in the medium may have been purified, for example, by reverse osmosis. In a preferred embodiment, the medium (such as water) contains less than about 50 ppm of mineral acid(s), such as less than about 40 ppm, less than about 30 ppm, less than about 20 ppm, less than about 10 ppm, less than about 5 ppm or less than about 1 ppm of mineral acid(s).

The medium may include an acid so long as it is not predominantly in its dissociated form. In one embodiment, the formulation further comprises an acid, wherein the ratio of (a) the concentration of the anions formed from the acid to (b) the concentration of the acid is less than about 0.5, such as less than about 0.4, less than about 0.3, less than about 0.2 or less than about 0.1. In a particular embodiment, the ratio of anion concentration to acid concentration is less than about 0.2 to 0.5. The anions present in the formulation may be derived from the acid in the medium. In one embodiment, the anion is a monovalent anion (such as an anion derived from acetic acid).

Isotonicity Agents

The isotonicity agent(s) included in the formulation are preferably substantially free of anions (e.g., substantially non-ionic), and more preferably are non-ionic. Suitable non-ionic isotonicity agents include, but are not limited to, polyols (e.g., a sugar alcohol such as a $C_3$-$C_6$ sugar alcohol), sugars (such as sucrose, fructose, dextrose, trehalose, or glucose), amino acids (such as glycine), and albumin. Suitable sugar alcohols include, but are not limited to, glycerol, erythritol, threitol, arabitol, xylitol, ribitol, sorbitol, mannitol, dulcitol and iditol. In one embodiment, the isotonicity agent is a sugar such as a glucose.

In one embodiment, the concentration of sugar (e.g., glucose) in the medium is at most about 300 mM, such as at most about 200, 100, 75, or 50 mM.

The amount of the isotonicity agent is preferably sufficient for the formulation to obtain an isotonic level.

In another embodiment, the formulation is free or substantially free of isotonicity agents.

Pharmaceutical Formulation

The concentration of lipid nanoparticles in the formulation may range from about 0.01 to about 50 mg/mL. In one embodiment, the concentration of lipid nanoparticles in the formulation ranges from about 0.1 to about 10 mg/mL, such as 0.5 to about 5 mg/mL. In another embodiment, the concentration of lipid nanoparticles in the formulation is about 0.5, about 0.75, about 1, about 1.5, about 2, about 2.5, about 3, about 4, or about 5 mg/mL.

The formulation may be administered parenterally, for example, intradermally, subcutaneously, intramuscularly, intravenously, or intraperitoneally. In one embodiment, the formulation is directly injected into a subject. In another embodiment, the formulation is added to an intravenous fluid which is intravenously administered. Because many intravenous fluids contain significant quantities of anions which may over time cause aggregation of LNPs, the formulation of the present invention is preferably added to the intravenous fluid shortly before (e.g., within 5, 10 or 15 minutes of) or simultaneously with the intravenous administration to the subject.

The formulation may further include additional pharmaceutically acceptable diluents, excipients, and/or carriers.

Example of excipients include, but are not limited to, isotonicity agents, pH adjusting and buffering agents. The formulation may also include lipid-protective agents which protect lipids against free-radical and lipid-peroxidative damages on storage. Such agents include lipophilic free-radical quenchers, such as α-tocopherol and water-soluble iron-specific chelators, such as ferrioxamine.

The formulation can be sterilized by known sterilization techniques. The aqueous solutions can then be packaged for use or filtered under aseptic conditions and lyophilized, the lyophilized preparation being combined with a sterile aqueous solution prior to administration.

The concentration of lipid nanoparticles in the formulation can range, for example, from less than about 0.01% (e.g., at or at least about 0.05-5%) to as much as 10 to 30% by weight. The dose of lipid nanoparticles is dependent on many factors, including the disorder and active pharmaceutical ingredient. In one embodiment, the dose of lipid nanoparticles administered may range from about 0.01 and about 50 mg per kilogram of body weight (e.g., from about 0.1 and about 5 mg/kg of body weight).

The lipid formulation or lipid nanoparticles can be provided in kit form. The kit will typically be comprised of a container that is compartmentalized for holding the various elements of the kit. The kit may contain the lipid nanoparticles or the formulation, such as in dehydrated or concentrated form, with instructions for their rehydration or dilution and administration.

Methods of Manufacture

The lipid nanoparticles may be prepared by an in-line mixing method as follows. In this method, both the lipids (e.g., the cationic lipid, non-cationic lipid, sterol, and aggregation reducing agent) and the nucleic acid are added in parallel into a mixing chamber. The mixing chamber can be a simple T-connector. This method is disclosed, for example, in International Publication No. WO 2010/088537, U.S. Pat. No. 6,534,018 and U.S. Pat. No. 6,855,277, U.S. Patent Publication No. 2007/0042031 and *Pharmaceuticals Research*, Vol. 22, No. 3, March 2005, p. 362-372, which are hereby incorporated by reference in their entirety.

In one embodiment, individual and separate stock solutions are prepared—one containing lipid (e.g., the cationic lipid, non-cationic lipid, sterol, and aggregation reducing agent) and the other an active pharmaceutical ingredient, such as a nucleic acid (e.g., siRNA). A lipid stock solution containing a cationic lipid, non-cationic lipid, sterol, and an aggregation reducing agent (e.g., a PEG-modified lipid) is prepared by solubilizing the lipids in a solution of an alcohol (e.g., ethanol) at, for example, a lipid concentration of 25 mg/mL. The nucleic acid (e.g., siRNA) is solubilized in acetate buffer, for example, at a concentration of 0.8 mg/mL. For small scale, 5 mL of each stock solution may be prepared.

Preferably, the stock solutions are completely clear, and the lipids are completely solubilized before combining them with the nucleic acid. The stock solutions may be heated to completely solubilize the lipids.

The individual stock solutions (i.e., the lipid stock solution and the nucleic acid stock solution) may be combined by pumping each solution to a T-junction (i.e., by in-line mixing). This results in the formation of the lipid nanoparticles.

Following the formation of the lipid nanoparticles, the medium of the lipid nanoparticles may be exchanged to one which is (a) non-ionic or substantially non-ionic and/or (b) free of or substantially free of anions. This exchange can be performed by dialysis or tangential flow filtration.

For example, the lipid nanoparticles may be dialyzed into reverse osmosis/deionized (RO/DI) water, and then concentrated (e.g., using centrifuge tubes). The dispersion medium can then be changed to, for example, 300 mM glucose by adding an appropriate stock solution, for example, to give final lipid nanoparticles at ~1 mg/mL (based on siRNA).

Alternatively, the medium may be exchanged as follows. The lipid nanoparticles are diluted into RO/DI water. The diluted lipid nanoparticles are then concentrated using tangential flow filtration. The concentration step includes washing with 10× larger volume-compared to concentrated formulation volume-of RO/DI water. The dispersion medium can then be changed to, for example, 300 mM glucose by adding an appropriate stock solution, for example, to give final lipid nanoparticles at ~1 mg/mL (based on siRNA).

EXAMPLES

The examples below are provided to describe specific embodiments of the present invention. By providing these specific examples, the applicants do not limit the scope and spirit of the present invention.

Example 1

Lipid nanoparticles having the components shown in Table 2 below were prepared.

TABLE 2

| Component | Mole Percentage (Based on 100% of the lipid components in the LNP) |
|---|---|
| 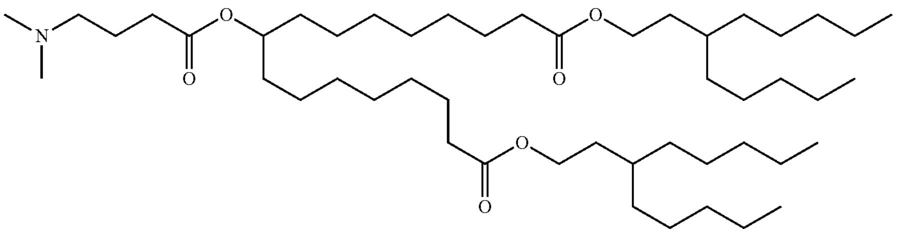 [SMILES: CCCCCC(CCCCC)CCOC(=O)CCCCCCCC(CCCCCCCC(=O)OCCC(CCCCC)CCCCC)OC(=O)CCCN(C)C] (Cationic Lipid) | 50% |
| Distearoylphosphatidylcholine (DSPC) | 10% |
| Cholesterol | 38.5% |

TABLE 2-continued

| Component | Mole Percentage (Based on 100% of the lipid components in the LNP) |
|---|---|
| PEG-DPG | 1.5% |
| siRNA (AD-1661) | — |

The ratio of cationic lipid to siRNA was 7.06. The ratio of total lipid to siRNA was 11.80.

The cationic lipid can be prepared by the methods described in U.S. Provisional Application Nos. 61/623,274, filed Apr. 12, 2012, and 61/568,133, filed Dec. 7, 2011, which are hereby incorporated by reference. The siRNA AD-1661 targets Factor VII and has the sequence shown below in Table 3.

TABLE 3

| Duplex # | Sequence 5'-3' | SEQ ID NO: | Target |
|---|---|---|---|
| AD-1661 | GGAfUfCAfUfCfUfCAAGfUfCfUfUAfC dTsdT | 1 | FVII |
| | GfUAAGAfCfUfUGAGAfUGAfUfCfCdT sdT | 2 | |

("G," "C," "A," "T" and "U" each refer to a ribonucleotide where the base is guanine, cytosine, adenine, thymidine and uracil, respectively. "dT" refers to a deoxyribonucleotide where the nucleobase is thymine, i.e., deoxyribothymine. "s" refers to phosphothioate. Lower case refers to 2'-OMe modification and Nf is a 2'F modified nucleobase.)

The lipid nanoparticles were prepared as follows. The cationic lipid, DSPC, cholesterol, and PEG-DPG in the ratio recited in Table 2 were solubilized in ethanol at a total lipid concentration of 25 mg/mL.

A siRNA stock solution was prepared by solubilizing the siRNA AD-1661 in a low pH acetate or citrate buffer (pH=4) at 0.8 mg/mL.

The stock solutions should be completely clear and the lipids should be completely solubilized before combining with the siRNA. Therefore, if it was determined appropriate, the stock solutions were heated to completely solubilize the lipids.

The individual stock solutions were combined by pumping each solution to a T-junction (i.e., by in-line mixing). Specifically, the ethanol solution (at 5 ml/min, via 0.01 in. PEEK tube) and aqueous buffer solution (at 15 mL/min, via 0.02 in. PEEK tube) were mixed through a T-junction (PEEK Tee body, IDEX).

After the T-junction a single tubing is placed where the combined stream will emit. Ethanol is removed and exchanged for PBS by dialysis. The lipid formulations are then concentrated using centrifugation or diafiltration to an appropriate working concentration.

Comparative Example 1

The procedure in Example 1 was repeated using 1-(monomethoxy-polyethyleneglycol)-2,3-dimyristoylglycerol (PEG-DMG) instead of PEG-DPG. The ratio of cationic lipid to siRNA was 7.06. The ratio of total lipid to siRNA was 11.79.

Example 2

The encapsulation efficiency for lipid nanoparticles in Example 1 and Comparative Example 1 was measured as follows.

The results are shown in Table 4 below.

TABLE 4

| Lipid Nanoparticles | Entrapment/Encapsulation Efficiency |
|---|---|
| Example 1 | 98 |
| Comparative Example 1 | 89 |

Example 3

In Vivo Evaluation of Lipid Nanoparticle Formulations

The formulations prepared in Example 1 and Comparative Example 1 were tested in mice for their anti-Factor VII activity as follows.

C57BL/6 mice (Charles River Labs, MA) received either PBS or one of the test formulations at dose of 0.03, 0.01 or 0.003 mg/kg via intravenous (bolus) injection. 24 hours after administration, Factor VII levels were measured in the serum using a chromogenic assay (Coaset Factor VII, DiaPharma Group, OH or Biophen FVII, Aniara Corporation, OH) according to the manufacturer protocols.

The results are shown in FIG. 1.

Example 4

The procedure in Example 1 was repeated except AD-18328, having the sequences shown in Table 5 below, was used as the siRNA.

TABLE 5

| Duplex # | Sequence 5'-3' | SEQ ID NO: | Target |
|---|---|---|---|
| AD-18328 | GuAAccAAGAGuAuuccAudTdT | 5 | TTR |
| | AUGGAAuACUCUUGGUuACdTdT | 6 | |

Comparative Example 2

The procedure in Example 4 was repeated except using 1-(monomethoxy-polyethyleneglycol)-2,3-dimyristoylglycerol (PEG-DMG) instead of PEG-DPG.

Example 5

In vivo Evaluation of Lipid Nanoparticle Formulations

The formulations prepared in Example 5 and Comparative Example 2 were tested in monkeys for their anti-TTR activity as follows.

Figure 2:
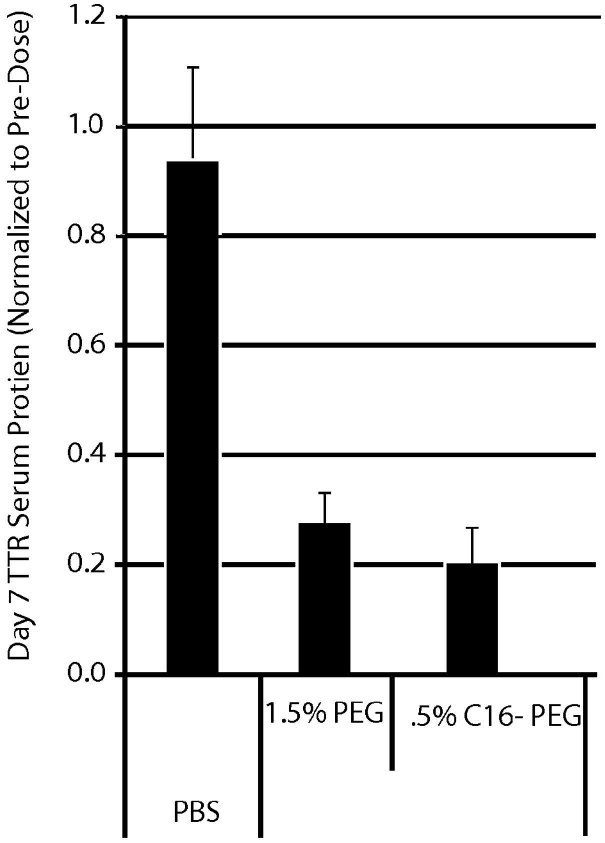
FIG. 2 shows the TTR serum protein level (normalized to pre-dose) 7 days after intravenous administration of the formulations prepared in Example 5 and Comparative Example 2 in monkeys.

The results on day 7 are shown in FIG. 2.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A pharmaceutical formulation for parenteral administration comprising (a) lipid nanoparticles in (b) a medium, wherein the formulation has one or more of the following characteristics:

(i) the medium is substantially free of anions, (ii) the medium is non-ionic or substantially non-ionic, and (iii) the formulation has a pH less than the pKa of the cationic lipid, wherein (i) the lipid nanoparticles comprise (a) a biodegradable cationic lipid;

(b) polyethylene glycol-dipalmitoylglycerol (PEG-DPG);

(c) a non-cationic lipid;

(d) an active pharmaceutical ingredient; and (e) an active pharmaceutical ingredient, and, wherein the lipid nanoparticles have a $d_{98}$ of less than about 150 nm.

2. The formulation of claim 1, wherein the formulation further comprises an acid, and the ratio of (a) the anion concentration from the acid to (b) the acid is less than about 0.5.

3. The formulation of claim 1, wherein the formulation further comprises a nonionic or substantially non-ionic isotonicity agent.

4. The formulation of claim 3, wherein the isotonicity agent is a polyol, sugar, amino acid, or albumin.

5. The formulation of claim 3, wherein the concentration of the isotonicity agent in the medium is at most about 300 mM.

6. The formulation of claim 1, wherein the lipid nanoparticles have a $d_{50}$ of less than about 50 nm.

7. The formulation of claim 1, wherein the lipid nanoparticles has a mean diameter of less than about 100 nm after about 1 month at 4° C.

* * * * *